(12) United States Patent
Baloglu et al.

(10) Patent No.: US 8,901,156 B2
(45) Date of Patent: Dec. 2, 2014

(54) COMPOUNDS AND METHODS

(75) Inventors: Erkan Baloglu, Cambridge, MA (US); Shomir Ghosh, Cambridge, MA (US); Mercedes Lobera, Cambridge, MA (US); Darby Schmidt, Cambridge, MA (US)

(73) Assignee: Tempero Pharmaceuticals, Inc., Cambridge, MA (US)

( * ) Notice: Subject to any disclaimer, the term of this patent is extended or adjusted under 35 U.S.C. 154(b) by 161 days.

(21) Appl. No.: 13/522,044

(22) PCT Filed: Jan. 13, 2011

(86) PCT No.: PCT/US2011/021089
§ 371 (c)(1),
(2), (4) Date: Jul. 13, 2012

(87) PCT Pub. No.: WO2011/088181
PCT Pub. Date: Jul. 21, 2011

(65) Prior Publication Data
US 2013/0059883 A1   Mar. 7, 2013

Related U.S. Application Data

(60) Provisional application No. 61/294,575, filed on Jan. 13, 2010.

(51) Int. Cl.
| | | |
|---|---|---|
| A01N 43/82 | (2006.01) | |
| A61K 31/41 | (2006.01) | |
| A01N 43/78 | (2006.01) | |
| A61K 31/425 | (2006.01) | |
| A01N 43/76 | (2006.01) | |
| A61K 31/42 | (2006.01) | |
| C07D 291/00 | (2006.01) | |
| C07D 285/08 | (2006.01) | |
| C07D 271/06 | (2006.01) | |
| C07D 249/08 | (2006.01) | |
| C07D 417/14 | (2006.01) | |
| A61K 31/497 | (2006.01) | |
| C07D 413/14 | (2006.01) | |
| C07D 413/12 | (2006.01) | |

(52) U.S. Cl.
CPC ............ *A61K 31/497* (2013.01); *C07D 417/14* (2013.01); *C07D 413/14* (2013.01); *C07D 271/06* (2013.01); *C07D 413/12* (2013.01)
USPC ........... 514/364; 514/365; 514/374; 514/383; 548/122; 548/128; 548/131; 548/262.2

(58) Field of Classification Search
None
See application file for complete search history.

(56) References Cited

U.S. PATENT DOCUMENTS

| 7,799,825 B2 | 9/2010 | Ferrigno et al. |
|---|---|---|
| 2009/0048228 A1 | 2/2009 | Attenni et al. |
| 2009/0076101 A1 | 3/2009 | Ferrigno et al. |

FOREIGN PATENT DOCUMENTS

| WO | WO 96/09822 A1 | 4/1996 |
|---|---|---|
| WO | WO 01/18045 A1 | 3/2001 |
| WO | WO 02/22577 A2 | 3/2002 |
| WO | WO 03/087057 A1 | 10/2003 |
| WO | WO 2006/102645 A1 | 9/2006 |
| WO | WO 2011/088187 A1 | 7/2011 |
| WO | WO 2011/088192 A1 | 7/2011 |
| WO | WO 2013/006408 A1 | 1/2013 |
| WO | WO 2013/008162 A1 | 1/2013 |

OTHER PUBLICATIONS

Lobera, et al. Nature Chemical Biology, 9: 319-328 (2013).
Lobera, et al. Supplementary Information, Nature Chemical Biology, 1-23 (2013). [Nature Chemical Biology: doi:10.1038/nchembio.1223].
Scarpelli, et al. Bioorganic & Medicinal Chemistry Letters, 18: 6078-6082 (2008).
Jones, et al. Bioorganic & Medicinal Chemistry Letters, 18: 3456-3461 (2008).
Muraglia, et al. Bioorganic & Medicinal Chemistry Letters, 18: 6083-6087 (2008).
Sheremetev, et al. Russian Chemical Bulletin (Translation of Izvestiya Akademii Nauk, Seriya Khimicheskaya), 53(3): 596-614 (2004).

*Primary Examiner* — Jeffrey S. Lundgren
*Assistant Examiner* — Michael Schmitt
(74) *Attorney, Agent, or Firm* — Kathryn A. Lutomski; John Lemanowicz

(57) ABSTRACT

Disclosed are compounds having the formula:

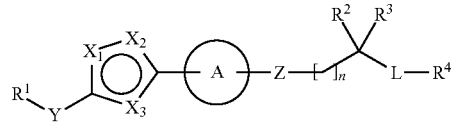

wherein $X_1$, $X_2$, $X_3$, $R^1$, $R^2$, $R^3$, $R^4$, Y, A, Z, L and n are as defined herein, and methods of making and using the same.

22 Claims, No Drawings

COMPOUNDS AND METHODS

This application is a §371 of International Application No. PCT/US2011/021089, filed 13 Jan. 2011, which claims the benefit of U.S. Provisional Application No. 61/294,575, filed 13 Jan. 2010, which is incorporated herein in its entirety.

FIELD OF THE INVENTION

The present invention relates to compounds that inhibit histone deacetylase (HDAC) enzymes, the preparation of these compounds, the use of these compounds in the treatment of diseases or conditions ameliorated by inhibition of HDAC activity and pharmaceutical compositions comprising these compounds.

BACKGROUND OF THE INVENTION

Chromatin organization involves DNA wound around histone octamers that form nucleosomes. Core histones with N-terminal tails extending from compact nucleosomal core particles can be acetylated or deacetylated at epsilon lysine residues affecting histone-DNA and histone-non-histone protein interactions. Histone deacetylases (HDACs) catalyze the deacetylation of histone and non-histone proteins and play an important role in epigenetic regulation. There are currently 18 known HDACs that are organized into three classes: class I HDACs (HDAC1, HDAC2, HDAC3, HDAC8 and HDAC11) are mainly localized to the nucleus; class II HDACs (HDAC4, HDAC5, HDAC6, HDAC7, HDAC9 and HDAC10), which shuttle between the nucleus and the cytoplasm; and class III HDACs (SIRT1-7), whose cellular localization includes various organelles.

Class II HDACs are further characterized as class IIa HDACs and class IIb HDACs.

HDAC9 is class IIa histone deacetylase highly expressed in human Tregs. HDAC9 deficiency: 1) increases Foxp3 expression (and other Treg markers), 2) increases Foxp3 and histone 3 acetylation, 3) increases Foxp3 DNA binding, 4) increases Treg numbers, 5) increases suppressive activity in vitro and in vivo, and 6) ameliorates murine colitis. Tregs which are deficient in HDAC9 induce permanent tolerance of fully mismatched cardiac allografts. In addition, HDAC9 inhibitors maybe useful for treatment of diseases and disorders associated with abnormal cell proliferation, differentiation and survival, e.g. breast and prostate tumors.

Preliminary data shows that targeting HDAC7, a class IIa histone deacetylase, enhances Treg suppression in vitro and in vivo. HDAC7 enhances FOXP3+ Treg function and induces long-term allograft survival.

Inhibition of HDAC6, a class IIb HDAC, has been shown to increase Treg suppressive function in vitro along with increased expression of FOXP3 protein and Treg associated genes including CTLA, IL-10, TNR18. HDAC6 inhibition in vivo decreased severity of colitis in the dextran sodium sulphate-induced colitis model and the $CD4_+CD62L_{high}$ adoptive transfer model of colitis. In addition, inhibition of HDAC6 with a subtherapeutic dose of rapamycin led to prolonged cardiac allograft survival.

Based on the above evidence, an orally available small molecule selective inhibitor of Class II HDAC activity (more specifically HDAC9 or HDAC7 or HDAC6) is expected to modulate autoimmune diseases through expansion and enhancement of Treg activity.

Inhibition of other Class II HDAC's for example HDAC4 and 5 impair myogenesis by modulating the stability and activity of HDAC-MEF2 complexes and maybe potentially useful for the treatment of muscle and heart diseases including cardiac hypertrophy and heart failure. Also, inhibition of Class II HDAC activity, represents a novel approach for disrupting or intervening in cell cycle regulation.

Class II HDAC inhibitors have therapeutic potential in the study and/or treatment of diseases or conditions ameliorated by modulating HDAC activity (in particular, cell proliferative diseases (such as cancer), diabetes (type I and/or type II diabetes), inflammation, cardiac disease, obesity, stroke, epilepsy, depression, immunological disease or viral or fungal infection.

Many HDAC inhibitors, however, inhibit all HDAC isoforms. It would be advantageous to identify HDAC inhibitors that inhibited one or more but not all HDAC isoforms.

SUMMARY OF THE INVENTION

The invention is directed to a compound according to Formula I:

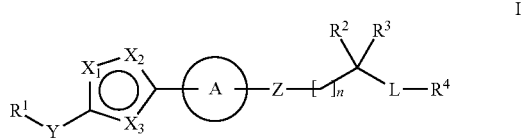

wherein:

$R^1$ is halo($C_1$-$C_4$)alkyl, wherein said halo($C_1$-$C_4$)alkyl contains at least 2 halo groups;

Y is a bond and $X_1$ is O, N or NH, $X_2$ is N or CH and $X_3$ is N or NH, or Y is —C(O)— and $X_1$ and $X_2$ are CH or N, $X_3$ is O or S, or Y is —C(O)— and $X_1$ is O, $X_2$ is CH or N, and $X_3$ is CH or N;

A is optionally substituted ($C_3$-$C_6$)cycloalkyl, phenyl, naphthyl, 4-7 membered heterocycloalkyl, 5-6 membered heteroaryl, or 9-10 membered heteroaryl, wherein any optionally substituted cycloalkyl, phenyl, naphthyl, heterocycloalkyl, or heteroaryl is optionally substituted by 1-3 groups independently selected from ($C_1$-$C_4$) alkyl, halogen, cyano, halo($C_1$-$C_4$)alkyl, ($C_1$-$C_4$)alkoxy, halo($C_1$-$C_4$)alkoxy, —$NR^AR^A$ and —(($C_1$-$C_4$)alkyl)$NR^AR^A$;

Z is —C(=O)$NR^X$—, —$NR^XC$(=O)$NR^X$, —$NR^XC$(=O)—, —$SO_2$—, —$SO_2NR^X$—, —$NR^XSO_2$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—;

n is 0-4;

when n is 0, $R^2$ and $R^3$ are independently selected from H and optionally substituted ($C_1$-$C_4$)alkyl, aryl($C_1$-$C_4$)alkyl-, and ($C_3$-$C_7$)cycloalkyl($C_1$-$C_4$)alkyl-, when n is 1-4, $R^2$ and $R^3$ are independently selected from H, fluoro, and optionally substituted ($C_1$-$C_4$)alkyl, aryl($C_1$-$C_4$)alkyl-, and ($C_3$-$C_7$)cycloalkyl($C_1$-$C_4$)alkyl-, wherein, when n is 1, $R^2$ is F and $R^3$ is H, then Z is —C(=O)$NR^X$—, —$NR^XC$(=O)$NR^X$, —$SO_2NR^X$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—, and when n is 1-4, $R^2$ is selected from —$NR^AR^B$, —($C_1$-$C_4$) alkyl-$NR^AR^B$, —$CONR^AR^B$, —($C_1$-$C_4$)alkyl-$CONR^AR^B$, —$CO_2H$, —($C_1$-$C_4$)alkyl-$CO_2H$, hydroxyl, hydroxy($C_1$-$C_4$) alkyl-, ($C_1$-$C_3$)alkoxy, and ($C_1$-$C_3$)alkoxy($C_1$-$C_4$)alkyl-, and $R^3$ is selected from H and optionally substituted ($C_1$-$C_4$)alkyl, aryl($C_1$-$C_4$)alkyl-, and ($C_3$-$C_7$)cycloalkyl($C_1$-$C_4$)alkyl-, wherein the aryl, cycloalkyl and each of the ($C_1$-$C_4$)alkyl moieties of said optionally substituted ($C_1$-$C_4$)alkyl, aryl($C_1$-

$C_4$)alkyl-, and ($C_3$-$C_7$)cycloalkyl($C_1$-$C_4$)alkyl- of any $R^2$ and $R^3$ are optionally substituted by 1, 2 or 3 groups independently selected from halogen, cyano, ($C_1$-$C_4$)alkyl, halo($C_1$-$C_4$)alkyl, ($C_1$-$C_4$)alkoxy, halo($C_1$-$C_4$)alkoxy, —$NR^A R^A$, —(($C_1$-$C_4$)alkyl)$NR^A R^A$, and hydroxyl;

or $R^2$ and $R^3$ taken together with the atom to which they are connected form an optionally substituted 4, 5, 6, or 7 membered cycloalkyl or heterocycloalkyl group, wherein said heterocycloalkyl group contains 1 or 2 heteroatoms independently selected from N, O and S and said optionally substituted cycloalkyl or heterocycloalkyl group is optionally substituted by 1, 2 or 3 substituents independently selected from ($C_1$-$C_4$)alkyl, halo($C_1$-$C_4$)alkyl, halogen, cyano, aryl ($C_1$-$C_4$)alkyl-, ($C_3$-$C_7$)cycloalkyl($C_1$-$C_4$)alkyl-, —$OR^Y$, —$NR^Y R^Y$, —$C(=O)OR^Y$, —$C(=O)NR^Y R^Y$, —$NR^Y C(=O) R^Y$, —$SO_2 NR^Y R^Y$, —$NR^Y SO_2 R^Y$, —$OC(=O)NR^Y R^Y$, —$NR^Y C(=O)OR^Y$, and —$NR^Y C(=O)NR^Y R^Y$; and L is 5-6 membered heteroaryl or phenyl which is substituted by $R^4$ and is optionally further substituted, wherein when L is further substituted, L is substituted by 1 or 2 substituents independently selected from halogen, cyano and ($C_1$-$C_4$)alkyl;

$R^4$ is H, ($C_1$-$C_4$)alkyl, halo, halo($C_1$-$C_4$)alkyl, ($C_1$-$C_4$)alkoxy, (($C_1$-$C_4$)alkyl)(($C_1$-$C_4$)alkyl)N($C_1$-$C_4$)alkoxy, (($C_1$-$C_4$)alkyl)(($C_1$-$C_4$)alkyl)N($C_1$-$C_4$)alkyl-, ($C_1$-$C_4$)haloalkoxy-, ($C_1$-$C_4$)alkylamino, optionally substituted ($C_3$-$C_6$)cycloalkyl, optionally substituted phenyl, optionally substituted 5-6 membered heterocycloalkyl, or optionally substituted 5-6 membered heteroaryl, wherein said optionally substituted cycloalkyl, phenyl, heterocycloalkyl or heteroaryl is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$)alkylthio-, halo($C_1$-$C_4$)alkoxy, hydroxyl, —$NR^A R^C$ and —(($C_1$-$C_4$)alkyl)$NR^A R^C$;

or L-$R^4$, taken together, form a 1,3-benzodioxolyl, 2,3-dihydro-1,4-benzodioxinyl, benzofuranyl, tetrahydroisoquinolyl or isoindolinyl group wherein said benzofuranyl, tetrahydroisoquinolyl or isoindolinyl group is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$)alkylthio-, halo($C_1$-$C_4$)alkoxy, hydroxyl, —$NR^A R^C$ and —(($C_1$-$C_4$)alkyl)$NR^A R^C$;

wherein each $R^A$ is independently selected from H and ($C_1$-$C_4$)alkyl;

$R^B$ is H, ($C_1$-$C_4$)alkyl, halo($C_1$-$C_4$)alkyl, C(=O)($C_1$-$C_4$)alkyl, —C(=O)O($C_1$-$C_4$)alkyl, —C(=O)$NH_2$, C(=O)NH($C_1$-$C_4$)alkyl, C(=O)N(($C_1$-$C_4$)alkyl)(($C_1$-$C_4$)alkyl), —$SO_2$($C_1$-$C_4$)alkyl, or $R^A$ and $R^B$ taken together with the atom to which they are attached form a 4-6 membered heterocyclic ring, optionally containing one additional heteroatom selected from N, O and S and optionally substituted by ($C_1$-$C_4$)alkyl;

$R^C$ is H, ($C_1$-$C_4$)alkyl, phenyl, 5-6 membered heterocycloalkyl, or 5-6 membered heteroaryl, or $R^A$ and $R^C$ taken together with the atom to which they are attached form a 4-8 membered heterocyclic ring, optionally containing one additional heteroatom selected from N, O and S and optionally substituted by ($C_1$-$C_4$)alkyl;

each $R^X$ is independently selected from H, ($C_1$-$C_6$)alkyl, and optionally substituted ($C_2$-$C_6$)alkyl, where said optionally substituted ($C_2$-$C_6$)alkyl is optionally substituted by hydroxyl, cyano, amino, ($C_1$-$C_4$)alkoxy, ($C_1$-$C_4$)alkyl)NH—, or (($C_1$-$C_4$)alkyl)(($C_1$-$C_4$)alkyl)N—; and each $R^Y$ is independently selected from H, ($C_1$-$C_4$)alkyl, phenyl, and —($C_1$-$C_4$)alkylphenyl;

or a salt thereof, or a salt, particularly a pharmaceutically acceptable salt, thereof, and is further directed to a pharmaceutical composition comprising the compound of Formula I, or a salt thereof, a method of inhibiting HDAC by contacting a HDAC with the compound of Formula I or a salt thereof, and a method of treating a subject having a disease or disorder mediated by inhibition of a HDAC comprising administering the compound of Formula I, or a salt thereof, or a pharmaceutical composition comprising the compound of Formula I, or a salt thereof, to the subject.

In one embodiment, a compound of Formula I excludes the following compounds:

N-[(4-fluorophenyl)methyl]-4-[5-(2,2,2-trifluoroacetyl)-2-thienyl]-benzamide

N-[(4-fluorophenyl)methyl]-3-[5-(2,2,2-trifluoroacetyl)-2-thienyl]-benzamide, 4-methoxy-N-[2-[3-(trifluoromethyl)-1H-1,2,4-triazol-5-yl]-3-thienyl]-benzeneacetamide, N-[(4-methoxyphenyl)methyl]-4-[5-(trichloromethyl)-1,2,4-oxadiazol-3-yl]-1,2,5-oxadiazol-3-amine, 4-(trifluoromethyl)-N-[3-(trifluoromethyl)-4-[5-(trifluoromethyl)-1,2,4-oxadiazol-3-yl]phenyl]-benzenepropanamide, 3-[4-(trifluoromethyl)phenyl]-N-{3-(trifluoromethyl)-4-[5-(trifluoromethyl)-1,2,4-oxadiazol-3-yl]phenyl}propanamide, 3-{7-methyl-2-[4-(3-methyl-5-isoxazolyl)butyl]-1-benzofuran-5-yl}-5-(trifluoromethyl)-1,2,4-oxadiazole, 1-[3-(3-methyl-5-isoxazolyl)propyl]-5-[5-(trifluoromethyl)-1,2,4-oxadiazol-3-yl]-1H-indole, 7-methyl-1-[4-(3-methyl-5-isoxazolyl)butyl]-5-[5-(trifluoromethyl)-1,2,4-oxadiazol-3-yl]-1H-indole, 7-methyl-1-[5-(3-methyl-5-isoxazolyl)pentyl]-5-[5-(trifluoromethyl)-1,2,4-oxadiazol-3-yl]-1H-indole, 7-methyl-1-[3-(3-methyl-5-isoxazolyl)propyl]-5-[5-(trifluoromethyl)-1,2,4-oxadiazol-3-yl]-2,3-dihydro-1H-indole, or N-(phenylmethyl)-4-[5-(trifluoromethyl)-1,2,4-oxadiazol-3-yl]-1,2,5-oxadiazol-3-amine;

or a salt thereof.

The invention is further directed to a pharmaceutical composition comprising a compound of the invention. The invention is still further directed to methods of inhibiting HDAC enzymes and treatment of conditions associated therewith using a compound of the invention or a pharmaceutical composition comprising a compound of the invention.

DETAILED DESCRIPTION OF THE INVENTION

The alternative definitions for the various groups and substituent groups of Formula I provided throughout the specification are intended to particularly describe each compound species disclosed herein, individually, as well as groups of one or more compound species. The scope of this invention includes any combination of these group and substituent group definitions.

In one embodiment of this invention, $R^1$ is a fluoro-alkyl group containing at least 2 fluoro groups (atoms). In another embodiment, $R^1$ is a ($C_1$-$C_2$)alkyl group containing at least 2 fluoro groups. In a specific embodiment, $R^1$ is $CHF_2$ or $CF_3$; more specifically, $R^1$ is $CF_3$ In selected embodiments, when Y is a bond, $X_1$, $X_2$, and $X_3$, taken together with the atoms to which they are attached, form an oxadiazolyl ($X_1$ is O, $X_2$ and $X_3$ are N), oxazolyl ($X_1$ is O, $X_2$ is CH, $X_3$ is N), imidazolyl ($X_1$ is N or NH, $X_2$ is CH, $X_3$ is N or NH); or a triazolyl ($X_1$ is N or NH, $X_2$ is N, $X_3$ is N or NH) ring moiety. In specific embodiments, when Y is a bond, $X_1$, $X_2$, and $X_3$, taken together with the atoms to which they are attached form an oxadiazolyl ring moiety.

In selected embodiments, when Y is —C(O)—, $X_1$, $X_2$, and $X_3$, taken together with the atoms to which they are attached, form an thiazolyl ($X_3$ is S, $X_1$ is CH and $X_2$ is N or $X_3$ is S, $X_1$ is N and $X_2$ is CH), oxazolyl ($X_3$ is O, $X_1$ is CH and $X_2$ is N or $X_3$ is O, $X_1$ is N and $X_2$ is CH), thienyl ($X_1$ and $X_2$ are CH, $X_3$ is S) or furanyl ($X_1$ and $X_2$ are CH, $X_3$ is O) ring moiety. In specific embodiments, when Y is —C(O)—, $X_1$, $X_2$, and $X_3$, taken together with the atoms to which they are attached form a thienyl, thiazolyl or oxazolyl ring moiety, more specifically a thienyl moiety.

In selected embodiments, when Y is —C(O)—, $X_1$, $X_2$, and $X_3$, taken together with the atoms to which they are attached, form a furanyl or furyl ($X_1$ is O, $X_2$ and $X_3$ are CH), oxazolyl ($X_1$ is O, $X_2$ is CH, and $X_3$ is N), isoxazolyl ($X_1$ is O, $X_2$ is N, and $X_3$ is CH), or oxadiazolyl ($X_1$ is O, $X_2$ and $X_3$ are N) ring moiety. In specific embodiments, when Y is —C(O)—, $X_1$, $X_2$, and $X_3$, taken together with the atoms to which they are attached form a furanyl (furyl) ring moiety.

The invention is further directed to a compound of Formula (I-a):

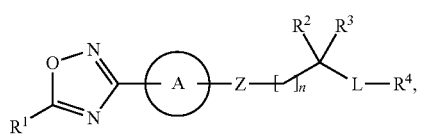
(I-a)

wherein $R^1$, $R^2$, $R^3$, $R^4$, A, Z, n and L are as defined herein.

The invention is still further directed to a compound of Formula (I-b):

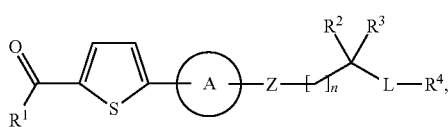
(I-b)

wherein $R^1$, $R^2$, $R^3$, $R^4$, A, Z, n and L are as defined herein.

The invention is further directed to a compound of Formula (I-c), (I-d) or (I-e):

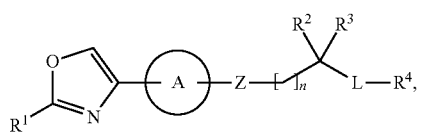
(I-c)

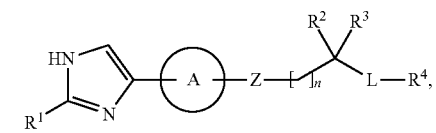
(I-d)

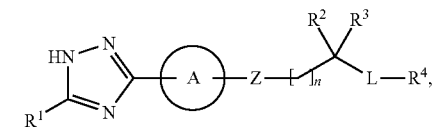
(I-e)

wherein $R^1$, $R^2$, $R^3$, $R^4$, A, Z, n and L are as defined herein.

The invention is still further directed to a compound of Formula (I-f), (I-g), (I-h), (I-i) or (I-j):

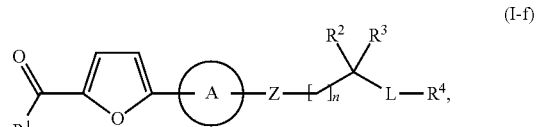
(I-f)

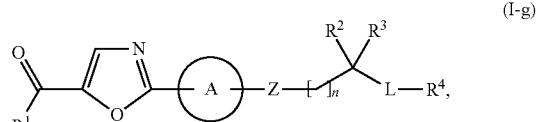
(I-g)

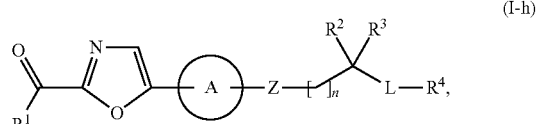
(I-h)

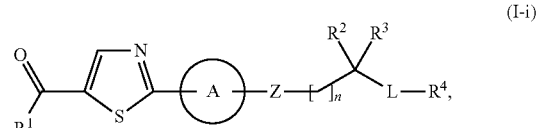
(I-i)

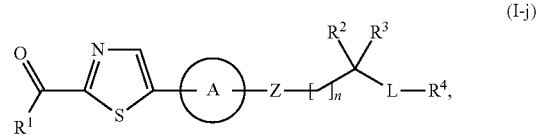
(I-j)

wherein $R^1$, $R^2$, $R^3$, $R^4$, A, Z, n and L are as defined herein.

The invention is still further directed to a compound of Formula (I-k), (I-l), (I-m), or (I-n):

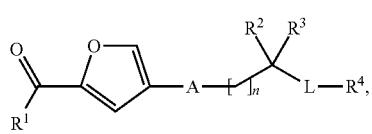
(I-k)

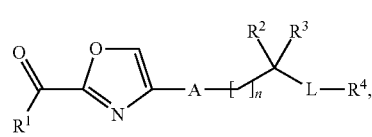
(I-l)

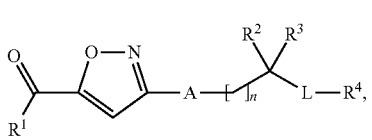
(I-m)

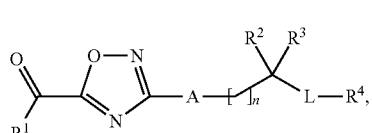
(I-n)

wherein $R^1$, $R^2$, $R^3$, $R^4$, A, n and L are as defined herein.

In another embodiment, A is a phenyl group optionally substituted by 1-2 groups independently selected from ($C_1$-$C_4$)alkyl, halogen, cyano, halo($C_1$-$C_4$)alkyl, ($C_1$-$C_4$)alkoxy, halo($C_1$-$C_4$)alkoxy, —$NR^AR^A$ and —(($C_1$-$C_4$)alkyl)$NR^AR^A$. In further embodiments, A is a phenyl group optionally substituted by 1 group selected from methyl, ethyl, fluoro, chloro, trifluoromethyl, methoxy, ethoxy, trifluoromethoxy, cyano, —NR$^A$R$^A$ and —((C$_1$-C$_4$)alkyl)NR$^A$R$^A$, where each R$^A$ is independently H or methyl. In specific embodiments, A is an unsubstituted phenyl group or a phenyl group substituted by an ethyl, fluoro, cyano or methoxy group.

In yet another embodiment, A is a cyclopropyl, cyclopentyl or cyclohexyl group, optionally substituted by 1-2 groups independently selected from (C$_1$-C$_4$)alkyl, (C$_1$-C$_4$)alkoxy, —NR$^A$R$^A$ and —((C$_1$-C$_4$)alkyl)NR$^A$R$^A$. In further embodiments, A is a cyclopropyl, cyclopentyl or cyclohexyl group, optionally substituted by 1-2 groups independently selected from methyl, ethyl, tert-butyl, methoxy, ethoxy, —NR$^A$R$^A$ and ((C$_1$-C$_4$)alkyl)NR$^A$R$^A$, where each R$^A$ is independently H or methyl. In selected embodiments of this invention, A is a cyclopropyl, cyclopentyl or cyclohexyl group.

In another embodiment of this invention, A is naphthyl, optionally substituted by 1-2 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, —NR$^A$R$^A$ and —((C$_1$-C$_4$)alkyl)NR$^A$R$^A$.

In another embodiment of this invention, A is a 4-7 membered heterocycloalkyl group optionally substituted by 1-3 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, oxo, —NR$^A$R$^A$ and —((C$_1$-C$_4$)alkyl)NR$^A$R$^A$.

In another embodiment of this invention, A is a 9-10 membered heteroaryl optionally substituted by 1-2 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, oxo, —NR$^A$R$^A$ and —((C$_1$-C$_4$)alkyl)NR$^A$R$^A$. In selected embodiments, A is isoquinolyl, indazolyl, tetrahydroisoquinolinonyl, isoindolinonyl, and indolinyl.

In further embodiments, A is a 5-6 membered heteroaryl optionally substituted by 1-2 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, —NR$^A$R$^A$ and —((C$_1$-C$_4$)alkyl)NR$^A$R$^A$. In still further embodiments, A is a 5-6 membered heteroaryl optionally substituted by 1 group selected from methyl, ethyl, fluoro, trifluoromethyl, —NR$^A$R$^A$ and —((C$_1$-C$_4$)alkyl)NR$^A$R$^A$, where each R$^A$ is independently H or methyl and the 5-6 membered heteroaryl contains 1 ring heteroatom selected form N, O and S and optionally contains 1 additional ring nitrogen atom. In selected embodiments, A is oxazolyl, pyrazolyl, or thienyl optionally substituted by a methyl group. In other selected embodiments, A is pyrazolyl or thienyl, optionally substituted by a methyl group. In specific embodiments, A is thienyl. In other specific embodiments, A is oxazolyl.

In yet other embodiments, A is a pyridyl or pyridyl-N-oxide group optionally substituted by 1-2 groups independently selected from (C$_1$-C$_4$)alkyl, halogen, cyano, halo(C$_1$-C$_4$)alkyl, (C$_1$-C$_4$)alkoxy, halo(C$_1$-C$_4$)alkoxy, —NR$^A$R$^A$ and —((C$_1$-C$_4$)alkyl)NR$^A$R$^A$. In further embodiments, A is a pyridyl or pyridyl-N-oxide group optionally substituted by 1 group selected from methyl, ethyl, fluoro, chloro, trifluoromethyl, methoxy, ethoxy, trifluoromethoxy, cyano, —NR$^A$R$^A$ and —((C$_1$-C$_4$)alkyl)NR$^A$R$^A$, where each R$^A$ is independently H or methyl. In selected embodiments, A is pyridyl or pyridyl-N-oxide. In specific embodiments, A is pyridyl.

In another embodiment of this invention, Z is C(═O)NR$^X$—, —NR$^X$C(═O)NR$^X$, or —NR$^X$C(═O)—; particularly C(═O)NR$^X$— or —NR$^X$C(═O)—. In another embodiment of this invention, Z is —SO$_2$NR$^X$— or —NR$^X$SO$_2$—. In another embodiment of this invention, Z is —NHCH(CF$_3$)— or —CH(CF$_3$)NH—. In another embodiment of this invention, Z is —CH(CF$_3$)— or —(C$_1$-C$_4$)alkyl-. In another embodiment of this invention, Z is —NR$^X$— or —(C$_1$-C$_3$)alkyl-NR$^X$—.

For each of the above embodiments of Z, R$^X$, or for —NR$^X$C(═O)NR$^X$, each R$^X$, may be independently selected from H, (C$_1$-C$_4$)alkyl, and optionally substituted (C$_2$-C$_4$) alkyl, where said optionally substituted (C$_2$-C$_4$)alkyl is optionally substituted by hydroxyl, cyano, amino, (C$_1$-C$_4$) alkoxy, (C$_1$-C$_4$)alkyl)NH—, or ((C$_1$-C$_4$)alkyl)((C$_1$-C$_4$)alkyl) N—. For each of the above embodiments of Z, R$^X$, or for —NR$^X$C(═O)NR$^X$, each R$^X$, may be independently selected from H, methyl, ethyl, tert-butyl, hydroxyethyl-, methoxymethyl-, cyanoethyl-, N-methylaminoethyl- and dimethylaminoethyl-. In specific embodiments, each R$^X$ is independently H, methyl or cyanoethyl, more specifically, R$^X$ is H or methyl.

In particular embodiments, Z is —C(═O)NR$^X$—, —SO$_2$—, —SO$_2$NR$^X$—, —CH(CF$_3$)NH—, methyl (methylenyl), ethyl (ethylenyl), —NR$^X$—, or —(C$_1$-C$_3$)alkyl-NR$^X$—, where each R$^X$ is independently H, methyl or ethyl. In specific embodiments, each R$^X$ is H. In selected embodiments, Z is —C(═O)NH—, —SO$_2$NH—, —CH(CF$_3$)NH—, ethyl (ethylenyl), —CH$_2$NH—, —CH$_2$N(CH$_2$CH$_3$)—, —CH(CH$_3$)N(CH$_2$CH$_3$)—, or —CH(CH$_3$)NH—. In specific embodiments, Z is —C(═O)NH— or —CH$_2$NH—.

In another embodiment of this invention, n is 0-4; particularly 0-3. In specific embodiments, n is 1 or n is 0.

In another embodiment, one of R$^2$ and R$^3$ is other than hydrogen. In yet another embodiment, both R$^2$ and R$^3$ are C$_{1-4}$ alkyl (e.g., methyl). In a still further embodiment, one of R$^2$ and R$^3$ is H and the other of R$^2$ and R$^3$ is C$_{1-4}$ alkyl (e.g., methyl). In a further embodiment, R$^2$ and R$^3$ taken together with the atom to which they are connected form an optionally substituted 4, 5, or 6 membered cycloalkyl or heterocycloalkyl group, wherein said heterocycloalkyl group contains 1 heteroatom selected from N, O and S and said optionally substituted cycloalkyl or heterocycloalkyl group is optionally substituted by a substituent selected from (C$_1$-C$_4$)alkyl, halo (C$_1$-C$_4$)alkyl, halogen, cyano, aryl(C$_1$-C$_2$)alkyl-, (C$_3$-C$_6$)cycloalkyl(C$_1$-C$_2$)alkyl-, —OR$^{Ya}$, —NR$^{Ya}$R$^{Yb}$, —C(═O) OR$^{Ya}$, —C(═O)NR$^{Ya}$R$^{Yb}$, —NR$^{Yb}$C(═O)R$^{Ya}$, —SO$_2$NR$^{Ya}$R$^{Yb}$, and —NR$^{Yb}$SO$_2$R$^{Ya}$, where R$^{Ya}$ is selected from H, (C$_1$-C$_4$)alkyl, phenyl(C$_1$-C$_2$)alkyl- and (C$_3$-C$_6$)cycloalkyl(C$_1$-C$_2$)alkyl-, and each R$^{Yb}$ is independently selected from H and (C$_1$-C$_4$)alkyl, specifically H and methyl.

In another embodiment of this invention, when n is O, R$^2$ and R$^3$ are independently selected from H and optionally substituted (C$_1$-C$_4$)alkyl, phenyl(C$_1$-C$_2$)alkyl-, and (C$_3$-C$_6$) cycloalkyl(C$_1$-C$_2$)alkyl-.

In another embodiment, when n is 1, R$^2$ and R$^3$ are independently selected from H and optionally substituted (C$_1$-C$_4$) alkyl, phenyl(C$_1$-C$_2$)alkyl-, and (C$_3$-C$_6$)cycloalkyl(C$_1$-C$_2$) alkyl-.

In another embodiment, when n is 1, R$^2$ is F and R$^3$ is H, then Z is —C(═O)NH—, —NHC(═O)NH—, —SO$_2$NH—, —NHCH(CF$_3$)—, —CH(CF$_3$)NH—, —CH(CF$_3$)—, —(C$_1$-C$_4$)alkyl-, —NH—, or —CH$_2$NH—; more specifically, Z is —C(═O)NH— or —CH$_2$NH—.

In another embodiment, when n is 2-4, R$^2$ and R$^3$ are independently selected from H, fluoro, and optionally substituted (C$_1$-C$_4$)alkyl, phenyl(C$_1$-C$_4$)alkyl-, and (C$_3$-C$_6$)cycloalkyl(C$_1$-C$_4$)alkyl-.

In another embodiment of this invention, when n is 1-4, R$^2$ is selected from amino, (C$_1$-C$_4$)alkylamino, ((C$_1$-C$_3$)alkyl) ((C$_1$-C$_3$)alkyl)amino, amino(C$_1$-C$_4$)alkyl, (C$_1$-C$_3$)alkylamino(C$_1$-C$_4$)alkyl, ((C$_1$-C$_3$)alkyl)((C$_1$-C$_3$)alkyl)amino (C$_1$-C$_4$)alkyl, (substituted(C$_1$-C$_3$)alkyl)((C$_1$-C$_3$)alkyl)amino $(C_1-C_4)$alkyl (where said substituted $(C_1-C_3)$alkyl moiety is substituted by —C(=O)OH, —C(=O)O$(C_1-C_4)$alkyl, or 1-8 fluoro groups), aminocarbonyl$(C_1-C_4)$alkyl, $(C_1-C_3)$alkylaminocarbonyl$(C_1-C_4)$alkyl, $((C_1-C_3)$alkyl)$((C_1-C_3)$alkyl)aminocarbonyl$(C_1-C_4)$alkyl, hydroxyl, hydroxy$(C_1-C_4)$alkyl-, $(C_1-C_4)$alkoxy, and $(C_1-C_4)$alkoxy$(C_1-C_4)$alkyl- and $R^3$ is selected from H and optionally substituted $(C_1-C_4)$alkyl, aryl$(C_1-C_4)$alkyl-, and $(C_3-C_7)$cycloalkyl$(C_1-C_4)$alkyl-.

In another embodiment of this invention, when n is 1-4, $R^2$ is selected from amino, hydroxyl, and $(C_1-C_4)$alkoxy, and $R^3$ is selected from H and optionally substituted $(C_1-C_4)$alkyl, phenyl$(C_1-C_2)$alkyl-, and $(C_3-C_6)$cycloalkyl$(C_1-C_2)$alkyl-. In another embodiment, n is 1-3, $R^2$ is hydroxyl and $R^3$ is H or methyl; more specifically, n is 1, $R^2$ is hydroxyl and $R^3$ is H or methyl. In another embodiment of this invention, (for any value of n) $R^2$ and $R^3$ are independently selected from H and optionally substituted $(C_1-C_4)$alkyl, phenyl$(C_1-C_2)$alkyl-, and $(C_3-C_6)$cycloalkyl$(C_1-C_2)$alkyl-.

In another embodiment of this invention, (for any value of n) $R^2$ is selected from H and optionally substituted $(C_1-C_4)$alkyl, phenyl$(C_1-C_2)$alkyl-, and $(C_3-C_6)$cycloalkyl$(C_1-C_2)$alkyl- and $R^3$ is selected from H and methyl.

In specific embodiments of this invention (for any value of n), $R^2$ and $R^3$ are independently selected from H and methyl. In more specific embodiments, both $R^2$ and $R^3$ are H or both $R^2$ and $R^3$ are methyl.

In another embodiment of this invention, the aryl, phenyl, cycloalkyl and each of the $(C_1-C_4)$alkyl or $(C_1-C_2)$alkyl moieties of said optionally substituted $(C_1-C_4)$alkyl, aryl$(C_1-C_4)$alkyl-, phenyl $(C_1-C_4)$alkyl-, $(C_3-C_7)$cycloalkyl$(C_1-C_4)$alkyl- and $(C_3-C_6)$cycloalkyl$(C_1-C_2)$alkyl- of any $R^2$ and $R^3$ are optionally substituted by 1, 2 or 3 halogen (specifically fluorine) groups and/or 1 or 2 groups independently selected from cyano, $(C_1-C_4)$alkyl, halo$(C_1-C_4)$alkyl, $(C_1-C_4)$alkoxy, halo$(C_1-C_4)$alkoxy, $NR^AR^A$, —$((C_1-C_4)$alkyl)$NR^AR^A$, and hydroxyl.

In another embodiment of this invention, $R^2$ and $R^3$ taken together with the atom to which they are connected form an optionally substituted 4, 5, or 6 membered cycloalkyl or heterocycloalkyl group, wherein said heterocycloalkyl group contains 1 heteroatom selected from N, O and S and said optionally substituted cycloalkyl or heterocycloalkyl group is optionally substituted by a substituent selected from $(C_1-C_4)$alkyl, halo$(C_1-C_4)$alkyl, halogen, cyano, aryl$(C_1-C_2)$alkyl-, $(C_3-C_6)$cycloalkyl$(C_1-C_2)$alkyl-, $OR^{Ya}$, —$NR^{Ya}R^{Yb}$, C(=O)$OR^{Ya}$, —C(=O)$NR^{Ya}R^{Yb}$, —$NR^{Yb}$C(=O)$R^{Ya}$, —$SO_2NR^{Ya}R^{Yb}$, and —$NR^{Yb}SO_2R^{Ya}$, where $R^{Ya}$ is selected from H, $(C_1-C_4)$alkyl phenyl$(C_1-C_2)$alkyl- and $(C_3-C_6)$cycloalkyl$(C_1-C_2)$alkyl-, and each $R^{Yb}$ is independently selected from H and $(C_1-C_4)$alkyl, specifically H and methyl.

In specific embodiments of this invention, $R^2$ and $R^3$ taken together with the atom to which they are connected form an optionally substituted 4, 5 or 6 membered cycloalkyl or heterocycloalkyl group, wherein said heterocycloalkyl group contains 1 heteroatom selected from N and O and said optionally substituted cycloalkyl or heterocycloalkyl group is optionally substituted by a substituent selected from $(C_1-C_4)$alkyl, aryl$(C_1-C_2)$alkyl-, and $(C_3-C_6)$cycloalkyl$(C_1-C_2)$alkyl-.

In selected embodiments of this invention, $R^2$ and $R^3$ taken together with the atom to which they are connected form a tetrahydropyranyl, 2,2-dimethyl-tetrahydropyranyl, cyclopentyl, 1-methyl-piperidinyl, cyclopropyl, cyclohexyl, 1-ethyl-piperidinyl, tetrahydrofuranyl, piperidinyl, 1-methyl-pyrrolidinyl, 1-benzyl-pyrrolidinyl, 1-cyclopropylm-ethyl-pyrrolidinyl, oxetanyl, azetidinyl, 1-methyl-azetidinyl, 1-benzyl-azetidinyl, or 1-cyclopropylmethyl-azetidinyl group.

In specific embodiments of this invention, $R^2$ and $R^3$ taken together with the atom to which they are connected form a tetrahydropyranyl, 2,2-dimethyl-tetrahydropyranyl, cyclopentyl, 1-methyl-piperidinyl group.

In another embodiment of this invention, L is 5-6 membered heteroaryl or phenyl which is substituted by $R^4$ and is optionally further substituted, wherein when L is further substituted, L is substituted by 1 or 2 substituents independently selected from halogen, cyano and methyl.

In another embodiment of this invention, L is a 5-membered heteroaryl, pyridyl or phenyl which is substituted by $R^4$ and is optionally further substituted, wherein when L is further substituted, L is substituted by 1 substituent selected from chloro, fluoro, cyano and methyl.

In selected embodiments, L is pyrazolyl, oxadiazolyl, 1-methyl-imidazolyl, thiazolyl, thienyl, triazolyl, pyridyl, phenyl, oxazolyl or isoxazolyl, any of which is substituted by a methyl group.

In specific embodiments, L is thiazolyl, thienyl, triazolyl, pyridyl, phenyl, or oxazolyl, any of which is substituted by a methyl group.

In another embodiment of this invention, $R^4$ is H, halogen, $(C_1-C_4)$alkyl, halo$(C_1-C_2)$alkyl, $(C_1-C_2)$alkoxy, $((C_1-C_2)$alkyl)$((C_1-C_2)$alkyl)$N(C_1-C_3)$alkoxy-, $((C_1-C_2)$alkyl)$((C_1-C_2)$alkyl)$N(C_1-C_3)$alkyl-, $(C_1-C_2)$haloalkyl, $(C_1-C_3)$alkylamino, optionally substituted $(C_3-C_6)$cycloalkyl, optionally substituted phenyl, optionally substituted 5-6 membered heterocycloalkyl, or optionally substituted 5-6 membered heteroaryl, where said optionally substituted cycloalkyl, phenyl, heterocycloalkyl or heteroaryl is optionally substituted by 1 or 2 groups independently selected from $(C_1-C_4)$alkyl, halogen, cyano, halo$(C_1-C_2)$alkyl, $(C_1-C_2)$alkoxy, halo$(C_1-C_2)$alkoxy, hydroxyl, —$NR^AR^C$ and —$((C_1-C_4)$alkyl)$NR^AR^C$.

In a selected embodiments, $R^4$ is H, methyl, bromo, trifluoromethyl, dimethylaminoethoxy-, dimethylaminopropyl-, and optionally substituted pyridyl, cyclohexyl, piperidinyl, piperazinyl, imidazolyl, thienyl, or phenyl, where the pyridyl, cyclohexyl, piperidinyl, piperizinyl, imidazolyl, thienyl, or phenyl are optionally substituted by 1-2 substituents independently selected from methyl, chloro, bromo, fluoro, trifluoromethyl, methoxy, and cyano.

In a selected embodiments, $R^4$ is H, methyl, bromo, trifluoromethyl, dimethylaminoethoxy-, phenyl, 4-chlorophenyl, 2-bromophenyl-, 4-fluorophenyl, 4-cyanophenyl, 3-trifluoromethylphenyl, 4-methoxyphenyl, cyclohexyl, imidazolyl, thienyl, pyrid-2-yl, pyrid-3-yl, or pyrid-4-yl.

In other embodiments of this invention, L-$R^4$, taken together, form a 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl group, optionally substituted with 1 or 2 groups independently selected from methyl, trifluoromethyl, chloro, fluoro, cyano, methoxy, phenyl, and morpholinylpropyl-.

In selected embodiments of this invention, L-$R^4$, taken together, form a 1,3-benzodioxolyl, tetrahydroisoquinolyl or isoindolinyl group.

In another embodiment of this invention, each $R^A$ and $R^C$ is independently selected from H and $(C_1-C_4)$alkyl; specifically each $R^A$ and $R^C$ is independently selected from H, methyl and ethyl.

In another embodiment of this invention, each $R^Y$ is independently selected from H, $(C_1-C_4)$alkyl, phenyl, and —$(C_1$-

$C_4$)alkylphenyl; specifically each $R^Y$ is independently selected from H, methyl, ethyl, phenyl, benzyl and -ethylphenyl.

As used herein, the term "alkyl" represents a saturated, straight or branched hydrocarbon moiety, which may be unsubstituted or substituted by one, or more of the substituents defined herein. Exemplary alkyls include, but are not limited to methyl (Me), ethyl (Et), n-propyl, isopropyl, n-butyl, isobutyl, sec-butyl, t-butyl, n-pentyl, iso-pentyl (3-methyl-butyl), neo-pentyl (2,2-dimethylpropyl), etc. The term "$C_1$-$C_4$" refers to an alkyl containing from 1 to 4 carbon atoms.

When the term "alkyl" is used in combination with other substituent groups, such as "haloalkyl" or "cycloalkyl-alkyl" or "arylalkyl", the term "alkyl" is intended to encompass a divalent straight or branched-chain hydrocarbon radical. For example, "arylalkyl" is intended to mean the radical alkylaryl, wherein the alkyl moiety thereof is a divalent straight or branched-chain carbon radical and the aryl moiety thereof is as defined herein, and is represented by the bonding arrangement present in a benzyl group (—$CH_2$-phenyl).

In addition, the term "alkyl" may be used to define a divalent substituent, such as a group bonded to two other groups. In this instance, the term "alkyl" is intended to encompass a divalent straight or branched-chain hydrocarbon radical. For example, "pentyl" is intended to represent a pentylene diradical wherein the pentyl moiety is any one of a divalent straight (—$CH_2CH_2CH_2CH_2CH_2$—) or branched (—$CH_2CH(CH_3)CH_2CH_2$—, —$CH_2CH_2CH(CH_2CH_3)$—, —$CH_2CH_2C(CH_3)_2$—) chain 5-carbon radical.

As used herein, the term "cycloalkyl" refers to a non-aromatic, saturated, cyclic hydrocarbon ring. The term "($C_3$-$C_8$)cycloalkyl" refers to a non-aromatic cyclic hydrocarbon ring having from three to eight ring carbon atoms. Exemplary "($C_3$-$C_8$)cycloalkyl" groups useful in the present invention include cyclopropyl, cyclobutyl, cyclopentyl, cyclohexyl, cycloheptyl, and cyclooctyl.

"Alkoxy" refers to a group containing an alkyl radical attached through an oxygen linking atom. The term "($C_1$-$C_4$)alkoxy" refers to a straight- or branched-chain hydrocarbon radical having at least 1 and up to 4 carbon atoms attached through an oxygen linking atom. Exemplary "($C_1$-$C_4$)alkoxy" groups useful in the present invention include, but are not limited to, methoxy, ethoxy, n-propoxy, isopropoxy, n-butoxy, s-butoxy, and t-butoxy.

"Aryl" represents a group or moiety comprising an aromatic, monovalent monocyclic or bicyclic hydrocarbon radical containing from 6 to 10 carbon ring atoms, which may be unsubstituted or substituted by one or more of the substituents defined herein, and to which may be fused one or more cycloalkyl rings, which may be unsubstituted or substituted by one or more substituents defined herein.

Generally, in the compounds of this invention, aryl is phenyl.

Heterocyclic groups may be heteroaryl or heterocycloalkyl groups. "Heterocycloalkyl" represents a group or moiety comprising a stable, non-aromatic, monovalent monocyclic or bicyclic radical, which is saturated or partially unsaturated, containing 3 to 10 ring atoms, which includes 1 to 4 heteroatoms selected from nitrogen, oxygen and sulfur, and which may be unsubstituted or substituted by one or more of the substituents defined herein. The heterocycloalkyl may be attached by any atom of the monocyclic or bicyclic radical which results in the creation of a stable structure. This term encompasses bicyclic heterocycloalkyl moieties where the rings are joined at two atoms per ring, as exemplified by the bonding arrangement in 2,5-diazabicyclo[2.2.1]heptyl, 2-azabicyclo[2.2.1]heptyl, 2-oxa-5-azabicyclo[2.2.1]heptyl, 7-oxa-2-azabicyclo[2.2.1]heptyl, 2-thia-5-azabicyclo[2.2.1]heptyl, 7-azabicyclo[2.2.1]heptyl, 2,6-diazatricyclo[3.3.1.13,7]decyl, 2-azatricyclo[3.3.1.13,7]decyl, 2,4,9-triazatricyclo[3.3.1.13,7]decyl, 8-azabicyclo[3.2.1]octyl, 2,5-diazabicyclo[2.2.2]octyl, 2-azabicyclo[2.2.2]octyl, 3-azabicyclo[3.2.1]octyl, 8-azabicyclo[3.2.1]octyl, octahydro-1H-pyrrolo[3,2-b]pyridyl group. This term specifically excludes bicyclic heterocycloalkyl moieties where the rings are joined at a single atom per ring (spiro), as exemplified by the bonding arrangement in a 1-oxa-2-azaspiro[4.5]dec-2-en-3-yl group. Illustrative examples of heterocycloalkyls include, but are not limited to, azetidinyl, pyrrolidyl (or pyrrolidinyl), piperidinyl, piperazinyl, morpholinyl, tetrahydro-2H-1,4-thiazinyl, tetrahydrofuryl (or tetrahydrofuranyl), dihydrofuryl, oxazolinyl, thiazolinyl, pyrazolinyl, tetrahydropyranyl, dihydropyranyl, 1,3-dioxolanyl, 1,3-dioxanyl, 1,4-dioxanyl, 1,3-oxathiolanyl, 1,3-oxathianyl, 1,3-dithianyl, azabicylo[3.2.1]octyl, azabicylo[3.3.1]nonyl, azabicylo[4.3.0]nonyl, oxabicylo[2.2.1]heptyl and 1,5,9-triazacyclododecyl.

Generally, in the compounds of this invention, heterocycloalkyl groups are 5-membered and/or 6-membered heterocycloalkyl groups, such as pyrrolidyl (or pyrrolidinyl), tetrahydrofuryl (or tetrahydrofuranyl), tetrahydrothienyl, dihydrofuryl, oxazolinyl, thiazolinyl or pyrazolinyl, piperidyl (or piperidinyl), piperazinyl, morpholinyl, tetrahydropyranyl, dihydropyranyl, 1,3-dioxanyl, tetrahydro-2H-1,4-thiazinyl, 1,4-dioxanyl, 1,3-oxathianyl, and 1,3-dithianyl.

"Heteroaryl" represents a group or moiety comprising an aromatic monovalent monocyclic or bicyclic radical, containing 5 to 10 ring atoms, including 1 to 4 heteroatoms selected from nitrogen, oxygen and sulfur, which may be unsubstituted or substituted by one or more of the substituents defined herein. This term also encompasses bicyclic heterocyclic-aryl compounds containing an aryl ring moiety fused to a heterocycloalkyl ring moiety, containing 5 to 10 ring atoms, including 1 to 4 heteroatoms selected from nitrogen, oxygen and sulfur, which may be unsubstituted or substituted by one or more of the substituents defined herein. This term is also intended to encompass heterocyclic groups containing nitrogen and/or sulfur where the nitrogen or sulfur heteroatoms are optionally oxidized. Illustrative examples of heteroaryls include, but are not limited to, thienyl, pyrrolyl, imidazolyl, pyrazolyl, furyl (or furanyl), isothiazolyl, furazanyl, isoxazolyl, oxazolyl, oxadiazolyl, thiazolyl, pyridyl (or pyridinyl), pyridyl-N-oxide, pyrazinyl, pyrimidinyl, pyridazinyl, triazinyl, tetrazinyl, triazolyl, tetrazolyl, benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, tetrahydroisoquinolinyl, isoindolinyl, indolinyl, cinnolinyl, pteridinyl, isothiazolyl.

Some of the heteroaryl groups present in the compounds of this invention are 5-6 membered monocyclic heteroaryl groups. Selected 5-membered heteroaryl groups contain one nitrogen, oxygen or sulfur ring heteroatom, and optionally contain 1, 2 or 3 additional nitrogen ring atoms. Selected 6-membered heteroaryl groups contain 1, 2, 3 or 4 nitrogen ring heteroatoms. Selected 5- or 6-membered heteroaryl groups include thienyl, pyrrolyl, imidazolyl, pyrazolyl, furyl, isothiazolyl, furazanyl, isoxazolyl, oxazolyl, oxadiazolyl, thiazolyl, triazolyl, and tetrazolyl or pyridyl, pyrazinyl, pyrimidinyl, pyridazinyl, triazinyl and thiadiazolyl.

Some of the heteroaryl groups present in the compounds of this invention are 9-10 membered bicyclic heteroaryl groups.

Selected 9-membered heteroaryl groups contain one nitrogen, oxygen or sulfur ring heteroatom, and optionally contain 1, 2 or 3 additional nitrogen ring atoms. Selected 10-membered heteroaryl groups contain one nitrogen, oxygen or sulfur ring heteroatom, and optionally contain 1, 2, 3 or 4 additional nitrogen ring atoms. Selected 9-10 membered heteroaryl groups include benzo[b]thienyl, isobenzofuryl, 2,3-dihydrobenzofuryl, chromenyl, chromanyl, indolizinyl, isoindolyl, indolyl, indazolyl, purinyl, isoquinolyl, quinolyl, phthalazinyl, naphthridinyl, quinzolinyl, benzothiazolyl, benzimidazolyl, tetrahydroquinolinyl, cinnolinyl, pteridinyl.

The terms "halogen" and "halo" represent chloro, fluoro, bromo or iodo substituents. "Hydroxy" or "hydroxyl" is intended to mean the radical OH. The term "oxo" is intended to mean a keto diradical (=O), such as present on a pyrrolidin-2-one ring.

The compounds of the invention are only those which are contemplated to be "chemically stable" as will be appreciated by those skilled in the art.

Specifically, the invention is directed to a compound according to Formula (I-a):

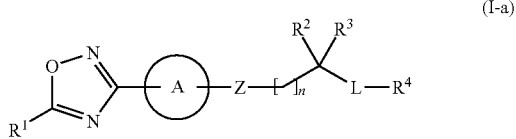

wherein:

$R^1$ is —$CF_3$;

A is optionally substituted ($C_3$-$C_6$)cycloalkyl, phenyl, naphthyl, 4-7 membered heterocycloalkyl, 5-6 membered heteroaryl, or 9-10 membered heteroaryl, wherein any optionally substituted cycloalkyl, phenyl, naphthyl, heterocycloalkyl, or heteroaryl is optionally substituted by 1-3 groups independently selected from ($C_1$-$C_4$)alkyl, halogen, cyano, halo($C_1$-$C_4$)alkyl, ($C_1$-$C_4$)alkoxy, halo($C_1$-$C_4$)alkoxy, —$NR^A R^A$ and —(($C_1$-$C_4$)alkyl)$NR^A R^A$;

Z is —C(=O)$NR^X$—, —$NR^X$C(=O)$NR^X$, —$NR^X$C(=O)—, —$SO_2$—, —$SO_2 NR^X$—, —$NR^X SO_2$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—;

n is 0-4;

when n is 0, $R^2$ and $R^3$ are independently selected from H and optionally substituted ($C_1$-$C_4$)alkyl, aryl($C_1$-$C_4$)alkyl-, and ($C_3$-$C_7$)cycloalkyl($C_1$-$C_4$)alkyl-, when n is 1-4, $R^2$ and $R^3$ are independently selected from H, fluoro, and optionally substituted ($C_1$-$C_4$)alkyl, aryl($C_1$-$C_4$)alkyl-, and ($C_3$-$C_7$)cycloalkyl($C_1$-$C_4$)alkyl-, wherein, when n is 1, $R^2$ is F and $R^3$ is H, then Z is —C(=O)$NR^X$—, —$NR^X$C(=O)$NR^X$, —$SO_2 NR^X$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—, and when n is 1-4, $R^2$ is selected from amino, hydroxyl, and ($C_1$-$C_4$)alkoxy, and $R^3$ is selected from H and optionally substituted ($C_1$-$C_4$)alkyl, aryl($C_1$-$C_4$)alkyl-, and ($C_3$-$C_7$)cycloalkyl($C_1$-$C_4$)alkyl-, wherein the aryl, cycloalkyl and each of the ($C_1$-$C_4$)alkyl moieties of said optionally substituted ($C_1$-$C_4$)alkyl, aryl($C_1$-$C_4$)alkyl-, and ($C_3$-$C_7$)cycloalkyl($C_1$-$C_4$)alkyl- of any $R^2$ and $R^3$ are optionally substituted by 1, 2 or 3 groups independently selected from halogen, cyano, ($C_1$-$C_4$)alkyl, halo($C_1$-$C_4$)alkyl, ($C_1$-$C_4$)alkoxy, halo($C_1$-$C_4$)alkoxy, halogen, —$NR^A R^A$, —(($C_1$-$C_4$)alkyl)$NR^A R^A$, ($C_1$-$C_4$)alkoxy, hydroxyl, cyano, halo($C_1$-$C_4$)alkyl, and halo($C_1$-$C_4$)alkoxy;

or $R^2$ and $R^3$ taken together with the atom to which they are connected form an optionally substituted 4, 5, 6, or 7 membered cycloalkyl or heterocycloalkyl group, wherein said heterocycloalkyl group contains 1 or 2 heteroatoms independently selected from N, O and S and said optionally substituted cycloalkyl or heterocycloalkyl group is optionally substituted by 1, 2 or 3 substituents independently selected from ($C_1$-$C_4$)alkyl, halo($C_1$-$C_4$)alkyl, halogen, cyano, aryl($C_1$-$C_4$)alkyl-, ($C_3$-$C_7$)cycloalkyl($C_1$-$C_4$)alkyl-, —$OR^Y$, —$NR^Y R^Y$, —C(=O)$OR^Y$, —C(=O)$NR^Y R^Y$, —$NR^Y$C(=O)$R^Y$, —$SO_2 NR^Y R^Y$, —$NR^Y SO_2 R^Y$, —OC(=O)$NR^Y R^Y$, —$NR^Y$C(=O)$OR^Y$, and —$NR^Y$C(=O)$NR^Y R^Y$; and L is 5-6 membered heteroaryl or phenyl which is substituted by $R^4$ and is optionally further substituted, wherein when L is further substituted, L is substituted by 1 or 2 substituents independently selected from halogen, cyano and ($C_1$-$C_4$)alkyl;

$R^4$ is H, ($C_1$-$C_4$)alkyl, halo, halo($C_1$-$C_4$)alkyl, ($C_1$-$C_4$)alkoxy, (($C_1$-$C_4$)alkyl)(($C_1$-$C_4$)alkyl)N($C_1$-$C_4$)alkoxy, (($C_1$-$C_4$)alkyl)(($C_1$-$C_4$)alkyl)N($C_1$-$C_4$)alkyl-, ($C_1$-$C_4$)haloalkoxy-, ($C_1$-$C_4$)alkylamino, optionally substituted ($C_3$-$C_6$)cycloalkyl, optionally substituted phenyl, optionally substituted 5-6 membered heterocycloalkyl, or optionally substituted 5-6 membered heteroaryl, wherein said optionally substituted cycloalkyl, phenyl, heterocycloalkyl or heteroaryl is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$)alkylthio-, halo($C_1$-$C_4$)alkoxy, hydroxyl, —$NR^A R^C$ and —(($C_1$-$C_4$)alkyl)$NR^A R^C$;

or L-$R^4$, taken together, form a 1,3-benzodioxolyl, 2,3-dihydro-1,4-benzodioxinyl, benzofuranyl, tetrahydroisoquinolyl or isoindolinyl group wherein said benzofuranyl, tetrahydroisoquinolyl or isoindolinyl group is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$)alkylthio-, halo($C_1$-$C_4$)alkoxy, hydroxyl, —$NR^A R^C$ and —(($C_1$-$C_4$)alkyl)$NR^A R^C$;

wherein each $R^A$ is independently selected from H and ($C_1$-$C_4$)alkyl;

$R^C$ is H, ($C_1$-$C_4$)alkyl, phenyl, 5-6 membered heterocycloalkyl, or 5-6 membered heteroaryl, or $R^A$ and $R^C$ taken together with the atom to which they are attached form an optionally substituted 4-8 membered heterocyclic ring, optionally containing one additional heteroatom selected from N, O and S;

each $R^X$ is independently selected from H, ($C_1$-$C_6$)alkyl, and optionally substituted ($C_2$-$C_6$)alkyl, where said optionally substituted ($C_2$-$C_6$)alkyl is optionally substituted by hydroxyl, cyano, amino, ($C_1$-$C_4$)alkoxy, ($C_1$-$C_4$)alkyl)NH—, or (($C_1$-$C_4$)alkyl)(($C_1$-$C_4$)alkyl)N—; and each $R^Y$ is independently selected from H, ($C_1$-$C_4$)alkyl, phenyl, and —($C_1$-$C_4$)alkylphenyl;

provided that the compound is not:

3-[4-(trifluoromethyl)phenyl]-N-{3-(trifluoromethyl)-4-[5-(trifluoromethyl)-1,2,4-oxadiazol-3-yl]phenyl}propanamido, 3-{7-methyl-2-[4-(3-methyl-5-isoxazolyl)butyl]-1-benzofuran-5-yl}-5-(trifluoromethyl)-1,2,4-oxadiazole, 1-[3-(3-methyl-5-isoxazolyl)propyl]-5-[5-(trifluoromethyl)-1,2,4-oxadiazol-3-yl]-1H-indole, 7-methyl-1-[4-(3-methyl-5-isoxazolyl)butyl]-5-[5-(trifluoromethyl)-1,2,4-oxadiazol-3-yl]-1H-indole, 7-methyl-1-[5-(3-methyl-5-isoxazolyl)pentyl]-5-[5-(trifluoromethyl)-1,2,4-oxadiazol-3-yl]-1H-indole, 7-methyl-1-[3-(3-methyl-5-isoxazolyl)propyl]-5-[5-(trifluoromethyl)-1,2,4-oxadiazol-3-yl]-2,3-dihydro-1H-indole, or N-(phenylmethyl)-4-[5-(trifluoromethyl)-1,2,4-oxadiazol-3-yl]-1,2,5-oxadiazol-3-amine;

or a salt, particularly a pharmaceutically acceptable salt, thereof.

Accordingly, the invention is further directed to a compound according to Formula I, wherein:

$R^1$ is $CHF_2$ or $CF_3$;

Y is a bond, $X_1$ is O, and $X_2$ and $X_3$ are N, or

Y is C(O)—, $X_1$ and $X_2$ are CH, and $X_3$ is S, or

Y is C(O)—, $X_1$ is O, and $X_2$ and $X_3$ are CH;

A is a phenyl group optionally substituted by 1 group selected from methyl, ethyl, fluoro, chloro, trifluoromethyl, methoxy, ethoxy, trifluoromethoxy, cyano, —$NR^A R^A$ and —$((C_1-C_4)alkyl)NR^A R^A$, or A is a cyclopropyl, cyclopentyl or cyclohexyl group, optionally substituted by 1-2 groups independently selected from methyl, ethyl, tert-butyl, methoxy, ethoxy, —$NR^A R^A$ and —$((C_1-C_4)alkyl)NR^A R^A$, or A is a 5-6 membered heteroaryl or a 9-10 membered heteroaryl optionally substituted by 1 group selected from methyl, ethyl, fluoro, trifluoromethyl, —$NR^A R^A$ and —$((C_1-C_4)alkyl)NR^A R^A$, where the 5-6 membered heteroaryl or 9-10 membered heteroaryl contains 1 ring heteroatom selected form N, O and S and optionally contains 1 additional ring nitrogen atom, where each $R^A$ is independently H or methyl;

Z is $C(=O)NR^X$—, —$NR^X C(=O)NR^X$, —$NR^X C(=O)$—, —$NHCH(CF_3)$—, —$CH(CF_3)NH$—, —$CH(CF_3)$—, —$(C_1-C_4)alkyl$-, or —$(C_1-C_4)alkylNR^X$—, where $R^X$ is H, $(C_1-C_4)alkyl$, or optionally substituted $(C_2-C_4)alkyl$, where said optionally substituted $(C_2-C_4)alkyl$ is optionally substituted by hydroxyl, cyano, amino, $(C_1-C_4)alkoxy$, $(C_1-C_4)alkyl)NH$—, or $((C_1-C_4)alkyl)((C_1-C_4)alkyl)N$—;

n is 0-3 and $R^2$ and $R^3$ are independently selected from H and optionally substituted $(C_1-C_4)alkyl$, phenyl$(C_1-C_2)alkyl$-, and $(C_3-C_6)cycloalkyl(C_1-C_2)alkyl$-, or n is 1-3 and $R^2$ is hydroxyl and $R^3$ is H or methyl, or n is 0-3 and $R^2$ and $R^3$ taken together with the atom to which they are connected form an optionally substituted 4, 5, or 6 membered cycloalkyl or heterocycloalkyl group, wherein said heterocycloalkyl group contains 1 heteroatom selected from N, O and S and said optionally substituted cycloalkyl or heterocycloalkyl group is optionally substituted by a substituent selected from $(C_1-C_4)alkyl$, halo$(C_1-C_4)alkyl$, halogen, cyano, aryl$(C_1-C_2)alkyl$-, $(C_3-C_6)cycloalkyl(C_1-C_2)alkyl$-, —$OR^{Ya}$, —$NR^{Ya}R^{Yb}$, —$C(=O)OR^{Ya}$, —$C(=O)NR^{Ya}R^{Yb}$, —$NR^{Yb}C(=O)R^{Ya}$, —$SO_2NR^{Ya}R^{Yb}$, and —$NR^{Yb}SO_2R^{Ya}$, where $R^{Ya}$ is selected from H, $(C_1-C_4)alkyl$ phenyl$(C_1-C_2)alkyl$- and $(C_3-C_6)cycloalkyl(C_1-C_2)alkyl$-, and each $R^{Yb}$ is independently selected from H and $(C_1-C_4)alkyl$;

L is 5-6 membered heteroaryl or phenyl which is substituted by $R^4$ and is optionally further substituted, wherein when L is further substituted, L is substituted by 1 or 2 substituents independently selected from halogen, cyano and methyl; and $R^4$ is H, halogen, $(C_1-C_4)alkyl$, halo$(C_1-C_2)alkyl$, $(C_1-C_2)alkoxy$, $((C_1-C_2)alkyl)((C_1-C_2)alkyl)N(C_1-C_3)alkoxy$-, $((C_1-C_2)alkyl)((C_1-C_2)alkyl)N(C_1-C_3)alkyl$-, $(C_1-C_2)haloalkyl$, $(C_1-C_3)alkylamino$, optionally substituted $(C_3-C_6)cycloalkyl$, optionally substituted phenyl, optionally substituted 5-6 membered heterocycloalkyl, or optionally substituted 5-6 membered heteroaryl, where said optionally substituted cycloalkyl, phenyl, heterocycloalkyl or heteroaryl is optionally substituted by 1 or 2 groups independently selected from $(C_1-C_4)alkyl$, halogen, cyano, halo$(C_1-C_2)alkyl$, $(C_1-C_2)alkoxy$, halo$(C_1-C_2)alkoxy$, hydroxyl, —$NR^A R^C$ and —$((C_1-C_4)alkyl)NR^A R^C$;

or a salt, particularly a pharmaceutically acceptable salt, thereof.

The invention is yet further directed to a compound as defined herein wherein:

n is 0-3 and $R^2$ and $R^3$ are independently selected from H and optionally substituted $(C_1-C_4)alkyl$, phenyl$(C_1-C_2)alkyl$-, and $(C_3-C_6)cycloalkyl(C_1-C_2)alkyl$-, or n is 1-3 and $R^2$ is hydroxyl and $R^3$ is H or methyl, or n is 0-3 and $R^2$ and $R^3$ taken together with the atom to which they are connected form an optionally substituted 4, 5 or 6 membered cycloalkyl or heterocycloalkyl group, wherein said heterocycloalkyl group contains 1 heteroatom selected from N and O and said optionally substituted cycloalkyl or heterocycloalkyl group is optionally substituted by a substituent selected from $(C_1-C_4)alkyl$, aryl$(C_1-C_2)alkyl$-, and $(C_3-C_6)cycloalkyl(C_1-C_2)alkyl$-;

$R^X$ is H, methyl or cyanoethyl;

L is a 5-membered heteroaryl, pyridyl or phenyl which is substituted by $R^4$ and is optionally further substituted, wherein when L is further substituted, L is substituted by 1 substituent selected from chloro, fluoro, cyano and methyl; and $R^4$ is H, methyl, bromo, trifluoromethyl, dimethylaminoethoxy-, dimethylaminopropyl-, and optionally substituted pyridyl, cyclohexyl, piperidinyl, piperazinyl, imidazolyl, thienyl, or phenyl, where the pyridyl, cyclohexyl, piperidinyl, piperizinyl, imidazolyl, thienyl, or phenyl are optionally substituted by 1-2 substituents independently selected from methyl, chloro, bromo, fluoro, trifluoromethyl, methoxy, and cyano;

or a salt, particularly a pharmaceutically acceptable salt, thereof.

The invention is specifically directed to a compound according to Formula I, wherein:

$R^1$ is $CHF_2$ or $CF_3$;

Y is a bond, $X_1$ is O, and $X_2$ and $X_3$ are N, or

Y is C(O)—, $X_1$ and $X_2$ are CH, and $X_3$ is S, or

Y is C(O)—, $X_1$ is O, and $X_2$ and $X_3$ are CH;

A is an unsubstituted phenyl group or a phenyl group substituted by an ethyl, fluoro, cyano or methoxy group, or a thienyl, pyridyl, cyclopropyl, cyclopentyl or cyclohexyl group;

Z is —$C(=O)NH$— or $CH_2NH$—;

n is 0 or 1 and both $R^2$ and $R^3$ are H or both $R^2$ and $R^3$ are methyl, or n is 1 and $R^2$ is hydroxyl and $R^3$ is H or methyl, or n is 0 or 1 and $R^2$ and $R^3$ taken together with the atom to which they are connected form a tetrahydropyranyl, 2,2-dimethyl-tetrahydropyranyl, cyclopentyl, 1-methyl-piperidinyl group;

L is thiazolyl, thienyl, triazolyl, pyridyl, phenyl, or oxazolyl, any of which is optionally substituted by a methyl group;

$R^4$ is H, methyl, bromo, trifluoromethyl, dimethylaminoethoxy-, phenyl, 4-chlorophenyl, 2-bromophenyl-, 4-fluorophenyl, 4-cyanophenyl, 3-trifluoromethylphenyl, 4-methoxyphenyl, cyclohexyl, imidazolyl, thienyl, pyrid-2-yl, pyrid-3-yl, or pyrid-4-yl; or L-$R^4$, taken together, form a 1,3-benzodioxolyl, tetrahydroisoquinolyl or isoindolinyl group;

or a salt, particularly a pharmaceutically acceptable salt, thereof.

The invention is more specifically directed to a compound according to Formula I, wherein:

$R^1$ is $CHF_2$ or $CF_3$;

Y is a bond, $X_1$ is O, and $X_2$ and $X_3$ are N;

A is an unsubstituted phenyl or pyridyl group;

Z is —C(=O)NH— or $CH_2NH$—;

n is 1;

$R^2$ and $R^3$ are both methyl, or $R^2$ is hydroxyl and $R^3$ is methyl, or $R^2$ and $R^3$ are both hydrogen, or $R^2$ is methyl and $R^3$ is hydrogen, or $R^2$ is hydroxyl and $R^3$ is hydrogen, or $R^2$ is dimethylamino and $R^3$ is H, or $R^2$ is N,N-dimethylaminoethyl and $R^3$ is H, or $R^2$ and $R^3$ taken together with the atom to which they are connected form a tetrahydropyranyl, 2,2-dimethyl-tetrahydropyranyl, or a 1-methyl-piperidinyl group;

L is thiazolyl, thienyl, triazolyl, pyridyl, phenyl, or oxazolyl, any of which is optionally substituted by a methyl group;

$R^4$ is phenyl, optionally substituted by halo (chloro or fluoro), cyano, halo($C_1$-$C_2$)alkyl, or ($C_1$-$C_2$)alkoxy;

or a salt, particularly a pharmaceutically acceptable salt, thereof.

As used herein, the term "compound(s) of the invention" means a compound of formula (I) (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

As used herein, the term "optionally substituted" means unsubstituted groups or rings (e.g., cycloalkyl, heterocycle, and heteroaryl rings) and groups or rings substituted with one or more specified substituents.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral centers may be used as racemic mixtures, scalemic mixtures, or as diaseteromerically or enantiomerically pure materials.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formula I are preferably pharmaceutically acceptable salts. Suitable pharmaceutically acceptable salts include those described by Berge, Bighley and Monkhouse, J. Pharm. Sci (1977) 66, pp 1-19. Salts encompassed within the term "pharmaceutically acceptable salts" refer to non-toxic salts of the compounds of this invention.

Typically, a salt may be readily prepared by using a desired acid or base as appropriate. The salt may precipitate from solution and be collected by filtration or may be recovered by evaporation of the solvent.

When a compound of the invention is a base (contain a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, and the like, or with a pyranosidyl acid, such as glucuronic acid or galacturonic acid, or with an alpha-hydroxy acid, such as citric acid or tartaric acid, or with an amino acid, such as aspartic acid or glutamic acid, or with an aromatic acid, such as benzoic acid or cinnamic acid, or with a sulfonic acid, such as p-toluenesulfonic acid, methanesulfonic acid, ethanesulfonic acid or the like.

Suitable addition salts are formed from acids which form non-toxic salts and examples include acetate, p-aminobenzoate, ascorbate, aspartate, benzenesulfonate, benzoate, bicarbonate, bismethylenesalicylate, bisulfate, bitartrate, borate, calcium edetate, camsylate, carbonate, clavulanate, citrate, cyclohexylsulfamate, edetate, edisylate, estolate, esylate, ethanedisulfonate, ethanesulfonate, formate, fumarate, gluceptate, gluconate, glutamate, glycollate, glycollylarsanilate, hexylresorcinate, hydrabamine, hydrobromide, hydrochloride, dihydrochloride, hydrofumarate, hydrogen phosphate, hydroiodide, hydromaleate, hydrosuccinate, hydroxynaphthoate, isethionate, itaconate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, oxaloacetate, pamoate (embonate), palmate, palmitate, pantothenate, phosphate/diphosphate, pyruvate, polygalacturonate, propionate, saccharate, salicylate, stearate, subacetate, succinate, sulfate, tannate, tartrate, teoclate, tosylate, triethiodide, trifluoroacetate and valerate.

Other exemplary acid addition salts include pyrosulfate, sulfite, bisulfite, decanoate, caprylate, acrylate, isobutyrate, caproate, heptanoate, propiolate, oxalate, malonate, suberate, sebacate, butyne-1,4-dioate, hexyne-1,6-dioate, chlorobenzoate, methylbenzoate, dinitrobenzoate, hydroxybenzoate, methoxybenzoate, phthalate, phenylacetate, phenylpropionate, phenylbutrate, lactate, γ-hydroxybutyrate, mandelate, and sulfonates, such as xylenesulfonate, propanesulfonate, naphthalene-1-sulfonate and naphthalene-2-sulfonate.

If an inventive basic compound is isolated as a salt, the corresponding free base form of that compound may be prepared by any suitable method known to the art, including treatment of the salt with an inorganic or organic base, suitably an inorganic or organic base having a higher $pK_a$ than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as N-methyl-D-glucamine, diethylamine, isopropylamine, trimethylamine, ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Compounds of the invention having both a basic and acidic moiety may be in the form of zwitterions, acid-addition salt of the basic moiety or base salts of the acidic moiety.

This invention also provides for the conversion of one pharmaceutically acceptable salt of a compound of this invention, e.g., a hydrochloride salt, into another pharmaceutically acceptable salt of a compound of this invention, e.g., a sodium salt.

For solvates of the compounds of Formula I, or salts thereof that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The subject invention also includes isotopically-labeled compounds which are identical to those recited in formula (I) but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^3H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^3H$ or $^{14}C$ have been incorporated, are useful in drug and/or substrate tissue distribution assays. Tritiated, ie. $^3H$, and carbon-14, ie. $^{14}C$, isotopes are particularly preferred for their ease of preparation and detectability. $^{11}C$ and $^{18}F$ isotopes are particularly useful in PET (positron emission tomography).

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The compounds of Formula I may be obtained by using synthetic procedures illustrated in the Schemes below or by drawing on the knowledge of a skilled organic chemist. The synthesis provided in these Schemes are applicable for producing compounds of the invention having a variety of different $R^1$ and $R^2$ groups employing appropriate precursors, which are suitably protected if needed, to achieve compatibility with the reactions outlined herein. Subsequent deprotection, where needed, affords compounds of the nature generally disclosed. While the Schemes are shown with compounds only of Formula I, they are illustrative of processes that may be used to make the compounds of the invention.

Intermediates (compounds used in the preparation of the compounds of the invention) may also be present as salts. Thus, in reference to intermediates, the phrase "compound(s) of formula (number)" means a compound having that structural formula or a pharmaceutically acceptable salt thereof.

Specific compounds of this invention include the compounds of Examples 1-141.

Representative compounds of this invention include:

N-((4-(4-phenylthiazol-2-yl)tetrahydro-2H-pyran-4-yl)methyl)-3-(5-(trifluoromethyl)-1,2,4-oxadiazol-3-yl)benzamide, N-(4-(2-(dimethylamino)ethoxy)benzyl)-3-(5-(trifluoromethyl)-1,2,4-oxadiazol-3-yl)benzamide, N-(2-(2-(dimethylamino)ethoxy)benzyl)-3-(5-(trifluoromethyl)-1,2,4-oxadiazol-3-yl)benzamide, N-(4-(1H-imidazol-1-yl)benzyl)-3-(5-(trifluoromethyl)-1,2,4-oxadiazol-3-yl)benzamide, N-(2-cyanoethyl)-N-(pyridin-3-ylmethyl)-3-(5-(trifluoromethyl)-1,2,4-oxadiazol-3-yl)benzamide, 3-(5-(trifluoromethyl)-1,2,4-oxadiazol-3-yl)-N-((4-(4-(trifluoromethyl)phenyl)tetrahydro-2H-pyran-4-yl)methyl)benzamide, 1-(4-(4-phenylthiazol-2-yl)tetrahydro-2H-pyran-4-yl)-N-(3-(5-(trifluoromethyl)-1,2,4-oxadiazol-3-yl)benzyl)methanamine, N-((4-(4-phenylthiazol-2-yl)tetrahydro-2H-pyran-4-yl)methyl)-5-(5-(trifluoromethyl)-1,2,4-oxadiazol-3-yl)nicotinamide, N-((4-(4-phenylthiophen-2-yl)tetrahydro-2H-pyran-4-yl)methyl)-3-(5-(trifluoromethyl)-1,2,4-oxadiazol-3-yl)benzamide, N-((1-(4-phenylthiazol-2-yl)cyclopentyl)methyl)-3-(5-(trifluoromethyl)-1,2,4-oxadiazol-3-yl)benzamide, N-((4-(3-phenyl-1H-1,2,4-triazol-5-yl)tetrahydro-2H-pyran-4-yl)methyl)-3-(5-(trifluoromethyl)-1,2,4-oxadiazol-3-yl)benzamide,
N-((4-(2-phenylthiazol-4-yl)tetrahydro-2H-pyran-4-yl)methyl)-3-(5-(trifluoromethyl)-1,2,4-oxadiazol-3-yl)benzamide,
N-((4-(4-(4-methoxyphenyl)thiazol-2-yl)tetrahydro-2H-pyran-4-yl)methyl)-3-(5-(trifluoromethyl)-1,2,4-oxadiazol-3-yl)benzamide,
N-((4-(4-(4-chlorophenyl)thiazol-2-yl)tetrahydro-2H-pyran-4-yl)methyl)-3-(5-(trifluoromethyl)-1,2,4-oxadiazol-3-yl)benzamide,
N-(2-methyl-2-(4-phenylthiazol-2-yl)propyl)-3-(5-(trifluoromethyl)-1,2,4-oxadiazol-3-yl)benzamide,
N-((1-methyl-4-(4-phenylthiazol-2-yl)piperidin-4-yl)methyl)-3-(5-(trifluoromethyl)-1,2,4-oxadiazol-3-yl)benzamide,
N-((4-(4-(4-fluorophenyl)thiazol-2-yl)tetrahydro-2H-pyran-4-yl)methyl)-3-(5-(trifluoromethyl)-1,2,4-oxadiazol-3-yl)benzamide,
N-((4-(5-methyl-4-phenylthiazol-2-yl)tetrahydro-2H-pyran-4-yl)methyl)-3-(5-(trifluoromethyl)-1,2,4-oxadiazol-3-yl)benzamide,
N-((4-(4-cyclohexylthiazol-2-yl)tetrahydro-2H-pyran-4-yl)methyl)-3-(5-(trifluoromethyl)-1,2,4-oxadiazol-3-yl)benzamide,
N-((4-(4-(pyridin-2-yl)thiazol-2-yl)tetrahydro-2H-pyran-4-yl)methyl)-3-(5-(trifluoromethyl)-1,2,4-oxadiazol-3-yl)benzamide,
N-((4-(4-(pyridin-4-yl)thiazol-2-yl)tetrahydro-2H-pyran-4-yl)methyl)-3-(5-(trifluoromethyl)-1,2,4-oxadiazol-3-yl)benzamide,
N-((4-(4-phenylthiazol-2-yl)tetrahydro-2H-pyran-4-yl)methyl)-5-(5-(trifluoromethyl)-1,2,4-oxadiazol-3-yl)thiophene-2-carboxamide,
N-((4-(4-(thiophen-2-yl)thiazol-2-yl)tetrahydro-2H-pyran-4-yl)methyl)-3-(5-(trifluoromethyl)-1,2,4-oxadiazol-3-yl)benzamide,
N-(2-(4-(4-fluorophenyl)thiazol-2-yl)-2-methylpropyl)-3-(5-(trifluoromethyl)-1,2,4-oxadiazol-3-yl)benzamide,
N-(2-(4-(4-chlorophenyl)thiazol-2-yl)-2-methylpropyl)-3-(5-(trifluoromethyl)-1,2,4-oxadiazol-3-yl)benzamide,
3-fluoro-N-(2-(4-(4-fluorophenyl)thiazol-2-yl)-2-methylpropyl)-5-(5-(trifluoromethyl)-1,2,4-oxadiazol-3-yl)benzamide,
3-cyano-N-((4-(4-phenylthiazol-2-yl)tetrahydro-2H-pyran-4-yl)methyl)-5-(5-(trifluoromethyl)-1,2,4-oxadiazol-3-yl)benzamide,
3-methoxy-N-((4-(4-phenylthiazol-2-yl)tetrahydro-2H-pyran-4-yl)methyl)-5-(5-(trifluoromethyl)-1,2,4-oxadiazol-3-yl)benzamide,
N-(2-(4-(4-fluorophenyl)thiazol-2-yl)ethyl)-3-(5-(trifluoromethyl)-1,2,4-oxadiazol-3-yl)benzamide,
N-((4-(4-(4-cyanophenyl)thiazol-2-yl)tetrahydro-2H-pyran-4-yl)methyl)-3-(5-(trifluoromethyl)-1,2,4-oxadiazol-3-yl)benzamide,
N-((4-(4-(4-fluorophenyl)thiazol-2-yl)-2,2-dimethyltetrahydro-2H-pyran-4-yl)methyl)-3-(5-(trifluoromethyl)-1,2,4-oxadiazol-3-yl)benzamide,
N-((4-(4-phenylthiazol-2-yl)tetrahydro-2H-pyran-4-yl)methyl)-3-(5-(trifluoromethyl)-1,2,4-oxadiazol-3-yl)benzenesulfonamide,
3-ethyl-N-((4-(4-phenylthiazol-2-yl)tetrahydro-2H-pyran-4-yl)methyl)-5-(5-(trifluoromethyl)-1,2,4-oxadiazol-3-yl)benzamide,
N-((4-(3-bromophenyl)tetrahydro-2H-pyran-4-yl)methyl)-3-(5-(trifluoromethyl)-1,2,4-oxadiazol-3-yl)benzamide,
3-(5-(trifluoromethyl)-1,2,4-oxadiazol-3-yl)-N-((4-(4-(4-(trifluoromethyl)phenyl)thiazol-2-yl)tetrahydro-2H-pyran-4-yl)methyl)benzamide,
N-(2-methyl-2-(4-(4-(trifluoromethyl)phenyl)thiazol-2-yl)propyl)-3-(5-(trifluoromethyl)-1,2,4-oxadiazol-3-yl)benzamide,
N-((4-(4-phenylthiazol-2-yl)tetrahydro-2H-pyran-4-yl)methyl)-2-(5-(trifluoromethyl)-1,2,4-oxadiazol-3-yl)cyclopropanecarboxamide,
N-((1-methyl-4-(2-phenylthiazol-4-yl)piperidin-4-yl)methyl)-5-(5-(trifluoromethyl)-1,2,4-oxadiazol-3-yl)nicotinamide,
N-(2-(2-(4-chlorophenyl)thiazol-4-yl)-2-methylpropyl)-5-(5-(trifluoromethyl)-1,2,4-oxadiazol-3-yl)nicotinamide,
N-((4-(2-(4-chlorophenyl)thiazol-4-yl)-1-methylpiperidin-4-yl)methyl)-5-(5-(trifluoromethyl)-1,2,4-oxadiazol-3-yl)nicotinamide,
N-(2-(2-(4-chlorophenyl)thiazol-4-yl)-2-methylpropyl)-3-(5-(trifluoromethyl)-1,2,4-oxadiazol-3-yl)benzamide,
N-(2-(2-(4-chlorophenyl)thiazol-4-yl)ethyl)-5-(5-(trifluoromethyl)-1,2,4-oxadiazol-3-yl)nicotinamide,
N-(2-(4-(4-chlorophenyl)thiazol-2-yl)-2-methylpropyl)-2-(5-(trifluoromethyl)-1,2,4-oxadiazol-3-yl)isonicotinamide,
N-(2-(2-(4-fluorophenyl)thiazol-4-yl)-2-methylpropyl)-3-(5-(trifluoromethyl)-1,2,4-oxadiazol-3-yl)benzamide,
N-(2-(2-(4-fluorophenyl)thiazol-4-yl)-2-methylpropyl)-5-(5-(trifluoromethyl)-1,2,4-oxadiazol-3-yl)nicotinamide,
N-(2-(4-(4-chlorophenyl)thiazol-2-yl)-2-methylpropyl)-6-(5-(trifluoromethyl)-1,2,4-oxadiazol-3-yl)picolinamide,
N-(2-(dimethylamino)-2-(4-phenylthiazol-2-yl)ethyl)-3-(5-(trifluoromethyl)-1,2,4-oxadiazol-3-yl)benzamide,
N-(2-(3-phenyl-1H-1,2,4-triazol-5-yl)ethyl)-3-(5-(trifluoromethyl)-1,2,4-oxadiazol-3-yl)benzamide,
N-((1-(4-phenylthiazol-2-yl)cyclopropyl)methyl)-3-(5-(trifluoromethyl)-1,2,4-oxadiazol-3-yl)benzamide,
3-(4-(4-fluorophenyl)thiazol-2-yl)-N-(3-(5-(trifluoromethyl)-1,2,4-oxadiazol-3-yl)phenyl)propanamide,
N-(2-(2-(4-chlorophenyl)thiazol-4-yl)ethyl)-3-(5-(trifluoromethyl)-1,2,4-oxadiazol-3-yl)benzamide,
N-((4-phenylthiazol-2-yl)methyl)-3-(5-(trifluoromethyl)-1,2,4-oxadiazol-3-yl)benzamide,
N-(2-(4-(4-fluorophenyl)thiazol-2-yl)ethyl)-5-(5-(trifluoromethyl)-1,2,4-oxadiazol-3-yl)nicotinamide,
N-(2-(4-(4-chlorophenyl)thiazol-2-yl)ethyl)-3-(5-(trifluoromethyl)-1,2,4-oxadiazol-3-yl)benzamide,
N-(2-(4-(4-chlorophenyl)thiazol-2-yl)ethyl)-5-(5-(trifluoromethyl)-1,2,4-oxadiazol-3-yl)nicotinamide,
N-((4-(3,4-dihydroisoquinolin-2(1H)-yl)tetrahydro-2H-pyran-4-yl)methyl)-3-(5-(trifluoromethyl)-1,2,4-oxadiazol-3-yl)benzamide,
N-methyl-N-((4-(4-phenylthiazol-2-yl)tetrahydro-2H-pyran-4-yl)methyl)-3-(5-(trifluoromethyl)-1,2,4-oxadiazol-3-yl)benzamide,
N-(2-(2-(4-fluorophenyl)thiazol-4-yl)ethyl)-5-(5-(trifluoromethyl)-1,2,4-oxadiazol-3-yl)nicotinamide,
N-(2-(2-(4-fluorophenyl)thiazol-4-yl)ethyl)-3-(5-(trifluoromethyl)-1,2,4-oxadiazol-3-yl)benzamide,
N-(2-(4-(4-fluorophenyl)thiazol-2-yl)-2-methylpropyl)-5-(5-(trifluoromethyl)-1,2,4-oxadiazol-3-yl)nicotinamide,
2,2,2-trifluoro-N-((4-(4-phenylthiazol-2-yl)tetrahydro-2H-pyran-4-yl)methyl)-1-(3-(5-(trifluoromethyl)-1,2,4-oxadiazol-3-yl)phenyl)ethanamine,
N-(2-(3-(4-fluorophenyl)-1H-1,2,4-triazol-5-yl)ethyl)-3-(5-(trifluoromethyl)-1,2,4-oxadiazol-3-yl)benzamide,
N-(2-(3-(4-chlorophenyl)-1H-1,2,4-triazol-5-yl)ethyl)-3-(5-(trifluoromethyl)-1,2,4-oxadiazol-3-yl)benzamide,
N-(2-methyl-2-(3-phenyl-1H-1,2,4-triazol-5-yl)propyl)-3-(5-(trifluoromethyl)-1,2,4-oxadiazol-3-yl)benzamide,
N-(2-methyl-2-(3-phenyl-1H-1,2,4-triazol-5-yl)propyl)-5-(5-(trifluoromethyl)-1,2,4-oxadiazol-3-yl)nicotinamide,
N-(2-(3-(4-fluorophenyl)-1H-1,2,4-triazol-5-yl)-2-methylpropyl)-3-(5-(trifluoromethyl)-1,2,4-oxadiazol-3-yl)benzamide, N-(2-(3-(4-fluorophenyl)-1H-1,2,4-triazol-5-yl)-2-methylpropyl)-5-(5-(trifluoromethyl)-1,2,4-oxadiazol-3-yl)nicotinamide,
N-(2-(3-(4-chlorophenyl)-1H-1,2,4-triazol-5-yl)-2-methylpropyl)-3-(5-(trifluoromethyl)-1,2,4-oxadiazol-3-yl)benzamide,
N-(2-(4-(4-chlorophenyl)thiazol-2-yl)-2-methylpropyl)-6-methyl-5-(5-(trifluoromethyl)-1,2,4-oxadiazol-3-yl)nicotinamide,
N-(3-(4-phenylthiazol-2-yl)propyl)-3-(5-(trifluoromethyl)-1,2,4-oxadiazol-3-yl)benzamide,
N-(2-(2-(4-fluorophenyl)oxazol-4-yl)ethyl)-5-(5-(trifluoromethyl)-1,2,4-oxadiazol-3-yl)nicotinamide,
N-(2-(5-phenylthiazol-2-yl)ethyl)-3-(5-(trifluoromethyl)-1,2,4-oxadiazol-3-yl)benzamide,
N-(2-(2-(4-fluorophenyl)oxazol-4-yl)propyl)-3-(5-(trifluoromethyl)-1,2,4-oxadiazol-3-yl)benzamide,
N-(2-(2-(3-fluorophenyl)oxazol-4-yl)ethyl)-5-(5-(trifluoromethyl)-1,2,4-oxadiazol-3-yl)nicotinamide,
N-(2-(4-(4-chlorophenyl)thiazol-2-yl)-2-methylpropyl)-2-methyl-5-(5-(trifluoromethyl)-1,2,4-oxadiazol-3-yl)nicotinamide,
N-(2-methyl-2-(5-phenylthiazol-2-yl)propyl)-3-(5-(trifluoromethyl)-1,2,4-oxadiazol-3-yl)benzamide,
N-((4-([1,1'-biphenyl]-3-yl)tetrahydro-2H-pyran-4-yl)methyl)-3-(5-(trifluoromethyl)-1,2,4-oxadiazol-3-yl)benzamide,
N-((4-([1,1'-biphenyl]-3-yl)tetrahydro-2H-pyran-4-yl)methyl)-5-(5-(trifluoromethyl)-1,2,4-oxadiazol-3-yl)nicotinamide,
N-(2-(4-fluorophenyl)oxazol-4-yl)methyl)-3-(5-(trifluoromethyl)-1,2,4-oxadiazol-3-yl)benzamide,
N-((4-(2-(4-fluorophenyl)oxazol-4-yl)-1-methylpiperidin-4-yl)methyl)-3-(5-(trifluoromethyl)-1,2,4-oxadiazol-3-yl)benzamide,
N-(2-methyl-2-(2-phenyloxazol-4-yl)propyl)-3-(5-(trifluoromethyl)-1,2,4-oxadiazol-3-yl)benzamide,
2-(2-(4-fluorophenyl)oxazol-4-yl)-2-methyl-N-(3-(5-(trifluoromethyl)-1,2,4-oxadiazol-3-yl)benzyl)propan-1-amine,
3-(3-(4-(4-phenylthiazol-2-yl)butyl)phenyl)-5-(trifluoromethyl)-1,2,4-oxadiazole,
N-(2-methyl-2-(5-phenyloxazol-2-yl)propyl)-3-(5-(trifluoromethyl)-1,2,4-oxadiazol-3-yl)benzamide,
N-(2-(2-phenylthiazol-5-yl)ethyl)-3-(5-(trifluoromethyl)-1,2,4-oxadiazol-3-yl)benzamide,
N-(2-methyl-2-(2-phenylthiazol-5-yl)propyl)-3-(5-(trifluoromethyl)-1,2,4-oxadiazol-3-yl)benzamide,
N-((4-(2-(4-chlorophenyl)thiazol-4-yl)-1-methylpiperidin-4-yl)methyl)-3-(5-(trifluoromethyl)-1,2,4-oxadiazol-3-yl)benzamide,
N-(2-(2-(4-fluorophenyl)oxazol-4-yl)-2-methylpropyl)-3-(5-(2,2,2-trifluoroacetyl)thiophen-2-yl)benzamide,
N-(2-(2-(4-fluorophenyl)oxazol-4-yl)-2-methylpropyl)-5-(5-(2,2,2-trifluoroacetyl)thiophen-2-yl)nicotinamide,
N-((4-(2-(4-chlorophenyl)thiazol-4-yl)-1-methylpiperidin-4-yl)methyl)-3-(5-(2,2,2-trifluoroacetyl)thiophen-2-yl)benzamide,
2-fluoro-N-(2-(2-(4-fluorophenyl)oxazol-4-yl)-2-methylpropyl)-5-(5-(trifluoromethyl)-1,2,4-oxadiazol-3-yl)benzamide,
N-(2-(2-(4-fluorophenyl)oxazol-4-yl)-2-methylpropyl)-2-(5-(trifluoromethyl)-1,2,4-oxadiazol-3-yl)oxazole-4-carboxamide,
N-(2-(1-methyl-2-phenyl-1H-imidazol-5-yl)propyl)-5-(5-(trifluoromethyl)-1,2,4-oxadiazol-3-yl)nicotinamide,
N-(2-(2-(4-fluorophenyl)oxazol-4-yl)-2-hydroxyethyl)-3-(5-(trifluoromethyl)-1,2,4-oxadiazol-3-yl)benzamide,
5-(5-(difluoromethyl)-1,2,4-oxadiazol-3-yl)-N-(2-(2-(4-fluorophenyl)oxazol-4-yl)-2-methylpropyl)nicotinamide,
N-(2-(dimethylamino)-2-(2-(4-fluorophenyl)oxazol-4-yl)ethyl)-3-(5-(trifluoromethyl)-1,2,4-oxadiazol-3-yl)benzamide hydrochloride,
N-(2-(3-(4-fluorophenyl)-1H-1,2,4-triazol-5-yl)-2-methylpropyl)-5-(5-(2,2,2-trifluoroacetyl)thiophen-2-yl)nicotinamide,
N-(2-(2-(4-fluorophenyl)oxazol-4-yl)-2-methylpropyl)-2-methoxy-5-(5-(trifluoromethyl)-1,2,4-oxadiazol-3-yl)benzamide,
N-(2-(2-(4-fluorophenyl)oxazol-5-yl)-2-methylpropyl)-3-(5-(trifluoromethyl)-1,2,4-oxadiazol-3-yl)benzamide,
N-(4-(dimethylamino)-2-(2-(4-fluorophenyl)oxazol-4-yl)butyl)-3-(5-(trifluoromethyl)-1,2,4-oxadiazol-3-yl)benzamide,
N-(4-(dimethylamino)-2-(2-(4-fluorophenyl)oxazol-4-yl)butyl)-5-(5-(trifluoromethyl)-1,2,4-oxadiazol-3-yl)nicotinamide,
N-(2-(2-(4-fluorophenyl)oxazol-4-yl)-2-hydroxyethyl)-5-(5-(trifluoromethyl)-1,2,4-oxadiazol-3-yl)nicotinamide,
N-((4-(2-(4-chlorophenyl)oxazol-4-yl)-1-methylpiperidin-4-yl)methyl)-3-(5-(trifluoromethyl)-1,2,4-oxadiazol-3-yl)benzamide,
2-(2-(4-chlorophenyl)oxazol-4-yl)-2-methyl-N-(3-(5-(trifluoromethyl)-1,2,4-oxadiazol-3-yl)benzyl)propan-1-amine,
N-(2-(2-(4-fluorophenyl)oxazol-5-yl)ethyl)-3-(5-(trifluoromethyl)-1,2,4-oxadiazol-3-yl)benzamide,
N-((4-([1,1'-biphenyl]-3-yl)-1-methylpiperidin-4-yl)methyl)-3-(5-(trifluoromethyl)-1,2,4-oxadiazol-3-yl)benzamide,
N-(2-(2-(4-methoxyphenyl)oxazol-4-yl)ethyl)-5-(5-(trifluoromethyl)-1,2,4-oxadiazol-3-yl)nicotinamide,
2-chloro-N-(2-(2-(4-fluorophenyl)oxazol-4-yl)-2-methylpropyl)-5-(5-(trifluoromethyl)-1,2,4-oxadiazol-3-yl)benzamide,
N-(2-(2-(4-fluorophenyl)oxazol-4-yl)-2-methylpropyl)-3-(5-(trifluoromethyl)-1,2,4-oxadiazol-3-yl)benzamide,
N-(3-(2-(4-fluorophenyl)oxazol-4-yl)-3-hydroxypropyl)-3-(5-(trifluoromethyl)-1,2,4-oxadiazol-3-yl)benzamide,
N-(2-(2-(4-cyanophenyl)oxazol-4-yl)ethyl)-5-(5-(trifluoromethyl)-1,2,4-oxadiazol-3-yl)nicotinamide,
N-(2-(2-(2-fluorophenyl)oxazol-4-yl)ethyl)-5-(5-(trifluoromethyl)-1,2,4-oxadiazol-3-yl)nicotinamide,
3-(5-(2,2-difluoroacetyl)thiophen-2-yl)-N-(2-(2-(4-fluorophenyl)oxazol-4-yl)-2-methylpropyl)benzamide,
N-(2-(2-(4-fluorophenyl)oxazol-4-yl)-2-methylpropyl)-3-(5-(2,2,2-trifluoroacetyl)thiazol-2-yl)benzamide,
N-(2-(1-methyl-2-phenyl-1H-imidazol-4-yl)propyl)-5-(5-(trifluoromethyl)-1,2,4-oxadiazol-3-yl)nicotinamide,
N-(2-(2-(4-fluorophenyl)oxazol-4-yl)-2-methylpropyl)-3-(5-(2,2,2-trifluoroacetyl)furan-2-yl)benzamide,
N-(2-(2-(4-fluorophenyl)oxazol-4-yl)-2-methoxyethyl)-3-(5-(trifluoromethyl)-1,2,4-oxadiazol-3-yl)benzamide,
N-(2-(4-(4-fluorophenyl)thiazol-2-yl)propyl)-3-(5-(trifluoromethyl)-1,2,4-oxadiazol-3-yl)benzamide,
N-((4-(4-phenylthiazol-2-yl)tetrahydro-2H-pyran-4-yl)methyl)-3-(5-(2,2,2-trifluoroacetyl)thiophen-2-yl)benzamide,
N-(2-(2-(4-fluorophenyl)oxazol-4-yl)ethyl)-3-(5-(trifluoromethyl)-1,2,4-oxadiazol-3-yl)benzamide,
N-(2-(2-(4-fluorophenyl)oxazol-4-yl)-2-methylpropyl)-5-(5-(trifluoromethyl)-1,2,4-oxadiazol-3-yl)nicotinamide, N-(2-([1,1'-biphenyl]-3-yl)-2-methylpropyl)-3-(5-(trifluoromethyl)-1,2,4-oxadiazol-3-yl)benzamide,
N-(2-(4-fluoro-[1,1'-biphenyl]-3-yl)-2-methylpropyl)-3-(5-(trifluoromethyl)-1,2,4-oxadiazol-3-yl)benzamide,
N-((4-(4-(3,5-difluorophenyl)thiazol-2-yl)tetrahydro-2H-pyran-4-yl)methyl)-3-(5-(trifluoromethyl)-1,2,4-oxadiazol-3-yl)benzamide,
N-(2-(4-(3,5-difluorophenyl)thiazol-2-yl)-2-methylpropyl)-3-(5-(trifluoromethyl)-1,2,4-oxadiazol-3-yl)benzamide,
N-(2-(2-phenyloxazol-4-yl)ethyl)-3-(5-(trifluoromethyl)-1,2,4-oxadiazol-3-yl)benzamide,
N-(2-(2-phenyloxazol-4-yl)ethyl)-5-(5-(trifluoromethyl)-1,2,4-oxadiazol-3-yl)nicotinamide,
N-(2-(2-(4-chlorophenyl)oxazol-4-yl)ethyl)-3-(5-(trifluoromethyl)-1,2,4-oxadiazol-3-yl)benzamide,
N-(2-(2-(4-chlorophenyl)oxazol-4-yl)ethyl)-5-(5-(trifluoromethyl)-1,2,4-oxadiazol-3-yl)nicotinamide,
N-(2-methyl-2-(2-phenyloxazol-4-yl)propyl)-5-(5-(trifluoromethyl)-1,2,4-oxadiazol-3-yl)nicotinamide,
N-(2-(2-(4-chlorophenyl)oxazol-4-yl)-2-methylpropyl)-3-(5-(trifluoromethyl)-1,2,4-oxadiazol-3-yl)benzamide,
N-(2-(3-phenyl-1,2,4-oxadiazol-5-yl)ethyl)-3-(5-(trifluoromethyl)-1,2,4-oxadiazol-3-yl)benzamide,
N-(2-methyl-2-(3-phenyl-1H-pyrazol-5-yl)propyl)-3-(5-(trifluoromethyl)-1,2,4-oxadiazol-3-yl)benzamide,
N-(2-(2-(4-fluorophenyl)oxazol-4-yl)propyl)-5-(5-(trifluoromethyl)-1,2,4-oxadiazol-3-yl)nicotinamide,
N-(2-(4-(4-chlorophenyl)thiazol-2-yl)-2-methylpropyl)-5-(5-(trifluoromethyl)-1,2,4-oxadiazol-3-yl)nicotinamide,
N-((4-([1,1'-biphenyl]-3-yl)-1-methylpiperidin-4-yl)methyl)-5-(5-(trifluoromethyl)-1,2,4-oxadiazol-3-yl)nicotinamide,
N-(2-(2-(4-fluorophenyl)oxazol-4-yl)-2-methylpropyl)-3-(4-(2,2,2-trifluoroacetyl)thiophen-2-yl)benzamide,
N-(2-(2-(4-fluorophenyl)oxazol-4-yl)-2-hydroxypropyl)-3-(5-(trifluoromethyl)-1,2,4-oxadiazol-3-yl)benzamide,
N-(2-(2-(4-fluorophenyl)oxazol-4-yl)-2-methylpropyl)-3-(5-(2,2,2-trifluoroacetyl)furan-3-yl)benzamide,
N-(2-(2-(4-fluorophenyl)oxazol-4-yl)-2-methylpropyl)-3-(5-(2,2,2-trifluoroacetyl)thiophen-3-yl)benzamide,
N-((4-(4-phenylthiazol-2-yl)tetrahydro-2H-pyran-4-yl)methyl)-3-(5-(2,2,2-trifluoroacetyl)-1,2,4-oxadiazol-3-yl)benzamide,
and salts, particularly pharmaceutically acceptable salts, thereof.

Particular compounds of this invention include:
N-((4-(4-phenylthiazol-2-yl)tetrahydro-2H-pyran-4-yl)methyl)-3-(5-(trifluoromethyl)-1,2,4-oxadiazol-3-yl)benzamide,
N-(2-methyl-2-(2-phenyloxazol-4-yl)propyl)-3-(5-(trifluoromethyl)-1,2,4-oxadiazol-3-yl)benzamide,
N-(2-(3-(4-fluorophenyl)-1H-1,2,4-triazol-5-yl)-2-methylpropyl)-5-(5-(trifluoromethyl)-1,2,4-oxadiazol-3-yl)nicotinamide,
N-(2-(2-(4-fluorophenyl)oxazol-4-yl)-2-methylpropyl)-3-(5-(trifluoromethyl)-1,2,4-oxadiazol-3-yl)benzamide,
N-(2-(dimethylamino)-2-(2-(4-fluorophenyl)oxazol-4-yl)ethyl)-3-(5-(trifluoromethyl)-1,2,4-oxadiazol-3-yl)benzamide,
N-(2-(2-(4-fluorophenyl)oxazol-4-yl)-2-hydroxyethyl)-3-(5-(trifluoromethyl)-1,2,4-oxadiazol-3-yl)benzamide,
N-(2-(3-(4-Fluorophenyl)-1H-1,2,4-triazol-5-yl)-2-methylpropyl)-5-(5-(2,2,2-trifluoroacetyl)thiophen-2-yl)nicotinamide,
N-(4-(dimethylamino)-2-(2-(4-fluorophenyl)oxazol-4-yl)butyl)-3-(5-(trifluoromethyl)-1,2,4-oxadiazol-3-yl)benzamide,
N-(2-(2-(4-fluorophenyl)oxazol-4-yl)-2-methylpropyl)-3-(5-(2,2,2-trifluoroacetyl)thiazol-2-yl)benzamide,
N-(2-(2-(4-fluorophenyl)oxazol-4-yl)-2-hydroxypropyl)-3-(5-(trifluoromethyl)-1,2,4-oxadiazol-3-yl)benzamide,
(3-(5-(4-fluorophenyl)oxazol-2-yl)piperidin-1-yl)(3-(5-(trifluoromethyl)-1,2,4-oxadiazol-3-yl)phenyl)methanone, and salts, particularly pharmaceutically acceptable salts, thereof.

Compound names were generated using the software naming program ChemDraw 11.0 available from CambridgeSoft Corporation, 100 CambridgePark Drive, Cambridge, Mass. 02140, USA (http://www.cambridgesoft.com).

The compounds of Formula I can be prepared according to the methods outlined below.

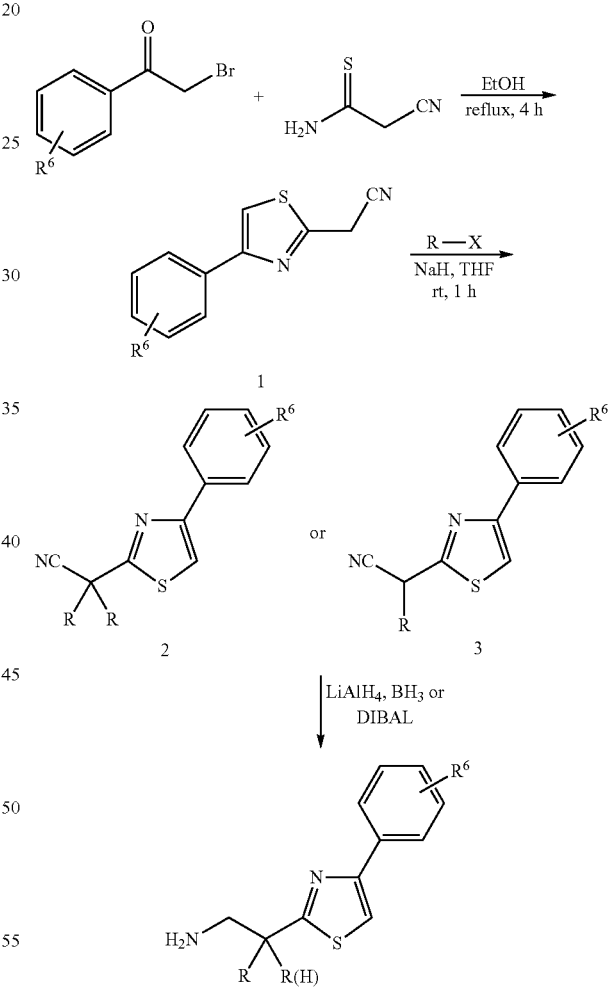

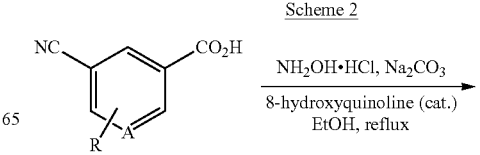

27
-continued
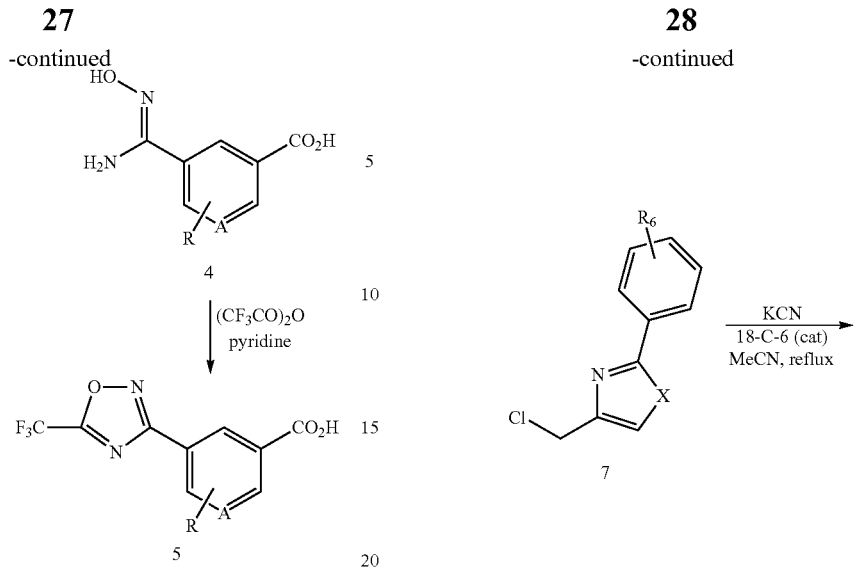
Scheme 3
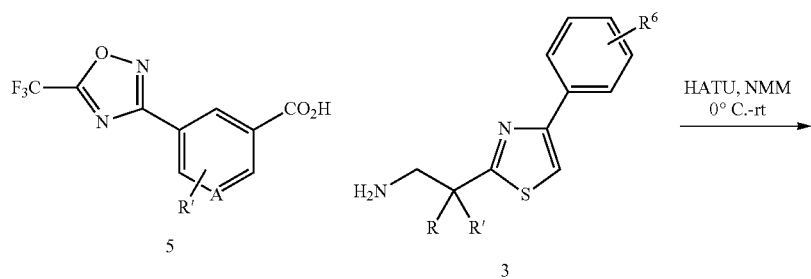
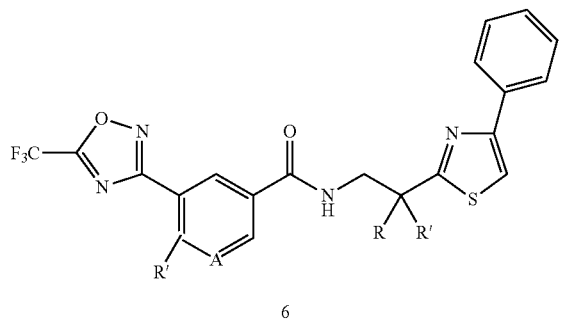
Scheme 4
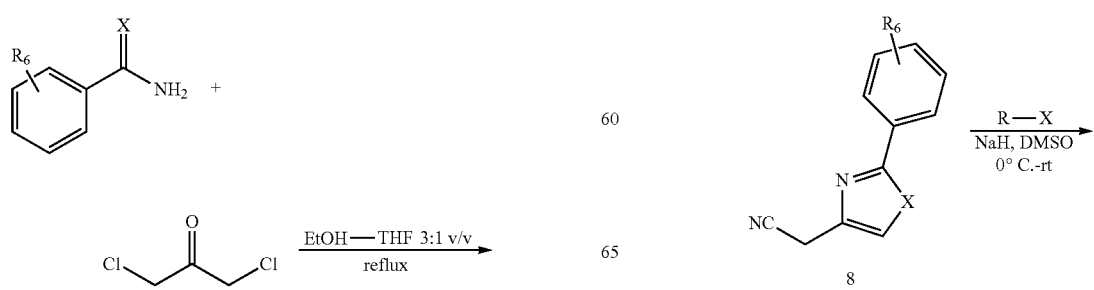

-continued

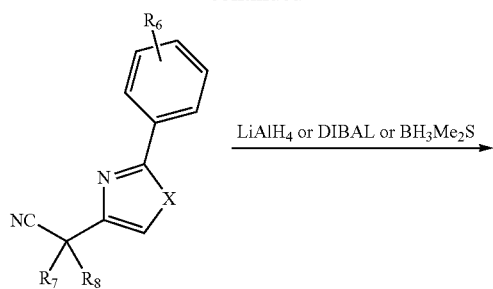

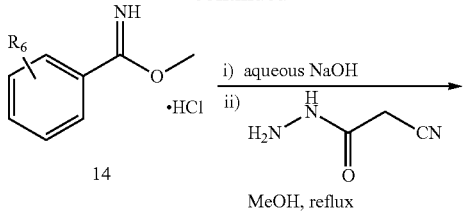

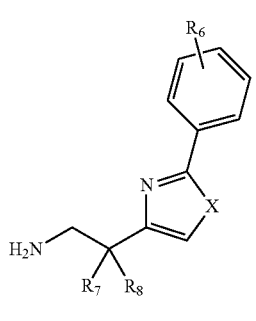

Scheme 5

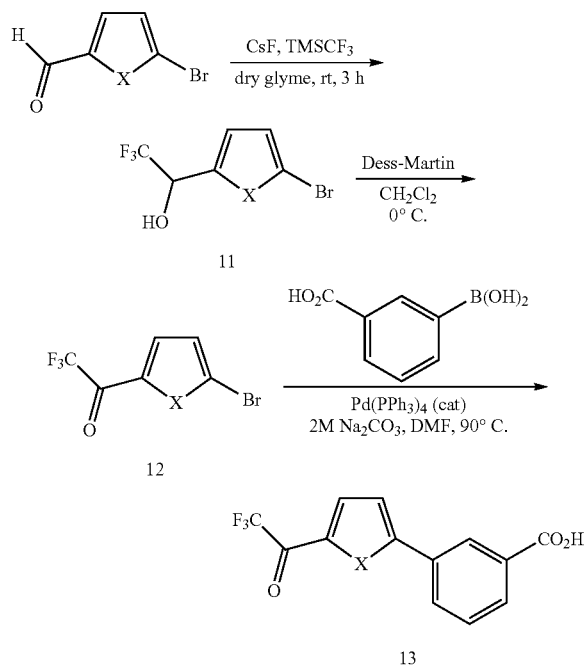

Scheme 6

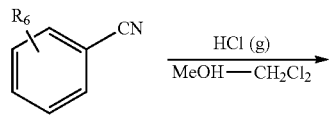

The invention also includes various deuterated forms of the compounds of Formula I. Each available hydrogen atom attached to a carbon atom may be independently replaced with a deuterium atom. A person of ordinary skill in the art will know how to synthesize deuterated forms of the compounds of Formula I. For example, deuterated alkyl groups (e.g., N-(deutero-methyl)amines) may be prepared by conventional techniques (see for example: methyl-$d_3$-amine available from Aldrich Chemical Co., Milwaukee, Wis., Cat. No. 489, 689-2). Employing such compounds will allow for the preparation of compounds of Formula I in which various hydrogen atoms of the N-methyl groups are replaced with a deuterium atom.

The present invention is directed to a method of inhibiting an HDAC which comprises contacting the acetylase with a compound of Formula I or a salt thereof, particularly a pharmaceutically acceptable salt thereof. This invention is also directed to a method of treatment of an HDAC-mediated disease or disorder comprising administering a therapeutically effective amount of the compound of Formula I or a salt thereof, particularly a pharmaceutically acceptable salt thereof, to a patient, specifically a human, in need thereof. As used herein, "patient" refers to a mammal, specifically, a human. A therapeutically "effective amount" is intended to mean that amount of a compound that, when administered to a patient in need of such treatment, is sufficient to effect treatment, as defined herein. Thus, e.g., a therapeutically effective amount of a compound of Formula I, or a pharmaceutically acceptable salt thereof, is a quantity of an inventive agent that, when administered to a human in need thereof, is sufficient to inhibit the activity of HDAC such that a disease condition which is mediated by that activity is reduced, alleviated or prevented. The amount of a given compound that will correspond to such an amount will vary depending upon factors such as the particular compound (e.g., the potency (pXC$_{50}$), efficacy (EC$_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmaceutical characteristics), disease or condition and its severity and the specific composition and method being used, but can nevertheless be determined by one of skill in the art.

"Treating" or "treatment" is intended to mean at least the mitigation of a disease condition in a patient, where the disease condition is caused or mediated by HDAC. The methods of treatment for mitigation of a disease condition include the use of the compounds in this invention in any conventionally acceptable manner, for example for prevention, retardation, prophylaxis, therapy or cure of a disease.

In one embodiment, this invention is directed to a method of treating, ameliorating, or preventing an autoimmune disorder, an immunological disease, an inflammatory disorder, transplant/graft rejection (e.g., allograft), lymphopenia, or graft-versus-host disease (GvHD) in a patient, specifically in a human, comprising administering to the patient a compound of this invention, in an amount sufficient to increase the level and/or activity of a Treg cell or a population of Treg cells in the patient, thereby treating, ameliorating, or preventing the autoimmune disorder, inflammatory disorder, transplant/graft rejection, lymphopenia, or GvHD in the patient.

Additional examples of diseases and conditions that may be treated by the compounds of this invention include but not limited to type II diabetes mellitus, coronary artery disease, allergies and allergic reactions, and sepsis/toxic shock.

Exemplary autoimmune disorders include, but are not limited to, multiple sclerosis, juvenile idiopathic arthritis, psoriatic arthritis, hepatitis C virus-associated mixed cryoglobulinemia, polymyositis, dermatomyositis, polyglandular syndrome type II, autoimmune liver disease, Kawasaki disease, myasthenia gravis, immunodysregulation polyendocrinopathy enteropathy X-linked syndrome (IPEX (syndrome)), type I diabetes, psoriasis, hypothyroidism, hemolytic anemia, autoimmune polyendocrinopathy-candidiasis-ectodermal dystrophy (APECED), thrombocytopenia, spondyloarthritis, Sjogren's syndrome, rheumatoid arthritis, inflammatory bowel disease (IBD), Crohn's disease, ulcerative colitis, eczema, gastritis, or thyroiditis. As part of a nonlimiting list, the inflammatory disorder can be contact hypersensitivity, atopic dermatitis or Still disease.

Additional examples of autoimmune diseases include but are not limited to autoimmune diseases include osteoarthritis, systemic sclerosis, sarcoidosis, insulin dependent diabetes mellitus (IDDM, type I diabetes), reactive arthritis, scleroderma, vasculitis, Wegener's granulomatosis, Hashimoto's disease, scleroderma, oophoritis, Lupus (SLE), Grave's disease, asthma, cryoglobulinemia, primary biliary sclerosis, pemphigus vulgaris, hemolytic anemia and pernicious anemia.

Examples of transplant/graft rejection (e.g., allograft), lymphopenia, or graft-versus-host disease (GvHD) are those arising from cell, tissue and organ transplantation procedures, such as therapeutic cell transplants such as stem cells, muscle cells such as cardiac cells, islet cells, liver cells, bone marrow transplants, skin grafts, bone grafts, lung transplants, kidney transplants, liver transplants, and heart transplants.

Other examples of diseases and conditions that may be treated by the compounds of this invention include but are not limited to cystic fibrosis, osteoporosis, obesity, epilepsy, depression, thalassemia, sickle cell anemia, amyotrophic lateral sclerosis (ALS) and hyperalgesia, cardiac disease (e.g., stroke, hypertension, atherothrombotic diseases, artherosclerosis or limitation of infarct size in acute coronary syndrome), diseases or disorders involving muscular atrophy, gentamicin-induced hearing loss, drug resistance (e.g., drug resistance in osteosarcoma and colon cancer cells), infectious diseases, and immune deficiency/immunocompromised patients. Examples of infectious diseases relate to various pathogen infections such as viral, fungal, bacterial, mycoplasm, and infections by unicellular and multicellular eukaryotic organisms. Common human pathogens include but are not limited to HIV, HSV, HPV, Hepatitis A, B and C viruses, influenza, denge, zostrella, rubella, RSV, rotavirus, gram positive, gram negative, streptococcus, tetanus, staphalococcus, tuberculosis, listeria, and malaria.

In another embodiment, this invention is directed to inhibitors of HDAC and their use to stop or reduce the growth of neoplastic cells, e.g., cancer cells and tumor cells.

The growth of cancer cells and/or tumor cells that are found in the following cancer types may be reduced by treatment with a compound of this invention: carcinoma (e.g., adenocarcinoma), heptaocellular carcinoma, sarcoma, myeloma (e.g., multiple myeloma), treating bone disease in multiple myeloma, leukemia, childhood acute lymphoblastic leukemia and lymphoma (e.g., cutaneous cell lymphoma), and mixed types of cancers, such as adenosquamous carcinoma, mixed mesodermal tumor, carcinosarcoma, and teratocarcinoma.

In one aspect of the invention, breast or prostate cancers or tumors are treated using the HDAC inhibitors of this invention.

Other cancers that may be treated using the compounds of this invention include, but are not limited to, bladder cancer, breast cancer, prostate cancer, stomach cancer, lung cancer, colon cancer, rectal cancer, colorectal cancer, liver cancer, endometrial cancer, pancreatic cancer, cervical cancer, ovarian cancer; head and neck cancer, and melanoma.

The inhibitors of the invention may be employed alone or in combination with standard anti-cancer regimens for neoplastic cell, e.g., tumor and cancer, treatments.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Treatment of HDAC-mediated disease conditions may be achieved using the compounds of this invention as a monotherapy, or in dual or multiple combination therapy, such as in combination with other agents, for example, in combination with one or more of the following agents: DNA methyltransferase inhibitors, acetyl transferase enhancers, proteasome or HSP90 inhibitors, and one or more immunosuppressants that do not activate the T suppressor cells including but are not limited to corticosteroids, rapamycin, Azathioprine, Mycophenolate, Cyclosporine, Mercaptopurine (6-MP), basiliximab, daclizumab, sirolimus, tacrolimus, Muromonab-CD3, cyclophosphamide, and methotrexate, which are administered in effective amounts as is known in the art.

The compounds of the invention will normally, but not necessarily, be formulated into a pharmaceutical composition prior to administration to a patient. Accordingly, in another aspect the invention is directed to pharmaceutical compositions comprising a compound of the invention and a pharmaceutically-acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula I or a salt, particularly a pharmaceutically acceptable salt, thereof). When prepared in unit dosage form, the pharmaceutical compositions may contain from 1 mg to 1000 mg of a compound of this invention.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional pharmaceutically active compounds.

As used herein, "pharmaceutically-acceptable excipient" means a material, composition or vehicle involved in giving form or consistency to the composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically-acceptable are avoided. In addition, each excipient must of course be of sufficiently high purity to render it pharmaceutically-acceptable.

The compounds of the invention and the pharmaceutically-acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising an effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the following experimental descriptions, the following abbreviations may be used:

| Abbreviation | Meaning |
|---|---|
| AcOH | acetic acid |
| aq | aqueous |
| brine | saturated aqueous NaCl |
| $CH_2Cl_2$ | methylene chloride |
| $CH_3CN$ or MeCN | acetonitrile |
| $CH_3NH_2$ | methylamine |
| d | day |
| DMF | N,N-dimethylformamide |
| DMSO | dimethylsulfoxide |
| equiv | equivalents |
| Et | ethyl |
| $Et_3N$ | triethylamine |
| $Et_2O$ | diethyl ether |
| EtOAc | ethyl acetate |
| h, hr | hour |
| HCl | hydrochloric acid |
| i-$Pr_2$NEt | N',N'-diisopropylethylamine |
| KOt-Bu | potassium tert-butoxide |
| LCMS | liquid chromatography-mass spectroscopy |
| Me | methyl |
| MeOH or $CH_3OH$ | methanol |
| $MgSO_4$ | magnesium sulfate |
| min | minute |
| MS | mass spectrum |
| μw | microwave |
| $NaBH_4$ | sodium borohydride |
| $Na_2CO_3$ | sodium carbonate |
| $NaHCO_3$ | sodium bicarbonate |
| NaOH | sodium hydroxide |
| $Na_2SO_4$ | sodium sulfate |
| $NH_4Cl$ | ammonium chloride |
| $NiCl_2 \cdot 6H_2O$ | nickel (II) chloride hexahydrate |
| NMP | N-methyl-2-pyrrolidone |
| Ph | phenyl |
| rt | room temperature |
| satd | saturated |
| SCX | strong cation exchange |
| SPE | solid phase extraction |
| TFA | trifluoroacetic acid |
| THF | tetrahydrofuran |
| $t_R$ | retention time |

Example 1

Step 1: 2-(4-Phenylthiazol-2-yl)acetonitrile

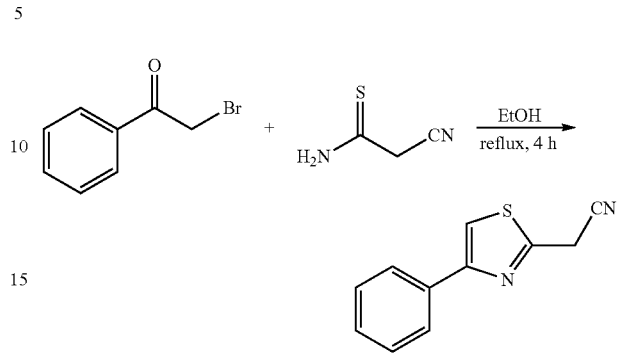

A mixture of 2-bromoacetophenone (2 g, 10 mmol) and 2-cyanothioacetamide (1 g, 10 mmol) in EtOH (25 mL) was heated to 80° C. for 4 h. The reaction mixture was cooled to room temperature and poured into an aqueous ammonia solution (final pH was >7). The mixture was then extracted with EtOAc and the organic layer was washed with $H_2O$ and brine. Solvent was removed under reduced pressure and the crude product was purified by flash column chromatography (silica gel 230-400 mesh, eluent 8% EtOAc in petroleum ether) to afford 2-(4-phenylthiazol-2-yl)acetonitrile (1.5 g, yield 75%) as a yellow solid: $^1$H NMR (300 MHz, $CDCl_3$) δ 7.88-7.91 (m, 2H), 7.49 (s, 1H), 7.27-7.48 (m, 3H), 4.19 (s, 2H). MS (ESI) m/z: Calculated for $C_{11}H_8N_2S$: 200.04. found: 201.2 $(M+H)^+$.

Step 2: 4-(4-Phenylthiazol-2-yl)tetrahydro-2H-pyran-4-carbonitrile

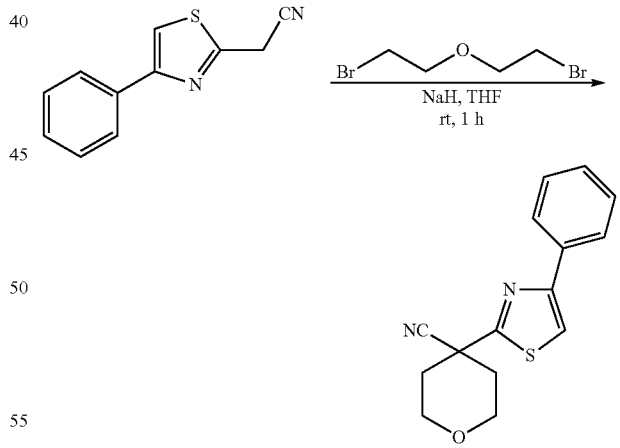

A solution of 2-(4-phenylthiazol-2-yl)acetonitrile (0.84 g, 4.19 mmol) in THF (25 mL) was cooled to 0° C. NaH was added (0.5 g, 60% dispersion in oil) portionwise over 10 min. The resulting mixture was allowed to warm up to room temperature and stirred for 20 min. 2-Bromoethyl ether (1.58 mL, 12.5 mmol) was added dropwise. The reaction mixture was further stirred at room temperature for 1 h and then quenched with saturated $NH_4Cl$ solution. The reaction mixture was diluted with EtOAc and the organic layer was washed with $H_2O$ and brine. The organic layer was dried over anhydrous sodium sulfate and concentrated under reduced pressure. The residue was purified by column chromatography (silica gel 60-120 mesh, eluent 4-8% EtOAc in petroleum ether) to afford 4-(4-phenylthiazol-2-yl)tetrahydro-2H-pyran-4-carbonitrile (0.97 g, yield 85%) as a yellow solid: $^1$H NMR (300 MHz, CDCl$_3$) δ 7.91-7.94 (m, 2H), 7.51 (s, 1H), 7.37-7.48 (m, 3H), 4.07-4.14 (m, 2H), 3.87-3.96 (m, 2H), 2.32-2.43 (m, 4H). MS (ESI) m/z: Calculated for C$_{15}$H$_{14}$N$_2$OS: 270.08. found: 271.2 (M+H)$^+$.

Step 3: (4-(4-Phenyithiazol-2-yl)tetrahydro-2H-pyran-4-yl)methanamine

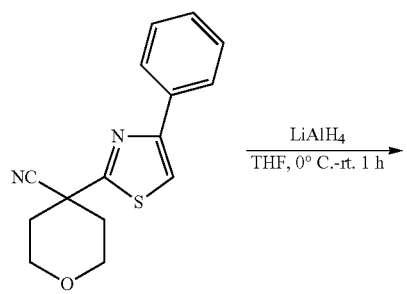

To a suspension of LiAlH$_4$ (220 mg, 5.9 mmol) in dry THF (10 mL) was added a solution of 4-(4-phenylthiazol-2-yl)tetrahydro-2H-pyran-4-carbonitrile (400 mg, 1.47 mmol) in dry THF (10 mL) at 0° C. The reaction mixture was stirred at room temperature for 1 h and then quenched carefully with water and diluted with EtOAc. The organic layer was washed with brine, dried over anhydrous sodium sulfate and concentrated under reduced pressure. The residue was purified by column chromatography (neutral alumina, eluent 5% MeOH in CHCl$_3$) to afford (4-(4-phenylthiazol-2-yl)tetrahydro-2H-pyran-4-yl)methanamine (150 mg, yield 37%): $^1$H NMR (400 MHz, CDCl$_3$) δ 7.89-7.91 (m, 2H), 7.48 (s, 1H), 7.33-7.46 (m, 3H), 3.89-3.93 (m, 2H), 3.63-3.69 (m, 2H), 3.03 (s, 2H), 2.30-2.33 (m, 2H), 1.90-1.97 (m, 2H). MS (ESI) m/z: Calculated for C$_{15}$H$_{18}$N$_2$OS: 274.11. found: 275.2 (M+H)$^+$.

Step 4: 3-(N'-Hydroxycarbamimidoyl)benzoic acid

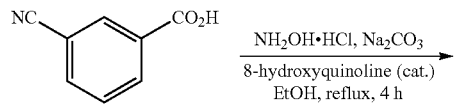

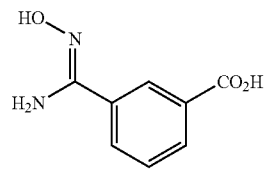

8-Hydroxyquinoline (5 mg, 0.03 mmol) was added to a solution of 3-cyanobenzoic acid (1 g, 6.8 mmol) in 50 mL ethanol. To this reaction mixture were added first hydroxylamine hydrochloric acid (950 mg, 13.6 mmol) in water (8 mL) followed by sodium carbonate (1.2 g, 10.9 mmol) in water (12 mL). The mixture was heated to reflux for 4 h. After removal of ethanol under reduced pressure, the residue was diluted with water, and the aqueous solution was acidified with 10% HCl to pH ~3. The white precipitate was filtrated, washed with water and acetone and then dried under reduced pressure to afford compound 3-(N'-hydroxycarbamimidoyl)benzoic acid (1 g, yield 82%): $^1$H NMR (400 MHz, CDCl$_3$) δ 13.03 (br s, 1H), 9.76 (s, 1H), 8.27-8.26 (m, 1H), 7.95-7.89 (m, 2H), 7.53 (t, J=7.8 Hz, 1H), 5.94 (br s, 2H). MS (ESI) m/z: Calculated for C$_8$H$_8$N$_2$O$_3$: 180.05. found: 180.9 (M+H)$^+$.

Step 5: 3-(5-(Trifluoromethyl)-1,2,4-oxadiazol-3-yl)benzoic acid

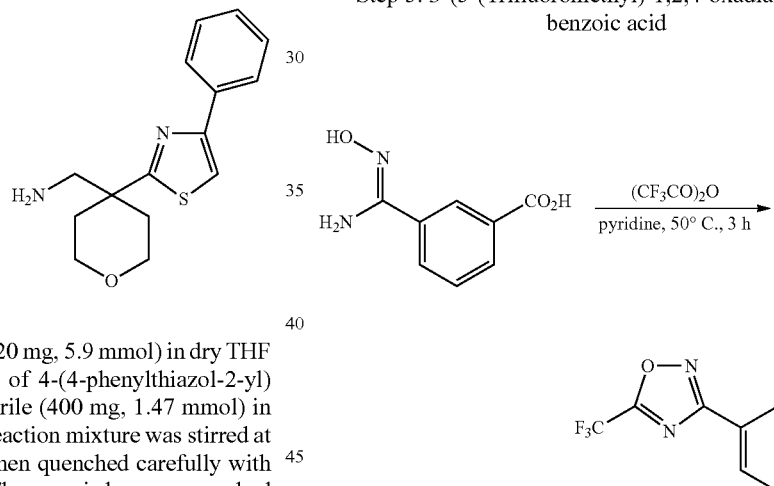

A solution of compound 3-(N'-hydroxycarbamimidoyl)benzoic acid (1 g, 5.6 mmol) in anhydrous pyridine (15 mL) was cooled to 0° C. and trifluoroacetic anhydride (2.3 mL, 16.7 mmol) was added dropwise. The reaction mixture was slowly warmed to room temperature and further heated to 50° C. for 3 h. The reaction mixture was poured into ice-water and adjusted to pH ~4 by addition of 1.5N HCl. The product was extracted with EtOAc and the solvent removed under reduced pressure. The crude product was purified by column chromatography [silica gel 60-120 mesh, eluent: 10% EtOAc in petroleum ether] to afford 3-(5-(trifluoromethyl)-1,2,4-oxadiazol-3-yl)benzoic acid (400 mg, yield 28%): $^1$H NMR (400 MHz, CDCl$_3$) δ 13.44 (br s, 1H), 8.56 (s, 1H), 8.30 (d, J=7.9 Hz, 1H), 8.21 (d, J=7.9 Hz, 1H), 7.78 (t, J=7.8 Hz, 1H). MS (ESI) m/z: Calculated for C$_{10}$H$_5$F$_3$N$_2$O$_3$: 258.03. found: 257 (M−H)$^−$.

Step 6: N-((4-(4-Phenylthiazol-2-yl)tetrahydro-2H-pyran-4-yl)methyl)-3-(5-(trifluoromethyl)-1,2,4-oxadiazol-3-yl)benzamide

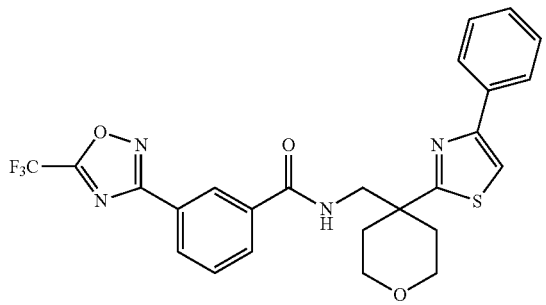 [SMILES: O=C(NCC1(c2nc(-c3ccccc3)cs2)CCOCC1)c1cccc(-c2noc(C(F)(F)F)n2)c1]

A mixture of 3-(5-(trifluoromethyl)-1,2,4-oxadiazol-3-yl)benzoic acid (52 mg, 0.202 mmole), (4-(4-phenylthiazol-2-yl)tetrahydro-2H-pyran-4-yl)methanamine (50 mg, 0.184 mmole), and EDCI (38.5 mg, 0.202 mmole) in $CH_2Cl_2$ (2 ml) was stirred at room temperature for 8 h. The reaction mixture was then diluted with methylene chloride (10 ml), washed with water (5 ml), dried over $MgSO_4$ and concentrated under reduced pressure. The residue was purified by ISCO (silica gel, elute: 2% methanol in $CH_2Cl_2$) to give N-((4-(4-phenylthiazol-2-yl)tetrahydro-2H-pyran-4-yl)methyl)-3-(5-(trifluoromethyl)-1,2,4-oxadiazol-3-yl)benzamide as a white solid product (59 mg, 62% yield): $^1$H NMR (CDCl$_3$, 500 MHz): 8.49 (s, 1H), 8.22 (d, J=7.5 Hz, 1H), 7.98 (d, J=8.5 Hz, 1H), 7.88 (d, J=8 Hz, 2H), 7.56-7.53 (m, 2H), 7.52 (s, 1H), 7.369-7.31 (m, 3H), 3.97-3.93 (m, 2H), 3.91 (d, J=5.5 Hz, 2H), 3.77-3.74 (m, 2H), 2.36-2.28 (m, 2H), 2.06-2.04 (m, 2H). MS (ESI) m/z: Calculated for $C_{25}H_{21}F_3N_4O_3S$: 514.13. found: 515.1 (M−H)$^+$.

Examples 2-6 were synthesized from 3-(5-(trifluoromethyl)-1,2,4-oxadiazol-3-yl)benzoic acid and readily available amines in a similar manner as part of a screening collection and characterized by LCMS and $^1$H NMR.

| Example No. | Compound Structure | Compound Name |
| --- | --- | --- |
| 2 | 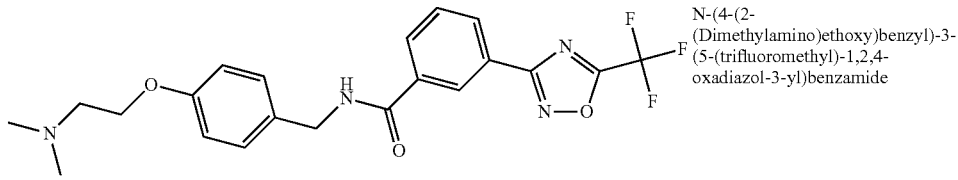 | N-(4-(2-(Dimethylamino)ethoxy)benzyl)-3-(5-(trifluoromethyl)-1,2,4-oxadiazol-3-yl)benzamide |
| 3 | 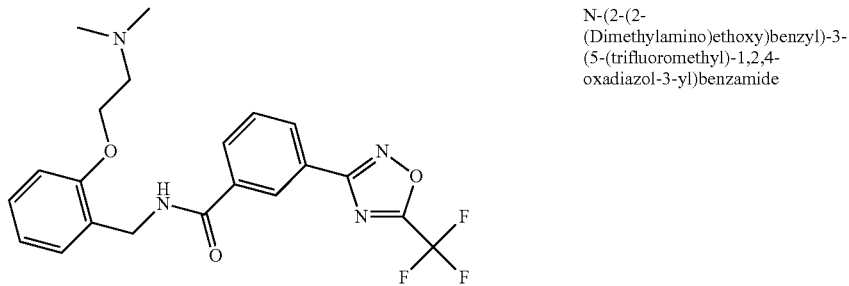 | N-(2-(2-(Dimethylamino)ethoxy)benzyl)-3-(5-(trifluoromethyl)-1,2,4-oxadiazol-3-yl)benzamide |
| 4 | 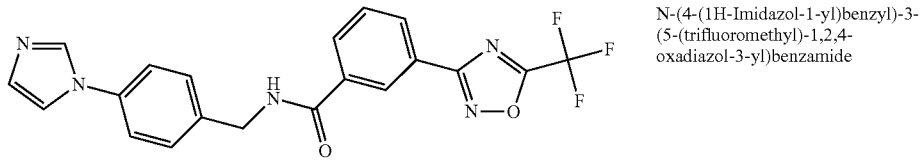 | N-(4-(1H-Imidazol-1-yl)benzyl)-3-(5-(trifluoromethyl)-1,2,4-oxadiazol-3-yl)benzamide |
| 5 | 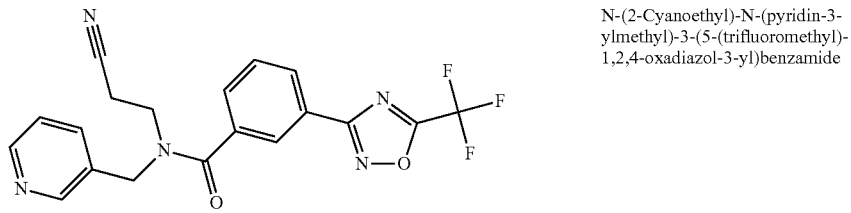 | N-(2-Cyanoethyl)-N-(pyridin-3-ylmethyl)-3-(5-(trifluoromethyl)-1,2,4-oxadiazol-3-yl)benzamide |

| Example No. | Compound Structure | Compound Name |
|---|---|---|
| 6 | 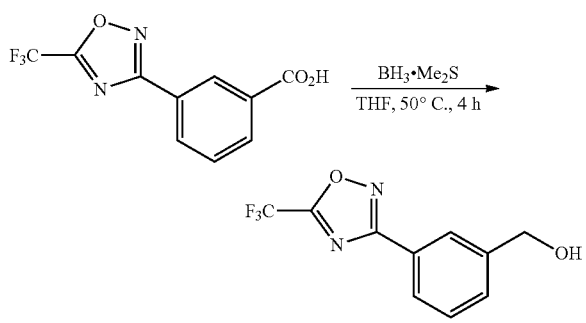 | 3-(5-(Trifluoromethyl)-1,2,4-oxadiazol-3-yl)-N-((4-(4-(trifluoromethyl)phenyl)tetrahydro-2H-pyran-4-yl)methyl)benzamide |

Example 7

(3-(5-(Trifluoromethyl)-1,2,4-oxadiazol-3-yl)phenyl)methanol

Borane dimethyl sulfide complex (0.3 mL, 2.9 mmol) was added to a stirred solution of 3-(5-(trifluoromethyl)-1,2,4-oxadiazol-3-yl)benzoic acid (0.5 g, 1.9 mmol) in dry THF (10 mL) at 0° C. The reaction mixture was slowly warmed to room temperature and further heated to 50° C. for 4 h. Reaction mixture was then carefully quenched with dry MeOH and concentrated under reduced pressure. The crude product was purified by column chromatography (silica 60-120 mesh, eluent 10-15% EtOAc in petroleum ether) to get pure alcohol compound (3-(5-(trifluoromethyl)-1,2,4-oxadiazol-3-yl)phenyl)methanol (190 mg, yield 41%): $^1$H NMR (400 MHz, CDCl$_3$) δ 8.14 (m, 1H), 8.06 (d, J=7.5 Hz, 1H), 7.61-7.51 (m, 2H), 4.81 (s, 2H)

3-(5-(Trifluoromethyl)-1,2,4-oxadiazol-3-yl)benzaldehyde

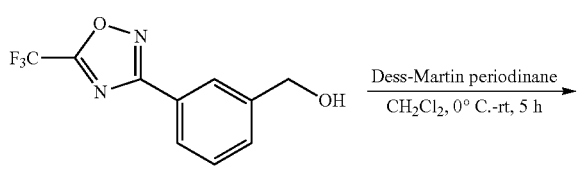

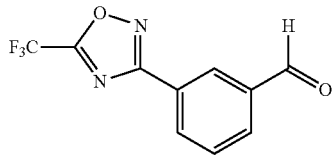

A solution of compound 3-(5-(trifluoromethyl)-1,2,4-oxadiazol-3-yl)phenyl)methanol (150 mg, 0.6 mmol) in dry CH$_2$Cl$_2$ (10 mL) was purged with argon for 10 min and Dess-Martin periodinane (0.39 g, 0.9 mmol) was added to the solution at 0° C. The reaction mixture was allowed to come to room temperature and stirred for 5 h. The reaction mixture was then quenched with saturated sodium thiosulfate solution and extracted with CH$_2$Cl$_2$. The organic layer was washed with brine and dried over anhydrous sodium sulfate. The solvent was concentrated under reduced pressure to yield 3-(5-(trifluoromethyl)-1,2,4-oxadiazol-3-yl)benzaldehyde (140 mg, crude) which was carried through without further purification. $^1$H NMR (400 MHz, CDCl$_3$) δ 10.13 (s, 1H), 8.64 (s, 1H), 8.41-8.39 (dt, J=7.8 Hz, 1.5 Hz, 1H), 8.13-8.11 (dt, J=7.8 Hz, 1.5 Hz, 1H), 7.76 (t, J=7.7 Hz, 1H).

1-(4-(4-Phenylthiazol-2-yl)tetrahydro-2H-pyran-4-yl)-N-(3-(5-(trifluoromethyl)-1,2,4-oxadiazol-3-yl)benzyl)methanamine -continued

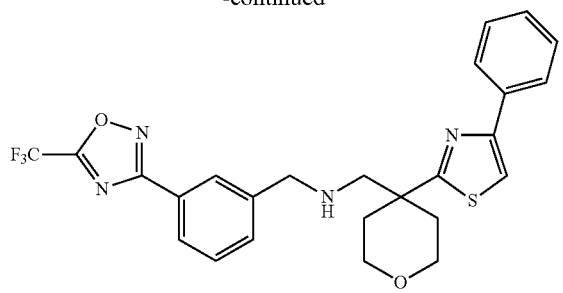

Sodium triacetoxy borohydride (200 mg, 0.9 mmol) was added to a solution of 3-(5-(trifluoromethyl)-1,2,4-oxadiazol-3-yl)benzaldehyde (140 mg, 0.6 mmol) and (4-(4-phenylthiazol-2-yl)tetrahydro-2H-pyran-4-yl)methanamine (170 mg, 0.6 mmol) in dry dichloroethane (20 mL) at 0° C. under nitrogen atmosphere and stirred at room temperature for 8 h. The reaction mixture was carefully quenched with 10% NaHCO$_3$ solution and extracted with EtOAc. The organic layer was washed with brine, dried over anhydrous Na$_2$SO$_4$ and concentrated under reduced pressure. The crude product was purified by column chromatography (silica 60-120 mesh, eluent 20-25% EtOAc in petroleum ether) to get 1-(4-(4-phenylthiazol-2-yl)tetrahydro-2H-pyran-4-yl)-N-(3-(5-(trifluoromethyl)-1,2,4-oxadiazol-3-yl)benzyl)methanamine (65 mg, yield 22%): $^1$H NMR (400 MHz, CDCl$_3$) δ 7.98 (m, 2H), 7.89 (d, J=7.6 Hz, 2H), 7.48 (s, 1H), 7.46-7.27 (m, 5H), 3.86-3.81 (m, 4H), 3.69-3.64 (m, 2H), 2.91 (s, 2H), 2.36 (m, 2H), 2.03-1.97 (ddd, J=13.7 Hz, 9.7 Hz, 4 Hz, 2H). MS (ESI) m/z: Calculated for C$_{25}$H$_{23}$F$_3$N$_4$O$_2$S: 500.15. found: 501.0 (M–H)$^-$.

Example 8

Methyl-5-bromonicotinate

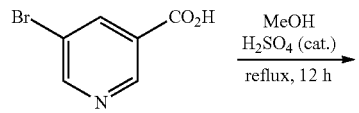

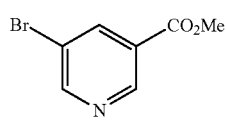

A solution of 5-bromonicotinic acid (10 g, 49.5 mmol) in MeOH (200 mL) was cooled to 0° C. and conc. H$_2$SO$_4$ (5 mL) was added dropwise. The reaction mixture was heated to reflux for 12 h. After completion, the reaction mixture was concentrated under reduced pressure, diluted with water and the aqueous layer was washed with EtOAc. The resulting mixture was poured over an aqueous saturated NaHCO$_3$ solution to adjust the pH 7-8, it was then extracted with EtOAc and the organic layer was dried over anhydrous Na$_2$SO$_4$. Solvent was evaporated under reduced pressure to get the solid product methyl 5-bromonicotinate as an off-white solid (7 g, yield 66%): $^1$H NMR (400 MHz, CDCl$_3$) δ 9.14 (s, 1H), 8.86 (s, 1H), 8.45 (s, 1H), 3.98 (s, 3H)

Methyl 5-cyanonicotinate

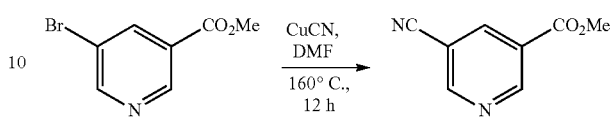

CuCN (5.22 g, 58.3 mmol) was added to a solution of methyl 5-bromonicotinate (6 g, 27.8 mmol) in dry DMF (150 mL). The solution was purged with argon and heated to 160° C. for 12 h under argon atmosphere. The reaction mixture was cooled to room temperature and then quenched with saturated NH$_4$Cl solution. Further EtOAc was added and the reaction mixture was stirred for 10 min. The reaction mixture was filtered through a Celite plug, the organic layer was separated, washed with water and brine, and dried over anhydrous Na$_2$SO$_4$. Solvent was evaporated under reduced pressure to get methyl-5-cyano-nicotinate as greenish-white solid (2.7 g, yield 60%): $^1$H NMR (300 MHz, DMSO-d$_6$) δ 9.29-9.27 (m, 2H), 8.77 (s, 1H), 3.91 (s, 3H)

3-Cyanonicotinic acid

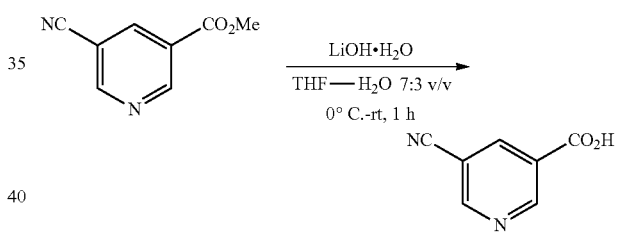

LiOH (150 mg, 6.2 mmol) was added to solution of methyl 5-cyanonicotinate (1 g, 6.17 mmol) in THF—H$_2$O (7:3 v/v, 50 mL) at 0° C. The reaction mixture was stirred at room temperature for 1 h. THF was then removed under reduced pressure and the reaction mixture was diluted with water and washed with EtOAc. The resulting reaction mixture was acidified with 1.5N HCl to pH 3-4. The mixture was extracted with EtOAc and the organic layer was dried over anhydrous Na$_2$SO$_4$. Solvent was evaporated under reduced pressure to get 3-cyanonicotinic acid as an off-white solid (0.7 g, yield 78%): $^1$H NMR (300 MHz, DMSO-d$_6$) δ 13.9 (br s, 1H), 9.27 (s, 1H), 9.23 (s, 2H), 8.71 (s, 1H). MS (ESI) m/z: Calculated for C$_7$H$_4$N$_2$O$_2$: 148.03. found: 147.0 (M–H)$^-$.

5-(N'-Hydroxycarbamimidoyl)nicotinic acid

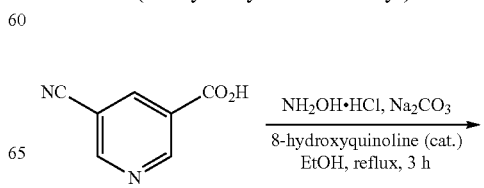

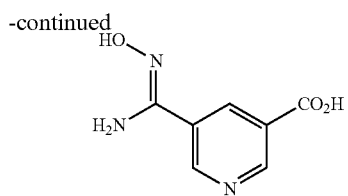

This compound was synthesized from 5-cyanonicotinic acid as described in example 1 step 4 (330 mg, yield 54%): $^1$H NMR (400 MHz, DMSO-$d_6$) δ 13.54 (br s, 1H), 9.98 (s, 1H), 9.16 (m, 2H), 8.49 (s, 1H), 6.11 (br s, 2H). MS (ESI) m/z: Calculated for $C_7H_7N_3O_3$: 181.05. found: 182.2 (M+H)$^+$.

6-(6-(Trifluoromethyl)-1,2,4-oxadiazol-3-yl)nicotinic acid

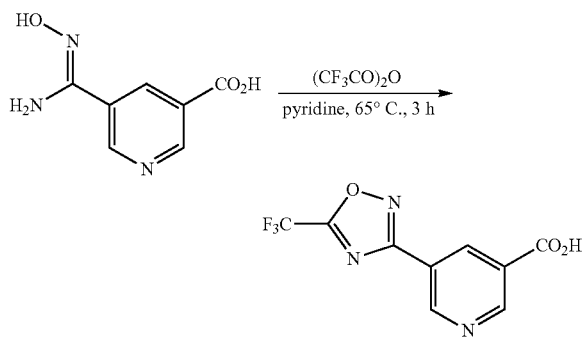

This compound was synthesized from 5-(N'-hydroxycarbamimidoyl)nicotinic acid as described in example 1 step 5 (260 mg, yield 63%). $^1$H NMR (400 MHz, DMSO-$d_6$) δ 13.93 (br s, 1H), 9.43 (d, J=2.1 Hz, 1H), 9.31 (d, J=2.1 Hz, 1H), 8.77 (t, J=2.1 Hz, 1H). MS (ESI) m/z: Calculated for $C_9H_4F_3N_3O_3$: 259.02. found: 258.0 (M−H)$^−$.

Step 6: N-((4-(4-Phenyithiazol-2-yl)tetrahydro-2H-pyran-4-yl)methyl)-6-(6-(trifluoromethyl)-1,2,4-oxadiazol-3-yl)nicotinamide To a stirred solution of compound 5-(5-(trifluoromethyl)-1,2,4-oxadiazol-3-yl)nicotinic acid (100 mg, 0.4 mmol) in dry DMF (5 mL) were added HATU (180 mg, 0.46 mmol) followed by hydrochloride salt of (4-(4-phenylthiazol-2-yl)tetrahydro-2H-pyran-4-yl)methanamine (120 mg, 0.4 mmol) and NMM (0.12 mL, 1.1 mmol) at 0° C. The reaction mixture was slowly warmed to room temperature and stirred for further 10 h. The reaction mixture was diluted with EtOAc. The organic layer was washed with water and brine solution, dried over anhydrous sodium sulfate, and concentrated under reduced pressure. The crude product was purified by column chromatography (silica 60-120 mesh, eluent 50-60% EtOAc in petroleum ether) to get pure product N-((4-(4-phenylthiazol-2-yl)tetrahydro-2H-pyran-4-yl)methyl)-5-(5-(trifluoromethyl)-1,2,4-oxadiazol-3-yl)nicotinamide (70 mg, yield 37%): $^1$H NMR (400 MHz, CDCl$_3$) δ 9.43 (d, J=2 Hz, 1H), 9.21 (br s, 1H), 8.76 (br s, 1H), 7.87 (d, J=7 Hz, 2H), 7.75 (br s, 1H), 7.53 (s, 1H), 7.41-7.32 (m, 3H), 3.99-3.95 (m, 2H), 3.79-3.74 (m, 2H), 2.35-2.32 (m, 2H), 2.07-2.03 (m, 2H). MS (ESI) m/z: Calculated for $C_{24}H_{20}F_3N_5O_3S$: 515.12. found: 516.0 (M+H)$^+$.

Example 9

5-((4-Phenyithiophen-2-yl)methylene)-2-thioxothiazolidin-4-one

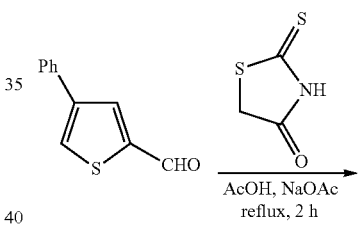

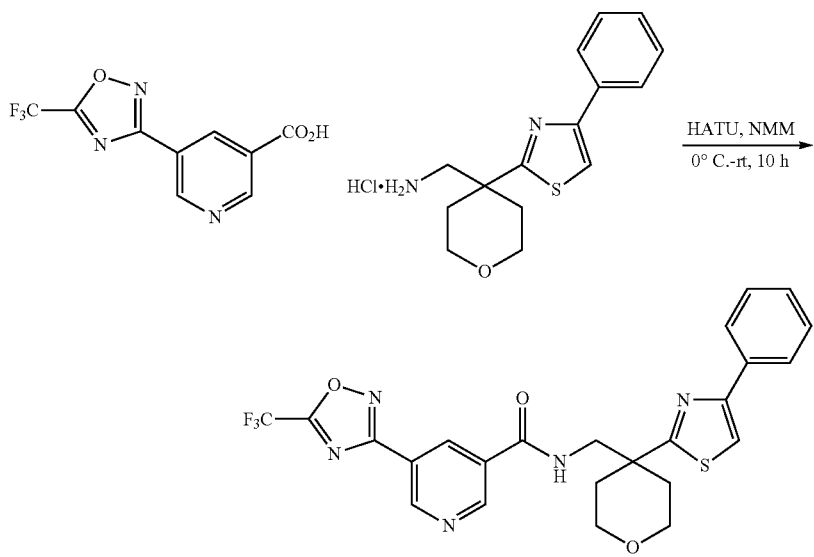

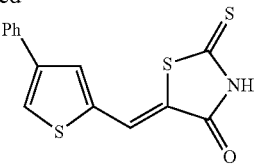

A solution of 4-phenyl thiophene-2-carboxaldehyde (1 g, 5.3 mmol) and rhodanine (700 mg, 5.3 mmol) in 10 mL of glacial acetic acid was heated with anhydrous sodium acetate (1.22 g, 14.8 mmol) for 2 h. The reaction mixture was then poured into cold water. The precipitate was filtered, washed with water and dried under reduced pressure to get 5-((4-phenylthiophen-2-yl)methylene)-2-thioxothiazolidin-4-one (1.4 g, yield 87%). MS (ESI) m/z: Calculated for $C_{14}H_9NOS_3$: 302.98. found: 302.0 (M−H)⁻. The crude product was carried through without further purification.

3-(4-Phenylthiophen-2-yl)-2-thioxopropanoic acid

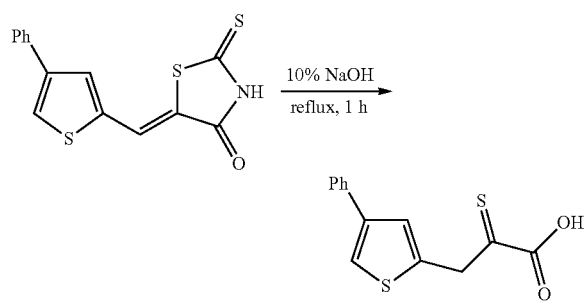

A suspension of product 5-((4-phenylthiophen-2-yl)methylene)-2-thioxothiazolidin-4-one (1.4 g, 4.6 mmol) in 12 mL of 10% aqueous NaOH was heated to 95° C. for 1 h. The solution was cooled to room temperature and diluted with water. The aqueous phase was washed with EtOAc, and acidified with 10% HCl. The precipitate that was formed was filtered, washed with water and dried under reduced pressure to get the product 3-(4-phenylthiophen-2-yl)-2-thioxopropanoic acid (0.9 g, yield 74%). MS (ESI) m/z: Calculated for $C_{13}H_{10}O_2S_2$: 262.01. found: 261.0 (M−H)⁻. The crude product was carried through without further purification 2-(Hydroxyimino)-3-(4-phenylthiophen-2-yl)propanoic acid

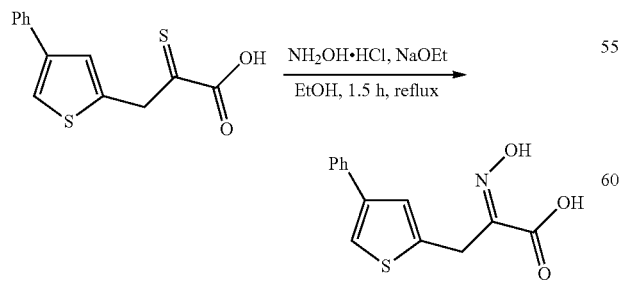

3-(4-Phenylthiophen-2-yl)-2-thioxopropanoic acid (0.9 g, 3.4 mmol), hydroxylamine hydrochloride (740 mg, 10.6 mmol), and an ethanolic solution sodium ethoxide [prepared from 0.4 g of sodium and 30 mL of absolute ethanol] was refluxed for 1.5 h. Solvent was removed under reduced pressure and the residue was diluted with water and acidified with 1.5N HCl to adjust the pH of the solution ~3. The solid product was extracted with EtOAc. The organic layer was dried over anhydrous Na₂SO₄, then removal of the solvent under reduced pressure yielded 2-(hydroxyimino)-3-(4-phenylthiophen-2-yl)propanoic acid (0.8 g, yield 89%) as an off-white solid. ¹H NMR (400 MHz, MeOD) δ 7.59-7.57 (m, 2H), 7.37-7.33 (m, 3H), 7.24-7.23 (m, 2H), 3.31 (s, 2H). MS (ESI) m/z: Calculated for $C_{13}H_{11}NO_3S$: 262.05. found: 262.0 (M+H)⁺.

2-(4-Phenylthiophen-2-yl)acetonitrile

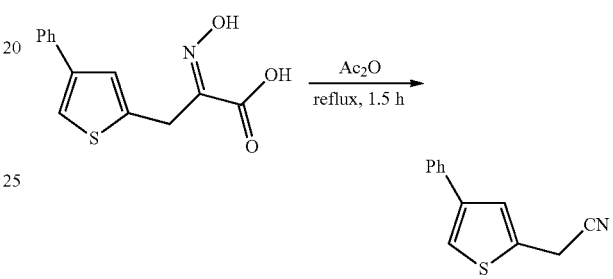

2-(Hydroxyimino)-3-(4-phenylthiophen-2-yl)propanoic acid (0.8 g, 3.1 mmol) was heated in acetic anhydride (5 mL) for 1.5 h. The reaction mixture was cooled to room temperature and treated with water. The product was extracted with EtOAc and the organic layer was washed with H₂O and brine, dried over anhydrous Na₂SO₄ and concentrated under reduced pressure. The residue was purified by column chromatography (silica gel 60-120 mesh, eluent 10-15% EtOAc in petroleum ether) to afford 2-(4-phenylthiophen-2-yl)acetonitrile (0.45 g, yield 73%) as a pale yellow solid. ¹H NMR (400 MHz, CDCl₃) δ 7.57-7.53 (m, 2H), 7.43-7.39 (m, 2H), 7.37-7.36 (m, 2H), 7.34-7.30 (m, 1H), 3.96 (s, 2H).

4-(4-Phenylthiophen-2-yl)tetrahydro-2H-pyran-4-carbonitrile

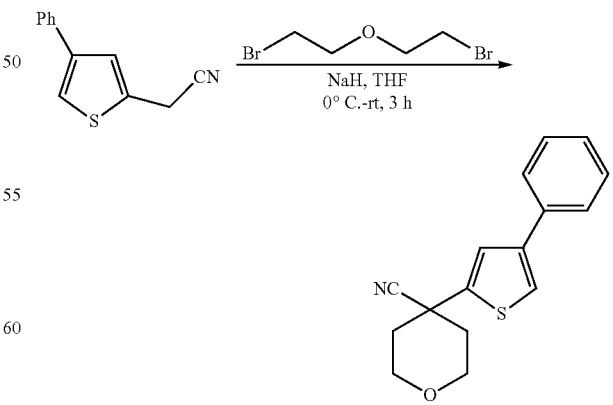

This compound was synthesized from 2-(4-phenylthiophen-2-yl)acetonitrile as described in example 1 step 2 (0.32 g, yield 68%) as a yellow solid. ¹H NMR (400 MHz, CDCl$_3$) δ 7.59-7.57 (dd, J=8.2 Hz, 1.1 Hz, 2H), 7.45-7.40 (m, 4H), 7.35-7.31 (m, 1H), 4.11-4.07 (m, 2H), 3.93-3.86 (td, J=12 Hz, 2.4 Hz, 2H), 2.29-2.15 (m, 4H).

(4-(4-Phenylthiophen-2-yl)tetrahydro-2H-pyran-4-yl)methanamine

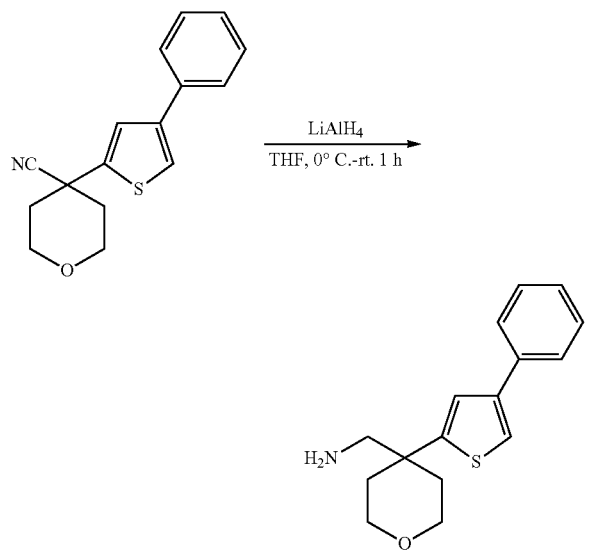 [SMILES: N#CC1(c2cc(-c3ccccc3)cs2)CCOCC1 ; "LiAlH4" ; NCC1(c2cc(-c3ccccc3)cs2)CCOCC1]

This compound was synthesized from 4-(4-phenylthiophen-2-yl)tetrahydro-2H-pyran-4-carbonitrile as described in example 1 step 3 (210 mg, yield 65%). $^1$H NMR (400 MHz, CDCl$_3$) δ 7.61-7.59 (d, J=7.3 Hz, 2H), 7.43-7.30 (m, 4H), 7.19-7.18 (d, J=1 Hz, 1H), 3.86-3.82 (m, 2H), 3.62-3.57 (m, 2H), 2.69 (br s, 2H), 2.11-1.96 (m, 2H), 1.81-1.74 (m, 2H). MS (ESI) m/z: Calculated for C$_{16}$H$_{19}$NOS: 273.12. found: 274.2 (M+H)$^+$.

N-((4-(4-Phenylthiophen-2-yl)tetrahydro-2H-pyran-4-yl)methyl)-3-(5-(trifluoromethyl)-1,2,4-oxadiazol-3-yl)benzamide

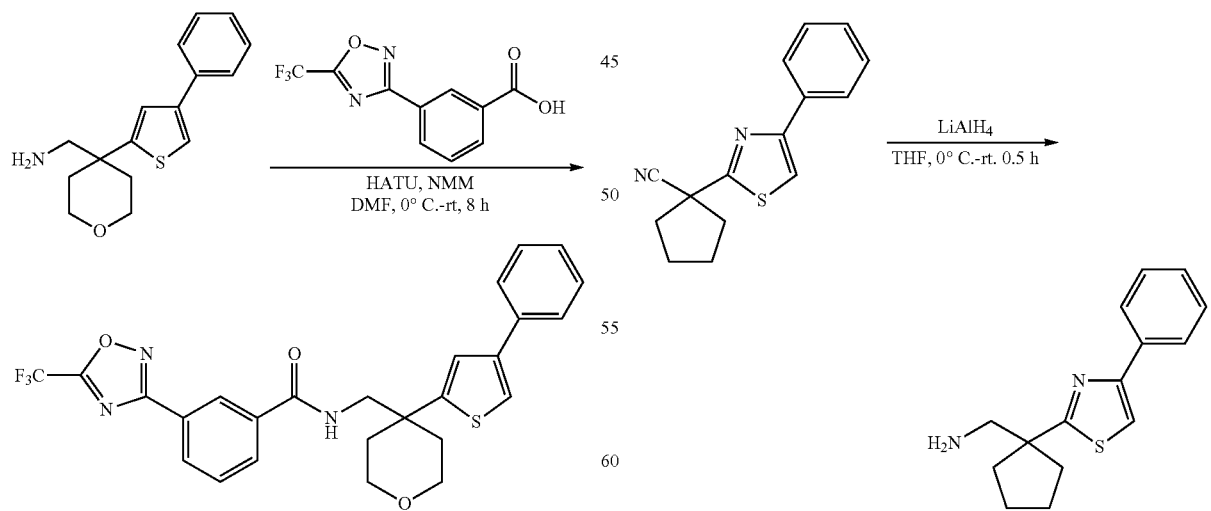

This compound was synthesized from (4-(4-phenylthiophen-2-yl)tetrahydro-2H-pyran-4-yl)methanamine and 3-(5-(trifluoromethyl)-1,2,4-oxadiazol-3-yl)benzoic acid as described in example 8 step 6 (80 mg, yield 20%). $^1$H NMR (400 MHz, CDCl$_3$) δ 8.43 (m, 1H), 8.25 (d, J=7.8 Hz, 1H), 7.96 (d, J=7.8 Hz, 1H), 7.62-7.58 (m, 3H), 7.45 (d, J=1.2 Hz, 1H), 7.40 (t, J=7.7 Hz, 2H), 7.31 (m, 1H), 7.23 (d, J=1.5 Hz, 1H), 6.15 (t, J=6.5 Hz, 1H), 3.96-3.91 (dt, J=11.9 Hz, 4.2 Hz, 2H), 3.74 (d, J=6.4 Hz, 2H), 3.71-3.66 (m, 2H), 2.18-2.14 (m, 2H), 2.08-2.03 (m, 2H). MS (ESI) m/z: Calculated for C$_{26}$H$_{22}$F$_3$N$_3$O$_3$S: 513.13. found: 514.2 (M+H)$^+$.

Example 10

1-(4-Phenylthiazol-2-yl)cyclopentanecarbonitrile

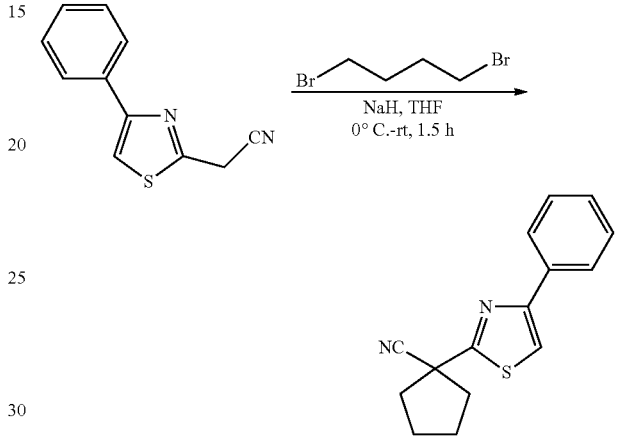

This compound was synthesized from 2-(4-phenylthiazol-2-yl)acetonitrile as described in example 1 step 2 using 1,4-dibromobutane (580 mg, yield 91%). $^1$H NMR (300 MHz, CDCl$_3$) δ 7.93-7.92 (m, 2H), 7.90-7.33 (m, 4H), 2.58-2.49 (m, 4H), 2.06-2.00 (m, 4H). MS (ESI) m/z: Calculated for C$_{16}$H$_{14}$N$_2$S: 254.09. found: 255.2 (M+H)$^+$.

(1-(4-Phenylthiazol-2-yl)cyclopentyl)methanamine

This compound was synthesized from 1-(4-phenylthiazol-2-yl)cyclopentanecarbonitrile as described in example 1 step 3 (250 mg, yield 42%). $^1$H NMR (400 MHz, DMSO-d$_6$) δ 7.96-7.93 (m, 3H), 7.44-7.40 (m, 2H), 7.33-7.29 (m, 1H), 2.85 (s, 2H), 2.06-3.01 (m, 2H), 1.94-1.87 (m, 2H), 1.73-1.66 (m, 6H). MS (ESI) m/z: Calculated for $C_{15}H_{18}N_2S$: 258.12. found: 259.2 (M+H)+.

N-((1-(4-Phenylthiazol-2-yl)cyclopentyl)methyl)-3-(5-(trifluoromethyl)-1,2,4-oxadiazol-3-yl)benzamide

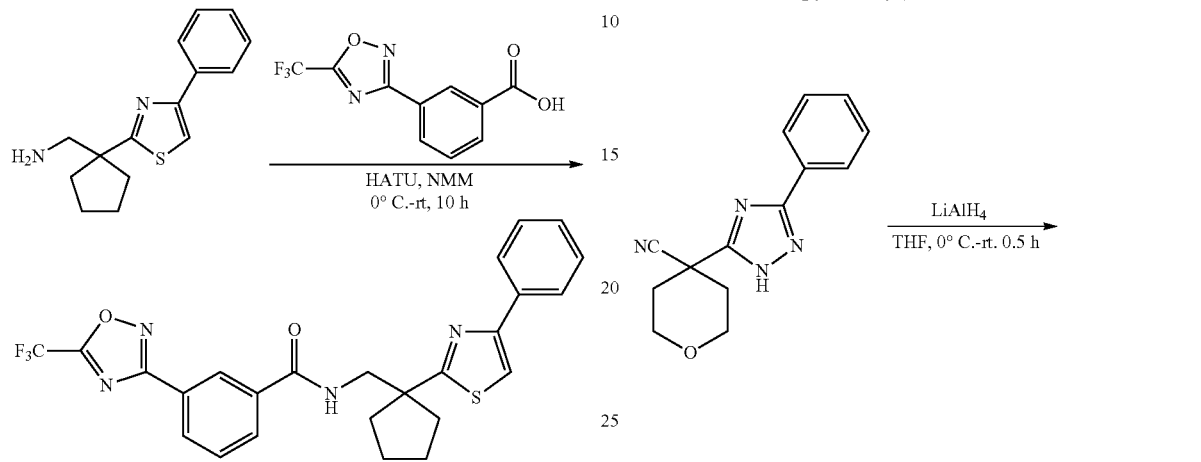

This compound was synthesized from (1-(4-phenylthiazol-2-yl)cyclopentyl)methanamine and 3-(5-(trifluoromethyl)-1, 2,4-oxadiazol-3-yl)benzoic acid as described in example 8 step 6 (65 mg, yield 34%). $^1$H NMR (400 MHz, DMSO-d$_6$) 8.78 (m, 1H), 8.44 (s, 1H), 8.19 (d, J=7.6 Hz, 1H), 8.06 (d, J=7.9 Hz, 1H), 7.98 (s, 1H), 7.93 (d, J=7.3 Hz, 2H), 7.71 (t, J=7.9 Hz, 1H), 7.39 (m, 2H), 7.30 (m, 1H), 3.69 (d, J=6.2 Hz, 2H), 2.19 (m, 2H), 2.07 (m, 2H), 1.76 (m, 2H), 1.64 (m, 2H). MS (ESI) m/z: Calculated for $C_{25}H_{21}F_3N_4O_2S$: 498.13. found: 499.2 (M+H)+.

Example 11

4-(3-Phenyl-1H-1,2,4-triazol-5-yl)tetrahydro-2H-pyran-4-carbonitrile

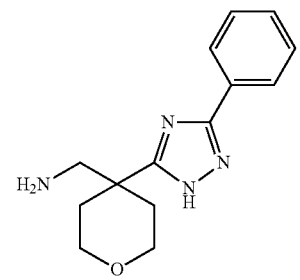

This compound was synthesized from (5-phenyl-2H-[1,2,4]triazol-3-yl)-acetonitrile as described in example 1 step 2 (0.22 g, yield 16%). $^1$H NMR (300 MHz, CDCl$_3$) δ 7.96-7.92 (dd, J=6.6 Hz, 3.1 Hz, 2H), 7.54-7.49 (m, 3H), 4.09-4.03 (dt, J=12.1 Hz, 3.7 Hz, 2H), 3.95-3.87 (m, 2H), 2.44-2.38 (m, 2H), 2.29-2.25 (m, 2H). MS (ESI) m/z: Calculated for $C_{14}H_{14}N_4O$: 254.12. found: 255.2 (M+H)+.

(4-(3-Phenyl-1H-1,2,4-triazol-5-yl)tetrahydro-2H-pyran-4-yl)methanamine

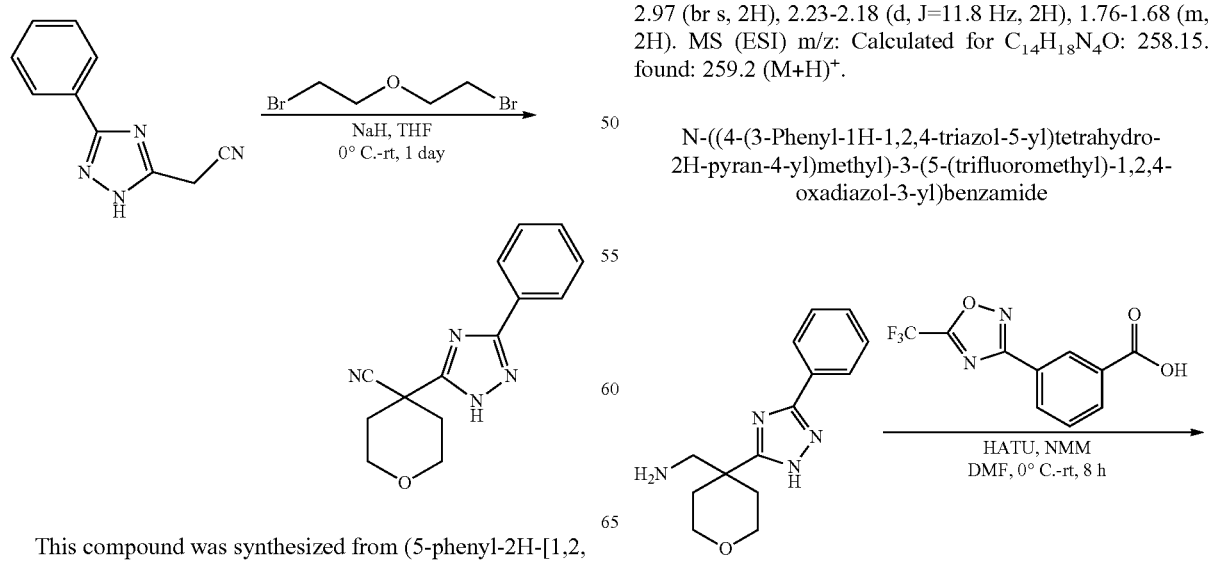

This compound was synthesized from 4-(3-phenyl-1H-1, 2,4-triazol-5-yl)tetrahydro-2H-pyran-4-carbonitrile as described in example 1 step 3 (170 mg, crude). $^1$H NMR (300 MHz, DMSO-d$_6$) δ 8.05-8.02 (dd, J=8.0 Hz, 1.4 Hz, 2H), 7.51-7.40 (m, 3H), 3.76-3.72 (m, 2H), 3.42-3.38 (m, 2H), 2.97 (br s, 2H), 2.23-2.18 (d, J=11.8 Hz, 2H), 1.76-1.68 (m, 2H). MS (ESI) m/z: Calculated for $C_{14}H_{18}N_4O$: 258.15. found: 259.2 (M+H)+.

N-((4-(3-Phenyl-1H-1,2,4-triazol-5-yl)tetrahydro-2H-pyran-4-yl)methyl)-3-(5-(trifluoromethyl)-1,2,4-oxadiazol-3-yl)benzamide

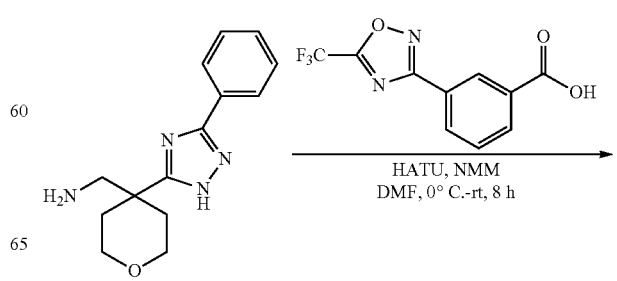

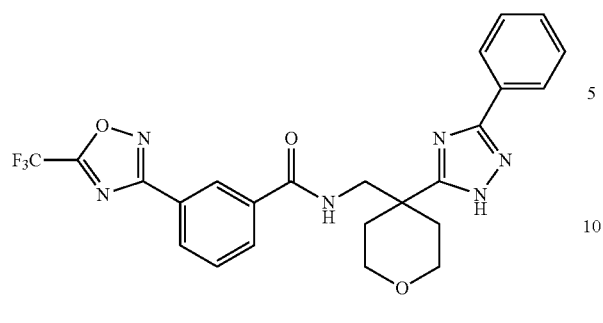

This compound was synthesized from (4-(3-phenyl-1H-1,2,4-triazol-5-yl)tetrahydro-2H-pyran-4-yl)methanamine and 3-(5-(trifluoromethyl)-1,2,4-oxadiazol-3-yl)benzoic acid as described in example 8 step 6 (80 mg, yield 24%). $^1$H NMR (400 MHz, CDCl$_3$) δ 8.56 (s, 1H), 8.25 (d, J=7.8 Hz, 1H), 8.11 (d, J=7.8 Hz, 1H), 8.02 (dd, J=7.3 Hz, 1.8 Hz, 2H), 7.89 (br s, 1H), 7.62 (t, J=7.8 Hz, 1H), 7.46 (m, 3H), 3.97-3.92 (dt, J=11.9 Hz, 4.5 Hz, 2H), 3.83 (d, J=5.8 Hz, 2H), 3.71-3.66 (m, 2H), 2.44-2.42 (d, J=13.6 Hz, 2H), 1.96-1.89 (ddd, J=13.4 Hz, 9.2 Hz, 3.5 Hz, 2H). MS (ESI) m/z: Calculated for C$_{24}$H$_{21}$F$_3$N$_6$O$_3$: 498.16. found: 499.2 (M+H)$^+$.

Example 12

4-(2-Phenylthiazol-4-yl)tetrahydro-2H-pyran-4-carbonitrile

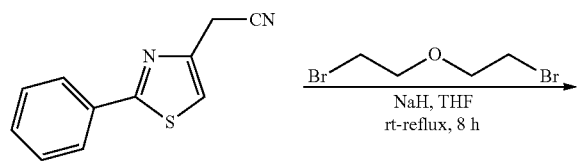

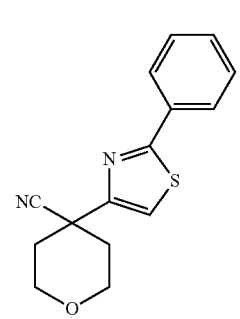

This compound was synthesized from (2-phenyl-thiazol-4-yl)-acetonitrile as described in example 1 step 2 (0.53 g, yield 79%) as a yellow solid. $^1$H NMR (300 MHz, CDCl$_3$) δ 7.98-7.94 (dd, J=6.5 Hz, 3.2 Hz, 2H), 7.47-7.43 (m, 3H), 7.33 (s, 1H), 4.12-4.08 (ddd, J=12.3 Hz, 3.9 Hz, 1.5 Hz, 2H), 3.93-3.85 (td, J=12.3 Hz, 2.1 Hz, 2H), 2.49-2.38 (ddd, J=13.7 Hz, 12.3 Hz, 4.5 Hz, 2H), 2.18-2.13 (dd, J=13.6 Hz, 2.0 Hz, 2H). MS (ESI) m/z: Calculated for C$_{15}$H$_{14}$N$_2$OS: 270.08. found: 271.2 (M+H)$^+$.

(4-(2-Phenylthiazol-4-yl)tetrahydro-2H-pyran-4-yl)methanamine

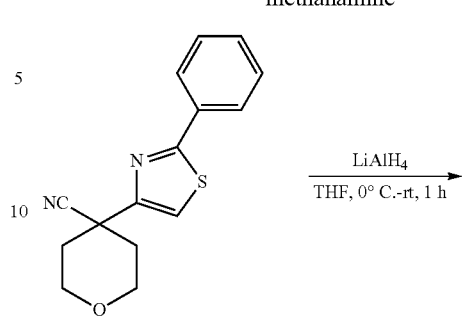

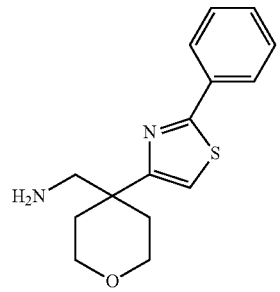

This compound was synthesized from 4-(2-phenylthiazol-4-yl)tetrahydro-2H-pyran-4-carbonitrile as described in example 1 step 3 (380 mg, yield 72%). $^1$H NMR (400 MHz, CDCl$_3$) δ 7.96-7.94 (dd, J=7.5 Hz, 2.0 Hz, 2H), 7.47-7.41 (m, 3H), 6.99 (s, 1H), 3.89-3.84 (dt, J=11.7 Hz, 4.0 Hz, 2H), 3.58-3.52 (m, 2H), 2.91 (s, 2H), 2.31-2.28 (d, J=13.8 Hz, 2H), 1.87-1.80 (ddd, J=13.9 Hz, 10.2 Hz, 4.3 Hz, 2H). MS (ESI) m/z: Calculated for C$_{15}$H$_{18}$N$_2$OS: 274.11. found: 275.2 (M+H)$^+$.

N-((4-(2-Phenylthiazol-4-yl)tetrahydro-2H-pyran-4-yl)methyl)-3-(5-(trifluoromethyl)-1,2,4-oxadiazol-3-yl)benzamide

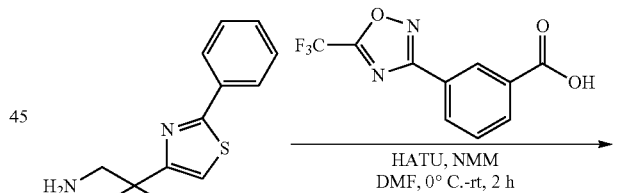

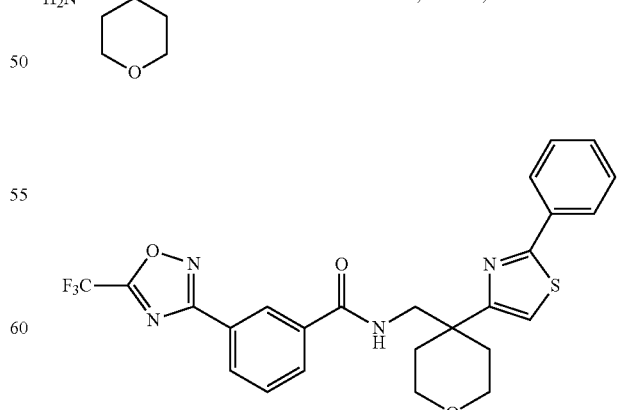

This compound was synthesized from (4-(2-phenylthiazol-4-yl)tetrahydro-2H-pyran-4-yl)methanamine and 3-(5-(trifluoromethyl)-1,2,4-oxadiazol-3-yl)benzoic acid as described in example 8 step 6 (85 mg, yield 45%). $^1$H NMR (400 MHz, DMSO-d$_6$) δ 8.56 (t, J=6.2 Hz, 1H), 8.41 (m, 1H), 8.18 (d, J=7.8 Hz, 1H), 8.05 (d, J=7.6 Hz, 1H), 7.91-7.89 (m, 2H), 7.69-7.65 (t, J=7.8 Hz, 1H), 7.53 (s, 1H), 7.46-7.43 (dd, J=4.8 Hz, 1.9 Hz, 3H), 3.79-3.76 (m, 2H), 3.54-3.52 (d, J=6.2 Hz, 2H), 3.37 (m, 2H), 2.26-2.22 (d, J=13.8 Hz, 2H), 1.89-1.84 (m, 2H). MS (ESI) m/z: Calculated for C$_{24}$H$_{21}$F$_3$N$_4$O$_3$S: 514.13. found: 515.0 (M+H)$^+$.

Example 13

2-(4-(4-Methoxyphenyl)thiazol-2-yl)acetonitrile

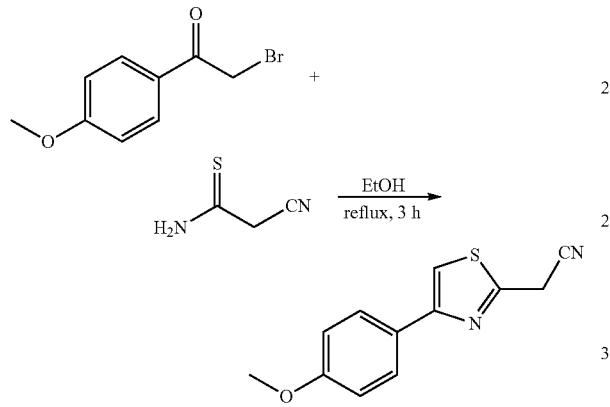

This compound was synthesized from 2-bromo-1-(4-methoxyphenyl)ethanone and 2-cyanothioacetamide as described in example 1 step 1 (1.5 g, yield 75%). $^1$H NMR (300 MHz, CDCl$_3$) δ 7.83 (d, J=8.9 Hz, 2H), 7.35 (s, 1H), 6.98 (d, J=8.9 Hz, 2H), 4.17 (s, 2H), 3.86 (s, 3H). MS (ESI) m/z: Calculated for C$_{12}$H$_{10}$N$_2$OS: 230.05. found: 231.2 (M+H)$^+$.

4-(4-(4-Methoxyphenyl)thiazol-2-yl)tetrahydro-2H-pyran-4-carbonitrile

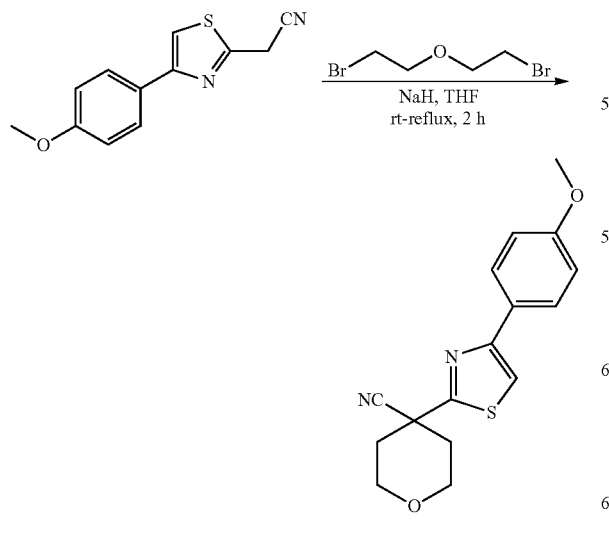

This compound was synthesized from 2-(4-(4-methoxyphenyl)thiazol-2-yl)acetonitrile as described in example 1 step 2 (1.6 g, yield 82%). $^1$H NMR (400 MHz, CDCl$_3$) δ 7.86 (d, J=8.8 Hz, 2H), 7.36 (s, 1H), 6.97 (d, J=8.8 Hz, 2H), 4.11-4.07 (m, 2H), 3.96-3.87 (dd, J=11.3 Hz, 2.5 Hz, 2H), 3.86 (s, 3H), 2.41-2.31 (m, 4H). MS (ESI) m/z: Calculated for C$_{16}$H$_{16}$N$_2$O$_2$S: 300.09. found: 301.2 (M+H)$^+$.

(4-(4-(4-Methoxyphenyl)thiazol-2-yl)tetrahydro-2H-pyran-4-yl)methanamine

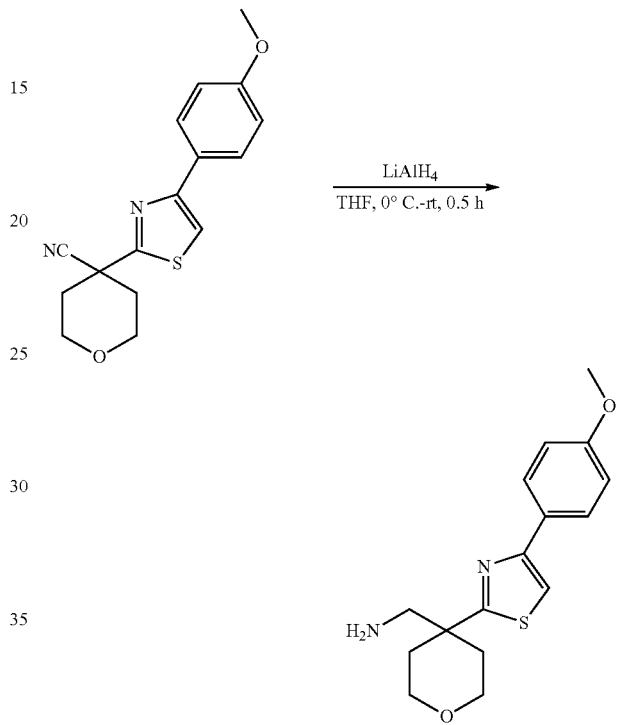

This compound was synthesized from 4-(4-(4-methoxyphenyl)thiazol-2-yl)tetrahydro-2H-pyran-4-carbonitrile as described in example 1 step 3 (200 mg, yield 40%). $^1$H NMR (300 MHz, CDCl$_3$) δ 7.86 (d, J=8.8 Hz, 2H), 7.33 (s, 1H), 6.97 (d, J=8.8 Hz, 2H), 3.93-3.88 (m, 5H), 3.68-3.59 (m, 2H), 2.97 (s, 2H), 2.33 (m, 2H), 1.94-1.86 (m, 2H). MS (ESI) m/z: Calculated for C$_{16}$H$_{20}$N$_2$O$_2$S: 304.12. found: 305.2 (M+H)$^+$.

N-((4-(4-(4-Methoxyphenyl)thiazol-2-yl)tetrahydro-2H-pyran-4-yl)methyl)-3-(5-(trifluoromethyl)-1,2,4-oxadiazol-3-yl)benzamide

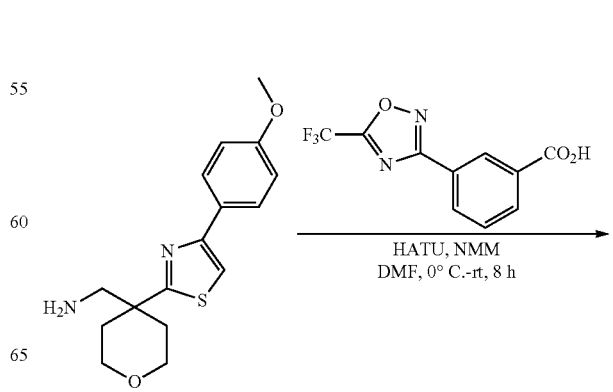

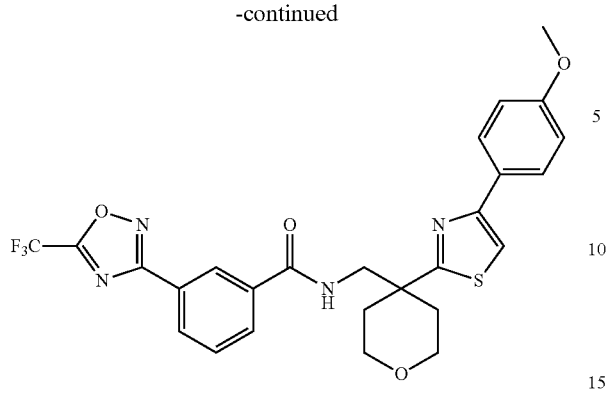

This compound was synthesized from (4-(4-(4-methoxyphenyl)thiazol-2-yl)tetrahydro-2H-pyran-4-yl)methanamine and 3-(5-(trifluoromethyl)-1,2,4-oxadiazol-3-yl)benzoic acid as described in example 8 step 6 (80 mg, yield 38%). $^1$H NMR (400 MHz, DMSO-d$_6$) δ 8.78 (t, J=6.3 Hz, 1H), 8.43 (s, 1H), 8.20 (d, J=7.9 Hz, 1H), 8.07 (d, J=7.9 Hz, 1H), 7.91 (s, 1H), 7.86 (d, J=8.9 Hz, 2H), 7.71 (t, J=7.8 Hz, 1H), 6.95 (d, J=8.5 Hz, 2H), 3.86 (m, 2H), 3.77 (s, 3H), 3.58 (d, J=6.4 Hz, 2H), 3.43 (t, J=10.5 Hz, 2H), 3.33 (s, 2H), 2.25 (d, J=14 Hz, 2H), 2.02 (m, 2H). MS (ESI) m/z: Calculated for C$_{26}$H$_{23}$F$_3$N$_4$O$_4$S: 544.14. found: 545.2 (M+H)$^+$.

Example 14

2-(4-(4-Chlorophenyl)thiazol-2-yl)acetonitrile

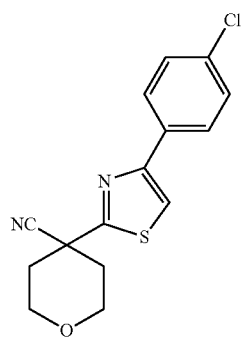

This compound was synthesized from 2-(4-(4-chlorophenyl)thiazol-2-yl)acetonitrile as described in example 1 step 2 (1.15 g, yield 86%). $^1$H NMR (300 MHz, CDCl$_3$) δ 7.88 (d, J=8.6 Hz, 2H), 7.50 (s, 1H), 7.43 (d, J=8.6 Hz, 2H), 4.14-4.07 (dt, J=12.3 Hz, 3.4 Hz, 2H), 3.95-3.86 (m, 2H), 2.45-2.30 (m, 4H). MS (ESI) m/z: Calculated for C$_{15}$H$_{13}$ClN$_2$OS: 304.04. found: 305.0 (M+H)$^+$.

(4-(4-(4-Chlorophenyl)thiazol-2-yl)tetrahydro-2H-pyran-4-yl)methanamine

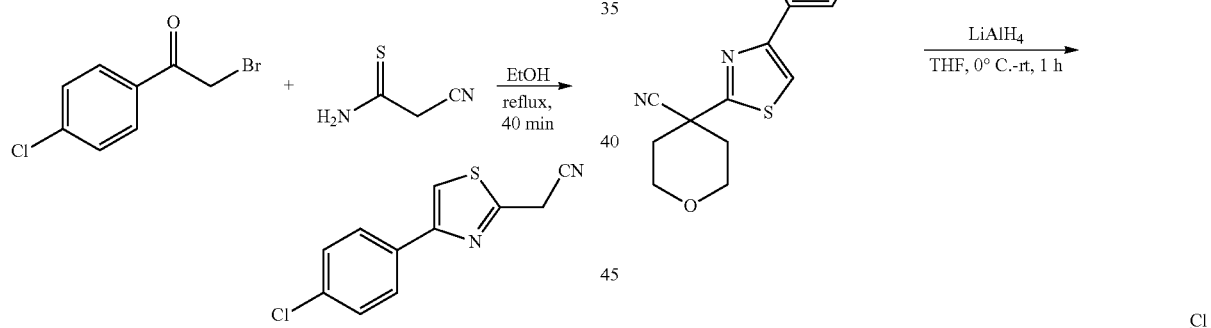

This compound was synthesized from 2-bromo-1-(4-chlorophenyl)ethanone and 2-cyanothioacetamide as described in example 1 step 1 (1.51 g, yield 75%). $^1$H NMR (300 MHz, CDCl$_3$) δ 7.84 (d, J=8.8 Hz, 2H), 7.49 (s, 1H), 7.43 (d, J=8.8 Hz, 2H), 4.18 (s, 2H). MS (ESI) m/z: Calculated for C$_{11}$H$_7$ClN$_2$S: 234.00. found: 235.0 (M+H)$^+$.

4-(4-(4-Chlorophenyl)thiazol-2-yl)tetrahydro-2H-pyran-4-carbonitrile

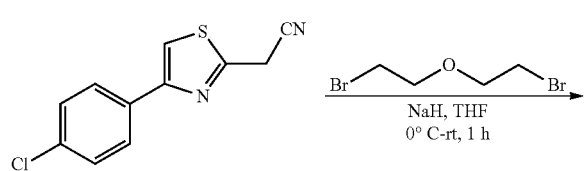

This compound was synthesized 4-(4-(4-chlorophenyl)thiazol-2-yl)tetrahydro-2H-pyran-4-carbonitrile as described in example 1 step 3 (250 mg, yield 50%). $^1$H NMR (400 MHz, DMSO-d$_6$) δ 8.14 (s, 1H), 7.99 (d, J=8.5 Hz, 2H), 7.52 (d, J=8.5 Hz, 2H), 3.79-3.75 (m, 2H), 3.47-3.42 (m, 2H), 2.81 (s, 2H), 2.13 (d, J=13.7 Hz, 2H), 1.91-1.83 (m, 2H). MS (ESI) m/z: Calculated for C$_{15}$H$_{17}$ClN$_2$OS: 308.08. found: 309.2 (M+H)$^+$.

N-((4-(4-(4-Chlorophenyl)thiazol-2-yl)tetrahydro-2H-pyran-4-yl)methyl)-3-(5-(trifluoromethyl)-1,2,4-oxadiazol-3-yl)benzamide

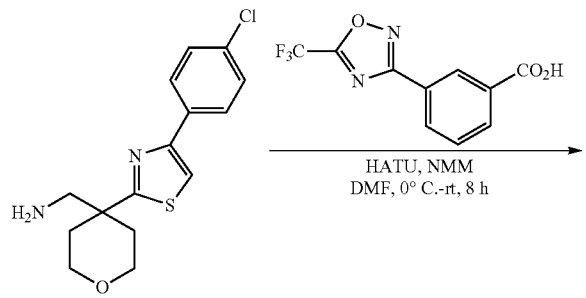

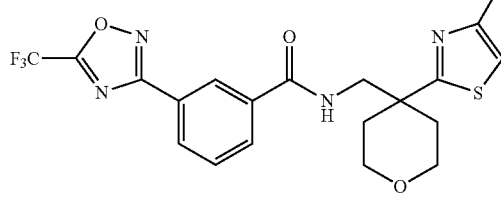

This compound was synthesized (4-(4-(4-chlorophenyl)thiazol-2-yl)tetrahydro-2H-pyran-4-yl)methanamine and 3-(5-(trifluoromethyl)-1,2,4-oxadiazol-3-yl)benzoic acid as described in example 8 step 6 (75 mg, yield 42%). $^1$H NMR (400 MHz, CDCl$_3$) δ 8.47 (s, 1H), 8.26 (d, J=7.8 Hz, 1H), 7.99 (d, J=9 Hz, 1H), 7.83 (m, 2H), 7.59 (t, J=7.8 Hz, 1H), 7.52 (s, 1H), 7.42 (t, J=5.4 Hz, 1H), 7.35 (d, J=8.5 Hz, 2H), 3.99-3.94 (m, 2H), 3.58 (d, J=5.8 Hz, 2H), 3.77-3.71 (m, 2H), 2.35-2.29 (m, 2H), 2.08-2.05 (m, 2H). MS (ESI) m/z: Calculated for C$_{26}$H$_{20}$ClF$_3$N$_4$O$_3$S: 548.09. found: 549.0 (M+H)$^+$.

Example 15

2-Methyl-2-(4-phenylthiazol-2-yl)propanenitrile

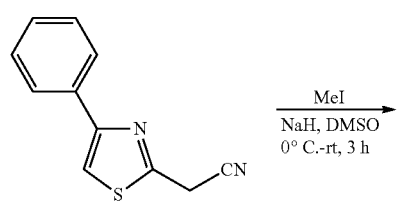

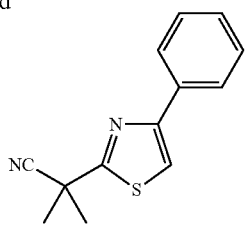

This compound was synthesized from 2-(4-phenylthiazol-2-yl)acetonitrile as described in example 1 step 2 using iodomethane (250 mg, crude). $^1$H NMR (300 MHz, CDCl$_3$) δ 7.94-7.91 (m, 2H), 7.47 (s, 1H), 7.46-7.36 (m, 3H), 1.93 (s, 6H).

2-Methyl-2-(4-phenylthiazol-2-yl)propan-1-amine

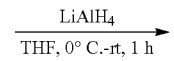

This compound was synthesized from 2-methyl-2-(4-phenylthiazol-2-yl)propanenitrile as described in example 1 step 3 (100 mg, yield 45%). $^1$H NMR (400 MHz, DMSO-d$_6$) δ 7.95-7.93 (m, 3H), 7.44-7.40 (t, J=7.3 Hz, 2H), 7.33-7.31 (m, 1H), 2.81 (s, 2H), 1.35 (s, 6H). MS (ESI) m/z: Calculated for C$_{13}$H$_{16}$N$_2$S: 232.10. found: 233.2 (M+H)$^+$.

N-(2-Methyl-2-(4-phenylthiazol-2-yl)propyl)-3-(5-(trifluoromethyl)-1,2,4-oxadiazol-3-yl)benzamide

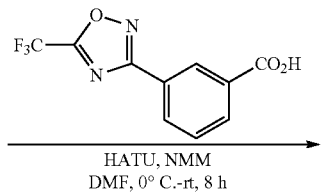

-continued

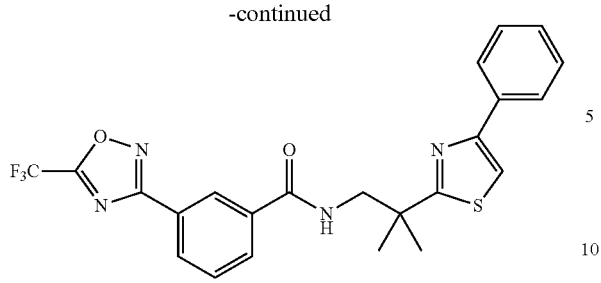

This compound was synthesized from 2-methyl-2-(4-phenylthiazol-2-yl)propan-1-amine and 3-(5-(trifluoromethyl)-1,2,4-oxadiazol-3-yl)benzoic acid as described in example 8 step 6 (75 mg, yield 38%). $^1$H NMR (400 MHz, MeOD) δ 8.52 (t, J=1.8 Hz, 1H), 8.27 (d, J=7.8 Hz, 1H), 8.03 (d, J=8.0 Hz, 1H), 7.92-7.90 (m, 2H), 7.69 (s, 1H), 7.67-7.63 (t, J=7.8 Hz, 1H), 7.36-7.29 (m, 2H), 7.28-7.26 (m, 1H), 3.79 (d, J=6.3 Hz, 2H), 1.58 (s, 6H). MS (ESI) m/z: Calculated for $C_{23}H_{19}F_3N_4O_2S$: 472.12. found: 473.0 (M+H)$^+$.

Example 16

1-Methyl-4-(4-phenylthiazol-2-yl)piperidine-4-carbonitrile

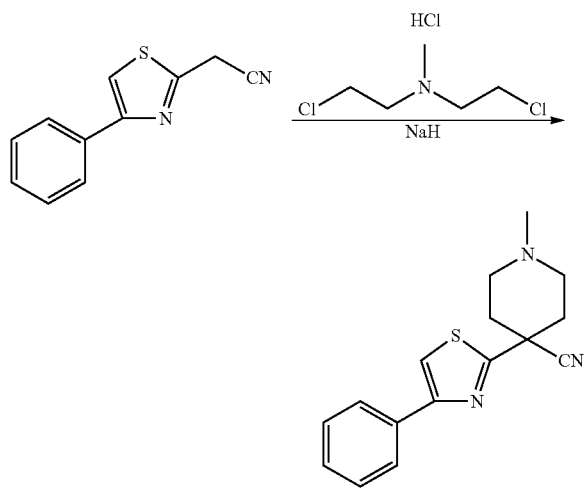

This compound was synthesized from 2-(4-phenylthiazol-2-yl)acetonitrile as described in example 1 step 2 using 2-chloro-N-(2-chloroethyl)-N-methylethanamine hydrochloride and heating the reaction mixture at 60° C. overnight (200 mg, 40% yield). MS (ESI) m/z: Calculated for $C_{16}H_{17}N_3S$: 283.11. found: 284.1 (M+H)$^+$.

Step 1b: Alternate synthesis of 1-methyl-4-(4-phenylthiazol-2-yl)piperidine-4-carbonitrile

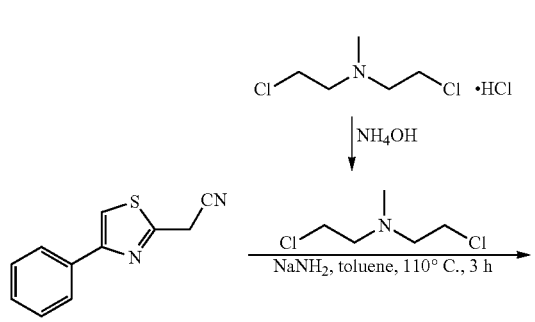

-continued

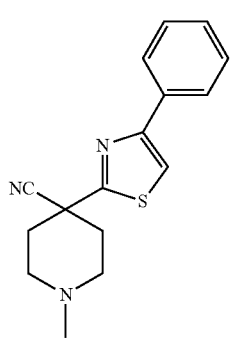

Sodium amide (878 mg, 22.4 mmol) was suspended in toluene (15 mL) and cooled to 0° C. To this suspension was added dropwise a solution of (4-phenyl-thiazol-2-yl)-acetonitrile (1.5 g, 7.4 mmol) in toluene (10 mL) while maintaining the temperature at 0° C. The reaction mixture was stirred for 20 min. Separately the bis-(2-chloroethyl)methylamine hydrochloride (1.45 g, 7.4 mmol) was taken in water (8 mL), cooled to 0° C., and basified with aqueous ammonia solution (adjusted to pH of the solution to ~8). The oily layer was separated out from the aqueous layer and the organic product was extracted with toluene. The toluene layer was dried over sodium hydroxide pellets. The dry toluene solution of bis-(2-chloroethyl)methylamine was added to the reaction mixture at 0° C. The reaction mixture was allowed to warm up to room temperature and further heated to 110° C. for 3 h. The reaction mixture was then cooled to room temperature, diluted with EtOAc, and extracted with EtOAc. The combined extracts were washed with water and brine, dried over anhydrous sodium sulfate and concentrated under reduced pressure. The crude product was purified by column chromatography (silica gel 60-120 mesh, eluent 5% MeOH in $CH_2Cl_2$) to afford 1-methyl-4-(4-phenylthiazol-2-yl)piperidine-4-carbonitrile (350 mg, yield 17%). $^1$H NMR (400 MHz, DMSO-d$_6$) δ 8.22 (s, 1H), 7.99-7.97 (m, 2H), 7.49-7.44 (m, 2H), 7.40-7.36 (m, 1H), 2.92-2.90 (m, 2H), 2.40-2.37 (m, 2H), 2.31-2.16 (m, 7H). MS (ESI) m/z: Calculated for $C_{16}H_{17}N_3S$: 283.11. found: 284.2 (M+H)$^+$.

(1-Methyl-4-(4-phenylthiazol-2-yl)piperidin-4-yl)methanamine

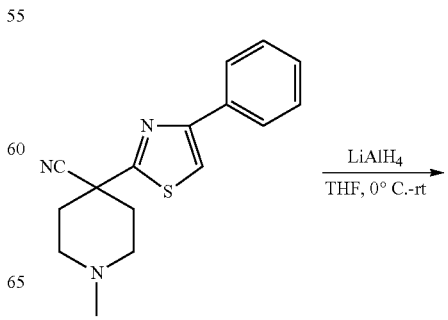

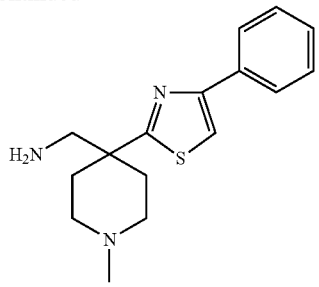

This compound was synthesized from 1-methyl-4-(4-phenylthiazol-2-yl)piperidine-4-carbonitrile as described in example 1 step 3 (200 mg, crude). MS (ESI) m/z: Calculated for $C_{16}H_{21}N_3S$: 287.15. found: 288.1 (M+H)$^+$.

N-((1-Methyl-4-(4-phenylthiazol-2-yl)piperidin-4-yl)methyl)-3-(5-(trifluoromethyl)-1,2,4-oxadiazol-3-yl)benzamide

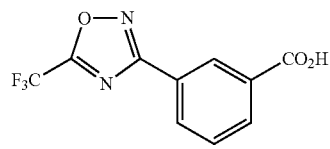

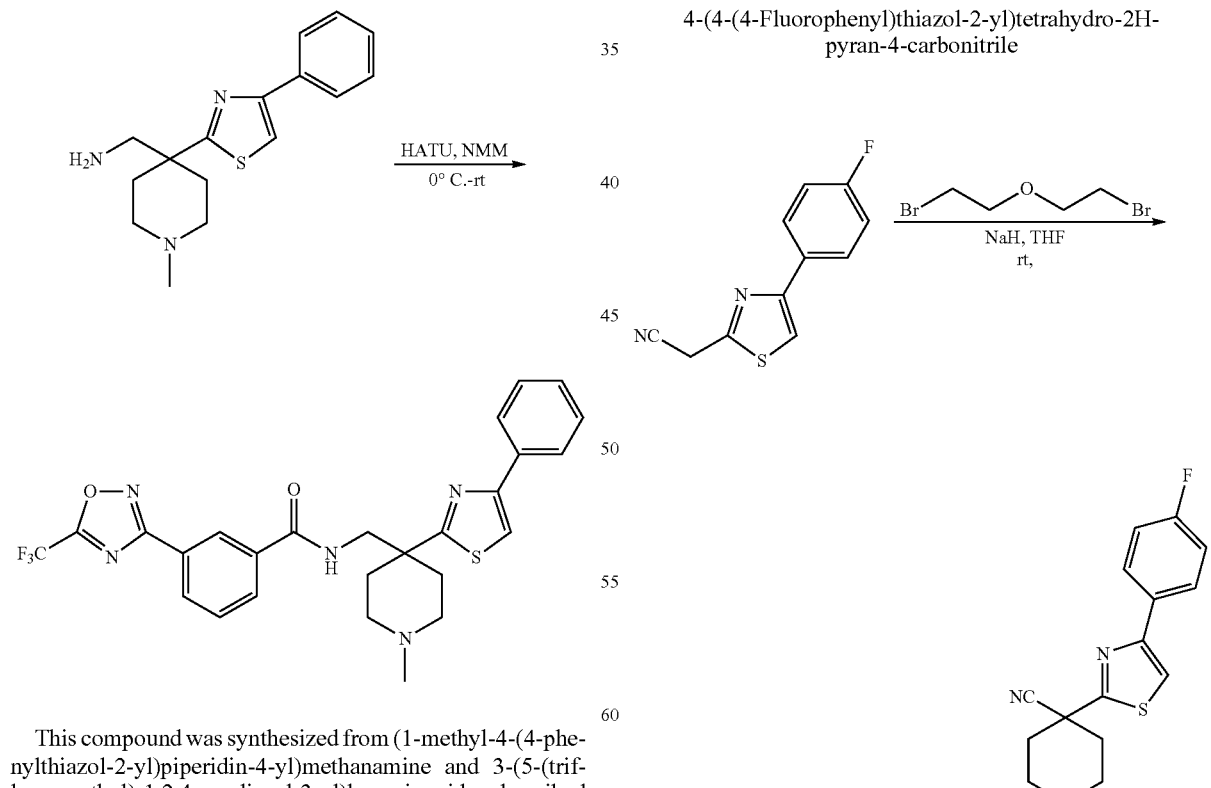

This compound was synthesized from (1-methyl-4-(4-phenylthiazol-2-yl)piperidin-4-yl)methanamine and 3-(5-(trifluoromethyl)-1,2,4-oxadiazol-3-yl)benzoic acid as described in example 8 step 6 (9 mg, 23% yield): $^1$H NMR (300 MHz, CDCl$_3$) δ 8.51 (s, 1H), 8.21 (d, J=7.5 Hz, 1H), 7.98 (d, J=7.5 Hz, 1H), 7.86 (d, J=6.3 Hz, 1H), 7.78 (m, 1H), 7.54 (t, J=6.2 Hz, 2H), 7.48 (s, 1H), 7.34-7.25 (m, 2H), 3.86 (s, 2H), 2.69 (m, 2H), 2.57 (m, 4H), 2.34 (s, 3H), 2.13 (m, 2H). MS (ESI) m/z: Calculated for $C_{26}H_{24}F_3N_5O_2S$: 527.16. found: 528.1 (M+H)$^+$.

Example 17

2-(4-(4-Fluorophenyl)thiazol-2-yl)acetonitrile

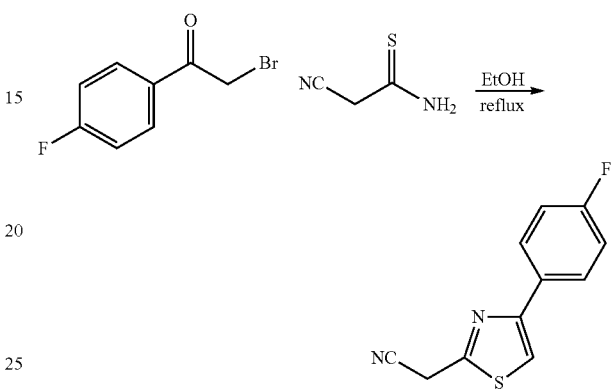

This compound was synthesized from 2-bromo-1-(4-fluorophenyl)ethanone and 2-cyanothioacetamide as described in example 1 step 1 (3.2 g, yield 72%). MS (ESI) m/z: Calculated for $C_{11}H_7FN_2S$: 218.03. found: 219.0 (M+H)$^+$.

4-(4-(4-Fluorophenyl)thiazol-2-yl)tetrahydro-2H-pyran-4-carbonitrile

This compound was synthesized from 2-(4-(4-fluorophenyl)thiazol-2-yl)acetonitrile as described in example 1 step 2

(3.0 g, yield 66%). MS (ESI) m/z: Calculated for $C_{15}H_{13}FN_2OS$: 288.07. found: 289.0 (M+H)$^+$.

(4-(4-(4-Fluorophenyl)thiazol-2-yl)tetrahydro-2H-pyran-4-yl)methanamine

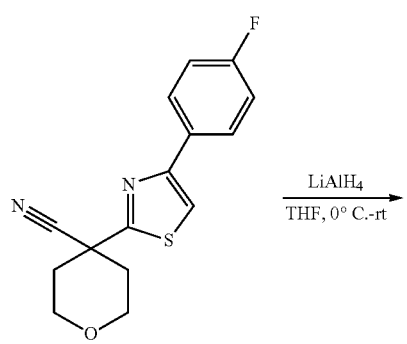

This compound was synthesized from 4-(4-(4-fluorophenyl)thiazol-2-yl)tetrahydro-2H-pyran-4-carbonitrile as described in example 1 step 3 (600 mg, crude) and it was carried through without further purification. MS (ESI) m/z: Calculated for $C_{15}H_{17}FN_2OS$: 292.10. found: 293.1 (M+H)$^+$.

N-((4-(4-(4-Fluorophenyl)thiazol-2-yl)tetrahydro-2H-pyran-4-yl)methyl)-3-(5-(trifluoromethyl)-1,2,4-oxadiazol-3-yl)benzamide

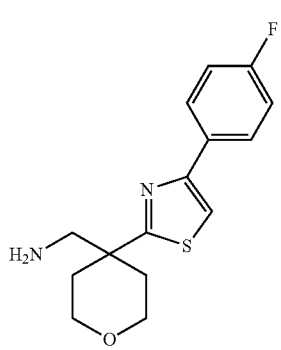

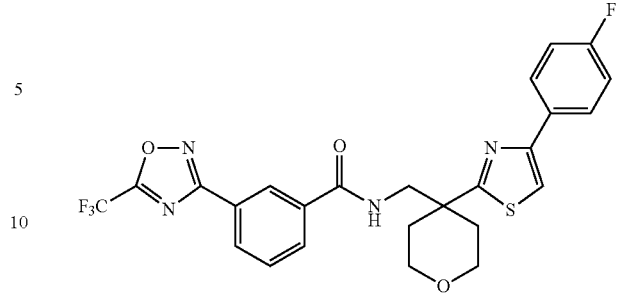

This compound was synthesized from (4-(4-(4-fluorophenyl)thiazol-2-yl)tetrahydro-2H-pyran-4-yl)methanamine and 3-(5-(trifluoromethyl)-1,2,4-oxadiazol-3-yl)benzoic acid as described in example 8 step 6 (11 mg, 27% yield): $^1$H NMR (300 MHz, CDCl$_3$) δ 8.45 (s, 1H), 8.23 (d, J=6.4 Hz, 1H), 7.98 (d, J=6.4 Hz, 1H), 7.85 (t, J=5.1 Hz, 2H), 7.55 (t, J=7.7 Hz, 1H), 7.25 (s, 1H), 7.04 (t, J=7.7 Hz, 2H) 3.94 (m, 2H), 3.87 (m, 2H), 3.21 (m, 2H), 2.28 (m, 2H), 2.04 (m, 2H). MS (ESI) m/z: Calculated for $C_{25}H_{20}F_4N_4O_3S$: 532.12. found: 533.2 (M+H)$^+$.

Example 18

2-(5-Methyl-4-phenylthiazol-2-yl)acetonitrile

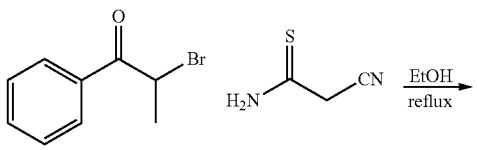

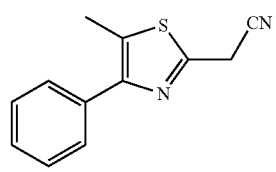

This compound was synthesized from 2-bromo-1-phenylpropan-1-one and 2-cyanothioacetamide as described in example 1 step 1 (1.7 g, 56% yield %). MS (ESI) m/z: Calculated for $C_{12}H_{10}N_2S$: 214.06. found: 215.0 (M+H)$^+$.

4-(5-Methyl-4-phenylthiazol-2-yl)tetrahydro-2H-pyran-4-carbonitrile

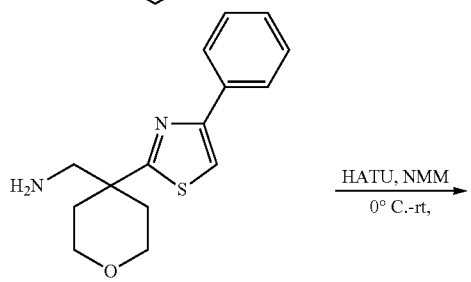 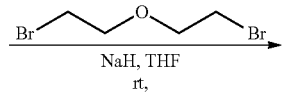

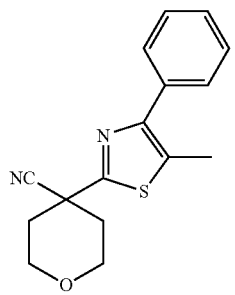

This compound was synthesized from 2-(5-methyl-4-phenylthiazol-2-yl)acetonitrile as described in example 1 step 2 (3.0 g, yield 66%). MS (ESI) m/z: Calculated for C₁₆H₁₆N₂OS: 284.10. found: 258.1 (M+H)⁺.

(4-(5-Methyl-4-phenylthiazol-2-yl)tetrahydro-2H-pyran-4-yl)methanamine

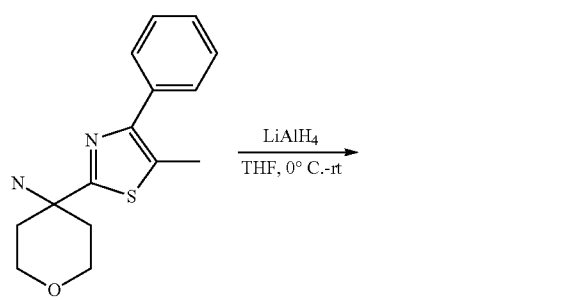

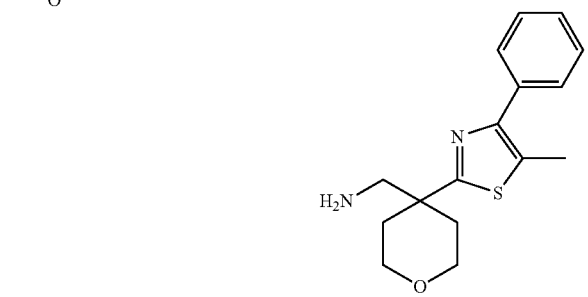

This compound was synthesized from 4-(5-methyl-4-phenylthiazol-2-yl)tetrahydro-2H-pyran-4-carbonitrile as described in example 1 step 3 (600 mg, crude) and it was carried through without further purification. MS (ESI) m/z: Calculated for C₁₆H₂₀N₂OS: 288.13. found: 289.1 (M+H)⁺.

N-((4-(5-Methyl-4-phenylthiazol-2-yl)tetrahydro-2H-pyran-4-yl)methyl)-3-(5-(trifluoromethyl)-1,2,4-oxadiazol-3-yl)benzamide

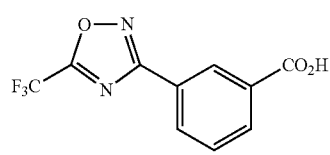

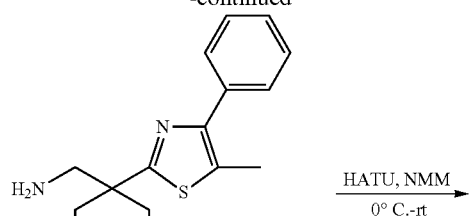

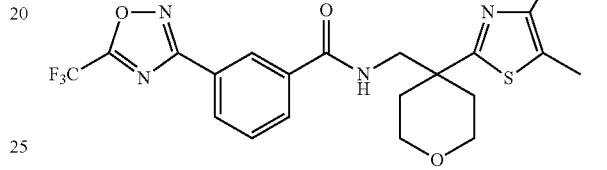

This compound was synthesized from (4-(5-methyl-4-phenylthiazol-2-yl)tetrahydro-2H-pyran-4-yl)methanamine and 3-(5-(trifluoromethyl)-1,2,4-oxadiazol-3-yl)benzoic acid as described in example 8 step 6 (55 mg, 89% yield): ¹H NMR (300 MHz, CDCl₃) δ 8.48 (t, J=1.1 Hz, 1H), 8.23 (dt, J=6.2 Hz, 1.1, 1H), 7.98 (dt, J=7.9 Hz, 1.1 Hz, 1H), 7.74 (bs, 1H), 7.64 (m, 2H), 7.49 (t, J=7.7 Hz, 1H), 7.39-7.29 (m, 2H), 3.92 (m, 2H), 3.85 (d, J=5.7 Hz, 2H), 3.74 (m, 2H), 2.59 (s, 3H), 2.24 (m, 2H), 1.95 (m, 2H). MS (ESI) m/z: Calculated for C₂₆H₂₃F₃N₄O₃S: 528.14. found: 529.1 (M+H)⁺.

Example 19

2-(4-Cyclohexylthiazol-2-yl)acetonitrile

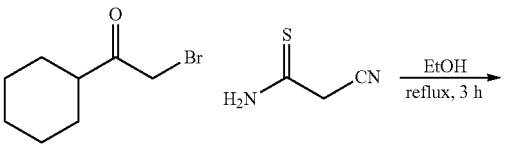

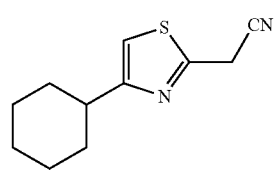

This compound was synthesized from 2-bromo-1-cyclohexylethanone and 2-cyanothioacetamide as described in example 1 step 1 (0.4 g, yield 80%). ¹H NMR (300 MHz, CDCl₃) δ 6.88 (s, 1H), 4.11 (s, 2H), 2.74 (m, 1H), 2.06-2.04

(m, 2H), 1.84-1.72 (m, 4H), 1.44-1.31 (m, 4H). MS (ESI) m/z: Calculated for $C_{11}H_{14}N_2S$: 206.09. found: 207.2 (M+H)$^+$.

4-(4-Cyclohexylthiazol-2-yl)tetrahydro-2H-pyran-4-carbonitrile

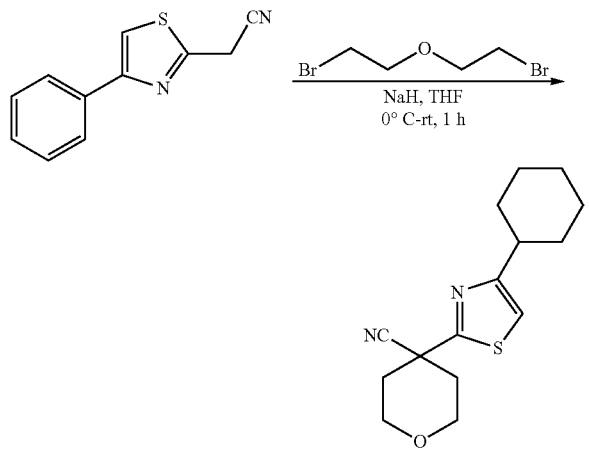

This compound was synthesized from 2-(4-cyclohexylthiazol-2-yl)acetonitrile as described in example 1 step 2 (0.3 g, yield 60%) as a yellow solid. $^1$H NMR (400 MHz, CDCl$_3$) δ 6.87 (s, 1H), 4.07-4.03 (dt, J=12.2 Hz, 3.3 Hz, 2H), 3.90-3.83 (m, 2H), 2.77 (m, 1H), 2.35-2.25 (m, 4H), 2.08-2.06 (d, J=6.0 Hz, 2H), 1.83-1.72 (m, 4H), 1.43-1.33 (m, 4H). MS (ESI) m/z: Calculated for $C_{16}H_{20}N_2OS$: 276.13. found: 277.2 (M+H)$^+$.

(4-(4-Cyclohexylthiazol-2-yl)tetrahydro-2H-pyran-4-yl)methanamine

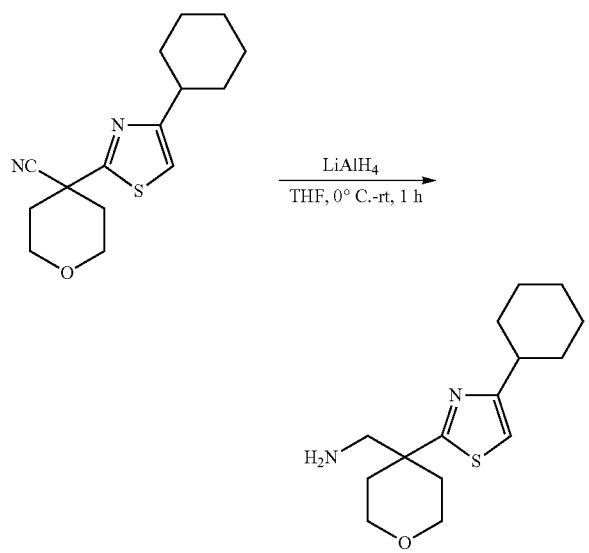

This compound was synthesized from 4-(4-cyclohexylthiazol-2-yl)tetrahydro-2H-pyran-4-carbonitrile as described in example 1 step 3 (120 mg, yield 40%). $^1$H NMR (400 MHz, DMSO-d$_6$) δ 7.14 (s, 1H), 3.75-3.69 (m, 2H), 3.39-3.34 (m, 4H), 2.69 (m, 1H), 2.03 (m, 4H), 1.83-1.67 (m, 6H), 1.43 (m, 4H). MS (ESI) m/z: Calculated for $C_{16}H_{24}N_2OS$: 280.16. found: 281.2 (M+H)$^+$.

N-((4-(4-Cyclohexylthiazol-2-yl)tetrahydro-2H-pyran-4-yl)methyl)-3-(5-(trifluoromethyl)-1,2,4-oxadiazol-3-yl)benzamide

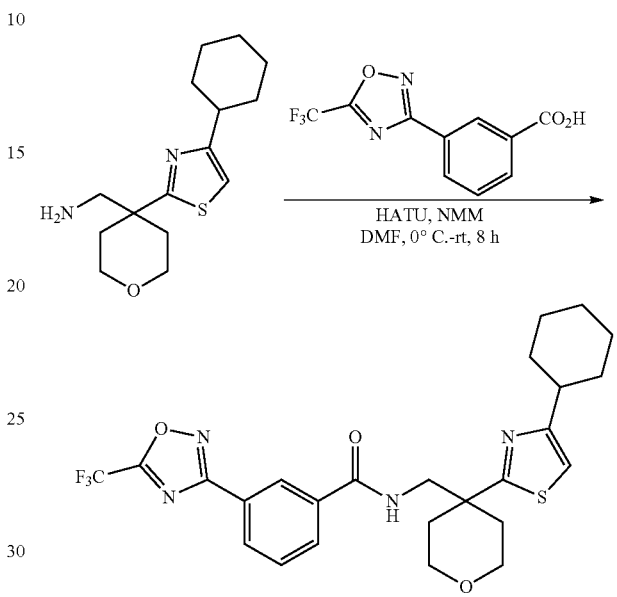

This compound was synthesized from (4-(4-cyclohexylthiazol-2-yl)tetrahydro-2H-pyran-4-yl)methanamine and 3-(5-(trifluoromethyl)-1,2,4-oxadiazol-3-yl)benzoic acid as described in example 8 step 6 (70 mg, yield 32%). $^1$H NMR (400 MHz, MeOD) δ 8.50 (t, J=1.5 Hz, 1H), 8.29 (dt, J=7.8 Hz, 1.4 Hz, 1H), 7.98 (m, 1H), 7.67 (t, J=7.8 Hz, 1H), 7.05 (s, 1H), 3.90-3.86 (dt, J=11.8 Hz, 3.9 Hz, 2H), 3.65 (s, 2H), 3.55-3.49 (m, 2H), 2.69 (m, 1H), 2.35 (d, J=13.8 Hz, 2H), 2.04-1.96 (m, 4H), 1.76-1.73 (m, 2H), 1.39 (m, 6H). MS (ESI) m/z: Calculated for $C_{25}H_{27}F_3N_4O_3S$: 520.18. found: 521.2 (M+H)$^+$.

Example 20

2-(4-(Pyridin-2-yl)thiazol-2-yl)acetonitrile

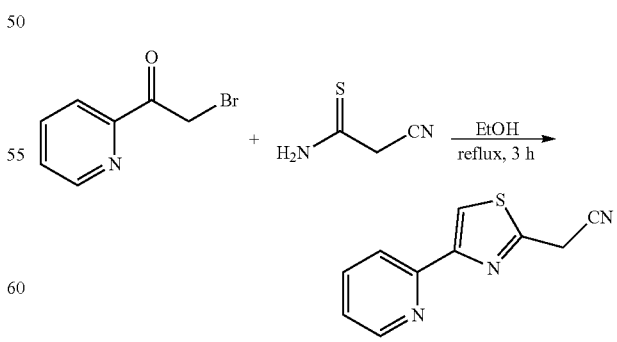

This compound was synthesized from 2-bromo-1-(pyridin-2-yl)ethanone and 2-cyanothioacetamide as described in example 1 step 1 (0.37 g, yield 73%): $^1$H NMR (400 MHz, CDCl$_3$) δ 8.65 (d, J=5.5 Hz, 1H), 8.15 (m, 2H), 7.84 (t, J=8.4

Hz, 1H), 7.30 (m, 1H), 4.21 (s, 2H). MS (ESI) m/z: Calculated for $C_{10}H_7N_3S$: 201.04. found: 202.2 (M+H)$^+$.

4-(4-(Pyridin-2-yl)thiazol-2-yl)tetrahydro-2H-pyran-4-carbonitrile

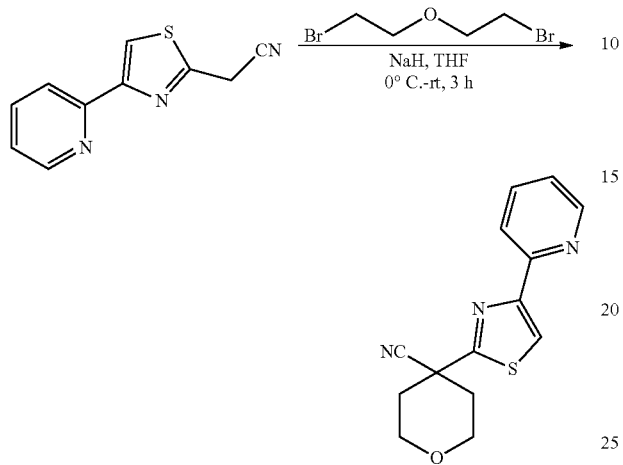

This compound was synthesized from 2-(4-(pyridin-2-yl)thiazol-2-yl)acetonitrile as described in example 1 step 2 (0.37 g, yield 74%): $^1$H NMR (300 MHz, CDCl$_3$) δ 8.64 (d, J=3.9 Hz, 1H), 8.18 (m, 2H), 7.83 (td, J=7.8 Hz, 1.8 Hz, 1H), 7.29 (m, 1H), 4.14-4.08 (m, 2H), 3.96-3.87 (m, 2H), 2.46-2.32 (m, 4H). MS (ESI) m/z: Calculated for $C_{14}H_{13}N_3OS$: 271.08. found: 272.2 (M+H)$^+$.

(4-(4-(Pyridin-2-yl)thiazol-2-yl)tetrahydro-2H-pyran-4-yl)methanamine

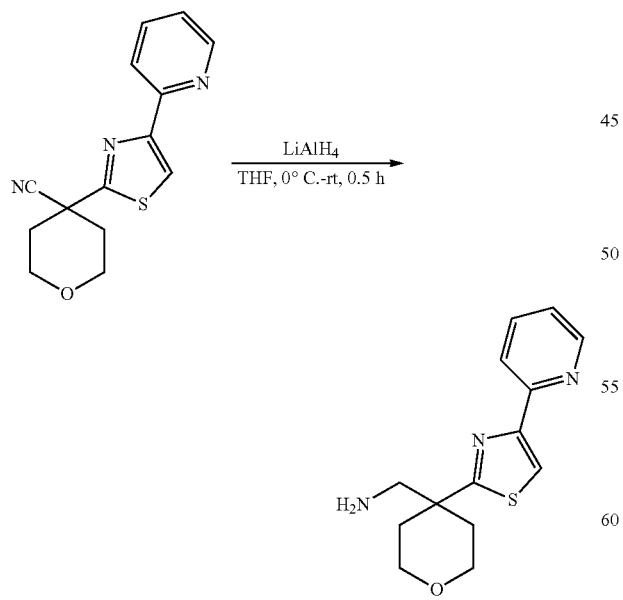

This compound was synthesized from 4-(4-(pyridin-2-yl)thiazol-2-yl)tetrahydro-2H-pyran-4-carbonitrile as described in example 1 step 3 (150 mg, crude), and it was carried through without any further purification. MS (ESI) m/z: Calculated for $C_{14}H_{17}N_3OS$: 275.11. found: 276.2 (M+H)$^+$.

N-((4-(4-(Pyridin-2-yl)thiazol-2-yl)tetrahydro-2H-pyran-4-yl)methyl)-3-(5-(trifluoromethyl)-1,2,4-oxadiazol-3-yl)benzamide This compound was synthesized from (4-(4-(pyridin-2-yl)thiazol-2-yl)tetrahydro-2H-pyran-4-yl)methanamine and 3-(5-(trifluoromethyl)-1,2,4-oxadiazol-3-yl)benzoic acid as described in example 8 step 6 (35 mg, yield 13%). $^1$H NMR (400 MHz, MeOD) δ 8.54 (d, J=5.5 Hz, 1H), 8.44 (m, 1H), 8.25 (d, J=8.0 Hz, 1H), 8.17 (s, 1H), 8.11 (d, J=8.0 Hz, 1H), 7.97 (d, J=7.8 Hz, 1H), 7.79 (td, J=7.7 Hz, 1.6 Hz, 1H), 7.62 (t, J=7.8 Hz, 1H), 7.32 (m, 1H), 3.97-3.93 (dt, J=11.8 Hz, 3.8 Hz, 2H), 3.75 (m, 2H), 3.62-3.56 (m, 2H), 2.47-2.44 (m, 2H), 2.12-2.08 (ddd, J=14.1 Hz, 10.5 Hz, 4.3 Hz, 2H). MS (ESI) m/z: Calculated for $C_{24}H_{20}F_3N_5O_3S$: 515.12. found: 516.0 (M+H)$^+$.

Example 21

2-(4-(Pyridin-4-yl)thiazol-2-yl)acetonitrile

This compound was synthesized from 2-bromo-1-(pyridin-4-yl)ethanone and 2-cyanothioacetamide as described in example 1 step 1 (0.23 g, yield 46%): $^1$H NMR (300 MHz, MeOD) δ 8.59 (m, 2H), 8.24 (s, 1H), 7.98 (m, 2H), 4.44 (s, 2H). MS (ESI) m/z: Calculated for $C_{10}H_7N_3OS$: 201.01. found: 202.2 $(M+H)^+$.

4-(4-(Pyridin-4-yl)thiazol-2-yl)tetrahydro-2H-pyran-4-carbonitrile

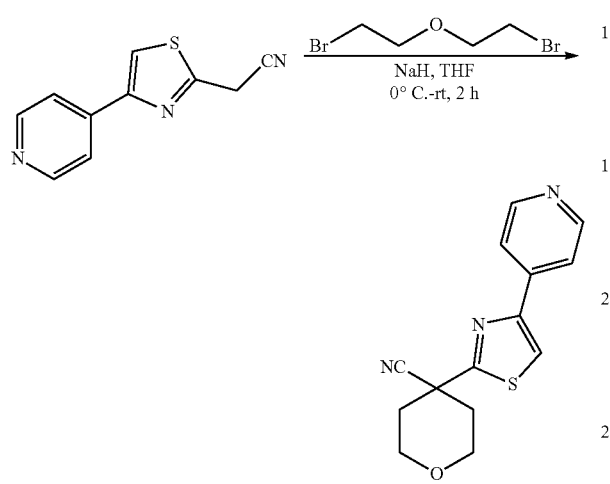

This compound was synthesized from 2-(4-(pyridin-4-yl)thiazol-2-yl)acetonitrile as described in example 1 step 2 (0.18 g, yield 58%): $^1$H NMR (300 MHz, MeOD) δ 8.60 (m, 2H), 8.29 (s, 1H), 7.99 (m, 2H), 4.10-4.04 (dt, J=12.2 Hz, 3.1 Hz, 2H), 3.88-3.79 (m, 2H), 2.37-2.33 (m, 4H). MS (ESI) m/z: Calculated for $C_{14}H_{13}N_3OS$: 271.08. found: 272.2 $(M+H)^+$.

(4-(4-(Pyridin-4-yl)thiazol-2-yl)tetrahydro-2H-pyran-4-yl)methanamine

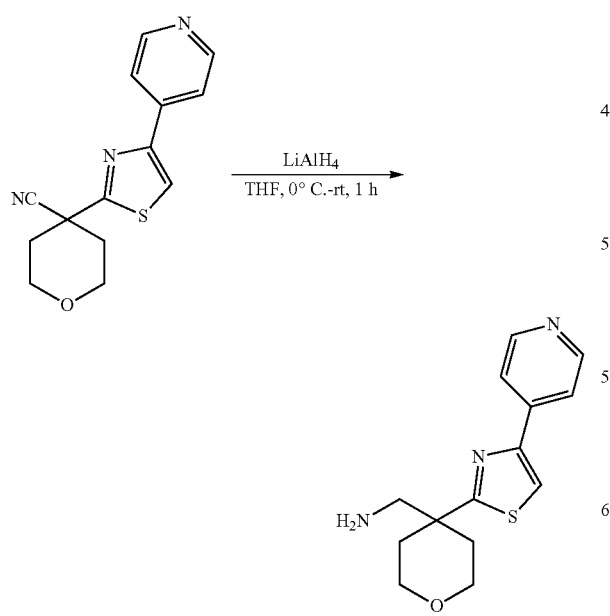

This compound was synthesized from 4-(4-(pyridin-4-yl)thiazol-2-yl)tetrahydro-2H-pyran-4-carbonitrile as described in example 1 step 3 (90 mg, crude), and it was carried through without any further purification. $^1$H NMR (300 MHz, DMSO-$d_6$) δ 8.63 (m, 2H), 8.42 (s, 1H), 7.90 (m, 2H), 3.79-3.74 (m, 2H), 3.51-3.42 (m, 2H), 2.79 (s, 2H), 2.14-2.10 (m, 2H), 1.89-1.82 (m, 2H). MS (ESI) m/z: Calculated for $C_{14}H_{17}N_3OS$: 275.11. found: 276.2 $(M+H)^+$.

N-((4-(4-(Pyridin-4-yl)thiazol-2-yl)tetrahydro-2H-pyran-4-yl)methyl)-3-(5-(trifluoromethyl)-1,2,4-oxadiazol-3-yl)benzamide

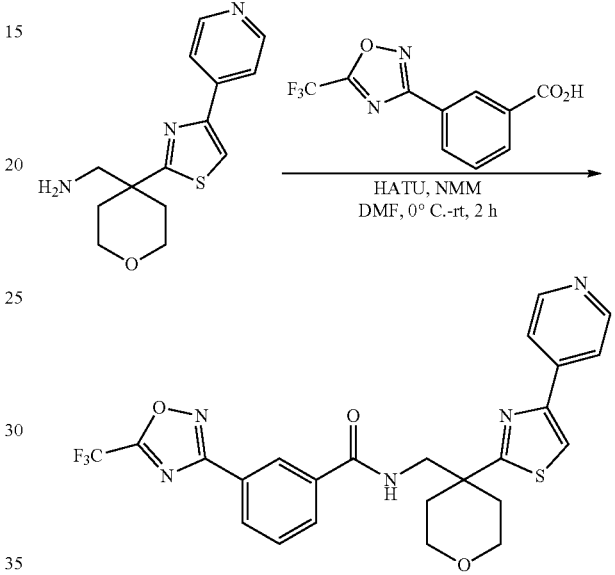

This compound was synthesized from (4-(4-(pyridin-4-yl)thiazol-2-yl)tetrahydro-2H-pyran-4-yl)methanamine and 3-(5-(trifluoromethyl)-1,2,4-oxadiazol-3-yl)benzoic acid as described in example 8 step 6 (60 mg, yield 38%): $^1$H NMR (400 MHz, DMSO-$d_6$) δ 8.82 (t, J=6.3 Hz, 1H), 8.57 (d, J=5.8 Hz, 2H), 8.45 (s, 1H), 8.40 (s, 1H), 8.19 (d, J=7.9 Hz, 1H), 8.05 (d, J=7.9 Hz, 1H), 7.87 (d, J=5.8 Hz, 2H), 7.70 (t, J=7.8 Hz, 1H), 3.87-3.84 (dt, J=12.1 Hz, 3.4 Hz, 2H), 3.59-3.58 (d, J=6.1 Hz, 2H), 3.42 (m, 2H), 2.28-2.24 (d, J=13.4 Hz, 2H), 2.04-1.96 (m, 2H). MS (ESI) m/z: Calculated for $C_{24}H_{20}F_3N_6O_3S$: 515.12. found: 516.0 $(M+H)^+$.

Example 22

Methyl 5-((hydroxyimino)methyl)thiophene-2-carboxylate

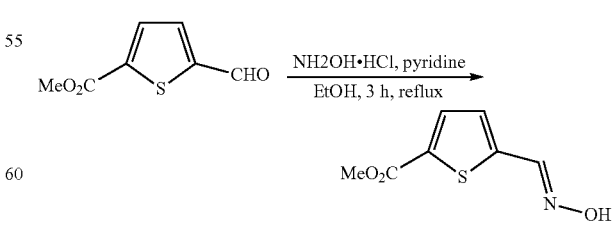

Hydroxylamine hydrochloride (420 mg, 6.1 mmol) and pyridine (0.5 mL) were added to a solution of methyl 5-formylthiophene-2-carboxylate (690 mg, 4.1 mmol) in EtOH (25 mL). The reaction mixture was refluxed for 3 h, cooled to room temperature and concentrated under reduced pressure. The residue was dissolved in diethyl ether, the organic layer was washed with water and brine, and dried over anhydrous sodium sulfate. The solvent was removed under reduced pressure to get product methyl 5-((hydroxyimino)methyl)thiophene-2-carboxylate (440 mg, yield 60%), which was carried through without any further purification. $^1$H NMR (400 MHz, DMSO-d$_6$) δ 12.5 (s, 1H), 7.98 (s, 1H), 7.78 (d, J=4.1 Hz, 1H), 7.51 (d, J=4.1 Hz, 1H), 3.82 (s, 3H). MS (ESI) m/z: Calculated for C$_7$H$_7$NO$_3$S: 185.01. found: 186.0 (M+H)$^+$.

Methyl 5-cyanothiophene-2-carboxylate

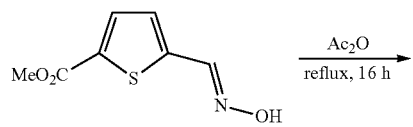

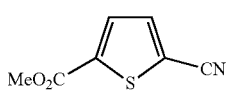

A solution of methyl 5-((hydroxyimino)methyl)thiophene-2-carboxylate (440 mg, 2.4 mmol) in acetic anhydride (10 mL) was refluxed for 16 h. After completion, the reaction mixture was cooled to room temperature, concentrated under reduced pressure and the residue was dissolved in diethyl ether. The organic layer was washed with 10% aqueous NaOH solution, water and brine, and dried over anhydrous sodium sulfate. The solvent was removed under reduced pressure to yield methyl 5-cyanothiophene-2-carboxylate (5-cyano-thiophene-2-carboxylic acid methyl ester) (400 mg, yield 90%) which was carried through without any further purification. $^1$H NMR (400 MHz, DMSO-d$_6$) δ 7.77 (d, J=4.2 Hz, 1H), 7.60 (d, J=4.1 Hz, 1H), 3.95 (s, 3H).

Methyl and ethyl 5-(N'-hydroxycarbamimidoyl)thiophene-2-carboxylate

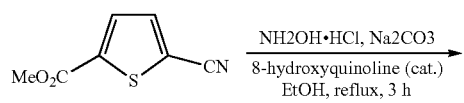

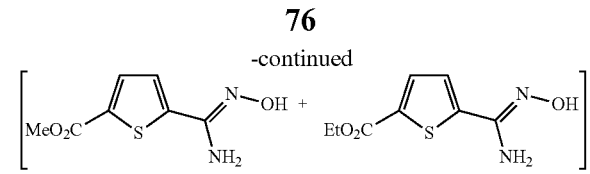

This mixture of compounds was synthesized from methyl 5-cyanothiophene-2-carboxylate as described in example 1 step 4 and it was isolated as a mixture of methyl and ethyl esters (2:3 ratio), and it was carried through without any further purification. MS (ESI) m/z: Calculated for C$_7$H$_8$N$_2$O$_3$S: 200.03. found: 201.2 (M+H)$^+$. (methyl ester); Calculated for C$_8$H$_{10}$N$_2$O$_3$S: 214.04. found: 215.0 (M+H)$^+$. (ethyl ester)

Methyl and ethyl 5-(5-(trifluoromethyl)-1,2,4-oxadiazol-3-yl)thiophene-2-carboxylate

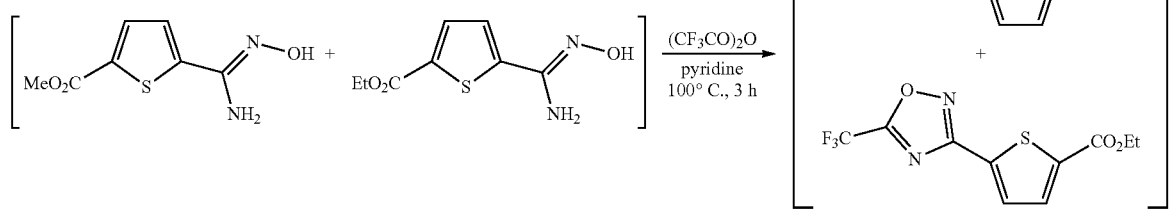

This mixture of compounds was synthesized from a mixture of methyl and ethyl 5-(N'-hydroxycarbamimidoyl)thiophene-2-carboxylate as described in example 1 step 5 and it was isolated as a mixture of methyl and ethyl esters (2:3 ratio), and it was carried through without any further purification. MS (ESI) m/z: Calculated for C$_9$H$_5$F$_3$N$_2$O$_3$S: 278.00. found: 278.0 (M)$^-$. (methyl ester); Calculated for C$_{10}$H$_7$F$_3$N$_2$O$_3$S: 292.01. found: 292.0 (M)$^-$. (ethyl ester)

5-(5-(Trifluoromethyl)-1,2,4-oxadiazol-3-yl)thiophene-2-carboxylic acid

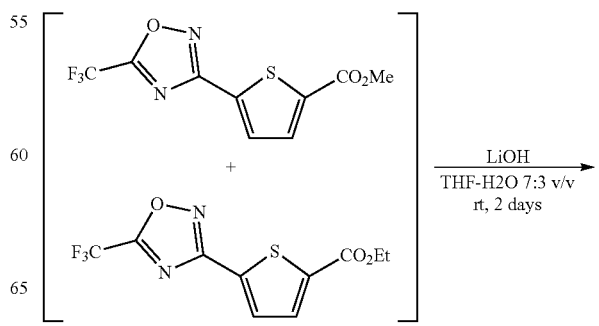

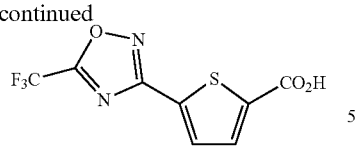

LiOH (37 mg) was added to a solution of a mixture of compounds methyl and ethyl 5-(5-(trifluoromethyl)-1,2,4-oxadiazol-3-yl)thiophene-2-carboxylate (300 mg) in THF:H$_2$O (10 mL, 7:3 v/v) and the mixture was stirred at room temperature for 2 days. The reaction mixture was then diluted with water and the aqueous layer was washed with EtOAc. The aqueous layer was acidified to pH ~4, extracted with EtOAc. The combined extracts were concentrated under reduced pressure to yield 5-(5-(trifluoromethyl)-1,2,4-oxadiazol-3-yl)thiophene-2-carboxylic acid (60 mg), which was carried through without any further purification. $^1$H NMR (400 MHz, DMSO-d$_6$) δ 13.78 (br s, 1H), 8.01-7.94 (m, 1H), 7.84-7.79 (dd, J=18.2 Hz, 3.8 Hz, 1H). MS (ESI) m/z: Calculated for C$_8$H$_3$F$_3$N$_2$O$_3$S: 263.98. found: 263.0 (M−H)$^-$.

N-((4-(4-Phenyithiazol-2-yl)tetrahydro-2H-pyran-4-yl)methyl)-5-(5-(trifluoromethyl)-1,2,4-oxadiazol-3-yl)thiophene-2-carboxamide

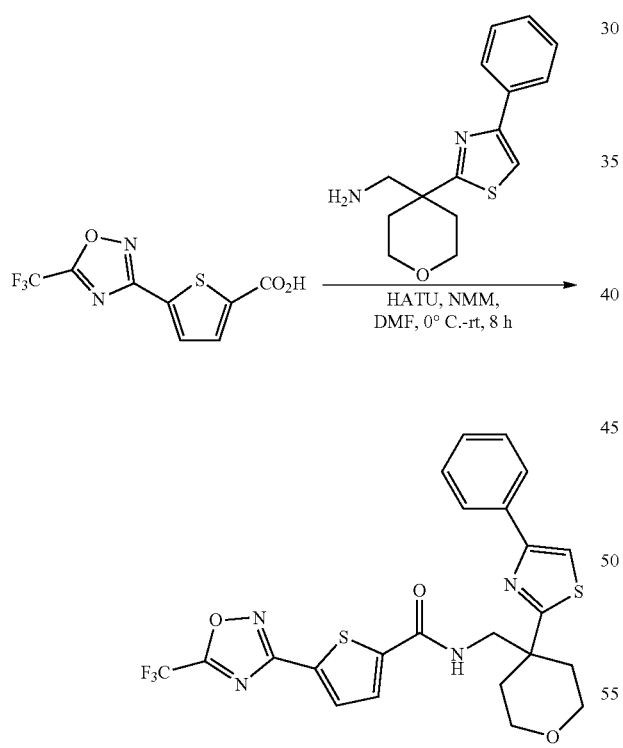

This compound was synthesized from (4-(4-phenylthiazol-2-yl)tetrahydro-2H-pyran-4-yl)methanamine and 5-(5-(trifluoromethyl)-1,2,4-oxadiazol-3-yl)thiophene-2-carboxylic acid as described in example 8 step 6 (25 mg, yield 22%): $^1$H NMR (400 MHz, CDCl$_3$) δ 7.96 (d, J=7.3 Hz, 2H), 7.78 (m, J=4.0 Hz, 1H), 7.62 (br s, 1H), 7.53-7.48 (m, 4H), 7.42-7.38 (m, 1H), 3.97-3.91 (m, 2H), 3.86 (d, J=5.5 Hz, 2H), 3.78-3.73 (ddd, J=11.6 Hz, 7.5 Hz, 3.5 Hz, 2H), 2.33-2.27 (ddd, J=13.6 Hz, 7.0 Hz, 3.5 Hz, 2H), 2.06-1.99 (ddd, J=13.8 Hz, 7.3 Hz, 3.3 Hz, 2H). MS (ESI) m/z: Calculated for C$_{23}$H$_{19}$F$_3$N$_4$O$_3$S$_2$: 520.09. found: 521.0 (M+H)$^+$.

Example 23

2-(4-(Thiophen-2-yl)thiazol-2-yl)acetonitrile

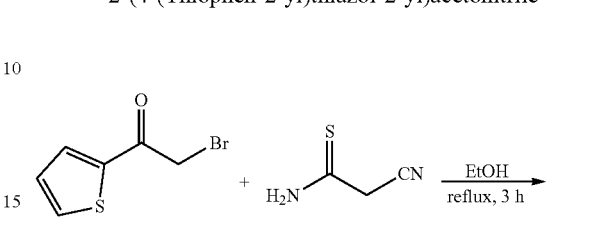

This compound was synthesized from 2-bromo-1-(thiophen-2-yl)ethanone and 2-cyanothioacetamide as described in example 1 step 1 (0.25 g, yield 49%): $^1$H NMR (400 MHz, CDCl$_3$) δ 7.47 (d, J=3.4 Hz, 1H), 7.36 (s, 1H), 7.33 (d, J=5.1 Hz, 1H), 7.09 (t, J=4.2 Hz, 1H), 4.17 (s, 2H). MS (ESI) m/z: Calculated for C$_9$H$_6$N$_2$S$_2$: 206.00. found: 207.0 (M+H)$^+$.

4-(4-(Thiophen-2-yl)thiazol-2-yl)tetrahydro-2H-pyran-4-carbonitrile

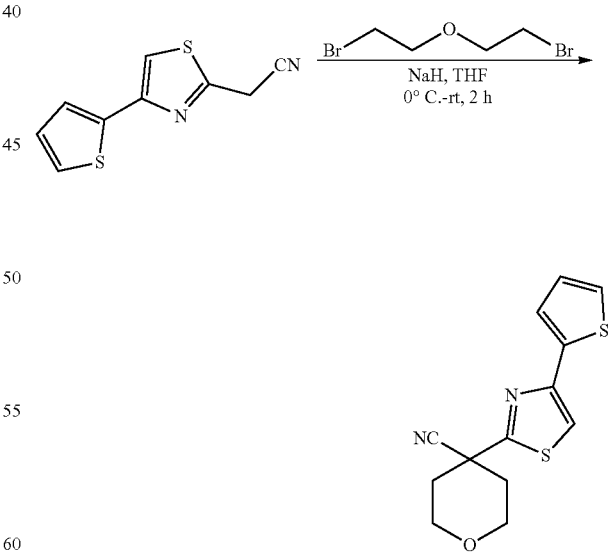

This compound was synthesized from 2-(4-(thiophen-2-yl)thiazol-2-yl)acetonitrile as described in example 1 step 2 (0.2 g, yield 60%): $^1$H NMR (300 MHz, CDCl$_3$) δ 7.49-7.47 (dd, J=3.6 Hz, 1.2 Hz, 1H), 7.36 (s, 1H), 7.32 (dd, J=5.2 Hz, 1.2 Hz, 1H), 7.09-7.07 (dd, J=5.0 Hz, 3.5 Hz, 1H), 4.13-4.07

(m, 2H), 3.94-3.85 (td, J=11.8 Hz, 2.5 Hz, 2H), 2.46-2.33 (m, 4H). MS (ESI) m/z: Calculated for $C_{13}H_{12}N_2OS_2$: 276.04. found: 277.0 (M+H)+.

(4-(4-(Thiophen-2-yl)thiazol-2-yl)tetrahydro-2H-pyran-4-yl)methanamine

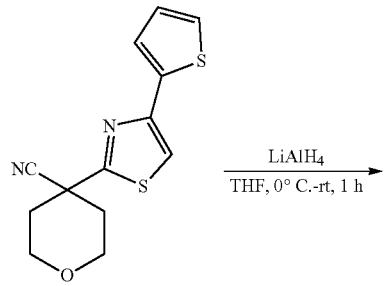

This compound was synthesized from 4-(4-(thiophen-2-yl)thiazol-2-yl)tetrahydro-2H-pyran-4-carbonitrile as described in example 1 step 3 (80 mg, yield 40%): $^1$H NMR (400 MHz, DMSO-$d_6$) δ 7.88 (s, 1H), 7.54-7.47 (m, 2H), 7.10-7.08 (m, 1H), 3.76-3.72 (m, 2H), 3.49-3.39 (m, 2H), 2.79 (s, 2H), 2.08-1.96 (m, 2H), 1.87-1.81 (m, 2H). MS (ESI) m/z: Calculated for $C_9H_6N_2S_2$: 280.07. found: 281.2 (M+H)+.

N-((4-(4-(Thiophen-2-yl)thiazol-2-yl)tetrahydro-2H-pyran-4-yl)methyl)-3-(5-(trifluoromethyl)-1,2,4-oxadiazol-3-yl)benzamide

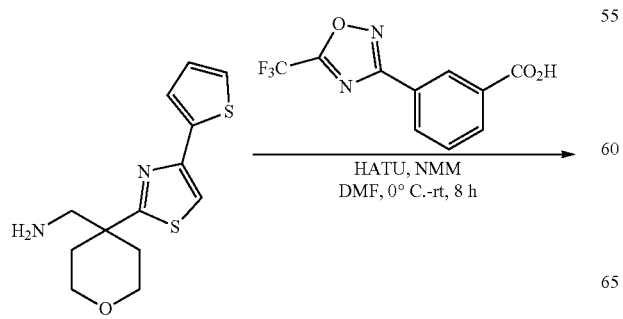

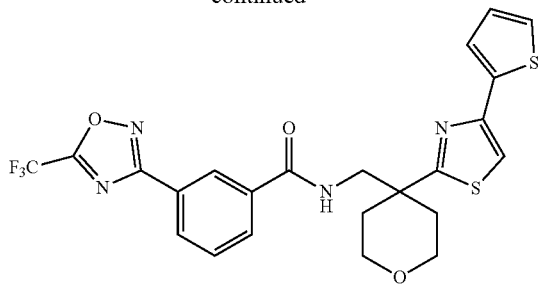

This compound was synthesized from (4-(4-(thiophen-2-yl)thiazol-2-yl)tetrahydro-2H-pyran-4-yl)methanamine and 3-(5-(trifluoromethyl)-1,2,4-oxadiazol-3-yl)benzoic acid as described in example 8 step 6 (70 mg, yield 46%): $^1$H NMR (400 MHz, MeOD) δ 8.47 (t, J=1.5 Hz, 1H), 8.26 (m, 1H), 8.00 (dt, J=7.8 Hz, 1.4 Hz, 1H), 7.63-7.61 (m, 2H), 7.46 (dd, J=3.8 Hz, 1.0 Hz, 1H), 7.29 (dd, J=5.0 Hz, 1.0 Hz, 1H), 7.01 (dd, J=5.0 Hz, 3.8 Hz, 1H), 3.95-3.92 (dt, J=11.9 Hz, 4.0 Hz, 2H), 3.71 (s, 2H), 3.62-3.56 (m, 2H), 2.42-2.38 (d, J=13.8 Hz, 2H), 2.08-2.02 (ddd, J=14.3 Hz, 10.4 Hz, 4.4 Hz, 2H), MS (ESI) m/z: Calculated for $C_{23}H_{19}F_3N_4O_3S_2$: 520.09. found: 521.0 (M+H)+.

Example 24

2-(4-(4-Fluorophenyl)thiazol-2-yl)-2-methylpropanenitrile

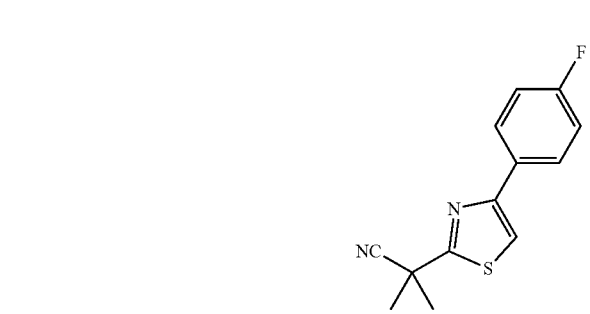

This compound was synthesized from 2-(4-(4-fluorophenyl)thiazol-2-yl)acetonitrile using iodomethane as described in example 1 step 2, and it was used directly without any purification in the next step. $^1$H NMR (CDCl$_3$) δ 7.88 (2H, m), 7.39 (1H, s), 7.10 (2H, m), 1.90 (6H, s). MS (ESI) m/z: Calculated for $C_{13}H_{11}FN_2S$: 246.06. found: 247.0 (M+H)⁺.

2-(4-(4-Fluorophenyl)thiazol-2-yl)-2-methylpropan-1-amine

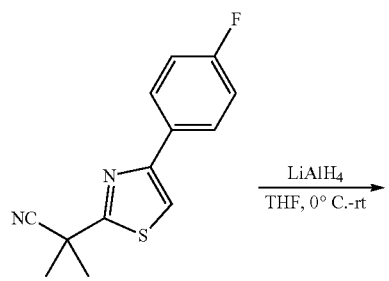

This compound was synthesized from 2-(4-(4-fluorophenyl)thiazol-2-yl)-2-methylpropanenitrile as described in example 1 step 3 (29 mg, 6% yield). ¹H NMR (DMSO-d₆) δ 7.98-7.94 (2H, m), 7.92 (1h, s), 7.26-7.22 (2H, m), 2.77 (2H, s), 1.33 (6H, s); MS (ESI) m/z: Calculated for $C_{13}H_{16}FN_2S$: 250.09. found: 251.1 (M+H)⁺.

Step 6: N-(2-(4-(4-Fluorophenyl)thiazol-2-yl)-2-methylpropyl)-3-(5-(trifluoromethyl)-1,2,4-oxadiazol-3-yl)benzamide

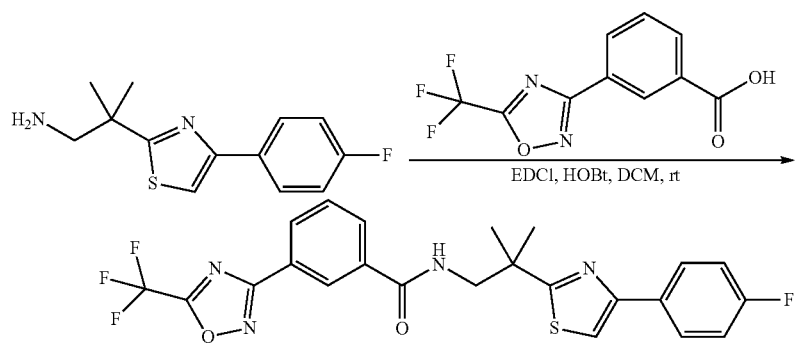

2-(4-(4-Fluorophenyl)thiazol-2-yl)-2-methylpropan-1-amine (140 mg, 0.56 mmol), 3-(5-(trifluoromethyl)-1,2,4-oxadiazol-3-yl)benzoic acid (144.37 mg, 0.56 mmol), N-(3-dimethylaminopropyl)-N'-ethylcarbodiimide hydrochloride (EDCI) (214.42 mg, 1.12 mmol), and 1-hydroxybenzotriazole (HOBt) (120.91 mg, 0.89 mmol) were dissolved in dichloromethane (3 mL) at room temperature. Diisopropylethylamine (DIEA) (0.39 mL, 2.24 mmol) was then introduced at room temperature and the reaction mixture was stirred at room temperature for 2 h. The reaction mixture was diluted with dichloromethane (60 mL) and washed with water (1×20 mL) and brine (1×20 mL). The organic layer was then dried over anhydrous sodium sulfate and concentrated under reduced pressure to give the crude product. The crude product was then purified on Combiflash ISCO (0-30% Ethyl Acetate: Hexanes) to give the desired product (164 mg, 60% yield). ¹H NMR (CDCl₃) δ 8.52 (1H, t), 8.22 (1H, dt), 8.12 (1H, t), 8.03 (1H, dt), 7.85-7.81 (2H, m), 7.57 (1H, d), 7.35 (1H, s), 7.05-7.00 (2H, m), 3.80 (2H, d, J=4 Hz), 1.55 (6H, s); MS (ESI) m/z: Calculated for $C_{23}H_{18}F_4N_4O_2S$: 490.11. found: 491.1 (M+H)⁺.

Example 25

2-(4-(4-Chlorophenyl)thiazol-2-yl)-2-methylpropanenitrile

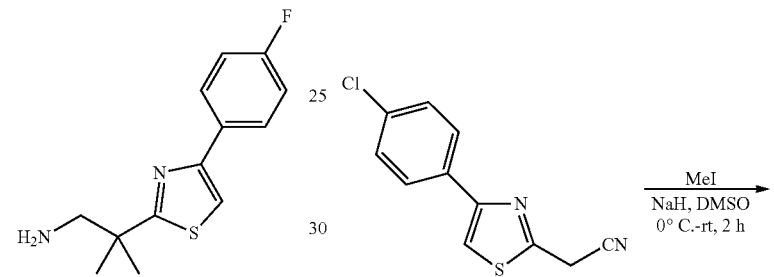

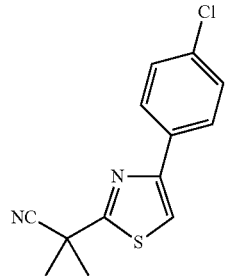

This compound was synthesized from 2-(4-(4-chlorophenyl)thiazol-2-yl)acetonitrile using iodomethane as described in example 1 step 2 (470 mg, yield 94%): ¹H NMR (400 MHz, CDCl₃) δ 7.86-7.85 (d, J=8.5 Hz, 2H), 7.46 (s, 1H), 7.41-7.39 (d, J=8.5 Hz, 2H), 1.92 (s, 6H). MS (ESI) m/z: Calculated for $C_{13}H_{11}ClN_2S$: 262.03. found: 263.0 (M+H)⁺.

2-(4-(4-Chlorophenyl)thiazol-2-yl)-2-methylpropan-1-amine

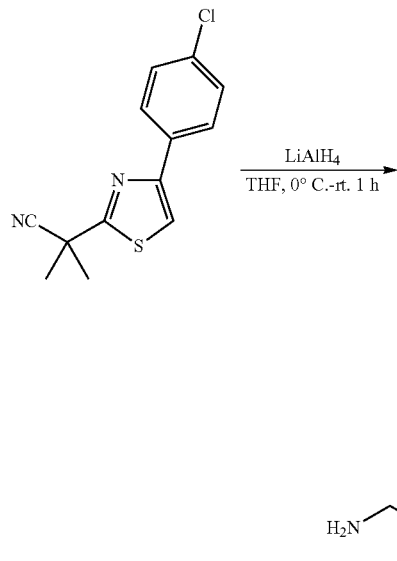

This compound was synthesized from 2-(4-(4-chlorophenyl)thiazol-2-yl)-2-methylpropanenitrile as described in example 1 step 3 (120 mg, yield 47%): $^1$H NMR (400 MHz, DMSO-d$_6$) δ 8.04 (d, J=1.2 Hz, 1H), 7.98 (dd, J=8.4 Hz, J=1.7 Hz, 2H), 7.51-7.48 (dd, J=8.5 Hz, J=1.5 Hz, 2H), 2.81 (s, 2H), 1.37 (s, 6H). MS (ESI) m/z: Calculated for C$_{13}$H$_{15}$ClN$_2$S: 266.06. found: 267.2 (M+H)$^+$.

N-(2-(4-(4-Chlorophenyl)thiazol-2-yl)-2-methylpropyl)-3-(5-(trifluoromethyl)-1,2,4-oxadiazol-3-yl)benzamide

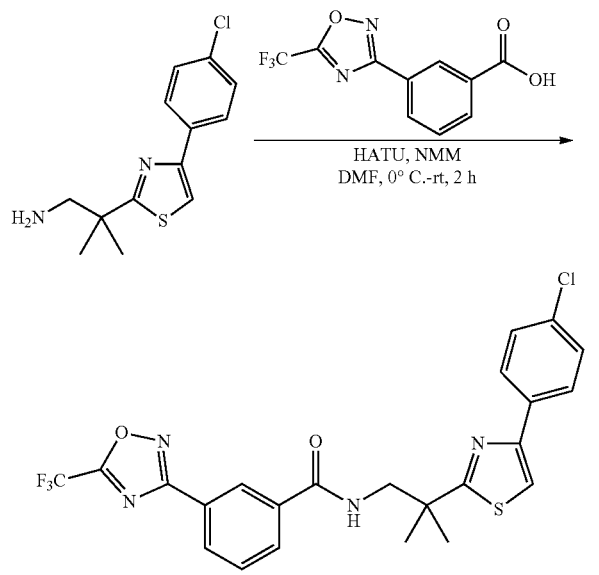

This compound was synthesized from 2-(4-(4-chlorophenyl)thiazol-2-yl)-2-methylpropan-1-amine and 3-(5-(trifluoromethyl)-1,2,4-oxadiazol-3-yl)benzoic acid as described in example 8 step 6 (80 mg, yield 35%): $^1$H NMR (400 MHz, CDCl$_3$) δ 8.54 (m, 1H), 8.27 (d, J=7.8 Hz, 1H), 8.10-8.04 (m, 2H), 7.82-7.80 (d, J=8.5 Hz, 2H), −7.62-7.58 (t, J=7.8 Hz, 1H), 7.42 (s, 1H), 7.33 (d, J=8.5 Hz, 2H), 3.82 (d, J=5.8 Hz, 2H), 1.58 (s, 6H). MS (ESI) m/z: Calculated for C$_{23}$H$_{18}$ClF$_3$N$_4$O$_2$S: 506.08. found: 507.0 (M+H)$^+$.

Example 26

3-Fluoro-5-(N′-hydroxycarbamimidoyl)benzoic acid

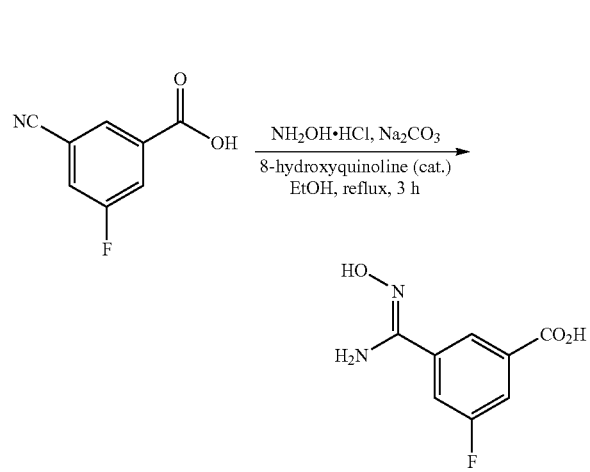

This compound was synthesized from 3-cyano-5-fluorobenzoic acid as described in example 1 step 4 (442 mg, yield 37%) and it was carried through without further purification. MS (ESI) m/z: Calculated for C$_8$H$_7$FN$_2$O$_3$: 198.04. found: 199.1 (M+H)$^+$.

3-Fluoro-5-(5-(trifluoromethyl)-1,2,4-oxadiazol-3-yl)benzoic acid

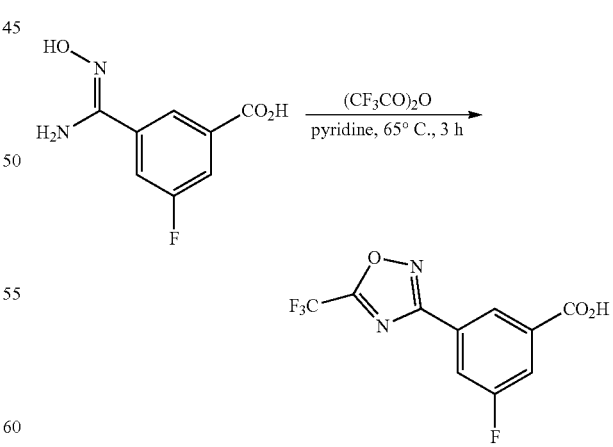

This compound was synthesized from 3-fluoro-5-(N′-hydroxycarbamimidoyl)benzoic acid as described in example 1 step 5 (351 mg, yield 51%) and it was carried through without further purification. MS (ESI) m/z: Calculated for C$_{10}$H$_4$F$_4$N$_2$O$_2$: 276.02. found: 277.1 (M+H)$^+$.

3-Fluoro-N-(2-(4-(4-fluorophenyl)thiazol-2-yl)-2-methylpropyl)-5-(5-(trifluoromethyl)-1,2,4-oxadiazol-3-yl)benzamide

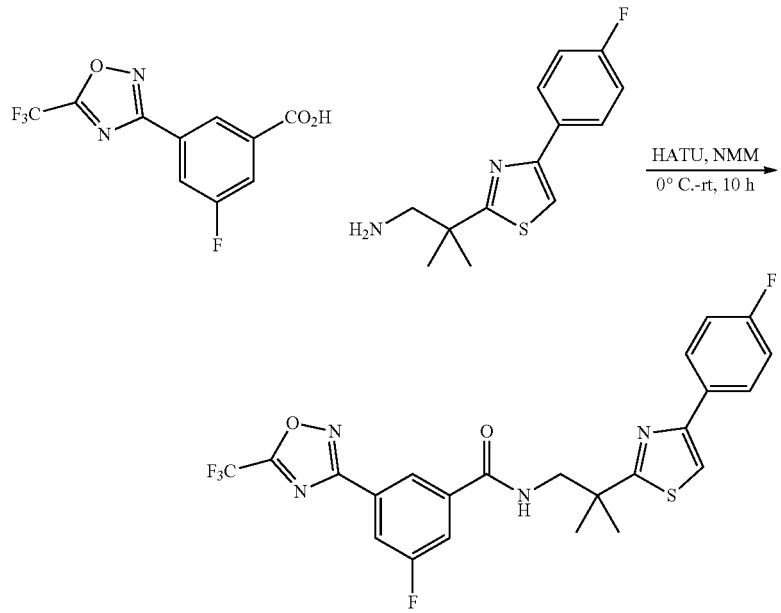

This compound was synthesized from 2-(4-(4-fluorophenyl)thiazol-2-yl)-2-methylpropan-1-amine and 3-fluoro-5-(5-(trifluoromethyl)-1,2,4-oxadiazol-3-yl)benzoic acid as described in example 8 step 6 (23 mg, yield 32%): $^1$H NMR (400 MHz, CDCl$_3$) δ 8.32 (br s, 1H), 8.23 (br t, J=5 Hz, 1H), 7.94 (br d, J=8 Hz, 1H), 7.86-7.75 (m, 3H), 7.06-7.00 (m, 2H), 3.78 (d, J=4 Hz, 2H), 1.55, (s, 6H). MS (ESI) m/z: Calculated for C$_{23}$H$_{17}$F$_6$N$_4$O$_2$S: 508.10. found: 509.1 (M+H)$^+$.

Example 27

Methyl 3,5-dicyanobenzoate

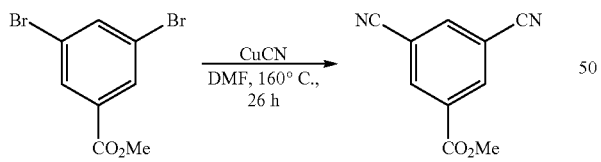

3,5-Dibromomethylbenzoate (1 g, 3.4 mmol) was dissolved in dry DMF (35 mL) and copper cyanide (1.2 g, 13.6 mmol) was added. The reaction mixture was heated to 160° C. under argon atmosphere for 26 h, allowed to cool down to room temperature and then quenched with saturated ammonium chloride solution. The reaction mixture was diluted with EtOAc and filtered through a Celite plug. The filtrate was diluted with EtOAc and the organic layer was washed with water and brine. The solvent was evaporated under reduced pressure to get the crude methyl 3,5-dicyanobenzoate (400 mg, crude, confirmed by GC-MS), which was carried through without further purification.

3,5-Dicyanobenzoic acid

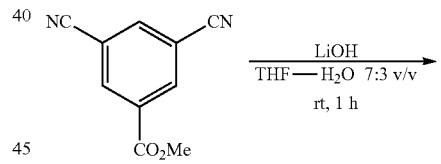

Methyl 3,5-dicyanobenzoate (400 mg, 2.1 mmol) was dissolved in THF—H$_2$O (7:3 v/v, 30 mL), the solution was cooled to 0° C. and LiOH (51 mg, 2.1 mmol) was added. The reaction mixture was allowed to warm up to room temperature and stirred for 1 h. THF was removed under reduced pressure and the aqueous layer was washed with EtOAc, acidified to pH ~2-3 using 1.5N HCl, and extracted with EtOAc. The organic layer was dried over anhydrous sodium sulfate and the solvent was removed under reduced pressure. The crude product was purified by column chromatography (silica 60-120 mesh, eluent 20% MeOH in CHCl$_3$) to get pure product 3,5-dicyanobenzoic acid (100 mg, yield 28%): $^1$H NMR (400 MHz, DMSO-d$_6$) δ 8.53 (s, 1H), 8.50 (s, 2H). MS (ESI) m/z: Calculated for C$_9$H$_4$N$_2$O$_2$: 172.03. found: 171.2 (M−H)$^-$.

3-Cyano-5-(N'-hydroxycarbamimidoyl)benzoic acid

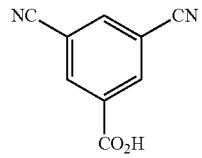

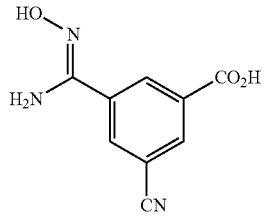

This compound was synthesized from 3,5-dicyanobenzoic acid as described in example 1 step 4 (120 g, crude), and it was carried through without any further purification. MS (ESI) m/z: Calculated for C$_9$H$_7$N$_3$O$_3$: 205.05. found: 204.0 (M−H)$^-$.

3-Cyano-5-(5-(trifluoromethyl)-1,2,4-oxadiazol-3-yl)benzoic acid

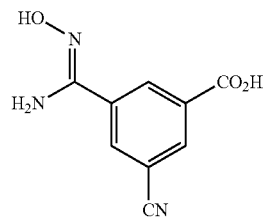

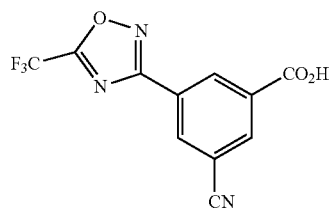

This compound was synthesized from 3-cyano-5-(N'-hydroxycarbamimidoyl)benzoic acid as described in example 1 step 5 (45 mg, yield 27%): $^1$H NMR (400 MHz, DMSO-d$_6$) δ 8.79 (s, 1H), 8.39 (s, 2H). MS (ESI) m/z: Calculated for C$_9$H$_4$N$_2$O$_2$: 283.02. found: 282.0 (M−H)$^-$.

3-Cyano-N-((4-(4-phenylthiazol-2-yl)tetrahydro-2H-pyran-4-yl)methyl)-5-(5-(trifluoromethyl)-1,2,4-oxadiazol-3-yl)benzamide

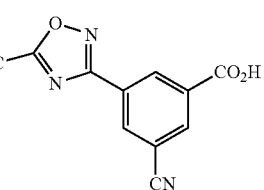
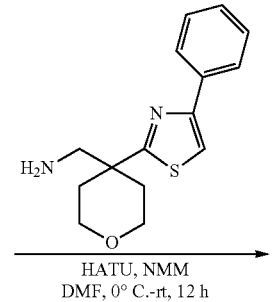

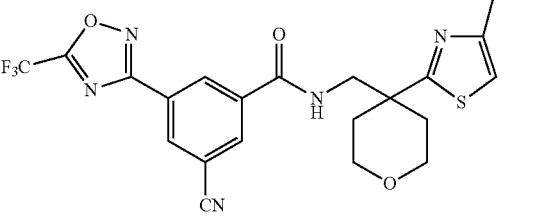

This compound was synthesized from (4-(4-phenylthiazol-2-yl)tetrahydro-2H-pyran-4-yl)methanamine and 3-cyano-5-(5-(trifluoromethyl)-1,2,4-oxadiazol-3-yl)benzoic acid as described in example 8 step 6 (25 mg, yield 30%): $^1$H NMR (400 MHz, MeOD) δ 8.63 (t, J=1.6 Hz, 1H), 8.52 (t, J=1.5 Hz, 1H), 8.25 (t, J=1.6 Hz, 1H), 7.87-7.85 (m, 2H), 7.81 (s, 1H), 7.32-7.28 (m, 2H), 7.25-7.21 (m, 1H), 3.97-3.92 (m, 2H), 3.71 (s, 2H), 3.62-3.58 (td, J=11.4 Hz, 2.1 Hz, 2H), 2.48-2.44 (d, J=13.3 Hz, 2H), 2.11-2.04 (ddd, J=14.3 Hz, 10.5 Hz, 4.3 Hz, 2H). MS (ESI) m/z: Calculated for C$_{26}$H$_{20}$F$_3$N$_5$O$_3$S: 539.12. found: 540.0 (M+H)$^+$.

Example 28

3-(N'-Hydroxycarbamimidoyl)-8-methoxybenzoic acid

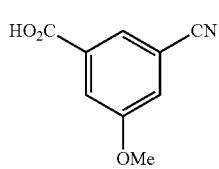

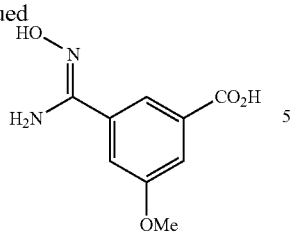

This compound was synthesized from 3-cyano-5-methoxybenzoic acid as described in example 1 step 4 (500 mg, yield 84%): $^1$H NMR (400 MHz, DMSO-$d_6$) δ 11.27 (br s, 1H), 9.07 (br s, 2H), 7.83 (s, 1H), 7.68 (s, 1H), 7.55 (m, 1H), 3.89 (s, 3H). MS (ESI) m/z: Calculated for $C_9H_{10}N_2O_4$: 210.06. found: 211.2 (M+H)$^+$.

3-Methoxy-8-(5-(trifluoromethyl)-1,2,4-oxadiazol-3-yl)benzoic acid

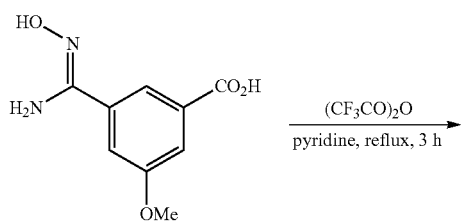

This compound was synthesized from 3-(N'-hydroxycarbamimidoyl)-5-methoxybenzoic acid as described in example 1 step 5 (170 mg, yield 40%), and it was carried through without any further purification. $^1$H NMR (400 MHz, DMSO-$d_6$) δ 8.16 (t, J=1.3 Hz, 1H), 7.74 (dd, J=2.6 Hz, 1.5 Hz, 1H), 7.69 (dd, J=2.6 Hz, 1.5 Hz, 1H), 3.91 (s, 3H). MS (ESI) m/z: Calculated for $C_{11}H_7F_3N_2O_4$: 288.04. found: 287.0 (M–H)$^-$.

3-Methoxy-N-((4-(4-phenylthiazol-2-yl)tetrahydro-2H-pyran-4-yl)methyl)-5-(5-(trifluoromethyl)-1,2,4-oxadiazol-3-yl)benzamide

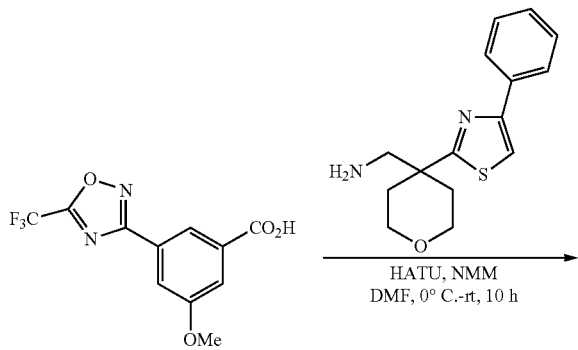

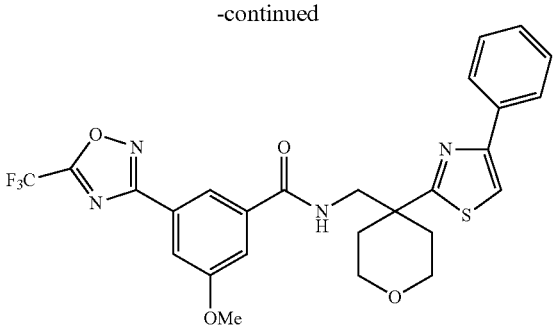

This compound was synthesized from (4-(4-phenylthiazol-2-yl)tetrahydro-2H-pyran-4-yl)methanamine and 3-methoxy-5-(5-(trifluoromethyl)-1,2,4-oxadiazol-3-yl)benzoic acid as described in example 8 step 6 (70 mg, yield 46%): $^1$H NMR (400 MHz, CDCl$_3$) δ 8.75 (t, J=6.3 Hz, 1H), 8.08 (s, 1H), 8.02 (s, 1H), 7.91 (d, J=7.0 Hz, 2H), 7.63 (m, 1H), 7.57 (m, 1H), 7.38-7.35 (m, 2H), 7.30-7.26 (m, 1H), 3.85 (s, 3H), 3.83 (m, 2H), 3.56 (d, J=6.5 Hz, 2H), 3.41-3.36 (m, 2H), 2.23 (d, J=13.5 Hz, 2H), 2.01-1.94 (m, 2H). MS (ESI) m/z: Calculated for $C_{26}H_{23}F_3N_4O_4S$: 544.14. found: 545.2 (M+H)$^+$.

Example 29

2-(4-(4-Fluorophenyl)thiazol-2-yl)ethanamine

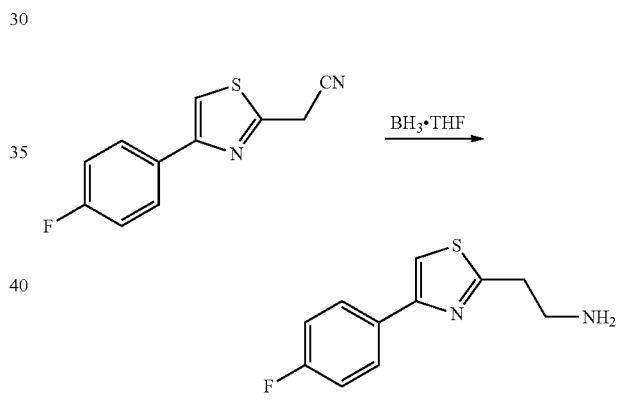

2-(4-(4-fluorophenyl)thiazol-2-yl)acetonitrile (400 mg, 1.83 mmol) was dissolved in tetrahydrofuran (10 mL) at room temperature. Borane tetrahydrofuran complex solution (1M in tetrahydrofuran, 9.16 mL, 9.16 mmol) was added and the reaction mixture was stirred for 1 h at room temperature. The reaction mixture was cooled to 0° C. and quenched with methanol (5 eq., 0.4 mL). The reaction was allowed to warm to room temperature and 2N HCl was added until the reaction mixture was confirmed acidic by a pH paper. The reaction mixture was then refluxed at 65° C. for 30 min. The reaction mixture was then allowed to cool to room temperature and was concentrated under reduced pressure. The solid obtained was triturated with ether (2×20 mL) and dichloromethane (2×20 mL). The remaining solid was dissolved in water (50 mL) and basified to pH ~11 with NaOH pellets. The aqueous mixture was then extracted with ether (2×100 mL). The organic layer was dried over anhdrous sodium sulfate and concentrated under reduced pressure to give the crude product, which was used directly without any purification in the next step (100 mg, 25% yield). MS (ESI) m/z: Calculated for $C_{11}H_{11}FN_2S$: 222.06. found: 223.1 (M+H)$^+$.

N-(2-(4-(4-Fluorophenyl)thiazol-2-yl)ethyl)-3-(5-(trifluoromethyl)-1,2,4-oxadiazol-3-yl)benzamide

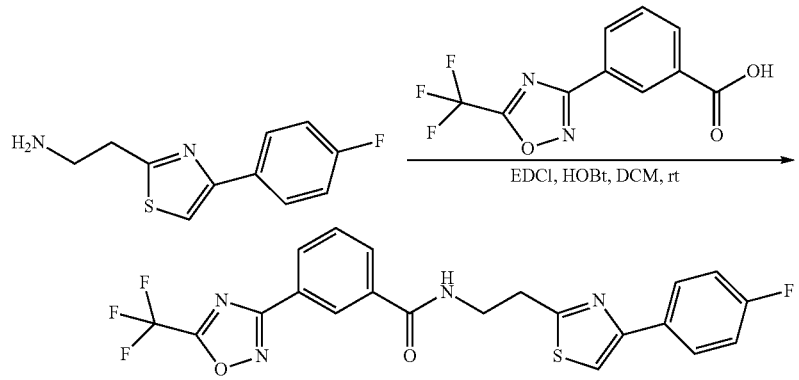

This compound was synthesized from 2-(4-(4-fluorophenyl)thiazol-2-yl)ethanamine and 3-(5-(trifluoromethyl)-1,2,4-oxadiazol-3-yl)benzoic acid as described in example 26 step 6 (180 mg, 86% yield). $^1$H NMR (CDCl$_3$) δ 8.51 (1H, t), 8.22 (1H, dt), 8.04 (1H, dt), 7.85-7.81 (2H, m), 7.64 (1H, m), 7.59 (1H, t), 7.31 (1H, s), 7.06-7.02 (2H, m), 3.97 (2H, q), 3.35 (2H, t); MS (ESI) m/z: Calculated for C$_{21}$H$_{14}$F$_4$N$_4$O$_2$S: 462.08. found: 463.1 (M+H)$^+$.

Example 30

2-(4-(4-Bromophenyl)thiazol-2-yl)acetonitrile

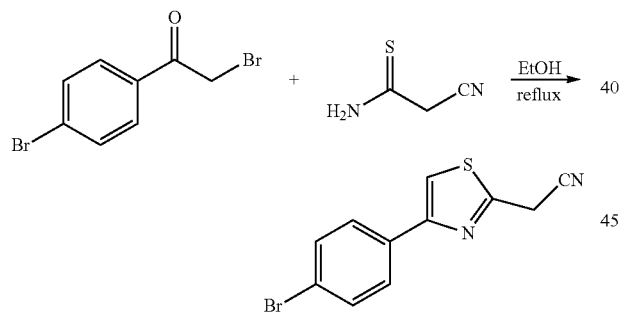

This compound was synthesized from 2-bromo-1-(4-bromophenyl)ethanone and 2-cyanothioacetamide as described in example 1 step 1 (2.4 g, 48% yield), and it was carried through without further purification. MS (ESI) m/z: Calculated for C$_{11}$H$_7$BrN$_2$S: 277.95. found: 279.0 (M+H)$^+$.

4-(4-(4-Bromophenyl)thiazol-2-yl)tetrahydro-2H-pyran-4-carbonitrile

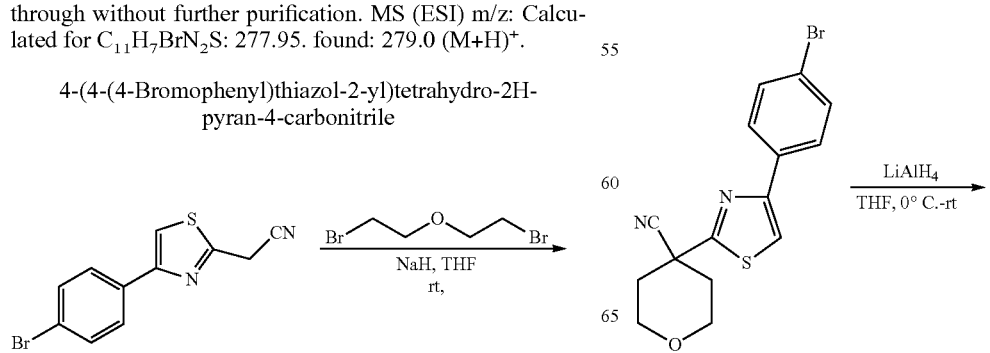

-continued

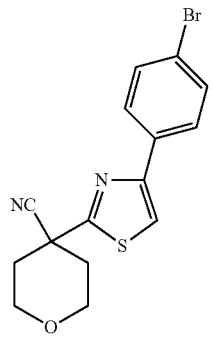

This compound was synthesized from 2-(4-(4-bromophenyl)thiazol-2-yl)acetonitrile as described in example 1 step 2 (1.9 g, yield 80%). MS (ESI) m/z: Calculated for C$_{15}$H$_{13}$BrN$_2$OS: 347.99. found: 349.0 (M+H)$^+$.

(4-(4-(4-Bromophenyl)thiazol-2-yl)tetrahydro-2H-pyran-4-yl)methanamine

-continued

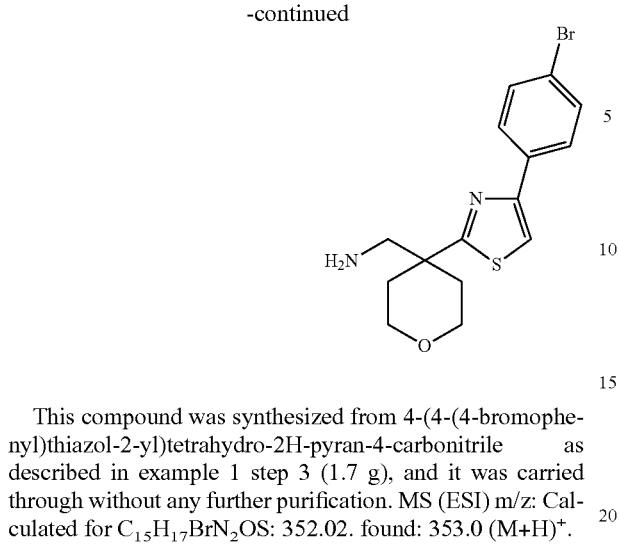

This compound was synthesized from 4-(4-(4-bromophenyl)thiazol-2-yl)tetrahydro-2H-pyran-4-carbonitrile as described in example 1 step 3 (1.7 g), and it was carried through without any further purification. MS (ESI) m/z: Calculated for $C_{15}H_{17}BrN_2OS$: 352.02. found: 353.0 (M+H)$^+$.

4-(2-(4-(Aminomethyl)tetrahydro-2H-pyran-4-yl)thiazol-4-yl)benzonitrile (4-(4-(4-Bromophenyl)thiazol-2-yl)tetrahydro-2H-pyran-4-yl)methanamine (200 mg, 0.56 mmol), zinc cyanide (53 mg, 0.45 mmol), and DMF (2 mL) were placed in microwave tube and degassed. 1,1'-Bis(diphenylphosphino)ferrocene-palladium(II)dichloride (41 mg, 0.05 mmol) was added. Reaction was microwaved at 200° C. for 10 min intervals until complete. The reaction was quenched with ammonium hydroxide/water (1:4) and washed with ethyl acetate. Organic layer was dried over sodium sulfate. Crude was purified using silica chromatography with an ethyl acetate wash followed by 10% Methanol in dichloromethane with 1% triethylamine to yield 4-(2-(4-(aminomethyl)tetrahydro-2H-pyran-4-yl)thiazol-4-yl)benzonitrile (20 mg, 10% yield). MS (ESI) m/z: Calculated for $C_{16}H_{17}N_3OS$: 299.11. found: 300.1 (M+H)$^+$.

N-((4-(4-(4-Cyanophenyl)thiazol-2-yl)tetrahydro-2H-pyran-4-yl)methyl)-3-(5-(trifluoromethyl)-1,2,4-oxadiazol-3-yl)benzamide

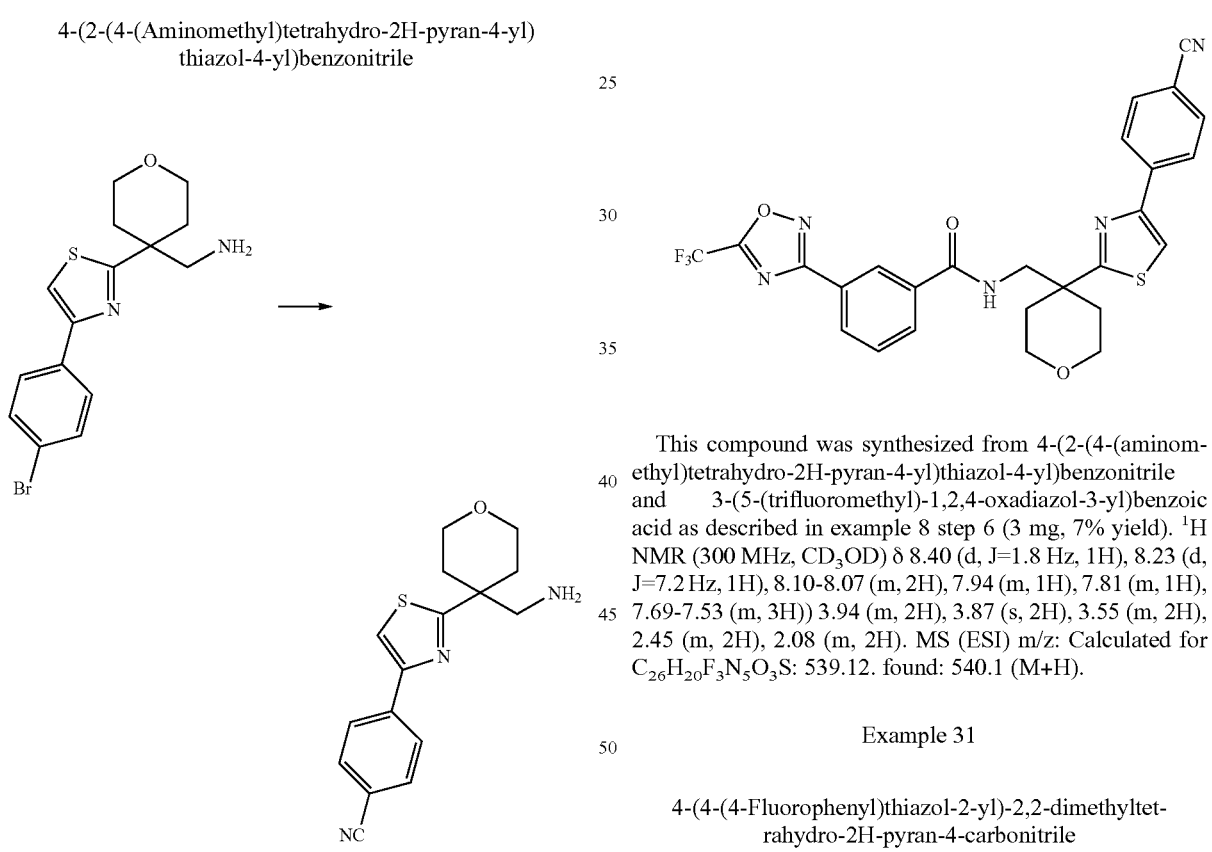

This compound was synthesized from 4-(2-(4-(aminomethyl)tetrahydro-2H-pyran-4-yl)thiazol-4-yl)benzonitrile and 3-(5-(trifluoromethyl)-1,2,4-oxadiazol-3-yl)benzoic acid as described in example 8 step 6 (3 mg, 7% yield). $^1$H NMR (300 MHz, CD$_3$OD) δ 8.40 (d, J=1.8 Hz, 1H), 8.23 (d, J=7.2 Hz, 1H), 8.10-8.07 (m, 2H), 7.94 (m, 1H), 7.81 (m, 1H), 7.69-7.53 (m, 3H)) 3.94 (m, 2H), 3.87 (s, 2H), 3.55 (m, 2H), 2.45 (m, 2H), 2.08 (m, 2H). MS (ESI) m/z: Calculated for $C_{26}H_{20}F_3N_5O_3S$: 539.12. found: 540.1 (M+H).

Example 31

4-(4-(4-Fluorophenyl)thiazol-2-yl)-2,2-dimethyltetrahydro-2H-pyran-4-carbonitrile

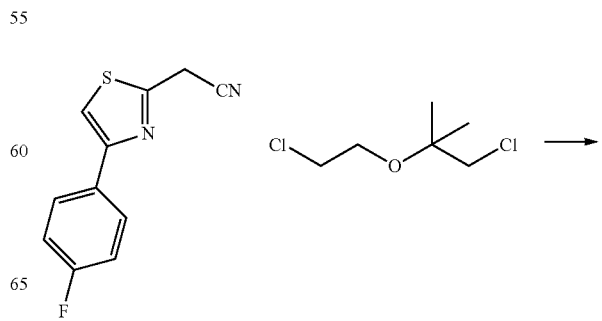

-continued

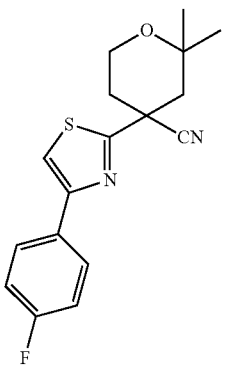

2-(4-(4-Fluorophenyl)thiazol-2-yl)acetonitrile (325 mg, 1.5 mmol), potassium carbonate (617 mg, 4.47 mmol), and 1-chloro-2-(2-chloroethoxy)-2-methylpropane (254 mg, 1.5 mmol) in DMF (5 mL) were microwaved at 160° C. for 5 min then 20 min. A second addition of potassium carbonate and 1-chloro-2-(2-chloroethoxy)-2-methylpropane was made and then the reaction was microwaved again for 30 min two times. The reaction was diluted with ethyl acetate and washed with water. The organic layer was dried over sodium sulfate and purified on silica using a gradient of 0-30% ethyl acetate/hexanes to afford 4-(4-(4-Fluorophenyl)thiazol-2-yl)-2,2-dimethyltetrahydro-2H-pyran-4-carbonitrile (228 mg, 48% yield). MS (ESI) m/z: Calculated for $C_{17}H_{17}FN_2OS$: 316.10. found: 317.1 (M+H)$^+$.

(4-(4-(4-Fluorophenyl)thiazol-2-yl)-2,2-dimethyltetrahydro-2H-pyran-4-yl)methanamine

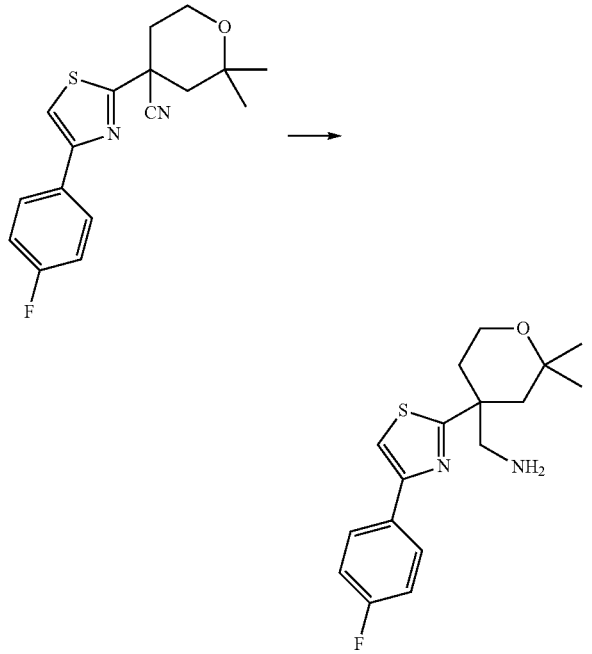 [SMILES: CC1(C)CC(C#N)(c2nc(-c3ccc(F)cc3)cs2)CCO1 ; CC1(C)CC(CN)(c2nc(-c3ccc(F)cc3)cs2)CCO1]

This compound was synthesized from 4-(4-(4-fluorophenyl)thiazol-2-yl)-2,2-dimethyltetrahydro-2H-pyran-4-carbonitrile as described in example 1 step 3 (100 mg), and it was carried through without any further purification. MS (ESI) m/z: Calculated for $C_{17}H_{21}FN_2OS$: 320.14. found: 321.1 (M+H)$^+$.

N-((4-(4-(4-Fluorophenyl)thiazol-2-yl)-2,2-dimethyltetrahydro-2H-pyran-4-yl)methyl)-3-(5-(trifluoromethyl)-1,2,4-oxadiazol-3-yl)benzamide

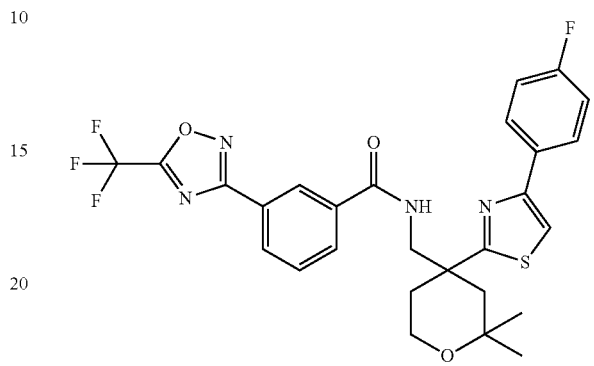

This compound was synthesized from (4-(4-(4-fluorophenyl)thiazol-2-yl)-2,2-dimethyltetrahydro-2H-pyran-4-yl)methanamine and 3-(5-(trifluoromethyl)-1,2,4-oxadiazol-3-yl)benzoic acid as described in example 8 step 6 (7 mg, yield 17%): $^1$H NMR (500 MHz, CD$_3$OD) δ 8.41 (t, J=1 Hz, 1H), 8.23 (d, J=4 Hz, 1H), 7.96-7.90 (m, 3H), 7.76 (s, 1H), 7.61 (t, J=7.7 Hz, 1H), 7.69-7.04 (t, J=8.8 Hz, 2H), 3.88 (m, 2H), 3.60 (s, 2H), 2.52 (m, 2H), 1.95 (m, 2H), 1.29 (s, 3H), 0.81 (s, 3H). MS (ESI) m/z: Calculated for $C_{27}H_{24}F_4N_4O_3S$: 560.15. found: 561.1 (M+H)$^+$.

Example 32

3-Cyanobenzene-1-sulfonyl chloride

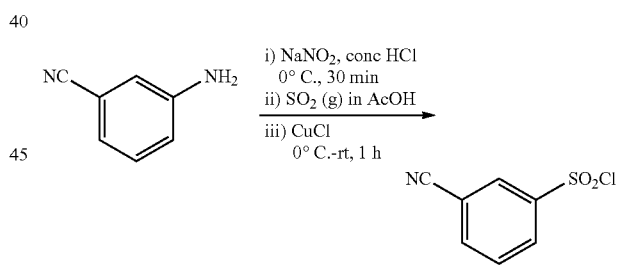

3-Aminobenzonitrile (2.5 g, 21 mmol) was dissolved in conc. HCl (20 mL) and water (20 mL), cooled to 0° C. and a solution of sodium nitrite (1.5 g, 22 mmol) in water (5 mL) was added dropwise. The reaction mixture was stirred for 10 min to complete the diazonium salt formation. In a separate flask was added copper(I) chloride (0.2 g) over a saturated solution of sulfur dioxide in AcOH (25 mL) and stirred at 0° C. for 10 min. The resulting solution was added dropwise to the diazonium salt and stirred at 0° C. for 1 h. The reaction mixture poured into ice water and the product was extracted with tert-butylmethylether. The combined organic layer was washed with water and brine. The crude product was purified by column chromatography (silica gel 60-120 mesh using 5% EtOAc in petroleum ether) to get the pure 3-cyanobenzene-1-sulfonyl chloride (1.9 g, yield 45%) as an off-white solid. $^1$H NMR (300 MHz, CDCl$_3$) δ 8.35 (t, J=1.5 Hz, 1H), 8.31-8.27 (m, 1H), 8.06-8.02 (m, 1H), 7.82 (t, J=7.9 Hz, 1H).

3-Cyano-N-((4-(4-phenylthiazol-2-yl)tetrahydro-2H-pyran-4-yl)methyl)benzenesulfonamide

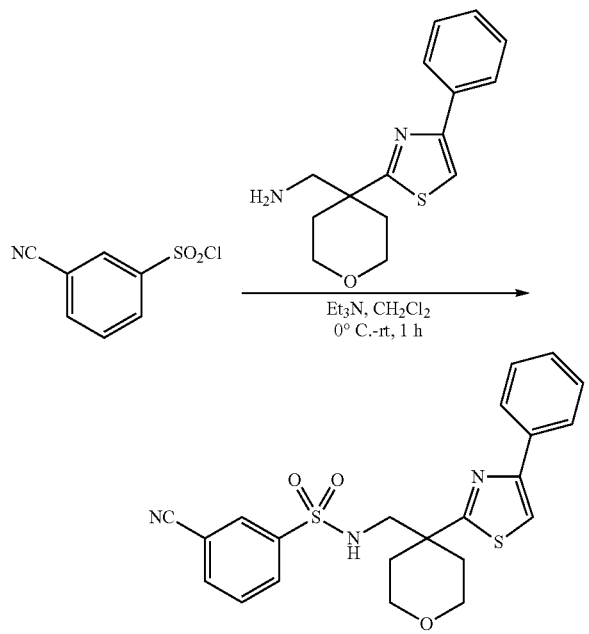

Et$_3$N (0.15 mL, 1.43 mmol) was added dropwise to an ice cold solution of (4-(4-phenylthiazol-2-yl)tetrahydro-2H-pyran-4-yl)methanamine (130 mg, 0.48 mmol) in dry CH$_2$Cl$_2$ (3 mL). The resulting reaction mixture was stirred at 0° C. for 5 min, then a solution of 3-cyanobenzene-1-sulfonyl chloride (105 mg, 0.52 mmol) in dry CH$_2$Cl$_2$ (2 mL) was added dropwise. The reaction mixture was further stirred at room temperature for 1 h. The reaction mixture was diluted with CH$_2$Cl$_2$ and the organic layer was washed with H$_2$O and brine, dried over anhydrous sodium sulfate and concentrated under reduced pressure. The residue was purified by column chromatography (silica gel 60-120 mesh, eluent 35% EtOAc in petroleum ether) to afford compound 3-cyano-N-((4-(4-phenylthiazol-2-yl)tetrahydro-2H-pyran-4-yl)methyl)benzenesulfonamide (0.13 g, yield 61%) as an off-white solid. $^1$H NMR (300 MHz, CDCl$_3$) δ 8.03-7.98 (m, 2H), 7.85-7.76 (m, 3H), 7.59-7.54 (m, 1H), 7.50-7.38 (m, 4H), 3.87-3.79 (m, 2H), 3.74-3.66 (m, 2H), 3.36 (s, 2H), 2.27-2.19 (ddd, J=13.5 Hz, 6.7 Hz, 3.5 Hz, 2H), 2.01-1.93 (ddd, J=13.8 Hz, 7.5 Hz, 3.7 Hz, 2H). MS (ESI) m/z: Calculated for C$_{22}$H$_{21}$N$_3$O$_3$S$_2$: 439.10. found: 440.0 (M+H)$^+$.

N'-Hydroxy-3-(N-((4-(4-phenylthiazol-2-yl)tetrahydro-2H-pyran-4-yl)methyl)sulfamoyl)benzimidamide

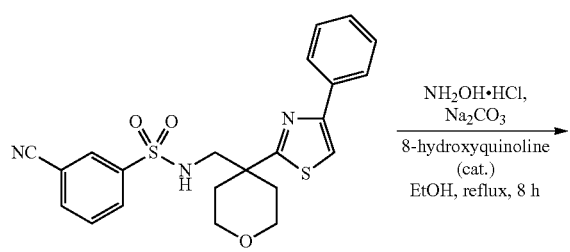

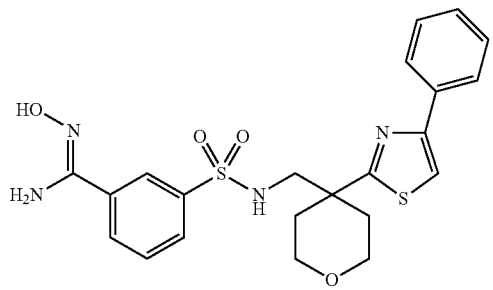

This compound was synthesized from 3-cyano-N-((4-(4-phenylthiazol-2-yl)tetrahydro-2H-pyran-4-yl)methyl)benzenesulfonamide as described in example 1 step 4 (125 mg, yield 89%) and it was carried through without further purification, $^1$H NMR (400 MHz, DMSO-d$_6$) δ 9.83 (s, 1H), 8.08 (m, 2H), 7.95 (d, J=7.0 Hz, 2H), 7.86 (d, J=7.9 Hz, 1H), 7.79 (t, J=6.7 Hz, 1H), 7.74 (d, J=7.9 Hz, 1H), 7.55 (m, 1H), 7.44 (m, 2H), 7.34 (m, 1H), 5.96 (s, 2H), 3.78 (m, 2H), 3.41 (t, J=10.2 Hz, 2H), 3.01 (d, J=6.7 Hz, 2H), 2.15-2.12 (m, 2H), 1.94-1.87 (m, 2H). MS (ESI) m/z: Calculated for C$_{22}$H$_{24}$N$_4$O$_2$S$_2$: 472.12. found: 473.2 (M+H)$^+$.

N-((4-(4-Phenylthiazol-2-yl)tetrahydro-2H-pyran-4-yl)methyl)-3-(5-(trifluoromethyl)-1,2,4-oxadiazol-3-yl)benzenesulfonamide

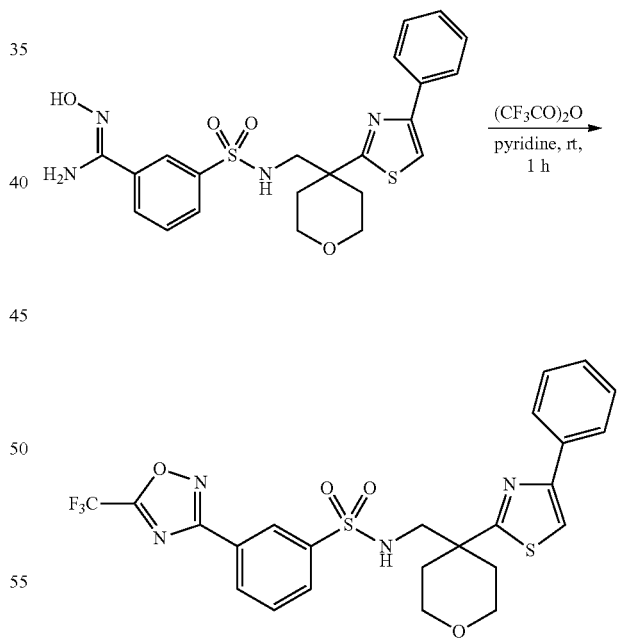

This compound was synthesized from N'-hydroxy-3-(N-((4-(4-phenylthiazol-2-yl)tetrahydro-2H-pyran-4-yl)methyl)sulfamoyl)benzimidamide as described in example 1 step 5 (80 mg, yield 57%). $^1$H NMR (400 MHz, DMSO-d$_6$) δ 8.32 (s, 1H), 8.22 (d, J=7.6 Hz, 1H), 8.05 (t, J=6.9 Hz, 1H), 7.999 (m, 2H), 7.89 (d, J=7.3 Hz, 2H), 7.76 (t, J=7.8 Hz, 1H), 7.40 (m, 2H), 7.30 (m, 1H), 3.79-3.76 (m, 2H), 3.39 (t, J=10.8 Hz, 2H), 3.11 (d, J=6.7 Hz, 2H), 2.16-2.13 (m, 2H), 1.93-1.86

(m, 2H). MS (ESI) m/z: Calculated for $C_{24}H_{21}F_3N_4O_2S_2$: 550.10. found: 551.0 (M+H)$^+$.

Example 33

3-Bromo-5-(methoxycarbonyl)benzoic acid

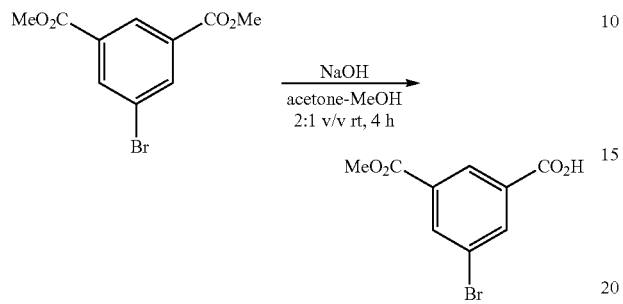

Dimethyl-5-bromoisophthalate (3 g, 11.0 mmol) was dissolved in acetone-$H_2O$ (2:1 v/v, 60 mL) and NaOH (0.40 g, 11.0 mmol) was added. The reaction mixture was allowed to stir for 4 h. Acetone was removed under reduced pressure and the aqueous layer was washed with EtOAc, acidified to pH ~2-3 using 1.5N HCl, and extracted with EtOAc. The organic layer was dried over anhydrous sodium sulfate and the solvent was removed under reduced pressure to yield 3-bromo-5-(methoxycarbonyl)benzoic acid (2.55 g, yield 89%): $^1$H NMR (300 MHz, DMSO-$d_6$) δ 13.75 (br s, 1H), 8.40 (d, J=1.0 Hz, 1H), 8.26 (d, J=1.4 Hz, 1H), 8.23 (d, J=1.0 Hz, 1H), 3.89 (s, 3H). MS (ESI) m/z: Calculated for $C_9H_7BrO_4$: 257.95. found: 258.0 (M+H)$^+$.

Methyl 3-bromo-5-(methoxy(methyl)carbamoyl)benzoate

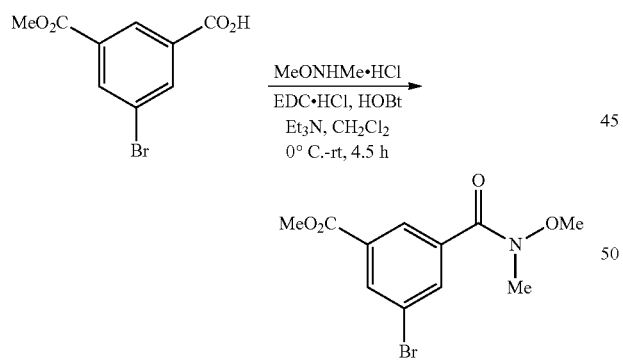

N,O-Dimethylhydroxylamine hydrochloride (1.15 g, 11.8 mmol) was dissolved in $CH_2Cl_2$ (50 mL) and $Et_3N$ (4.8 mL, 34.4 mmol) was added. The solution was stirred for 30 min. The resultant solution was cooled to 0° C. and compound 3-bromo-5-(methoxycarbonyl)benzoic acid (2.55 g, 9.84 mmol) was added followed by EDC.HCl (3.77 g, 19.6 mmol) and HOBt (0.26 g, 1.96 mmol). The reaction mixture was allowed to come to room temperature and stirred for another 4 h. After completion, the reaction mixture was diluted with $CH_2Cl_2$. The organic layer was washed with water and brine solution and dried over anhydrous sodium sulfate. Solvent was removed under reduced pressure and the crude product was purified by column chromatography (silica 60-120 mesh, eluent 20% EtOAc in petroleum ether) to get methyl 3-bromo-5-(methoxy(methyl)carbamoyl)benzoate (2.3 g, yield 77%) as colorless liquid. $^1$H NMR (400 MHz, CDCl$_3$) δ 8.29 (m, 1H), 8.27 (t, J=1.8 Hz, 1H), 8.02 (t, J=1.6 Hz, 1H), 3.95 (s, 3H), 3.57 (s, 3H), 3.39 (s, 3H). MS (ESI) m/z: Calculated for $C_{11}H_{12}BrNO_4$: 300.99. found: 302.0 (M+H)$^+$.

Methyl 3-acetyl-5-bromobenzoate

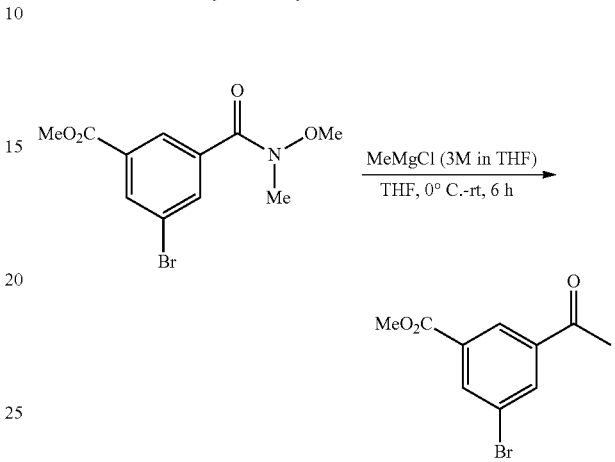

The compound methyl 3-bromo-5-(methoxy(methyl)carbamoyl)benzoate (2.3 g, 7.6 mmol) was dissolved in dry THF (50 mL), solution was cooled to 0° C. and methylmagnesium chloride (3M in THF, 2.5 mL, 7.6 mmol)) was added dropwise. The reaction mixture was slowly allowed to come to room temperature and stirred further for 6 h. The reaction mixture was cooled to 0° C. and quenched with saturated $NH_4Cl$ solution. The product was extracted with EtOAc. The organic layer was washed with water and brine and dried over anhydrous sodium sulfate. The solvent was removed under reduced pressure. The crude product was purified by column chromatography (silica 60-120 mesh, eluent 5% EtOAc in petroleum ether) to get methyl 3-acetyl-5-bromobenzoate (0.95 g, yield 49%) as a white solid. $^1$H NMR (400 MHz, CDCl$_3$) δ 8.51 (t, J=1.3 Hz, 1H), 8.37 (t, J=1.7 Hz, 1H), 8.28 (t, J=1.6 Hz, 1H), 3.97 (s, 3H), 2.65 (s, 3H).

3-Bromo-5-ethylbenzoic acid

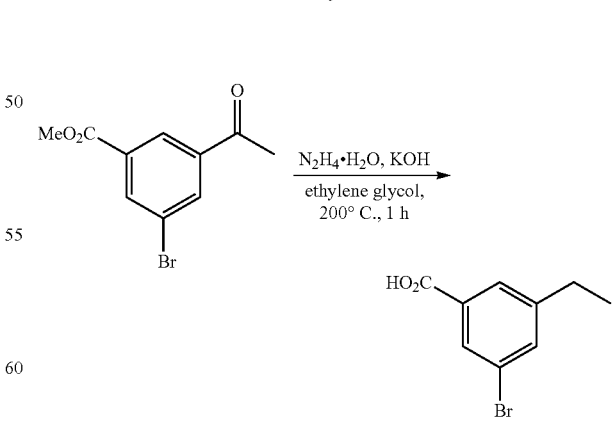

The compound methyl 3-acetyl-5-bromobenzoate (1.2 g, 4.8 mmol) was dissolved in ethylene glycol (10 mL) and KOH (0.41 g, 7.3 mmol) followed by hydrazine hydrate (0.44 mL, 7.3 mmol) were added. The reaction mixture was heated to 200° C. for 1 h. The reaction mixture was cooled to room temperature and diluted with water. The pH of the aqueous layer was adjusted to 2-3 using 1.5N HCl. The product was extracted with EtOAc. The organic layer was washed with water and brine and dried over anhydrous sodium sulfate. The solvent was removed under reduced pressure. The crude product was purified by column chromatography (silica 60-120 mesh, eluent 50% EtOAc in petroleum ether) to yield 3-bromo-5-ethylbenzoic acid (0.95 g, yield 89%) as a yellow solid. $^1$H NMR (300 MHz, CDCl$_3$) δ 8.07 (m, 1H), 7.88 (m, 1H), 7.59 (m, 1H), 2.73 (q, J=7.6 Hz, 2H), 1.28 (t, J=7.6 Hz, 3H). MS (ESI) m/z: Calculated for C$_9$H$_9$BrO$_2$: 227.98. found: 229.0 (M+H)$^+$.

Methyl 3-bromo-5-ethylbenzoate

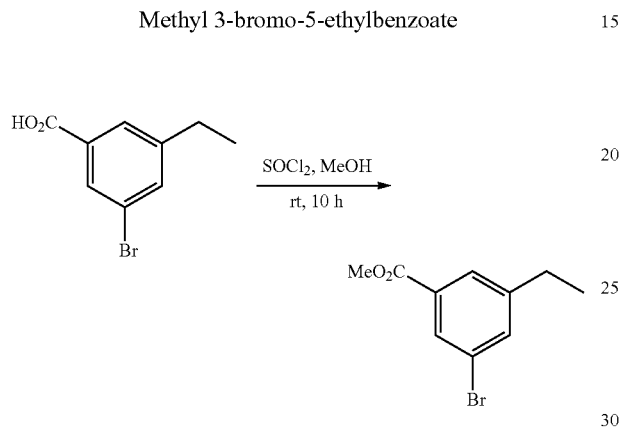

The compound 3-bromo-5-ethylbenzoic acid (0.95 g, 4.14 mmol) was dissolved in MeOH (50 mL), reaction mixture was cooled to 0° C. and SOCl$_2$ (0.5 mL) was added. The reaction mixture was allowed to stir at room temperature for 10 h. The reaction mixture was concentrated under reduced pressure and diluted with CH$_2$Cl$_2$. The organic layer was washed with 10% NaHCO$_3$ solution, water and brine. The organic phase was dried over anhydrous sodium sulfate and solvent was removed under reduced pressure. Methyl 3-bromo-5-ethylbenzoate (0.92 g, yield 92%) was isolated as colorless liquid and carried through without further purification. $^1$H NMR (300 MHz, CDCl$_3$) δ 7.99 (t, J=1.6 Hz, 1H), 7.81 (d, J=1.4 Hz, 1H), 7.54 (t, J=1.6 Hz, 1H), 3.92 (s, 3H), 2.69 (q, J=7.6 Hz, 2H), 1.26 (t, J=7.6 Hz, 3H).

Methyl 3-cyano-5-ethylbenzoate

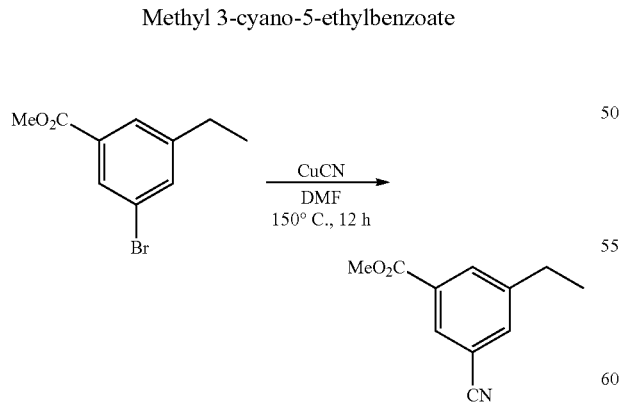

The product methyl 3-bromo-5-ethylbenzoate (0.9 g, 3.7 mmol) was dissolved in dry DMF (50 mL) and copper cyanide (0.84 g, 9.43 mmol) was added. The reaction mixture was heated to 150° C. under argon atmosphere for 12 h (monitored by TLC; petroleum ether/EtOAc 9:1). The reaction mixture was allowed to come to room temperature and then quenched with saturated ammonium chloride solution. The reaction mixture was diluted with EtOAc and filtered through a Celite bed. The filtrate was diluted with EtOAc and the organic layer was washed with water and brine. The solvent was evaporated under reduced pressure. The crude product was purified by column chromatography (silica 60-120 mesh, eluent 5% EtOAc in petroleum ether) to get methyl 3-cyano-5-ethylbenzoate (0.27 g, yield 39%) as colorless liquid, which was carried through without further purification.

3-Cyano-5-ethylbenzoic acid

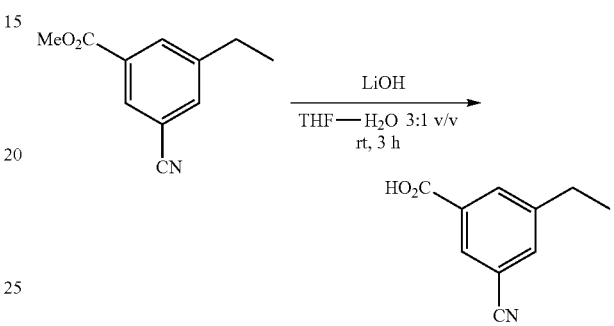

The compound methyl 3-cyano-5-ethylbenzoate (270 mg, 1.42 mmol) was dissolved in THF—H$_2$O (7:3 v/v, 10 mL), solution was cooled to 0° C. and LiOH (59 mg, 1.42 mmol) was added. The reaction mixture was allowed to come to room temperature and stirred for 3 h (monitored by TLC; petroleum ether/EtOAc 1:1). Solvent THF was removed under reduced pressure and the aqueous layer was washed with EtOAc to remove the non-polar impurities. The pH of the aqueous layer was adjusted to 2-3 using 1.5N HCl. The product was extracted with EtOAc. The organic layer was dried over anhydrous sodium sulfate and the solvent was removed under reduced pressure to yield 3-cyano-5-ethylbenzoic acid (200 mg, yield 80%), which was carried through without further purification. $^1$H NMR (400 MHz, CDCl$_3$) δ 8.23 (m, 1H), 8.17 (m, 1H), 7.74 (m, 1H), 2.81 (q, J=7.6 Hz, 2H), 1.32 (t, J=7.6 Hz, 3H).

3-Ethyl-5-(N'-hydroxycarbamimidoyl)benzoic acid

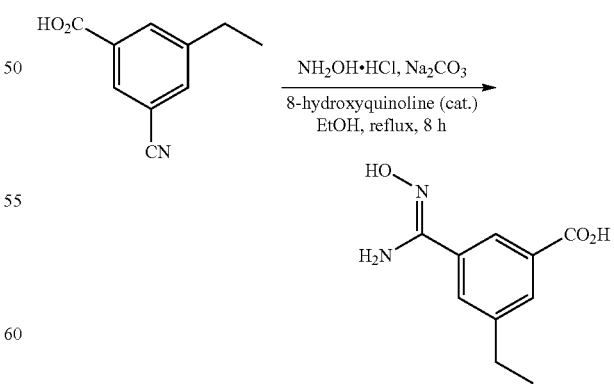

This compound was synthesized from 3-cyano-5-ethylbenzoic acid as described in example 1 step 4 (200 mg, crude), and it was carried through without further purification.

3-Ethyl-5-(5-(trifluoromethyl)-1,2,4-oxadiazol-3-yl)benzoic acid

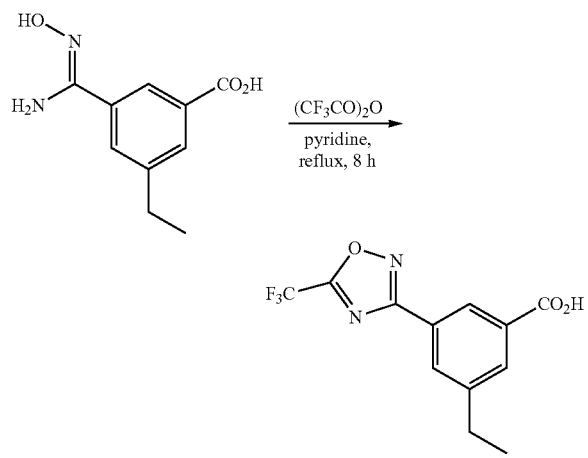

This compound was synthesized from 3-ethyl-5-(N'-hydroxycarbamimidoyl)benzoic acid as described in example 1 step 5 (130 mg, yield 52%). $^1$H NMR (300 MHz, CDCl$_3$) δ 8.69 (m, 1H), 8.21 (m, 1H), 8.17 (m, 1H), 2.85 (q, J=7.6 Hz, 2H), 1.33 (t, J=7.6 Hz, 3H). MS (ESI) m/z: Calculated for C$_{12}$H$_9$F$_3$N$_2$O$_3$: 286.06. found: 285.0 (M–H)$^-$.

3-Ethyl-N-((4-(4-phenylthiazol-2-yl)tetrahydro-2H-pyran-4-yl)methyl)-5-(5-(trifluoromethyl)-1,2,4-oxadiazol-3-yl)benzamide

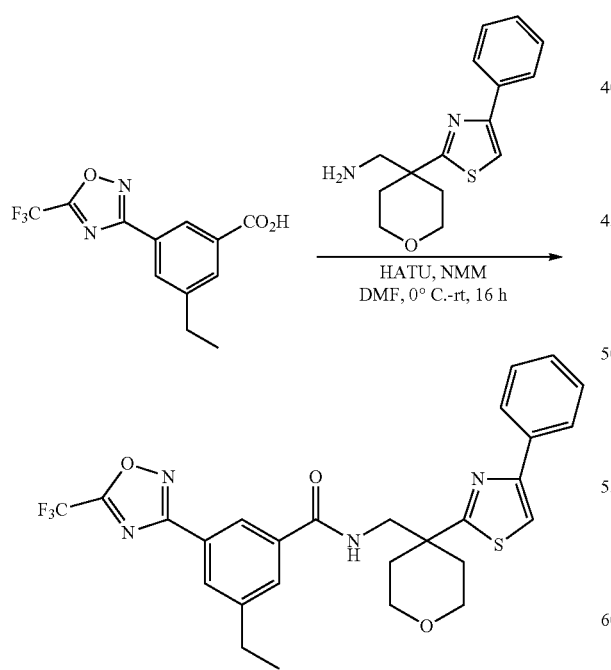

This compound was synthesized from (4-(4-phenylthiazol-2-yl)tetrahydro-2H-pyran-4-yl)methanamine and 3-ethyl-5-(5-(trifluoromethyl)-1,2,4-oxadiazol-3-yl)benzoic acid as described in example 8 step 6 (85 mg, yield 45%). $^1$H NMR (400 MHz, CDCl$_3$) δ 8.29 (s, 1H), 8.05 (s, 1H), 7.89 (m, 2H), 7.80 (s, 1H), 7.52 (m, 2H), 7.37-7.29 (m, 3H), 4.00-3.94 (m, 2H), 3.89 (d, J=5.5 Hz, 2H), 3.78-3.72 (ddd, J=11.7 Hz, 7.8 Hz, 3.3 Hz, 2H), 2.69 (q, J=7.7 Hz, 2H), 2.36-2.30 (ddd, J=13.6 Hz, 6.5 Hz, 3.3 Hz, 2H), 2.08-2.02 (ddd, J=13.6 Hz, 7.7 Hz, 3.3 Hz, 2H), 1.23 (t, J=7.7 Hz, 3H). MS (ESI) m/z: Calculated for C$_{27}$H$_{25}$F$_3$N$_4$O$_3$S: 542.16. found: 543.2 (M+H)$^+$.

Example 34

4-(3-Bromophenyl)tetrahydro-2H-pyran-4-carbonitrile

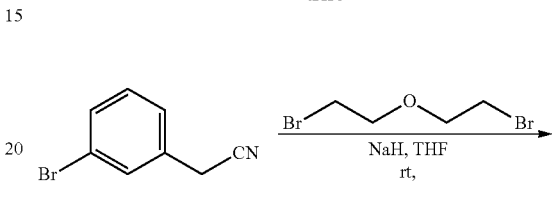

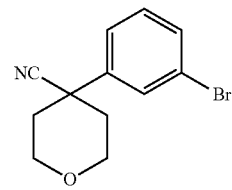

This compound was synthesized from 2-(3-bromophenyl)acetonitrile as described in example 1 step 2 (1.3 g, 65% yield). MS (ESI) m/z: Calculated for C$_{12}$H$_{12}$BrNO: 265.01. found: 266.0 (M+H)$^+$.

(4-(3-Bromophenyl)tetrahydro-2H-pyran-4-yl)methanamine

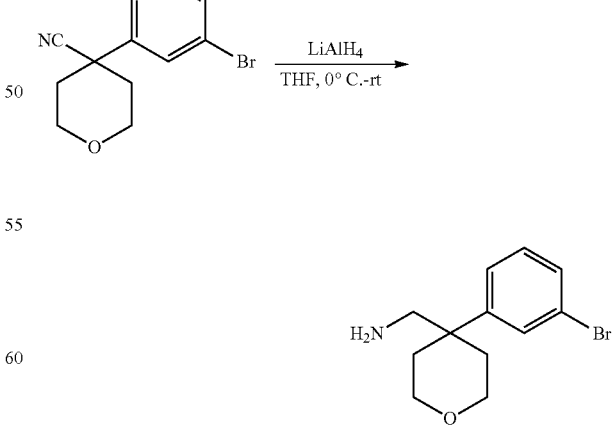

This compound was synthesized from 4-(3-bromophenyl)tetrahydro-2H-pyran-4-carbonitrile as described in example 1 step 3 (1.3 g, crude), and it was carried through without further purification. MS (ESI) m/z: Calculated for $C_{12}H_{16}BrNO$: 269.04. found: 270.0 (M+H)+.

N-((4-(3-Bromophenyl)tetrahydro-2H-pyran-4-yl)methyl)-3-(5-(trifluoromethyl)-1,2,4-oxadiazol-3-yl)benzamide

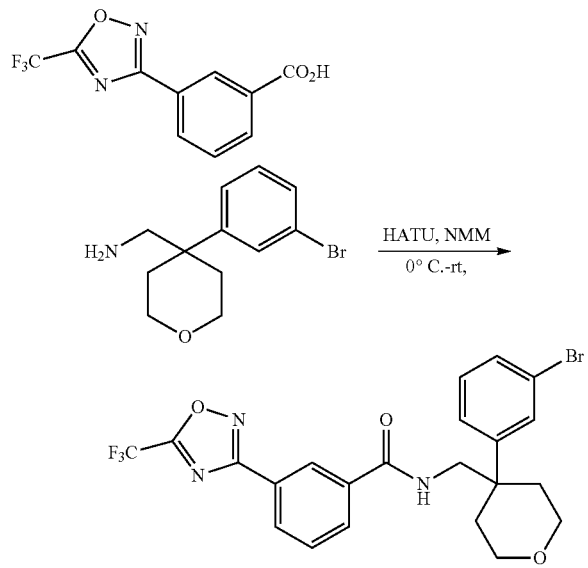

This compound was synthesized from (4-(3-bromophenyl)tetrahydro-2H-pyran-4-yl)methanamine and 3-(5-(trifluoromethyl)-1,2,4-oxadiazol-3-yl)benzoic acid as described in example 8 step 6 (40 mgs, 34% yield). $^1$H NMR (300 MHz, CDCl$_3$) δ 8.30-8.22 (m, 2H) 7.86 (d, J=3.7 Hz, 1H), 7.60 (t, J=3.7 Hz, 1H), 7.52-7.44 (m, 2H), 7.38-7.30 (m, 2H), 3.90 (m, 2H), 3.71 (d, J=3.3 Hz, 2H), 3.64 (m, 2H), 2.13 (m, 2H), 2.02 (m, 2H). MS (ESI) m/z: Calculated for $C_{22}H_{19}BrF_3N_3O_3$: 509.06. found: 509.9 (M+H)+.

Example 35

2-(4-(4-(Trifluoromethyl)phenyl)thiazol-2-yl)acetonitrile

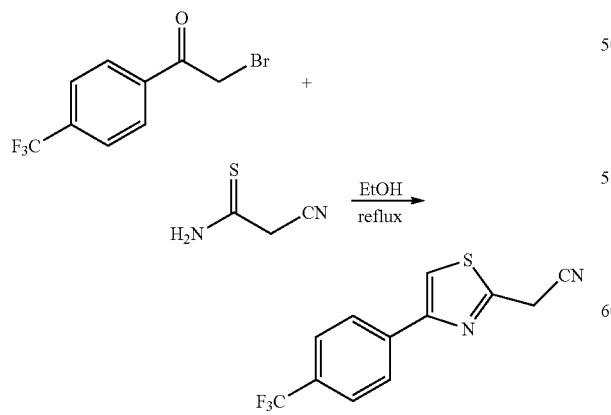

This compound was synthesized from 2-bromo-1-(4-(trifluoromethyl)phenyl)ethanone and 2-cyanothioacetamide as described in example 1 step 1 (2.4 g, 48% yield), and it was carried through without further purification. MS (ESI) m/z: Calculated for $C_{12}H_7F_3N_2S$: 268.03. found: 269.0 (M+H)+.

4-(4-(4-(Trifluoromethyl)phenyl)thiazol-2-yl)tetrahydro-2H-pyran-4-carbonitrile

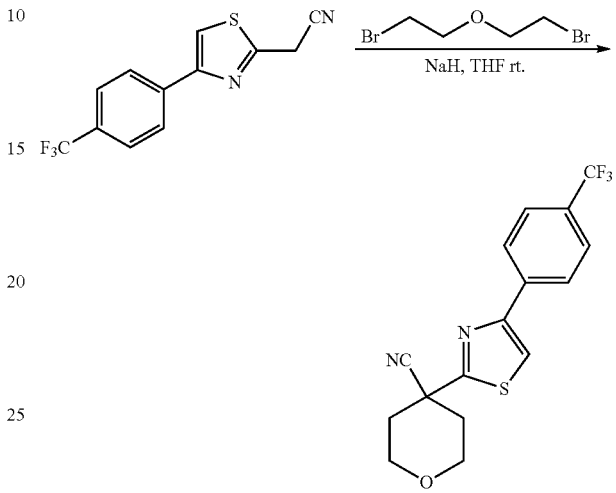

This compound was synthesized from 2-(4-(4-(trifluoromethyl)phenyl)thiazol-2-yl)acetonitrile as described in example 1 step 2 (690 mg, yield 98%), and it was carried through without further purification. MS (ESI) m/z: Calculated for $C_{16}H_{13}F_3N_2OS$: 338.07. found: 339.1 (M+H)+.

(4-(4-(4-(Trifluoromethyl)phenyl)thiazol-2-yl)tetrahydro-2H-pyran-4-yl)methanamine

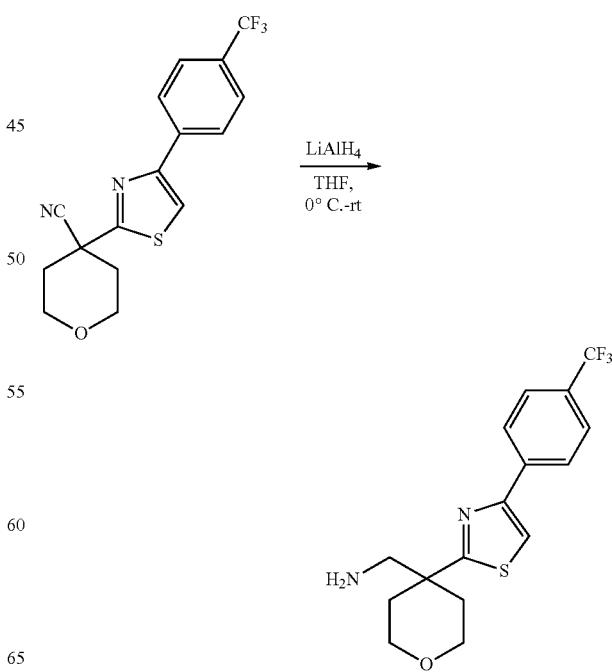

107

This compound was synthesized from 4-(4-(4-(trifluoromethyl)phenyl)thiazol-2-yl)tetrahydro-2H-pyran-4-carbonitrile as described in example 1 step 3. The material was carried through without further purification. MS (ESI) m/z: Calculated for $C_{16}H_{17}F_3N_2OS$: 342.10. found: 343.1 $(M+H)^+$.

3-(5-(Trifluoromethyl)-1,2,4-oxadiazol-3-yl)-N-((4-(4-(4-(trifluoromethyl)phenyl)thiazol-2-yl)tetrahydro-2H-pyran-4-yl)methyl)benzamide

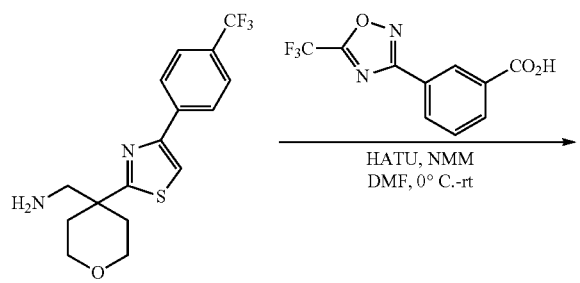

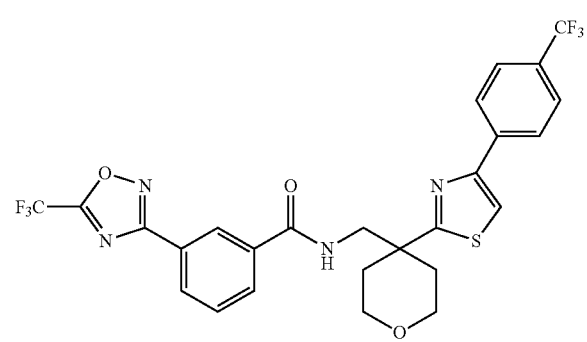

This compound was synthesized from (4-(4-(4-(trifluoromethyl)phenyl)thiazol-2-yl)tetrahydro-2H-pyran-4-yl)methanamine and 3-(5-(trifluoromethyl)-1,2,4-oxadiazol-3-yl)benzoic acid as described in example 8 step 6 (9 mgs, 19% yield). $^1$H NMR (300 MHz, CDCl$_3$) δ 8.44 (s, 1H), 8.24 (d, J=7.7 Hz, 1H), 8.00 (m, 2H), 7.65-7.58 (m, 4H), 7.36 (s, 1H), 4.02-3.78 (m, 4H), 3.74 (m, 2H), 2.30 (m, 2H), 2.05 (m, 2H). MS (ESI) m/z: Calculated for $C_{26}H_{20}F_6N_4O_3S$: 582.12. found: 583.1 $(M+H)^+$.

Example 36

2-Methyl-2-(4-(4-(trifluoromethyl)phenyl)thiazol-2-yl)propanenitrile

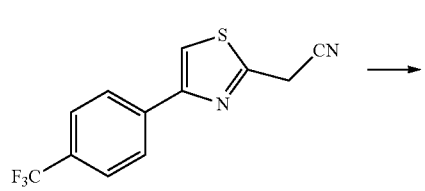

108

-continued

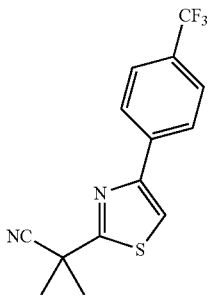

This compound was synthesized from 2-(4-(4-(trifluoromethyl)phenyl)thiazol-2-yl)acetonitrile using iodomethane as described in example 1 step 2 (620 mg, yield 73%) and it was carried through without further purification. MS (ESI) m/z: Calculated for $C_{14}H_{11}F_3N_2S$: 296.06. found: 297.0 $(M+H)^+$.

2-Methyl-2-(4-(4-(trifluoromethyl)phenyl)thiazol-2-yl)propan-1-amine

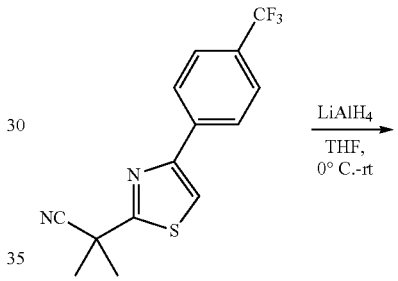

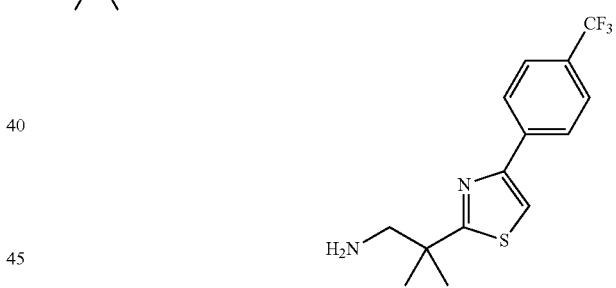

This compound was synthesized from 2-methyl-2-(4-(4-(trifluoromethyl)phenyl)thiazol-2-yl)propanenitrile as described in example 1 step 3. The material was carried through without further purification. MS (ESI) m/z: Calculated for $C_{14}H_{15}F_3N_2S$: 300.09. found: 301.1 $(M+H)^+$.

N-(2-Methyl-2-(4-(4-(trifluoromethyl)phenyl)thiazol-2-yl)propyl)-3-(5-(trifluoromethyl)-1,2,4-oxadiazol-3-yl)benzamide

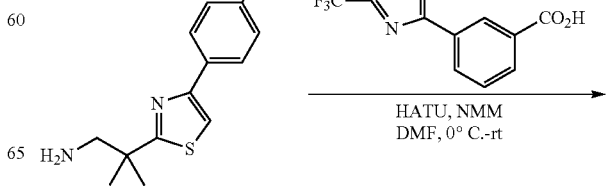

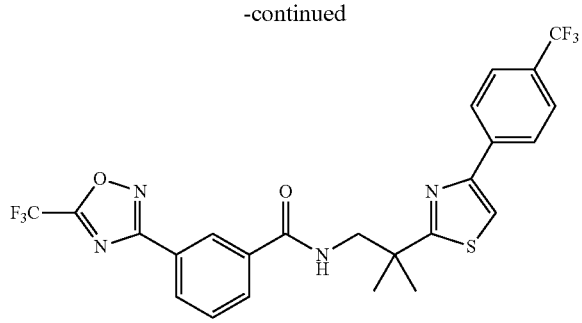

This compound was synthesized from 2-methyl-2-(4-(4-(trifluoromethyl)phenyl)thiazol-2-yl)propan-1-amine and 3-(5-(trifluoromethyl)-1,2,4-oxadiazol-3-yl)benzoic acid as described in example 8 step 6 (10 mgs, 24% yield). $^1$H NMR (300 MHz, CDCl$_3$) δ 8.51 (s, 1H), 8.25 (d, J=7.4 Hz, 1H), 8.09-7.96 (m, 4H), 7.64-7.53 (m, 3H), 3.82 (bs, 2H), 1.56 (s, 6H). MS (ESI) m/z: Calculated for C$_{24}$H$_{18}$F$_6$N$_4$O$_2$S: 540.11. found: 541.1 (M+H)$^+$.

Example 37

1-(2-Ethoxy-2-oxoethyl)tetrahydro-1H-thiophenium bromide

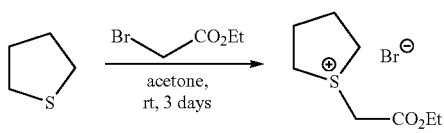 [SMILES: C1CCSC1 ; CCOC(=O)CBr ; CCOC(=O)C[S+]1CCCC1 ; [Br-]]

Tetrahydrothiophene (10 g, 113 mmol) and ethyl bromoacetate (13 mL, 113 mmol) were taken in acetone (50 mL) and stirred at room temperature for 3 days. The precipitate was filtered, washed with acetone and air dried to get 1-(2-ethoxy-2-oxoethyl)tetrahydro-1H-thiophenium bromide (23 g, yield 82%), which was carried through without further purification.

Ethyl 2-cyanocyclopropanecarboxylate

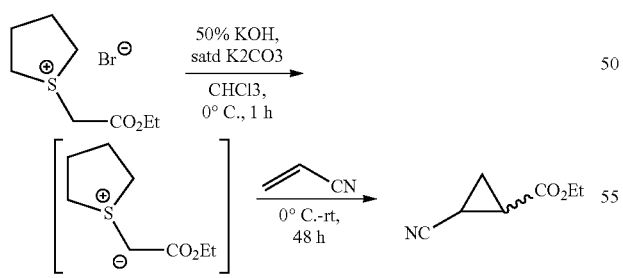

50% KOH solution (16 mL) and saturated K$_2$CO$_3$ solution (60 mL) were added to a cooled solution of compound get 1-(2-ethoxy-2-oxoethyl)tetrahydro-1H-thiophenium bromide (23 g, 90 mmol) in CHCl$_3$ (70 mL). The mixture was stirred at 0° C. for 1 h. The organic layer was separated and the aqueous layer was further extracted with CHCl$_3$. The combined organic extracts were dried over anhydrous sodium sulfate and the solvent was removed under reduced pressure to get the zwitterionic intermediate (11 g, yield 76%). This crude intermediate was dissolved in CHCl$_3$ (100 mL) and cooled to 0° C. Acrylonitrile (4 mL, 68.3 mmol) was added to the reaction mixture and the mixture was further stirred at room temperature for 48 h. The solvent was evaporated under reduced pressure and the crude product was purified by column chromatography (silica 60-120 mesh, eluent 30% EtOAc in petroleum ether) to get ethyl 2-cyanocyclopropanecarboxylate (5 g, yield 53%). $^1$H NMR (300 MHz, CDCl$_3$) δ 4.19 (q, J=7.0 Hz, 2H), 2.29-2.23 (ddd, J=8.8 Hz, 6.0 Hz, 4.3 Hz, 1H), 1.96-1.91 (ddd, J=9.1 Hz, 6.4 Hz, 4.3 Hz, 1H), 1.56-1.45 (m, 2H), 1.30 (t, J=7.0 Hz, 3H)

2-Cyanocyclopropanecarboxylic acid

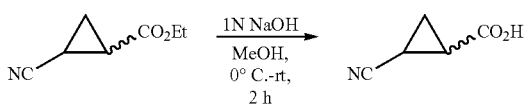

Ethyl 2-cyanocyclopropanecarboxylate (5 g, 35.9 mmol) was dissolved in MeOH (20 mL) and 1N NaOH (35 mL) was added. The reaction mixture was stirred at room temperature for 2 h. After completion of the reaction MeOH was evaporated under reduced pressure. The pH of the aqueous layer was adjusted to 2-3 using 1.5N HCl. The white precipitate was collected by filtration and dried under reduced pressure to get 2-cyanocyclopropanecarboxylic acid (3.3 g, yield 85%): $^1$H NMR (400 MHz, DMSO-d$_6$) δ 12.78 (br s, 1H), 2.26-2.21 (ddd, J=8.8 Hz, 6.0 Hz, 4.3 Hz, 1H), 2.14-2.09 (ddd, J=9.4 Hz, 6.2 Hz, 4.4 Hz, 1H), 1.53-1.48 (m, 1H), 1.36-1.32 (m, 1H). MS (ESI) m/z: Calculated for C$_5$H$_6$NO$_2$: 111.03. found: 110.2 (M−H)$^−$.

2-Cyano-N-((4-(4-phenylthiazol-2-yl)tetrahydro-2H-pyran-4-yl)methyl)cyclopropanecarboxamide

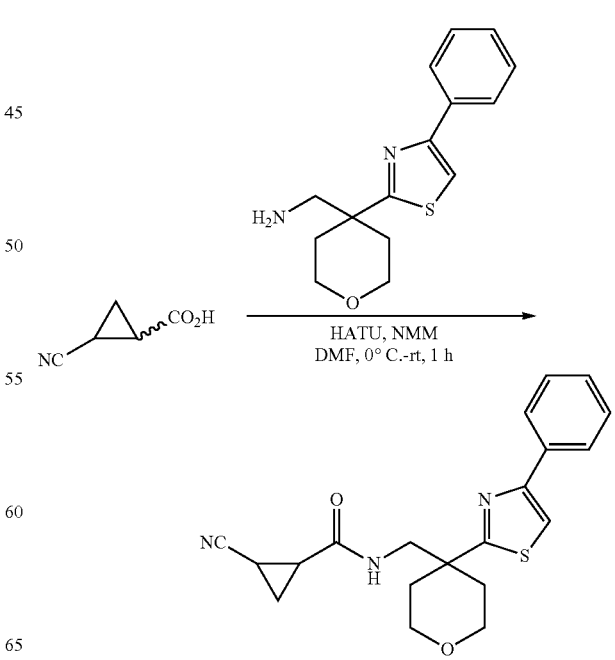

This compound was synthesized from (4-(4-phenylthiazol-2-yl)tetrahydro-2H-pyran-4-yl)methanamine and 2-cyano-cyclopropanecarboxylic acid as described in example 8 step 6 (90 mg, yield 29%): $^1$H NMR (400 MHz, CDCl$_3$) δ 7.92 (m, 2H), 7.52-7.46 (m, 3H), 7.41-7.37 (m, 1H), 6.72 (t, J=5.3 Hz, 1H), 3.92-3.86 (m, 2H), 3.75-3.68 (m, 4H), 2.30-2.22 (dddd, J=13.2 Hz, 9.8 Hz, 6.5 Hz, 3.4 Hz, 2H), 1.99-1.89 (m, 4H), 1.52-1.47 (ddd, J=9.1 Hz, 5.8 Hz, 4.6 Hz, 1H), 1.38-1.33 (ddd, J=8.6 Hz, 6.1 Hz, 4.9 Hz, 1H). MS (ESI) m/z: Calculated for C$_{20}$H$_{21}$N$_3$O$_2$S: 367.14. found: 368.2 (M+H)$^+$.

2-(N'-Hydroxycarbamimidoyl)-N-((4-(4-phenylthiazol-2-yl)tetrahydro-2H-pyran-4-yl)methyl)cyclopropanecarboxamide

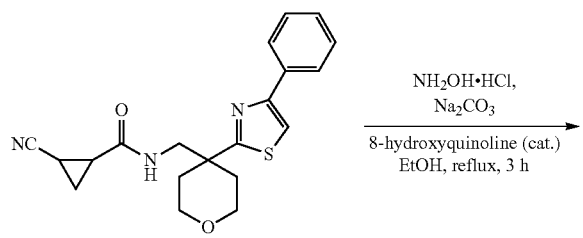

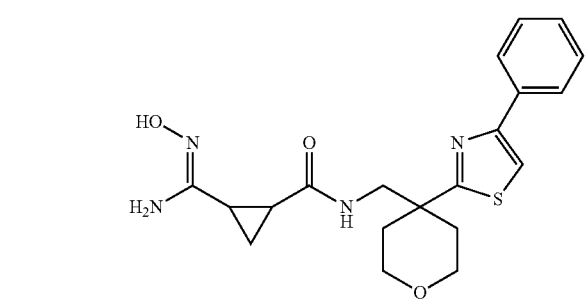

This compound was synthesized from 2-cyano-N-((4-(4-phenylthiazol-2-yl)tetrahydro-2H-pyran-4-yl)methyl)cyclopropanecarboxamide as described in example 1 step 4 (90 mg, crude) and it was used carried through without further purification. MS (ESI) m/z: Calculated for C$_{20}$H$_{24}$N$_4$O$_3$S: 400.16. found: 401.2 (M+H)$^+$.

N-((4-(4-Phenylthiazol-2-yl)tetrahydro-2H-pyran-4-yl)methyl)-2-(5-(trifluoromethyl)-1,2,4-oxadiazol-3-yl)cyclopropanecarboxamide

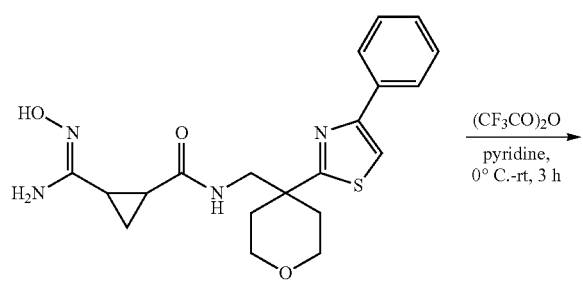

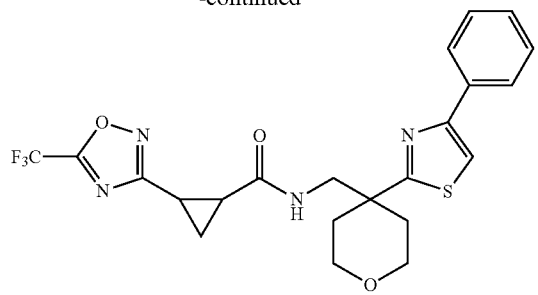

This compound was synthesized from 2-(N'-hydroxycarbamimidoyl)-N-((4-(4-phenylthiazol-2-yl)tetrahydro-2H-pyran-4-yl)methyl)cyclopropanecarboxamide as described in example 1 step 5 (45 mg, yield 45%): $^1$H NMR (400 MHz, MeOD) δ 7.94 (m, 2H), 7.77 (s, 1H), 7.38 (m, 2H), 7.30 (m, 1H), 3.92-3.88 (dt, J=12.0 Hz, 3.8 Hz, 2H), 3.61-3.50 (m, 4H), 2.55-2.48 (ddd, J=9.2 Hz, 5.6 Hz, 4.0 Hz, 1H), 2.35 (d, J=13.8 Hz, 2H), 2.31-2.27 (ddd, J=8.7 Hz, 5.7 Hz, 4.1 Hz, 1H), 2.02-1.94 (m, 2H), 1.51-1.47 (m, 1H), 1.39-1.34 (m, 1H). MS (ESI) m/z: Calculated for C$_{22}$H$_{21}$F$_3$N$_4$O$_3$S: 478.13. found: 479.2 (M+H)$^+$.

Example 38

2-Chloro-N-(2-chloroethyl)-N-methylethanamine hydrochloride

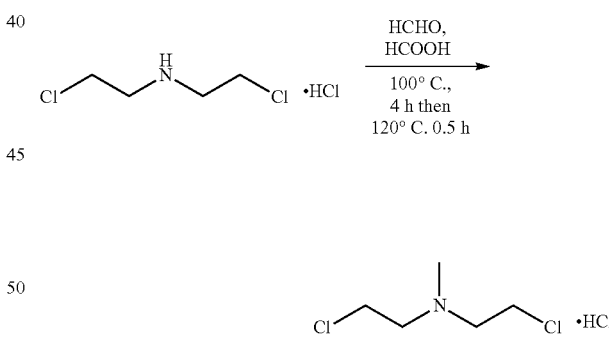

1,5-Dichloroazapentane hydrochloride (1.0 g, 5.6 mmol) was taken in formic acid (0.43 mL, 11.2 mmol). A formaldehyde solution (1.2 mL, 37% in water) was added and the reaction mixture was heated to 100° C. for 4 h and then to 120° C. for 0.5 h. The reaction mixture was cooled to room temperature and the solvent was removed under reduced pressure. The crude mixture was washed with hexane to afford 2-chloro-N-(2-chloroethyl)-N-methylethanamine hydrochloride (1.0 g, yield 92%) as a white solid. $^1$H NMR (300

MHz, DMSO-d6) δ 11.21 (br s, 1H), 4.04-4.00 (t, J=6.8 Hz, 4H), 3.54-3.48 (m, 4H), 2.82 (s, 3H).

1-Methyl-4-(2-phenylthiazol-4-yl)piperidine-4-carbonitrile

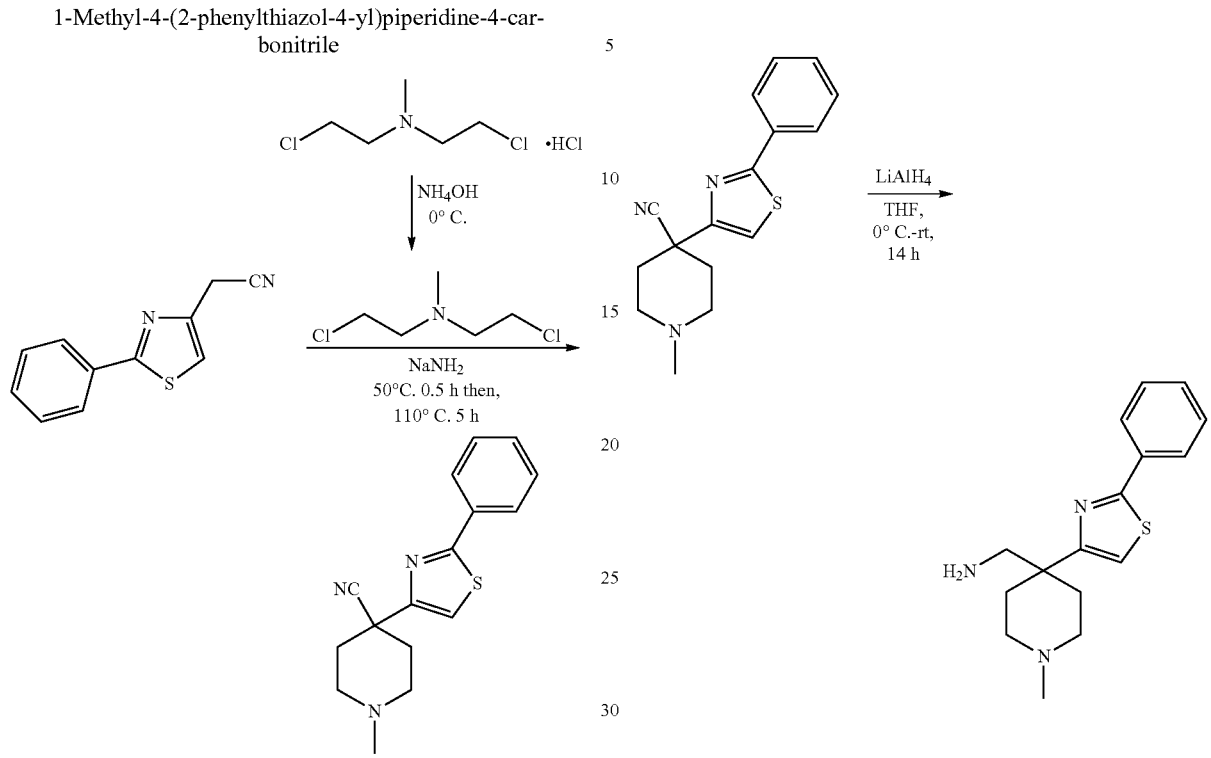

This compound was synthesized from (2-phenyl-thiazol-4-yl)-acetonitrile and 2-chloro-N-(2-chloroethyl)-N-methyl-ethanamine hydrochloride as described in example 16 step 1b (135 mg, yield 25%). $^1$H NMR (300 MHz, CDCl3) δ 7.97-7.94 (m, 2H), 7.45-7.43 (m, 3H), 7.30 (s, 1H), 3.00-2.96 (m, 2H), 2.53-2.40 (m, 7H), 2.25-2.20 (m, 2H). MS (ESI) m/z: Calculated for $C_{16}H_{17}N_3S$: 283.11. found: 284.2 (M+H)$^+$.

(1-Methyl-4-(2-phenylthiazol-4-yl)piperidin-4-yl)methanamine

This compound was synthesized from 1-methyl-4-(2-phenylthiazol-4-yl)piperidine-4-carbonitrile as described in example 1 step 3 (110 mg) and it was carried through without further purification. MS (ESI) m/z: Calculated for $C_{16}H_{21}N_3S$: 287.15. found: 288.2 (M+H)$^+$.

N-((1-Methyl-4-(2-phenylthiazol-4-yl)piperidin-4-yl)methyl)-5-(5-(trifluoromethyl)-1,2,4-oxadiazol-3-yl)nicotinamide

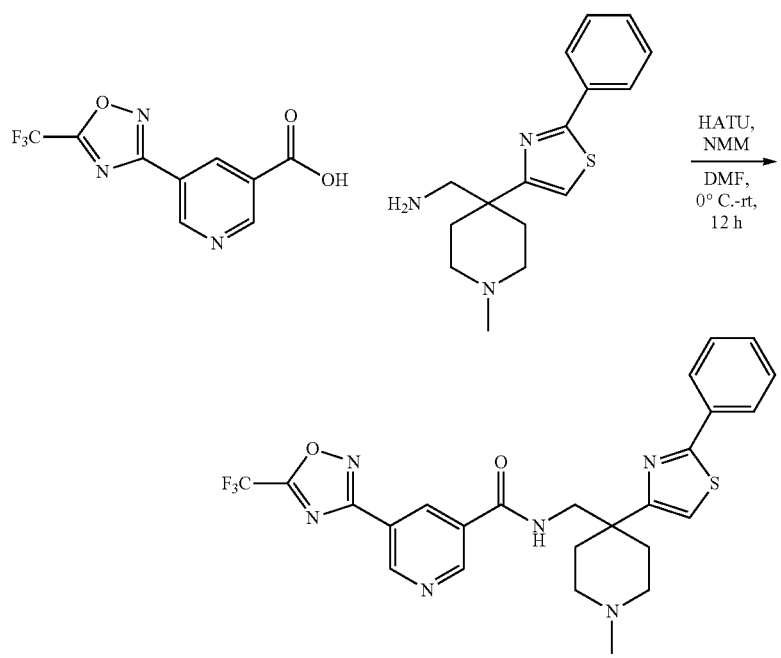

This compound was synthesized from (1-methyl-4-(2-phenylthiazol-4-yl)piperidin-4-yl)methanamine and 5-(5-(trifluoromethyl)-1,2,4-oxadiazol-3-yl)nicotinic acid as described in example 8 step 6 (15 mg, yield 8%). $^1$H NMR (400 MHz, CDCl$_3$) δ 9.43 (d, J=1.5 Hz, 1H), 9.22 (d, J=1.8 Hz, 1H), 8.76 (m, 1H), 7.92-7.90 (m, 3H), 7.42-7.41 (m, 3H), 7.19 (s, 1H), 3.92-3.87 (m, 2H), 3.00 (m, 2H), 2.84 (m, 2H), 2.57 (m, 5H), 2.25 (m, 2H). MS (ESI) m/z: Calculated for C$_{25}$H$_{23}$F$_3$N$_6$O$_2$S: 528.55. found: 529.2 (M+H)$^+$.

Example 39

4-(Chloromethyl)-2-(4-chlorophenyl)thiazole

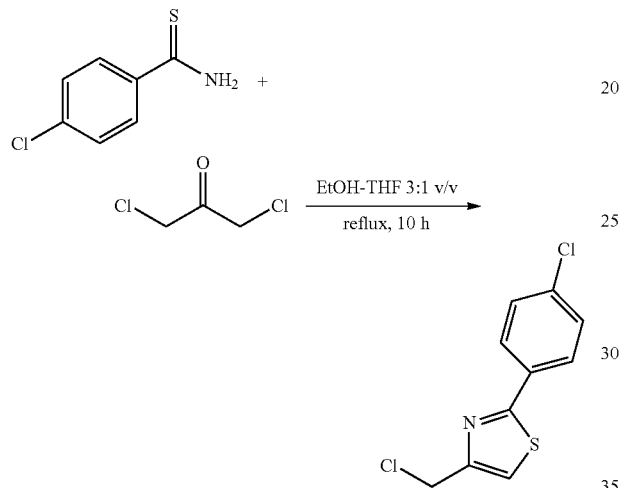

A mixture of 4-chlorothiobenzamide (0.5 g, 2.9 mmol) and 1,3-dichloroacetone (0.4 g, 3.18 mmol) in EtOH-THF (20 mL-10 mL) was heated to 85° C. for 10 h. The reaction mixture was cooled to room temperature and quenched with 10% NaHCO$_3$ solution. The organic product was extracted with EtOAc and the organic layer was washed with H$_2$O and brine, and dried over anhydrous sodium sulfate. The solvent was removed under reduced pressure and the crude product was purified by column chromatography (silica gel 60-120 mesh, eluent 3-5% EtOAc in petroleum ether) to afford 4-(chloromethyl)-2-(4-chlorophenyl)thiazole (0.55 g, yield 77%) as a white solid. $^1$H NMR (400 MHz, CDCl$_3$) δ 7.91-7.88 (m, 2H), 7.44-7.41 (m, 2H), 7.33 (s, 1H), 4.75 (s, 2H). MS (ESI) m/z: Calculated for C$_{10}$H$_7$Cl$_2$NS: 242.97. found: 244.0 (M+H)$^+$.

2-(2-(4-Chlorophenyl)thiazol-4-yl)acetonitrile

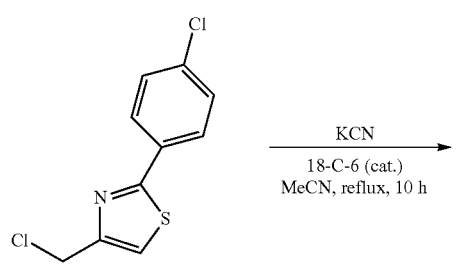

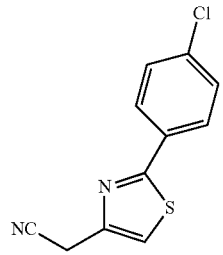

A catalytic amount of 18-crown-6-ether (20 mg) was added to a solution of 4-(chloromethyl)-2-(4-chlorophenyl)thiazole (0.55 g, 2.25 mmol) in acetonitrile (20 mL), followed by potassium cyanide (0.22 g, 3.37 mmol) and the reaction mixture was refluxed for 10 h. The reaction mixture was then quenched with water and the organic product extracted with EtOAc. The combined extracts were washed with H$_2$O and brine, dried over anhydrous sodium sulfate and concentrated under reduced pressure. The crude product was purified by column chromatography (silica gel 60-120 mesh, eluent 15% EtOAc in petroleum ether) to afford 2-(2-(4-chlorophenyl)thiazol-4-yl)acetonitrile (0.43 g, yield 82%) as an off-white solid. $^1$H NMR (300 MHz, CDCl$_3$) δ 7.89-7.86 (d, J=8.6 Hz, 2H), 7.45-7.42 (d, J=8.6 Hz, 2H), 7.32 (m, 1H), 3.96 (s, 2H). MS (ESI) m/z: Calculated for C$_{11}$H$_7$ClN$_2$S: 234.00. found: 235.0 (M+H)$^+$.

2-(2-(4-Chlorophenyl)thiazol-4-yl)-2-methylpropanenitrile

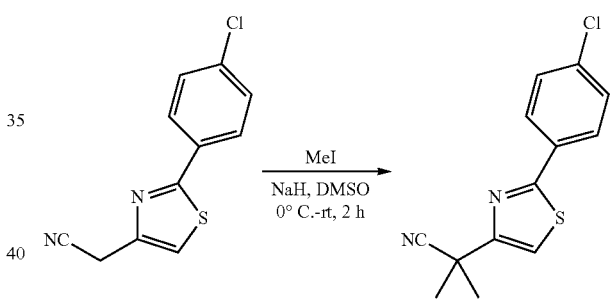

This compound was synthesized from 2-(2-(4-chlorophenyl)thiazol-4-yl)acetonitrile using iodomethane as described in example 1 step 2 (0.15 g, yield 70%) as a pale yellow solid. $^1$H NMR (300 MHz, CDCl$_3$) δ 7.92-7.88 (d, J=8.6 Hz, 2H), 7.44-7.41 (d, J=8.6 Hz, 2H), 7.29 (s, 1H), 1.82 (s, 6H). MS (ESI) m/z: Calculated for C$_{13}$H$_{11}$ClN$_2$S: 262.03. found: 263.0 (M+H)$^+$.

2-(2-(4-Chlorophenyl)thiazol-4-yl)-2-methylpropan-1-amine

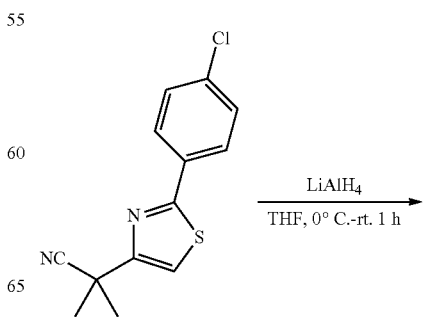

-continued

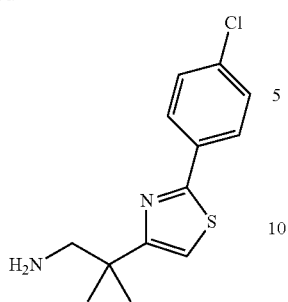

This compound was synthesized from 2-(2-(4-Chlorophenyl)thiazol-4-yl)-2-methylpropanenitrile as described in example 1 step 3, (60 mg, yield 40%). $^1$H NMR (400 MHz, CDCl$_3$) δ 7.90-7.88 (d, J=8.6 Hz, 2H), 7.42-7.40 (d, J=8.6 Hz, 2H), 6.99 (s, 1H), 2.98 (s, 2H), 1.39 (s, 6H). MS (ESI) m/z: Calculated for C$_{13}$H$_{15}$ClN$_2$S: 266.06. found: 267.0 (M+H)$^+$.

N-(2-(2-(4-chlorophenyl)thiazol-4-yl)-2-methylpropyl)-5-(5-(trifluoromethyl)-1,2,4-oxadiazol-3-yl)nicotinamide

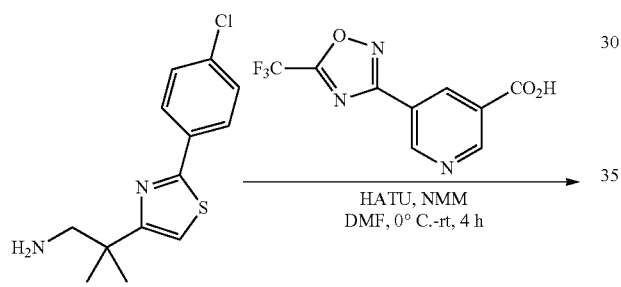

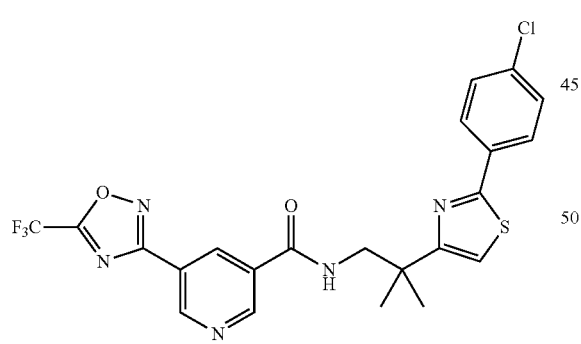

This compound was synthesized from 2-(2-(4-chlorophenyl)thiazol-4-yl)-2-methylpropan-1-amine and 5-(5-(trifluoromethyl)-1,2,4-oxadiazol-3-yl)nicotinic acid as described in example 8 step 6 (50 mg, yield 51%). $^1$H NMR (400 MHz, CDCl$_3$) δ 9.46 (d, J=1.5 Hz, 1H), 9.24 (d, J=1.8 Hz, 1H), 8.79 (m, 1H), 8.22 (t, J=4.5 Hz, 1H), 7.85-7.83 (d, J=8.5 Hz, 2H), 7.38-7.36 (d, J=8.5 Hz, 2H), 7.09 (s, 1H), 3.72 (d, J=5.5 Hz, 2H), 1.50 (s, 6H). MS (ESI) m/z: Calculated for C$_{22}$H$_{17}$ClF$_3$N$_5$O$_2$S: 507.07. found: 508.0 (M+H)$^+$.

Example 40

4-(2-(4-Chlorophenyl)thiazol-4-yl)-1-methylpiperidine-4-carbonitrile

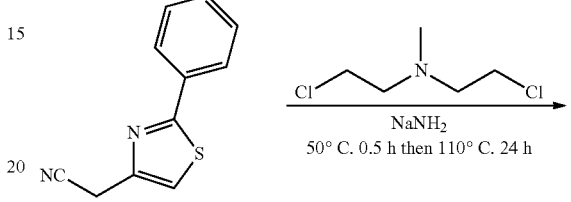

This compound was synthesized from 2-(2-(4-chlorophenyl)thiazol-4-yl)acetonitrile and 2-chloro-N-(2-chloroethyl)-N-methylethanamine hydrochloride as described in example 16 step 1b (350 mg, yield 32%). $^1$H NMR (300 MHz, CDCl$_3$) δ 7.91-7.88 (d, J=8.6 Hz, 2H), 7.43-7.40 (d, J=8.6 Hz, 2H), 7.32 (s, 1H), 3.03-2.98 (m, 2H), 2.57-2.38 (m, 7H), 2.26-2.21 (m, 2H). MS (ESI) m/z: Calculated for C$_{16}$H$_{16}$ClN$_3$S: 317.08. found: 318.2 (M+H)$^+$.

(4-(2-(4-Chlorophenyl)thiazol-4-yl)-1-methylpiperidin-4-yl)methanamine

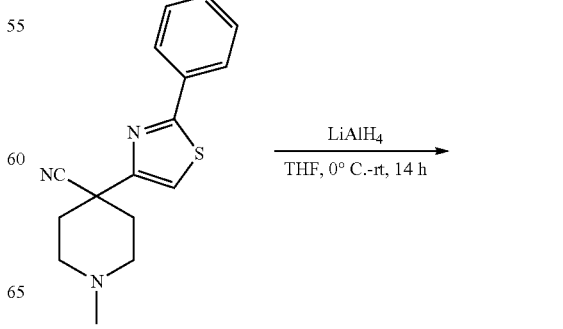

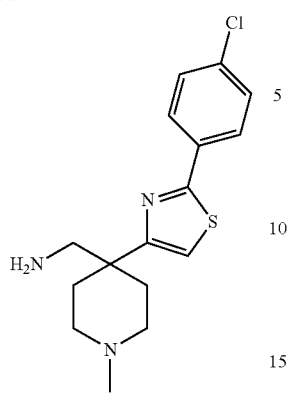

This compound was synthesized from 4-(2-(4-chlorophenyl)thiazol-4-yl)-1-methylpiperidine-4-carbonitrile as described in example 1 step 3 (130 mg, crude) and it was carried through without further purification. MS (ESI) m/z: Calculated for $C_{16}H_{20}ClN_3S$: 321.11. found: 322.2 $(M+H)^+$.

N-((4-(2-(4-Chlorophenyl)thiazol-4-yl)-1-methylpiperidin-4-yl)methyl)-5-(5-(trifluoromethyl)-1,2,4-oxadiazol-3-yl)nicotinamide

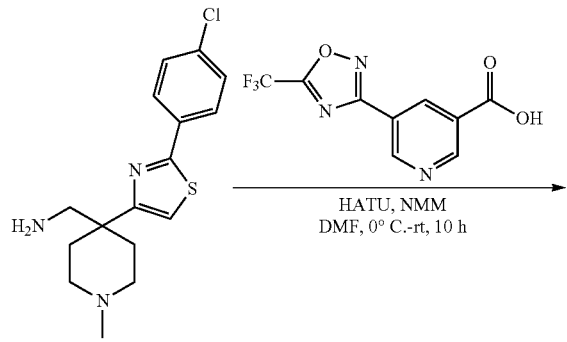

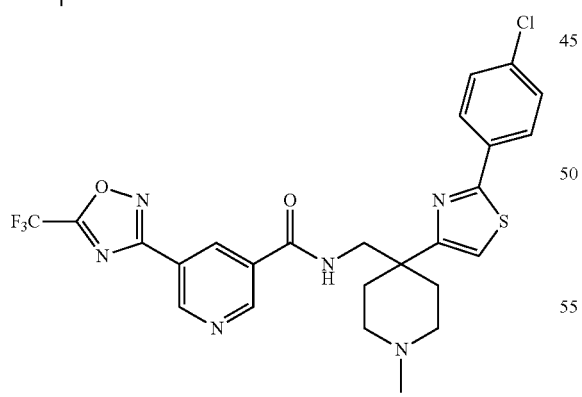

This compound was synthesized from (4-(2-(4-chlorophenyl)thiazol-4-yl)-1-methylpiperidin-4-yl)methanamine and 5-(5-(trifluoromethyl)-1,2,4-oxadiazol-3-yl)nicotinic acid as described in example 8 step 6 (17 mg, yield 11%). $^1$H NMR (400 MHz, MeOD) δ 9.36 (d, J=2.0 Hz, 1H), 9.09 (d, J=2.0 Hz, 1H), 8.72 (t, J=2.0 Hz, 1H), 7.95-7.93 (d, J=8.5 Hz, 2H), 7.59 (br s, 1H), 7.44-7.42 (d, J=8.6 Hz, 2H), 3.73 (m, 2H), 3.50-3.49 (m, 2H), 2.87-2.83 (m, 7H), 2.21-2.16 (m, 2H). MS (ESI) m/z: Calculated for $C_{25}H_{22}ClF_3N_6O_2S$: 562.12. found: 563.2 $(M+H)^+$.

Example 41

N-(2-(2-(4-chlorophenyl)thiazol-4-yl)-2-methylpropyl)-3-(5-(trifluoromethyl)-1,2,4-oxadiazol-3-yl)benzamide

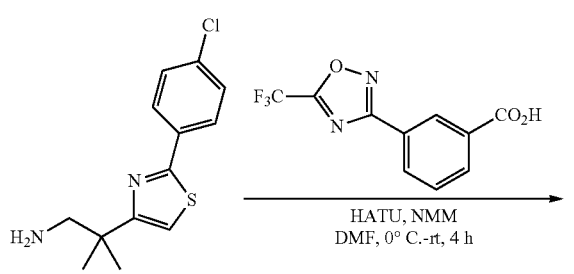

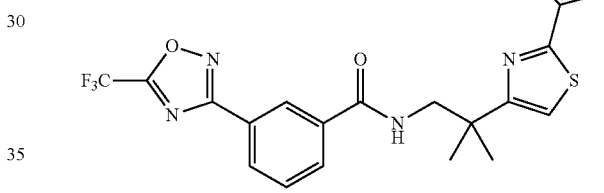

This compound was synthesized from 2-(2-(4-chlorophenyl)thiazol-4-yl)-2-methylpropan-1-amine and 3-(5-(trifluoromethyl)-1,2,4-oxadiazol-3-yl)benzoic acid as described in example 8 step 6 (75 mg, yield 25%). $^1$H NMR (400 MHz, CDCl$_3$) δ 8.53 (m, 1H), 8.27-8.25 (m, 1H), 8.10-8.05 (m, 2H), 7.86-7.84 (d, J=8.5 Hz, 2H), 7.62-7.59 (t, J=7.8 Hz, 1H), 7.33-7.31 (d, J=8.5 Hz, 2H), 7.08 (s, 1H), 3.71-3.69 (d, J=5.3 Hz, 2H), 1.49 (s, 6H). MS (ESI) m/z: Calculated for $C_{23}H_{18}ClF_3N_4O_2S$: 506.08. found: 507.0 $(M+H)^+$.

Example 42

2-(2-(4-Chlorophenyl)thiazol-4-yl)ethanamine

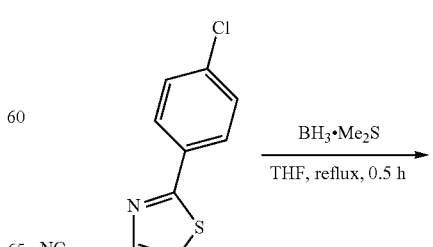

-continued

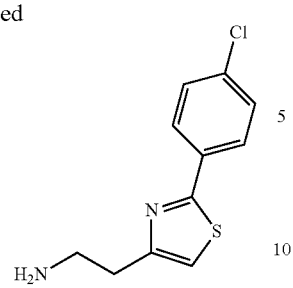

Borane dimethyl sulfide complex (0.24 mL, 2.5 mmol) was added to a solution of 2-(2-(4-chlorophenyl)thiazol-4-yl)acetonitrile (150 mg, 0.63 mmol) in dry THF (15 mL) at room temperature. The reaction mixture was refluxed for 0.5 h and then quenched carefully with methanol. The reaction mixture was concentrated under reduced pressure and diluted with EtOAc. The organic layer was washed with brine, dried over anhydrous sodium sulfate and concentrated under reduced pressure to afford 2-(2-(4-chlorophenyl)thiazol-4-yl)ethanamine (150 mg, crude) which was used as such for the next step.

N-(2-(2-(4-Chlorophenyl)thiazol-4-yl)ethyl)-5-(5-(trifluoromethyl)-1,2,4-oxadiazol-3-yl)nicotinamide

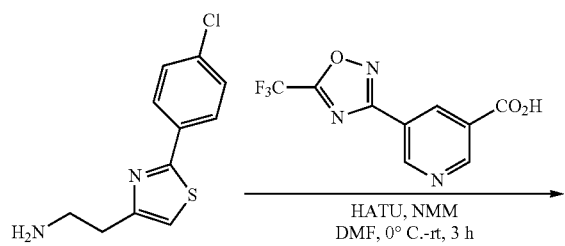

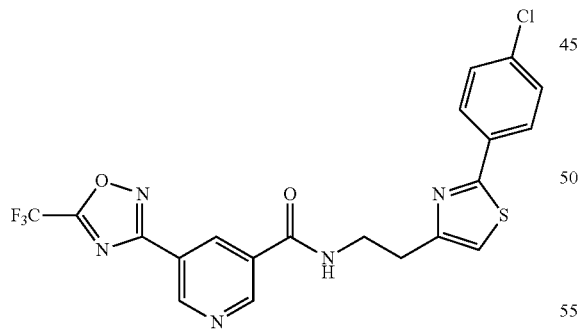

This compound was synthesized from 2-(2-(4-chlorophenyl)thiazol-4-yl)ethanamine and 5-(5-(trifluoromethyl)-1,2,4-oxadiazol-3-yl)nicotinic acid as described in example 8 step 6 (13 mg, yield 23%). $^1$H NMR (400 MHz, CDCl$_3$) δ 9.46 (m, 1H), 9.25 (m, 1H), 8.81-8.80 (t, J=2 Hz, 1H), 7.87-7.84 (m, 2H), 7.40-7.37 (m, 2H), 7.08 (s, 1H), 3.93-3.89 (m, 2H), 3.16-3.13 (m, 2H). MS (ESI) m/z: Calculated for C$_{20}$H$_{13}$ClF$_3$N$_5$O$_2$S: 479.04. found: 480.0 (M+H)$^+$.

Example 43

Methyl 2-cyanoisonicotinate

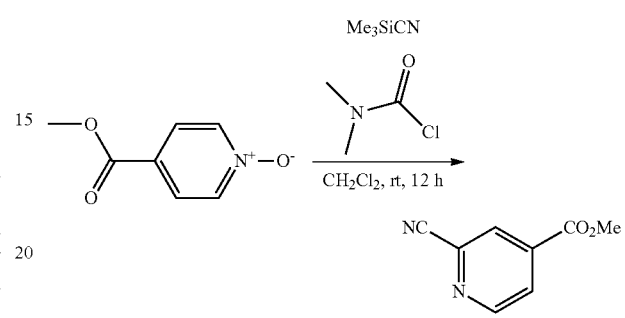

Trimethylsilyl cyanide (3.8 g, 0.0386 mol) and dimethylcarbamyl chloride (5.0 g, 0.0483 mol) were added to a solution of methylisonicotinate N-oxide (5.0 g, 0.0322 mol) in dry CH$_2$Cl$_2$ (50 mL) at room temperature. The reaction mixture was stirred at room temperature for 12 h and then quenched with 10% K$_2$CO$_3$ solution. The organic product was extracted with CH$_2$Cl$_2$ and the organic layer was washed with H$_2$O and brine, dried over anhydrous Na$_2$SO$_4$ and concentrated under reduced pressure. The crude product was purified by flash column chromatography (silica 230-400 mesh, eluent 1-2% MeOH in CH$_2$Cl$_2$) to afford methyl 2-cyanoisonicotinate (1.75 g, yield 33%) as an off-white solid. $^1$H NMR (400 MHz, DMSO-d$_6$) δ 8.97-8.95 (d, J=5.0 Hz, 1H), 8.41 (m, 1H), 8.15-8.13 (dd, J=4.8 Hz, 1.6 Hz, 1H), 3.92 (s, 3H).

2-Cyanoisonicotinic acid

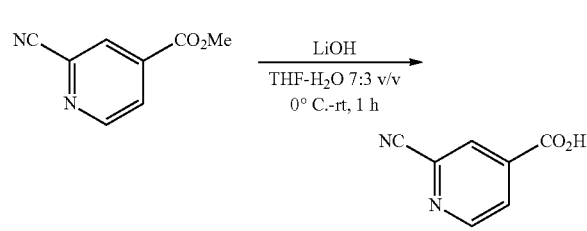

Lithium hydroxide (96 mg, 4.0 mmol) was added to a solution of methyl 2-cyanoisonicotinate (0.6 g, 3.7 mmol) in THF—H$_2$O (20 mL, 7:3 v/v) at 0° C. The reaction mixture was allowed to warm up to room temperature and further stirred for 1 h. The reaction mixture was concentrated under reduced pressure and then diluted with water. The aqueous layer was washed with EtOAc. The pH of the aqueous layer was adjusted to ~3 using 1.5N HCl and the organic product was extracted with EtOAc. The organic layer was dried over anhydrous Na$_2$SO$_4$ and concentrated under reduced pressure to afford 2-cyanoisonicotinic acid (490 mg, yield 89%) as a white solid. $^1$H NMR (300 MHz, DMSO-d$_6$) δ 14.11 (br s, 1H), 8.93-8.91 (dd, J=4.9 Hz, 0.8 Hz, 1H), 8.34 (d, J=0.9 Hz, 1H), 8.11-8.10 (m, 1H). MS (ESI) m/z: Calculated for $C_7H_4N_2O_2$: 148.03. found: 147.2 (M−H)⁻.

2-(N'-Hydroxycarbamimidoyl)isonicotinic acid

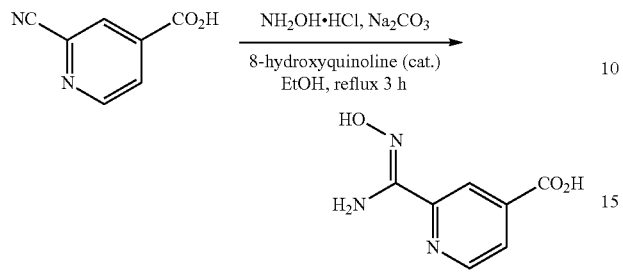

This compound was synthesized from 2-cyanoisonicotinic acid as described in example 1 step 4 (500 mg, crude), which was carried through without further purification. ¹H NMR (400 MHz, DMSO-$d_6$) δ 10.86 (br s, 1H), 10.36 (br s, 2H), 10.13 (br s, 1H), 8.87-8.86 (d, J=4.9 Hz, 1H), 8.44 (s, 1H), 7.99-7.98 (d, J=4.9 Hz, 1H). MS (ESI) m/z: Calculated for $C_7H_7N_3O_3$: 181.05. found: 182.2 (M+H)⁺.

2-(5-(Trifluoromethyl)-1,2,4-oxadiazol-3-yl)isonicotinic acid

This compound was synthesized from 2-(N'-hydroxycarbamimidoyl)isonicotinic acid as described in example 1 step 5 (200 mg, yield 23%) as a white solid. ¹H NMR (400 MHz, DMSO-$d_6$) δ 14.11 (br s, 1H), 9.02-9.00 (dd, J=4.8 Hz, 0.7 Hz, 1H), 8.45 (m, 1H), 8.09-8.07 (dd, J=5.0 Hz, 1.5 Hz, 1H). MS (ESI) m/z: Calculated for $C_9H_4F_3N_3O_3$: 259.02. found: 260.0 (M+H)⁺.

N-(2-(4-(4-Chlorophenyl)thiazol-2-yl)-2-methylpropyl)-2-(5-(trifluoromethyl)-1,2,4-oxadiazol-3-yl)isonicotinamide This compound was synthesized from 2-(4-(4-chlorophenyl)thiazol-2-yl)-2-methylpropan-1-amine and 2-(5-(trifluoromethyl)-1,2,4-oxadiazol-3-yl)isonicotinic acid as described in example 8 step 6 (65 mg, yield 33%). ¹H NMR (400 MHz, CDCl₃) δ 8.94-8.92 (dd, J=5.0 Hz, 0.8 Hz, 1H), 8.50 (m, 1H), 8.39-8.36 (t, J=5.6 Hz, 1H), 7.88-7.86 (dd, J=5.0 Hz, 1.5 Hz, 1H), 7.79-7.77 (d, J=8.5 Hz, 2H), 7.44 (s, 1H), 7.35-7.33 (d, J=8.5 Hz, 2H), 3.83-3.82 (d, J=5.8 Hz, 2H), 1.57 (s, 6H). MS (ESI) m/z: Calculated for $C_{22}H_{17}ClF_3N_6O_2S$: 507.07. found: 508.0 (M+H)⁺.

Example 44

4-(Chloromethyl)-2-(4-fluorophenyl)thiazole

This compound was synthesized from 4-fluorothiobenzamide and 1,3-dichloroacetone as described in example 39 step 1 (0.65 g, yield 89%) as a white solid. ¹H NMR (400 MHz, CDCl₃) δ 7.96-7.93 (m, 2H), 7.30 (s, 1H), 7.16-7.12 (t, J=8.7 Hz, 2H), 4.75 (s, 2H). MS (ESI) m/z: Calculated for C$_{10}$H$_7$ClFNS: 227.00. found: 228.0 (M+H)$^+$.

2-(2-(4-Fluorophenyl)thiazol-4-yl)acetonitrile

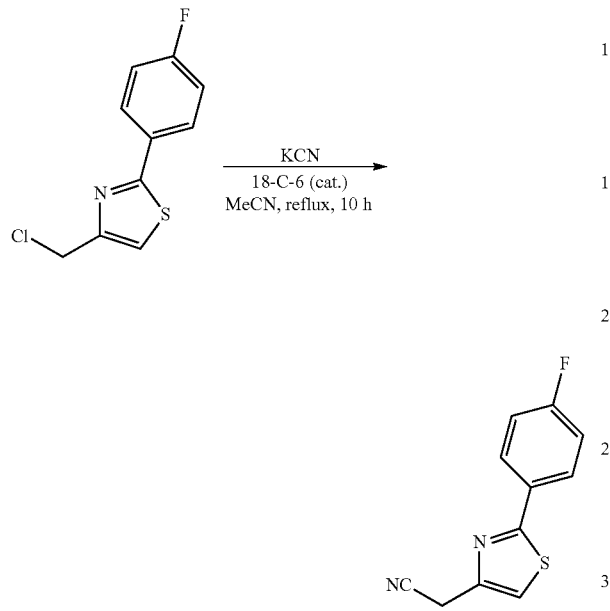

This compound was synthesized from 4-(chloromethyl)-2-(4-fluorophenyl)thiazole as described in example 39 step 2 (0.27 g, yield 80%) as an off-white solid. $^1$H NMR (400 MHz, CDCl$_3$) δ 7.95-7.91 (m, 2H), 7.30 (s, 1H), 7.17-7.13 (t, J=8.7 Hz, 2H), 3.95 (s, 2H). MS (ESI) m/z: Calculated for C$_{11}$H$_7$FN$_2$S: 218.03. found: 219.0 (M+H)$^+$.

2-(2-(4-Fluorophenyl)thiazol-4-yl)-2-methylpropanenitrile

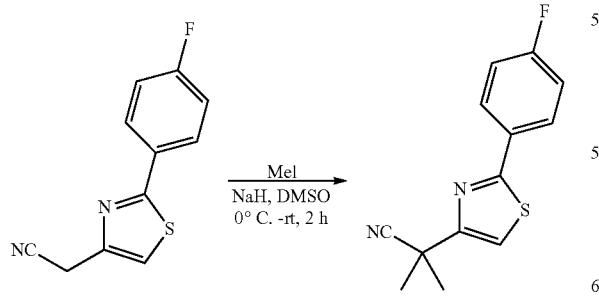

This compound was synthesized from 2-(2-(4-fluorophenyl)thiazol-4-yl)acetonitrile and methyl iodide as described in example 1 step 2 (250 mg, yield 75%). $^1$H NMR (400 MHz, CDCl$_3$) δ 7.98-7.94 (m, 2H), 7.41 (s, 1H), 7.17-7.12 (t, J=8.7 Hz, 2H), 1.82 (s, 6H). MS (ESI) m/z: Calculated for C$_{13}$H$_{11}$FN$_2$S: 246.06. found: 247.2 (M+H)$^+$.

2-(2-(4-Fluorophenyl)thiazol-4-yl)-2-methylpropan-1-amine

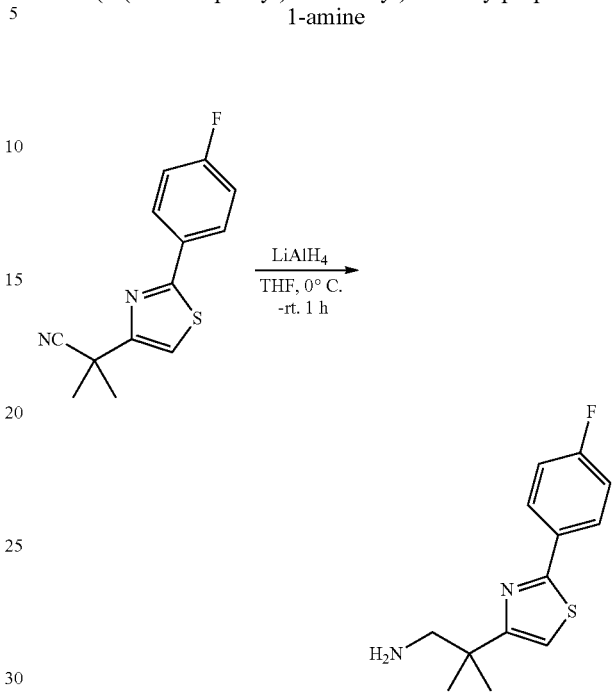

This compound was synthesized from 2-(2-(4-fluorophenyl)thiazol-4-yl)-2-methylpropanenitrile as described in example 1 step 3 (200 mg, crude) and it was carried through without further purification. MS (ESI) m/z: Calculated for C$_{13}$H$_{15}$FN$_2$S: 250.09. found: 251.2 (M+H)$^+$.

N-(2-(2-(4-Fluorophenyl)thiazol-4-yl)-2-methylpropyl)-3-(5-(trifluoromethyl)-1,2,4-oxadiazol-3-yl)benzamide

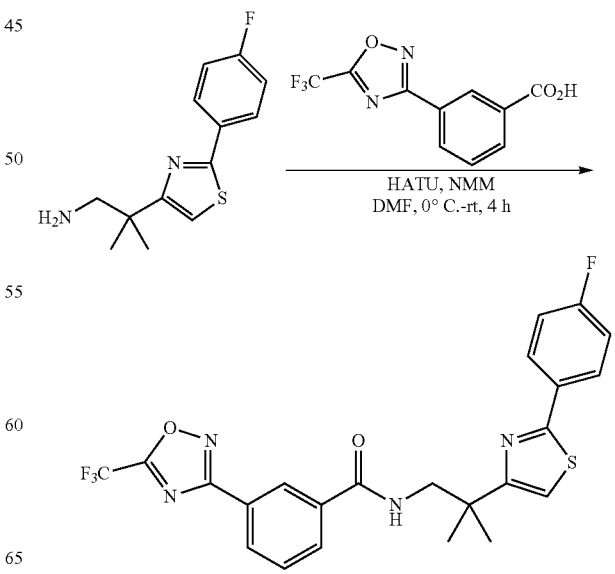

This compound was synthesized from 2-(2-(4-fluorophenyl)thiazol-4-yl)-2-methylpropan-1-amine and 3-(5-(trifluoromethyl)-1,2,4-oxadiazol-3-yl)benzoic acid as described in example 8 step 6 (55 mg, yield 30%). $^1$H NMR (400 MHz, CDCl$_3$) δ 8.53 (m, 1H), 8.26-8.24 (d, J=7.8 Hz, 1H), 8.13-8.11 (m, 1H), 8.07-8.05 (d, J=7.5 Hz, 1H), 7.92-7.89 (m, 2H), 7.62-7.58 (t, J=7.8 Hz, 1H), 7.06-7.02 (m, 3H), 3.71-3.69 (d, J=5.3 Hz, 2H), 1.49 (s, 6H). MS (ESI) m/z: Calculated for C$_{23}$H$_{18}$F$_4$N$_4$O$_2$S: 490.11. found: 491.0 (M+H)$^+$.

Example 45

N-(2-(2-(4-Fluorophenyl)thiazol-4-yl)-2-methylpropyl)-5-(5-(trifluoromethyl)-1,2,4-oxadiazol-3-yl)nicotinamide

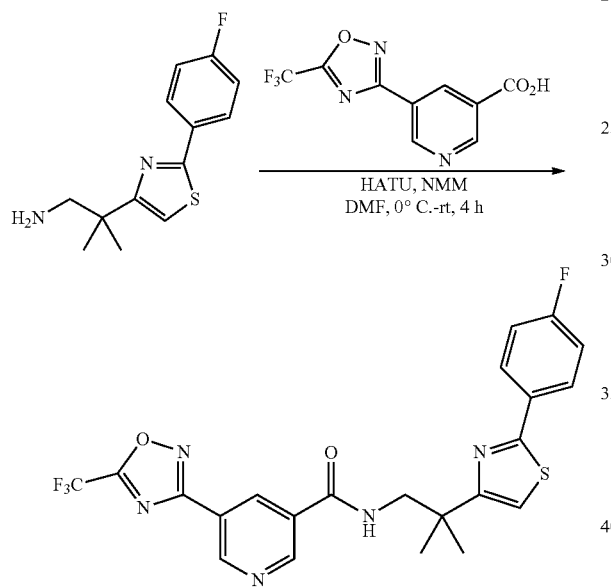

This compound was synthesized from 2-(2-(4-fluorophenyl)thiazol-4-yl)-2-methylpropan-1-amine and 5-(5-(trifluoromethyl)-1,2,4-oxadiazol-3-yl)nicotinic acid as described in example 8 step 6 (50 mg, yield 26%). $^1$H NMR (400 MHz, MeOD) δ 9.36 (d, J=2.0 Hz, 1H), 9.11 (d, J=2.3 Hz, 1H), 8.77-8.76 (t, J=2.1 Hz, 1H), 8.00-7.96 (m, 2H), 7.30 (s, 1H), 7.18-7.14 (t, J=8.8 Hz, 2H), 3.75 (s, 2H), 1.50 (s, 6H). MS (ESI) m/z: Calculated for C$_{22}$H$_{17}$F$_4$N$_5$O$_2$S: 491.10. found: 492.0 (M+H)$^+$.

Example 46

6-((Benzyloxy)carbonyl)picolinic acid

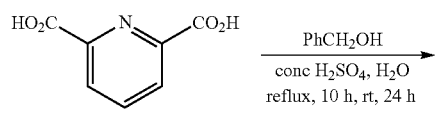

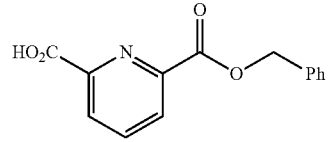

A mixture of 2,6-pyridinedicarboxylic acid (10 g, 0.06 mol) and benzyl alcohol (68 mL, 0.66 mol) were taken in water (25 mL), and concentrated H$_2$SO$_4$ (3.5 mL) was added. The reaction mixture was refluxed for 10 h and further allowed to stir at room temperature for 24 h. The reaction mixture was concentrated under reduced pressure and the organic product was extracted with CHCl$_3$. The solvent was removed under reduced pressure and the crude product was purified by column chromatography (silica gel 60-120 mesh, eluent 5% MeOH in CH$_2$Cl$_2$) to afford 6-((benzyloxy)carbonyl)picolinic acid (4.6 g, yield 30%) as a white solid. $^1$H NMR (400 MHz, DMSO-d$_6$) δ 13.54 (br s, 1H), 8.29-8.24 (m, 2H), 8.20-8.16 (m, 1H), 7.52-7.50 (m, 2H), 7.44-7.36 (m, 3H), 5.43 (s, 2H). MS (ESI) m/z: Calculated for C$_{14}$H$_{11}$NO$_4$: 257.07. found: 258.2 (M+H)$^+$.

6-Carbamoylpicolinic acid

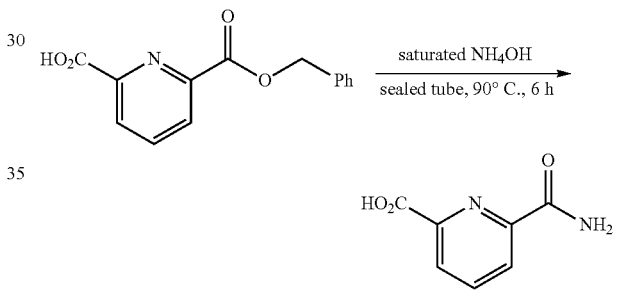

A solution of 6-((benzyloxy)carbonyl)picolinic acid (3.0 g, 11.7 mmol) in saturated NH$_4$OH (100 mL) was heated in a sealed tube at 90° C. for 6 h and monitored by TLC (CHCl$_3$/MeOH 8:2 v/v). The reaction mixture was evaporated to dryness to get the 6-carbamoylpicolinic acid (1.8 g, yield 94%) as a white solid, which was carried through without further purification. MS (ESI) m/z: Calculated for C$_7$H$_6$N$_2$O$_3$: 166.04. found: 167.0 (M+H)$^+$.

6-Cyanopicolinic acid

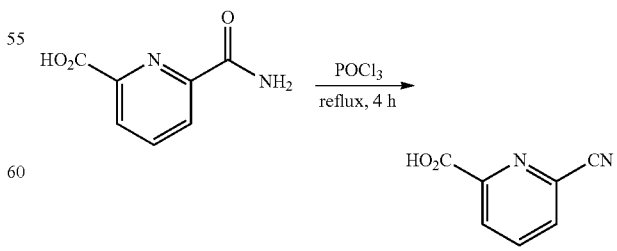

6-Carbamoylpicolinic acid (1.0 g, 6.0 mmol) was taken in phosphorus oxychloride (20 mL) and heated to reflux for 4 h. Excess POCl$_3$ was removed under reduced pressure and the residue was quenched with ice water. The organic product was extracted with EtOAc and the solvent was removed under reduced pressure to afford 6-cyanopicolinic acid (500 mg, yield 56%), which was carried through without further purification. $^1$H NMR (300 MHz, DMSO-$d_6$) δ 8.31-8.28 (m, 2H), 8.26-8.21 (m, 1H). MS (ESI) m/z: Calculated for $C_7H_4N_2O_2$: 148.03. found: 147.2 (M−H)$^-$.

6-(N'-Hydroxycarbamimidoyl)picolinic acid

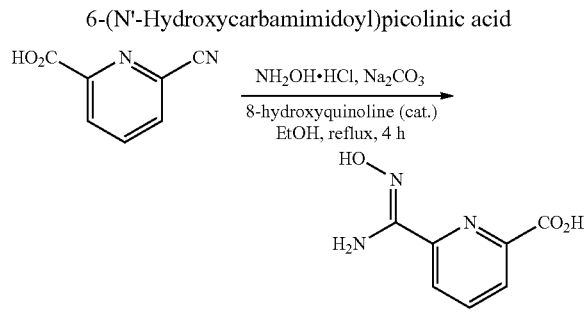

This compound was synthesized from 6-cyanopicolinic acid as described in example 1 step 4 (500 mg, crude), which was carried through without further purification. $^1$H NMR (400 MHz, $D_2O$) δ 8.31-8.29 (m, 1H), 8.18-8.14 (t, J=7.8 Hz, 1H), 8.07-8.05 (m, 1H).

6-(5-(Trifluoromethyl)-1,2,4-oxadiazol-3-yl)picolinic acid

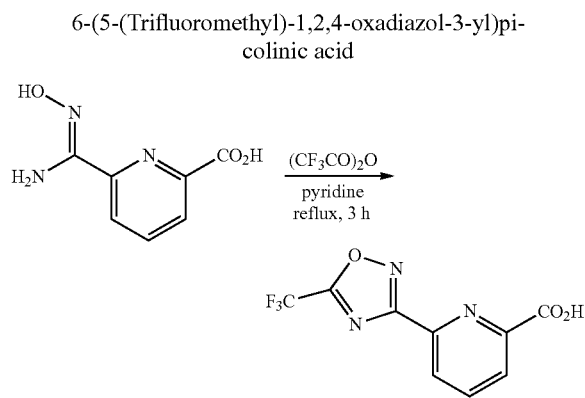

This compound was synthesized from 6-(N'-hydroxycarbamimidoyl)picolinic acid as described in example 1 step 5 (110 mg, yield 20%) as an off-white solid. $^1$H NMR (400 MHz, DMSO-$d_6$) δ 13.64 (br s, 1H), 8.36-8.34 (m, 1H), 8.27-8.25 (m, 2H). MS (ESI) m/z: Calculated for $C_6H_4F_3N_3O_3$: 259.02. found: 260.0 (M+H)$^+$.

N-(2-(4-(4-Chlorophenyl)thiazol-2-yl)-2-methylpropyl)-6-(5-(trifluoromethyl)-1,2,4-oxadiazol-3-yl)picolinamide

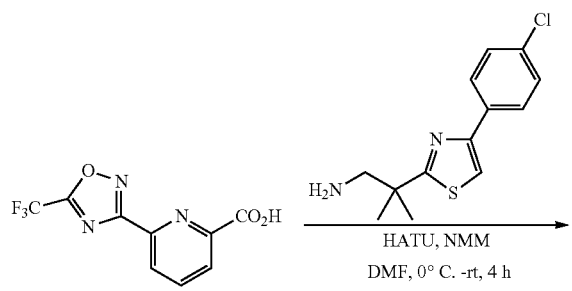

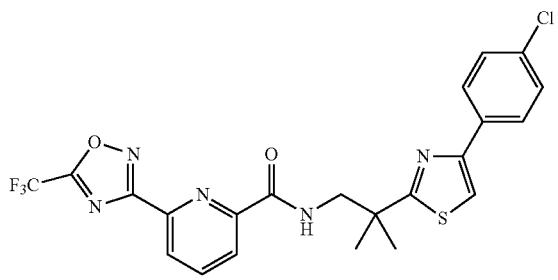

This compound was synthesized from 6-(5-(trifluoromethyl)-1,2,4-oxadiazol-3-yl)picolinic acid and 2-(4-(4-chlorophenyl)thiazol-2-yl)-2-methylpropan-1-amine as described in example 8 step 6 (55 mg, yield 56%). $^1$H NMR (400 MHz, CDCl$_3$) δ 8.87-8.85 (m, 1H), 8.43-8.41 (dd, J=7.8 Hz, 1 Hz, 1H), 8.27-8.24 (dd, J=7.8 Hz, 1.3 Hz, 1H), 8.10-8.06 (m, 1H), 7.89-7.87 (d, J=8.5 Hz, 2H), 7.41 (s, 1H), 7.32-7.29 (d, J=8.8 Hz, 2H), 3.91-3.89 (d, J=6.5 Hz, 2H), 1.56 (s, 6H). MS (ESI) m/z: Calculated for $C_{22}H_{17}ClF_3N_6O_2S$: 507.07. found: 508.0 (M+H)$^+$.

Example 47

(4-Phenylthiazol-2-yl)methanol

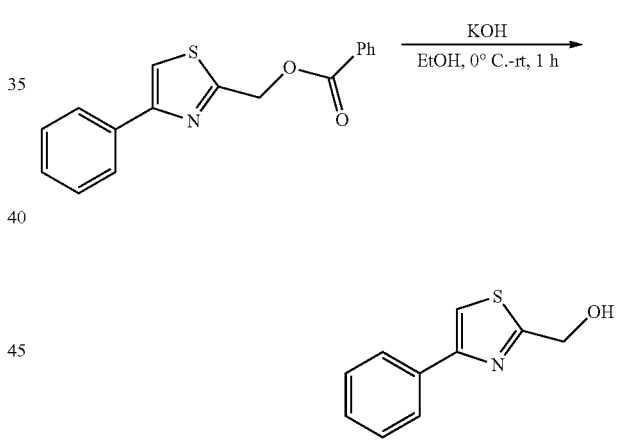

Potassium hydroxide (1.06 g, 18.84 mmol) was added to an ice cooled solution of benzoic acid (4-phenylthiazol-2-yl)methyl benzoate (3.71 g, 12.56 mmol) in EtOH (40 mL). The reaction mixture was slowly warmed to room temperature and allowed to stir for 1 h. The reaction mixture was concentrated under reduced pressure and then diluted with water. The organic product was extracted with EtOAc, washed with brine, dried over anhydrous sodium sulfate, and concentrated under reduced pressure. The crude product was purified by column chromatography (silica 60-120 mesh, eluant 10% EtOAc in petroleum ether) to get the pure (4-phenylthiazol-2-yl)methanol (2.1 g, yield 87%). $^1$H NMR (400 MHz, CDCl$_3$) δ 7.89-7.87 (m, 2H), 7.46-7.41 (m, 3H), 7.37-7.33

(m, 1H), 5.01 (s, 2H). MS (ESI) m/z: Calculated for $C_{10}H_9NOS$: 191.04. found: 192.2 $(M+H)^+$.

4-Phenylthiazole-2-carbaldehyde

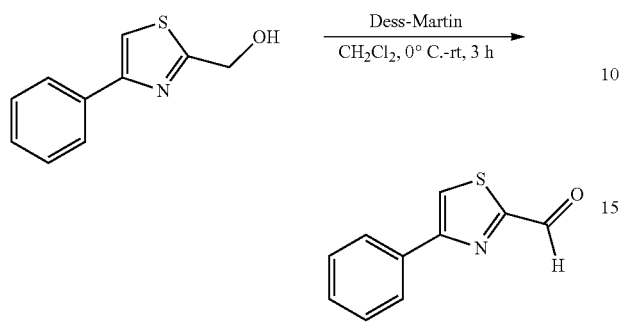

A solution of (4-phenylthiazol-2-yl)methanol (2.1 g, 10.98 mmol) in dry $CH_2Cl_2$ (50 mL) was purged with argon for 10 min and Dess-Martin periodinane (7.0 g, 16.5 mmol) was added to the solution at 0° C. The reaction mixture was allowed to warm up to room temperature and further stirred for 3 h (monitored by TLC, petroleum ether/EtOAc 8:2 v/v). The reaction mixture was then quenched with saturated sodium thiosulfate solution. The organic product was extracted with $CH_2Cl_2$, and the organic layer was washed with brine, dried over anhydrous sodium sulfate, and concentrated under reduced pressure to yield aldehyde 4-phenylthiazole-2-carbaldehyde (1.95 g, yield 94%), which was carried through without further purification. $^1H$ NMR (300 MHz, $CDCl_3$) δ 10.08 (m, 1H), 7.98-7.95 (m, 2H), 7.90 (m, 1H), 7.52-7.39 (m, 3H). MS (ESI) m/z: Calculated for $C_{10}H_7NOS$: 189.02. found: 190.0 $(M+H)^+$.

2-(Dimethylamino)-2-(4-phenylthiazol-2-yl)acetonitrile

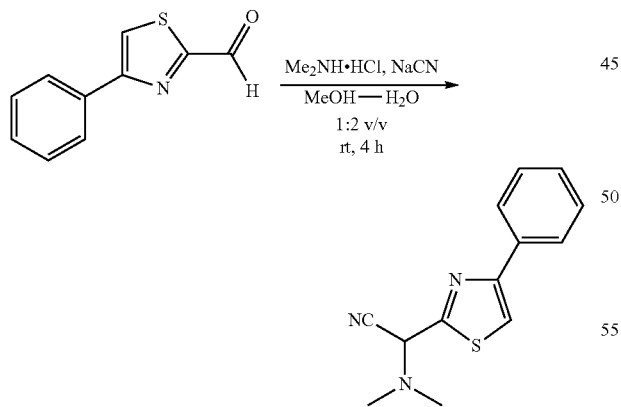

Sodium cyanide (124 mg, 2.53 mmol) was added to a solution of dimethylamine hydrochloride (280 mg, 3.43 mmol) in water (10 mL), followed by the addition of a solution of 4-phenylthiazole-2-carbaldehyde (400 mg, 2.11 mmol) in methanol (20 mL) while maintaining the temperature at −25° C. The reaction mixture was further stirred for 4 h at same temperature, then it was diluted with water and the organic product was extracted with EtOAc. The organic layer was washed with brine, dried over anhydrous sodium sulfate, and concentrated under reduced pressure to get the crude product, which was purified by column chromatography (silica 60-120 mesh, eluant 15% EtOAc in petroleum ether), to yield 2-(dimethylamino)-2-(4-phenylthiazol-2-yl)acetonitrile (160 mg, yield 31%). $^1H$ NMR (400 MHz, $CDCl_3$) δ 7.97-7.94 (m, 2H), 7.57 (s, 1H), 7.46-7.42 (m, 2H), 7.38-7.33 (m, 1H), 5.12 (s, 1H), 2.50 (s, 6H). MS (ESI) m/z: Calculated for $C_{13}H_{13}N_3S$: 243.08. found: 244.2 $(M+H)^+$.

N,N-Dimethyl-1-(4-phenylthiazol-2-yl)ethane-1,2-diamine

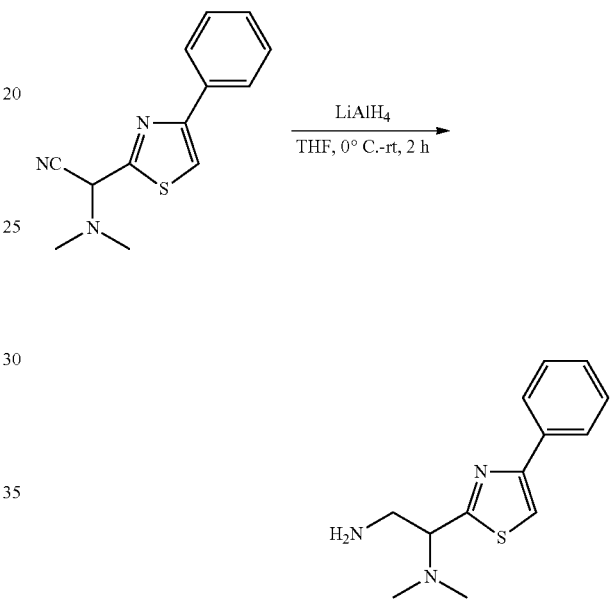

This compound was synthesized from 2-(dimethylamino)-2-(4-phenylthiazol-2-yl)acetonitrile as described in example 1 step 3 (130 mg, crude) and it was carried through without further purification. MS (ESI) m/z: Calculated for $C_{13}H_{17}N_3S$: 247.11. found: 248.2 $(M+H)^+$.

N-(2-(Dimethylamino)-2-(4-phenylthiazol-2-yl)ethyl)-3-(5-(trifluoromethyl)-1,2,4-oxadiazol-3-yl)benzamide

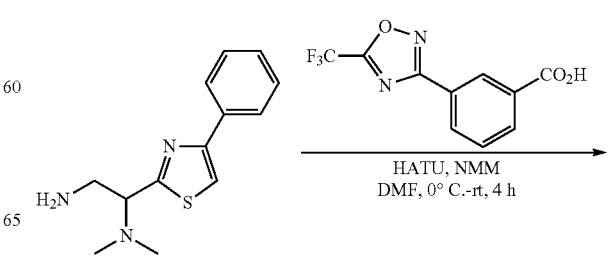

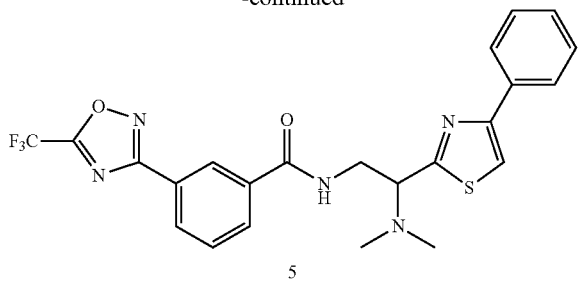

5

This compound was synthesized from N,N-dimethyl-1-(4-phenylthiazol-2-yl)ethane-1,2-diamine and 3-(5-(trifluoromethyl)-1,2,4-oxadiazol-3-yl)benzoic acid as described in example 8 step 6 (16 mg, yield 17%). $^1$H NMR (400 MHz, CDCl$_3$) δ 8.57-8.56 (t, J=1.5 Hz, 1H), 8.26-8.23 (dt, J=7.8 Hz, 1.4 Hz, 1H), 8.07-8.05 (dt, J=7.8 Hz, 1.4 Hz, 1H), 7.91-7.87 (m, 3H), 7.63-7.59 (t, J=7.8 Hz, 1H), 7.51 (s, 1H), 7.42-7.38 (m, 2H), 7.36-7.31 (m, 1H), 4.35-4.29 (ddd, J=13.2 Hz, 6.6 Hz, 5.5 Hz, 1H), 4.15-4.12 (m, 1H), 3.85-3.78 (ddd, J=13.0 Hz, 8.3 Hz, 4.6 Hz, 1H), 2.51 (s, 6H). MS (ESI) m/z: Calculated for C$_{23}$H$_{20}$F$_3$N$_5$O$_2$S: 487.13. found: 488.2 (M+H)$^+$.

Example 48

2-(3-Phenyl-1H-1,2,4-triazol-5-yl)ethanamine

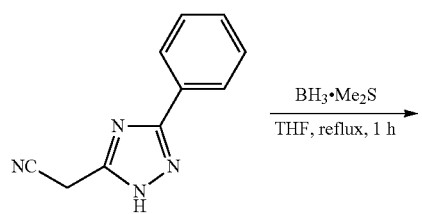

Borane dimethyl sulfide complex (0.2 mL, 2.16 mmol) was added to a solution of compound 2-(3-phenyl-1H-1,2,4-triazol-5-yl)acetonitrile (100 mg, 0.54 mmol) in dry THF (5 mL) at room temperature. The reaction mixture was refluxed for 1 h, then quenched carefully with methanol and again heated to reflux for 0.5 h. The reaction mixture was concentrated under reduced pressure and then diluted with EtOAc. The organic layer was washed with brine, dried over anhydrous sodium sulfate and concentrated under reduced pressure to afford 2-(3-phenyl-1H-1,2,4-triazol-5-yl)ethanamine (130 mg, crude), which was carried through without further purification. MS (ESI) m/z: Calculated for C$_{10}$H$_{12}$N$_4$: 188.11. found: 189.2 (M+H)$^+$.

N-(2-(3-Phenyl-1H-1,2,4-triazol-5-yl)ethyl)-3-(5-(trifluoromethyl)-1,2,4-oxadiazol-3-yl)benzamide

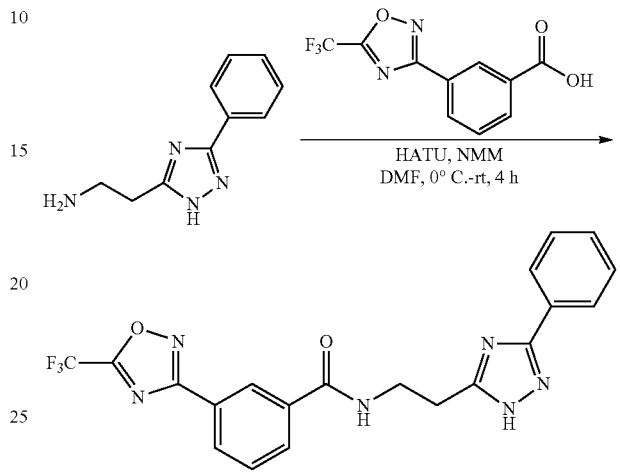

This compound was synthesized from 2-(3-phenyl-1H-1,2,4-triazol-5-yl)ethanamine and 3-(5-(trifluoromethyl)-1,2,4-oxadiazol-3-yl)benzoic acid as described in example 8 step 6 (17 mg, yield 21%). $^1$H NMR (400 MHz, CDCl$_3$) δ 8.53 (s, 1H), 8.21-8.19 (d, J=7.8 Hz, 1H), 8.06-8.04 (t, J=7.8 Hz, 1H), 8.01-7.99 (m, 2H), 7.89 (m, 1H), 7.58-7.54 (d, J=7.8 Hz, 1H), 7.40-7.39 (m, 3H), 4.00-3.95 (q, J=5.9 Hz, 2H), 3.24-3.21 (d, J=6.1 Hz, 2H). MS (ESI) m/z: Calculated for C$_{20}$H$_{15}$F$_3$N$_6$O$_2$: 428.12. found: 429.2 (M+H)$^+$.

Example 49

1-(4-Phenylthiazol-2-yl)cyclopropanecarbonitrile

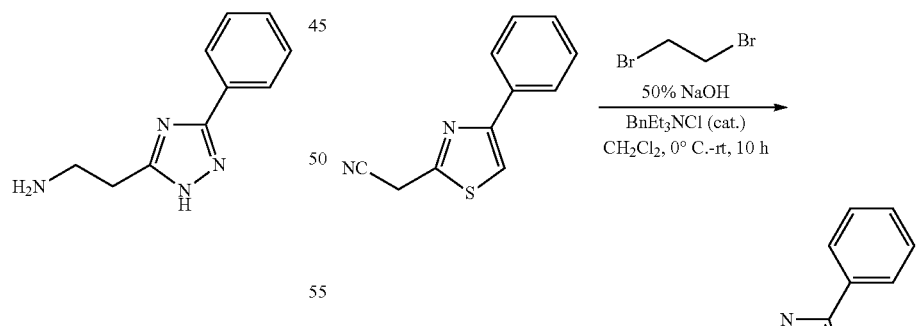

Benzyltriethyl ammonium chloride (34 mg, 0.15 mmol) and 50% aqueous NaOH solution (0.59 g dissolved in 1 mL of water) were added to a solution of 2-(4-phenylthiazol-2-yl)acetonitrile (0.3 g, 1.5 mmol) in CH$_2$Cl$_2$ (10 mL). The reaction mixture was cooled at 0° C. and 1,2-dibromoethane (0.15 mL, 1.79 mmol) was added dropwise. The reaction mixture was allowed to warm up to room temperature and stirred for 10 h. The reaction mixture was diluted with CH$_2$Cl$_2$ and the organic layer was washed with H$_2$O and brine, dried over anhydrous sodium sulfate and concentrated under reduced pressure. The residue was purified by column chromatography (silica gel 60-120 mesh, eluent 5% EtOAc in petroleum ether) to afford 1-(4-phenylthiazol-2-yl)cyclopropanecarbonitrile (0.14 g, yield 41%) as an off-white solid. $^1$H NMR (300 MHz, CDCl$_3$) δ 7.86-7.83 (m, 2H), 7.45-7.34 (m, 4H), 2.02-1.95 (m, 2H), 1.93-1.86 (m, 2H). MS (ESI) m/z: Calculated for C$_{13}$H$_{10}$N$_2$S: 226.06. found: 227.2 (M+H)$^+$.

(1-(4-Phenylthiazol-2-yl)cyclopropyl)methanamine

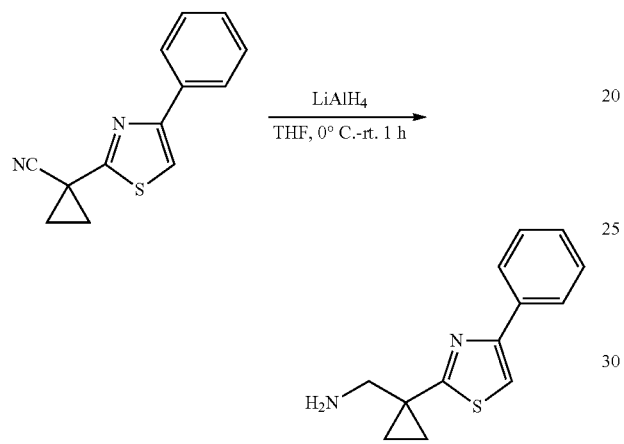

This compound was synthesized from 1-(4-phenylthiazol-2-yl)cyclopropanecarbonitrile as described in example 1 step 3 (59 mg, yield 42%) as a pale yellow liquid. $^1$H NMR (400 MHz, CDCl$_3$) δ 7.91-7.89 (m, 2H), 7.44-7.40 (m, 2H), 7.35-7.33 (m, 1H), 7.30 (s, 1H), 3.11 (s, 2H), 1.26-1.24 (m, 2H), 1.11-1.09 (m, 2H). MS (ESI) m/z: Calculated for C$_{13}$H$_{14}$N$_2$S: 230.09. found: 231.2 (M+H)$^+$.

N-((1-(4-Phenylthiazol-2-yl)cyclopropyl)methyl)-3-(5-(trifluoromethyl)-1,2,4-oxadiazol-3-yl)benzamide

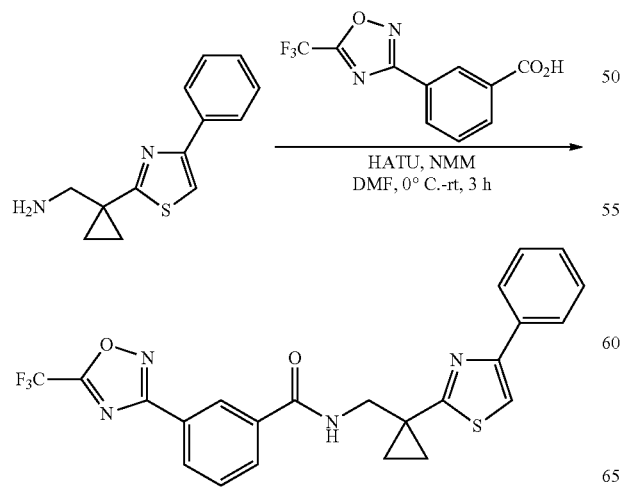

This compound was synthesized from (1-(4-phenylthiazol-2-yl)cyclopropyl)methanamine and 3-(5-(trifluoromethyl)-1,2,4-oxadiazol-3-yl)benzoic acid as described in example 8 step 6 (47 mg, yield 49%). $^1$H NMR (400 MHz, CDCl$_3$) δ 8.59 (s, 1H), 8.25-8.23 (m, 2H), 8.09-8.07 (m, 1H), 7.90-7.88 (m, 2H), 7.63-7.59 (t, J=7.9 Hz, 1H), 7.41-7.38 (m, 2H), 7.35-7.33 (m, 1H), 7.32 (s, 1H), 3.93 (d, J=5.5 Hz, 2H), 1.42-1.39 (m, 2H), 1.23-1.20 (m, 2H). MS (ESI) m/z: Calculated for C$_{23}$H$_{17}$F$_3$N$_4$O$_2$S: 470.10. found: 471.0 (M+H)$^+$.

Example 50

N'-Hydroxy-3-nitrobenzimidamide

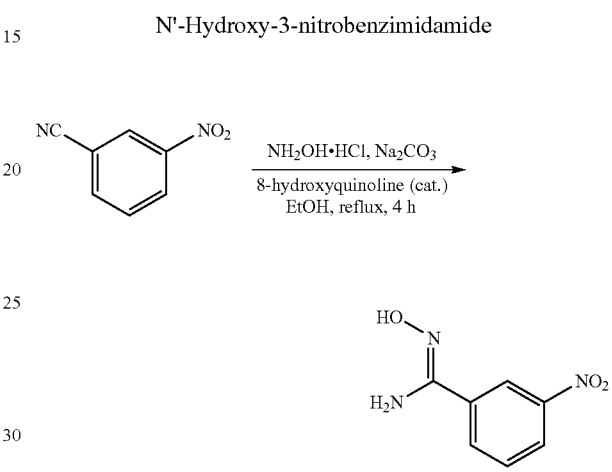

This compound was synthesized from 3-nitrobenzonitrile as described in example 1 step 4 (5.5 g, crude) and it was carried through without further purification. $^1$H NMR (300 MHz, DMSO-d$_6$) δ 9.96 (s, 1H), 8.50 (d, J=1.3 Hz, 1H), 8.23-8.19 (m, 1H), 8.12-8.10 (m, 1H), 7.67 (t, J=8.0 Hz, 1H), 6.09 (m, 2H). MS (ESI) m/z: Calculated for C$_7$H$_7$N$_3$O$_3$: 181.05. found: 182.2 (M+H)$^+$.

3-(3-Nitrophenyl)-5-(trifluoromethyl)-1,2,4-oxadiazole

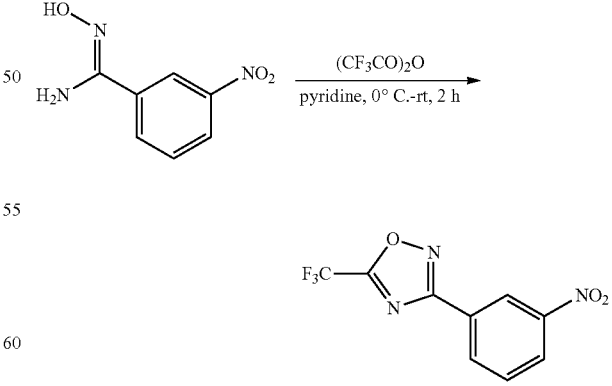

This compound was synthesized from N'-hydroxy-3-nitrobenzimidamide as described in example 1 step 5 (1.6 g, yield 56%) and it was carried through without further purification. $^1$H NMR (300 MHz, DMSO-d$_6$) δ 8.72 (t, J=1.9 Hz, 1H), 8.53-8.48 (m, 2H), 7.93 (t, J=8.0 Hz, 1H). MS (ESI) m/z: Calculated for $C_9H_4F_3N_3O_3$: 259.02. found: 260.0 (M+H)$^+$.

3-(5-(Trifluoromethyl)-1,2,4-oxadiazol-3-yl)aniline

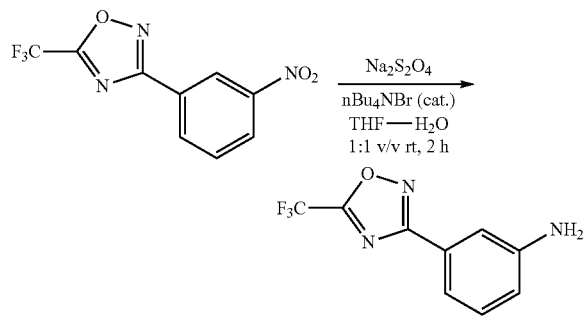

Sodium dithionite (1.61 g, 9.2 mmol) and a catalytic amount of tetra-n-butylammonium bromide (20 mg) were added to a solution of 3-(3-nitrophenyl)-5-(trifluoromethyl)-1,2,4-oxadiazole (1.6 g, 6.1 mmol) in THF—$H_2O$ (30 mL, 1:1 v/v), and the reaction mixture was stirred at room temperature for 2 h and monitored by TLC (petroleum ether/EtOAc 1:1). Solvent was removed under reduced pressure and the product was extracted with EtOAc. The organic layer was washed with brine, dried over anhydrous sodium sulfate and concentrated under reduced pressure. The crude product was purified by column chromatography (silica gel 60-120 mesh, eluent 30-35% EtOAc in petroleum ether) to afford 3-(5-(trifluoromethyl)-1,2,4-oxadiazol-3-yl)aniline (0.8 g, yield 57%). $^1$H NMR (300 MHz, CDCl$_3$) δ 7.52-7.49 (dt, J=7.7 Hz, 1.2 Hz, 1H), 7.42 (m, 1H), 7.30 (t, J=8.0 Hz, 1H), 6.89-6.86 (ddd, J=7.9 Hz, 2.4 Hz, 0.9 Hz, 1H), 3.87 (br s, 2H). MS (ESI) m/z: Calculated for $C_9H_6F_3N_3O$: 229.05. found: 230.0 (M+H)$^+$.

Methyl 4-amino-4-thioxobutanoate

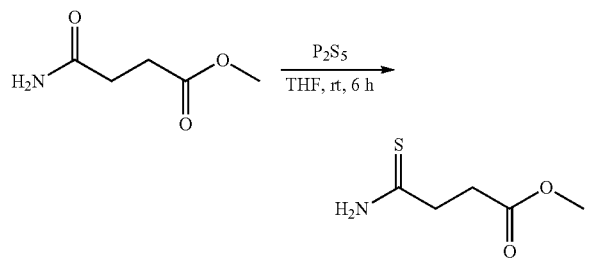

Methyl succinamate (2 g, 15.2 mmol) was dissolved in dry THF (50 mL) and $P_2S_5$ (3.4 g, 15.2 mmol) was added and the reaction mixture was stirred at room temperature for 6 h. The reaction mixture was filtered through a sintered funnel and the clear filtrate was concentrated under reduced pressure to get the crude product, which was further purified by column chromatography (silica gel 60-120 mesh, eluent 50% EtOAc in petroleum ether) to afford methyl 4-amino-4-thioxobutanoate (1.25 g, yield 53%) as a white solid. $^1$H NMR (300 MHz, CDCl$_3$) δ 7.27 (br s, 2H), 3.72 (s, 3H), 2.96-2.85 (m, 4H). MS (ESI) m/z: Calculated for $C_5H_9NO_2S$: 147.04. found: 148.2 (M+H)$^+$.

Ethyl 3-(4-(4-fluorophenyl)thiazol-2-yl)propanoate

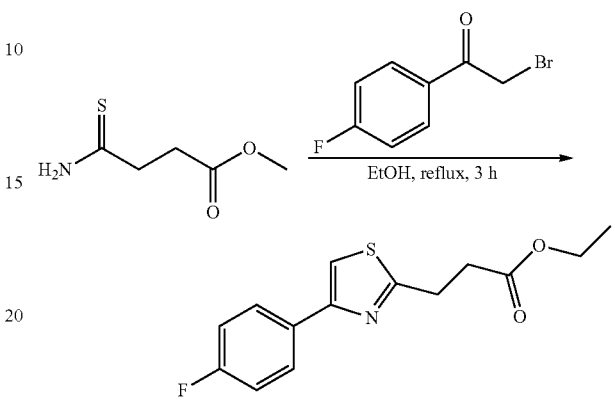

A mixture of methyl 4-amino-4-thioxobutanoate (0.3 g, 2.03 mmol) and 2-bromo-4-fluoroacetophenone (0.440 g, 2.03 mmol) in EtOH (10 mL) was refluxed for 3 h. The reaction mixture was cooled to room temperature and solvent was removed under reduced pressure. The organic product was extracted with EtOAc and the organic layer was washed with brine, dried over anhydrous sodium sulfate, and concentrated under reduced pressure. The crude product was purified by column chromatography (silica gel 60-120 mesh, eluent 8-10% EtOAc in petroleum ether) to afford ethyl 3-(4-(4-fluorophenyl)thiazol-2-yl)propanoate (0.45 g, crude containing 7% of methyl ester product), which was carried through without further purification. $^1$H NMR (300 MHz, CDCl$_3$) δ 7.88-7.83 (m, 2H), 7.28 (s, 1H), 7.13-7.07 (t, J=8.8 Hz, 2H), 4.22-4.15 (q, J=7.0 Hz, 2H), 3.40-3.35 (t, J=7.3 Hz, 2H), 2.93-2.88 (t, J=7.3 Hz, 2H), 1.30-1.25 (t, J=7.1 Hz, 3H). MS (ESI) m/z: Calculated for $C_{14}H_{14}FNO_2S$: 279.07. found: 280.2 (M+H)$^+$.

3-(4-(4-Fluorophenyl)thiazol-2-yl)propanoic acid

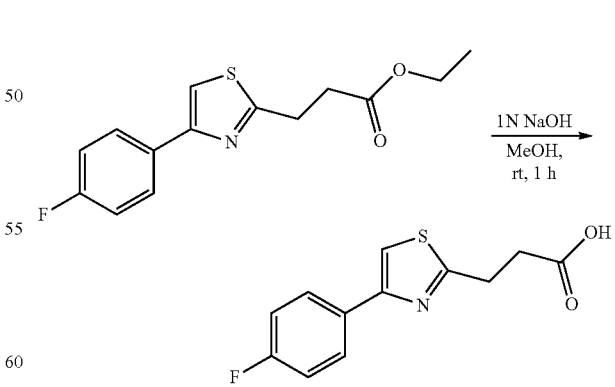

1N NaOH (5 mL) was added to an ice-cooled solution of crude ethyl 3-(4-(4-fluorophenyl)thiazol-2-yl)propanoate (450 mg, 1.61 mmol) in MeOH (5 mL) and the solution was allowed to stir at room temperature for 1 h. Solvent was evaporated and the reaction mixture was diluted with water.

The aqueous layer was washed with EtOAc and the pH of the aqueous solution was adjusted to ~2 using 1N HCl. The organic product was extracted with EtOAc and the organic layer was dried over anhydrous sodium sulfate and concentrated under reduced pressure to yield 3-(4-(4-fluorophenyl) thiazol-2-yl)propanoic acid (320 mg, yield 79%) as a white solid. $^1$H NMR (300 MHz, DMSO-$d_6$) δ 12.29 (br s, 1H), 7.99-7.96 (m, 2H), 7.93 (s, 1H), 7.28-7.22 (t, J=9.0 Hz, 2H), 3.25-3.20 (t, J=7.1 Hz, 2H), 2.78-2.74 (t, J=7.1 Hz, 2H). MS (ESI) m/z: Calculated for $C_{12}H_{10}FNO_2S$: 251.04. found: 252.2 (M+H)$^+$.

3-(4-(4-Fluorophenyl)thiazol-2-yl)-N-(3-(5-(trifluoromethyl)-1,2,4-oxadiazol-3-yl)phenyl)propanamide

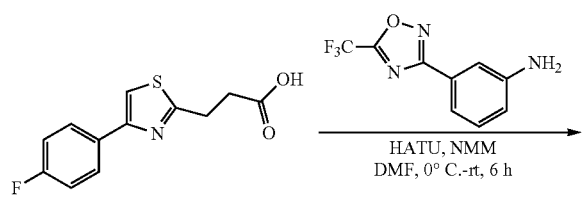

This compound was synthesized from 3-(5-(trifluoromethyl)-1,2,4-oxadiazol-3-yl)aniline and 3-(4-(4-fluorophenyl)thiazol-2-yl)propanoic acid as described in example 8 step 6 (80 mg, yield 43%). $^1$H NMR (400 MHz, CDCl$_3$) δ 8.80 (br s, 1H), 8.11 (s, 1H), 7.88-7.83 (m, 4H), 7.48-7.44 (t, J=7.9 Hz, 1H), 7.33 (s, 1H), 7.14-7.10 (t, J=8.7 Hz, 2H), 3.52-3.48 (m, 2H), 3.04-3.01 (m, 2H). MS (ESI) m/z: Calculated for $C_{21}H_{14}F_4N_4O_2S$: 462.08. found: 463.0 (M+H)$^+$.

Example 51

N-(2-(2-(4-Chlorophenyl)thiazol-4-yl)ethyl)-3-(5-(trifluoromethyl)-1,2,4-oxadiazol-3-yl)benzamide

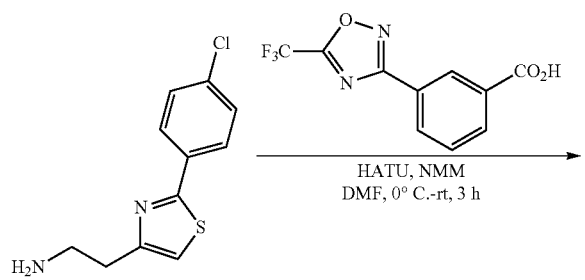

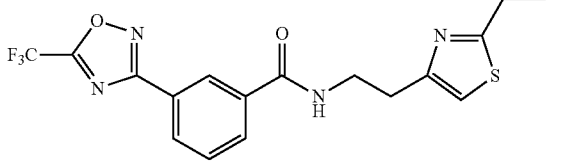

This compound was synthesized from 2-(2-(4-chlorophenyl)thiazol-4-yl)ethanamine and 3-(5-(trifluoromethyl)-1,2,4-oxadiazol-3-yl)benzoic acid as described in example 8 step 6 (40 mg, yield 22%). $^1$H NMR (400 MHz, CDCl$_3$) δ 8.53 (t, J=1.5 Hz, 1H), 8.27-8.25 (dt, J=7.8 Hz, 1.3 Hz, 1H), 8.09-8.07 (dt, J=7.8 Hz, 1.4 Hz, 1H), 7.89-7.87 (m, 2H), 7.68 (m, 1H), 7.62 (t, J=7.8 Hz, 1H), 7.36-7.34 (m, 2H), 7.09 (s, 1H), 3.92-3.87 (m, 2H), 3.16 (t, J=6.0 Hz, 2H). MS (ESI) m/z: Calculated for $C_{21}H_{14}ClF_3N_4O_2S$: 478.05. found: 479.0 (M+H)$^+$.

Example 52

N-((4-Phenylthiazol-2-yl)methyl)benzamide

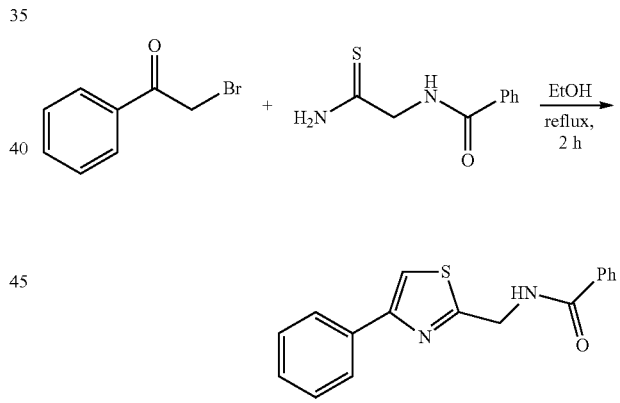

A mixture of N-(2-amino-2-thioxoethyl)benzamide (300 mg, 1.54 mmol) and 2-bromoacetophenone (305 mg, 1.54 mmol) in EtOH (10 mL) was heated to 80° C. for 2 h. The reaction mixture was cooled to room temperature and the solvent was evaporated under reduced pressure. The concentrated reaction mixture was diluted with EtOAc and the organic layer was washed with H$_2$O and brine, and concentrated under reduced pressure to yield N-((4-phenylthiazol-2-yl)methyl)benzamide (0.4 g, yield 88%) as a white solid, which was carried through without further purification. $^1$H NMR (400 MHz, CDCl$_3$) δ 8.69 (br s, 1H), 8.04-8.01 (dd, J=7.8 Hz, 1.5 Hz, 2H), 7.99-7.97 (m, 2H), 7.64 (s, 1H), 7.56-7.52 (m, 4H), 7.48-7.44 (m, 2H), 5.34 (d, J=6 Hz, 2H). MS (ESI) m/z: Calculated for $C_{17}H_{14}N_2OS$: 294.08. found: 295.0 (M+H)$^+$.

(4-Phenylthiazol-2-yl)methanamine

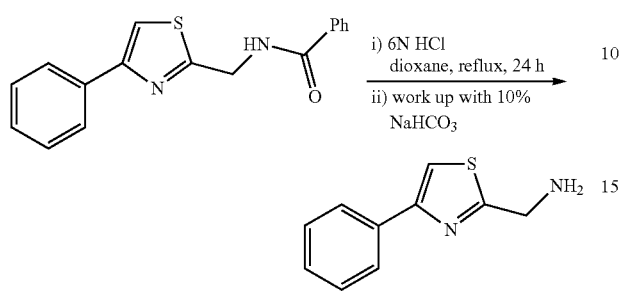

6N HCl (4.5 mL) was added to a solution of N-((4-phenylthiazol-2-yl)methyl)benzamide (150 mg, 0.51 mmol) in dioxane (10 mL) and the reaction mixture was stirred at 100° C. for 24 h (reaction monitored by TLC, eluant CHCl$_3$/MeOH). Reaction mixture was concentrated under reduced pressure and the residue was dissolved in water. The aqueous layer was washed twice with EtOAc. The pH of the aqueous layer was then adjusted to pH ~9 using 10% NaHCO$_3$ and the organic product was extracted with EtOAc. The organic layer was washed with brine and concentrated under reduced pressure to yield (4-phenylthiazol-2-yl)methanamine (75 mg, yield 77%) as orange colored liquid, which was carried through without further purification. $^1$H NMR (300 MHz, CDCl$_3$) δ 7.91-7.88 (m, 2H), 7.45-7.40 (m, 3H), 7.36-7.31 (m, 1H), 4.25 (br s, 2H), 3.79-3.75 (m, 1H), 3.68-3.63 (m, 1H). MS (ESI) m/z: Calculated for $C_{10}H_{10}N_2S$: 190.06. found: 191.2 (M+H)$^+$.

N-((4-Phenylthiazol-2-yl)methyl)-3-(5-(trifluoromethyl)-1,2,4-oxadiazol-3-yl)benzamide

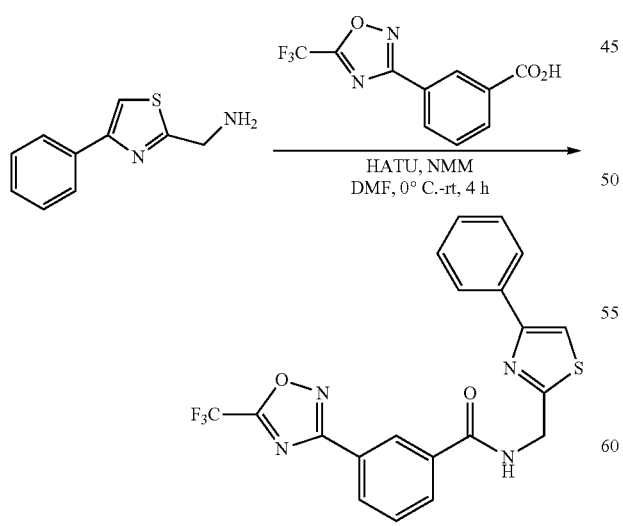

This compound was synthesized from (4-phenylthiazol-2-yl)methanamine and 3-(5-(trifluoromethyl)-1,2,4-oxadiazol-3-yl)benzoic acid as described in example 8 step 6 (60 mg, yield 38%) as a white solid. $^1$H NMR (400 MHz, CDCl$_3$) δ 8.59 (m, 1H), 8.31-8.29 (dd, J=7.8 Hz, 1.0 Hz, 1H), 8.12-8.10 (m, 1H), 7.91-7.89 (m, 2H), 7.67 (t, J=7.8 Hz, 1H), 7.47 (s, 1H), 7.44 (t, J=7.5 Hz, 2H), 7.38-7.34 (m, 1H), 7.23 (t, J=4.8 Hz, 1H), 5.04 (d, J=5.5 Hz, 2H). MS (ESI) m/z: Calculated for $C_{20}H_{13}F_3N_4O_2S$: 430.07. found: 431.0 (M+H)$^+$.

Example 53

N-(2-(4-(4-Fluorophenyl)thiazol-2-yl)ethyl)-5-(5-(trifluoromethyl)-1,2,4-oxadiazol-3-yl)nicotinamide

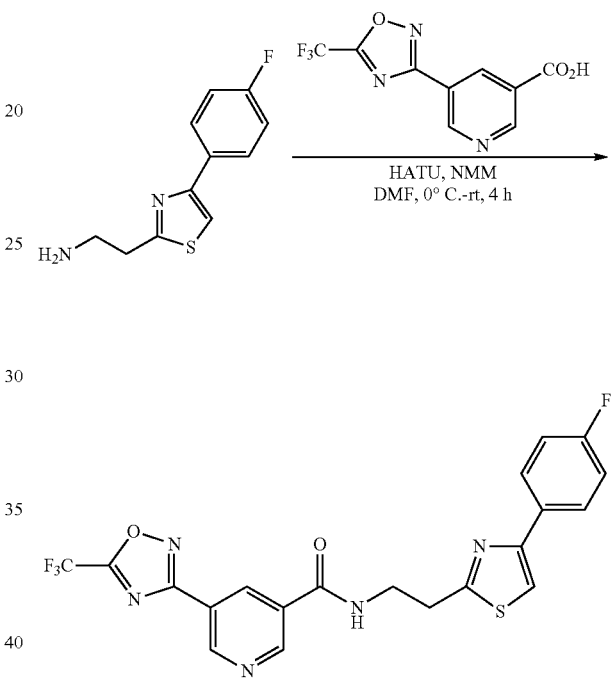

This compound was synthesized from 2-(4-(4-fluorophenyl)thiazol-2-yl)ethanamine and 5-(5-(trifluoromethyl)-1,2,4-oxadiazol-3-yl)nicotinic acid as described in example 8 step 6 (50 mg, yield 29%). $^1$H NMR (400 MHz, CDCl$_3$) δ 9.45 (d, J=1.3 Hz, 1H), 9.24 (d, J=1.5 Hz, 1H), 8.80 (t, J=2.1 Hz, 1H), 7.86-7.82 (m, 3H), 7.35 (s, 1H), 7.11-7.07 (m, 2H), 4.05-4.00 (q, J=5.7 Hz, 2H), 3.41-3.38 (m, 2H). MS (ESI) m/z: Calculated for $C_{20}H_{13}F_4N_5O_2S$: 463.07. found: 464.0 (M+H)$^+$.

Example 54

2-(4-(4-Chlorophenyl)thiazol-2-yl)ethanamine

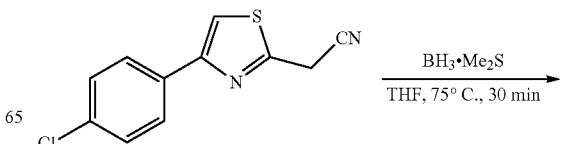

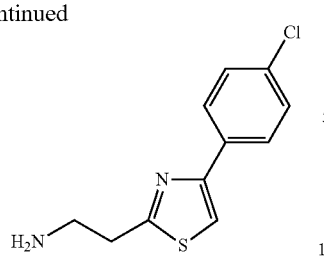

This compound was synthesized from 2-(4-(4-chlorophenyl)thiazol-2-yl)acetonitrile as described in example 42 step 1 (400 mg, crude) and it was carried through without further purification. MS (ESI) m/z: Calculated for $C_{11}H_{11}ClN_2S$: 238.03. found: 239.0 (M+H)$^+$.

N-(2-(4-(4-Chlorophenyl)thiazol-2-yl)ethyl)-3-(5-(trifluoromethyl)-1,2,4-oxadiazol-3-yl)benzamide

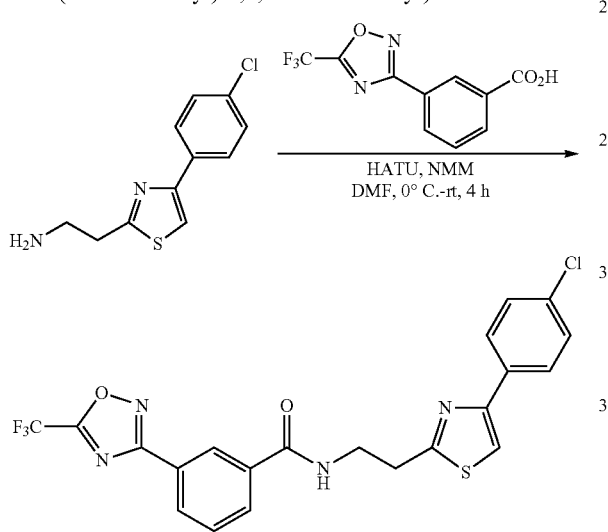

This compound was synthesized from 2-(4-(4-chlorophenyl)thiazol-2-yl)ethanamine and 3-(5-(trifluoromethyl)-1,2,4-oxadiazol-3-yl)benzoic acid as described in example 8 step 6 (30 mg, yield 16%). $^1$H NMR (400 MHz, CDCl$_3$) δ 8.53 (s, 1H), 8.26 (d, J=7.8 Hz, 1H), 8.06 (d, J=7.8 Hz, 1H), 7.81 (d, J=8.6 Hz, 2H), 7.64-7.60 (m, 2H), 7.39 (s, 1H), 7.34 (d, J=8.6 Hz, 2H), 4.02-3.97 (q, J=5.8 Hz, 2H), 3.39-3.36 (t, J=5.9 Hz, 2H). MS (ESI) m/z: Calculated for $C_{21}H_{14}ClF_3N_4O_2S$: 478.05. found: 479.0 (M+H)$^+$.

Example 55

N-(2-(4-(4-Chlorophenyl)thiazol-2-yl)ethyl)-5-(5-(trifluoromethyl)-1,2,4-oxadiazol-3-yl)nicotinamide

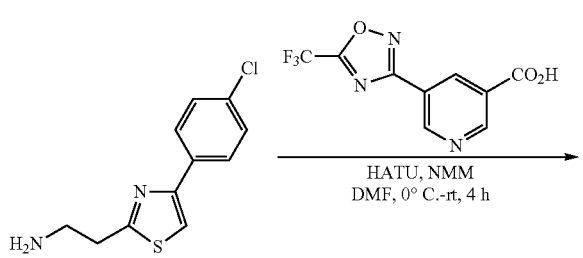

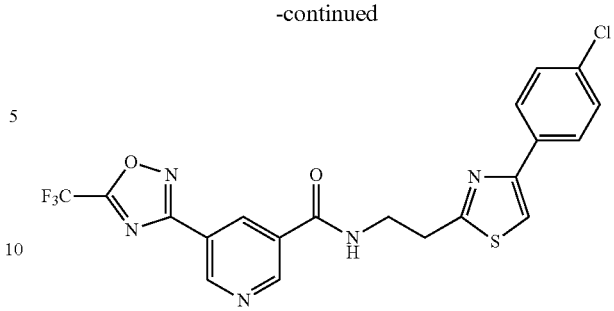

This compound was synthesized from 2-(4-(4-chlorophenyl)thiazol-2-yl)ethanamine and 5-(5-(trifluoromethyl)-1,2,4-oxadiazol-3-yl)nicotinic acid as described in example 8 step 6 (65 mg, yield 35%). $^1$H NMR (400 MHz, CDCl$_3$) δ 9.46 (d, J=1.8 Hz, 1H), 9.24 (d, J=1.8 Hz, 1H), 8.80 (t, J=2.1 Hz, 1H), 7.82-7.80 (m, 3H), 7.41 (s, 1H), 7.38-7.36 (m, 2H), 4.05-4.01 (q, J=5.8 Hz, 2H), 3.43-3.40 (t, J=5.9 Hz, 2H). MS (ESI) m/z: Calculated for $C_{20}H_{13}ClF_3N_5O_2S$: 479.04. found: 480.0 (M+H)$^+$.

Example 56

4-(3,4-Dihydroisoquinolin-2(1H)-yl)tetrahydro-2H-pyran-4-carbonitrile

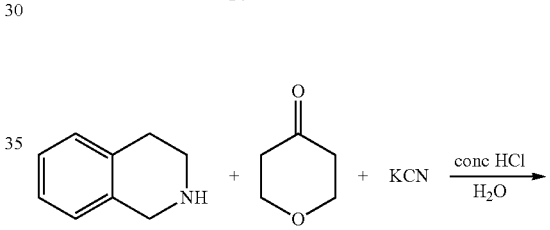

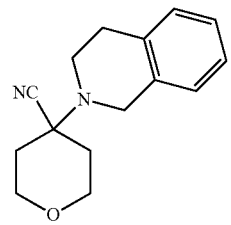

3,4,5,6-Tetrahydro-4H-pyran-4-one (0.37 g, 3.75 mmol) was added to a solution of 1,2,3,4-tetrahydroisoquinoline (0.47 mL, 3.75 mmol) in conc. HCl (0.4 mL) diluted with ice water (1.5 mL), followed by a solution of KCN (0.24 g, 3.75 mmol) dissolved in water (2 mL), and the reaction mixture was stirred at room temperature for 2 h. The reaction mixture was then diluted with water and the organic product was extracted with EtOAc. The organic layer was washed with H$_2$O and brine, dried over anhydrous Na$_2$SO$_4$ and concentrated under reduced pressure. The residue was purified by column chromatography (silica 60-120 mesh, eluent 6% EtOAc in petroleum ether) to afford 4-(3,4-dihydroisoquinolin-2(1H)-yl)tetrahydro-2H-pyran-4-carbonitrile (300 mg, yield 33%). $^1$H NMR (300 MHz, CDCl$_3$) δ 7.19-7.11 (m, 3H), 7.07-7.05 (m, 1H), 4.10-4.04 (dt, J=12.3 Hz, 3.5 Hz, 2H), 3.87 (s, 2H), 3.76-3.68 (m, 2H), 2.97-2.91 (m, 4H), 2.28-2.23

(dd, J=13.3 Hz, 1.4 Hz, 2H), 1.93-1.84 (td, J=12.4 Hz, 4.2 Hz, 2H). MS (ESI) m/z: Calculated for $C_{15}H_{18}N_2O$: 242.14. found: 243.2 (M+H)+.

(4-(3,4-Dihydroisoquinolin-2(1H)-yl)tetrahydro-2H-pyran-4-yl)methanamine

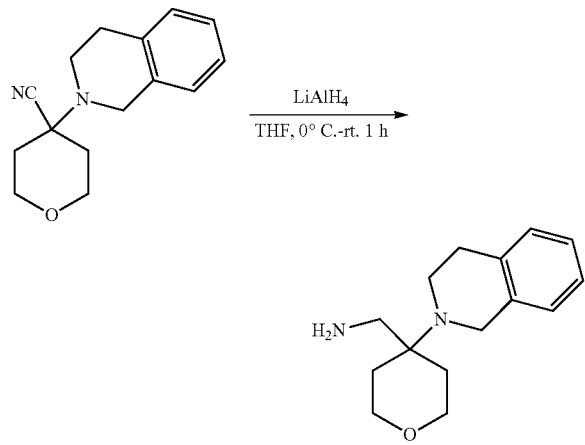

This compound was synthesized from 4-(3,4-dihydroisoquinolin-2(1H)-yl)tetrahydro-2H-pyran-4-carbonitrile as described in example 1 step 3 (80 mg, yield 26%). $^1$H NMR (300 MHz, CDCl$_3$) δ 7.15-7.12 (m, 3H), 7.06-7.03 (m, 1H), 3.90 (s, 2H), 3.87-3.84 (m, 2H), 3.65-3.58 (ddd, J=11.3 Hz, 8.1 Hz, 3.2 Hz, 2H), 2.94-2.85 (m, 6H), 1.99-1.91 (m, 2H), 1.65-1.62 (m, 2H). MS (ESI) m/z: Calculated for $C_{15}H_{22}N_2O$: 246.17. found: 247.2 (m+H)+.

N-((4-(3,4-Dihydroisoquinolin-2(1H)-yl)tetrahydro-2H-pyran-4-yl)methyl)-3-(5-(trifluoromethyl)-1,2,4-oxadiazol-3-yl)benzamide

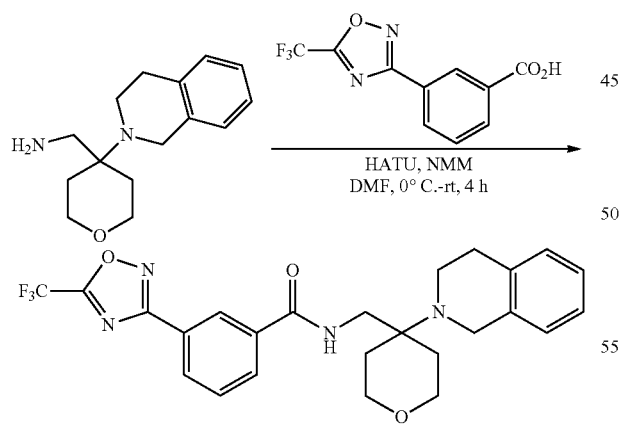

This compound was synthesized from (4-(3,4-dihydroisoquinolin-2(1H)-yl)tetrahydro-2H-pyran-4-yl)methan amine and 3-(5-(trifluoromethyl)-1,2,4-oxadiazol-3-yl)benzoic acid as described in example 8 step 6 (40 mg, yield 30%). $^1$H NMR (400 MHz, CDCl$_3$) δ 8.45 (s, 1H), 8.22 (d, J=7.8 Hz, 1H), 7.91-7.89 (d, J=7.5 Hz, 1H), 7.59-7.55 (t, J=7.8 Hz, 1H), 7.17-7.15 (m, 3H), 7.12-7.07 (m, 2H), 3.96-3.93 (m, 4H), 3.86-3.85 (d, J=4.8 Hz, 2H), 3.74-3.68 (m, 2H), 2.95 (m, 4H), 2.15-2.07 (m, 2H), 1.58-1.55 (m, 2H). MS (ESI) m/z: Calculated for $C_{25}H_{25}F_3N_4O_3$: 486.19. found: 487.2 (M+H)+.

Example 57

N-Methyl-1-(4-(4-phenylthiazol-2-yl)tetrahydro-2H-pyran-4-yl)methanamine

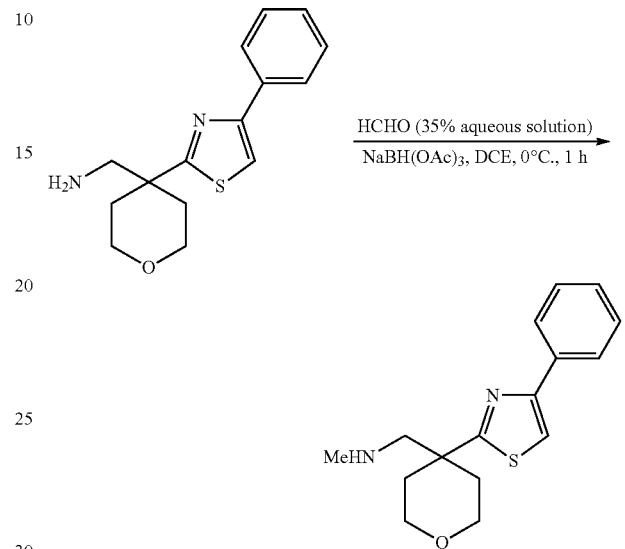

(4-(4-phenylthiazol-2-yl)tetrahydro-2H-pyran-4-yl) methanamine (300 mg, 1.1 mmol) was dissolved in 1,2-dichloroethane (30 mL) and cooled to 0° C. Formaline solution (~0.1 mL, 35%) was added to the solution, followed by sodiumtriacetoxy borohydride (0.16 g, 0.76 mmol). The reaction mixture was further stirred for 45 min maintaining the same temperature. The reaction mixture was then quenched with 10% NaHCO$_3$ solution and diluted with CH$_2$Cl$_2$. The organic layer was separated, dried over anhydrous Na$_2$SO$_4$, and concentrated under reduced pressure. The residue was purified by column chromatography (silica 60-120 mesh, eluent 10-20% MeOH in CHCl$_3$) to afford N-methyl-1-(4-(4-phenylthiazol-2-yl)tetrahydro-2H-pyran-4-yl)methanamine (120 mg, yield 38%). $^1$H NMR (300 MHz, CDCl$_3$) δ 7.90-7.88 (m, 2H), 7.48 (s, 1H), 7.44-7.34 (m, 3H), 3.93-3.86 (m, 2H), 3.75-3.67 (ddd, J=12.0 Hz, 8.9 Hz, 3.0 Hz, 2H), 3.01 (s, 2H), 2.49 (s, 3H), 2.36-2.39 (m, 2H), 2.09-2.01 (m, 2H). MS (ESI) m/z: Calculated for $C_{16}H_{20}N_2OS$: 288.13. found: 289.2 (M+H)+.

N-Methyl-N-((4-(4-phenylthiazol-2-yl)tetrahydro-2H-pyran-4-yl)methyl)-3-(5-(trifluoromethyl)-1,2,4-oxadiazol-3-yl)benzamide

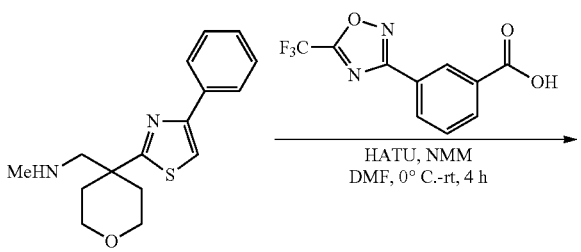

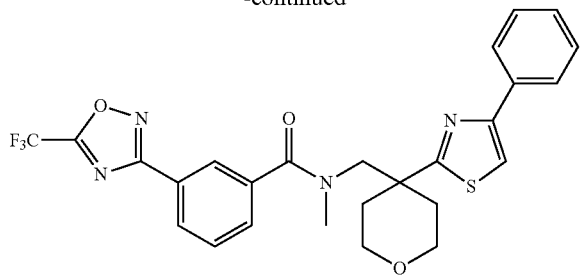

This compound was synthesized from N-methyl-1-(4-(4-phenylthiazol-2-yl)tetrahydro-2H-pyran-4-yl)methanamine and 3-(5-(trifluoromethyl)-1,2,4-oxadiazol-3-yl)benzoic acid as described in example 8 step 6 (30 mg, yield 14%). $^1$H NMR (400 MHz, CDCl$_3$) δ 8.13-8.09 (m, 2H), 7.96-7.94 (m, 2H), 7.57-7.55 (m, 2H), 7.48-7.41 (m, 3H), 7.36-7.32 (m, 1H), 3.99-3.96 (m, 2H), 3.92 (s, 2H), 3.66-3.60 (m, 2H), 2.53 (s, 3H), 2.48-2.44 (m, 2H), 2.23-2.16 (m, 2H). MS (ESI) m/z: Calculated for C$_{26}$H$_{23}$F$_3$N$_4$O$_3$S: 528.14. found: 529.2 (M+H)$^+$.

Example 58

2-(2-(4-Fluorophenyl)thiazol-4-yl)ethanamine

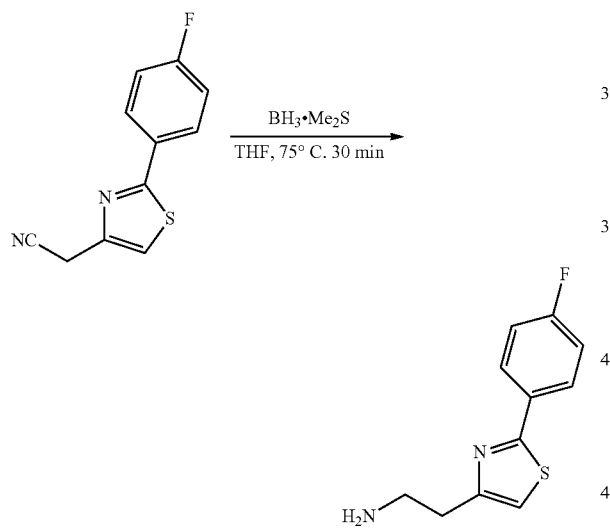

This compound was synthesized from 2-(2-(4-fluorophenyl)thiazol-4-yl)acetonitrile as described in example 42 step 1 (150 mg, crude) and it was carried through without further purification. MS (ESI) m/z: Calculated for C$_{11}$H$_{11}$FN$_2$S: 222.06. found: 223.0 (M+H)$^+$.

N-(2-(2-(4-Fluorophenyl)thiazol-4-yl)ethyl)-5-(5-(trifluoromethyl)-1,2,4-oxadiazol-3-yl)nicotinamide

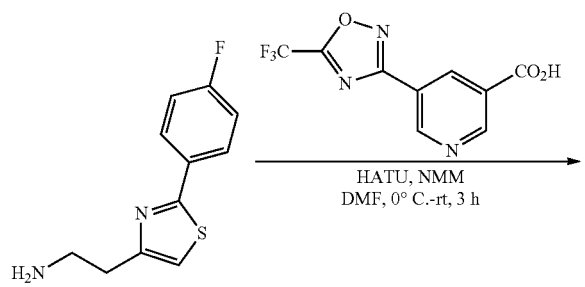

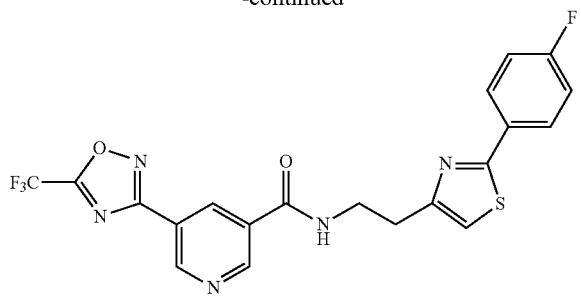

This compound was synthesized from 2-(2-(4-fluorophenyl)thiazol-4-yl)ethanamine and 5-(5-(trifluoromethyl)-1,2,4-oxadiazol-3-yl)nicotinic acid as described in example 8 step 6 (30 mg, yield 17%). $^1$H NMR (400 MHz, DMSO-d$_6$) δ 9.45 (br s, 1H), 9.26 (br s, 1H), 8.82 (t, J=2.0 Hz, 1H), 7.96-7.92 (m, 3H), 7.14-7.08 (m, 3H), 3.94-3.89 (m, 2H), 3.19-3.16 (m, 2H). MS (ESI) m/z: Calculated for C$_{20}$H$_{13}$F$_4$N$_5$O$_2$S: 463.07. found: 464.0 (M+H)$^+$.

Example 59

N-(2-(2-(4-Fluorophenyl)thiazol-4-yl)ethyl)-3-(5-(trifluoromethyl)-1,2,4-oxadiazol-3-yl)benzamide

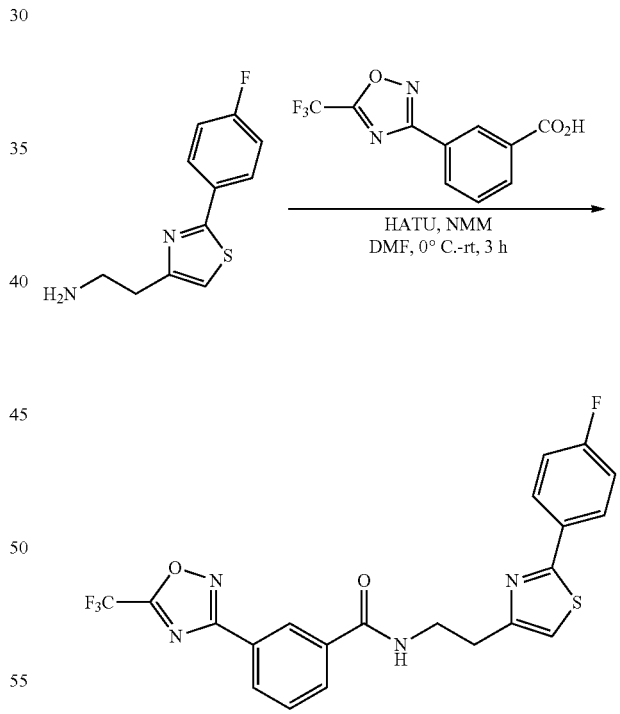

This compound was synthesized from 2-(2-(4-fluorophenyl)thiazol-4-yl)ethanamine and 3-(5-(trifluoromethyl)-1,2,4-oxadiazol-3-yl)benzoic acid as described in example 8 step 6 (60 mg, yield 45%). $^1$H NMR (400 MHz, CDCl$_3$) δ 8.53 (t, J=1.4 Hz, 1H), 8.27-8.24 (dt, J=7.9 Hz, 1.3 Hz, 1H), 8.09-8.06 (dt, J=7.6 Hz, 1.6 Hz, 1H), 7.94-7.90 (m, 2H), 7.70 (m, 1H), 7.63-7.59 (t, J=7.8 Hz, 1H), 7.09-7.05 (m, 3H), 3.91-

3.86 (m, 2H), 3.16-3.13 (t, J=6.0 Hz, 2H). MS (ESI) m/z: Calculated for $C_{21}H_{14}F_4N_4O_2S$: 462.08. found: 463.0 $(M+H)^+$.

Example 60

N-(2-(4-(4-Fluorophenyl)thiazol-2-yl)-2-methylpropyl)-6-(6-(trifluoromethyl)-1,2,4-oxadiazol-3-yl)nicotinamide

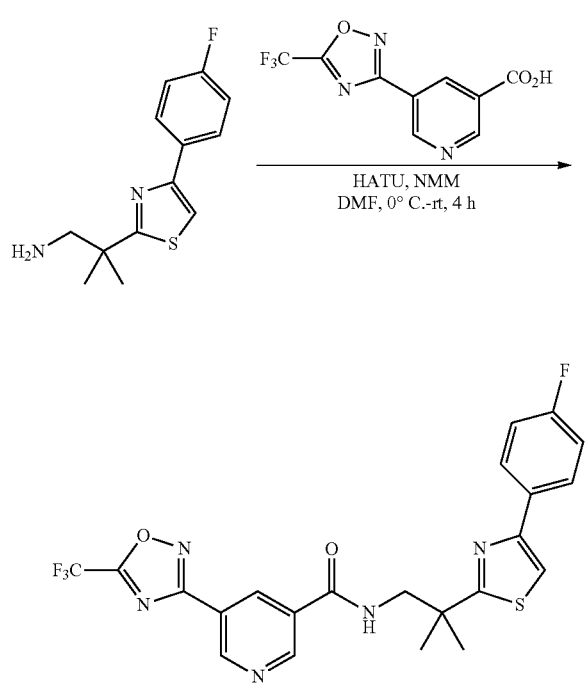

This compound was synthesized from 2-(4-(4-fluorophenyl)thiazol-2-yl)-2-methylpropan-1-amine and 5-(5-(trifluoromethyl)-1,2,4-oxadiazol-3-yl)nicotinic acid as described in example 8 step 6 (55 mg, yield 42%). $^1$H NMR (400 MHz, CDCl$_3$) δ 9.45 (s, 1H), 9.24 (s, 1H), 8.79 (m, 1H), 8.25 (m, 1H), 7.85-7.81 (dd, J=8.6 Hz, 5.4 Hz, 2H), 7.37 (s, 1H), 7.10-7.06 (t, J=8.6 Hz, 2H), 3.84 (d, J=5.6 Hz, 2H), 1.57 (s, 6H). MS (ESI) m/z: Calculated for $C_{22}H_{17}F_4N_5O_2S$: 491.10. found: 492.0 $(M+H)^+$.

Example 61

3-(2,2,2-Trifluoro-1-(((4-(4-phenylthiazol-2-yl)tetrahydro-2H-pyran-4-yl)methyl)imino)ethyl)benzonitrile

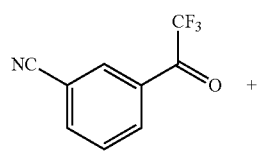

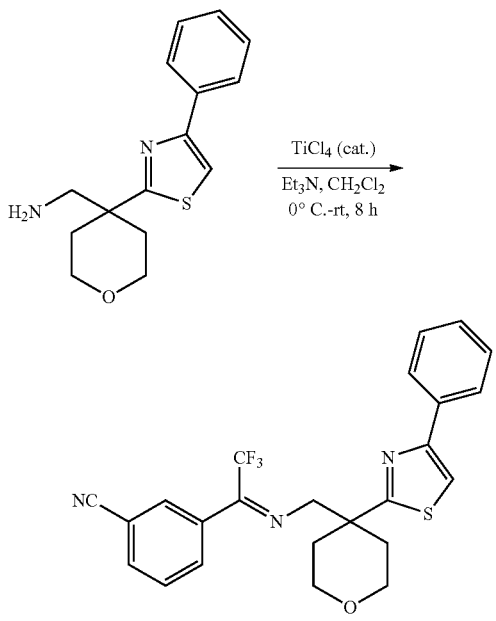

Triethylamine (1.0 mL, 2.7 mmol) was added to a solution of 3-cyano-2,2,2-trifluoroacetophenone (0.48 g, 2.4 mmol) and (4-(4-phenylthiazol-2-yl)tetrahydro-2H-pyran-4-yl)methanamine (0.66 g, 2.4 mmol) in dry CH$_2$Cl$_2$ (25 mL), followed by a solution of titanium tetrachloride in CH$_2$Cl$_2$ (1.2 mL, 1.2 mmol, 1M solution in CH$_2$Cl$_2$) at 0° C. and the reaction mixture was warmed to room temperature and further stirred for 8 h. The reaction was concentrated under reduced pressure and the organic product was extracted with EtOAc. The organic layer was washed with water and brine solution, dried over anhydrous sodium sulfate and the solvent was removed under reduced pressure to get 3-(2,2,2-trifluoro-1-(((4-(4-phenylthiazol-2-yl)tetrahydro-2H-pyran-4-yl)methyl)imino)ethyl)benzonitrile (0.6 g, crude), which was carried through without further purification. $^1$H NMR (400 MHz, CDCl$_3$) δ 7.88-7.85 (m, 2H), 7.70-7.67 (m, 1H), 7.50 (s, 1H), 7.46-7.41 (m, 3H), 7.39-7.36 (m, 1H), 7.23 (s, 1H), 7.07 (d, J=8.0 Hz, 1H), 3.93-3.88 (dt, J=11.9 Hz, 4.0 Hz, 2H), 3.66-3.62 (m, 4H), 2.43-2.40 (m, 2H), 2.15-2.00 (ddd, J=14.1 Hz, 10.3 Hz, 4.3 Hz, 2H). MS (ESI) m/z: Calculated for $C_{24}H_{20}F_3N_3OS$: 455.13. found: 456.2 $(M+H)^+$.

3-(2,2,2-Trifluoro-1-(((4-(4-phenylthiazol-2-yl)tetrahydro-2H-pyran-4-yl)methyl)amino)ethyl)benzonitrile

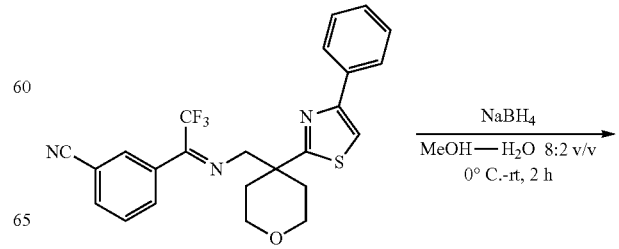

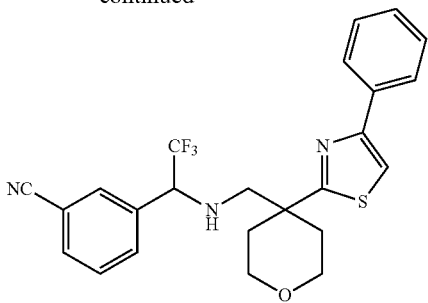

3-(2,2,2-trifluoro-1-(((4-(4-phenylthiazol-2-yl)tetrahydro-2H-pyran-4-yl)methyl)imino)ethyl)benzonitrile (600 mg, 1.3 mmol) was dissolved in MeOH—H$_2$O (20 mL, 8:2 v/v) and cooled to 0° C. Sodium borohydride (250 mg, 6.6 mmol) was added to this solution portionwise. The reaction mixture was allowed to warm up to room temperature, stirred for 2 h, and then quenched with water and concentrated under reduced pressure to remove the MeOH. The aqueous mixture was diluted with EtOAc and the organic layer was washed with H$_2$O and brine, dried over anhydrous sodium sulfate and concentrated under reduced pressure. The crude product was purified by column chromatography (silica gel 60-120 mesh, eluant 15-20% EtOAc in petroleum ether) to afford 3-(2,2,2-trifluoro-1-(((4-(4-phenylthiazol-2-yl)tetrahydro-2H-pyran-4-yl)methyl)amino)ethyl)benzonitrile (300 mg, yield 50%). $^1$H NMR (300 MHz, CDCl$_3$) δ 7.89-7.86 (m, 2H), 7.63-7.60 (dt, J=7.6 Hz, 1.4 Hz, 1H), 7.55-7.51 (m, 2H), 7.50 (s, 1H), 7.47-7.41 (m, 3H), 7.39-7.36 (m, 0.1H), 4.16-4.03 (m, 1H), 3.84-3.74 (m, 2H), 3.71-3.61 (m, 2H), 2.95 (d, J=11.4 Hz, 1H), 2.76 (d, J=11.4 Hz, 1H), 2.36-2.24 (m, 2H), 2.01-1.92 (ddd, J=13.5 Hz, 9.0 Hz, 4.1 Hz, 2H). MS (ESI) m/z: Calculated for C$_{24}$H$_{22}$F$_3$N$_3$OS: 457.14. found: 458.2 (M+H)$^+$.

N'-Hydroxy-3-(2,2,2-trifluoro-1-(((4-(4-phenylthiazol-2-yl)tetrahydro-2H-pyran-4-yl)methyl)amino)ethyl)benzimidamide

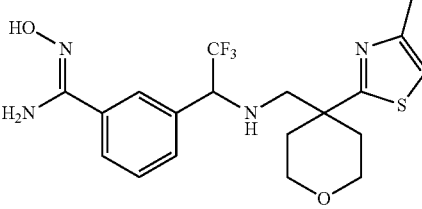

This compound was synthesized from 3-(2,2,2-trifluoro-1-(((4-(4-phenylthiazol-2-yl)tetrahydro-2H-pyran-4-yl)methyl)amino)ethyl)benzonitrile acid as described in example 1 step 4 (300 mg, crude), which was carried through without further purification. MS (ESI) m/z: Calculated for C$_{24}$H$_{25}$F$_3$N$_4$O$_2$S: 490.17. found: 491.2 (M+H)$^+$.

2,2,2-Trifluoro-N-((4-(4-phenylthiazol-2-yl)tetrahydro-2H-pyran-4-yl)methyl)-1-(3-(5-(trifluoromethyl)-1,2,4-oxadiazol-3-yl)phenyl)ethanamine

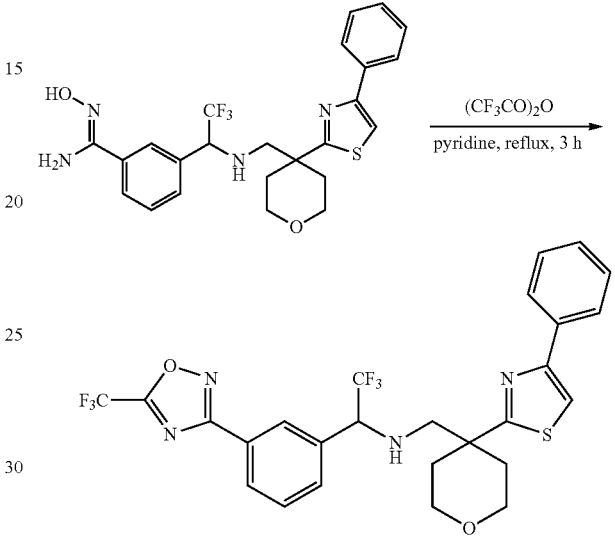

This compound was synthesized from N'-hydroxy-3-(2,2,2-trifluoro-1-(((4-(4-phenylthiazol-2-yl)tetrahydro-2H-pyran-4-yl)methyl)amino)ethyl)benzimidamide acid as described in example 1 step 5 (70 mg, yield 20%). $^1$H NMR (400 MHz, DMSO-d$_6$) δ 8.11-8.09 (dt, J=7.2 Hz, 1.7 Hz, 1H), 8.05 (s, 1H), 7.85-7.83 (m, 2H), 7.53-7.49 (m, 2H), 7.47 (s, 1H), 7.42-7.38 (m, 2H), 7.35-7.31 (m, 1H), 4.15-4.10 (q, J=7.2 Hz, 1H), 3.81-3.74 (m, 2H), 3.70-3.62 (m, 2H), 2.99-2.96 (m, 1H), 2.86-2.83 (m, 1H), 2.33-2.27 (m, 2H), 2.04-1.93 (ddd, J=13.4 Hz, 9.0 Hz, 4.0 Hz, 2H). MS (ESI) m/z: Calculated for C$_{26}$H$_{22}$F$_6$N$_4$O$_2$S: 568.14. found: 569.2 (M+H)$^+$.

Example 62

Methyl 4-fluorobenzimidate hydrochloride

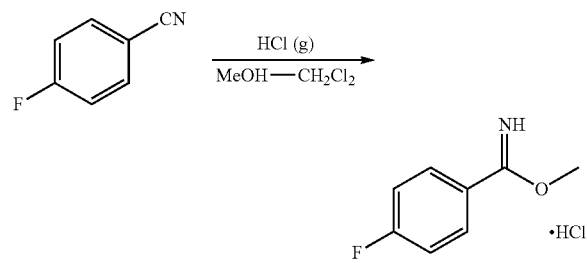

Dry HCl (g) was bubbled through a solution of 4-fluorobenzonitrile (5.0 g, 0.041 mol) in dry MeOH—CH$_2$Cl$_2$ (20 mL, 1:1 v/v) until saturation. The clear solution was kept at 0° C. for 2 days to crystallize methyl 4-fluorobenzimidate as hydrochloride salt, which was isolated by filtration (2.8 g, yield 36%). $^1$H NMR (400 MHz, DMSO-d$_6$) δ 7.95-7.92 (m, 2H), 7.38 (br s, 1H), 7.29-7.25 (m, 2H), 3.06 (s, 3H). MS (ESI) m/z: Calculated for C$_8$H$_8$FNO: 153.06. found: 154.2 (M+H)$^+$.

2-(3-(4-Fluorophenyl)-1H-1,2,4-triazol-5-yl)acetonitrile

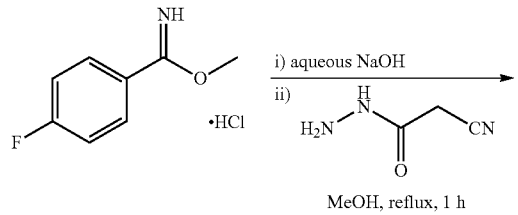

2-Cyanoacetohydrazide (172 mg, 1.74 mmol) and NaOH (66 mg, 1.66 mmol) were added to a solution of methyl 4-fluorobenzimidate hydrochloride (300 mg, 1.58 mmol) in dry MeOH (5 mL) and the mixture was heated to reflux for 1 h. The reaction mixture was concentrated under reduced pressure and the residue obtained was diluted with EtOAc. The organic layer was washed with water and brine, dried over anhydrous sodium sulfate, and concentrated under reduced pressure. The crude product was purified by column chromatography (silica 60-120 mesh, eluant 20-25% EtOAc in petroleum ether) to yield 2-(3-(4-fluorophenyl)-1H-1,2,4-triazol-5-yl)acetonitrile (150 mg, yield 47%). $^1$H NMR (400 MHz, DMSO-d$_6$) δ 8.04-7.99 (m, 2H), 7.39-7.33 (m, 2H), 4.11 (s, 2H). MS (ESI) m/z: Calculated for C$_{10}$H$_7$FN$_4$: 202.07. found: 203.2 (M+H)$^+$.

2-(3-(4-Fluorophenyl)-1H-1,2,4-triazol-5-yl)ethanamine

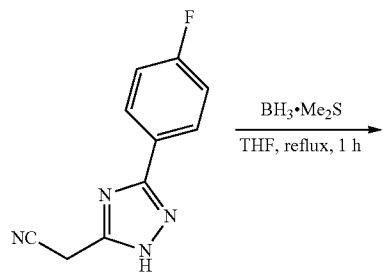

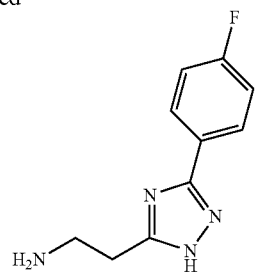

This compound was synthesized from 2-(3-(4-fluorophenyl)-1H-1,2,4-triazol-5-yl)acetonitrile as described in example 42 step 1 (40 mg, crude) and it was carried through without further purification. MS (ESI) m/z: Calculated for C$_{10}$H$_{11}$FN$_4$: 206.10. found: 207.2 (M+H)$^+$.

N-(2-(3-(4-Fluorophenyl)-1H-1,2,4-triazol-5-yl)ethyl)-3-(5-(trifluoromethyl)-1,2,4-oxadiazol-3-yl)benzamide

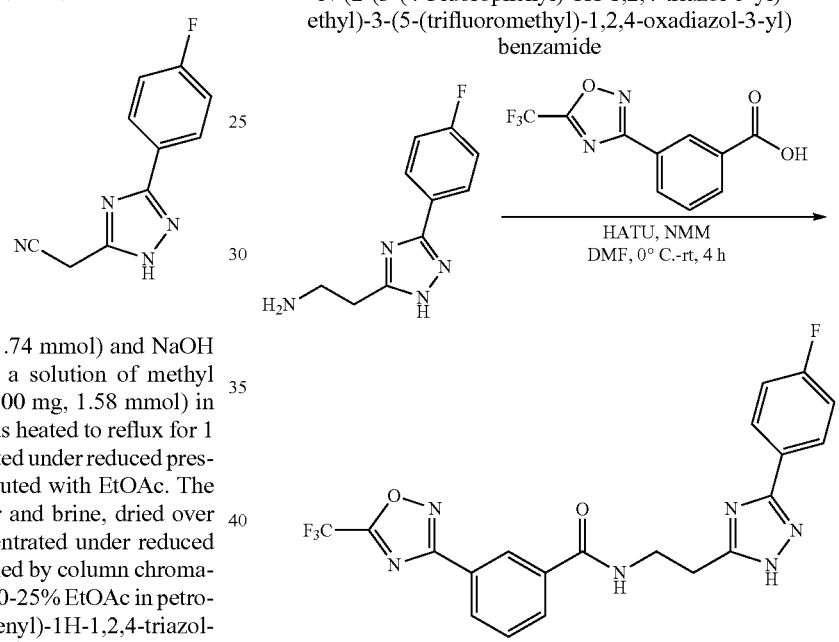

This compound was synthesized from 2-(3-(4-fluorophenyl)-1H-1,2,4-triazol-5-yl)ethanamine and 3-(5-(trifluoromethyl)-1,2,4-oxadiazol-3-yl)benzoic acid as described in example 8 step 6 (11 mg, yield 13%). $^1$H NMR (400 MHz, CDCl$_3$) δ 8.52 (s, 1H), 8.26-8.24 (d, J=7.8 Hz, 1H), 8.07-8.03 (m, 3H), 7.67-7.59 (m, 2H), 7.13-7.09 (t, J=8.7 Hz, 2H), 4.01-3.96 (q, J=5.9 Hz, 2H), 3.24-3.21 (d, J=6.1 Hz, 2H). MS (ESI) m/z: Calculated for C$_{20}$H$_{14}$F$_4$N$_6$O$_2$: 446.11. found: 447.2 (M+H)$^+$.

Example 63

Methyl 4-chlorobenzimidate hydrochloride

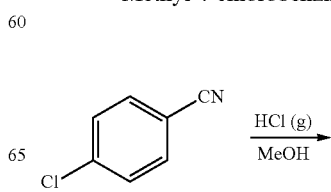

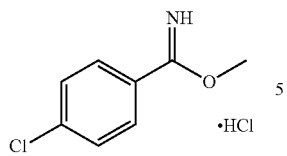

This compound was synthesized from 4-chlorobenzonitrile as described in example 62 step 1 (3.5 g, 47%). $^1$H NMR (400 MHz, DMSO-$d_6$) δ 7.95-7.92 (m, 2H), 7.38 (br s, 1H), 7.29-7.25 (m, 2H), 3.06 (s, 3H). MS (ESI) m/z: Calculated for $C_8H_8ClNO$: 169.02. found: 170.0 (M+H)$^+$.

2-(3-(4-Chlorophenyl)-1H-1,2,4-triazol-5-yl)acetonitrile

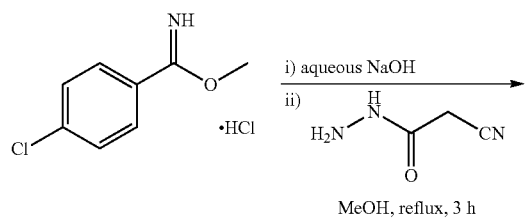

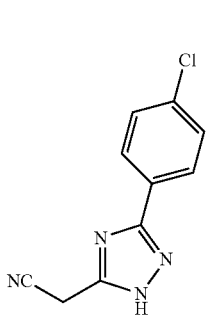

This compound was synthesized from methyl 4-chlorobenzimidate hydrochloride as described in example 62 step 2 (200 mg, yield 38%). $^1$H NMR (300 MHz, CDCl$_3$) δ 7.87-7.84 (m, 1H), 7.63-7.60 (m, 1H), 7.51-7.47 (m, 2H), 3.96 (s, 2H). MS (ESI) m/z: Calculated for $C_{10}H_7ClN_4$: 218.04. found: 219.0 (M+H)$^+$.

2-(3-(4-Chlorophenyl)-1H-1,2,4-triazol-5-yl)ethanamine

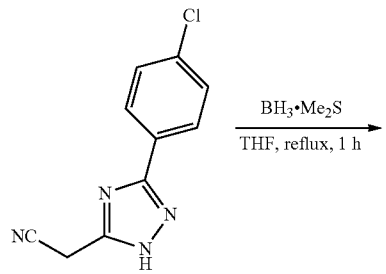

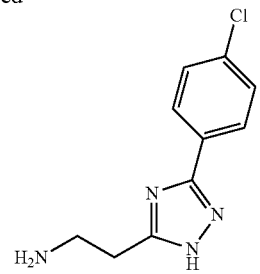

This compound was synthesized from 2-(3-(4-chlorophenyl)-1H-1,2,4-triazol-5-yl)acetonitrile as described in example 42 step 1 (90 mg, crude) and it was carried through without further purification. MS (ESI) m/z: Calculated for $C_{10}H_{11}ClN_4$: 222.07. found: 223.2 (M+H)$^+$.

N-(2-(3-(4-Chlorophenyl)-1H-1,2,4-triazol-5-yl) ethyl)-3-(5-(trifluoromethyl)-1,2,4-oxadiazol-3-yl) benzamide

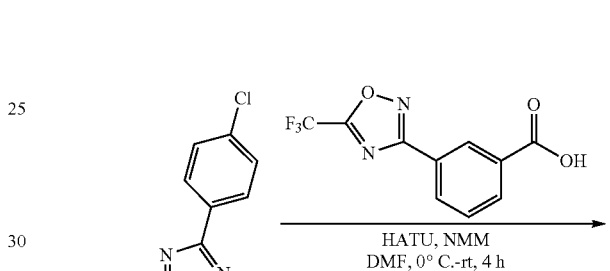

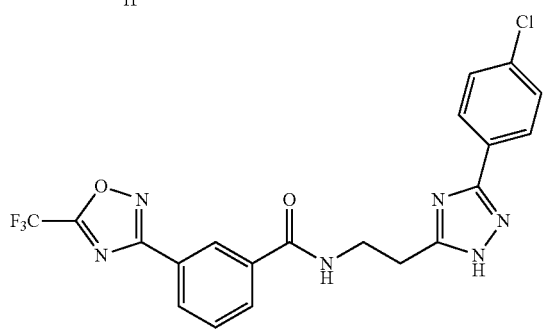

This compound was synthesized from 2-(3-(4-chlorophenyl)-1H-1,2,4-triazol-5-yl)ethanamine and 3-(5-(trifluoromethyl)-1,2,4-oxadiazol-3-yl)benzoic acid as described in example 8 step 6 (15 mg, yield 13%). $^1$H NMR (400 MHz, CDCl$_3$) δ 8.53 (s, 1H), 8.28-8.26 (d, J=7.8 Hz, 1H), 8.09-8.06 (m, 1H), 8.02-8.00 (d, J=8.5 Hz, 2H), 7.65-7.61 (t, J=7.8 Hz, 1H), 7.56-7.53 (m, 1H), 7.42-7.40 (d, J=8.5 Hz, 2H), 4.03-3.96 (q, J=6.0 Hz, 2H), 3.25-3.22 (d, J=6.0 Hz, 2H). MS (ESI) m/z: Calculated for $C_{20}H_{14}ClF_3N_6O_2$: 462.08. found: 463.0 (M+H)$^+$.

Example 64

Methyl 2-cyano-2-methylpropanoate

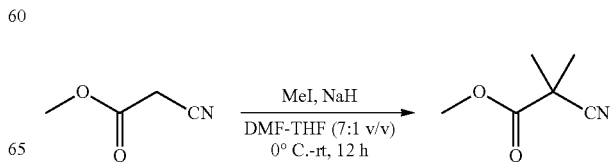

NaH (15.5 g, 60% dispersion in oil) was added portionwise over 10 min to the solution of ethyl cyanoacetate (20 g, 0.177 mol) in dry DMF (300 mL) at 0° C. The resulting reaction mixture was stirred at room temperature for 30 min and cooled again to 0° C. Methyl iodide (28 mL, 0.44 mol) in THF (50 mL) was added dropwise and the reaction mixture was stirred at room temperature for 12 h, and then quenched with saturated NH$_4$Cl solution. The mixture was then diluted with EtOAc; the organic layer was washed with H$_2$O and brine, dried over anhydrous Na$_2$SO$_4$, and concentrated under reduced pressure to afford crude product that was purified by column chromatography (silica gel 60-120 mesh, eluent 5% EtOAc in petroleum ether) to afford methyl 2-cyano-2-methylpropanoate (12 g, yield 48%) as a pale yellow solid.

2-Cyano-2-methylpropanehydrazide

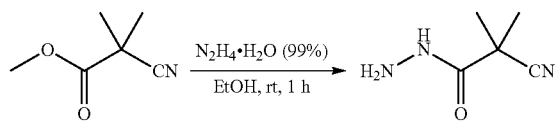

Hydrazine hydrate (1.8 mL, 35 mmol) was added to a solution of methyl 2-cyano-2-methylpropanoate (5.0 g, 35.0 mmol) in EtOH (5 mL), and the reaction mixture was stirred at room temperature for 1 h (monitored by TLC, eluant petroleum ether:EtOAc 7:3 v/v). The reaction mixture was diluted with diethyl ether and the precipitate formed was filtered. The clear filtrate was concentrated under reduced pressure to get 2-cyano-2-methylpropanehydrazide (1.75 g, yield 38%), which was carried through without further purification. MS (ESI) m/z: Calculated for C$_5$H$_9$N$_3$O: 127.07. found: 128.2 (M+H)$^+$.

2-Methyl-2-(3-phenyl-1H-1,2,4-triazol-5-yl)propanenitrile

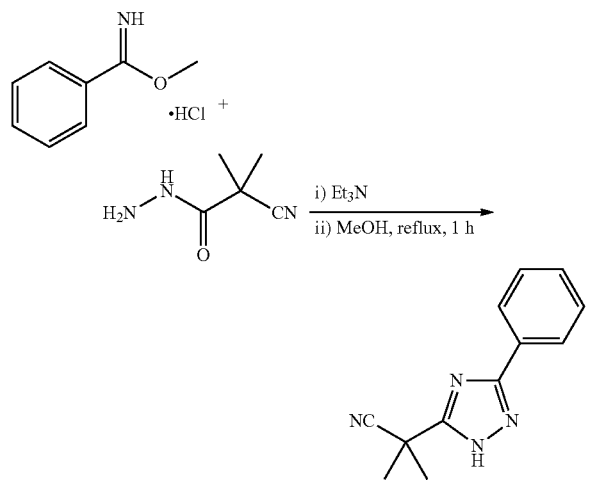

2-Cyano-2-methylpropanehydrazide (100 mg, 0.78 mmol) and Et$_3$N (0.1 mL, 0.86 mmol) were added to a solution of methyl benzimidate hydrochloride (100 mg, 0.58 mmol) in dry MeOH (10 mL), and the mixture was heated to reflux for 1 h. The reaction mixture was then concentrated under reduced pressure and the crude product was purified by column chromatography (silica 60-120 mesh, eluant 15% EtOAc in petroleum ether) to get 2-methyl-2-(3-phenyl-1H-1,2,4-triazol-5-yl)propanenitrile (80 mg, yield 51%). $^1$H NMR (300 MHz, MeOD) δ 7.98-7.95 (m, 2H), 7.52-7.50 (m, 3H), 1.82 (s, 6H). MS (ESI) m/z: Calculated for C$_{12}$H$_{12}$N$_4$: 212.11. found: 213.2 (M+H)$^+$.

2-Methyl-2-(3-phenyl-1H-1,2,4-triazol-5-yl)propan-1-amine

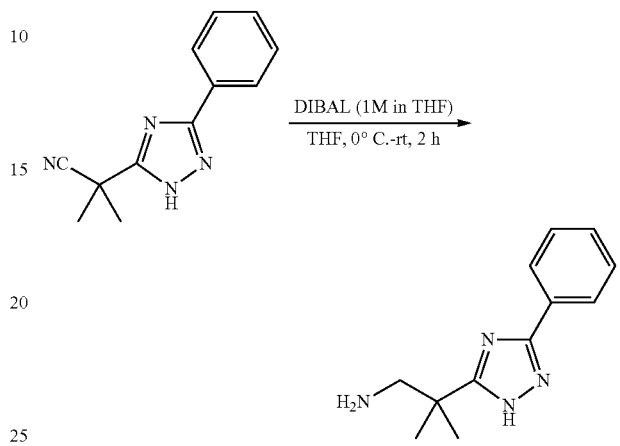

DIBAL-H (0.75 mL, 0.75 mmol, 1M in THF) was added to a solution of 2-methyl-2-(3-phenyl-1H-1,2,4-triazol-5-yl)propanenitrile (80 mg, 0.37 mmol) in dry THF (5 mL) at 0° C. The reaction mixture was allowed to warm up to room temperature and further stirred for 2 h. The reaction mixture was then quenched carefully with water and diluted with EtOAc. The organic layer was dried over anhydrous sodium sulfate and concentrated under reduced pressure to afford 2-methyl-2-(3-phenyl-1H-1,2,4-triazol-5-yl)propan-1-amine (70 mg, crude), which was carried through without further purification. MS (ESI) m/z: Calculated for C$_{12}$H$_{16}$N$_4$: 216.14. found: 217.2 (M+H)$^+$.

N-(2-Methyl-2-(3-phenyl-1H-1,2,4-triazol-5-yl)propyl)-3-(5-(trifluoromethyl)-1,2,4-oxadiazol-3-yl)benzamide

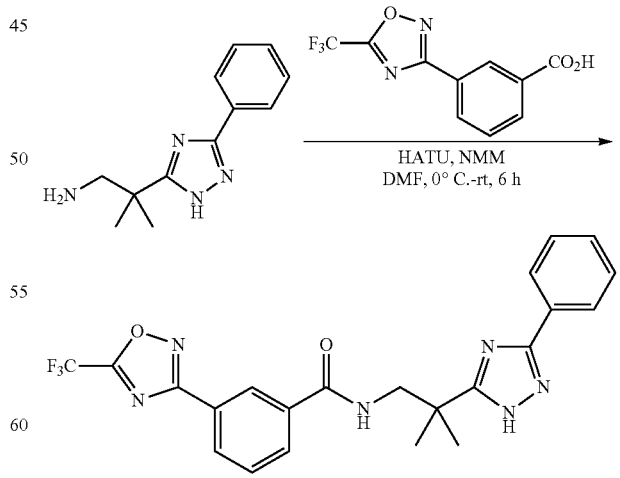

This compound was synthesized from 2-methyl-2-(3-phenyl-1H-1,2,4-triazol-5-yl)propan-1-amine and 3-(5-(trifluoromethyl)-1,2,4-oxadiazol-3-yl)benzoic acid as described in example 8 step 6 (35 mg, yield 25%). $^1$H NMR (400 MHz, MeOD) δ 8.55 (s, 1H), 8.29-8.27 (d, J=7.8 Hz, 1H), 8.06-7.97 (m, 3H), 7.71-7.67 (t, J=8.7 Hz, 1H), 7.50-7.41 (m, 3H), 3.75 (s, 2H), 1.54-1.51 (m, 6H). MS (ESI) m/z: Calculated for $C_{22}H_{19}F_3N_6O_2$: 456.15. found: 457.2 (M+H)$^+$.

Example 65

N-(2-Methyl-2-(3-phenyl-1H-1,2,4-triazol-5-yl)propyl)-5-(5-(trifluoromethyl)-1,2,4-oxadiazol-3-yl)nicotinamide

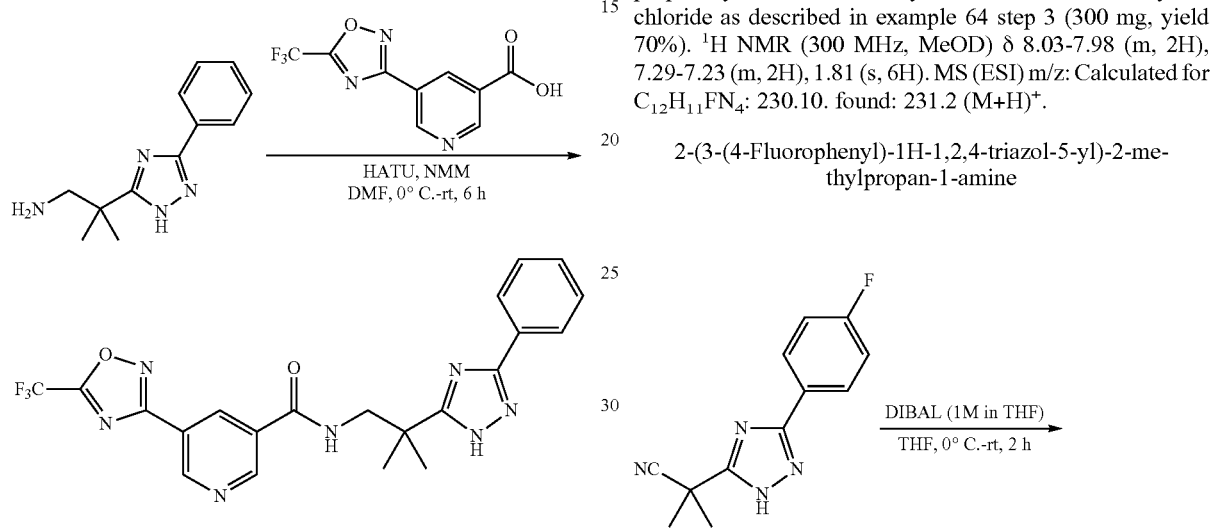

This compound was synthesized from 2-methyl-2-(3-phenyl-1H-1,2,4-triazol-5-yl)propan-1-amine and 5-(5-(trifluoromethyl)-1,2,4-oxadiazol-3-yl)nicotinic acid as described in example 8 step 6 (20 mg, yield 23%). $^1$H NMR (400 MHz, MeOD) δ 9.37 (m, 1H), 9.16 (m, 1H), 8.84-8.13 (m, 1H), 8.02-7.99 (m, 2H), 7.48-7.42 (m, 3H), 3.77 (s, 2H), 1.54 (m, 6H). MS (ESI) m/z: Calculated for $C_{21}H_{18}F_3N_7O_2$: 457.15. found: 458.2 (M+H)$^+$.

Example 66

2-(3-(4-Fluorophenyl)-1H-1,2,4-triazol-5-yl)-2-methylpropanenitrile

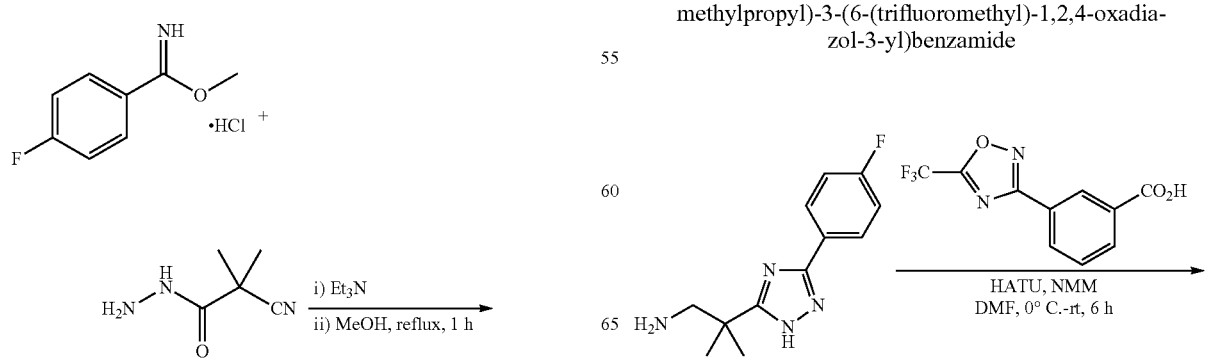

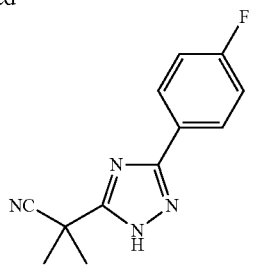

This compound was synthesized from 2-cyano-2-methylpropanehydrazide and methyl 4-fluorobenzimidate hydrochloride as described in example 64 step 3 (300 mg, yield 70%). $^1$H NMR (300 MHz, MeOD) δ 8.03-7.98 (m, 2H), 7.29-7.23 (m, 2H), 1.81 (s, 6H). MS (ESI) m/z: Calculated for $C_{12}H_{11}FN_4$: 230.10. found: 231.2 (M+H)$^+$.

2-(3-(4-Fluorophenyl)-1H-1,2,4-triazol-5-yl)-2-methylpropan-1-amine

This compound was synthesized from 2-(3-(4-fluorophenyl)-1H-1,2,4-triazol-5-yl)-2-methylpropanenitrile as described in example 64 step 4 (200 mg, crude) and it was carried through without further purification. MS (ESI) m/z: Calculated for $C_{12}H_{15}FN_4$: 234.13. found: 235.2 (M+H)$^+$.

N-(2-(3-(4-Fluorophenyl)-1H-1,2,4-triazol-5-yl)-2-methylpropyl)-3-(6-(trifluoromethyl)-1,2,4-oxadiazol-3-yl)benzamide -continued

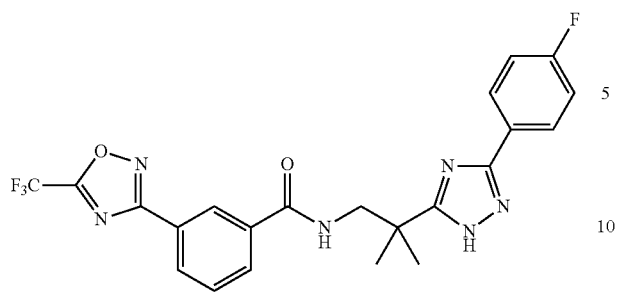

This compound was synthesized from 2-(3-(4-fluorophenyl)-1H-1,2,4-triazol-5-yl)-2-methylpropan-1-amine and 3-(5-(trifluoromethyl)-1,2,4-oxadiazol-3-yl)benzoic acid as described in example 8 step 6 (12 mg, yield 7%). $^1$H NMR (400 MHz, MeOD) δ 8.54 (s, 1H), 8.29-8.27 (d, J=7.8 Hz, 1H), 8.05-8.03 (m, 3H), 7.71-7.67 (t, J=7.8 Hz, 1H), 7.27-7.13 (m, 2H), 3.74 (s, 2H), 1.53-1.50 (m, 6H). MS (ESI) m/z: Calculated for $C_{22}H_{18}F_4N_6O_2$: 474.14. found: 475.2 (M+H)$^+$.

Example 67

N-(2-(3-(4-Fluorophenyl)-1H-1,2,4-triazol-5-yl)-2-methylpropyl)-5-(5-(trifluoromethyl)-1,2,4-oxadiazol-3-yl)nicotinamide

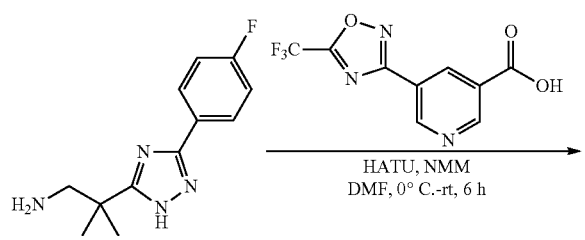

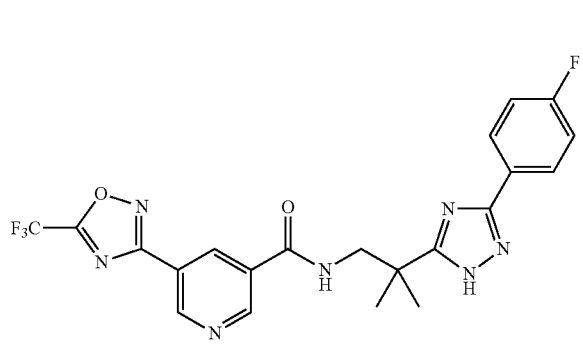

This compound was synthesized from 2-(3-(4-fluorophenyl)-1H-1,2,4-triazol-5-yl)-2-methylpropan-1-amine and 5-(5-(trifluoromethyl)-1,2,4-oxadiazol-3-yl)nicotinic acid as described in example 8 step 6 (20 mg, yield 11%). $^1$H NMR (400 MHz, MeOD) δ 9.38-9.37 (d, J=1.5 Hz, 1H), 9.15 (d, J=1.5 Hz, 1H), 8.82 (m, 1H), 8.06-8.02 (m, 2H), 7.21-7.17 (t, J=8.5 Hz, 2H), 3.76 (s, 2H), 1.53 (s, 6H). MS (ESI) m/z: Calculated for $C_{21}H_{17}F_4N_7O_2$: 475.14. found: 476.2 (M+H)$^+$.

Example 68

2-(3-(4-Chlorophenyl)-1H-1,2,4-triazol-6-yl)-2-methylpropanenitrile

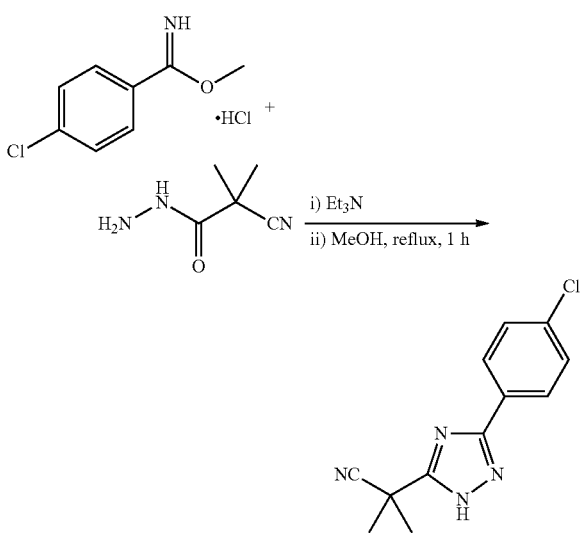

This compound was synthesized from 2-cyano-2-methylpropanehydrazide and methyl 4-chlorobenzimidate hydrochloride as described in example 64 step 3 (220 mg, yield 55%). $^1$H NMR (400 MHz, CDCl$_3$) δ 7.93-7.91 (m, 2H), 7.47-7.45 (m, 2H), 1.86 (s, 6H). MS (ESI) m/z: Calculated for $C_{12}H_{11}ClN_4$: 246.07. found: 245.2 (M–H)$^-$.

2-(3-(4-Chlorophenyl)-1H-1,2,4-triazol-5-yl)-2-methylpropan-1-amine

This compound was synthesized from 2-(3-(4-chlorophenyl)-1H-1,2,4-triazol-5-yl)-2-methylpropanenitrile as described in example 64 step 4 (140 mg, crude) and it was carried through without further purification. MS (ESI) m/z: Calculated for $C_{12}H_{15}ClN_4$: 250.10. found: 251.2 (M+H)⁺.

N-(2-(3-(4-Chlorophenyl)-1H-1,2,4-triazol-6-yl)-2-methylpropyl)-3-(5-(trifluoromethyl)-1,2,4-oxadiazol-3-yl)benzamide

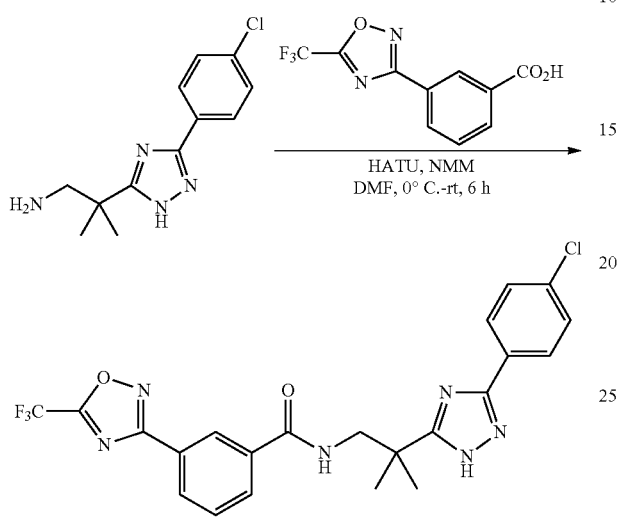

This compound was synthesized from 2-(3-(4-chlorophenyl)-1H-1,2,4-triazol-5-yl)-2-methylpropan-1-amine and 3-(5-(trifluoromethyl)-1,2,4-oxadiazol-3-yl)benzoic acid as described in example 8 step 6 (15 mg, yield 8%). ¹H NMR (400 MHz, CDCl₃) δ 8.59 (s, 1H), 8.30-8.28 (d, J=8.0 Hz, 1H), 8.14-8.12 (m, 1H), 8.06-8.04 (d, J=8.3 Hz, 2H), 7.93 (br s, 1H), 7.67-7.63 (t, J=7.7 Hz, 1H), 7.43-7.41 (d, J=8.5 Hz, 2H), 3.83-3.82 (m, 2H), 1.56 (s, 6H). MS (ESI) m/z: Calculated for $C_{22}H_{18}ClF_3N_6O_2$: 490.11. found: 491.2 (M+H)⁺.

Example 69

Ethyl 5-cyano-6-methylnicotinate

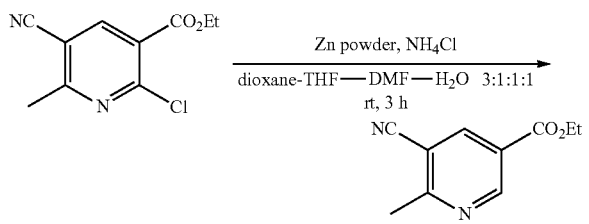

Ammonium chloride (3.58 g, 66.7 mmol in 10 mL water) was added to a solution of ethyl 2-chloro-5-cyano-6-methylnicotinate (1.0 g, 4.4 mmol) in dioxane-THF-DMF (50 mL, 3:1:1), followed by zinc powder (2.3 g, 35.6 mmol) portionwise at room temperature. The reaction mixture was allowed to stir at room temperature for 3 h, diluted with EtOAc, and filtered through a pad of Celite. The clear filtrate of organic layer was washed with H₂O and brine, dried over anhydrous Na₂SO₄, and concentrated under reduced pressure. The crude product was purified by column chromatography (silica 60-120 mesh, eluent 10-15% EtOAc in petroleum ether) to afford ethyl 5-cyano-6-methylnicotinate (230 mg, yield 27%) as a white solid. ¹H NMR (400 MHz, CDCl₃) δ 9.25 (d, J=2.0 Hz, 1H), 8.49 (d, J=2.0 Hz, 1H), 7.27 (s, 1H), 4.47-4.42 (q, J=7.2 Hz, 2H), 2.86 (s, 3H), 1.45-1.41 (t, J=7.0 Hz, 3H). MS (ESI) m/z: Calculated for $C_{10}H_{10}N_2O_2$: 190.07. found: 191.2 (M+H)⁺.

5-Cyano-6-methylnicotinic acid

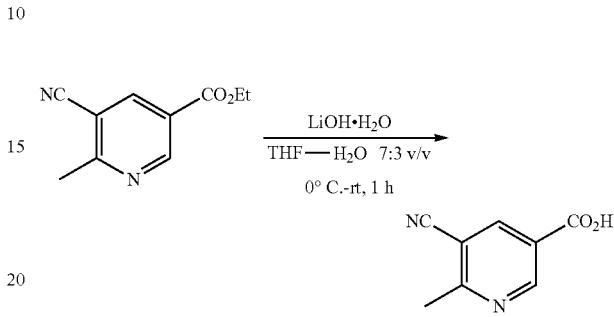

This compound was synthesized from ethyl 5-cyano-6-methylnicotinate as described in example 43 step 2 (150 mg, yield 76%) as a white solid. ¹H NMR (300 MHz, DMSO-d₆) δ 13.77 (br s, 1H), 9.13-9.12 (d, J=2.0 Hz, 1H), 8.61-8.60 (d, J=2.0 Hz, 1H), 2.74 (s, 3H). MS (ESI) m/z: Calculated for $C_8H_6N_2O_2$: 162.04. found: 161.2 (M+H)⁺.

5-(N'-Hydroxycarbamimidoyl)-6-methylnicotinic acid

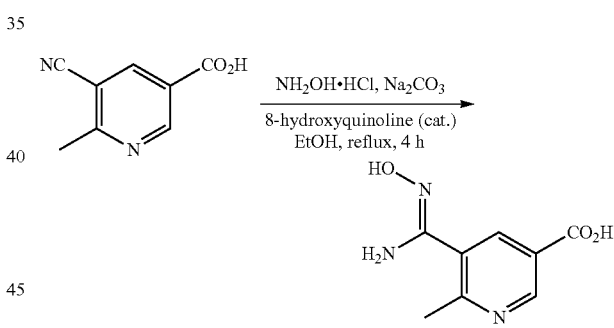

This compound was synthesized from 5-cyano-6-methylnicotinic acid as described in example 1 step 4 (130 mg, crude) and it was carried through without further purification. MS (ESI) m/z: Calculated for $C_8H_9N_3O_3$: 195.06. found: 196.2 (M+H)⁺.

6-Methyl-5-(5-(trifluoromethyl)-1,2,4-oxadiazol-3-yl)nicotinic acid

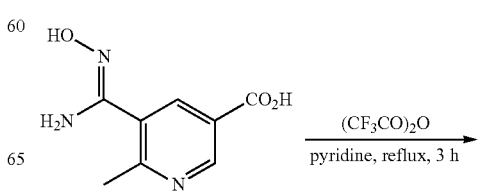

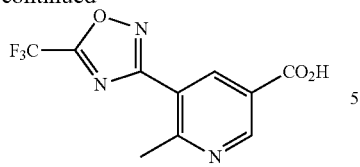

This compound was synthesized from 5-(N'-hydroxycarbamimidoyl)-6-methylnicotinic acid as described in example 1 step 5 (25 mg, yield 15%) as a white solid. $^1$H NMR (300 MHz, DMSO-$d_6$) δ 13.71 (br s, 1H), 9.14-9.13 (d, J=2.2 Hz, 1H), 8.69 (d, J=2.2 Hz, 1H), 2.86 (s, 3H). MS (ESI) m/z: Calculated for $C_{10}H_6F_3N_3O_3$: 273.04. found: 274.0 (M+H)$^+$.

N-(2-(4-(4-Chlorophenyl)thiazol-2-yl)-2-methylpropyl)-6-methyl-5-(5-(trifluoromethyl)-1,2,4-oxadiazol-3-yl)nicotinamide

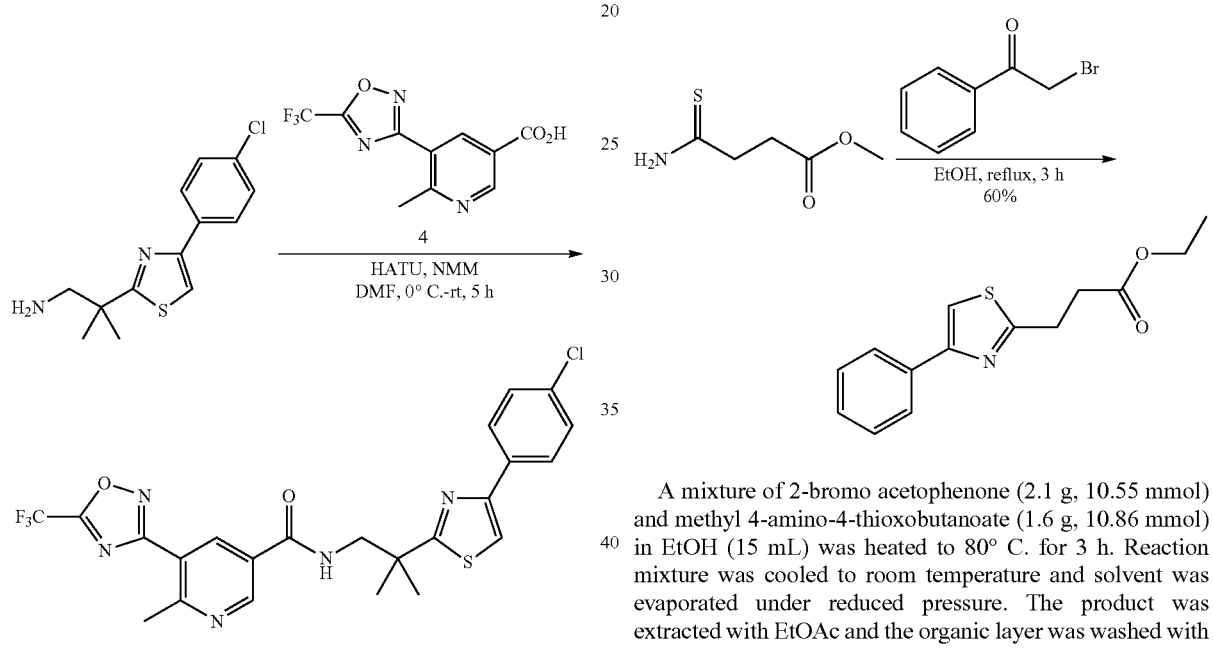

This compound was synthesized from 2-(4-(4-chlorophenyl)thiazol-2-yl)-2-methylpropan-1-amine and 6-methyl-5-(5-(trifluoromethyl)-1,2,4-oxadiazol-3-yl)nicotinic acid as described in example 8 step 6 (28 mg, yield 59%). $^1$H NMR (400 MHz, CDCl$_3$) δ 9.11 (br s, 1H), 8.80 (br s, 1H), 8.07 (br s, 1H), 7.79-7.77 (d, J=8.8 Hz, 2H), 7.43 (s, 1H), 7.35-7.33 (d, J=8.8 Hz, 2H), 3.86-3.84 (d, J=5.5 Hz, 2H), 3.02 (s, 3H), 1.57 (s, 6H). MS (ESI) m/z: Calculated for $C_{23}H_{19}ClF_3N_5O_2S$: 521.09. found: 522.0 (M+H)$^+$.

Example 70

Methyl 4-amino-4-thioxobutanoate

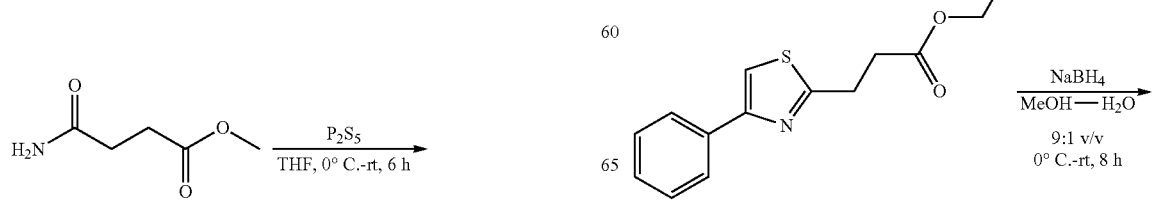

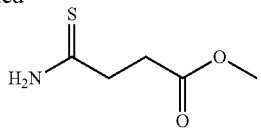

A solution of methyl succinamate (2.5 g, 0.019 mol) in THF (60 mL) was cooled to 0° C. and P$_2$S$_5$ (4.2 g, 0.019 mol) was added. The reaction mixture was warmed to room temperature and stirred for 6 h. The solvent was removed under reduced pressure and the crude product was purified by column chromatography (silica gel 60-120 mesh, eluent 35-40% EtOAc in petroleum ether) to afford methyl 4-amino-4-thioxobutanoate (1.6 g, yield 57%). $^1$H NMR (300 MHz, CDCl$_3$) δ 7.49 (br s, 2H), 3.72 (s, 3H), 2.95-2.86 (m, 4H). MS (ESI) m/z: Calculated for $C_5H_9NO_2S$: 147.04. found: 248.2 (M+H)$^+$.

Ethyl 3-(4-phenylthiazol-2-yl)propanoate

A mixture of 2-bromo acetophenone (2.1 g, 10.55 mmol) and methyl 4-amino-4-thioxobutanoate (1.6 g, 10.86 mmol) in EtOH (15 mL) was heated to 80° C. for 3 h. Reaction mixture was cooled to room temperature and solvent was evaporated under reduced pressure. The product was extracted with EtOAc and the organic layer was washed with H$_2$O and brine, dried over anhydrous Na$_2$SO$_4$, and concentrated under reduced pressure to afford ethyl 3-(4-phenylthiazol-2-yl)propanoate (1.1 g, yield 40%) as a white solid, which was carried through without further purification. $^1$H NMR (300 MHz, CDCl$_3$) δ 7.90-7.87 (m, 2H), 7.44-7.39 (m, 2H), 7.35-7.30 (m, 2H), 4.22-4.15 (q, J=7.2 Hz, 2H), 3.41-3.36 (t, J=7.5 Hz, 2H), 2.94-2.89 (t, J=7.3 Hz, 2H), 1.30-1.25 (t, J=7.1 Hz, 3H). MS (ESI) m/z: Calculated for $C_{14}H_{15}NO_2S$: 261.08. found: 262.2 (M+H)$^+$.

3-(4-Phenylthiazol-2-yl)propan-1-ol

-continued

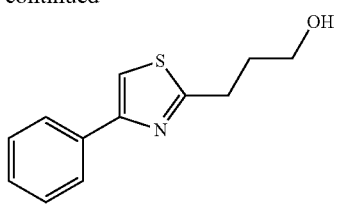

A solution of ethyl 3-(4-phenylthiazol-2-yl)propanoate (0.5 g, 1.91 mmol) in MeOH—H$_2$O (10 mL, 9:1 v/v) was cooled to 0° C. and sodium borohydride (0.29 g, 7.65 mmol) was added. The reaction mixture was warmed to room temperature and further stirred for 8 h. The mixture was quenched with ice water and the organic product was extracted with EtOAc. The combined extracts were washed with H$_2$O and brine, dried over anhydrous Na$_2$SO$_4$, and concentrated under reduced pressure to afford 3-(4-phenylthiazol-2-yl)propan-1-ol (0.4 g, yield 95%) as colorless liquid, which was carried through without further purification. $^1$H NMR (400 MHz, CDCl$_3$) δ 7.87-7.85 (m, 2H), 7.44-7.40 (m, 2H), 7.35-7.32 (m, 2H), 3.83-3.81 (t, J=5.8 Hz, 2H), 3.24-3.21 (m, 3H), 2.14-2.08 (m, 2H). MS (ESI) m/z: Calculated for C$_{12}$H$_{13}$NOS: 219.07. found: 220.2 (M+H)$^+$.

3-(4-Phenylthiazol-2-yl)propyl methanesulfonate

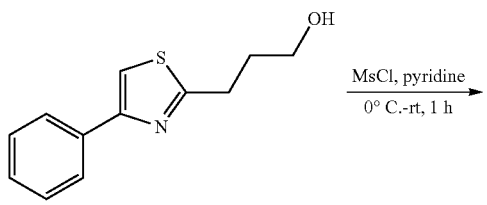

A solution of 3-(4-phenylthiazol-2-yl)propan-1-ol (0.4 g, 1.82 mmol) in dry pyridine (8 mL) was cooled to 0° C. and methanesulfonyl chloride (0.43 mL, 5.47 mmol) was added dropwise. The reaction mixture was allowed to warm up to room temperature, stirred for 1 h, and quenched with ice water. The organic product was extracted with EtOAc and organic layer was washed with brine, dried over anhydrous Na$_2$SO$_4$, and concentrated under reduced pressure to afford 3-(4-phenylthiazol-2-yl)propyl methanesulfonate (0.4 g, yield 74%) as a pale yellow liquid, which was carried through without further purification. $^1$H NMR (300 MHz, CDCl$_3$) δ 7.90-7.87 (m, 2H), 7.46-7.40 (m, 2H), 7.37-7.31 (m, 2H), 4.42-4.38 (t, J=6.1 Hz, 2H), 3.24-3.19 (t, J=7.2 Hz, 2H), 3.04 (s, 3H), 2.39-2.30 (m, 2H). MS (ESI) m/z: Calculated for C$_{13}$H$_{15}$NO$_3$S$_2$: 297.05. found: 298.0 (M+H)$^+$.

2-(3-Azidopropyl)-4-phenylthiazole

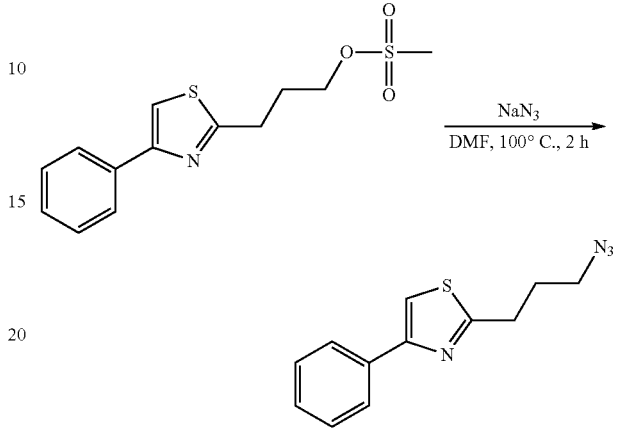

Sodium azide (263 mg, 4.05 mmol) was added to a solution of 3-(4-phenylthiazol-2-yl)propyl methanesulfonate (0.4 g, 1.35 mmol) in dry DMF (8 mL), and the reaction mixture was heated to 100° C. for 2 h. The mixture was allowed to cool down to room temperature and diluted with EtOAc. The organic product was extracted with EtOAc and the organic layer was washed with H$_2$O and brine, dried over anhydrous Na$_2$SO$_4$, and concentrated under reduced pressure to afford 2-(3-azidopropyl)-4-phenylthiazole (0.3 g, yield 91%) as a pale orange liquid, which was carried through without further purification. $^1$H NMR (300 MHz, CDCl$_3$) δ 7.91-7.89 (m, 2H), 7.46-7.41 (m, 2H), 7.36-7.31 (m, 2H), 3.49-3.44 (t, J=6.7 Hz, 2H), 3.20-3.15 (t, J=7.5 Hz, 2H), 2.21-2.12 (m, 2H). MS (ESI) m/z: Calculated for C$_{12}$H$_{12}$N$_4$S: 244.08. found: 245.2 (M+H)$^+$.

3-(4-Phenylthiazol-2-yl)propan-1-amine

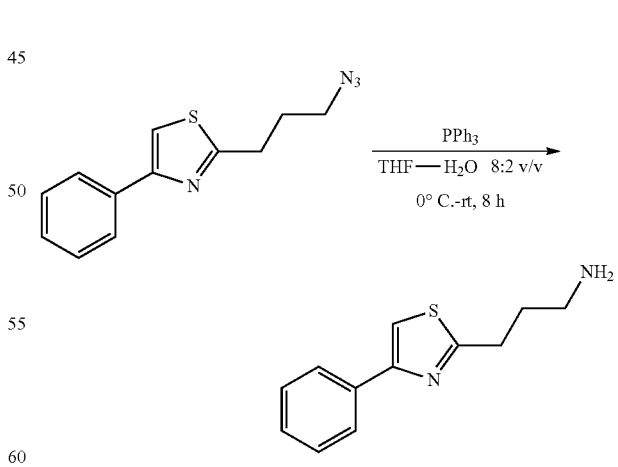

Triphenylphosphine (485 mg, 1.85 mmol) was added to a solution of 2-(3-azidopropyl)-4-phenylthiazole (0.3 g, 1.23 mmol) in THF—H$_2$O (10 mL, 8:2 v/v) at 0° C. The reaction mixture was allowed to warm up to room temperature, stirred for 8 h and then concentrated under reduced pressure. The residue was diluted with 1.5N HCl and the aqueous layer was washed with CH$_2$Cl$_2$. The pH of the aqueous layer was adjusted to ~8-9 using 10% NaOH solution and the organic product was extracted with CH$_2$Cl$_2$. The combined extracts were washed with brine, dried over anhydrous Na$_2$SO$_4$, and concentrated under reduced pressure to afford 3-(4-phenylthiazol-2-yl)propan-1-amine (240 mg, yield 89%) as a pale yellow liquid, which was carried through without further purification. MS (ESI) m/z: Calculated for C$_{12}$H$_{14}$N$_2$S: 218.09. found: 219.2 (M+H)$^+$.

N-(3-(4-Phenylthiazol-2-yl)propyl)-3-(5-(trifluoromethyl)-1,2,4-oxadiazol-3-yl)benzamide

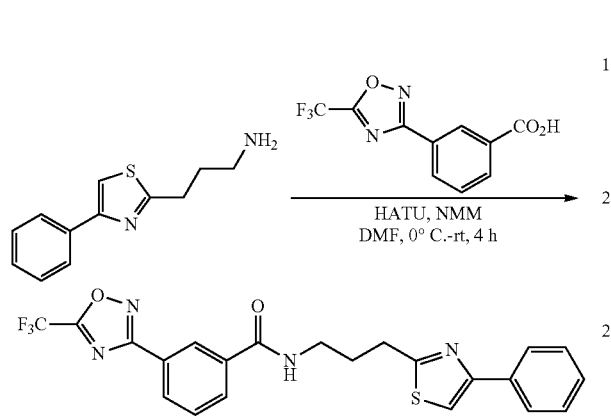

This compound was synthesized from 3-(4-phenylthiazol-2-yl)propan-1-amine and 3-(5-(trifluoromethyl)-1,2,4-oxadiazol-3-yl)benzoic acid as described in example 8 step 6 (100 mg, yield 70%). $^1$H NMR (400 MHz, CDCl$_3$) δ 8.40 (m, 1H), 8.17-8.14 (m, 1H), 7.96-7.94 (m, 1H), 7.80-7.78 (m, 2H), 7.45-7.41 (m, 1H), 7.34-7.29 (m, 4H), 3.70-3.66 (q, J=6.3 Hz, 2H), 3.27-3.23 (t, J=6.7 Hz, 2H), 2.29-2.23 (m, 2H). MS (ESI) m/z: Calculated for C$_{22}$H$_{17}$F$_3$N$_4$O$_2$S: 458.10. found: 459.2 (M+H)$^+$.

Example 71

4-(Chloromethyl)-2-(4-fluorophenyl)oxazole

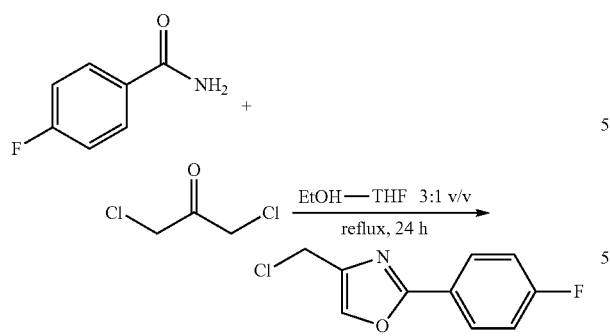

A mixture of 4-fluorobenzamide (2.5 g, 17.9 mmol) and 1,3-dichloroacetone (2.7 g, 21.6 mmol) in EtOH-THF (20 mL-10 mL) was heated to 85° C. for 24 h. The reaction mixture was cooled to room temperature and quenched with 10% NaHCO$_3$ solution. The organic product was extracted with EtOAc and the organic layer was washed with H$_2$O and brine, dried over anhydrous sodium sulfate and concentrated under reduced pressure. The crude product was purified by column chromatography (silica gel 60-120 mesh, eluent 6-10% EtOAc in petroleum ether) to afford 4-(chloromethyl)-2-(4-fluorophenyl)oxazole (1.2 g, yield 32%) as a white solid. $^1$H NMR (300 MHz, CDCl$_3$) δ 8.07-8.02 (m, 2H), 7.70 (m, 1H), 7.19-7.13 (t, J=8.8 Hz, 2H), 4.58 (m, 2H). MS (ESI) m/z: Calculated for C$_{10}$H$_7$ClNO: 211.02. found: 212.0 (M+H)$^+$.

2-(2-(4-Fluorophenyl)oxazol-4-yl)acetonitrile

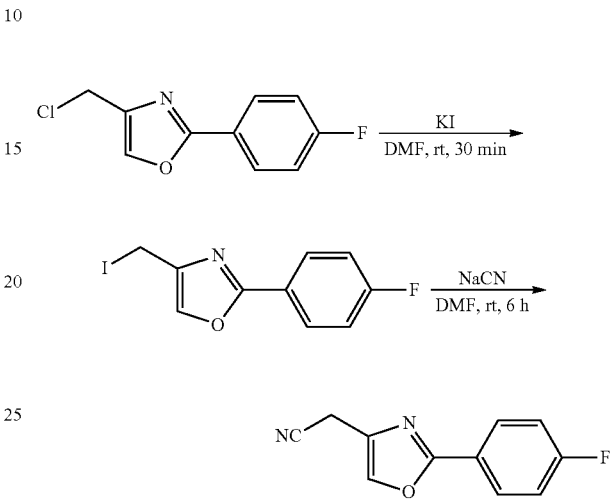

KI (3.14 g, 18.9 mmol) was added to a solution of 4-(chloromethyl)-2-(4-fluorophenyl)oxazole (1.0 g, 4.7 mmol) in dry DMF (20 mL) at room temperature. The reaction mixture was stirred for 30 min, diluted with EtOAc, and washed with water and brine. The organic layer was dried over anhydrous sodium sulfate and concentrated under reduced pressure to give crude 2-(4-fluorophenyl)-4-(iodomethyl)oxazole. The crude product was dissolved in DMF (20 mL) and sodium cyanide (0.46 g, 9.4 mmol) was added to the solution. The reaction mixture was stirred at room temperature for 6 h and quenched with water. The organic product was extracted with EtOAc and the organic layer was washed with H$_2$O and brine, dried over anhydrous sodium sulfate and concentrated under reduced pressure. The crude product was purified by column chromatography (silica gel 60-120 mesh, eluent 10-15% EtOAc in petroleum ether) to afford 2-(2-(4-fluorophenyl)oxazol-4-yl)acetonitrile (0.75 g, yield 78%) as an off-white solid. $^1$H NMR (300 MHz, CDCl$_3$) δ 8.05-8.00 (m, 2H), 7.73 (m, 1H), 7.20-7.14 (t, J=8.6 Hz, 2H), 3.73 (s, 2H). MS (ESI) m/z: Calculated for C$_{11}$H$_7$FN$_2$O: 202.05. found: 203.0 (M+H)$^+$.

2-(2-(4-Fluorophenyl)oxazol-4-yl)ethanamine

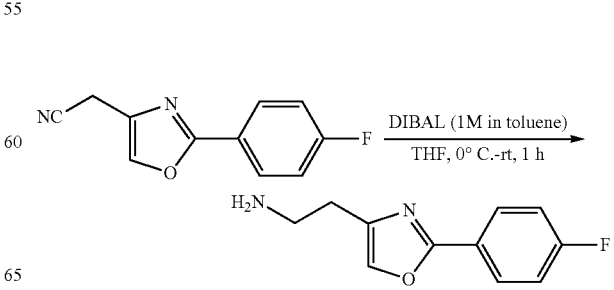

This compound was synthesized from 2-(2-(4-fluorophenyl)oxazol-4-yl)acetonitrile as described in example 64 step 4 (120 mg, crude) and it was carried through without further purification.

N-(2-(2-(4-Fluorophenyl)oxazol-4-yl)ethyl)-5-(5-(trifluoromethyl)-1,2,4-oxadiazol-3-yl)nicotinamide

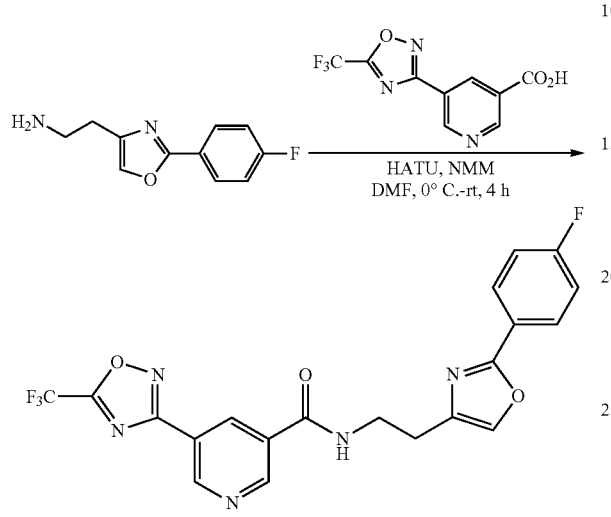

This compound was synthesized from 2-(2-(4-fluorophenyl)oxazol-4-yl)ethanamine and 5-(5-(trifluoromethyl)-1,2,4-oxadiazol-3-yl)nicotinic acid as described in example 8 step 6 (55 mg, yield 46%). $^1$H NMR (400 MHz, MeOD) δ 9.39 (d, J=2.0 Hz, 1H), 9.19 (d, J=2.0 Hz, 1H), 8.89 (t, J=2.0 Hz, 1H), 8.07-8.03 (m, 2H), 7.81 (s, 1H), 7.26-7.22 (m, 2H), 3.78-3.75 (t, J=6.9 Hz, 2H), 2.97-2.94 (t, J=6.9 Hz, 2H). MS (ESI) m/z: Calculated for $C_{20}H_{13}F_4N_5O_3$: 447.10. found: 448.2 (M+H)$^+$.

Example 72

Ethyl 2-oxo-2-((2-oxo-2-phenylethyl)amino)acetate

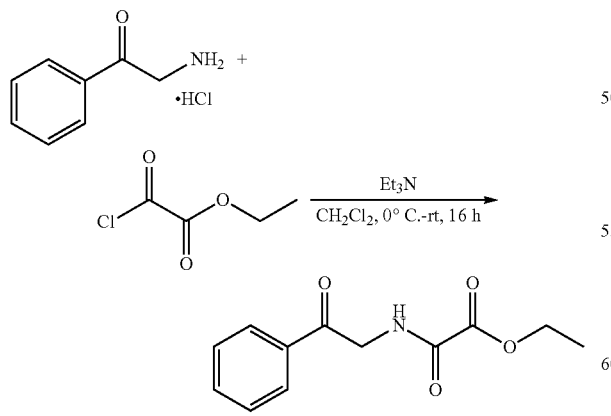

Triethylamine (36 mL, 262.1 mmol) was added to a solution of 2-aminoacetophenone hydrochloride (15.0 g, 87.39 mmol) in dry $CH_2Cl_2$ (300 mL), followed by ethyl chlorooxoacetate (10 mL, 87.39 mmol) at 0° C. The reaction mixture was allowed to warm up to room temperature and stirred for 16 h. The mixture was then diluted with water and extracted with EtOAc. The combined extracts were washed with $H_2O$ and brine, dried over anhydrous sodium sulfate and concentrated under reduced pressure. The crude product was purified by column chromatography (silica gel 60-120 mesh, eluent 20-30% EtOAc in petroleum ether) to afford ethyl 2-oxo-2-((2-oxo-2-phenylethyl)amino)acetate (13.5 g, yield 66%). $^1$H NMR (400 MHz, $CDCl_3$) δ 8.09 (br s, 1H), 8.02-8.00 (m, 2H), 7.68-7.64 (m, 1H), 7.55-7.51 (m, 2H), 4.85-4.84 (d, J=4.9 Hz, 2H), 4.44-4.39 (q, J=7.0 Hz, 2H), 1.44-1.41 (t, J=7.2 Hz, 3H). MS (ESI) m/z: Calculated for $C_{12}H_{13}NO_4$: 235.08. found: 236.2 (M+H)$^+$.

Ethyl 5-phenylthiazole-2-carboxylate

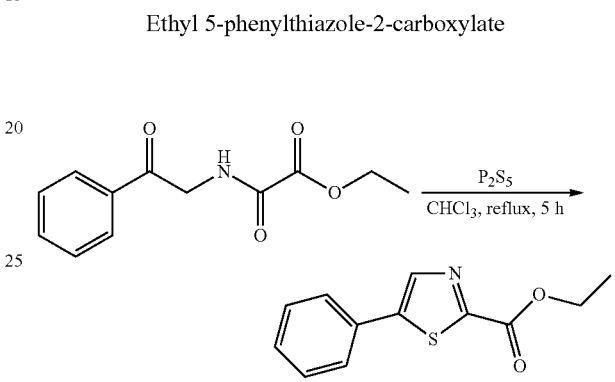

$P_2S_5$ (25.5 g, 114.7 mmol) was added to a solution of ethyl 2-oxo-2-((2-oxo-2-phenylethyl)amino)acetate (13.5 g, 57.39 mmol) in dry $CHCl_3$ (150 mL), and the resulting reaction mixture was heated to reflux for 5 h. The reaction mixture was quenched with water and the organic product was extracted with $CHCl_3$. The combined extracts were washed with $H_2O$ and brine, dried over anhydrous sodium sulfate, and concentrated under reduced pressure. The crude product was purified by column chromatography (silica gel 60-120 mesh, eluent 10-15% EtOAc in petroleum ether) to afford ethyl 5-phenylthiazole-2-carboxylate (10 g, yield 75%) as a white solid. $^1$H NMR (400 MHz, $CDCl_3$) δ 8.16 (s, 1H), 7.64-7.62 (m, 2H), 7.48-7.39 (m, 3H), 4.53-4.47 (q, J=7.0 Hz, 2H), 1.49-1.45 (t, J=7.2 Hz, 3H). MS (ESI) m/z: Calculated for $C_{12}H_{11}NO_2S$: 233.05. found: 234.0 (M+H)$^+$.

(5-Phenylthiazol-2-yl)methanol

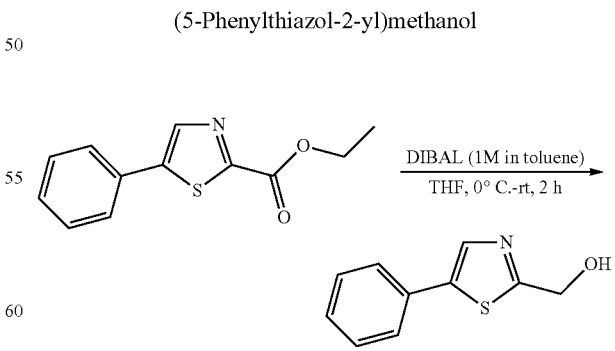

This compound was synthesized from ethyl 5-phenylthiazole-2-carboxylate as described in example 64 step 4 (3.5 g, yield 71%) and it was carried through without further purification. $^1$H NMR (300 MHz, $CDCl_3$) δ 7.89 (s, 1H), 7.57-7.54

(m, 2H), 7.44-7.35 (m, 3H), 4.97 (s, 2H). MS (ESI) m/z: Calculated for $C_{10}H_9NOS$: 191.04. found: 192.2 (M+H)$^+$.

2-(Bromomethyl)-5-phenylthiazole

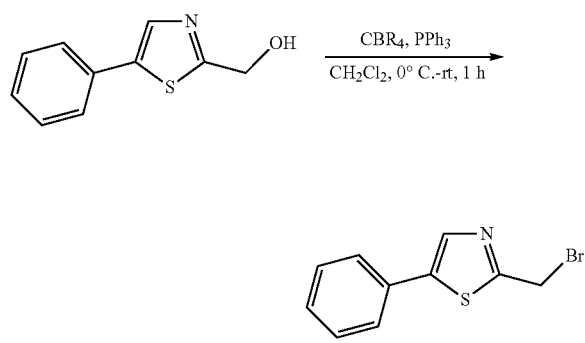

CBr$_4$ (8.65 g, 26.1 mmol) and Ph$_3$P (5.1 g, 19.6 mmol) were added to a solution of (5-phenylthiazol-2-yl)methanol (2.5 g, 13.07 mmol) in dry CH$_2$Cl$_2$ (30 mL) at 0° C. The resulting reaction mixture was stirred at room temperature for 1 h and then concentrated under reduced pressure. The residue was diluted with diethyl ether and filtered. The clear filtrate was removed under reduced pressure and the crude product was purified by column chromatography (silica gel 60-120 mesh, eluent 5-10% EtOAc in petroleum ether) to afford 2-(bromomethyl)-5-phenylthiazole (2 g, yield 60%). $^1$H NMR (300 MHz, CDCl$_3$) δ 7.89 (s, 1H), 7.57-7.55 (m, 2H), 7.45-7.36 (m, 3H), 4.76 (s, 2H). MS (ESI) m/z: Calculated for $C_{10}H_8BrNS$: 254.95. found: 256.0 (M+H)$^+$.

2-(5-Phenylthiazol-2-yl)acetonitrile

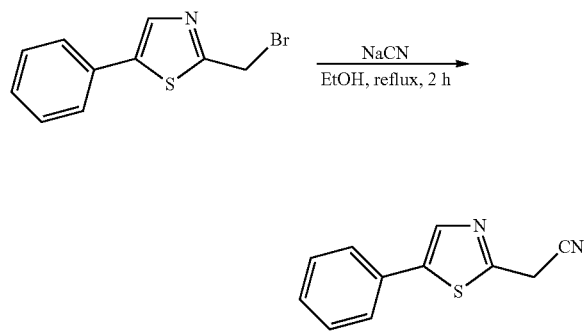

NaCN (0.46 g, 9.4 mmol) was added to a solution of 2-(bromomethyl)-5-phenylthiazole (2.0 g, 7.87 mmol) in dry EtOH (10 mL). The resulting reaction mixture was stirred at 70° C. for 2 h and then concentrated under reduced pressure, and diluted with ethyl acetate. The organic layer was washed with H$_2$O and brine, dried over anhydrous sodium sulfate, and concentrated under reduced pressure. The crude product was purified by column chromatography (silica gel 60-120 mesh, eluent 10% EtOAc in petroleum ether) to afford 2-(5-phenylthiazol-2-yl)acetonitrile (350 mg, yield 22%) as a white solid. $^1$H NMR (400 MHz, CDCl$_3$) δ 7.91 (s, 1H), 7.56-7.54 (m, 2H), 7.46-7.40 (m, 3H), 4.15 (s, 2H). MS (ESI) m/z: Calculated for $C_{11}H_8N_2S$: 200.04. found: 201.2 (M+H)$^+$.

2-(5-Phenylthiazol-2-yl)ethanamine

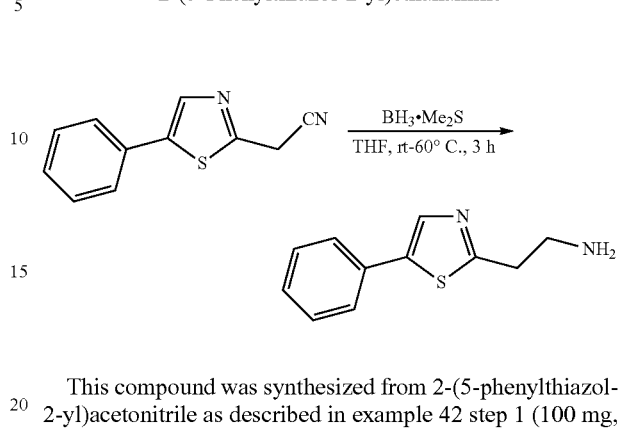

This compound was synthesized from 2-(5-phenylthiazol-2-yl)acetonitrile as described in example 42 step 1 (100 mg, crude) and it was carried through without further purification. MS (ESI) m/z: Calculated for $C_{11}H_{12}N_2S$: 204.07. found: 205.2 (M+H)$^+$.

N-(2-(5-Phenylthiazol-2-yl)ethyl)-3-(5-(trifluoromethyl)-1,2,4-oxadiazol-3-yl)benzamide

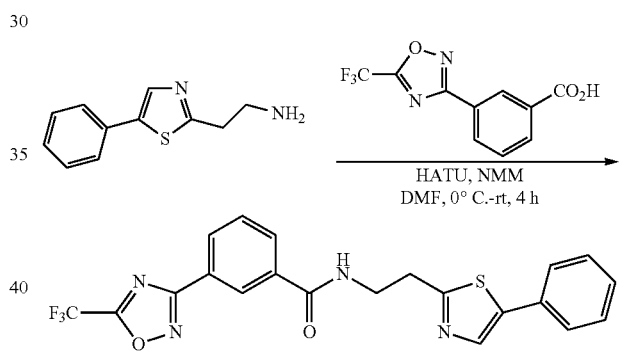

This compound was synthesized from 2-(5-phenylthiazol-2-yl)ethanamine and 3-(5-(trifluoromethyl)-1,2,4-oxadiazol-3-yl)benzoic acid as described in example 8 step 6 (7 mg, yield 5%). $^1$H NMR (400 MHz, MeOD) δ 8.60-8.59 (t, J=1.4 Hz, 1H), 8.31-8.28 (dt, J=7.8 Hz, 1.4 Hz, 1H), 8.08-8.05 (dt, J=7.9 Hz, 1.3 Hz, 1H), 7.96 (s, 1H), 7.72-7.68 (t, J=7.9 Hz, 1H), 7.61-7.59 (m, 2H), 7.43-7.39 (m, 2H), 7.36-7.32 (m, 1H), 3.85-3.82 (t, J=6.9 Hz, 2H), 3.40-3.36 (t, J=6.8 Hz, 2H). MS (ESI) m/z: Calculated for $C_{21}H_{15}F_3N_4O_2S$: 444.09. found: 445.0 (M+H)$^+$.

Example 73

2-(2-(4-Fluorophenyl)oxazol-4-yl)propanenitrile

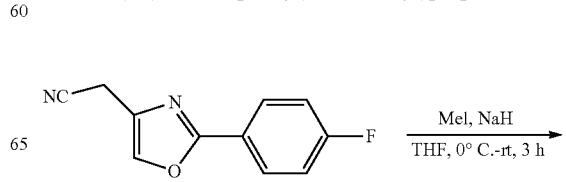

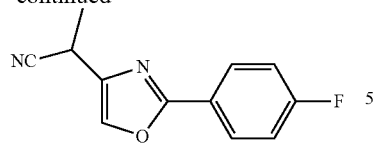

NaH (360 mg, 60% dispersion in oil) was added portionwise over 5 min to a solution of 2-(2-(4-fluorophenyl)oxazol-4-yl)acetonitrile (1.5 g, 7.42 mmol) in dry THF (60 mL) at 0° C. The resulting reaction mixture was slowly allowed to warm up to room temperature and stirred for 1 h. The reaction mixture was again cooled to 0° C. and a solution of methyl iodide (0.5 mL, 7.4 mmol) in dry THF (10 mL) was added dropwise at 0° C. over 30 min. The reaction mixture was stirred at 0° C. for 1 h and then at room temperature for another 1 h. The reaction mixture was quenched with saturated NH₄Cl solution, diluted with EtOAc and further extracted with EtOAc. The combined extracts were washed with H₂O and brine, dried over anhydrous Na₂SO₄, and concentrated under reduced pressure. The crude product was purified by column chromatography (silica 60-120 mesh, eluant 10% EtOAc in petroleum ether) to get 2-(2-(4-fluorophenyl)oxazol-4-yl)propanenitrile (360 mg, yield 23%). ¹H NMR (400 MHz, CDCl₃) δ 8.05-8.02 (m, 2H), 7.71-7.70 (d, J=1.1 Hz, 1H), 7.19-7.14 (t, J=8.7 Hz, 2H), 3.97-3.92 (m, 1H), 1.73-1.72 (d, J=7.2 Hz, 3H). MS (ESI) m/z: Calculated for $C_{12}H_{19}FN_2O$: 216.07. found: 216.9 (M+H)⁺.

2-(2-(4-Fluorophenyl)oxazol-4-yl)propan-1-amine

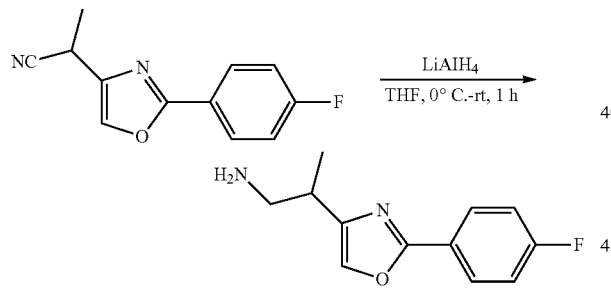

This compound was synthesized from 2-(2-(4-fluorophenyl)oxazol-4-yl)propanenitrile as described in example 1 step 3 (320 mg, crude) and it was carried through without further purification. MS (ESI) m/z: Calculated for $C_{12}H_{13}FN_2O$: 220.10. found: 220.8 (M+H)⁺.

N-(2-(2-(4-Fluorophenyl)oxazol-4-yl)propyl)-3-(5-(trifluoromethyl)-1,2,4-oxadiazol-3-yl)benzamide

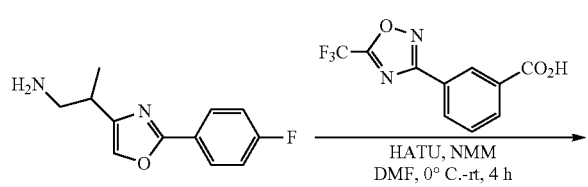

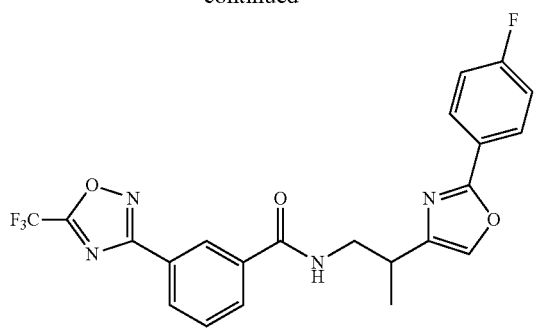

This compound was synthesized from 2-(2-(4-fluorophenyl)oxazol-4-yl)propan-1-amine and 3-(5-(trifluoromethyl)-1,2,4-oxadiazol-3-yl)benzoic acid as described in example 8 step 6 (95 mg, yield 36%) as a yellow solid. ¹H NMR (400 MHz, CDCl₃) δ 8.59-8.58 (t, J=1.5 Hz, 1H), 8.28-8.26 (dt, J=7.8 Hz, 1.3 Hz, 1H), 8.17-8.14 (dt, J=7.8 Hz, 1.4 Hz, 1H), 8.09-8.05 (m, 2H), 7.90 (m, 1H), 7.67-7.63 (t, J=7.8 Hz, 1H), 7.53 (d, J=0.8 Hz, 1H), 7.14-7.10 (m, 2H), 3.99-3.93 (ddd, J=13.2 Hz, 6.4 Hz, 4.3 Hz, 1H), 3.53-3.46 (ddd, J=13.2 Hz, 8.8 Hz, 4.3 Hz, 1H), 3.19-3.12 (m, 1H), 1.41-1.39 (d, J=7.0 Hz, 3H). MS (ESI) m/z: Calculated for $C_{22}H_{16}F_4N_4O_3$: 460.12. found: 461.1 (M+H)⁺.

Example 74

4-(Chloromethyl)-2-(3-fluorophenyl)oxazole

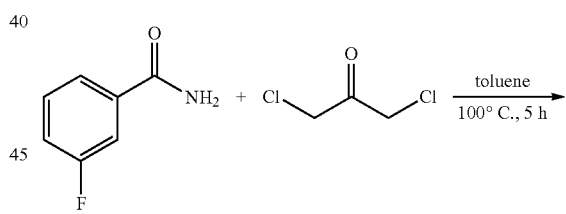

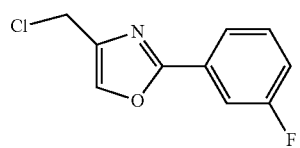

1,3-Dichloroacetone (3.65 g, 28.75 mmol) was added to a solution of 3-fluorobenzamide (2 g, 14.37 mmol) in dry toluene (20 mL). The resulting reaction mixture was stirred at 100° C. for 5 h. The reaction mixture was concentrated under reduced pressure and the crude product was purified by column chromatography (silica gel 60-120 mesh, eluent 10% EtOAc in petroleum ether) to afford 4-(chloromethyl)-2-(3-fluorophenyl)oxazole (1.2 g, yield 39%) as a yellow liquid.

NMR (300 MHz, CDCl₃) δ 7.85-7.83 (m, 1H), 7.77-7.73 (m, 2H), 7.48-7.41 (m, 1H), 7.20-7.14 (m, 1H), 4.58 (d, J=0.9 Hz, 2H).

2-(2-(3-Fluorophenyl)oxazol-4-yl)acetonitrile

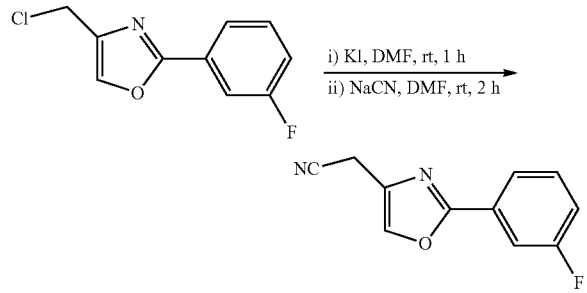

This compound was synthesized from 4-(chloromethyl)-2-(3-fluorophenyl)oxazole as described in example 71 step 2 (0.15 g, yield 35%). ¹H NMR (300 MHz, CDCl₃) δ 7.83-7.81 (m, 1H), 7.76-7.70 (m, 2H), 7.49-7.42 (m, 1H), 7.22-7.15 (m, 1H), 3.74 (s, 2H). MS (ESI) m/z: Calculated for C₁₁H₇FN₂O: 202.06. found: 203.2 (M+H)⁺.

2-(2-(3-Fluorophenyl)oxazol-4-yl)ethanamine

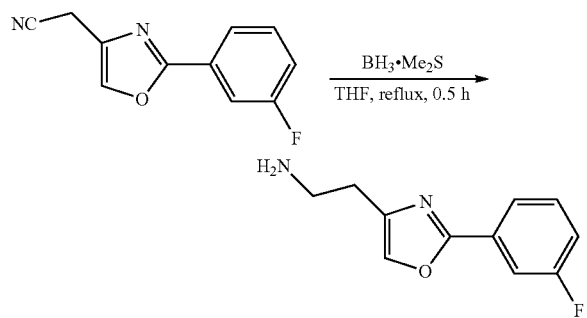

This compound was synthesized from 2-(2-(3-fluorophenyl)oxazol-4-yl)acetonitrile as described in example 42 step 1 (120 mg, crude) and it was carried through without further purification. MS (ESI) m/z: Calculated for C₁₁H₁₁FN₂O: 206.09. found: 206.9 (M+H)⁺.

N-(2-(2-(3-Fluorophenyl)oxazol-4-yl)ethyl)-5-(5-(trifluoromethyl)-1,2,4-oxadiazol-3-yl)nicotinamide

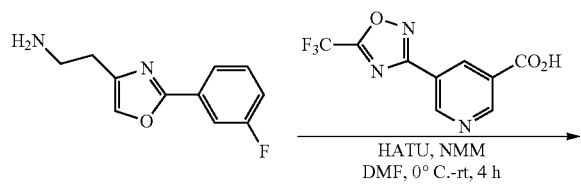

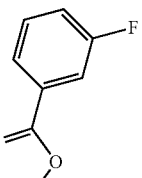

This compound was synthesized from 2-(2-(3-fluorophenyl)oxazol-4-yl)ethanamine and 5-(5-(trifluoromethyl)-1,2,4-oxadiazol-3-yl)nicotinic acid as described in example 8 step 6 (15 mg, yield 9%). ¹H NMR (400 MHz, MeOD) δ 9.39 (d, J=2.0 Hz, 1H), 9.19 (d, J=2.3 Hz, 1H), 8.90-8.88 (t, J=2.1 Hz, 1H), 7.84-7.82 (m, 2H), 7.72-7.69 (m, 1H), 7.54-7.49 (m, 1H), 7.26-7.21 (m, 1H), 3.79-3.76 (t, J=6.9 Hz, 2H), 2.98-2.95 (t, J=6.9 Hz, 2H). MS (ESI) m/z: Calculated for C₂₀H₁₃F₄N₅O₃: 447.10. found: 448.0 (M+H)⁺.

Example 75

Methyl 6-chloro-5-cyano-2-methylnicotinate

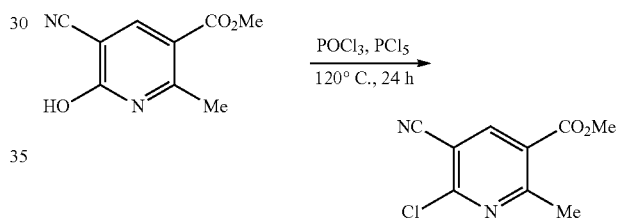

A mixture of methyl-5-cyano-6-hydroxy-2-methylnicotinate (2.0 g, 10.41 mmol), POCl₃ (40 mL) and PCl₅ (1.08 g, 5.2 mmol) was heated to 110° C. for 24 h. The reaction mixture was concentrated under reduced pressure and quenched with ice-water. The organic product was extracted with EtOAc and the organic layer was washed with H₂O and brine, dried over anhydrous sodium sulfate and concentrated under reduced pressure. The crude product was purified by column chromatography (silica gel 60-120 mesh, eluent 10-15% EtOAc in petroleum ether) to afford methyl 6-chloro-5-cyano-2-methylnicotinate (1.5 g, yield 68%). ¹H NMR (300 MHz, CDCl₃) δ 8.48 (s, 1H), 3.96 (s, 3H), 2.90 (s, 3H).

Methyl 5-cyano-2-methylnicotinate

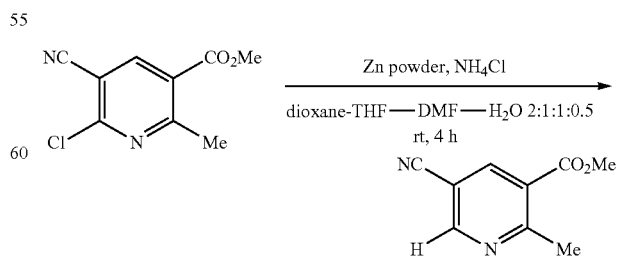

This compound was synthesized from methyl 6-chloro-5-cyano-2-methylnicotinate as described in example 69 step 1

(230 mg, yield 23%). $^1$H NMR (300 MHz, DMSO-$d_6$) δ 9.07-9.06 (d, J=2.2 Hz, 1H), 8.62-8.61 (d, J=2.2 Hz, 1H), 3.87 (m, 3H), 2.78 (s, 3H). MS (ESI) m/z: Calculated for $C_9H_8N_2O_2$: 176.06. found: 176.7 (M+H)$^+$.

5-Cyano-2-methylnicotinic acid

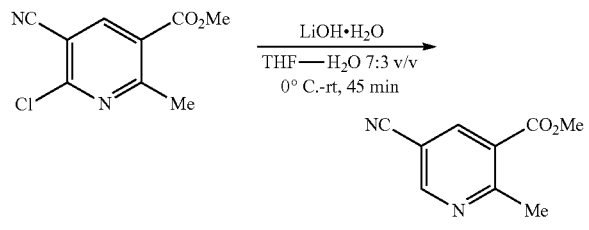

This compound was synthesized from methyl 5-cyano-2-methylnicotinate as described in example 69 step 2 (175 mg, yield 83%) as a white solid. $^1$H NMR (300 MHz, DMSO-$d_6$) δ 13.78 (br s, 1H), 9.02-9.01 (d, J=1.8 Hz, 1H), 8.56-8.55 (d, J=1.5 Hz, 1H), 2.78 (s, 3H). MS (ESI) m/z: Calculated for $C_8H_6N_2O_2$: 162.04. found: 160.6 (M−H)$^−$.

N-(2-(4-(4-Chlorophenyl)thiazol-2-yl)-2-methylpropyl)-5-cyano-2-methylnicotinamide

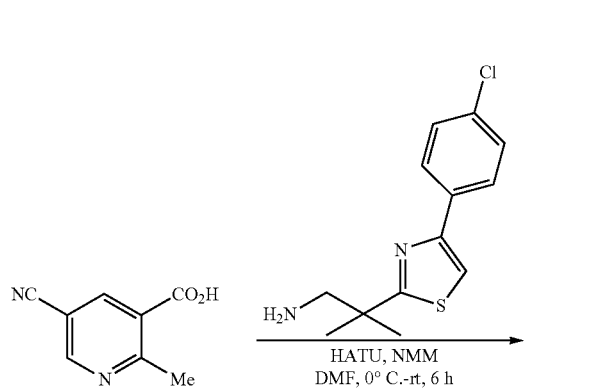

This compound was synthesized from 2-(4-(4-chlorophenyl)thiazol-2-yl)-2-methylpropan-1-amine and 5-cyano-2-methylnicotinic acid as described in example 8 step 6 (200 mg, yield 46%). $^1$H NMR (300 MHz, CDCl$_3$) δ 8.81 (m, 1H), 8.00-7.99 (m, 1H), 7.70-7.67 (m, 2H), 7.50-7.46 (m, 1H), 7.41-7.37 (m, 3H), 3.81-3.79 (d, J=5.7 Hz, 2H), 2.81 (s, 3H), 1.57 (s, 6H). MS (ESI) m/z: Calculated for $C_{21}H_{19}ClN_4OS$: 410.10. found: 411.1 (M+H)$^+$.

5-((2-(4-(4-Chlorophenyl)thiazol-2-yl)-2-methylpropyl)carbamoyl)-6-methylnicotinohydrazonic acid

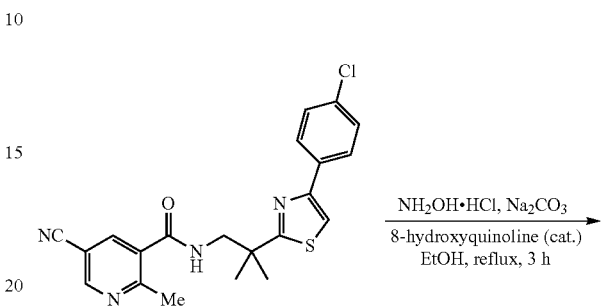

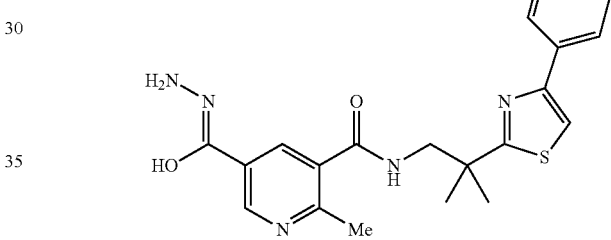

This compound was synthesized from methyl 5-cyano-2-methylnicotinate as described in example 1 step 4 (200 mg, crude) and it was carried through without further purification. $^1$H NMR (400 MHz, MeOD) δ 8.71-8.70 (d, J=2.3 Hz, 1H), 8.04-8.03 (d, J=2.3 Hz, 1H), 7.93-7.91 (d, J=8.5 Hz, 2H), 7.73 (s, 1H), 7.40-7.38 (d, J=8.5 Hz, 2H), 3.76 (s, 2H), 2.50 (br s, 3H), 1.58 (s, 6H). MS (ESI) m/z: Calculated for $C_{21}H_{22}ClN_5O_2S$: 443.12. found: 444.1 (M+H)$^+$.

N-(2-(4-(4-Chlorophenyl)thiazol-2-yl)-2-methylpropyl)-2-methyl-5-(5-(trifluoromethyl)-1,2,4-oxadiazol-3-yl)nicotinamide

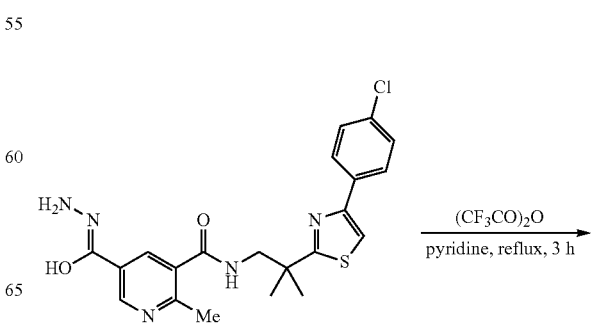

-continued

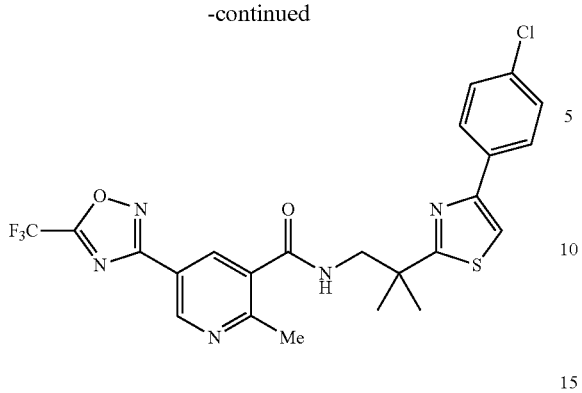

This compound was synthesized from 5-((2-(4-(4-chlorophenyl)thiazol-2-yl)-2-methylpropyl)carbamoyl)-6-methylnicotinohydrazonic acid as described in example 1 step 5 (20 mg, yield 9%). $^1$H NMR (400 MHz, MeOD) δ 9.14-9.13 (d, J=2.0 Hz, 1H), 8.34 (d, J=2.0 Hz, 1H), 7.93-7.91 (d, J=8.8 Hz, 2H), 7.74 (s, 1H), 7.35-7.33 (d, J=8.8 Hz, 2H), 3.80 (s, 2H), 2.58 (br s, 3H), 1.60 (s, 6H). MS (ESI) m/z: Calculated for $C_{23}H_{19}ClF_3N_5O_2S$: 521.09. found: 522.1 (M+H)$^+$.

Example 76

2-Methyl-2-(5-phenylthiazol-2-yl)propanenitrile

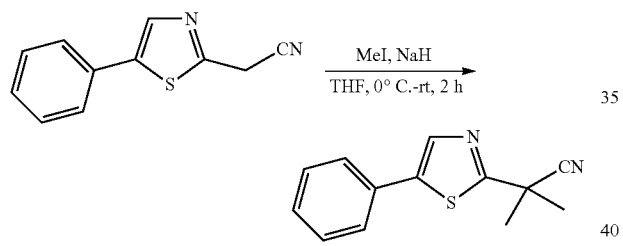

This compound was synthesized from 2-(5-phenylthiazol-2-yl)acetonitrile as described in example 1 step 2 using iodomethane (200 mg, yield 58%). $^1$H NMR (400 MHz, CDCl$_3$) δ 7.90 (s, 1H), 7.56-7.54 (m, 2H), 7.45-7.37 (m, 3H), 1.90 (s, 6H). MS (ESI) m/z: Calculated for $C_{13}H_{12}N_2S$: 228.07.10. found: 228.8 (M+H)$^+$.

2-Methyl-2-(5-phenylthiazol-2-yl)propan-1-amine

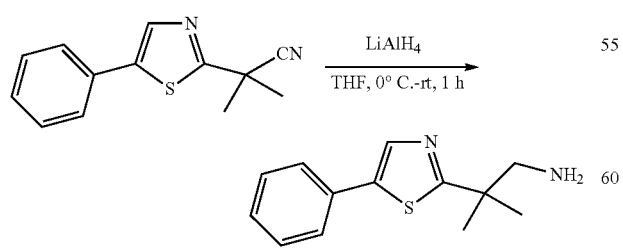

This compound was synthesized from 2-methyl-2-(5-phenylthiazol-2-yl)propanenitrile as described in example 1 step 3 (70 mg, yield 34%) and it was carried through without further purification. MS (ESI) m/z: Calculated for $C_{13}H_{16}N_2S$: 232.10. found: 233.2 (M+H)$^+$.

N-(2-Methyl-2-(5-phenylthiazol-2-yl)propyl)-3-(5-(trifluoromethyl)-1,2,4-oxadiazol-3-yl)benzamide

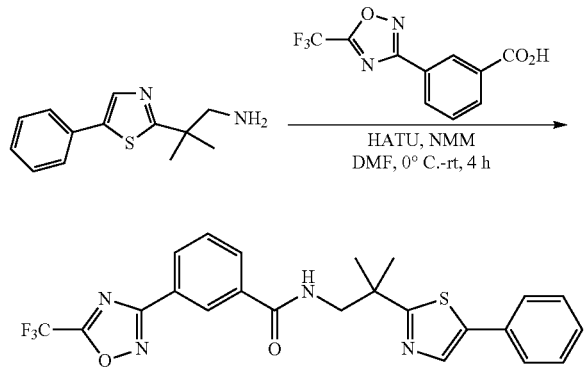

This compound was synthesized from 2-methyl-2-(5-phenylthiazol-2-yl)propan-1-amine and 3-(5-(trifluoromethyl)-1,2,4-oxadiazol-3-yl)benzoic acid as described in example 8 step 6 (20 mg, yield 17%). $^1$H NMR (400 MHz, MeOD) δ 8.55 (m, 1H), 8.29-8.27 (m, 1H), 8.03-8.01 (m, 1H), 7.96 (s, 1H), 7.98 (s, 1H), 7.71-7.67 (t, J=7.8 Hz, 1H), 7.63-7.61 (m, 2H), 7.43-7.39 (m, 2H), 7.35-7.32 (m, 1H), 3.75 (s, 2H), 1.56 (s, 6H). MS (ESI) m/z: Calculated for $C_{23}H_{19}F_3N_4O_2S$: 472.12. found: 473.1 (M+H)$^+$.

Example 77

2-([1,1'-Biphenyl]-3-yl)acetonitrile

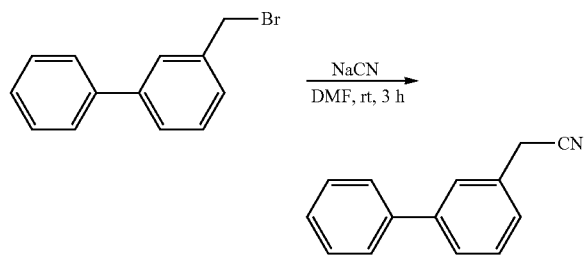

NaCN (1.1 g, 22.26 mmol) was added to a solution of 3-phenylbenzyl bromide (5.0 g, 20.23 mmol) in dry DMF (100 mL). The resulting reaction mixture was stirred at room temperature for 3 h and then quenched with water. The organic product was extracted with EtOAc and the combined extracts were washed with H$_2$O and brine, dried over anhydrous sodium sulfate and concentrated under reduced pressure. The crude product was purified by column chromatography (silica gel 60-120 mesh, eluent 5% EtOAc in petroleum ether) to afford 2-([1,1'-biphenyl]-3-yl)acetonitrile (3.8 g, yield 97%). $^1$H NMR (300 MHz, CDCl$_3$) δ 7.61-7.56 (m, 4H), 7.50-7.45 (m, 3H), 7.42-7.36 (m, 1H), 7.34-7.31 (m, 1H), 3.83 (s, 2H).

183

4-([1,1'Biphenyl]-3-yl)tetrahydro-2H-pyran-4-carbonitrile

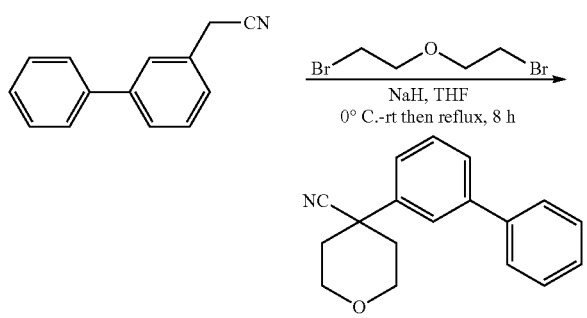

This compound was synthesized from 2-([1,1'-biphenyl]-3-yl)acetonitrile as described in example 1 step 2 using 2-bromoethyl ether (0.5 g, 73%). $^1$H NMR (300 MHz, CDCl$_3$) δ 7.72-7.71 (m, 1H), 7.62-7.57 (m, 3H), 7.51-7.45 (m, 4H), 7.42-7.37 (m, 1H), 4.15-4.10 (m, 2H), 3.99-3.91 (m, 2H), 2.28-2.20 (m, 4H).

(4-([1,1'-Biphenyl]-3-yl)tetrahydro-2H-pyran-4-yl)methanamine

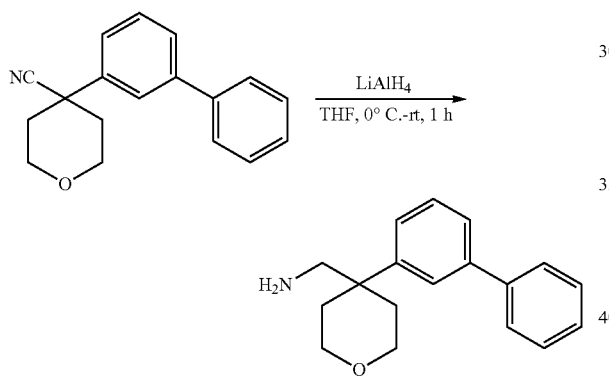

This compound was synthesized from 4-([1,1'-biphenyl]-3-yl)tetrahydro-2H-pyran-4-carbonitrile as described in example 1 step 3 (230 mg, yield 46%) as a pale yellow oil. $^1$H NMR (300 MHz, DMSO-d$_6$) δ 7.66-7.63 (m, 2H), 7.53-7.41 (m, 5H), 7.37-7.31 (m, 2H), 3.70-3.65 (m, 2H), 3.43-3.37 (m, 2H), 2.68 (s, 2H), 2.11-2.05 (m, 2H), 1.87-1.79 (m, 2H). MS (ESI) m/z: Calculated for C$_{18}$H$_{21}$NO: 267.16. found: 267.9 (M+H)$^+$.

N-((4-([1,1'-Biphenyl]-3-yl)tetrahydro-2H-pyran-4-yl)methyl)-3-(5-(trifluoromethyl)-1,2,4-oxadiazol-3-yl)benzamide

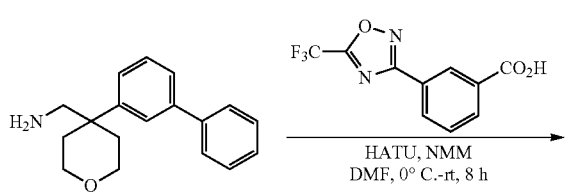

184

-continued

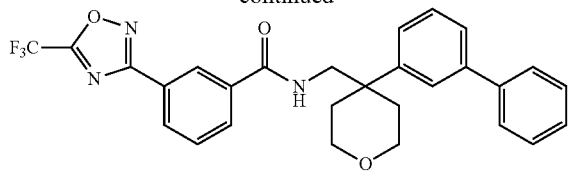

This compound was synthesized from (4-([1,1'-biphenyl]-3-yl)tetrahydro-2H-pyran-4-yl)methanamine and 3-(5-(trifluoromethyl)-1,2,4-oxadiazol-3-yl)benzoic acid as described in example 8 step 6 (110 mg, yield 56%) as a white solid. $^1$H NMR (400 MHz, CDCl$_3$) δ 8.28 (s, 1H), 8.23-8.21 (d, J=7.7 Hz, 1H), 7.86-7.84 (d, J=8.0 Hz, 1H), 7.58-7.55 (m, 6H), 7.45-7.37 (m, 4H), 5.85-5.82 (t, J=6.1 Hz, 1H), 3.96-3.91 (m, 2H), 3.79-3.78 (d, J=6.4 Hz, 2H), 3.74-3.69 (m, 2H), 2.27-2.22 (m, 2H), 2.10-2.04 (m, 2H). MS (ESI) m/z: Calculated for C$_{28}$H$_{24}$F$_3$N$_3$O$_3$: 507.18. found: 508.1 (M+H)$^+$.

Example 78

N-((4-([1,1'-Biphenyl]-3-yl)tetrahydro-2H-pyran-4-yl)methyl)-5-(5-(trifluoromethyl)-1,2,4-oxadiazol-3-yl)nicotinamide

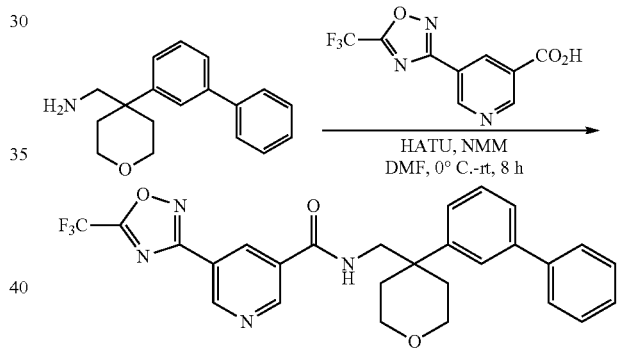

This compound was synthesized from (4-([1,1'-biphenyl]-3-yl)tetrahydro-2H-pyran-4-yl)methanamine and 5-(5-(trifluoromethyl)-1,2,4-oxadiazol-3-yl)nicotinic acid as described in example 8 step 6 (95 mg, yield 48%) as a white solid. $^1$H NMR (400 MHz, CDCl$_3$) δ 9.40 (br s, 1H), 8.97 (br s, 1H), 8.61-8.60 (t, J=1.9 Hz, 1H), 7.58-7.55 (m, 5H), 7.46-7.43 (t, J=7.5 Hz, 2H), 7.39-7.35 (m, 2H), 5.89-5.86 (t, J=6.1 Hz, 1H), 3.96-3.92 (m, 2H), 3.82-3.81 (d, J=6.1 Hz, 2H), 3.74-3.68 (m, 2H), 2.29-2.23 (m, 2H), 2.09-2.03 (m, 2H). MS (ESI) m/z: Calculated for C$_{27}$H$_{23}$F$_3$N$_4$O$_3$: 508.17. found: 507.2 (M-H)$^-$.

Example 79

2-(4-Fluorophenyl)-4-(iodomethyl)oxazole

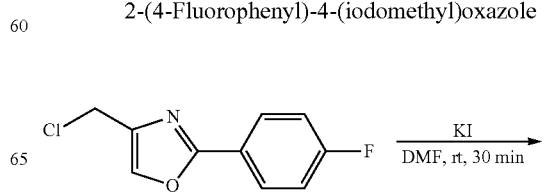

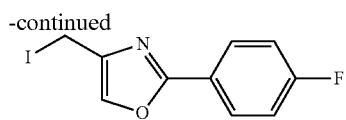

KI (3.14 g, 18.9 mmol) was added to a solution of 4-chloromethyl-2-(4-fluorophenyl)-oxazole (1 g, 4.7 mmol) in dry DMF (10 mL) at room temperature. The resulting reaction mixture was stirred for 30 min and then diluted with EtOAc. The mixture was extracted with EtOAc and the combined extracts were washed with water and brine, dried over anhydrous sodium sulfate, and concentrated under reduced pressure to get 2-(4-fluorophenyl)-4-(iodomethyl)oxazole (1.2 g, crude), which was carried through without further purification. $^1$H NMR (300 MHz, CDCl$_3$) δ 8.05-8.00 (m, 2H), 7.68 (s, 1H), 7.17-7.11 (m, 2H), 4.33 (s, 2H). MS (ESI) m/z: Calculated for $C_{10}H_7FINO$: 302.96. found: 304.0 (M+H)$^+$.

4-(Azidomethyl)-2-(4-fluorophenyl)oxazole

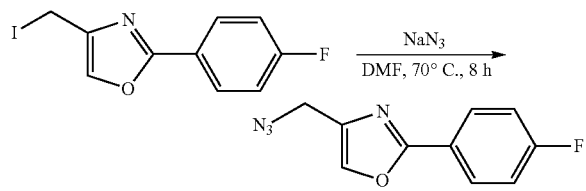

A solution of 2-(4-fluorophenyl)-4-(iodomethyl)oxazole (1.2 g, 3.96 mmol) in dry DMF (10 mL) was added sodium azide (515 mg, 7.9 mmol) and the reaction mixture was heated to 70° C. for 8 h. The reaction mixture was allowed to cool down to room temperature and diluted with EtOAc. The mixture was extracted with EtOAc and the combined extracts were washed with water and brine, dried over anhydrous Na$_2$SO$_4$, and concentrated under reduced pressure to afford 4-(azidomethyl)-2-(4-fluorophenyl)oxazole (0.73 g, yield 85%) as a pale orange liquid, which was carried through without further purification. $^1$H NMR (400 MHz, CDCl$_3$) δ 8.04-8.01 (m, 2H), 7.67 (s, 1H), 7.16-7.12 (m, 2H), 4.34 (s, 2H). MS (ESI) m/z: Calculated for $C_{10}H_7FN_4O$: 218.06. found: 219.2 (M+H)$^+$.

(2-(4-Fluorophenyl)oxazol-4-yl)methanamine

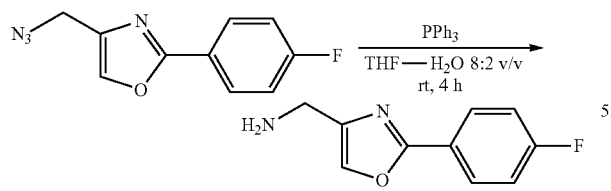

A solution of 4-(azidomethyl)-2-(4-fluorophenyl)oxazole (0.5 g, 2.3 mmol) in THF—H$_2$O (15 mL, 8:2 v/v) was cooled to 0° C. and triphenylphosphine (892 mg, 3.4 mmol) was added. The reaction mixture was allowed to warm up to room temperature and then stirred for 4 h. The reaction mixture was concentrated under reduced pressure and the residue was diluted with 1.5N HCl. The aqueous layer was washed with CH$_2$Cl$_2$ and then the pH of the aqueous layer was adjusted to ~8-9 using 10% NaOH solution. The organic product was extracted with CH$_2$Cl$_2$ and organic layer was washed with brine, dried over anhydrous Na$_2$SO$_4$, and concentrated under reduced pressure to afford (2-(4-fluorophenyl)oxazol-4-yl)methanamine (330 mg, yield 75%) as a pale yellow liquid, which was carried through without further purification. $^1$H NMR (400 MHz, DMSO-d$_6$) δ 8.01-7.98 (m, 2H), 7.94 (s, 1H), 7.38-7.34 (m, 2H), 3.65 (d, J=1.1 Hz, 2H). MS (ESI) m/z: Calculated for $C_{10}H_9FN_2O$: 192.07. found: 193.2 (M+H)$^+$.

N-((2-(4-Fluorophenyl)oxazol-4-yl)methyl)-3-(5-(trifluoromethyl)-1,2,4-oxadiazol-3-yl)benzamide

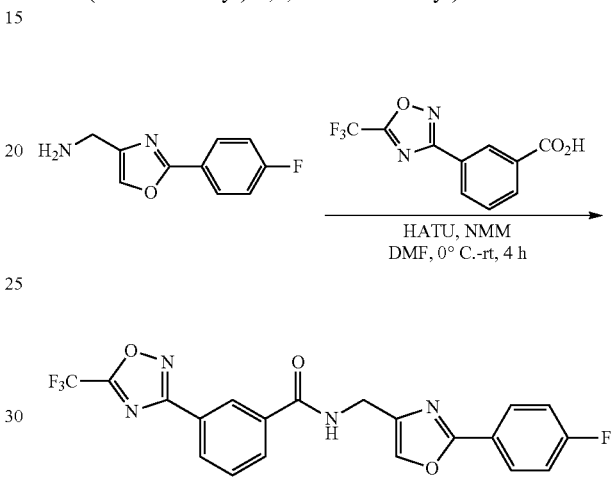

This compound was synthesized from (2-(4-fluorophenyl)oxazol-4-yl)methanamine and 3-(5-(trifluoromethyl)-1,2,4-oxadiazol-3-yl)benzoic acid as described in example 8 step 6 (65 mg, yield 26%) as a white solid. $^1$H NMR (400 MHz, DMSO-d$_6$) δ 9.35-9.32 (m, 1H), 8.60 (t, J=1.5 Hz, 1H), 8.25-8.19 (m, 2H), 8.12 (m, 1H), 8.04-8.00 (m, 2H), 7.77-7.73 (t, J=7.8 Hz, 1H), 7.41-7.36 (m, 2H), 4.48-4.47 (d, J=5.2 Hz, 2H). MS (ESI) m/z: Calculated for $C_{20}H_{12}F_4N_4O_3$: 432.08. found: 433.2 (M+H)$^+$.

Example 80

4-(2-(4-Fluorophenyl)oxazol-4-yl)-1-methylpiperidine-4-carbonitrile

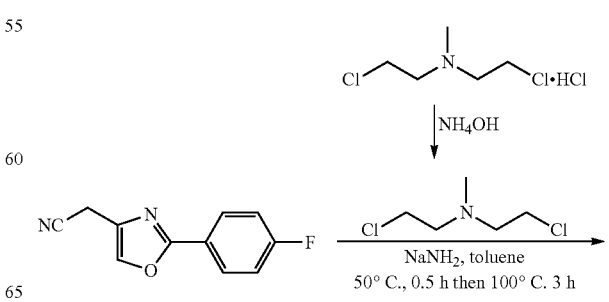

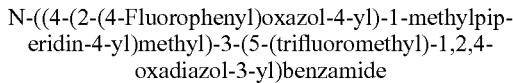

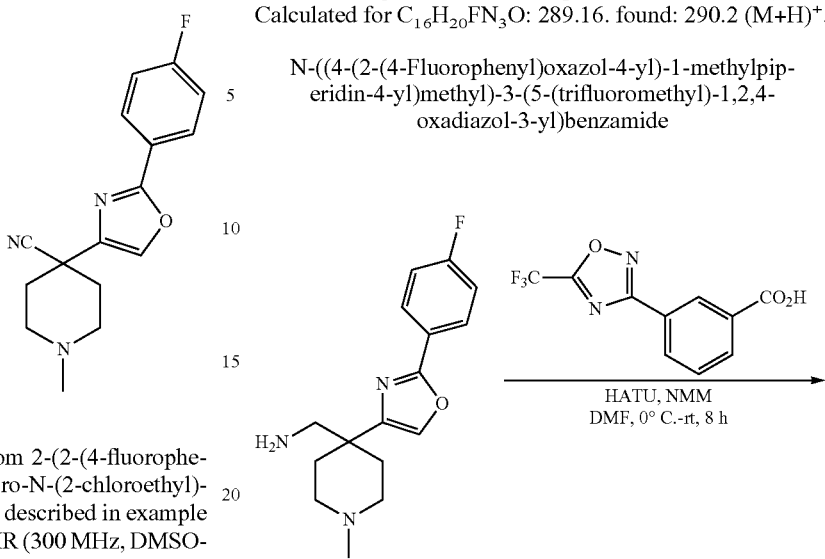

This compound was synthesized from 2-(2-(4-fluorophenyl)oxazol-4-yl)acetonitrile and 2-chloro-N-(2-chloroethyl)-N-methylethanamine hydrochloride as described in example 16 step 1b (430 mg, yield 30%). $^1$H NMR (300 MHz, DMSO-$d_6$) δ 8.30 (s, 1H), 8.05-8.00 (m, 2H), 7.41-7.35 (m, 2H), 2.83-2.79 (m, 2H), 2.26-2.18 (m, 7H), 2.04-1.94 (m, 2H). MS (ESI) m/z: Calculated for $C_{16}H_{16}FN_3O$: 285.13. found: 286.2 (M+H)$^+$.

(4-(2-(4-Fluorophenyl)oxazol-4-yl)-1-methylpiperidin-4-yl)methanamine

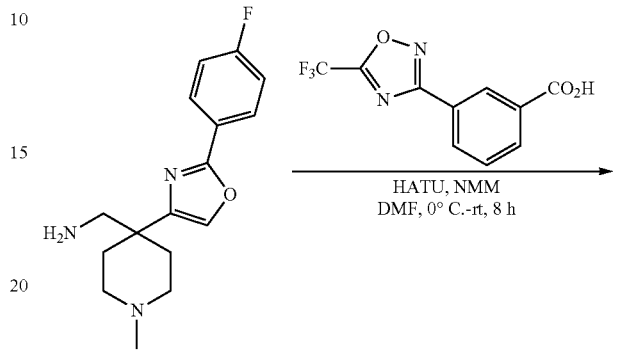

This compound was synthesized from 4-(2-(4-fluorophenyl)oxazol-4-yl)-1-methylpiperidine-4-carbonitrile as described in example 1 step 3 (170 mg, crude) and it was carried through without further purification. MS (ESI) m/z: Calculated for $C_{16}H_{20}FN_3O$: 289.16. found: 290.2 (M+H)$^+$.

N-((4-(2-(4-Fluorophenyl)oxazol-4-yl)-1-methylpiperidin-4-yl)methyl)-3-(5-(trifluoromethyl)-1,2,4-oxadiazol-3-yl)benzamide

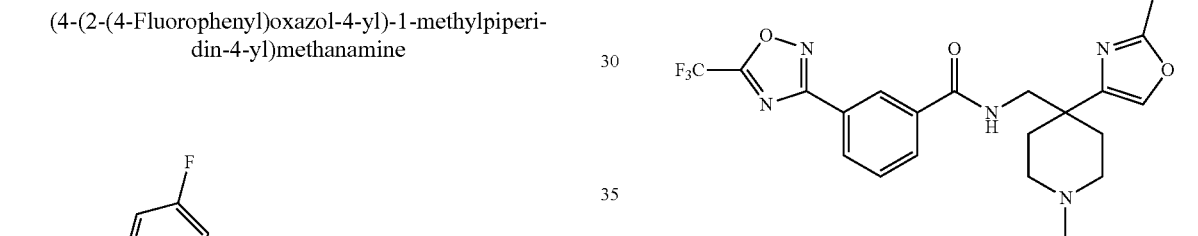

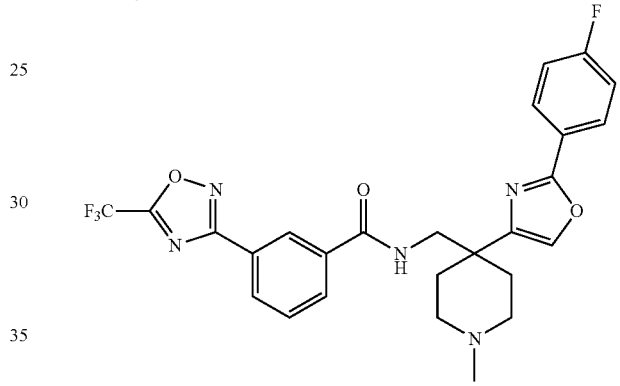

This compound was synthesized from (4-(2-(4-fluorophenyl)oxazol-4-yl)-1-methylpiperidin-4-yl)methanamine and 3-(5-(trifluoromethyl)-1,2,4-oxadiazol-3-yl)benzoic acid as described in example 8 step 6 (50 mg, yield 24%). $^1$H NMR (400 MHz, CDCl$_3$) δ 8.55 (s, 1H), 8.29-8.27 (m, 1H), 8.13-8.05 (m, 3H), 7.67-7.62 (m, 2H), 7.17-7.13 (t, J=8.7 Hz, 2H), 3.85-3.84 (m, 2H), 3.14-3.00 (m, 4H), 2.67 (m, 3H), 2.43-2.42 (m, 2H), 2.24-2.23 (m, 2H). MS (ESI) m/z: Calculated for $C_{26}H_{23}F_4N_5O_3$: 529.17. found: 530.2 (M+H)$^+$.

Example 81

4-(Chloromethyl)-2-phenyloxazole

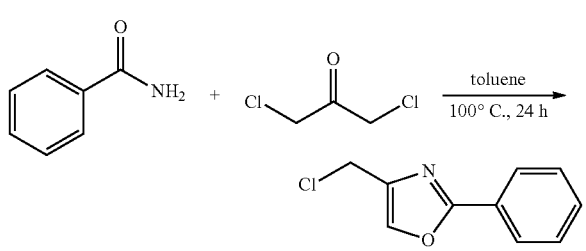

This compound was synthesized from 1,3-dichloroacetone and benzamide as described in example 71 step 1 (65 g, yield 68%) as a white solid. $^1$H NMR (300 MHz, CDCl$_3$) δ 8.06-

8.04 (m, 2H), 7.72 (m, 1H), 7.49-7.46 (m, 3H), 4.59 (d, J=1.1 Hz, 2H). MS (ESI) m/z: Calculated for $C_{10}H_8ClNO$: 193.03. found: 194.2 (M+H)$^+$.

2-(2-Phenyloxazol-4-yl)acetonitrile

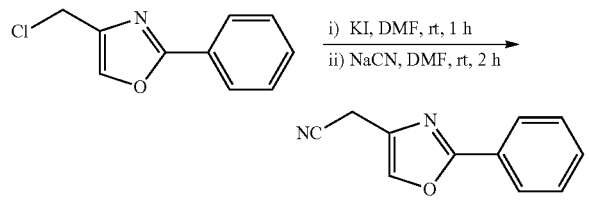

This compound was synthesized from 4-(chloromethyl)-2-phenyloxazole as described in example 71 step 2 (24 g, yield 50%) as a white solid. $^1$H NMR (300 MHz, CDCl$_3$) δ 8.04-8.01 (m, 2H), 7.74 (t, J=1.2 Hz, 1H), 7.49-7.46 (m, 3H), 3.74 (d, J=1.1 Hz, 2H). MS (ESI) m/z: Calculated for $C_{11}H_8N_2O$: 184.06. found: 185.2 (M+H)$^+$.

2-Methyl-2-(2-phenyloxazol-4-yl)propanenitrile

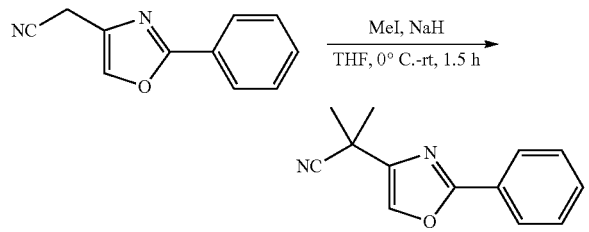

This compound was synthesized from 2-(2-phenyloxazol-4-yl)acetonitrile using iodomethane as described in example 1 step 2 (18 g, yield 65%) as a yellow solid. $^1$H NMR (300 MHz, CDCl$_3$) δ 8.06-8.03 (m, 2H), 7.68 (s, 1H), 7.48-7.46 (m, 3H), 1.77 (s, 6H). MS (ESI) m/z: Calculated for $C_{13}H_{12}N_2O$: 212.09. found: 213.2 (M+H)$^+$.

2-Methyl-2-(2-phenyloxazol-4-yl)propan-1-amine

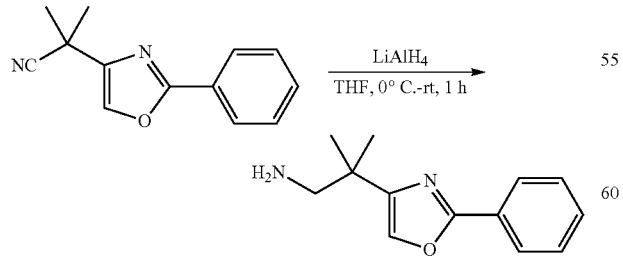

This compound was synthesized from 2-methyl-2-(2-phenyloxazol-4-yl)propanenitrile as described in example 1 step 3 (16.2 g, crude) and it was carried through without further purification. MS (ESI) m/z: Calculated for $C_{13}H_{16}N_2O$: 216.13. found: 217.2 (M+H)$^+$.

N-(2-Methyl-2-(2-phenyloxazol-4-yl)propyl)-3-(5-(trifluoromethyl)-1,2,4-oxadiazol-3-yl)benzamide

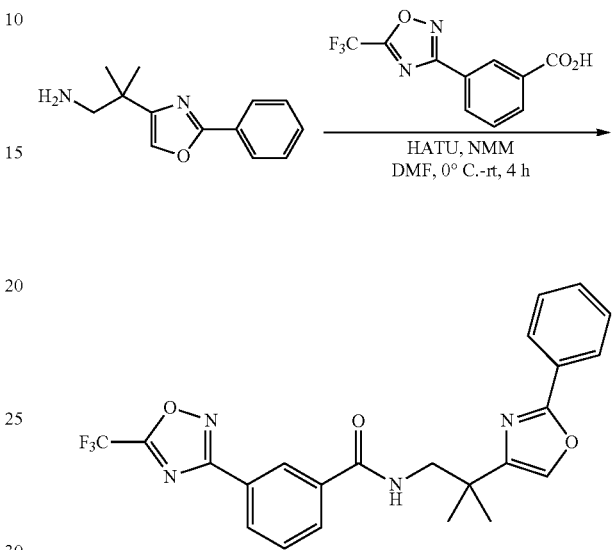

This compound was synthesized from 2-methyl-2-(2-phenyloxazol-4-yl)propan-1-amine and 3-(5-(trifluoromethyl)-1,2,4-oxadiazol-3-yl)benzoic acid as described in example 8 step 6 (15 g, yield 44%) as a white solid. $^1$H NMR (400 MHz, CDCl$_3$) δ 8.66 (t, J=1.5 Hz, 1H), 8.29-8.26 (m, 2H), 8.20-8.17 (dt, J=8.0 Hz, 1.2 Hz, 1H), 8.09-8.06 (m, 2H), 7.68-7.64 (t, J=7.9 Hz, 1H), 7.51 (s, 1H), 7.47-7.40 (m, 3H), 3.66 (d, J=5.6 Hz, 2H), 1.43 (s, 6H). MS (ESI) m/z: Calculated for $C_{23}H_{19}F_3N_4O_3$: 456.14. found: 457.2 (M+H)$^+$.

Example 82

2-(2-(4-Fluorophenyl)oxazol-4-yl)-2-methylpropanenitrile

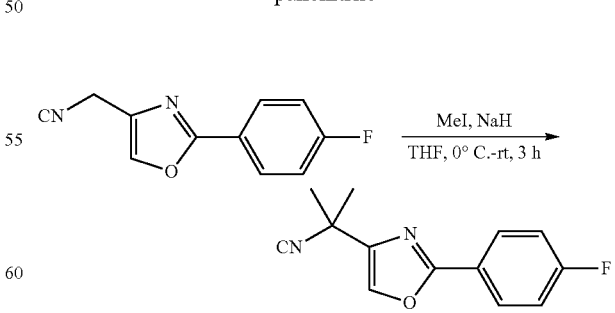

This compound was synthesized from 2-(2-(4-fluorophenyl)oxazol-4-yl)acetonitrile using iodomethane as described in example 1 step 2 (15 g, yield 66%) as a white solid. $^1$H NMR (300 MHz, CDCl$_3$) δ 8.07-8.02 (dd, J=8.9 Hz, 5.4 Hz, 2H), 7.66 (s, 1H), 7.19-7.13 (t, J=8.7 Hz, 2H), 1.76 (s, 6H). MS (ESI) m/z: Calculated for $C_{13}H_{11}FN_2O$: 230.09. found: 231.2 $(M+H)^+$.

2-(2-(4-Fluorophenyl)oxazol-4-yl)-2-methylpropan-1-amine

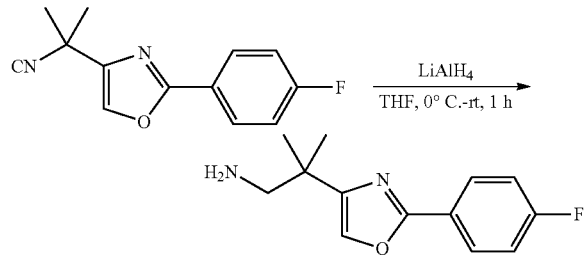

This compound was synthesized from 2-(2-(4-fluorophenyl)oxazol-4-yl)-2-methylpropanenitrile as described in example 1 step 3 (14 g, crude) and it was carried through without further purification. $^1$H NMR (300 MHz, MeOD) δ 8.07-8.03 (dd, J=8.9 Hz, 5.4 Hz, 2H), 7.73 (s, 1H), 7.26-7.20 (m, 2H), 2.85 (s, 2H), 1.31 (s, 6H). MS (ESI) m/z: Calculated for $C_{13}H_{15}FN_2O$: 234.12. found: 235.2 $(M+H)^+$.

2-(2-(4-Fluorophenyl)oxazol-4-yl)-2-methyl-N-(3-(5-(trifluoromethyl)-1,2,4-oxadiazol-3-yl)benzyl)propan-1-amine

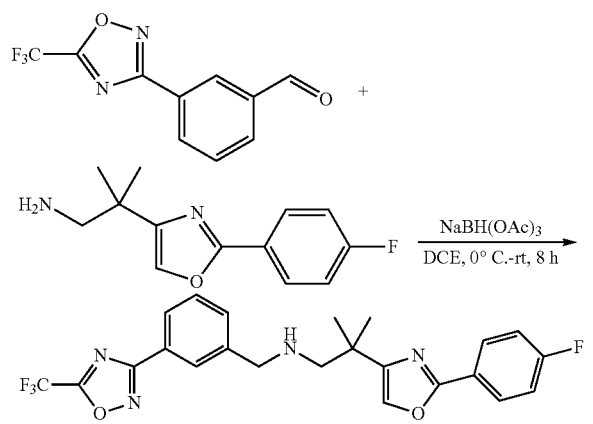

Sodiumtriacetoxy borohydride (197 mg, 0.9 mmol) was added to a solution of 3-(5-(trifluoromethyl)-1,2,4-oxadiazol-3-yl)benzaldehyde (150 mg, 0.62 mmol) and 2-(2-(4-fluorophenyl)oxazol-4-yl)-2-methylpropan-1-amine (150 mg, 0.64 mmol) in dry DCE (2 mL) at 0° C. under nitrogen atmosphere and stirred at room temperature for 8 h (monitored by TLC, petroleum ether/EtOAc 6:4). Reaction mixture was carefully quenched with 10% NaHCO$_3$ solution and the organic product was extracted with EtOAc. The combined extracts were washed with brine, dried over anhydrous Na$_2$SO, and concentrated under reduced pressure. The crude product was purified by column chromatography (silica 60-120 mesh, eluant 10-15% EtOAc in petroleum ether) to get 2-(2-(4-fluorophenyl)oxazol-4-yl)-2-methyl-N-(3-(5-(trifluoromethyl)-1,2,4-oxadiazol-3-yl)benzyl)propan-1-amine (50 mg, yield 18%). $^1$H NMR (400 MHz, MeOD) δ 8.01 (m, 2H), 7.96-7.92 (m, 3H), 7.67 (s, 1H), 7.54-7.52 (m, 1H), 7.49-7.45 (m, 1H), 7.20-7.15 (m, 1H), 3.82 (s, 2H), 2.76 (s, 2H), 1.32 (s, 6H). MS (ESI) m/z: Calculated for $C_{23}H_{20}F_4N_4O_2$: 460.15. found: 461.2 $(M+H)^+$.

Example 83

4-Phenylthiazol-2(3H)-one

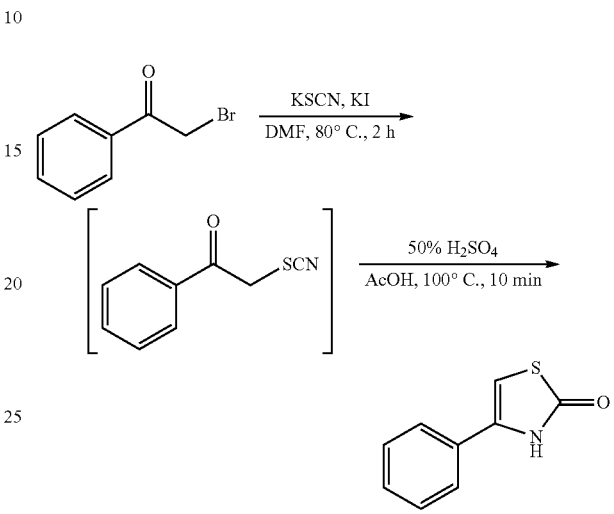

A suspension of 2-bromoacetophenone (5 g, 0.0251 mol), potassium thiocyanate (8.6 g, 0.088 mol) and potassium iodide (0.25 g, 0.0015 mol) in dry DMF (25 mL) was heated to 80° C. for 2 h. The reaction mixture was concentrated to dryness under reduced pressure and the residue was dissolved in glacial acetic acid (25 mL) and 50% aqueous H$_2$SO$_4$ was added to it. The reaction mixture was heated to 100° C. for 10 min. The reaction mixture was poured in ice water and the precipitate formed was filtered and dried under reduced pressure to get 4-phenylthiazol-2(3H)-one (3.3 g, yield 75%) as a brown solid, which was carried through without further purification.

2-Bromo-4-phenylthiazole

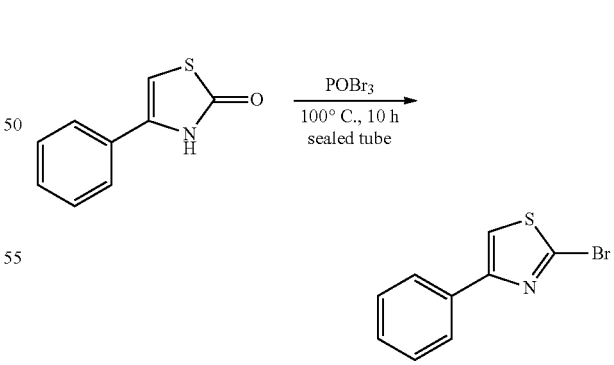

A mixture of 4-phenylthiazol-2(3H)-one (300 mg, 1.7 mmol) and POBr$_3$ (4.85 g, 17.0 mmol) was heated to 100° C. in a sealed tube for 10 h. The reaction mixture was poured in ice water and the organic product was extracted with EtOAc. The combined extracts were washed with brine, dried over anhydrous sodium sulfate, and concentrated under reduced pressure. The crude product was purified by column chromatography (silica 60-120 mesh, eluant 1% EtOAc in petroleum ether) to get 2-bromo-4-phenylthiazole (300 mg, yield 73%) as light brown colored liquid. $^1$H NMR (300 MHz, CDCl$_3$) δ 7.88-7.85 (m, 2H), 7.46-7.35 (m, 4H). MS (ESI) m/z: Calculated for C$_9$H$_6$BrNS: 240.94. found: 242.0 (M+H)$^+$.

3-(4,4-Dibromobut-3-en-1-yl)benzonitrile

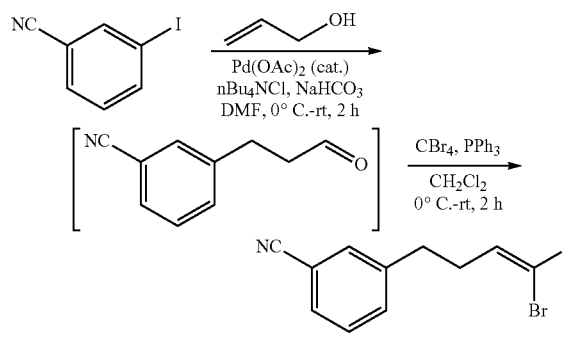

Tetrabutyl ammonium chloride (6.0 g, 21.83 mmol) and sodium bicarbonate (4.5 g, 54.5 mmol) were taken in dry DMF (15 mL) and cooled to 0° C. and 3-iodobenzonitrile (5.0 g, 21.83 mmol) was added. Allyl alcohol (2.2 mL, 32.7 mmol) was added to the reaction mixture, followed by a catalytic amount of Pd(OAc)$_2$ (146 mg, 0.65 mmol) and the mixture was stirred at 0° C. for 30 min. The reaction mixture was slowly warmed up to room temperature and further stirred for 2 h. The reaction mixture was diluted with water and the organic product was extracted with ether. The combined extracts were dried over anhydrous Na$_2$SO$_4$ and concentrated under reduced pressure to get the crude product aldehyde. The crude aldehyde (5.0 g, 31.4 mmol) was added to a cold solution of carbon tetrabromide (20.8 g, 62.8 mmol) and triphenyl phosphine (32.8 g, 125 mmol) in CH$_2$Cl$_2$ (100 mL) at 0° C. The reaction mixture was further stirred for 2 h maintaining the same temperature. The mixture was then diluted with hexane and the precipitate formed was filtered. The clear filtrate was concentrated to get the crude product which was purified by column chromatography (silica 60-120 mesh, eluant 10-15% EtOAc in petroleum ether) to get 3-(4,4-dibromobut-3-en-1-yl)benzonitrile (2.25 g, overall yield 33%) as a brown oil. $^1$H NMR (300 MHz, CDCl$_3$) δ 7.66-7.63 (dt, J=7.7 Hz, 1.3 Hz, 1H), 7.55-7.49 (m, 2H), 7.44-7.42 (m, 1H), 6.42-6.37 (t, J=7.2 Hz, 1H), 2.81-2.76 (m, 2H), 2.46-2.39 (q, J=7.4 Hz, 2H).

3-(But-3-yn-1-yl)benzonitrile

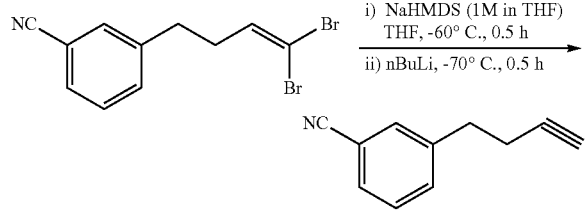

Sodium bis(trimethylsilyl)amide (10.7 mL, 10.7 mmol, 1 M in THF) was added dropwise to a solution of 3-(4,4-dibromobut-3-en-1-yl)benzonitrile (2.25 g, 7.14 mmol) in dry THF (45 mL) at −60° C. The reaction mixture was stirred for another 0.5 h maintaining the same temperature. The mixture was then cooled to −70° C. and n-BuLi (8.9 mL, 14.3 mmol, 1.6 M in hexane) was added dropwise. The reaction mixture was stirred for 0.5 h, quenched with saturated NH$_4$Cl solution, and extracted with EtOAc. The combined extracts were concentrated under reduced pressure to obtain the 3-(but-3-yn-1-yl)benzonitrile (600 mg, yield 54%). $^1$H NMR (300 MHz, CDCl$_3$) δ 7.55 (m, 1H), 7.53-7.51 (m, 1H), 7.48-7.39 (m, 2H), 2.90-2.85 (m, 2H), 2.54-2.48 (td, J=7.2 Hz, 2.6 Hz, 2H), 2.01-1.99 (t, J=2.6 Hz, 1H).

3-(4-(4-Phenylthiazol-2-yl)but-3-yn-1-yl)benzonitrile

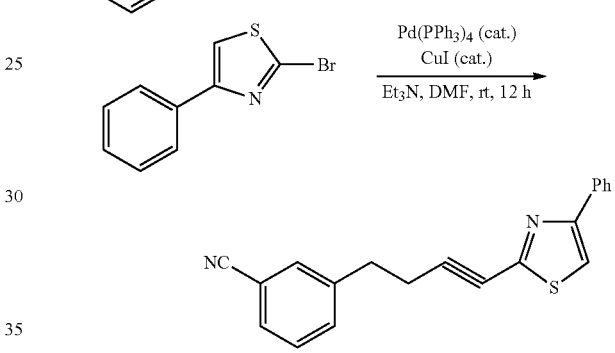

3-(But-3-yn-1-yl)benzonitrile (462 mg, 2.98 mmol) and 2-bromo-4-phenylthiazole (650 mg, 2.71 mmol) were taken in dry DMF (20 mL) and purged with nitrogen gas for 15 min. Et$_3$N (1.9 mL, 13.5 mmol) was added to the reaction mixture, followed by a catalytic amount of copper iodide (51 mg, 0.27 mmol) and Pd(PPh$_3$)$_4$ (115 mg, 0.1 mmol). The reaction mixture was stirred at room temperature for 12 h and then quenched with water. The organic product was extracted with EtOAc, and the combined extracts were concentrated under reduced pressure. The crude product was purified by column chromatography (silica 60-120 mesh, eluant 15-20% EtOAc in petroleum ether) to get 3-(4-(4-phenylthiazol-2-yl)but-3-yn-1-yl)benzonitrile (430 mg, yield 50%) as a pale yellow solid. $^1$H NMR (300 MHz, CDCl$_3$) δ 7.92-7.90 (m, 2H), 7.59-7.52 (m, 3H), 7.47-7.33 (m, 5H), 3.04-2.99 (m, 2H), 2.83-2.78 (m, 2H). MS (ESI) m/z: Calculated for C$_{20}$H$_{14}$N$_2$S: 314.09. found: 315.2 (M+H)$^+$.

3-(4-(4-Phenylthiazol-2-yl)butyl)benzonitrile

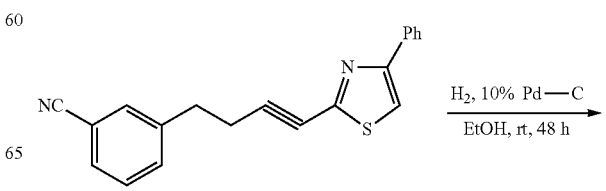

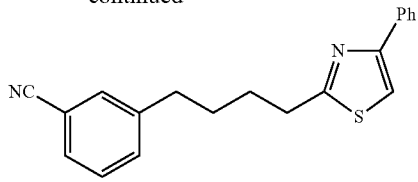

10% Palladium on charcoal (215 mg) was added to a solution of 3-(4-(4-phenylthiazol-2-yl)but-3-yn-1-yl)benzonitrile (430 mg, 1.37 mmol) in ethanol (15 mL), the reaction mixture was put under ~2 kg H$_2$-pressure for 48 h. The reaction mixture was filtered through a celite bed and washed thoroughly with EtOAc. The solvent was concentrated under reduced pressure to obtain 3-(4-(4-phenylthiazol-2-yl)butyl)benzonitrile (330 mg, 76%) as colorless viscous liquid. $^1$H NMR (300 MHz, CDCl$_3$) δ 7.90-7.87 (m, 2H), 7.50-7.33 (m, 8H), 3.13-3.08 (t, J=7.5 Hz, 2H), 2.75-2.70 (t, J=7.5 Hz, 2H), 1.93-1.85 (m, 2H), 1.83-1.75 (m, 2H). MS (ESI) m/z: Calculated for C$_{20}$H$_{18}$N$_2$S: 318.12. found: 319.2 (M+H)$^+$.

N'-Hydroxy-3-(4-(4-phenylthiazol-2-yl)butyl)benzimidamide

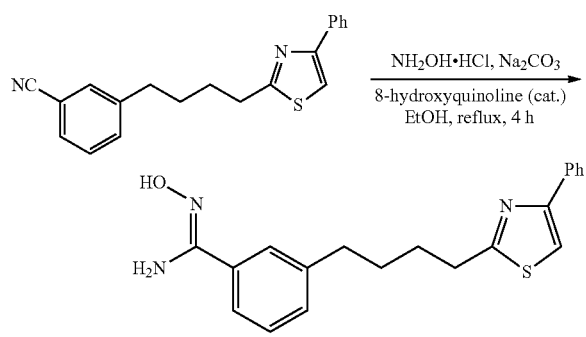

This compound was synthesized from 3-(4-(4-phenylthiazol-2-yl)butyl)benzonitrile as described in example 1 step 4 (290 mg, crude) and it was carried through without further purification. $^1$H NMR (300 MHz, DMSO-d$_6$) δ 9.55 (s, 1H), 7.92-7.90 (m, 2H), 7.51-7.39 (m, 5H), 7.33-7.18 (m, 3H), 5.74 (br s, 2H), 3.07-3.02 (t, J=6.9 Hz, 2H), 2.67-2.62 (t, J=7.1 Hz, 2H), 1.80-1.67 (m, 4H). MS (ESI) m/z: Calculated for C$_{20}$H$_{21}$N$_3$OS: 351.14. found: 352.2 (M+H)$^+$.

3-(3-(4-(4-Phenylthiazol-2-yl)butyl)phenyl)-5-(trifluoromethyl)-1,2,4-oxadiazole

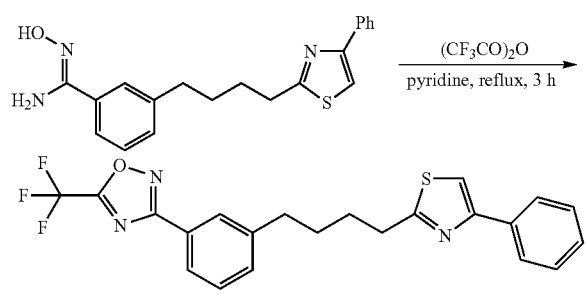

This compound was synthesized from N'-hydroxy-3-(4-(4-phenylthiazol-2-yl)butyl)benzimidamide as described in example 1 step 5 (70 mg, yield 20%) as a yellow liquid. $^1$H NMR (400 MHz, CDCl$_3$) δ 7.96-7.95 (m, 2H), 7.90-7.88 (m, 2H), 7.47-7.40 (m, 4H), 7.36-7.31 (m, 2H), 3.15-3.12 (t, J=7.5 Hz, 2H), 2.81-2.77 (t, J=7.5 Hz, 2H), 1.95-1.90 (m, 2H), 1.88-1.82 (m, 2H). MS (ESI) m/z: Calculated for C$_{22}$H$_{16}$F$_3$N$_3$OS: 429.11. found: 430.2 (M+H)$^+$.

Example 84

2-Diazo-1-phenylethanone

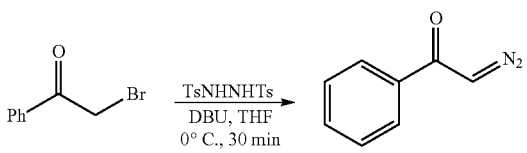

DBU (7.5 mL, 50.2 mmol) was added dropwise to a solution of 2-bromo-1-phenylethanone (2.0 g, 10.05 mmol) and N,N'-bis(p-toluenesulfonyl)hydrazine (6.8 g, 20.1 mmol) in dry THF (30 mL) at 0° C. The reaction mixture was stirred at 0° C. for 30 min, and quenched with aqueous saturated NaHCO$_3$ solution. The organic product was extracted with EtOAc and the combined extracts were washed with brine, dried over anhydrous sodium sulfate, and concentrated under reduced pressure. The crude product was purified by column chromatography (silica 60-120 mesh, eluant 10-15% EtOAc in petroleum ether) to get 2-diazo-1-phenylethanone (1.2 g, yield 82%) as a yellow solid. $^1$H NMR (300 MHz, CDCl$_3$) δ 7.78-7.76 (m, 2H), 7.56-7.53 (m, 1H), 7.48-7.43 (m, 2H), 5.91 (s, 1H).

2-(5-Phenyloxazol-2-yl)acetonitrile

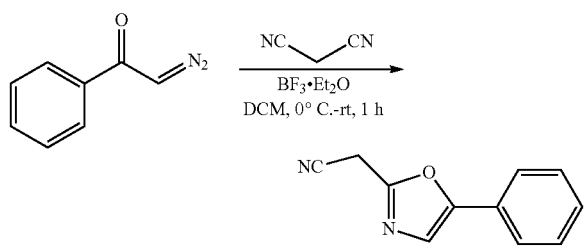

BF$_3$·Et$_2$O (1.1 mL, 8.5 mmol) was added dropwise to a solution of malononitrile (2.26 g, 34.2 mmol) in dry CH$_2$Cl$_2$ (20 mL) at 0° C., followed by addition of 2-diazo-1-phenylethanone (0.5 g, 3.4 mmol) in DCM (5 mL). The reaction mixture was stirred at room temperature for 1 h and then quenched with aqueous 10% NaOH solution. The organic product was extracted with EtOAc and the combined extracts were washed with brine, dried over anhydrous sodium sulfate, and concentrated under reduced pressure. The crude product was purified by column chromatography (silica 60-120 mesh, eluant 5-10% EtOAc in petroleum ether) to get 2-(5-phenyloxazol-2-yl)acetonitrile (200 mg, yield 32%) as a brown solid. $^1$H NMR (300 MHz, CDCl$_3$) δ 7.66-7.63 (m, 2H), 7.47-7.38 (m, 3H), 7.32 (s, 1H), 4.02 (s, 2H). MS (ESI) m/z: Calculated for $C_{11}H_8N_2O$: 184.06. found: 185.2 $(M+H)^+$.

2-Methyl-2-(5-phenyloxazol-2-yl)propanenitrile

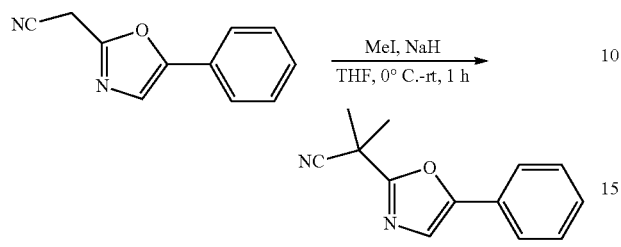

This compound was synthesized from 2-(5-phenyloxazol-2-yl)acetonitrile using iodomethane as described in example 1 step 2 (150 mg, yield 65%). $^1H$ NMR (300 MHz, $CDCl_3$) δ 7.66-7.64 (m, 2H), 7.47-7.36 (m, 3H), 7.29 (s, 1H), 1.88 (s, 6H). MS (ESI) m/z: Calculated for $C_{13}H_{12}N_2O$: 212.10. found: 213.2 $(M+H)^+$.

2-Methyl-2-(5-phenyloxazol-2-yl)propan-1-amine

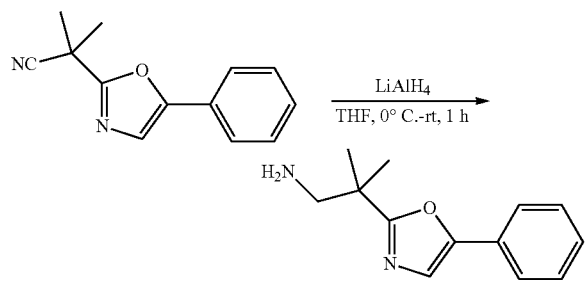

This compound was synthesized from 2-methyl-2-(5-phenyloxazol-2-yl)propanenitrile as described in example 1 step 3 (100 mg, crude) and it was carried through without further purification. MS (ESI) m/z: Calculated for $C_{13}H_{16}N_2O$: 216.13. found: 217.2 $(M+H)^+$.

N-(2-Methyl-2-(5-phenyloxazol-2-yl)propyl)-3-(5-(trifluoromethyl)-1,2,4-oxadiazol-3-yl)benzamide

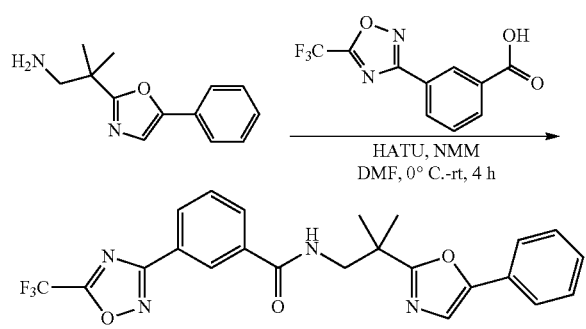

This compound was synthesized from 2-methyl-2-(5-phenyloxazol-2-yl)propan-1-amine and 3-(5-(trifluoromethyl)-1,2,4-oxadiazol-3-yl)benzoic acid as described in example 8 step 6 (18 mg, yield 10%) as a yellow viscous liquid. $^1H$ NMR (400 MHz, MeOD) δ 8.50-8.49 (t, J=1.8 Hz, 1H), 8.28-8.25 (dt, J=7.8 Hz, 1.4 Hz, 1H), 8.00-7.98 (dt, J=7.8 Hz, 1.5 Hz, 1H), 7.68-7.64 (m, 3H), 7.39-7.36 (m, 3H), 7.32-7.27 (m, 1H), 4.58 (s, 2H), 1.54 (s, 6H). MS (ESI) m/z: Calculated for $C_{23}H_{19}F_3N_4O_3$: 456.14. found: 457.2 $(M+H)^+$.

Example 85

Ethyl 2-phenylthiazole-5-carboxylate

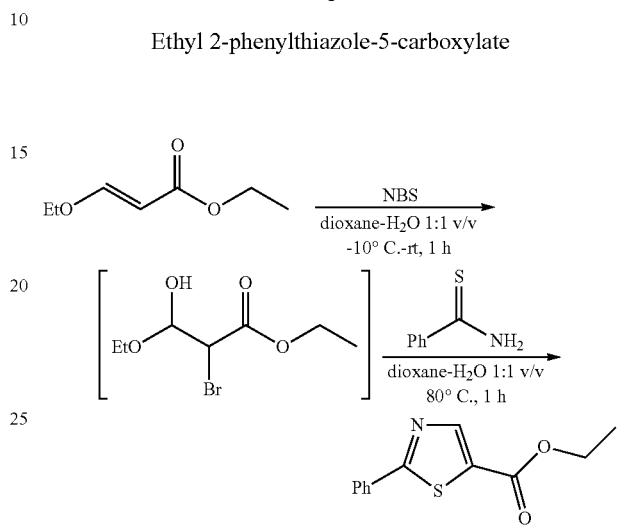

Ethyl-3-ethoxyacryalate (4.0 g, 27.7 mmol) was dissolved in dioxane-$H_2O$ (30 ml, 1:1 v/v) and cooled to −10° C. N-Bromosuccinimide (5.43 g, 30.5 mmol) was added to this solution and the reaction mixture was allowed to warm up to room temperature and further stirred for 1 h. Thiobenzamide (3.8 g, 27.7 mmol) was then added and the reaction mixture was further heated to 80° C. for 1 h. The reaction mixture was then cooled to room temperature and quenched with aqueous ammonia solution. The organic product was extracted with EtOAc and combined extracts were washed with $H_2O$ and brine, dried over anhydrous sodium sulfate, and concentrated under reduced pressure. The crude product was purified by column chromatography (silica gel 60-120 mesh, eluent 5-10% EtOAc in petroleum ether) to afford ethyl 2-phenylthiazole-5-carboxylate (1.1 g, yield 17%) as a yellow solid. $^1H$ NMR (300 MHz, $CDCl_3$) δ 8.43 (s, 1H), 8.01-7.98 (m, 2H), 7.48-7.48 (m, 3H), 4.44-4.37 (q, J=7.2 Hz, 2H), 1.44-1.39 (t, J=7.2 Hz, 3H). MS (ESI) m/z: Calculated for $C_{12}H_{11}NO_2S$: 233.05. found: 234.0 $(M+H)^+$.

(2-Phenylthiazol-5-yl)methanol

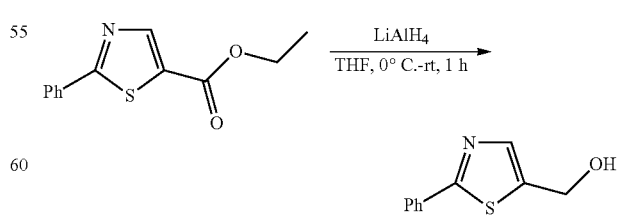

This compound was synthesized from ethyl 2-phenylthiazole-5-carboxylate as described in example 1 step 3 (390 mg, yield 95%) as a yellow solid. $^1H$ NMR (300 MHz, $CDCl_3$) δ 7.95-7.92 (m, 2H), 7.71 (s, 1H), 7.46-7.43 (m, 3H), 4.91 (s, 2H). MS (ESI) m/z: Calculated for C$_{10}$H$_9$NOS: 191.04. found: 192.2 (M+H)$^+$.

5-(Bromomethyl)-2-phenylthiazole

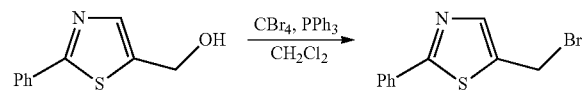

(2-phenylthiazol-5-yl)methanol (390 mg, 2.03 mmol) was dissolved in dry CH$_2$Cl$_2$ (10 mL) and cooled to 0° C. Triphenyl phosphine (800 mg, 3.05 mmol) was then added, followed by carbon tetrabromide (1.35 g, 4.07 mmol). The reaction mixture was allowed to warm up to room temperature and stirred for 1 h. The reaction mixture was then concentrated under reduced pressure and the crude product was purified by column chromatography (silica 60-120 mesh, eluant 5% EtOAc in petroleum ether) to get 5-(bromomethyl)-2-phenylthiazole (250 mg, yield 48%) as light yellow solid. $^1$H NMR (400 MHz, CDCl$_3$) δ 7.95-7.92 (m, 2H), 7.80 (s, 1H), 7.46-7.45 (m, 3H), 4.77 (s, 2H). MS (ESI) m/z: Calculated for C$_{10}$H$_8$BrNS: 254.95. found: 256.0 (M+H)$^+$.

2-(2-Phenylthiazol-5-yl)acetonitrile

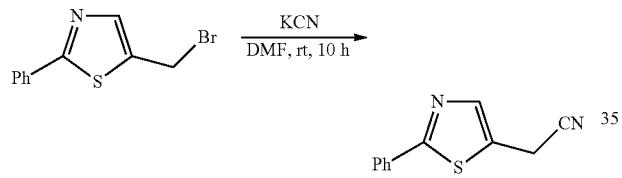

KCN (154 mg, 2.36 mmol) was added to a solution of 5-(bromomethyl)-2-phenylthiazole (400 mg, 1.57 mmol) in dry DMF (10 mL). The resulting reaction mixture was stirred at room temperature for 10 h. The mixture was then quenched with water and the organic product was extracted with EtOAc. The combined extracts were washed with H$_2$O and brine, dried over anhydrous sodium sulfate, and concentrated under reduced pressure. The crude product was purified by column chromatography (silica gel 60-120 mesh, eluent 20% EtOAc in petroleum ether) to afford 2-(2-phenylthiazol-5-yl)acetonitrile (230 mg, yield 73%) as a white solid. $^1$H NMR (300 MHz, CDCl$_3$) δ 7.94-7.90 (m, 2H), 7.76 (s, 1H), 7.47-7.45 (m, 3H), 3.98 (d, J=1.1 Hz, 2H). MS (ESI) m/z: Calculated for C$_{11}$H$_8$N$_2$S: 200.05. found: 201.2 (M+H)$^+$.

2-(2-Phenylthiazol-5-yl)ethanamine

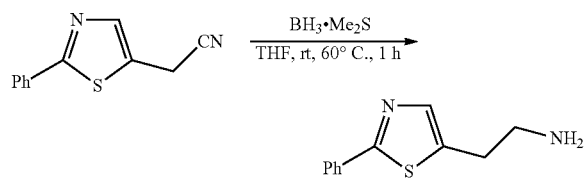

This compound was synthesized from 2-(2-phenylthiazol-5-yl)acetonitrile as described in example 42 step 1 (150 mg, crude) and it was carried through without further purification. MS (ESI) m/z: Calculated for C$_{11}$H$_{12}$N$_2$S: 204.08. found: 205.2 (M+H)$^+$.

N-(2-(2-Phenylthiazol-5-yl)ethyl)-3-(5-(trifluoromethyl)-1,2,4-oxadiazol-3-yl)benzamide

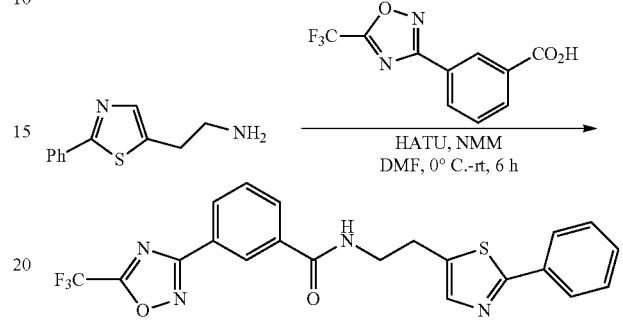

This compound was synthesized from 2-(2-phenylthiazol-5-yl)ethanamine and 3-(5-(trifluoromethyl)-1,2,4-oxadiazol-3-yl)benzoic acid as described in example 8 step 6 (35 mg, yield 27%) as an off white solid. $^1$H NMR (400 MHz, MeOD) δ 8.61 (t, J=1.5 Hz, 1H), 8.32-8.29 (dt, J=7.8 Hz, 1.3 Hz, 1H), 8.09-8.06 (dt, J=7.8 Hz, 1.5 Hz, 1H), 7.90-7.88 (m, 2H), 7.73-7.69 (t, J=7.9 Hz, 1H), 7.66 (s, 1H), 7.47-7.45 (m, 3H), 3.75-3.71 (t, J=6.8 Hz, 2H), 3.28-3.25 (t, J=6.8 Hz, 2H). MS (ESI) m/z: Calculated for C$_{21}$H$_{15}$F$_3$N$_4$O$_2$S: 444.09. found: 445.0 (M+H)$^+$.

Example 86

2-Methyl-2-(2-phenylthiazol-5-yl)propanenitrile

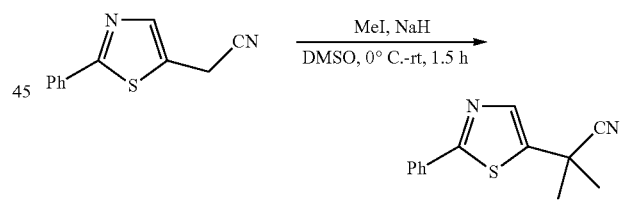

This compound was synthesized from 2-(2-phenylthiazol-5-yl)acetonitrile using iodomethane as described in example 1 step 2 (210 mg, yield 80%) as a yellow liquid. $^1$H NMR (400 MHz, CDCl$_3$) δ 7.93-7.90 (m, 2H), 7.79 (s, 1H), 7.47-7.45 (m, 3H), 1.86 (s, 6H). MS (ESI) m/z: Calculated for C$_{13}$H$_{12}$N$_2$S: 228.07. found: 229.2 (M+H)$^+$.

2-Methyl-2-(2-phenylthiazol-5-yl)propan-1-amine

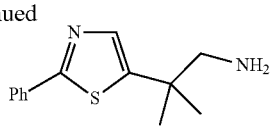

This compound was synthesized from 2-methyl-2-(2-phenylthiazol-5-yl)propanenitrile as described in example 1 step 3 (100 mg, crude) and it was carried through without further purification. MS (ESI) m/z: Calculated for $C_{13}H_{16}N_2S$: 232.10. found: 233.2 (M+H)⁺.

N-(2-Methyl-2-(2-phenylthiazol-5-yl)propyl)-3-(5-(trifluoromethyl)-1,2,4-oxadiazol-3-yl)benzamide

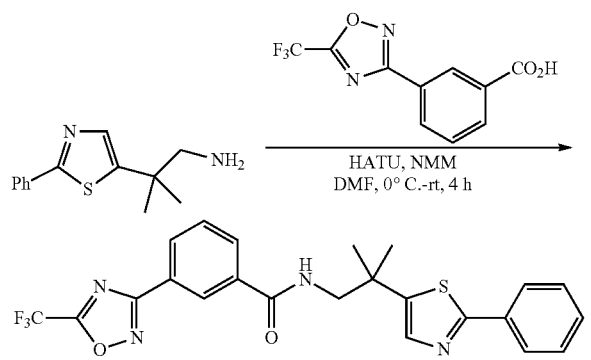

This compound was synthesized from 2-methyl-2-(2-phenylthiazol-5-yl)propan-1-amine and 3-(5-(trifluoromethyl)-1,2,4-oxadiazol-3-yl)benzoic acid as described in example 8 step 6 (70 mg, yield 51%). ¹H NMR (400 MHz, MeOD) δ 8.55 (t, J=1.6 Hz, 1H), 8.29-8.26 (dt, J=7.9 Hz, 1.3 Hz, 1H), 8.03-8.01 (dt, J=7.8 Hz, 1.5 Hz, 1H), 7.91-7.88 (m, 2H), 7.70-7.66 (m, 2H), 7.47-7.45 (m, 3H), 3.64 (s, 2H), 1.53 (s, 6H). MS (ESI) m/z: Calculated for $C_{23}H_{19}F_3N_4O_2S$: 472.12. found: 473.2 (M+H)⁺.

Example 87

N-((4-(2-(4-Chlorophenyl)thiazol-4-yl)-1-methylpiperidin-4-yl)methyl)-3-(5-(trifluoromethyl)-1,2,4-oxadiazol-3-yl)benzamide

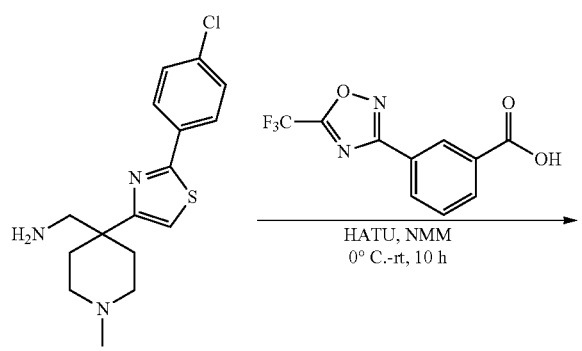

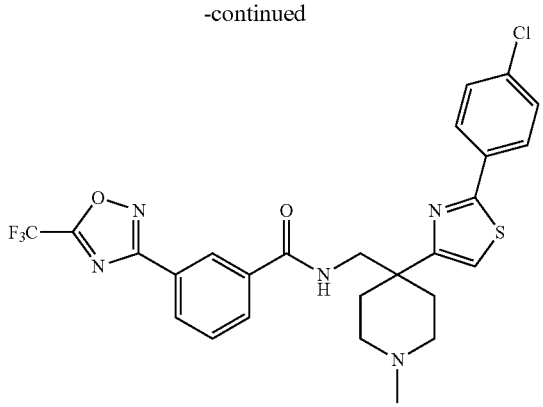

This compound was synthesized from (4-(2-(4-chlorophenyl)thiazol-4-yl)-1-methylpiperidin-4-yl)methanamine and 3-(5-(trifluoromethyl)-1,2,4-oxadiazol-3-yl)benzoic acid as described in example 8 step 6 (50 mg, yield 23%). ¹H NMR (400 MHz, DMSO-d₆) δ 8.54-8.51 (m, 1H), 8.39 (m, 1H), 8.18-8.16 (d, J=7.6 Hz, 1H), 8.04-8.02 (d, J=7.6 Hz, 1H), 7.91-7.89 (d, J=8.2 Hz, 2H), 7.69-7.65 (t, J=7.8 Hz, 1H), 7.52-7.49 (m, 3H), 3.49-3.48 (m, 2H), 2.66-2.63 (m, 2H), 2.31-2.28 (m, 2H), 2.12-2.04 (m, 5H), 1.90-1.84 (m, 2H). MS (ESI) m/z: Calculated for $C_{26}H_{23}ClF_3N_6O_2S$: 561.12. found: 562.0 (M+H)⁺.

Example 88

1-(5-Bromothiophen-2-yl)-2,2,2-trifluoroethanol

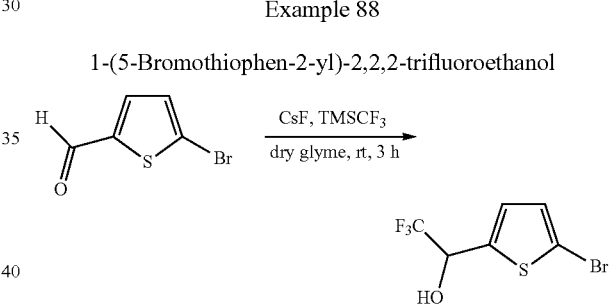

CsF (400 mg, 2.6 mmol) was added to a solution of 5-bromothiophene-2-carbaldehyde (5.0 g, 26.17 mmol) in dry 1,2-dimethoxyethane (20 mL), followed by trifluoromethyl trimethylsilane (4.6 mL, 31.4 mmol) dropwise at 0° C. The reaction mixture was stirred at room temperature for 3 h, quenched with 1.5N HCl, and stirred for an additional 30 min. The crude product was extracted with $CH_2Cl_2$. The combined extracts were dried over anhydrous $Na_2SO_4$, and concentrated under reduced pressure. The crude product was purified by column chromatography (silica 60-120 mesh, eluant 5-10% EtOAc in petroleum ether) to get 1-(5-bromothiophen-2-yl)-2,2,2-trifluoroethanol (4 g, yield 59%). ¹H NMR (400 MHz, CDCl₃) δ 7.01 (m, 1H), 6.95 (m, 1H), 5.23-5.18 (q, J=5.9 Hz, 1H), 3.07 (br s, 1H). MS (ESI) m/z: Calculated for $C_6H_4BrF_3OS$: 261.91. found: 260.7 (M−1)⁻.

1-(5-Bromothiophen-2-yl)-2,2,2-trifluoroethanone

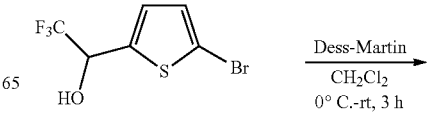

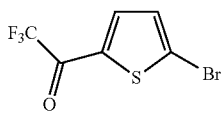

This compound was synthesized from 1-(5-bromothiophen-2-yl)-2,2,2-trifluoroethanol as described in example 47 step 2 (0.8 g, yield 42%). $^1$H NMR (400 MHz, CDCl$_3$) δ 7.72-7.71 (m, 1H), 7.24-7.23 (d, J=4.3 Hz, 1H).

3-(5-(2,2,2-Trifluoroacetyl)thiophen-2-yl)benzoic acid

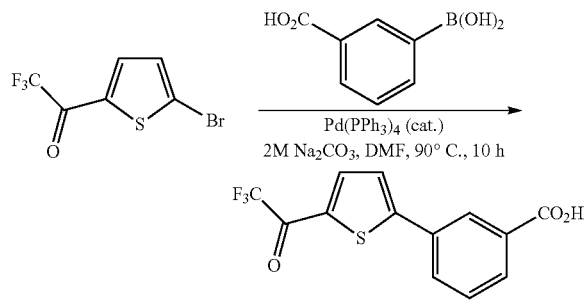

1-(5-Bromothiophen-2-yl)-2,2,2-trifluoroethanone (0.8 g, 3.09 mmol) and 3-carboxyphenylboronic acid (0.5 g, 3.01 mmol) were dissolved in DMF (10 mL) and the solution was purged with argon for 10 min. 2M aqueous solution of Na$_2$CO$_3$ (0.65 g, 6.17 mmol) and catalytic Pd(PPh$_3$)$_4$ (178 mg, 0.15 mmol) were added to the reaction mixture and heated to 90° C. for 10 h. The reaction mixture was cooled to room temperature, diluted with water and acidified to pH ~6 with 1.5 N HCl. The crude product was extracted with EtOAc. The combined extracts were dried over anhydrous Na$_2$SO$_4$ and concentrated under reduced pressure. The crude product was triturated with diethyl ether to get 3-(5-(2,2,2-trifluoroacetyl)thiophen-2-yl)benzoic acid (700 mg, yield 79%). $^1$H NMR (400 MHz, DMSO-d$_6$) δ 13.35 (br s, 1H), 8.31-8.30 (m, 1H), 8.16-8.11 (m, 2H), 8.04-8.02 (d, J=7.6 Hz, 1H), 7.93-7.92 (d, J=4.3 Hz, 1H), 7.67-7.63 (t, J=7.8 Hz, 1H). MS (ESI) m/z: Calculated for C$_{13}$H$_7$F$_3$O$_3$S: 300.01. found: 299.0 (M−1)$^−$.

N-(2-(2-(4-Fluorophenyl)oxazol-4-yl)-2-methylpropyl)-3-(5-(2,2,2-trifluoroacetyl)thiophen-2-yl)benzamide This compound was synthesized from 2-(2-(4-fluorophenyl)oxazol-4-yl)-2-methylpropan-1-amine and 3-(5-(2,2,2-trifluoroacetyl)thiophen-2-yl)benzoic acid as described in example 8 step 6 (8 mg, yield 5%). $^1$H NMR (400 MHz, DMSO-d$_6$) δ 8.53-8.50 (t, J=6.2 Hz, 1H), 8.21 (m, 1H), 8.17-8.16 (m, 1H), 8.03-7.98 (m, 4H), 7.93-7.91 (m, 1H), 7.88-7.87 (d, J=4.3 Hz, 1H), 7.63-7.59 (t, J=7.8 Hz, 1H), 7.34-7.30 (t, J=8.8 Hz, 2H), 3.52-3.50 (d, J=6.4 Hz, 2H), 1.29 (s, 6H).

Example 89

5-(5-(2,2,2-Trifluoroacetyl)thiophen-2-yl)nicotinic acid

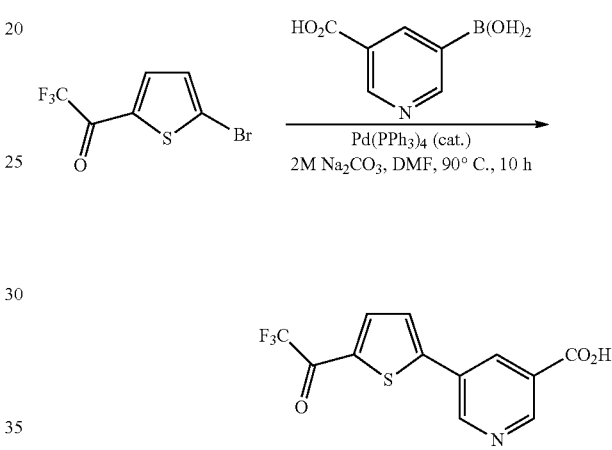

This compound was synthesized from 1-(5-bromothiophen-2-yl)-2,2,2-trifluoroethanone and 5-borononicotinic acid as described in example 88 step 3 (470 mg, yield 82%). $^1$H NMR (300 MHz, DMSO-d$_6$) δ 13.74 (br s, 1H), 9.30-9.29 (s, 1H), 9.11-9.10 (m, 1H), 8.59-8.58 (t, J=2.0 Hz, 1H), 8.20-8.19 (m, 1H), 8.07-8.05 (m, 1H).

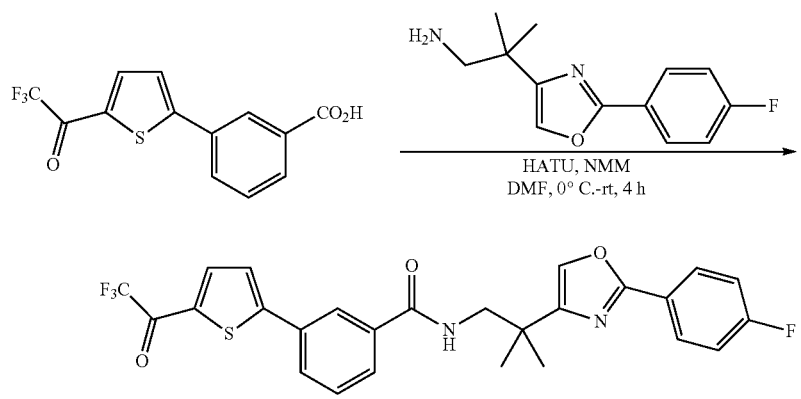

N-(2-(2-(4-Fluorophenyl)oxazol-4-yl)-2-methylpropyl)-5-(5-(2,2,2-trifluoroacetyl)thiophen-2-yl)nicotinamide

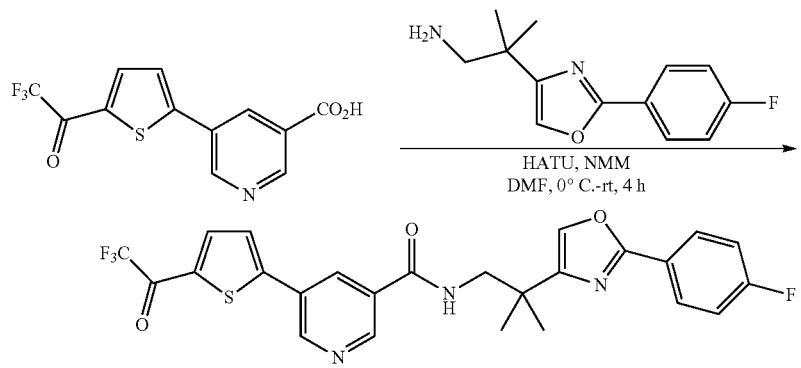

This compound was synthesized from 2-(2-(4-fluorophenyl)oxazol-4-yl)-2-methylpropan-1-amine and 5-(5-(2,2,2-trifluoroacetyl)thiophen-2-yl)nicotinic acid as described in example 8 step 6 (45 mg, yield 26%). $^1$H NMR (400 MHz, DMSO-$d_6$) δ 9.21 (d, J=2.1 Hz, 1H), 9.01 (s, 1H), 8.66-8.60 (m, 1H), 8.52-8.51 (t, J=2.0 Hz, 1H), 8.21-8.20 (m, 1H), 8.02-7.98 (m, 4H), 7.36-7.30 (m, 2H), 3.53-3.52 (d, J=6.1 Hz, 2H), 1.30 (s, 6H).

Example 90

N-((4-(2-(4-Chlorophenyl)thiazol-4-yl)-1-methylpiperidin-4-yl)methyl)-3-(5-(2,2,2-trifluoroacetyl)thiophen-2-yl)benzamide

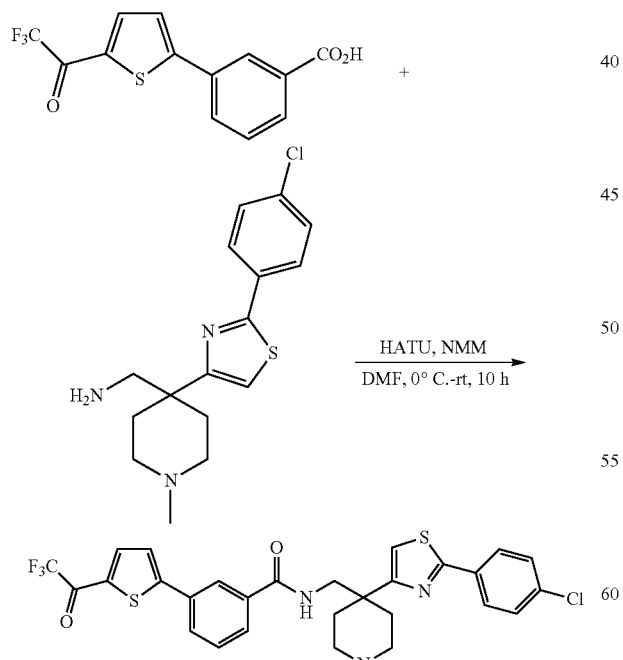

This compound was synthesized from (4-(2-(4-chlorophenyl)thiazol-4-yl)-1-methylpiperidin-4-yl)methanamine and 3-(5-(2,2,2-trifluoroacetyl)thiophen-2-yl)benzoic acid as described in example 8 step 6 (8.5 mg, yield 4%). $^1$H NMR (400 MHz, DMSO-$d_6$) δ 8.54 (m, 1H), 8.14-8.13 (m, 2H), 8.00-7.86 (m, 4H), 7.82-7.77 (m, 1H), 7.70 (m, 1H), 7.60-7.56 (m, 1H), 7.48-7.46 (m, 2H), 3.50 (m, 2H), 3.39-3.17 (m, 4H), 2.57 (m, 3H), 2.43 (m, 2H), 2.08 (m, 2H).

Example 91

5-Cyano-2-fluorobenzoic acid

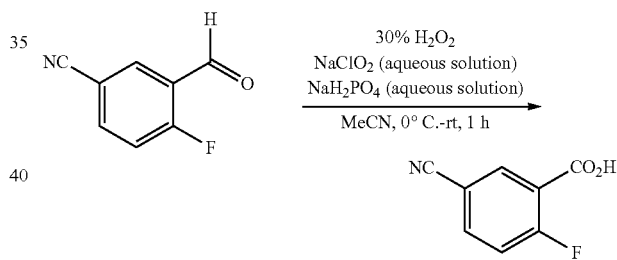

NaH$_2$PO$_4$ (87 mg, 0.724 mmol) in water (3.5 mL) was added to a solution of 5-cyano-2-fluorobenzaldehyde (500 mg, 3.35 mmol) in acetonitrile (7 mL), followed by 30% H$_2$O$_2$ (0.31 mL). Sodium chlorite (434 mg, 4.8 mmol) in water (3.5 mL) was added dropwise to this reaction mixture at 0° C. The mixture was stirred at room temperature for 1 h, quenched with aqueous sodium sulfite solution at 0° C. and then acidified with 1.5N HCl solution. The aqueous solution was extracted with EtOAc and the combined extracts were dried over anhydrous sodium sulfate, and concentrated under reduced pressure to afford 5-cyano-2-fluorobenzoic acid (500 mg, yield 90%). $^1$H NMR (300 MHz, DMSO-$d_6$) δ 13.79 (br s, 1H), 8.30-8.27 (dd, J=6.6 Hz, 2.2 Hz, 1H), 8.17-8.12 (ddd, J=8.6 Hz, 4.4 Hz, 2.3 Hz, 1H), 7.60-7.53 (dd, J=10.5 Hz, 8.8 Hz, 1H). MS (ESI) m/z: Calculated for C$_8$H$_4$FNO$_2$: 165.02. found: 163.6 (M−H)$^-$.

2-Fluoro-5-(N'-hydroxycarbamimidoyl)benzoic acid

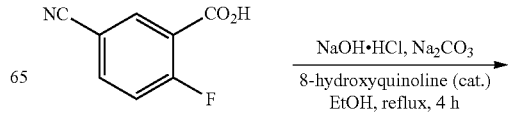

207

-continued

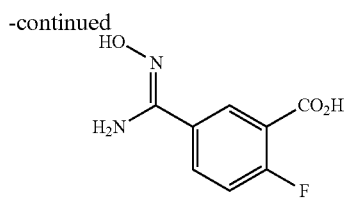

This compound was synthesized from 5-cyano-2-fluorobenzoic acid as described in example 1 step 4 (400 mg, crude) and it was carried through without further purification. ¹H NMR (400 MHz, DMSO-d₆) δ 13.72 (br s, 1H), 11.43 (br s, 1H), 10.39 (br s, 2H), 8.24-8.22 (m, 1H), 8.04-8.01 (m, 1H), 7.61-7.56 (t, J=9.6 Hz, 1H). MS (ESI) m/z: Calculated for C₈H₇FN₂O₃: 198.04. found: 198.8 (M+H)⁺.

2-Fluoro-5-(5-(trifluoromethyl)-1,2,4-oxadiazol-3-yl)benzoic acid

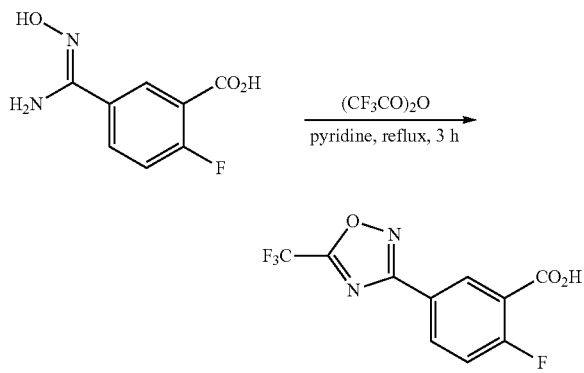

This compound was synthesized from 2-fluoro-5-(N' hydroxycarbamimidoyl)benzoic acid as described in example 1 step 5 (130 mg, yield 23%). ¹H NMR (300 MHz, DMSO-d₆) δ 13.72 (br s, 1H), 8.51-8.48 (dd, J=6.9 Hz, 2.3 Hz, 1H), 8.33-8.29 (m, 1H), 7.62-7.55 (dd, J=10.2 Hz, 8.9 Hz, 1H). MS (ESI) m/z: Calculated for C₁₀H₄F₄N₂O₃: 276.02. found: 274.8 (M-H)⁻.

2-Fluoro-N-(2-(2-(4-fluorophenyl)oxazol-4-yl)-2-methylpropyl)-5-(5-(trifluoromethyl)-1,2,4-oxadiazol-3-yl)benzamide

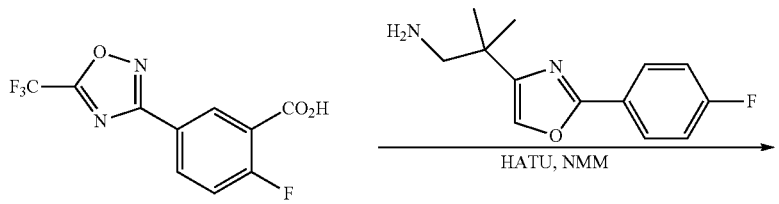

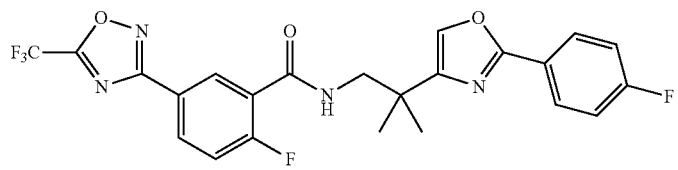

208

This compound was synthesized from 2-(2-(4-fluorophenyl)oxazol-4-yl)-2-methylpropan-1-amine and 2-fluoro-5-(5-(trifluoromethyl)-1,2,4-oxadiazol-3-yl)benzoic acid as described in example 8 step 6 (75 mg, yield 32%) as a yellow viscous liquid. ¹H NMR (400 MHz, MeOD) δ 8.46-8.43 (dd, J=6.8 Hz, 2.3 Hz, 1H), 8.29-8.25 (ddd, J=8.7 Hz, 4.8 Hz, 2.4 Hz, 1H), 8.09-8.05 (dd, J=9.0 Hz, 5.3 Hz, 2H), 7.77 (s, 1H), 7.47-7.42 (dd, J=10.3 Hz, 8.8 Hz, 1H), 7.25-7.20 (t, J=8.9 Hz, 2H), 3.67 (s, 2H), 1.41 (s, 6H). MS (ESI) m/z: Calculated for C₂₃H₁₇F₆N₄O₃: 492.12. found: 493.2 (M+H)⁺.

Example 92

(E)-ethyl 2-styryloxazole-4-carboxylate

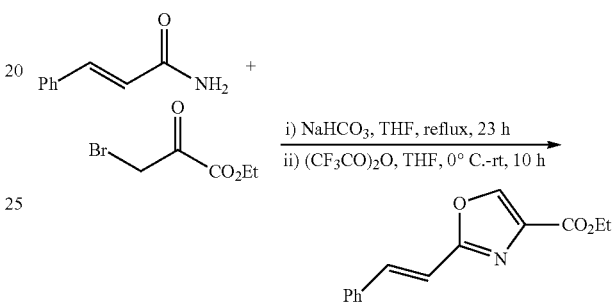

Ethyl bromopyruvate (10 mL, 81.55 mmol) was added dropwise to a solution of 3-phenylacrylamide (5 g, 33.97 mmol) and NaHCO₃ (11.42 g, 135.89 mmol) in anhydrous THF (120 mL) at 0° C. The reaction mixture was heated to reflux for 23 h. The mixture was then filtered through Celite and the solvent was removed under reduced pressure. The crude product was dissolved in anhydrous THF (80 mL) and trifluoroacetic anhydride (37 mL) was added dropwise at 0° C. The reaction mixture was stirred at room temperature for 10 h, and quenched with saturated NaHCO₃ solution at 0° C. The organic product was extracted with EtOAc, and the combined extracts were washed with brine, dried over anhydrous sodium sulfate and concentrated under reduced pressure. The crude product was purified by column chromatography (silica gel 60-120 mesh, eluent 10% EtOAc in petroleum ether) to afford (E)-ethyl 2-styryloxazole-4-carboxylate (4.22 g, yield 51%) as an off white solid. ¹H NMR (300 MHz, CDCl₃) δ 8.21 (s, 1H), 7.66-7.61 (d, J=16.4 Hz, 1H), 7.56-7.52 (m, 2H), 7.44-7.36 (m, 3H), 7.00-6.94 (d, J=16.4 Hz, 1H), 4.46-4.39

(q, J=7.0 Hz, 2H), 1.44-1.39 (t, J=7.0 Hz, 3H). MS (ESI) m/z: Calculated for $C_{14}H_{13}NO_3$: 243.09. found: 243.8 (M+H)$^+$.

Ethyl 2-formyloxazole-4-carboxylate

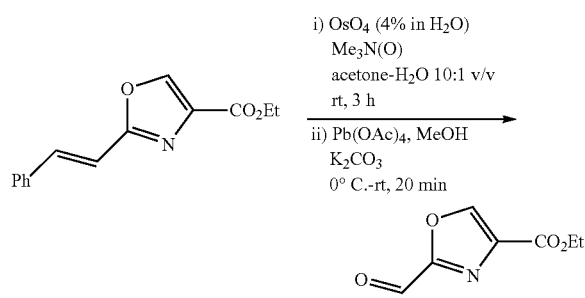

OsO$_4$ [10 mL, 0.41 mmol, 4% in H$_2$O] was added dropwise to a solution of (E)-ethyl 2-styryloxazole-4-carboxylate (4 g, 16.44 mmol) and trimethylamine N-oxide (1.84 g, 24.5 mmol) in acetone-H$_2$O (88 mL; 10:1 v/v). The reaction mixture was stirred at room temperature for 3 h and then concentrated under reduced pressure. The crude product was purified by column chromatography (silica gel 60-120 mesh, eluent 50% EtOAc in petroleum ether) to afford an intermediate (1.5 g, 5.41 mmol) which was dissolve in anhydrous benzene (30 mL). K$_2$CO$_3$ (0.85 g, 6.17 mmol) was added to the reaction mixture followed by Pb(OAc)$_4$ (2.73 g, 6.17 mmol). The reaction mixture was stirred at room temperature for 20 min and then quenched with saturated NaHCO$_3$ solution. The organic product was extracted with EtOAc. Solvent was removed under reduced pressure and the crude product was purified by column chromatography (silica gel 60-120 mesh, eluent 30% EtOAc in petroleum ether) to afford ethyl 2-formyloxazole-4-carboxylate (0.65 g, overall yield 24%) as an off white solid. $^1$H NMR (400 MHz, CDCl$_3$) δ 9.84 (s, 1H), 8.43 (s, 1H), 4.49-4.44 (q, J=7.0 Hz, 2H), 1.45-1.41 (t, J=7.0 Hz, 3H). MS (ESI) m/z: Calculated for $C_7H_7NO_4$: 169.04. found: 169.8 (M+H)$^+$.

Ethyl 2-cyanooxazole-4-carboxylate

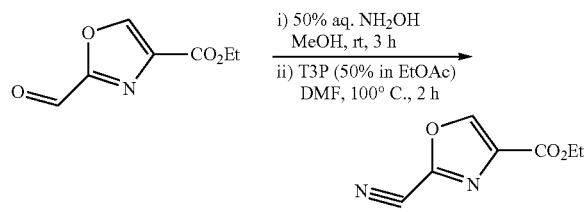

A solution of ethyl 2-formyloxazole-4-carboxylate (650 mg, 3.84 mmol) in methanol (25 mL) was cooled to 0° C. and 50% aqueous hydroxylamine (0.22 mL, 7.68 mmol) was added dropwise. The reaction mixture was stirred at room temperature for 3 h. Solvent was removed under reduced pressure and the crude product (0.52 g) obtained was dissolved in DMF (20 mL). T$_3$P (3.4 mL, 5.65 mmol; 50% in EtOAc) was added to the reaction mixture and heated to 100° C. for 2 h. The reaction mixture was quenched with saturated NaHCO$_3$ solution and the organic product was extracted with EtOAc. Solvent was removed under reduced pressure and the crude product was purified by column chromatography (silica gel 60-120 mesh, eluent 10% EtOAc in petroleum ether) to afford ethyl 2-cyanooxazole-4-carboxylate (0.34 g, yield 53%) as an off white solid. $^1$H NMR (300 MHz, CDCl$_3$) δ 8.39 (s, 1H), 4.48-4.41 (q, J=7.0 Hz, 2H), 1.44-1.39 (t, J=7.0 Hz, 3H).

Ethyl 2-(N'-hydroxycarbamimidoyl)oxazole-4-carboxylate

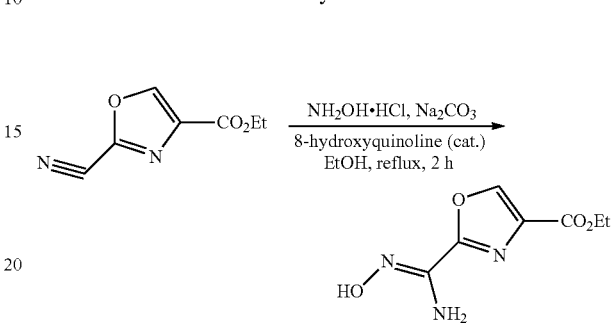

This compound was synthesized from ethyl 2-cyanooxazole-4-carboxylate as described in example 1 step 4 (500 mg, crude) and it was carried through without further purification. MS (ESI) m/z: Calculated for $C_7H_9N_3O_4$: 199.06. found: 199.8 (M+H)$^+$.

Ethyl 2-(5-(trifluoromethyl)-1,2,4-oxadiazol-3-yl)oxazole-4-carboxylate

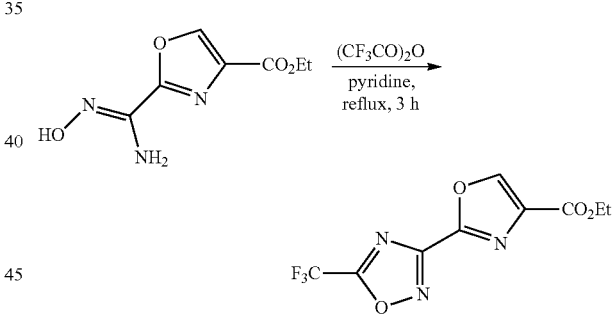

This compound was synthesized from ethyl 2-(N'-hydroxycarbamimidoyl)oxazole-4-carboxylate as described in example 1 step 5 (50 mg, yield 7%). $^1$H NMR (400 MHz, CDCl$_3$) δ 8.49 (s, 1H), 4.49-4.44 (q, J=7.0 Hz, 2H), 1.45-1.41 (t, J=7.0 Hz, 3H). MS (ESI) m/z: Calculated for $C_9H_6F_3N_3O_4$: 277.03. found: 277.9 (M+H)$^+$.

2-(5-(Trifluoromethyl)-1,2,4-oxadiazol-3-yl)oxazole-4-carboxylic acid

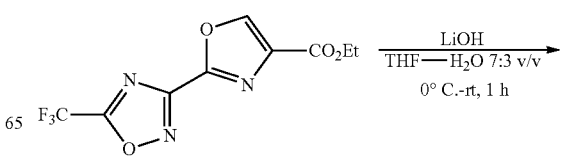

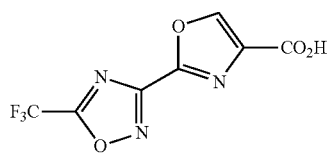

This compound was synthesized from ethyl 2-(5-(trifluoromethyl)-1,2,4-oxadiazol-3-yl)oxazole-4-carboxylate as described in example 43 step 2 (25 mg, 56%) as an off white solid. $^1$H NMR (400 MHz, DMSO-d$_6$) δ 13.65 (br s, 1H), 9.18 (s, 1H). MS (ESI) m/z: Calculated for $C_7H_2F_3N_3O_4$: 249.00. found: 248.0 (M−H)$^-$.

N-(2-(2-(4-Fluorophenyl)oxazol-4-yl)-2-methylpropyl)-2-(5-(trifluoromethyl)-1,2,4-oxadiazol-3-yl)oxazole-4-carboxamide

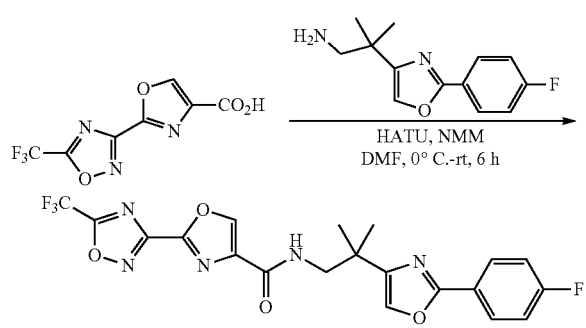

This compound was synthesized from 2-(2-(4-fluorophenyl)oxazol-4-yl)-2-methylpropan-1-amine and 2-(5-(trifluoromethyl)-1,2,4-oxadiazol-3-yl)oxazole-4-carboxylic acid as described in example 8 step 6 (6 mg, yield 13%). $^1$H NMR (400 MHz, CDCl$_3$) δ 8.88-8.86 (m, 1H), 8.49 (s, 1H), 8.25-8.21 (m, 2H), 7.46 (s, 1H), 7.23-7.19 (t, J=8.8 Hz, 2H), 3.62-3.60 (d, J=6.0 Hz, 2H), 1.39 (s, 6H). MS (ESI) m/z: Calculated for $C_{20}H_{15}F_4N_6O_4$: 465.11. found: 466.1 (M+H)$^+$.

Example 93

Methyl 1-methyl-2-phenyl-1H-imidazole-5-carboxylate

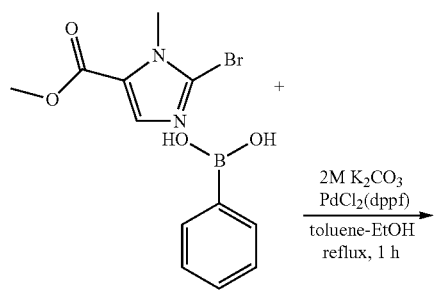

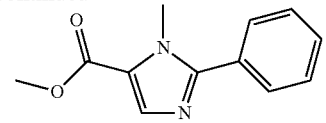

Methyl-2-bromo-1-methyl-1H-imidazole-5-carboxylate (1 g, 4.56 mmol) and phenylboronic acid (0.67 g, 5.48 mmol) were dissolved in toluene-EtOH (80 mL, 5:3 v/v) and the solution was purged with argon for 10 min. K$_2$CO$_3$ (10 mL, 2M solution) and catalytic PdCl$_2$(dppf) (82 mg, 0.12 mmol) were added and the reaction mixture was heated to 100° C. for 1 h. The reaction mixture was then cooled to room temperature and concentrated under reduced pressure. The residue was diluted with water and washed with EtOAc. The aqueous layer was acidified to pH ~6 using 1.5N HCl and the crude product was extracted with EtOAc. The combined extracts were dried over anhydrous Na$_2$SO$_4$, and concentrated under reduced pressure. The crude product was purified by column chromatography (silica 60-120 mesh, eluent 35-45% EtOAc in petroleum ether) to get methyl 1-methyl-2-phenyl-1H-imidazole-5-carboxylate (800 mg, yield 81%) as a pale yellow solid. $^1$H NMR (400 MHz, CDCl$_3$) δ 7.86 (s, 1H), 7.63-7.61 (m, 2H), 7.51-7.48 (m, 3H), 3.96 (s, 3H), 3.89 (s, 3H). MS (ESI) m/z: Calculated for $C_{12}H_{12}N_2O_2$: 216.09. found: 2168.8 (M+H)$^+$.

(1-Methyl-2-phenyl-1H-imidazol-5-yl)methanol

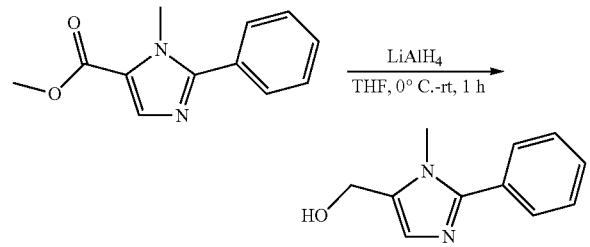

This compound was synthesized from 1-methyl-2-phenyl-1H-imidazole-5-carboxylate as described in example 1 step 3 (600 mg, yield 86%) as a white solid. $^1$H NMR (300 MHz, MeOD) δ 7.60-7.57 (m, 2H), 7.50-7.48 (m, 3H), 7.00 (s, 1H), 4.64 (s, 2H), 3.72 (s, 3H). MS (ESI) m/z: Calculated for $C_{11}H_{12}N_2O$: 188.09. found: 188.8 (M+H)$^+$.

5-(Chloromethyl)-1-methyl-2-phenyl-1H-imidazole hydrochloride

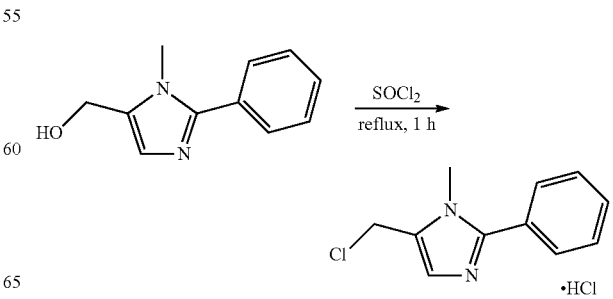

A solution of (1-methyl-2-phenyl-1H-imidazol-5-yl)methanol (0.600 g, 3.19 mmol) in dry SOCl$_2$ (11 mL) was refluxed at 80° C. for 1 h. The reaction mixture was concentrated under reduced pressure and the residue was co-evaporated with CH$_2$Cl$_2$, and then triturated with diethyl ether, filtered and dried under suction to afford 5-(chloromethyl)-1-methyl-2-phenyl-1H-imidazole hydrochloride (0.67 g, yield 86%) as a white solid. $^1$H NMR (300 MHz, MeOD) δ 7.79-7.79 (m, 6H), 4.98 (s, 2H), 3.93 (s, 3H).

2-(1-Methyl-2-phenyl-1H-imidazol-5-yl)acetonitrile

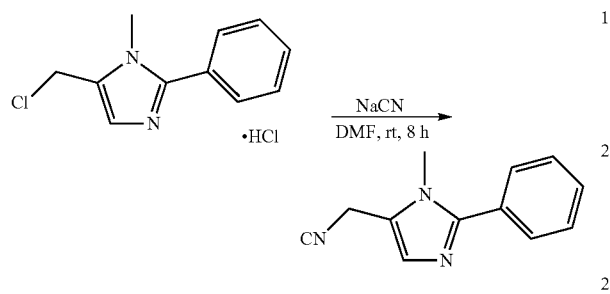

This compound was synthesized from 5-(chloromethyl)-1-methyl-2-phenyl-1H-imidazole hydrochloride as described in example 77 step 1 (400 mg, yield 90%). $^1$H NMR (300 MHz, CDCl$_3$) δ 7.61-7.58 (m, 2H), 7.49-7.44 (m, 3H), 7.12 (s, 1H), 3.79 (s, 2H), 3.71 (s, 3H). MS (ESI) m/z: Calculated for C$_{12}$H$_{11}$N$_3$: 197.10. found: 197.9 (M+H)$^+$.

2-(1-Methyl-2-phenyl-1H-imidazol-5-yl)propanenitrile

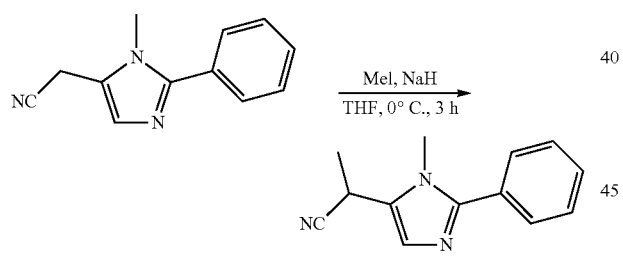

This compound was synthesized from 2-(1-methyl-2-phenyl-1H-imidazol-5-yl)acetonitrile as described in example 1 step 2 (170 mg, yield 53%) as colorless oil. $^1$H NMR (400 MHz, CDCl$_3$) δ 7.61-7.58 (m, 2H), 7.52-7.46 (m, 3H), 7.10 (m, 1H), 4.00-3.95 (q, J=7.2 Hz, 1H), 3.74 (s, 3H), 1.83-1.81 (d, J=7.2 Hz, 3H). MS (ESI) m/z: Calculated for C$_{13}$H$_{13}$N$_3$: 211.11. found: 211.9 (M+H)$^+$.

2-(1-Methyl-2-phenyl-1H-imidazol-5-yl)propan-1-amine

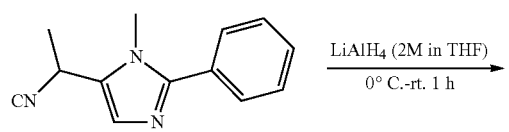

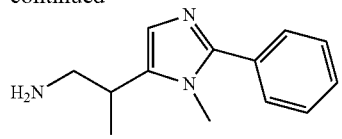

This compound was synthesized from 2-(1-methyl-2-phenyl-1H-imidazol-5-yl)propanenitrile as described in example 1 step 3 (155 mg, crude) and it was carried through without further purification. MS (ESI) m/z: Calculated for C$_{13}$H$_{17}$N$_3$: 215.14. found: 215.9 (M+H)$^+$.

N-(2-(1-Methyl-2-phenyl-1H-imidazol-5-yl)propyl)-5-(5-(trifluoromethyl)-1,2,4-oxadiazol-3-yl)nicotinamide

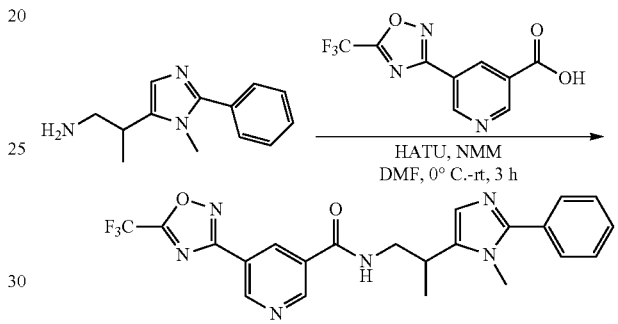

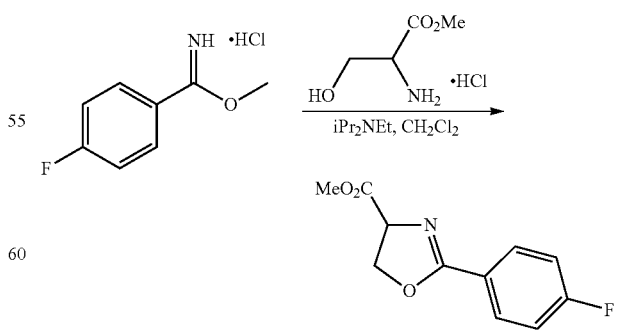

This compound was synthesized from 2-(1-methyl-2-phenyl-1H-imidazol-5-yl)propan-1-amine and 5-(5-(trifluoromethyl)-1,2,4-oxadiazol-3-yl)nicotinic acid as described in example 8 step 6 (35 mg, yield 28%). $^1$H NMR (400 MHz, DMSO-d$_6$) δ 9.36 (d, J=2.1 Hz, 1H), 9.28-9.26 (m, 2H), 8.84-8.83 (t, J=2.0 Hz, 1H), 7.65-7.63 (m, 2H), 7.50-7.42 (m, 4H), 6.92 (s, 1H), 3.70 (s, 3H), 3.66-3.61 (m, 1H), 3.32-3.28 (m, 1H), 3.22-3.17 (m, 1H), 1.33-1.32 (d, J=6.7 Hz, 3H). MS (ESI) m/z: Calculated for C$_{22}$H$_{19}$F$_3$N$_6$O$_2$: 456.15. found: 457.2 (M+H)$^+$.

Example 94

Methyl 2-(4-fluorophenyl)-4,5-dihydrooxazole-4-carboxylate

N,N-Diisopropylethylamine (11 mL, 63.3 mmol) was added dropwise to a solution of methyl 4-fluorobenzimidate hydrochloride (10 g, 52.74 mmol) and DL-serine methyl ester HCl salt (9.9 g, 63.63 mmol) in dry $CH_2Cl_2$ (200 mL) at 0° C. The reaction mixture was stirred at room temperature for 24 h and then concentrated under reduced pressure. The reaction mixture was diluted with $CH_2Cl_2$ and the organic layer was washed with $H_2O$ and brine, dried over anhydrous $Na_2SO_4$, and concentrated under reduced pressure to get methyl 2-(4-fluorophenyl)-4,5-dihydrooxazole-4-carboxylate (9.5 g, yield 81%) as an orange liquid. $^1$H NMR (300 MHz, $CDCl_3$) δ 8.02-7.97 (m, 2H), 7.13-7.07 (t, J=8.7 Hz, 2H), 4.98-4.92 (m, 1H), 4.73-4.57 (m, 2H), 3.83 (s, 3H). MS (ESI) m/z: Calculated for $C_{11}H_{10}FNO_3$: 223.06. found: 223.8 (M+H)$^+$.

Methyl 2-(4-fluorophenyl)oxazole-4-carboxylate

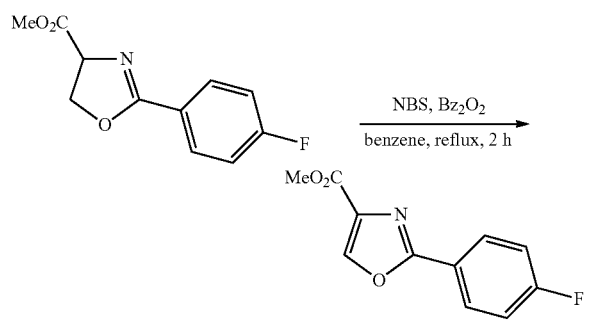

Benzoyl peroxide (0.49 g, 2.0 mmol) was added to a solution of methyl 2-(4-fluorophenyl)-4,5-dihydrooxazole-4-carboxylate (9.0 g, 40.3 mmol) in dry benzene (180 mL) and the mixture was refluxed for 15 min. N-bromosuccinimide (8.6 g, 48.3 mmol) was then added and the reaction mixture was refluxed for 2 h. The reaction mixture was quenched with ice-cold water and the crude product was extracted with EtOAc. The combined extracts were washed with 10% aqueous $NaHCO_3$ solution, $H_2O$ and brine, dried over anhydrous $Na_2SO_4$, and concentrated under reduced pressure. The crude product was purified by column chromatography (silica 60-120 mesh, eluant 10-15% EtOAc in petroleum ether) to get methyl 2-(4-fluorophenyl)oxazole-4-carboxylate (6 g, yield 67%) as a white solid. $^1$H NMR (400 MHz, $CDCl_3$) δ 8.29 (s, 1H), 8.14-8.10 (m, 2H), 7.19-7.15 (t, J=8.5 Hz, 2H), 3.96 (s, 3H). MS (ESI) m/z: Calculated for $C_{11}H_8FNO_3$: 221.05. found: 221.8 (M+H)$^+$.

(2-(4-Fluorophenyl)oxazol-4-yl)methanol

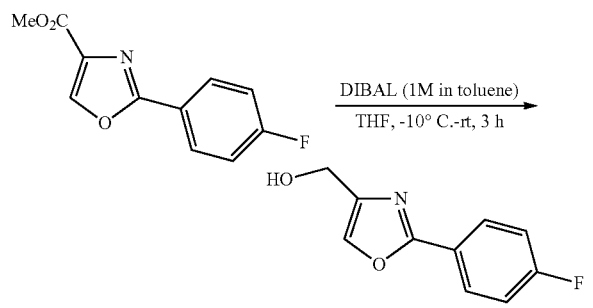

This compound was synthesized from methyl 2-(4-fluorophenyl)oxazole-4-carboxylate as described in example 64 step 4 (4.5 g, yield 86%) as a yellow solid. $^1$H NMR (300 MHz, $CDCl_3$) δ 8.06-8.01 (m, 2H), 7.65 (s, 1H), 7.18-7.12 (t, J=8.7 Hz, 2H), 4.68 (s, 2H). MS (ESI) m/z: Calculated for $C_{10}H_8FNO_2$: 193.05. found: 193.8 (M+H)$^+$.

2-(4-Fluorophenyl)oxazole-4-carbaldehyde

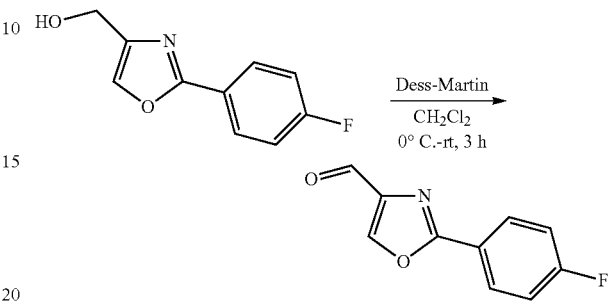

This compound was synthesized from (2-(4-fluorophenyl)oxazol-4-yl)methanol as described in example 47 step 2 (2.8 g, yield 63%) as a white solid. $^1$H NMR (300 MHz, $CDCl_3$) δ 10.01 (s, 1H), 8.32 (s, 1H), 8.14-8.10 (m, 2H), 7.23-7.17 (t, J=8.8 Hz, 2H). MS (ESI) m/z: Calculated for $C_{10}H_6FNO_2$: 191.04. found: 191.8 (M+H)$^+$.

2-(2-(4-Fluorophenyl)oxazol-4-yl)-2-hydroxyacetonitrile

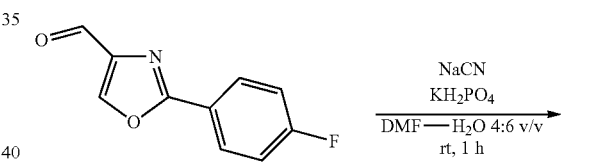

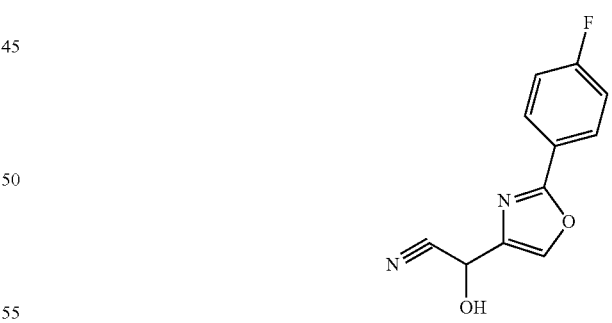

$KH_2PO_4$ (712 mg, 5.23 mmol) and NaCN (251 mg, 5.12 mmol) were added to a solution of 2-(4-fluorophenyl)oxazole-4-carbaldehyde (500 mg, 2.62 mmol) in DMF-$H_2O$ (10 mL, 4:6, v/v). The resulting reaction mixture was stirred at room temperature for 1 h, then diluted with water and extracted with EtOAc. The combined extracts were washed with $H_2O$ and brine, dried over anhydrous $Na_2SO_4$, and concentrated under reduced pressure to afford 2-(2-(4-fluorophenyl)oxazol-4-yl)-2-hydroxyacetonitrile (500 mg, yield 87%). $^1$H NMR (400 MHz, $CDCl_3$) δ 8.07-8.02 (m, 2H), 7.88 (s, 1H), 7.20-7.16 (t, J=8.8 Hz, 2H), 5.62 (s, 1H), 4.38 (br s, 1H). MS (ESI) m/z: Calculated for $C_{11}H_7FN_2O_2$: 218.05. found: 218.8 (M+H)$^+$.

2-Amino-1-(2-(4-fluorophenyl)oxazol-4-yl)ethanol

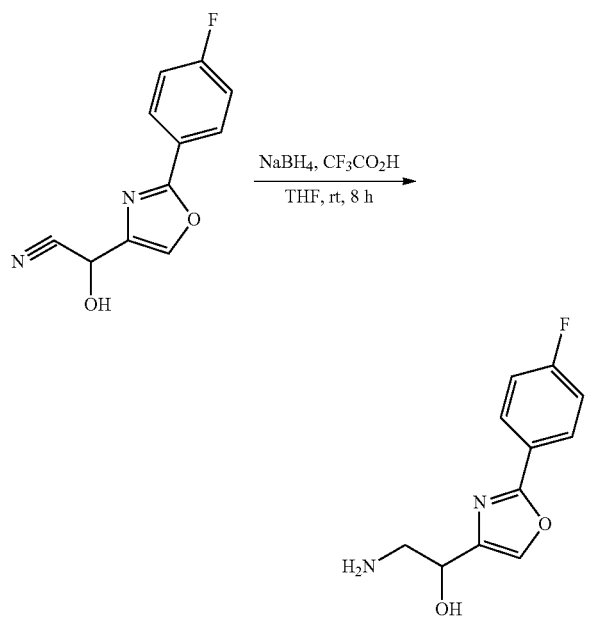

Trifluoroacetic acid (0.35 mL, 4.60 mmol) was added dropwise to a suspension of NaBH$_4$ (0.174 g, 4.60 mmol) in dry THF (10 mL) at 0° C., followed by addition of 2-(2-(4-fluorophenyl)oxazol-4-yl)-2-hydroxyacetonitrile (0.20 g, 0.92 mmol) also portionwise. The reaction mixture was stirred at room temperature for 8 h, and then concentrated under reduced pressure and diluted with ice-water. The mixture was acidified to pH ~2 using 1.5N HCl at 0° C. and then heated to 50° C. for 20 min. The solution was basified with aqueous NH$_4$OH solution and the organic product was extracted with CHCl$_3$. The combined extracts were washed with brine and concentrated under reduced pressure to afford 2-amino-1-(2-(4-fluorophenyl)oxazol-4-yl)ethanol (120 mg, crude), which was carried through without further purification. MS (ESI) m/z: Calculated for $C_{11}H_{11}FN_2O_2$: 222.08. found: 222.8 (M+H)$^+$.

N-(2-(2-(4-Fluorophenyl)oxazol-4-yl)-2-hydroxyethyl)-3-(5-(trifluoromethyl)-1,2,4-oxadiazol-3-yl)benzamide

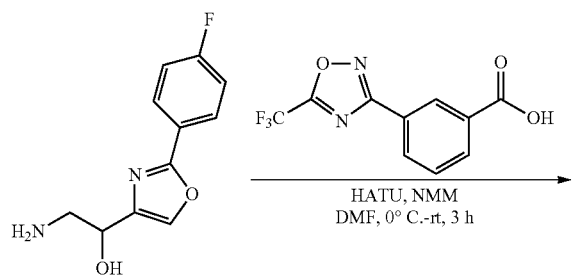

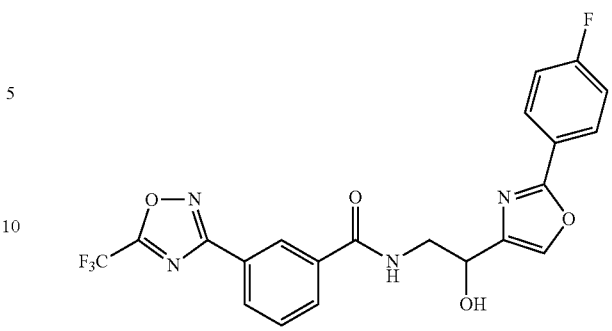

This compound was synthesized from 2-amino-1-(2-(4-fluorophenyl)oxazol-4-yl)ethanol and 3-(5-(trifluoromethyl)-1,2,4-oxadiazol-3-yl)benzoic acid as described in example 8 step 6 (70 mg, yield 39%). $^1$H NMR (400 MHz, CDCl$_3$) δ 8.51 (m, 1H), 8.28-8.26 (m, 1H), 8.08-8.01 (m, 3H), 7.73 (s, 1H), 7.66-7.62 (m, 1H), 7.17-7.08 (m, 3H), 5.05-5.03 (m, 1H), 4.12-4.06 (ddd, J=14.1 Hz, 6.3 Hz, 3.8 Hz, 1H), 3.91-3.85 (m, 1H), 3.77 (br s, 1H). MS (ESI) m/z: Calculated for $C_{21}H_{14}F_4N_4O_4$: 462.10. found: 463.1 (M+H)$^+$.

Example 95

5-(5-(Difluoromethyl)-1,2,4-oxadiazol-3-yl)nicotinic acid

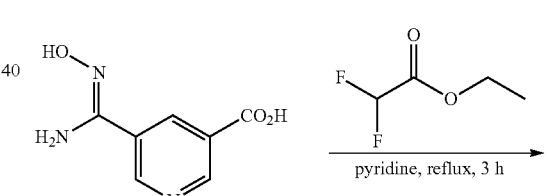

This compound was synthesized from 5-(N'-hydroxycarbamimidoyl)nicotinic acid using ethyl difluoroacetate as described in example 1 step 5 (100 mg, yield 30%). $^1$H NMR (400 MHz, DMSO-d$_6$) δ 13.94 (br s, 1H), 9.40 (d, J=2.1 Hz, 1H), 9.28 (d, J=2.1 Hz, 1H), 8.76-8.75 (t, J=2.1 Hz, 1H), 7.73-7.47 (m, 1H). MS (ESI) m/z: Calculated for $C_9H_6F_2N_3O_3$: 241.03. found: 241.8 (M+H)$^+$.

5-(5-(Difluoromethyl)-1,2,4-oxadiazol-3-yl)-N-(2-(2-(4-fluorophenyl)oxazol-4-yl)-2-methylpropyl)nicotinamide

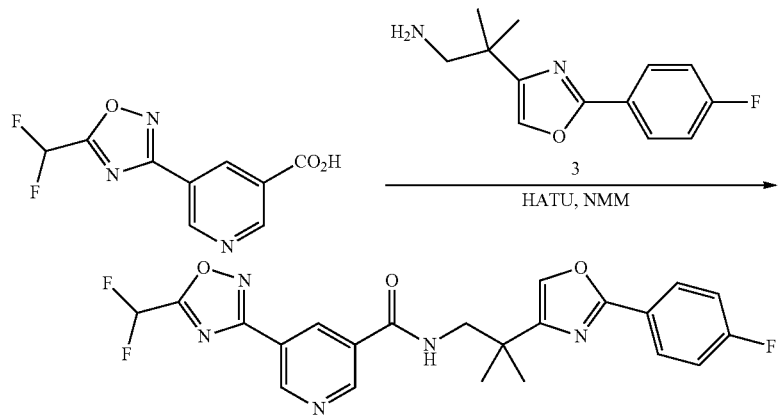

This compound was synthesized from 2-(2-(4-fluorophenyl)oxazol-4-yl)-2-methylpropan-1-amine and 5-(5-(difluoromethyl)-1,2,4-oxadiazol-3-yl)nicotinic acid as described in example 8 step 6 (45 mg, yield 24%). $^1$H NMR (400 MHz, DMSO-$d_6$) δ 9.32 (d, J=2.1 Hz, 1H), 9.20 (d, J=2.1 Hz, 1H), 8.82-8.78 (m, 1H), 8.75-8.74 (t, J=2.1 Hz, 1H), 8.04-8.00 (m, 3H), 7.74-7.48 (m, 1H), 7.38-7.33 (t, J=8.9 Hz, 2H), 3.55-3.53 (d, J=6.1 Hz, 2H), 1.31 (s, 6H). MS (ESI) m/z: Calculated for $C_{22}H_{18}F_3N_5O_3$: 457.14. found: 458.2 (M+H)$^+$.

Example 96

2-(Dimethylamino)-2-(2-(4-fluorophenyl)oxazol-4-yl)acetonitrile

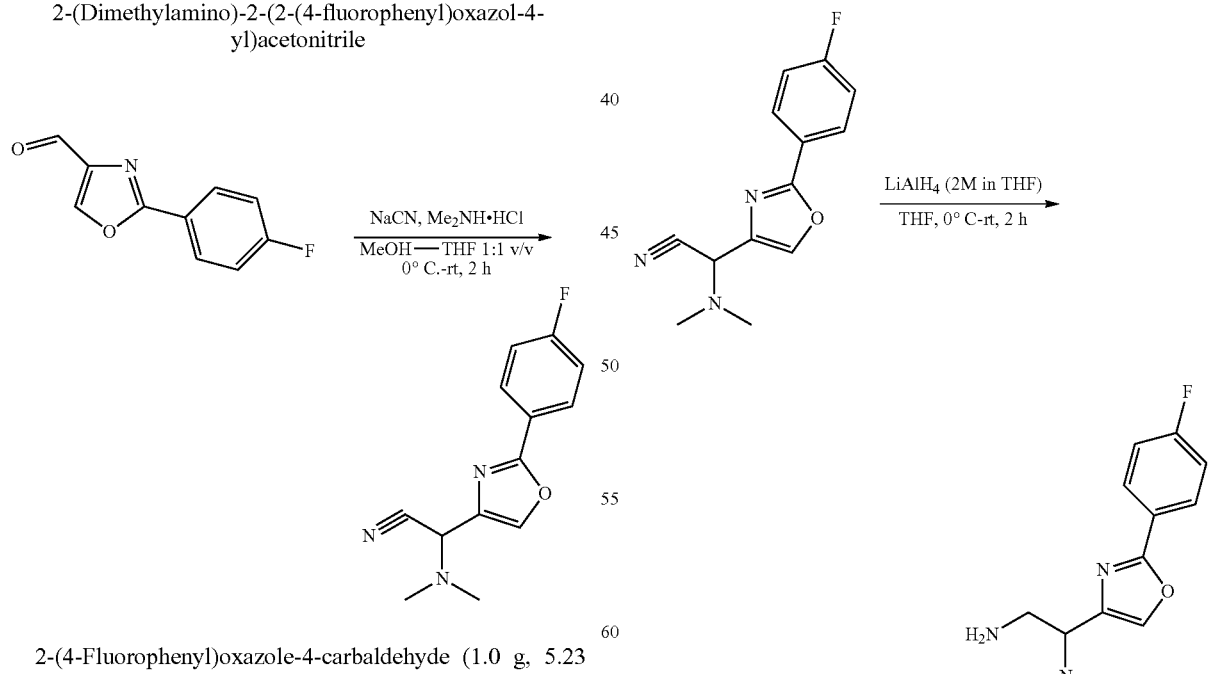

2-(4-Fluorophenyl)oxazole-4-carbaldehyde (1.0 g, 5.23 mmol) was dissolved in THF-MeOH (20 mL, 1:1 v/v). This solution was added to a solution of dimethylamine hydrochloride (470 mg, 5.7 mmol) and NaCN (640 mg, 13.0 mmol) in water. The resulting reaction mixture was stirred at room temperature for 2 h, and then diluted with water and extracted with EtOAc. The combined extracts were washed with $H_2O$ and brine, dried over anhydrous $Na_2SO_4$, and concentrated under reduced pressure to afford 2-(dimethylamino)-2-(2-(4-fluorophenyl)oxazol-4-yl)acetonitrile (1.0 g, crude) as a brown oil, which was used without further purification. MS (ESI) m/z: Calculated for $C_{13}H_{12}FN_3O$: 245.10. found: 245.9 (M+H)$^+$.

1-(2-(4-Fluorophenyl)oxazol-4-yl)-N1,N1-dimethylethane-1,2-diamine

This compound was synthesized from 2-(dimethylamino)-2-(2-(4-fluorophenyl)oxazol-4-yl)acetonitrile as described in example 1 step 3 (0.6 g) and it was carried through without further purification. MS (ESI) m/z: Calculated for $C_{13}H_{16}FN_3O$: 249.13. found: 249.9 $(M+H)^+$.

N-(2-(Dimethylamino)-2-(2-(4-fluorophenyl)oxazol-4-yl)ethyl)-3-(5-(trifluoromethyl)-1,2,4-oxadiazol-3-yl)benzamide hydrochloride

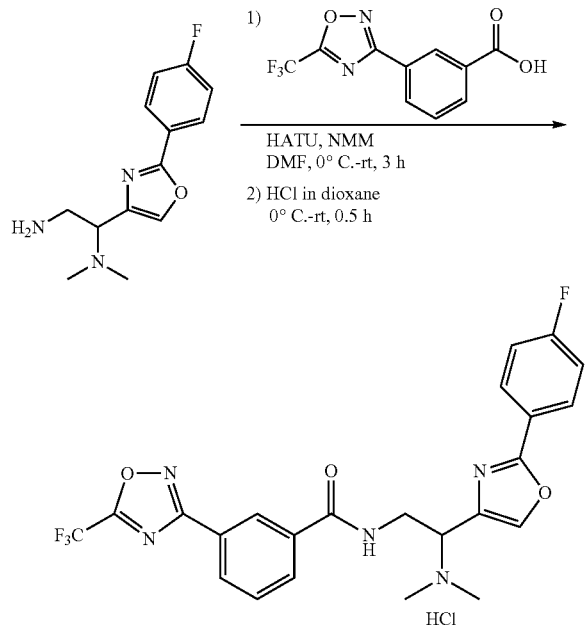

N-(2-(dimethylamino)-2-(2-(4-fluorophenyl)oxazol-4-yl)ethyl)-3-(5-(trifluoromethyl)-1,2,4-oxadiazol-3-yl)benzamide was synthesized from 1-(2-(4-fluorophenyl)oxazol-4-yl)-N1,N1-dimethylethane-1,2-diamine and 3-(5-(trifluoromethyl)-1,2,4-oxadiazol-3-yl)benzoic acid as described in example 8 step 6. The free base was then stirred with HCl in dioxane solution (4 mL) for 0.5 h at 0° C. to room temperature. The reaction mixture was concentrated and triturated with diethyl ether to afford N-(2-(dimethylamino)-2-(2-(4-fluorophenyl)oxazol-4-yl)ethyl)-3-(5-(trifluoromethyl)-1,2,4-oxadiazol-3-yl)benzamide hydrochloride (130 mg, yield 16%) as light brown solid. $^1$H NMR (400 MHz, DMSO-d$_6$) δ 10.39 (br s, 1H), 9.18-9.15 (t, J=5.6 Hz, 1H), 8.55-8.54 (m, 2H), 8.27-8.25 (m, 1H), 8.21-8.19 (m, 1H), 8.11-8.07 (m, 2H), 7.79-7.75 (t, J=7.8 Hz, 1H), 7.45-7.41 (t, J=8.9 Hz, 2H), 4.84-4.81 (t, J=6.1 Hz, 1H), 4.20-4.13 (m, 1H), 3.87-3.82 (m, 1H), 2.87-2.84 (dd, J=6.9 Hz, 5.0 Hz, 6H). MS (ESI) m/z: Calculated for $C_{23}H_{19}F_4N_5O_3$: 489.14. found: 490.2 $(M+H)^+$.

Example 97

N-(2-(3-(4-Fluorophenyl)-1H-1,2,4-triazol-5-yl)-2-methylpropyl)-5-(5-(2,2,2-trifluoroacetyl)thiophen-2-yl)nicotinamide

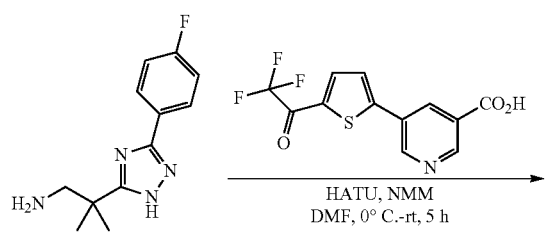

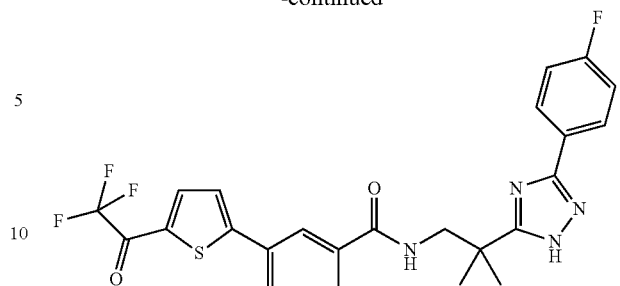

This compound was synthesized from 2-(3-(4-fluorophenyl)-1H-1,2,4-triazol-5-yl)-2-methylpropan-1-amine and 5-(5-(2,2,2-trifluoroacetyl)thiophen-2-yl)nicotinic acid as described in example 8 step 6 (28 mg, yield 20%) as a yellow viscous liquid. $^1$H NMR (400 MHz, DMSO-d$_6$) δ 9.20 (d, J=2.3 Hz, 1H), 9.01-8.98 (m, 1H), 8.80-8.77 (m, 1H), 8.51-8.48 (m, 1H), 8.21-8.19 (m, 1H), 8.01-7.96 (m, 4H), 7.24-7.19 (m, 2H), 3.59-3.57 (d, J=6.2 Hz, 2H), 1.42 (s, 6H). MS (ESI) m/z: Calculated for $C_{24}H_{19}F_4N_6O_2S$: 517.12. found: 516.4 $(M-H)^-$.

Example 98

Methyl 5-cyano-2-methoxybenzoate

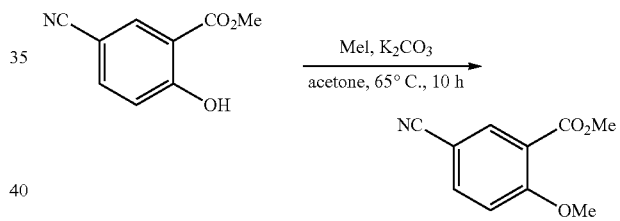

A solution of acid methyl 5-cyano-2-hydroxybenzoate (2 g, 11.2 mmol) in dry acetone (50 mL) was cooled to 0° C. and $K_2CO_3$ (2.34 g, 16.9 mmol) followed by MeI (1.1 mL, 16.9 mmol) were added dropwise. The reaction mixture was allowed to stir at 65° C. for 10 h and then diluted with EtOAc. The organic layer was washed with water and brine, dried over anhydrous sodium sulfate, and concentrated under reduced pressure to yield methyl 5-cyano-2-methoxybenzoate (600 mg, crude), which was carried through without further purification. $^1$H NMR (300 MHz, CDCl$_3$) δ 8.11 (d, J=2.2 Hz, 1H), 7.78-7.74 (dd, J=8.8 Hz, 2.2 Hz, 1H), 7.08-7.05 (d, J=8.8 Hz, 1H), 3.98 (s, 3H), 3.92 (s, 3H). MS (ESI) m/z: Calculated for $C_{10}H_9NO_3$: 191.06. found: 191.8 $(M+H)^+$.

5-Cyano-2-methoxybenzoic acid

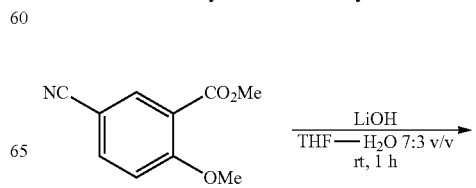

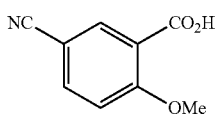

This compound was synthesized from 5-cyano-2-methoxybenzoic acid as described in example 43 step 2 (300 mg, yield 72%) as a white solid. $^1$H NMR (400 MHz, DMSO-$d_6$) δ 13.13 (br s, 1H), 8.02-8.01 (d, J=2.1 Hz, 1H), 7.99-7.96 (dd, J=8.8 Hz, 2.1 Hz, 1H), 7.32-7.30 (d, J=8.8 Hz, 1H), 3.90 (s, 3H). MS (ESI) m/z: Calculated for $C_9H_7NO_3$: 177.04. found: 175.6 (M−H)$^−$.

5-(N'-Hydroxycarbamimidoyl)-2-methoxybenzoic acid

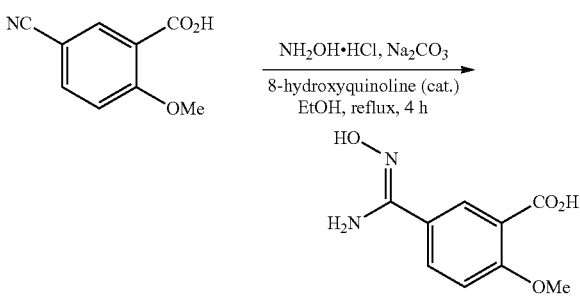

This compound was synthesized from 5-cyano-2-methoxybenzoic acid as described in example 1 step 4 (300 mg) and it was carried through without further purification. MS (ESI) m/z: Calculated for $C_9H_{10}N_2O_4$: 210.06. found: 210.8 (M+H)$^+$.

2-Methoxy-5-(5-(trifluoromethyl)-1,2,4-oxadiazol-3-yl)benzoic acid

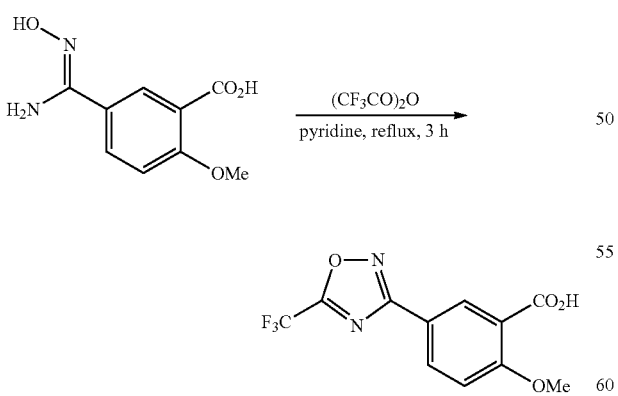

This compound was synthesized from 5-(N'-hydroxycarbamimidoyl)-2-methoxybenzoic acid as described in example 1 step 5 (40 mg, yield 35%). $^1$H NMR (300 MHz, DMSO-$d_6$) δ 13.05 (br s, 1H), 8.30-8.29 (d, J=2.2 Hz, 1H), 8.20-8.16 (dd, J=8.8 Hz, 2.2 Hz, 1H), 7.38-7.35 (d, J=8.8 Hz, 1H), 3.92 (s, 3H). MS (ESI) m/z: Calculated for $C_{11}H_7F_3N_2O_4$: 288.04. found: 286.7 (M−H)$^−$.

N-(2-(2-(4-Fluorophenyl)oxazol-4-yl)-2-methylpropyl)-2-methoxy-5-(5-(trifluoromethyl)-1,2,4-oxadiazol-3-yl)benzamide

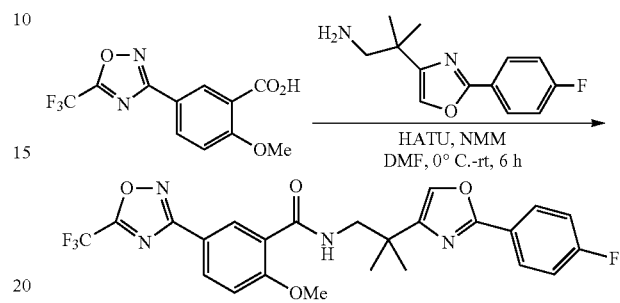

This compound was synthesized from 2-(2-(4-fluorophenyl)oxazol-4-yl)-2-methylpropan-1-amine and 2-methoxy-5-(5-(trifluoromethyl)-1,2,4-oxadiazol-3-yl)benzoic acid as described in example 8 step 6 (40 mg, yield 36%). $^1$H NMR (400 MHz, MeOD) δ 8.64-8.63 (d, J=2.3 Hz, 1H), 8.45-8.42 (t, J=5.6 Hz, 1H), 8.24-8.21 (dd, J=8.8 Hz, 2.4 Hz, 1H), 8.11-8.07 (m, 2H), 7.83 (s, 1H), 7.34-7.32 (d, J=8.8 Hz, 1H), 7.27-7.23 (t, J=8.8 Hz, 2H), 3.91 (s, 3H), 3.72-3.71 (m, 2H), 1.41 (s, 6H). MS (ESI) m/z: Calculated for $C_{24}H_{20}F_4N_4O_4$: 504.14. found: 505.2 (M+H)$^+$.

Example 99

2-(2-(4-Fluorophenyl)oxazol-5-yl)-2-methylpropanenitrile

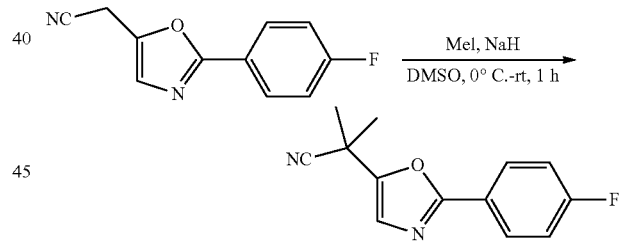

This compound was synthesized from 2-(2-(4-fluorophenyl)oxazol-5-yl)acetonitrile using iodomethane as described in example 1 step 2 (170 mg, yield 60%). $^1$H NMR (300 MHz, CDCl$_3$) δ 8.06-8.02 (m, 2H), 7.20-7.14 (t, J=8.7 Hz, 2H), 7.06 (s, 1H), 1.81 (s, 6H). MS (ESI) m/z: Calculated for $C_{13}H_{11}FN_2O$: 230.09. found: 230.9 (M+H)$^+$.

2-(2-(4-Fluorophenyl)oxazol-5-yl)-2-methylpropan-1-amine

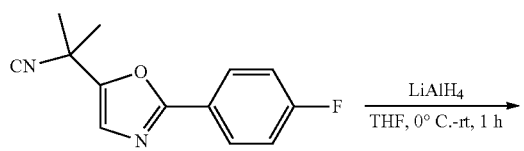

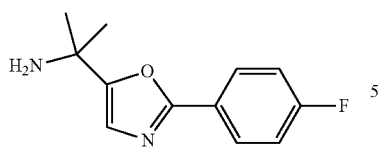

This compound was synthesized from 2-(2-(4-fluorophenyl)oxazol-5-yl)-2-methylpropanenitrile as described in example 1 step 3 (100 mg, crude) and it was carried through without further purification. MS (ESI) m/z: Calculated for $C_{13}H_{15}FN_2O$: 234.12. found: 235.2 (M+H)$^+$.

N-(2-(2-(4-Fluorophenyl)oxazol-5-yl)-2-methylpropyl)-3-(5-(trifluoromethyl)-1,2,4-oxadiazol-3-yl)benzamide

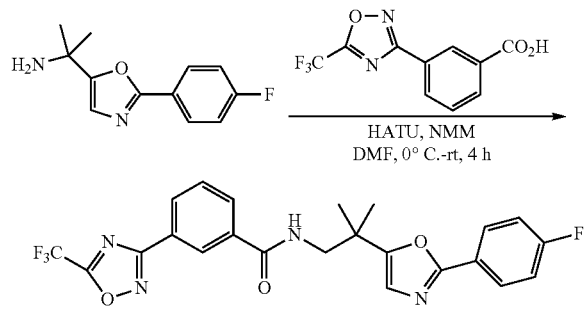

This compound was synthesized from 2-(2-(4-fluorophenyl)oxazol-5-yl)-2-methylpropan-1-amine and 3-(5-(trifluoromethyl)-1,2,4-oxadiazol-3-yl)benzoic acid as described in example 8 step 6 (30 mg, yield 15%). $^1$H NMR (400 MHz, MeOD) δ 8.48-8.47 (m, 1H), 8.28-8.25 (m, 1H), 8.00-7.97 (m, 3H), 7.68-7.64 (t, J=7.8 Hz, 1H), 7.21-7.16 (t, J=8.8 Hz, 2H), 7.00 (s, 1H), 3.66 (s, 2H), 1.46 (s, 6H). MS (ESI) m/z: Calculated for $C_{23}H_{18}F_4N_4O_3$: 474.13. found: 475.2 (M+H)$^+$.

Example 100

4-(Dimethylamino)-2-(2-(4-fluorophenyl)oxazol-4-yl)butanenitrile

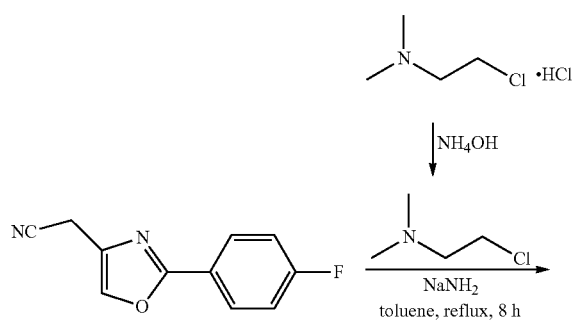

This compound was synthesized from 2-(2-(4-fluorophenyl)oxazol-4-yl)acetonitrile and 2-chloro-N,N-dimethylethanamine hydrochloride as described in example 16 step 1b (400 mg, yield 48%). $^1$H NMR (400 MHz, MeOD) δ 8.10-8.07 (m, 2H), 7.99 (m, 1H), 7.29-7.25 (t, J=8.9 Hz, 2H), 4.24-4.20 (t, J=7.3 Hz, 1H), 2.59-2.46 (m, 2H), 2.29 (s, 6H), 2.23-2.17 (m, 2H). MS (ESI) m/z: Calculated for $C_{15}H_{16}FN_3O$: 273.13. found: 274.2 (M+H)$^+$.

3-(2-(4-Fluorophenyl)oxazol-4-yl)-N1,N1-dimethylbutane-1,4-diamine

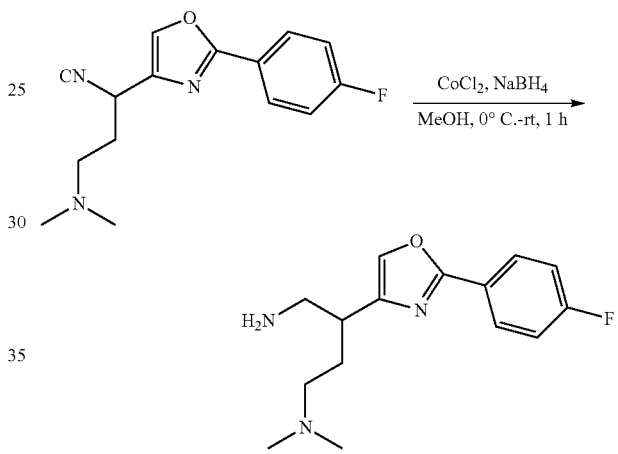

Cobalt (II) chloride (380 mg, 2.9 mmol) was added to a solution of 4-(dimethylamino)-2-(2-(4-fluorophenyl)oxazol-4-yl)butanenitrile (400 mg, 1.46 mmol) in dry methanol (10 mL) at 0° C., followed by sodium borohydride (550 mg, 14.6 mmol) portionwise. The resulting mixture was stirred at room temperature for 1 h, then quenched carefully with ice water, and filtered through a Celite bed. The filtrate was concentrated under reduced pressure to afford crude 3-(2-(4-fluorophenyl)oxazol-4-yl)-N1,N1-dimethylbutane-1,4-diamine (180 mg, crude), which was carried through without further purification. MS (ESI) m/z: Calculated for $C_{15}H_{20}FN_3O$: 277.16. found: 278.2 (M+H)$^+$.

N-(4-(Dimethylamino)-2-(2-(4-fluorophenyl)oxazol-4-yl)butyl)-3-(5-(trifluoromethyl)-1,2,4-oxadiazol-3-yl)benzamide

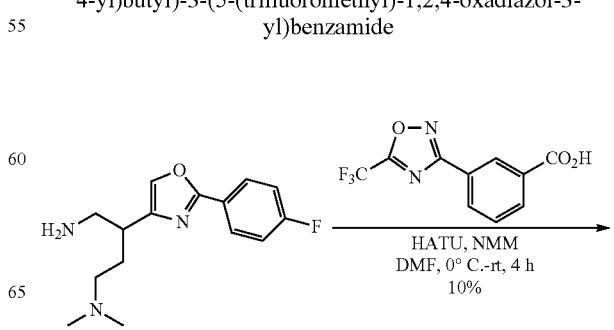

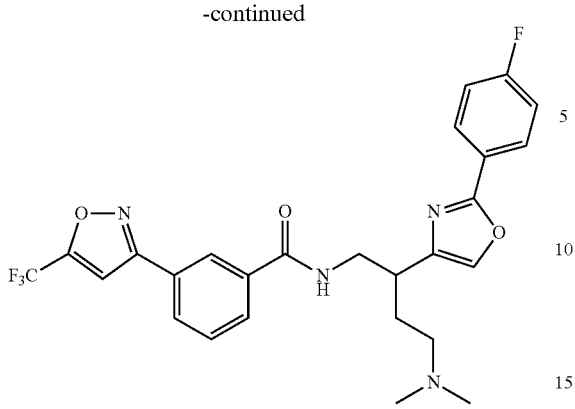

This compound was synthesized from 3-(2-(4-fluorophenyl)oxazol-4-yl)-N1,N1-dimethylbutane-1,4-diamine and 3-(5-(trifluoromethyl)-1,2,4-oxadiazol-3-yl)benzoic acid as described in example 8 step 6 (17 mg, yield 10%). $^1$H NMR (400 MHz, MeOD) δ 8.55-8.54 (t, J=1.5 Hz, 1H), 8.30-8.27 (m, 1H), 8.08-8.02 (m, 3H), 7.82 (s, 1H), 7.71-7.67 (t, J=7.8 Hz, 1H), 7.26-7.21 (t, J=8.9 Hz, 2H), 3.76-3.65 (m, 2H), 3.16-3.10 (m, 1H), 2.53-2.40 (m, 2H), 2.30 (m, 6H), 2.04-1.98 (m, 2H). MS (ESI) m/z: Calculated for $C_{24}H_{22}F_4N_6O_3$: 518.17. found: 519.2 (M+H)$^+$.

Example 101

N-(4-(Dimethylamino)-2-(2-(4-fluorophenyl)oxazol-4-yl)butyl)-5-(5-(trifluoromethyl)-1,2,4-oxadiazol-3-yl)nicotinamide

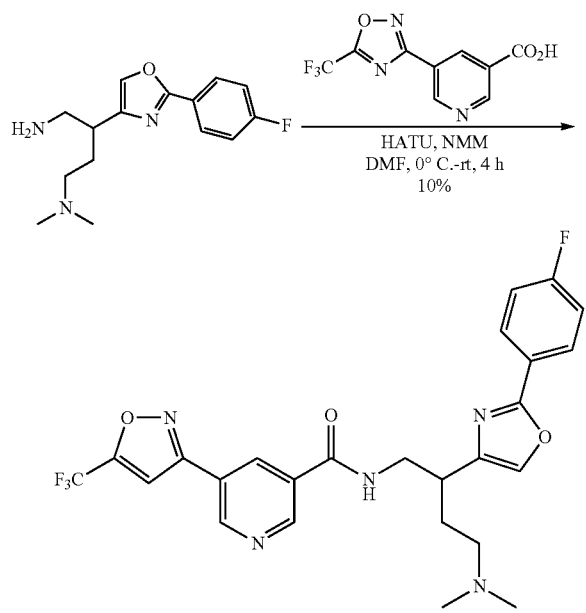

This compound was synthesized from 3-(2-(4-fluorophenyl)oxazol-4-yl)-N1,N1-dimethylbutane-1,4-diamine and 5-(5-(trifluoromethyl)-1,2,4-oxadiazol-3-yl)nicotinic acid as described in example 8 step 6 (16 mg, yield 10%). $^1$H NMR (400 MHz, MeOD) δ 9.39-9.38 (d, J=2.0 Hz, 1H), 9.16 (d, J=2.0 Hz, 1H), 8.85-8.84 (t, J=2.1 Hz, 1H), 8.08-8.05 (m, 2H), 7.84 (s, 1H), 7.26-7.22 (t, J=8.9 Hz, 2H), 3.79-3.66 (m, 2H), 3.18-3.11 (m, 1H), 2.63-2.46 (m, 2H), 2.37 (m, 6H), 2.06-2.00 (m, 2H). MS (ESI) m/z: Calculated for $C_{24}H_{22}F_4N_6O_3$: 518.17. found: 519.2 (M+H)$^+$.

Example 102

N-(2-(2-(4-Fluorophenyl)oxazol-4-yl)-2-hydroxyethyl)-5-(5-(trifluoromethyl)-1,2,4-oxadiazol-3-yl)nicotinamide

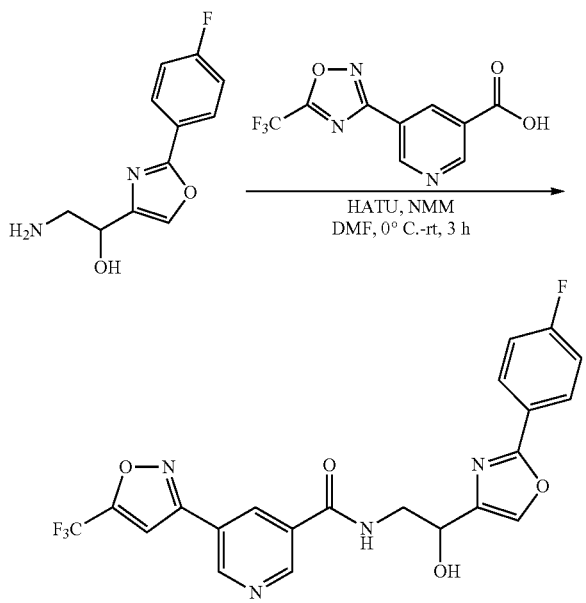

This compound was synthesized from 2-amino-1-(2-(4-fluorophenyl)oxazol-4-yl)ethanol and 5-(5-(trifluoromethyl)-1,2,4-oxadiazol-3-yl)nicotinic acid as described in example 8 step 6 (120 mg, yield 45%). $^1$H NMR (400 MHz, DMSO-d$_6$) δ 9.35 (d, J=1.8 Hz, 1H), 9.27 (d, J=1.8 Hz, 1H), 9.13-9.10 (t, J=5.6 Hz, 1H), 8.84-8.83 (t, J=1.8 Hz, 1H), 8.11 (s, 1H), 8.03-8.00 (dd, J=8.5 Hz, 5.5 Hz, 2H), 7.39-7.35 (t, J=8.9 Hz, 2H), 5.74-5.73 (d, J=5.2 Hz, 1H), 4.85-4.81 (m, 1H), 3.77-3.71 (m, 1H), 3.56-3.49 (m, 1H). MS (ESI) m/z: Calculated for $C_{20}H_{13}F_4N_5O_4$: 463.09. found: 464.0 (M+H)$^+$.

Example 103

4-(Chloromethyl)-2-(4-chlorophenyl)oxazole

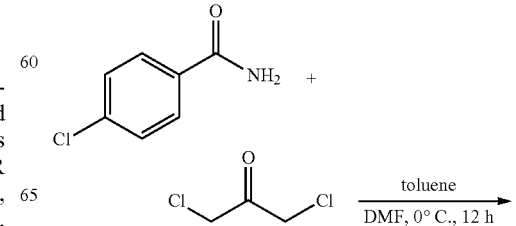

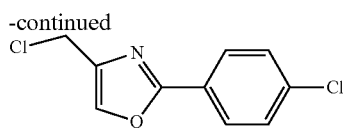

This compound was synthesized from 4-chlorobenzamide and 1,3-dichloroacetone as described in example 74 step 1 (3.4 g, yield 46%). $^1$H NMR (300 MHz, CDCl$_3$) δ 8.01-7.98 (d, J=8.8 Hz, 2H), 7.72 (s, 1H), 7.47-7.44 (d, J=8.8 Hz, 2H), 4.59 (d, J=0.9 Hz, 2H).

2-(2-(4-Chlorophenyl)oxazol-4-yl)acetonitrile

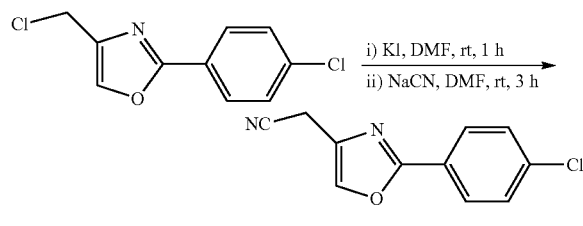

This compound was synthesized from 4-(chloromethyl)-2-(4-chlorophenyl)oxazole as described in example 71 step 2 (1.7 g, yield 53%). $^1$H NMR (300 MHz, CDCl$_3$) δ 7.98-7.95 (d, J=8.8 Hz, 2H), 7.75-7.74 (d, J=1.3 Hz, 1H), 7.47-7.44 (d, J=8.8 Hz, 2H), 3.73 (d, J=1.3 Hz, 2H). MS (ESI) m/z: Calculated for C$_{11}$H$_7$ClN$_2$O: 218.02. found: 219.0 (M+H)$^+$.

4-(2-(4-Chlorophenyl)oxazol-4-yl)-1-methylpiperidine-4-carbonitrile

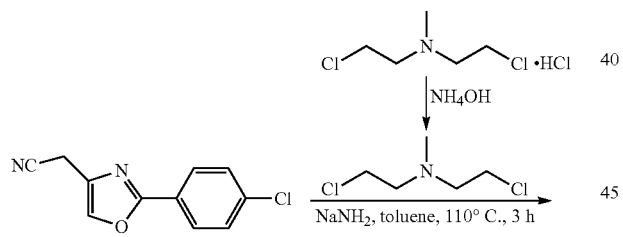

This compound was synthesized from 2-(2-(4-chlorophenyl)oxazol-4-yl)acetonitrile as described in example 16 step 1b (140 mg, yield 20%). $^1$H NMR (400 MHz, CDCl$_3$) δ 8.00-7.97 (m, 2H), 7.74 (s, 1H), 7.47-7.45 (m, 2H), 3.67-3.63 (m, 2H), 3.25-3.18 (m, 2H), 2.99-2.95 (m, 2H), 2.89 (s, 3H), 2.49-2.46 (m, 2H). MS (ESI) m/z: Calculated for C$_{16}$H$_{16}$ClN$_3$O: 301.10. found: 302.1 (M+H)$^+$.

(4-(2-(4-Chlorophenyl)oxazol-4-yl)-1-methylpiperidin-4-yl)methanamine

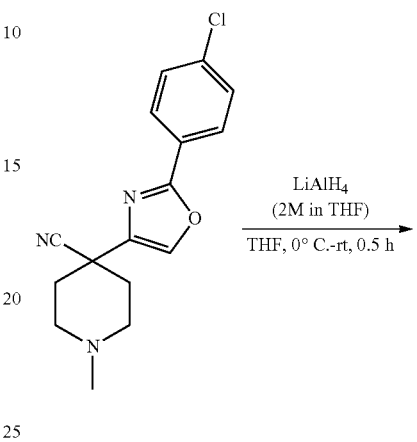

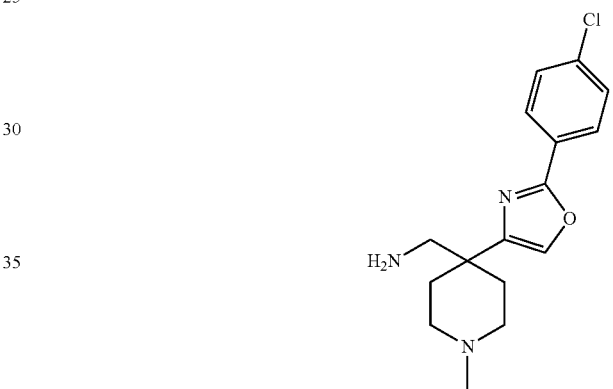

This compound was synthesized from 4-(2-(4-chlorophenyl)oxazol-4-yl)-1-methylpiperidine-4-carbonitrile as described in example 1 step 3 (100 mg, crude) and it was carried through without further purification. MS (ESI) m/z: Calculated for C$_{16}$H$_{20}$ClN$_3$O: 305.13. found: 306.2 (M+H)$^+$.

N-((4-(2-(4-Chlorophenyl)oxazol-4-yl)-1-methylpiperidin-4-yl)methyl)-3-(5-(trifluoromethyl)-1,2,4-oxadiazol-3-yl)benzamide hydrochloride

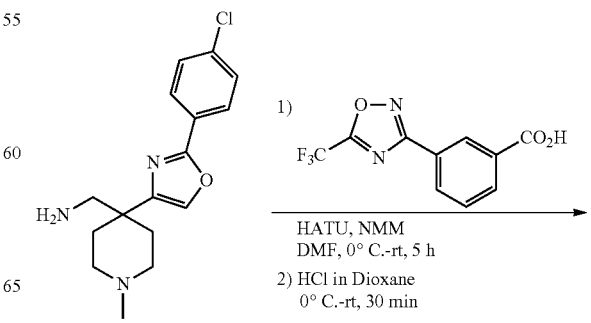

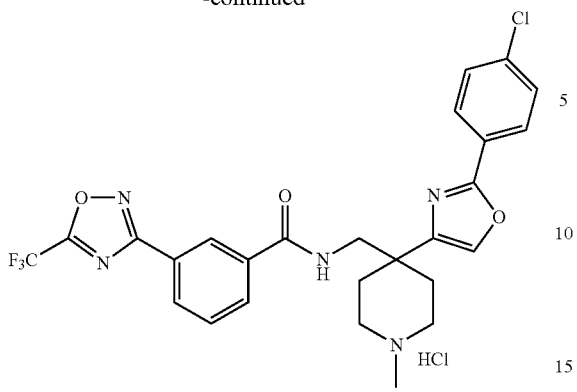

This compound was synthesized from (4-(2-(4-chlorophenyl)oxazol-4-yl)-1-methylpiperidin-4-yl)methanamine and 3-(5-(trifluoromethyl)-1,2,4-oxadiazol-3-yl)benzoic acid as described in example 96 step 3 (12 mg, yield 5%). $^1$H NMR (400 MHz, CDCl$_3$) [free amine] δ 8.56 (s, 1H), 8.28-8.26 (d, J=7.7 Hz, 1H), 8.13-8.11 (d, J=7.6 Hz, 1H), 8.02-8.00 (d, J=8.5 Hz, 2H), 7.79-7.75 (m, 1H), 7.66-7.62 (d, J=7.2 Hz, 1H), 7.57 (s, 1H), 7.42-7.40 (d, J=8.2 Hz, 2H), 3.77-3.76 (d, J=4.7 Hz, 2H), 2.79-2.77 (m, 2H), 2.59 (m, 2H), 2.42 (m, 3H), 2.22-2.21 (m, 2H), 2.08-2.04 (m, 2H). MS (ESI) m/z: Calculated for C$_{26}$H$_{23}$ClF$_3$N$_5$O$_3$: 545.14. found: 546.2 (M+H)$^+$.

Example 104

2-(2-(4-Chlorophenyl)oxazol-4-yl)-2-methylpropanenitrile

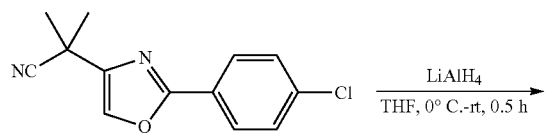

This compound was synthesized from 2-(2-(4-chlorophenyl)oxazol-4-yl)acetonitrile using iodomethane as described in example 1 step 2 (300 mg, yield 53%). $^1$H NMR (400 MHz, CDCl$_3$) δ 8.00-7.98 (d, J=8.7 Hz, 2H), 7.68 (s, 1H), 7.46-7.44 (d, J=8.7 Hz, 2H), 1.76 (s, 6H). MS (ESI) m/z: Calculated for C$_{13}$H$_{11}$ClN$_2$O: 246.06. found: 247.0 (M+H)$^+$.

2-(2-(4-Chlorophenyl)oxazol-4-yl)-2-methylpropan-1-amine

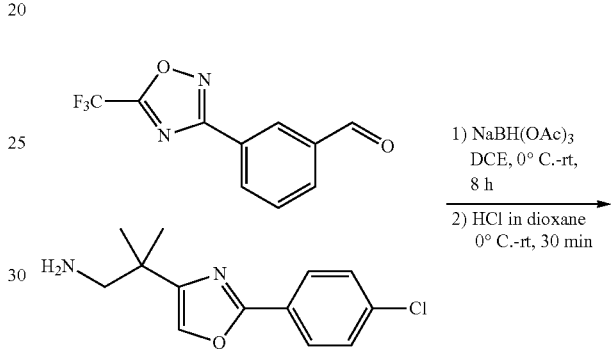

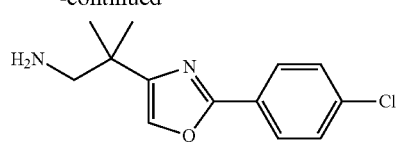

This compound was synthesized from 2-(2-(4-chlorophenyl)oxazol-4-yl)-2-methylpropanenitrile as described in example 1 step 3 (155 mg, yield 59%) and it was used without further purification. MS (ESI) m/z: Calculated for C$_{13}$H$_{16}$ClN$_2$O: 250.09. found: 251.1 (M+H)$^+$.

2-(2-(4-Chlorophenyl)oxazol-4-yl)-2-methyl-N-(3-(5-(trifluoromethyl)-1,2,4-oxadiazol-3-yl)benzyl)propan-1-amine hydrochloride

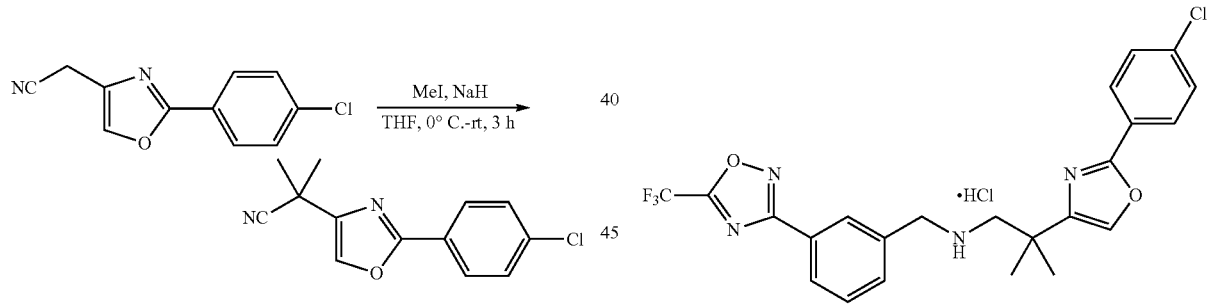

2-(2-(4-Chlorophenyl)oxazol-4-yl)-2-methyl-N-(3-(5-(trifluoromethyl)-1,2,4-oxadiazol-3-yl)benzyl)propan-1-amine was synthesized from 3-(5-(trifluoromethyl)-1,2,4-oxadiazol-3-yl)benzaldehyde and 2-(2-(4-chlorophenyl)oxazol-4-yl)-2-methylpropan-1-amine as described in example 7 step 3. The free amine was then treated with HCl in dioxane (2 M) at 0° C. and stirred at room temperature for 30 min. The reaction mixture was concentrated under reduced pressure. The crude was purified by washing with dry hexane to get 2-(2-(4-chlorophenyl)oxazol-4-yl)-2-methyl-N-(3-(5-(trifluoromethyl)-1,2,4-oxadiazol-3-yl)benzyl)propan-1-amine hydrochloride (20 mg, yield 6%). $^1$H NMR (400 MHz, DMSO-d$_6$) δ 8.87 (br s, 2H), 8.26 (s, 1H), 8.11-8.08 (m, 2H), 7.85-7.80 (m, 3H), 7.69-7.65 (t, J=7.6 Hz, 1H), 7.55-7.52 (d, J=8.5 Hz, 2H), 4.28 (br s, 2H), 3.12 (m, 2H), 1.33 (s, 6H). MS (ESI) m/z: Calculated for C$_{23}$H$_{20}$ClF$_3$N$_4$O$_2$: 476.12. found: 477.2 (M+H)$^+$.

Example 105

2-(2-(4-Fluorophenyl)oxazol-5-yl)ethanamine

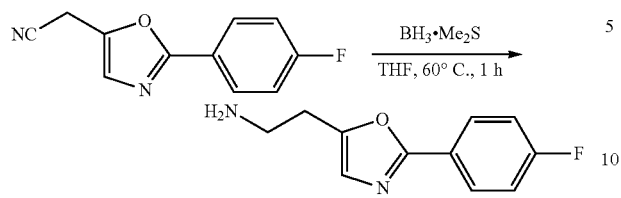

This compound was synthesized from 2-(2-(4-fluorophenyl)oxazol-5-yl)acetonitrile as described in example 42 step 1 (70 mg) and it was carried through without further purification. MS (ESI) m/z: Calculated for $C_{11}H_{11}FN_2O$: 206.09. found: 206.8 $(M+H)^+$.

N-(2-(2-(4-Fluorophenyl)oxazol-5-yl)ethyl)-3-(5-(trifluoromethyl)-1,2,4-oxadiazol-3-yl)benzamide

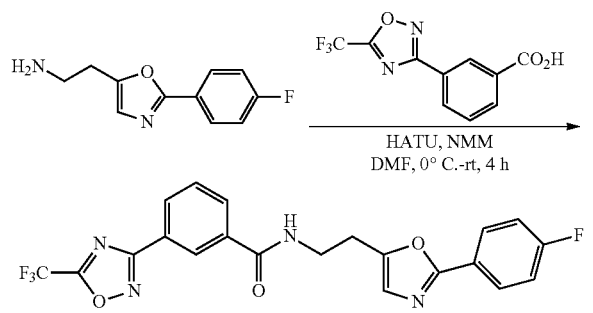

This compound was synthesized from 2-(2-(4-fluorophenyl)oxazol-5-yl)ethanamine and 3-(5-(trifluoromethyl)-1,2,4-oxadiazol-3-yl)benzoic acid as described in example 8 step 6 (28 mg, yield 20%). $^1$H NMR (400 MHz, MeOD) δ 8.56-8.55 (m, 1H), 8.30-8.28 (dq, J=7.8 Hz, 0.9 Hz, 1H), 8.06-8.04 (m, 1H), 8.00-7.96 (dd, J=9.0 Hz, 5.3 Hz, 2H), 7.71-7.69 (t, J=7.8 Hz, 1H), 7.21-7.17 (t, J=8.8 Hz, 2H), 7.03 (s, 1H), 3.78-3.75 (t, J=6.7 Hz, 2H), 3.15-3.12 (m, 2H). MS (ESI) m/z: Calculated for $C_{21}H_{14}F_4N_4O_3$: 446.10. found: 447.0 $(M+H)^+$.

Example 106

4-([1,1'-Biphenyl]-3-yl)-1-methylpiperidine-4-carbonitrile

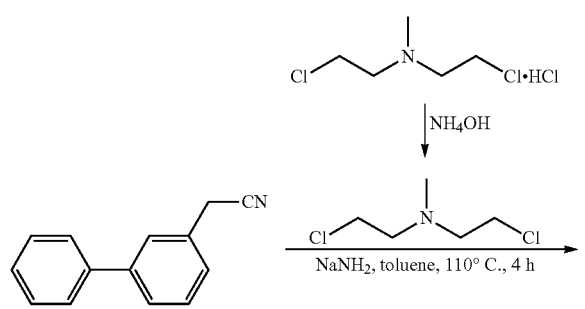

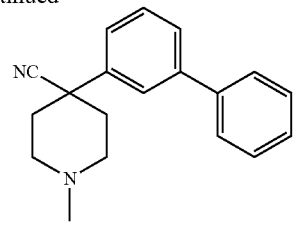

This compound was synthesized from 2-([1,1'-biphenyl]-3-yl)acetonitrile as described in example 16 step 1b (500 mg, yield 35%). $^1$H NMR (400 MHz, MeOD) δ 7.75 (m, 1H), 7.64-7.60 (m, 3H), 7.53-7.51 (m, 2H), 7.48-7.44 (m, 2H), 7.39-7.35 (m, 1H), 3.08-3.05 (m, 2H), 2.57-2.50 (m, 2H), 2.42 (s, 3H), 2.23-2.20 (m, 4H). MS (ESI) m/z: Calculated for $C_{19}H_{20}N_2$: 276.16. found: 277.0 $(M+H)^+$.

(4-([1,1'-Biphenyl]-3-yl)-1-methylpiperidin-4-yl)methanamine

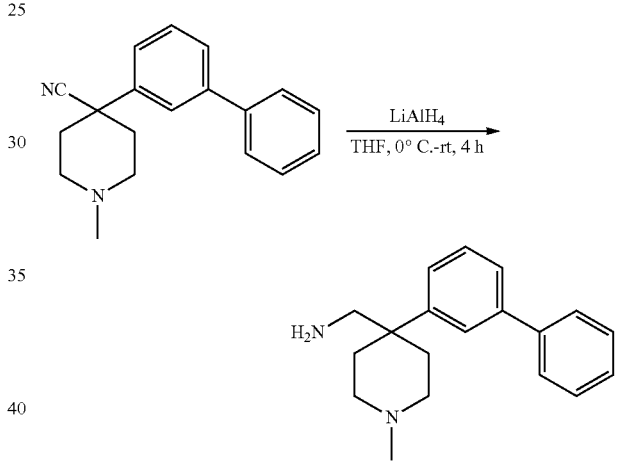

This compound was synthesized from 4-([1,1'-biphenyl]-3-yl)-1-methylpiperidine-4-carbonitrile as described in example 1 step 3 (250 mg, yield 50%). $^1$H NMR (400 MHz, MeOD) δ 7.63-7.58 (m, 3H), 7.52-7.42 (m, 4H), 7.39-7.32 (m, 2H), 2.77 (s, 2H), 2.69-2.66 (m, 2H), 2.37-2.27 (m, 4H), 2.22 (s, 3H), 1.91-1.86 (m, 2H). MS (ESI) m/z: Calculated for $C_{19}H_{24}N_2$: 280.19. found: 281.0 $(M+H)^+$.

N-((4-([1,1'-Biphenyl]-3-yl)-1-methylpiperidin-4-yl)methyl)-3-(5-(trifluoromethyl)-1,2,4-oxadiazol-3-yl)benzamide

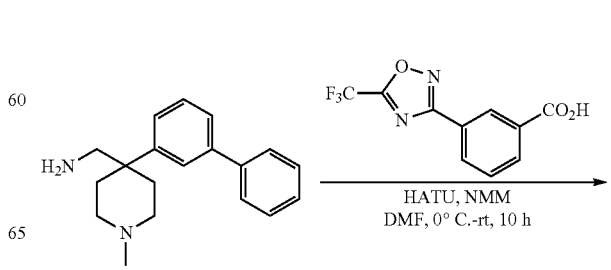

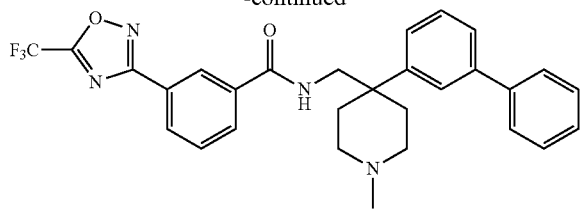

This compound was synthesized from (4-([1,1'-biphenyl]-3-yl)-1-methylpiperidin-4-yl)methanamine and 3-(5-(trifluoromethyl)-1,2,4-oxadiazol-3-yl)benzoic acid as described in example 8 step 6 (60 mg, yield 31%) as an off white solid. $^{1}$H NMR (400 MHz, MeOD) δ 8.39 (m, 1H), 8.23-8.21 (m, 1H), 7.90-7.88 (m, 1H), 7.64-7.54 (m, 4H), 7.49-7.47 (m, 3H), 7.39-7.36 (m, 2H), 7.31-7.28 (m, 1H), 3.60 (m, 2H), 2.79-2.76 (m, 2H), 2.42-2.30 (m, 4H), 2.23 (m, 3H), 2.11-2.06 (m, 2H). MS (ESI) m/z: Calculated for $C_{29}H_{27}F_3N_4O_2$: 520.21. found: 521.2 (M+H)$^{+}$.

Example 107

4-(Chloromethyl)-2-(4-methoxyphenyl)oxazole

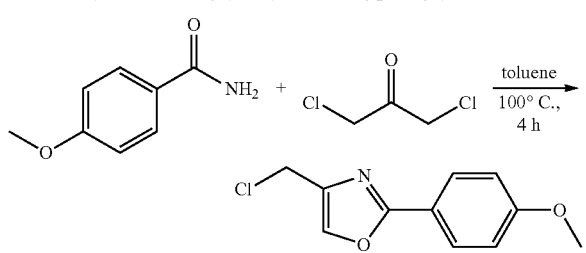

This compound was synthesized from 4-methoxybenzamide and 1,3-dichloroacetone as described in example 74 step 1 (2.3 g, yield 78%) as a yellow solid. $^{1}$H NMR (400 MHz, CDCl$_3$) δ 7.98-7.96 (d, J=8.3 Hz, 2H), 7.65 (s, 1H), 6.97-6.95 (d, J=8.3 Hz, 2H), 4.56 (s, 2H), 3.86 (s, 3H). MS (ESI) m/z: Calculated for $C_{11}H_{10}ClNO_2$: 223.04. found: 223.8 (M+H)$^{+}$.

2-(2-(4-Methoxyphenyl)oxazol-4-yl)acetonitrile

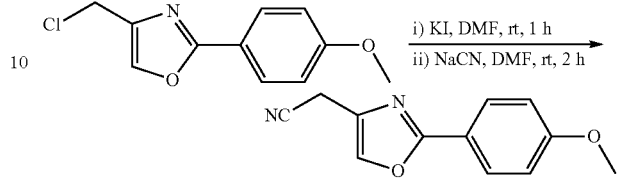

This compound was synthesized from 4-(chloromethyl)-2-(4-methoxyphenyl)oxazole as described in example 71 step 2 (0.65 g, yield 57%) as an off white solid. $^{1}$H NMR (300 MHz, CDCl$_3$) δ 7.97-7.94 (d, J=8.6 Hz, 2H), 7.69 (s, 1H), 6.99-6.97 (d, J=8.6 Hz, 2H), 3.87 (s, 3H), 3.71 (s, 2H). MS (ESI) m/z: Calculated for $C_{12}H_{10}N_2O_2$: 214.07. found: 214.8 (M+H)$^{+}$.

2-(2-(4-Methoxyphenyl)oxazol-4-yl)ethanamine

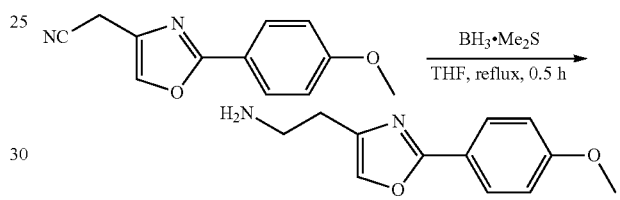

This compound was synthesized from 2-(2-(4-methoxyphenyl)oxazol-4-yl)acetonitrile as described in example 42 step 1 (130 mg, crude) and it was carried through without further purification. MS (ESI) m/z: Calculated for $C_{12}H_{14}N_2O_2$: 218.11. found: 218.8 (M+H)$^{+}$.

N-(2-(2-(4-Methoxyphenyl)oxazol-4-yl)ethyl)-5-(5-(trifluoromethyl)-1,2,4-oxadiazol-3-yl)nicotinamide

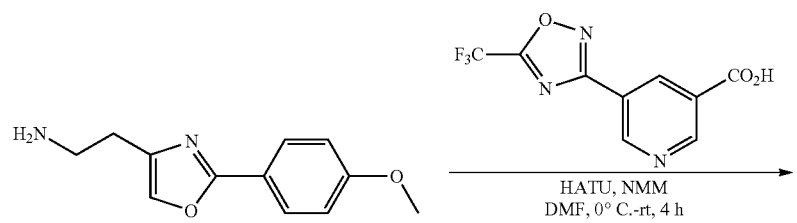

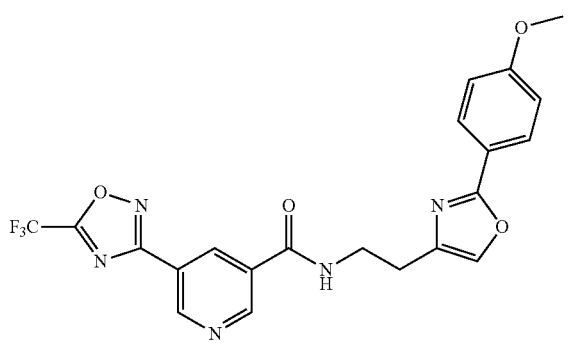

This compound was synthesized from 2-(2-(4-methoxyphenyl)oxazol-4-yl)ethanamine and 5-(5-(trifluoromethyl)-1,2,4-oxadiazol-3-yl)nicotinic acid as described in example 8 step 6 (35 mg, yield 19%) as a white solid. $^1$H NMR (400 MHz, CDCl$_3$) δ 9.47 (m, 1H), 9.34 (m, 1H), 8.90-8.89 (t, J=2.0 Hz, 1H), 8.08-8.06 (m, 1H), 8.03-8.00 (d, J=8.8 Hz, 2H), 7.55 (s, 1H), 6.99-6.97 (d, J=8.8 Hz, 2H), 3.88 (s, 3H), 3.87-3.84 (m, 2H), 2.96-2.93 (t, J=5.9 Hz, 2H). MS (ESI) m/z: Calculated for C$_{21}$H$_{16}$F$_3$N$_5$O$_4$: 459.12. found: 460.1 (M+H)$^+$.

Example 108

2-Chloro-5-cyanobenzoic acid

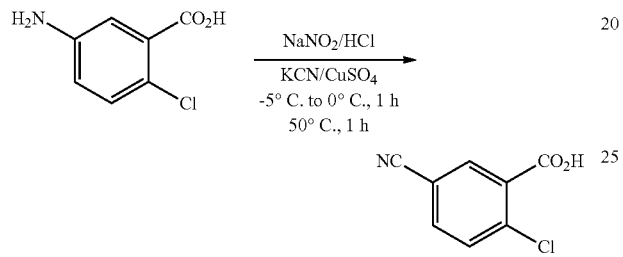

A solution of NaNO$_2$ (2.21 g, 32 mmol) in water (10 mL) was added to a solution of 5-amino-2-chlorobenzoic acid (5.0 g, 29.14 mmol) in water (40 mL) at 0° C., followed addition of by conc. HCl (10 mL) at −5° C. The reaction mixture was stirred at −5° C. for an additional 1 h and then the diazonium solution was added dropwise into a solution of potassium cuprotetracyanide [prepared by dropwise addition of a solution of KCN (10 g, 15.38 mmol) in water (18 mL) to a solution of CuSO$_4$ (7 g, 43.8 mmol) in water (12 mL) at 70° C.] at 50° C. for 1 h. The reaction mixture was acidified with 1.5 N HCl solution and the product was extracted with EtOAc. The combined extracts were washed with water and brine, dried over anhydrous sodium sulfate, and concentrated under reduced pressure. The crude product was purified by column chromatography (silica 60-120 mesh, eluant 1-2% MeOH in CHCl$_3$) to get 2-chloro-5-cyanobenzoic acid (1.8 g, yield 34%). $^1$H NMR (400 MHz, DMSO-d$_6$) δ 13.92 (br s, 1H), 8.24 (d, J=2.1 Hz, 1H), 8.02-7.99 (d, J=8.4 Hz, 2.1 Hz, 1H), 7.80-7.78 (d, J=8.2 Hz, 1H). MS (ESI) m/z: Calculated for C$_8$H$_4$ClNO$_2$: 180.99. found: 179.6 (M−H)$^−$.

2-Chloro-5-cyano-N-(2-(2-(4-fluorophenyl)oxazol-4-yl)-2-methylpropyl)benzamide

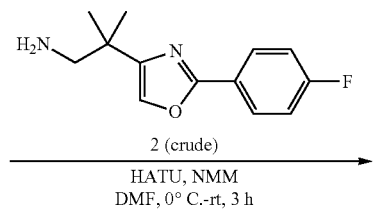

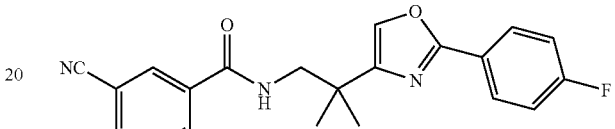

This compound was synthesized from 2-(2-(4-fluorophenyl)oxazol-4-yl)-2-methylpropan-1-amine and 2-chloro-5-cyanobenzoic acid as described in example 8 step 6 (300 mg, yield 44%). $^1$H NMR (400 MHz, CDCl$_3$) δ 8.02 (d, J=2.0 Hz, 1H), 7.98-7.95 (m, 2H), 7.66-7.63 (m, 1H), 7.56-7.54 (d, J=8.3 Hz, 1H), 7.48 (s, 1H), 7.39 (m, 1H), 7.17-7.13 (t, J=8.8 Hz, 2H), 3.68-3.66 (d, J=5.8 Hz, 2H), 1.41 (s, 6H). MS (ESI) m/z: Calculated for C$_{21}$H$_{17}$ClFN$_3$O$_2$: 397.10. found: 396.4 (M−H)$^−$.

4-Chloro-3-((2-(2-(4-fluorophenyl)oxazol-4-yl)-2-methylpropyl)carbamoyl)benzohydrazonic acid

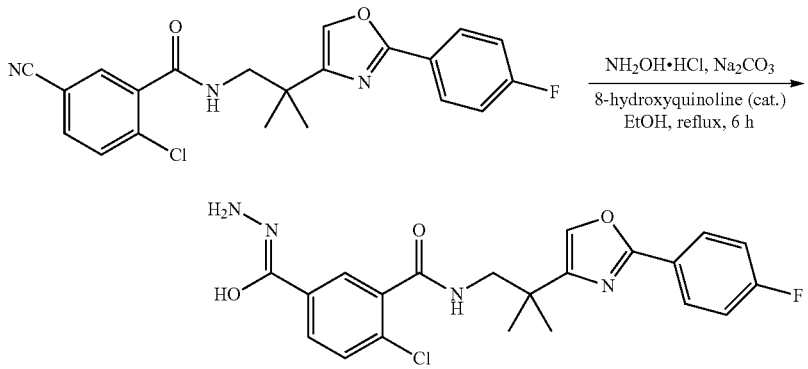

This compound was synthesized from 2-chloro-5-cyano-N-(2-(2-(4-fluorophenyl)oxazol-4-yl)-2-methylpropyl)benzamide as described in example 1 step 4 (230 mg, crude) and it was carried through without further purification. $^1$H NMR (300 MHz, MeOD) δ 8.06-8.02 (m, 2H), 7.74-7.73 (m, 2H), 7.67-7.63 (m, 1H), 7.46-7.43 (d, J=8.3 Hz, 1H), 7.24-7.18 (t, J=8.8 Hz, 2H), 3.61 (s, 2H), 1.40 (s, 6H). MS (ESI) m/z: Calculated for C$_{21}$H$_{20}$ClFN$_4$O$_3$: 430.12. found: 429.4 (M−H)$^−$.

2-Chloro-N-(2-(2-(4-fluorophenyl)oxazol-4-yl)-2-methylpropyl)-5-(5-(trifluoromethyl)-1,2,4-oxadiazol-3-yl)benzamide

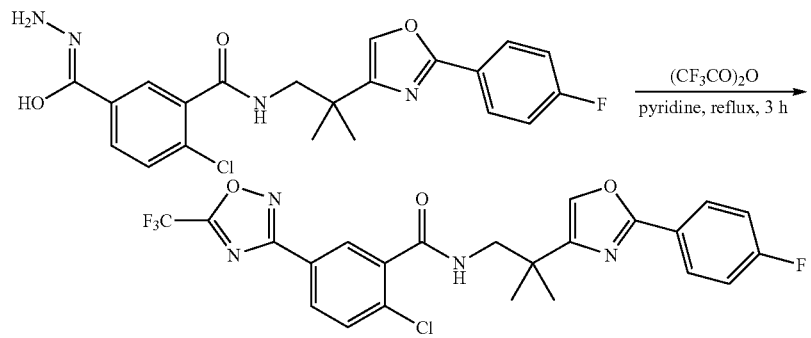

This compound was synthesized from 4-chloro-3-((2-(2-(4-fluorophenyl)oxazol-4-yl)-2-methylpropyl)carbamoyl)benzohydrazonic acid as described in example 1 step 5 (100 mg, yield 37%). $^1$H NMR (400 MHz, MeOD) δ 8.15-8.12 (m, 2H), 8.07-8.04 (m, 2H), 7.76 (s, 1H), 7.68-7.66 (m, 1H), 7.23-7.18 (m, 2H), 3.67 (s, 2H), 1.43 (s, 6H). MS (ESI) m/z: Calculated for $C_{23}H_{17}ClF_4N_4O_3$: 508.09. found: 509.1 (M+H)$^+$.

Example 109

N-(2-(2-(4-Fluorophenyl)oxazol-4-yl)-2-methylpropyl)-3-(5-(trifluoromethyl)-1,2,4-oxadiazol-3-yl)benzamide

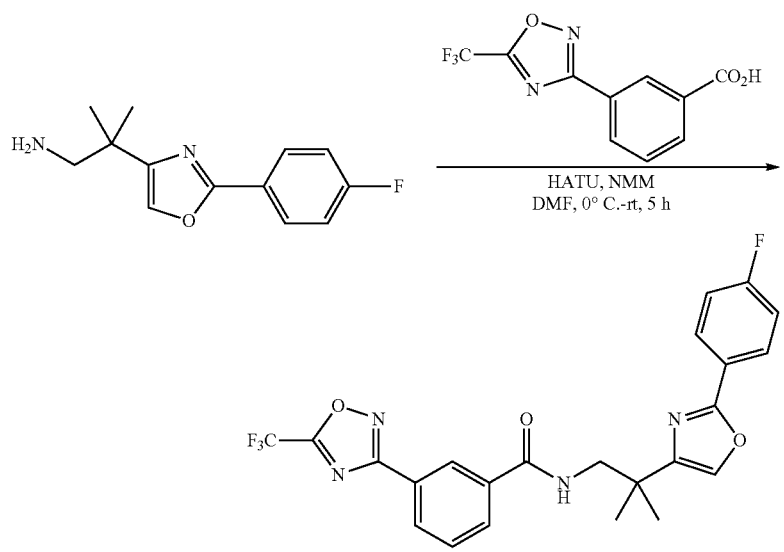

This compound was synthesized from 2-(2-(4-fluorophenyl)oxazol-4-yl)-2-methylpropan-1-amine and 3-(5-(trifluoromethyl)-1,2,4-oxadiazol-3-yl)benzoic acid as described in example 8 step 6 (18 mg, yield 12%). $^1$H NMR (400 MHz, MeOD) δ 8.55 (s, 1H), 8.29 (d, J=7.8 Hz, 1H), 8.09-8.05 (m, 3H), 7.78 (s, 1H), 7.71-7.68 (t, J=7.8 Hz, 1H), 7.24-7.19 (m, 2H), 3.66 (s, 2H), 1.41 (s, 6H). MS (ESI) m/z: Calculated for $C_{23}H_{16}F_4N_4O_3$: 474.13. found: 475.1 (M+H)$^+$.

Example 110

1-(2-(4-Fluorophenyl)oxazol-4-yl)ethanone

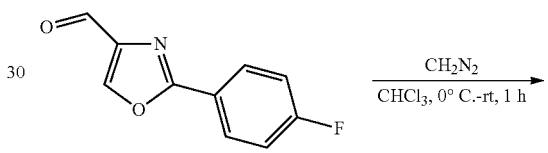

-continued

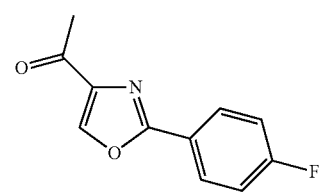

A solution of 2-(4-fluorophenyl)oxazole-4-carbaldehyde (400 mg, 2.09 mmol) in dry chloroform (5 mL) was cooled to 0° C. and a freshly prepared solution of diazomethane in ether (20 mL) was added. The reaction mixture was stirred for 1 h and quenched with 10% aqueous NaHCO$_3$ solution. The crude product was extracted with CH$_2$Cl$_2$ and the combined extracts were dried over anhydrous sodium sulfate, and concentrated under reduced pressure. The crude product was purified by column chromatography (silica gel 60-120 mesh, eluent 5-8% EtOAc in petroleum ether) to afford 1-(2-(4-fluorophenyl)oxazol-4-yl)ethanone (250 mg, yield 58%) as a white solid. $^1$H NMR (400 MHz, CDCl$_3$) δ 8.25 (s, 1H), 8.12-8.09 (m, 2H), 7.21-7.17 (t, J=8.7 Hz, 2H), 2.60 (s, 3H). MS (ESI) m/z: Calculated for C$_{11}$H$_8$FNO$_2$: 205.05. found: 205.9 (M+H)$^+$.

3-(2-(4-Fluorophenyl)oxazol-4-yl)-3-hydroxypropanenitrile

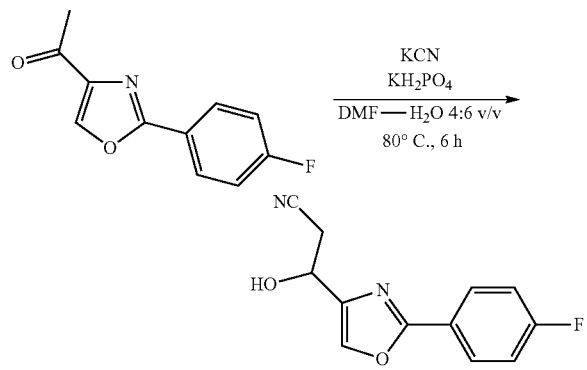

A solution of 1-(2-(4-fluorophenyl)oxazol-4-yl)ethanone (250 mg, 1.22 mmol) in DMF-H$_2$O (7 mL; 2:5 v/v) was cooled to 0° C. and KH$_2$PO$_4$ (327 mg, 2.4 mmol) was added, followed by KCN (116 mg, 1.8 mmol). The reaction mixture was stirred at 80° C. 10 h and then diluted with water. The organic product was extracted with EtOAc and the combined extracts were washed with H$_2$O and brine, dried over anhydrous sodium sulfate, and concentrated under reduced pressure. The crude product was purified by column chromatography (silica gel 60-120 mesh, eluent 8-12% EtOAc in petroleum ether) to afford 3-(2-(4-fluorophenyl)oxazol-4-yl)-3-hydroxypropanenitrile (60 mg, yield 21%) as a light yellow solid. $^1$H NMR (300 MHz, DMSO-d$_6$) δ 8.11 (d, J=0.7 Hz, 1H), 8.03-7.98 (dd, J=8.9 Hz, 5.4 Hz, 2H), 7.40-7.34 (t J=8.9 Hz, 2H), 6.13-6.12 (d, J=5.3 Hz, 1H), 4.93-4.87 (m, 1H), 2.98-2.93 (dd, J=8.9 Hz, 5.8 Hz, 2H). MS (ESI) m/z: Calculated for C$_{12}$H$_9$FN$_2$O$_2$: 232.06. found: 233.0 (M+H)$^+$.

3-Amino-1-(2-(4-fluorophenyl)oxazol-4-yl)propan-1-ol

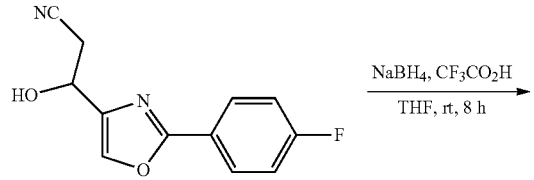

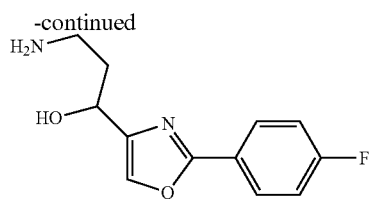

This compound was synthesized from 3-(2-(4-fluorophenyl)oxazol-4-yl)-3-hydroxypropanenitrile as described in example 94 step 6 (110 mg, crude) and it was carried through without further purification. MS (ESI) m/z: Calculated for C$_{12}$H$_{13}$FN$_2$O$_2$: 236.10. found: 237.0 (M+H)$^+$.

N-(3-(2-(4-Fluorophenyl)oxazol-4-yl)-3-hydroxypropyl)-3-(5-(trifluoromethyl)-1,2,4-oxadiazol-3-yl)benzamide

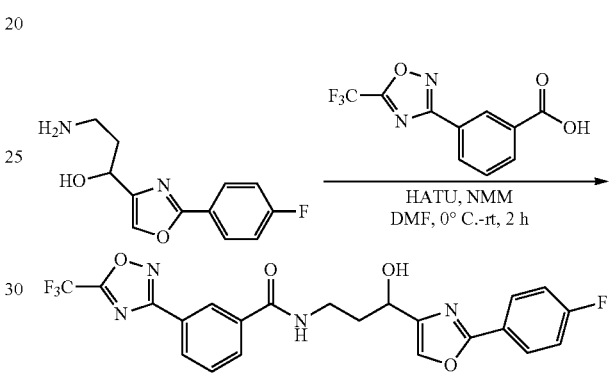

This compound was synthesized from 3-amino-1-(2-(4-fluorophenyl)oxazol-4-yl)propan-1-ol and 3-(5-(trifluoromethyl)-1,2,4-oxadiazol-3-yl)benzoic acid as described in example 8 step 6 (35 mg, yield 19%) as a white solid. $^1$H NMR (400 MHz, DMSO-d$_6$) 8.80-8.77 (t, J=5.3 Hz, 1H), 8.51 (s, 1H), 8.20-8.18 (d, J=7.6 Hz, 1H), 8.13-8.11 (d, J=7.9 Hz, 1H), 8.00 (s, 1H), 7.99-7.96 (dd, J=8.8 Hz, 5.5 Hz, 2H), 7.72-7.68 (t, J=7.8 Hz, 1H), 7.37-7.32 (t, J=8.8 Hz, 2H), 5.44-5.43 (d, J=5.2 Hz, 1H), 4.69-4.65 (m, 1H), 3.47-3.42 (m, 2H), 2.17-2.08 (m, 1H), 1.99-1.90 (m, 1H). MS (ESI) m/z: Calculated for C$_{22}$H$_{16}$F$_4$N$_4$O$_4$: 476.11. found: 477.1 (M+H)$^+$.

Example 111

2-(4-Bromophenyl)-4-(chloromethyl)oxazole

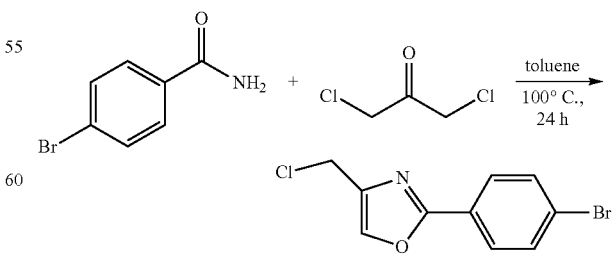

This compound was synthesized from 4-bromobenzamide and 1,3-dichloroacetone as described in example 74 step 1 (1.5 g, yield 14%) as a white solid. $^1$H NMR (400 MHz, CDCl$_3$) δ 7.92-7.89 (d, J=8.8 Hz, 2H), 7.71 (s, 1H), 7.61-7.59 (d, J=8.8 Hz, 2H), 4.57 (s, 2H). MS (ESI) m/z: Calculated for C$_{10}$H$_7$BrClNO: 272.94. found: 273.8 (M+H)$^+$.

2-(2-(4-Bromophenyl)oxazol-4-yl)acetonitrile

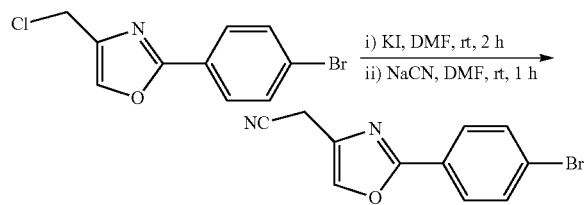

This compound was synthesized from 2-(4-bromophenyl)-4-(chloromethyl)oxazole as described in example 71 step 2 (1.4 g, yield 76%) as a off-white solid. $^1$H NMR (300 MHz, CDCl$_3$) δ 7.90-7.88 (d, J=8.8 Hz, 2H), 7.75-7.74 (t, J=1.3 Hz, 1H), 7.63-7.60 (d, J=8.8 Hz, 2H), 3.73 (d, J=1.3 Hz, 2H). MS (ESI) m/z: Calculated for C$_{11}$H$_7$BrN$_2$O: 261.97. found: 262.9 (M+H)$^+$.

2-(2-(4-Bromophenyl)oxazol-4-yl)ethanamine

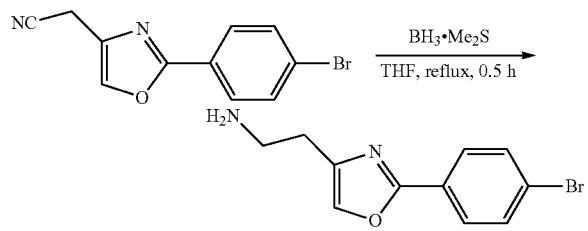

This compound was synthesized from 2-(2-(4-bromophenyl)oxazol-4-yl)acetonitrile as described in example 42 step 1 (0.4 g, yield 56%) as a yellow liquid. $^1$H NMR (300 MHz, DMSO-d$_6$) δ 8.02 (m, 1H), 7.89-7.86 (d, J=8.6 Hz, 2H), 7.73-7.71 (d, J=8.6 Hz, 2H), 2.96-2.91 (m, 2H), 2.73-2.68 (m, 2H). MS (ESI) m/z: Calculated for C$_{11}$H$_{11}$BrN$_2$O: 266.01. found: 267.1 (M+H)$^+$.

N-(2-(2-(4-Bromophenyl)oxazol-4-yl)ethyl)-2,2,2-trifluoroacetamide

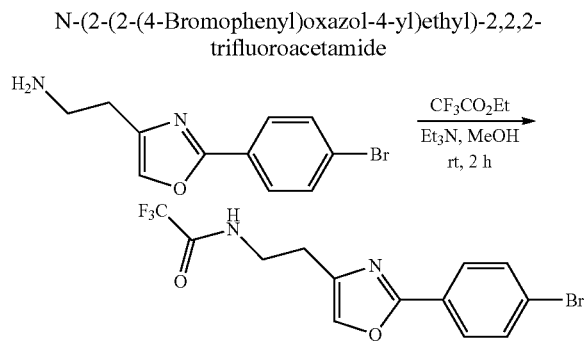

Triethylamine (0.31 mL, 2.24 mmol) was added to a solution of 2-(2-(4-bromophenyl)oxazol-4-yl)ethanamine (0.4 g, 1.49 mmol) in dry methanol (20 mL), followed by ethyl trifluoro acetate (0.27 mL, 2.25 mmol) dropwise at 0° C. The reaction mixture was slowly warmed to room temperature and further stirred for 2 h. The reaction mixture was then concentrated under reduced pressure. The reaction mixture was diluted with EtOAc and washed with water and brine, dried over anhydrous sodium sulfate, and concentrated under reduced pressure. The crude product was purified by column chromatography (silica gel 60-120 mesh, eluent 1% MeOH in CHCl$_3$) to afford N-(2-(2-(4-bromophenyl)oxazol-4-yl)ethyl)-2,2,2-trifluoroacetamide (0.26 g, yield 48%) as an off-white solid. $^1$H NMR (300 MHz, CDCl$_3$) δ 7.98-7.95 (d, J=8.6 Hz, 2H), 7.68-7.65 (d, J=8.6 Hz, 2H), 7.61 (m, 1H), 3.78-3.72 (m, 2H), 2.96-2.92 (t, J=6.1 Hz, 2H). MS (ESI) m/z: Calculated for C$_{13}$H$_{10}$BrF$_3$N$_2$O$_2$: 361.99. found: 362.5 (M+H)$^+$.

N-(2-(2-(4-Cyanophenyl)oxazol-4-yl)ethyl)-2,2,2-trifluoroacetamide

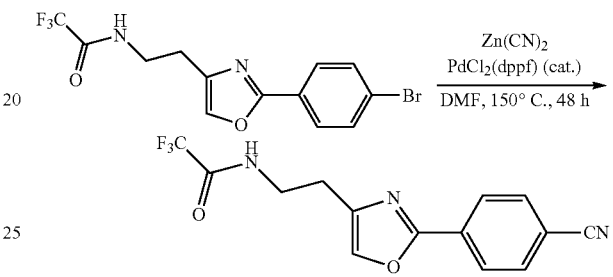

N-(2-(2-(4-Bromophenyl)oxazol-4-yl)ethyl)-2,2,2-trifluoroacetamide (200 mg, 0.55 mmol) was dissolved in dry DMF (10 mL) and the solution was purged with argon for 10 min. Zn(CN)$_2$ (97 mg, 0.83 mmol) and PdCl$_2$(dppf) (302 mg, 0.04 mmol) were added to the reaction mixture and heated to 150° C. for 48 h. The reaction mixture was filtered through Celite and the filtrate was concentrated under reduced pressure. The residue was diluted with water and the product was extracted with EtOAc. The combined extracts were dried over anhydrous sodium sulfate and concentrated under reduced pressure to get N-(2-(2-(4-cyanophenyl)oxazol-4-yl)ethyl)-2,2,2-trifluoroacetamide (150 mg), which was used for the next step without further purification. MS (ESI) m/z: Calculated for C$_{14}$H$_{10}$F$_3$N$_3$O$_2$: 309.07. found: 307.9 (M−H)$^-$.

4-(4-(2-Aminoethyl)oxazol-2-yl)benzonitrile

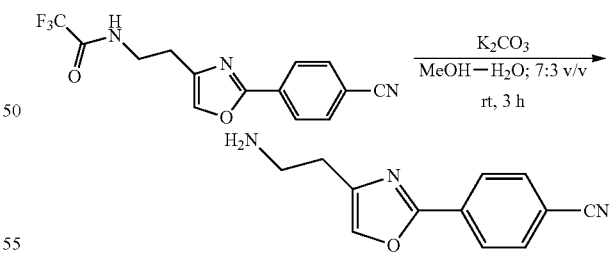

K$_2$CO$_3$ (0.20 g, 1.45 mmol) was added portionwise to a solution of N-(2-(2-(4-cyanophenyl)oxazol-4-yl)ethyl)-2,2,2-trifluoroacetamide (0.15 g, 0.49 mmol) in dry methanol:water (10 mL, 7:3 v/v). The reaction mixture was stirred at room temperature for 3 h and then diluted with water. The crude product was extracted with chloroform. The organic layer was dried over anhydrous Na$_2$SO$_4$ and concentrated under reduced pressure to get 4-(4-(2-aminoethyl)oxazol-2-yl)benzonitrile (80 mg), which was used for the next step without further purification. MS (ESI) m/z: Calculated for C$_{12}$H$_{11}$N$_3$O: 213.09. found: 214.0 (M+H)$^+$.

N-(2-(2-(4-Cyanophenyl)oxazol-4-yl)ethyl)-5-(5-(trifluoromethyl)-1,2,4-oxadiazol-3-yl)nicotinamide

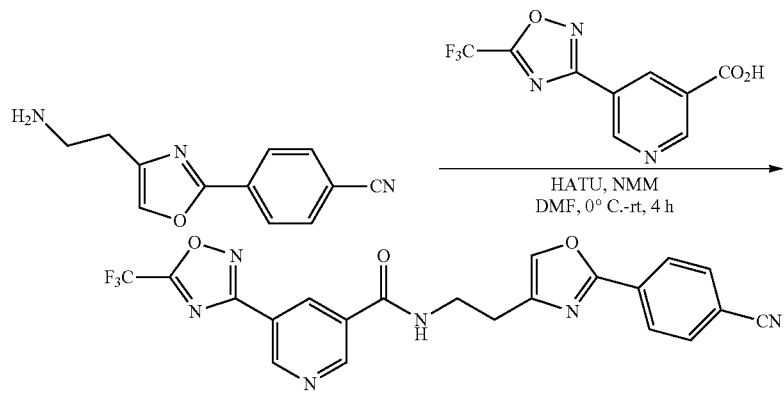

This compound was synthesized from 4-(4-(2-aminoethyl) oxazol-2-yl)benzonitrile and 5-(5-(trifluoromethyl)-1,2,4-oxadiazol-3-yl)nicotinic acid as described in example 8 step 6 (30 mg, yield 23%) as an off white solid. $^1$H NMR (400 MHz, CDCl$_3$) δ 9.69 (m, 1H), 9.47 (m, 1H), 9.18 (m, 1H), 8.18-8.16 (d, J=8.3 Hz, 2H), 7.78-7.76 (d, J=8.8 Hz, 2H), 7.71 (s, 1H), 3.92-3.91 (m, 2H), 3.05-3.02 (t, J=6.0 Hz, 2H). MS (ESI) m/z: Calculated for C$_{21}$H$_{13}$F$_3$N$_6$O$_3$: 454.10. found: 453.2 (M−H)$^-$.

Example 112

4-(Chloromethyl)-2-(2-fluorophenyl)oxazole

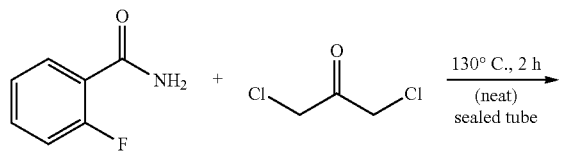

A mixture of 2-fluorobenzamide (500 mg, 3.59 mmol) and 1,3-dichloroacetone (1.82 g, 14.36 mmol) was heated to 130° C. for 2 h in a sealed tube. The reaction mixture was diluted with EtOAc and washed with water and brine. Solvent was removed under reduced pressure and the crude product was purified by column chromatography (silica gel 60-120 mesh, eluent 2-3% EtOAc in petroleum ether) to afford 4-(chloromethyl)-2-(2-fluorophenyl)oxazole (500 mg, yield 66%) as a white solid. $^1$H NMR (300 MHz, CDCl$_3$) δ 8.08-8.02 (td, J=7.6 Hz, 1.6 Hz, 1H), 7.78 (s, 1H), 7.50-7.43 (m, 1H), 7.28-7.18 (m, 2H), 4.61 (d, J=0.7 Hz, 2H). MS (ESI) m/z: Calculated for C$_{10}$H$_7$ClFNO: 211.02. found: 211.9 (M+H)$^+$.

2-(2-(2-Fluorophenyl)oxazol-4-yl)acetonitrile

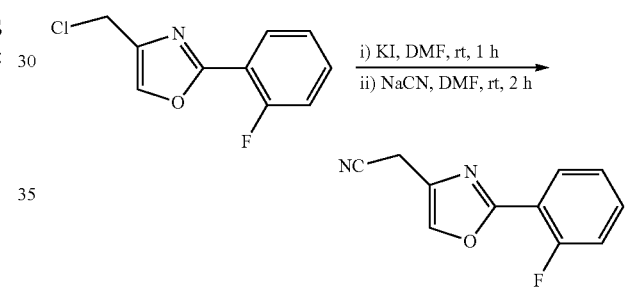

This compound was synthesized from 4-(chloromethyl)-2-(2-fluorophenyl)oxazole as described in example 71 step 2 (0.2 g, yield 29%) as a white solid. $^1$H NMR (300 MHz, CDCl$_3$) δ 8.05-8.00 (td, J=7.6 Hz, 1.8 Hz, 1H), 7.82-7.81 (t, J=1.3 Hz, 1H), 7.50-7.45 (m, 1H), 7.30-7.20 (m, 2H), 3.77 (d, J=1.1 Hz, 2H). MS (ESI) m/z: Calculated for C$_{11}$H$_7$FN$_2$O: 202.05. found: 202.9 (M+H)$^+$.

2-(2-(2-Fluorophenyl)oxazol-4-yl)ethanamine

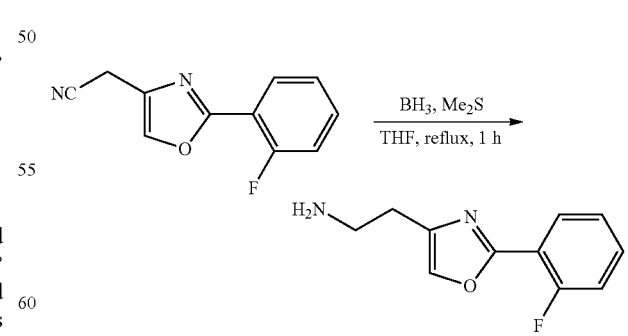

This compound was synthesized from 2-(2-(2-fluorophenyl)oxazol-4-yl)acetonitrile as described in example 42 step 1 (100 mg, crude) and it was carried through without further purification. MS (ESI) m/z: Calculated for C$_{11}$H$_{11}$FN$_2$O: 206.09. found: 207.0 (M+H)$^+$.

N-(2-(2-(2-Fluorophenyl)oxazol-4-yl)ethyl)-5-(5-(trifluoromethyl)-1,2,4-oxadiazol-3-yl)nicotinamide

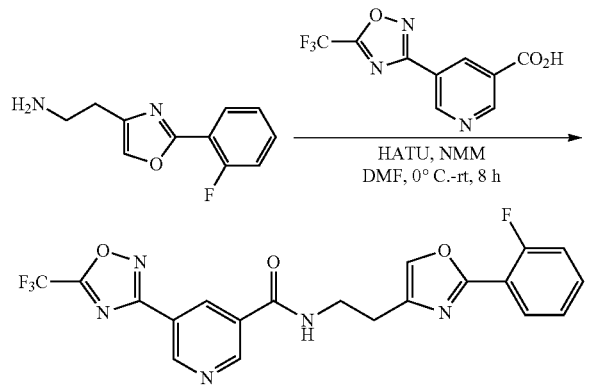

This compound was synthesized from 2-(2-(2-fluorophenyl)oxazol-4-yl)ethanamine and 5-(5-(trifluoromethyl)-1,2,4-oxadiazol-3-yl)nicotinic acid as described in example 8 step 6 (10 mg, yield 6%) as a white solid. $^1$H NMR (400 MHz, MeOD) δ 9.39 (d, J=2.0 Hz, 1H), 9.20 (d, J=2.0 Hz, 1H), 8.90-8.89 (t, J=2.0 Hz, 1H), 8.03-7.99 (td, J=7.7 Hz, 1.8 Hz, 1H), 7.89 (s, 1H), 7.56-7.51 (m, 1H), 7.33-7.25 (m, 2H), 3.80-3.76 (t, J=6.9 Hz, 2H), 3.00-2.97 (t, J=6.9 Hz, 2H). MS (ESI) m/z: Calculated for $C_{20}H_{13}F_4N_5O_3$: 447.10. found: 448.1 (M+H)$^+$.

Example 113

1-(5-Bromothiophen-2-yl)-2,2-difluoroethanone

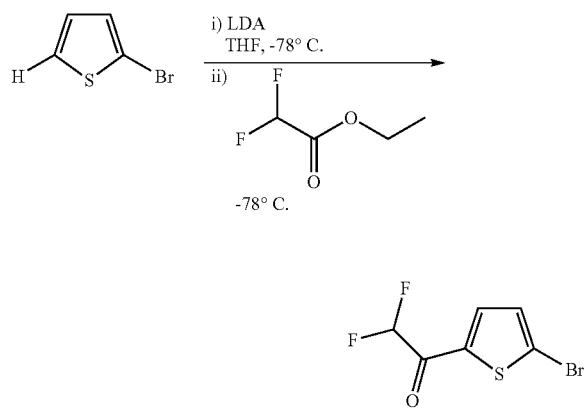

A solution of 2-bromothiophene (0.5 g, 3.00 mmol) in dry THF (5 mL) was cooled to −78° C. and freshly prepared lithium diisopropylamide (prepared from diisopropyl amine (0.5 mL, 3.60 mmol) and nBuLi (2.3 mL, 3.60 mmol, 1.6M in THF) was added dropwise. The reaction mixture was stirred at −78° C. for 1 h. Ethyl difluoro acetate (409 mg, 3.30 mmol) was added dropwise at −78° C. and the reaction mixture was stirred for 1 h, then slowly warmed up to room temperature and quenched with saturated NH$_4$Cl solution. The organic product was extracted with EtOAc and dried over anhydrous sodium sulfate. The solvent was concentrated under reduced pressure to get 1-(5-bromothiophen-2-yl)-2,2-difluoroethanone (500 mg, yield 69%). $^1$H NMR (400 MHz, CDCl$_3$) δ 7.77-7.75 (m, 1H), 7.21-7.20 (d, J=4.1 Hz, 1H), 6.27-6.00 (m, 1H).

3-(5-(2,2-Difluoroacetyl)thiophen-2-yl)benzoic acid

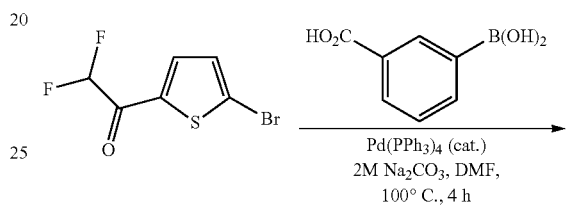

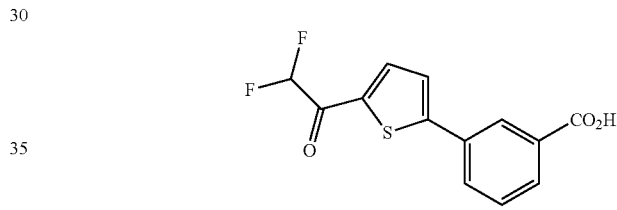

This compound was synthesized from 1-(5-bromothiophen-2-yl)-2,2-difluoroethanone as described in example 88 step 3 (300 mg, yield 51%) as a brown solid. $^1$H NMR (300 MHz, DMSO-d$_6$) δ 13.24 (br s, 1H), 8.28 (s, 1H), 8.15-8.14 (d, J=4.2 Hz, 1H), 8.09-8.06 (m, 1H), 8.01-7.99 (m, 1H), 7.88-7.87 (d, J=4.2 Hz, 1H), 7.65-7.60 (t, J=7.8 Hz, 1H), 7.20-6.85 (m, 1H). MS (ESI) m/z: Calculated for $C_{13}H_8F_2O_3S$: 282.02. found: 280.8 (M−H)$^-$.

3-(5-(2,2-Difluoroacetyl)thiophen-2-yl)-N-(2-(2-(4-fluorophenyl)oxazol-4-yl)-2-methylpropyl)benzamide

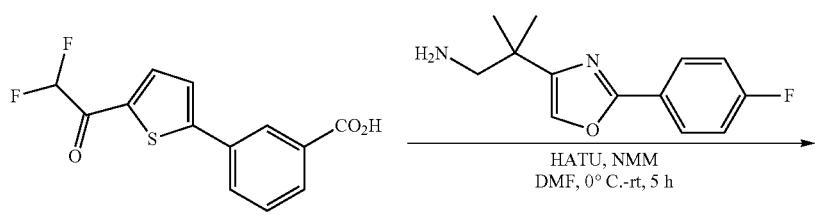

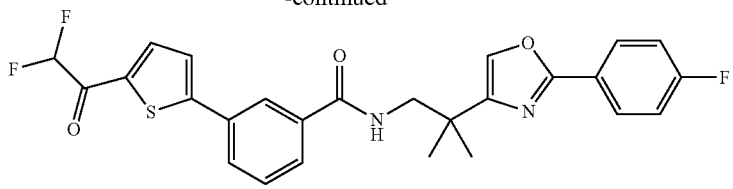

This compound was synthesized from 2-(2-(4-fluorophenyl)oxazol-4-yl)-2-methylpropan-1-amine and 3-(5-(2,2-difluoroacetyl)thiophen-2-yl)benzoic acid as described in example 8 step 6 (60 mg, yield 34%). $^1$H NMR (400 MHz, DMSO-$d_6$) δ 8.51-8.48 (t, J=6.2 Hz, 1H), 8.19-8.15 (m, 2H), 8.02-7.97 (m, 3H), 7.90-7.88 (m, 1H), 7.84-7.83 (d, J=4.3 Hz, 1H), 7.61-7.57 (t, J=7.8 Hz, 1H), 7.35-7.31 (t, J=8.8 Hz, 2H), 7.16-6.90 (m, 1H), 3.52-3.50 (d, J=6.4 Hz, 2H), 1.29 (s, 6H). MS (ESI) m/z: Calculated for $C_{26}H_{21}F_3N_2O_3S$: 498.12. found: 499.1 (M+H)$^+$.

Example 114

1-(2-Bromothiazol-5-yl)-2,2,2-trifluoroethanol

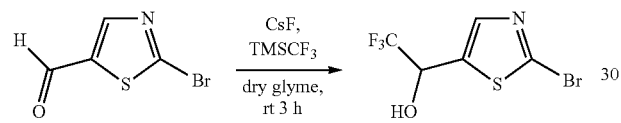

This compound was synthesized from 2-bromothiazole-5-carbaldehyde as described in example 88 step 1 (0.6 g, yield 44%). $^1$H NMR (300 MHz, CDCl$_3$) δ 7.63 (s, 1H), 5.37-5.29 (m, 1H), 3.54 (d, J=5.0 Hz, 1H).

1-(2-Bromothiazol-5-yl)-2,2,2-trifluoroethanone

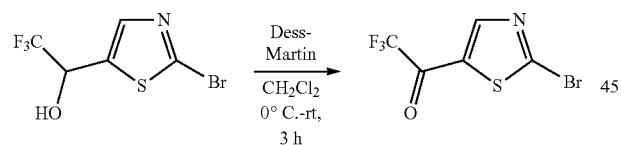

This compound was synthesized from 1-(2-bromothiazol-5-yl)-2,2,2-trifluoroethanol as described in example 47 step 2 (0.35 g, yield 59%). $^1$H NMR (300 MHz, CDCl$_3$) δ 8.32 (m, 1H). MS (ESI) m/z: Calculated for $C_5HBrF_3NOS$: 260.89. found: 261.0 (M+H)$^+$.

3-(5-(2,2,2-Trifluoroacetyl)thiazol-2-yl)benzoic acid

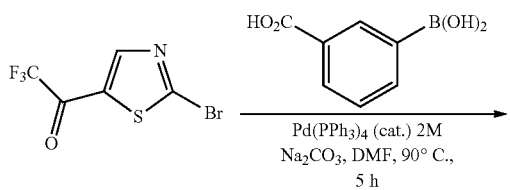

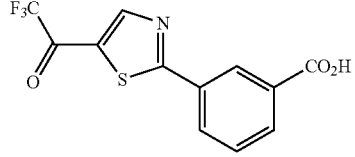

This compound was synthesized from 1-(2-bromothiazol-5-yl)-2,2,2-trifluoroethanone as described in example 88 step 3 (120 mg, crude) and it was carried through without further purification. MS (ESI) m/z: Calculated for $C_{12}H_6F_3NO_3S$: 301.00. found: 299.9 (M−H)$^-$.

N-(2-(2-(4-Fluorophenyl)oxazol-4-yl)-2-methylpropyl)-3-(5-(2,2,2-trifluoroacetyl)thiazol-2-yl)benzamide

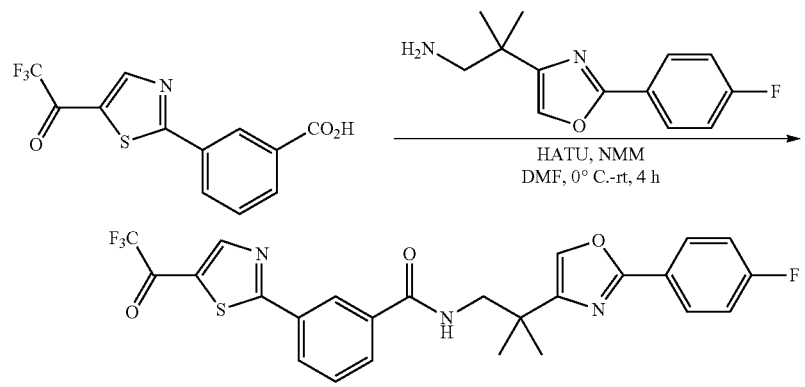

This compound was synthesized from 2-(2-(4-fluorophenyl)oxazol-4-yl)-2-methylpropan-1-amine and 3-(5-(2,2,2-trifluoroacetyl)thiazol-2-yl)benzoic acid as described in example 8 step 6 (7 mg, yield 3%). ¹H NMR (400 MHz, DMSO-d₆) δ 8.56-8.53 (t, J=5.5 Hz, 1H), 8.35 (m, 1H), 8.28 (m, 2H), 8.10-8.08 (m, 1H), 8.02-8.00 (m, 2H), 7.94 (m, 1H), 7.61-7.57 (t, J=7.8 Hz, 1H), 7.35-7.31 (t, J=8.7 Hz, 2H), 3.51-3.50 (d, J=5.8 Hz, 2H), 1.29 (s, 6H). MS (ESI) m/z: Calculated for $C_{26}H_{19}F_4N_3O_3S$: 517.11. found: 516.1 (M−H)⁻.

Example 115

4-(((tert-Butyldiphenylsilyl)oxy)methyl)-2-phenyl-1H-imidazole

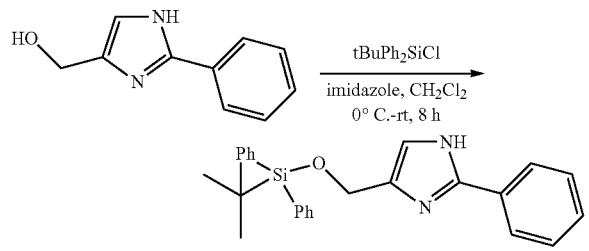

ᵗBuPh₂SiCl (5.5 g, 19.9 mmol) was added dropwise to a suspension of 2-phenyl-1H-imidazole-4-methanol (2.9 g, 16.65 mmol) and imidazole (1.7 g, 24.97 mmol) in dry CH₂Cl₂ (60 mL) at 0° C. The reaction mixture was allowed to warm up to room temperature and stirred for 8 h. The reaction mixture was diluted with CH₂Cl₂ and the organic layer was washed with 10% NaHCO₃ solution, water and brine. The organic layer was dried over anhydrous Na₂SO₄ and concentrated under reduced pressure to yield 4-(((tert-butyldiphenylsilyl)oxy)methyl)-2-phenyl-1H-imidazole (5.7 g, yield 83%), which was carried through without further purification. ¹H NMR (300 MHz, CDCl₃) δ 7.77-7.69 (m, 6H), 7.46-7.37 (m, 9H), 6.95 (m, 1H), 4.81 (s, 2H), 1.09 (s, 9H). MS (ESI) Calculated for $C_{26}H_{28}N_2OSi$: 412.20. found: 413.3 (M+H)⁺.

4-(((tert-Butyldiphenylsilyl)oxy)methyl)-1-methyl-2-phenyl-1H-imidazole

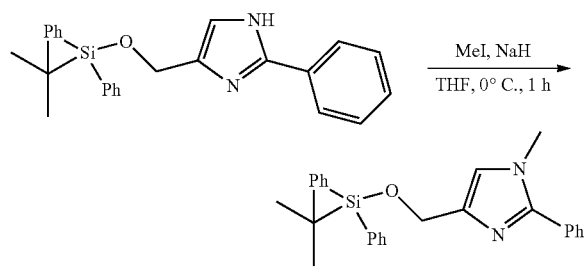

This compound was synthesized from 4-(((tert-butyldiphenylsilyl)oxy)methyl)-2-phenyl-1H-imidazole as described in example 1 step 2 (1.25 g, yield 21%) as a yellow viscous liquid. ¹H NMR (400 MHz, CDCl₃) δ 7.82-7.75 (m, 3H), 7.69-7.67 (m, 4H), 7.61-7.60 (m, 2H), 7.46-7.41 (m, 6H), 6.95 (s, 1H), 5.14 (d, J=1.3 Hz, 2H), 3.88 (s, 3H), 1.13 (s, 9H). MS (ESI) m/z: Calculated for $C_{27}H_{30}N_2OSi$: 426.21. found: 427.3 (M+H)⁺.

(1-Methyl-2-phenyl-1H-imidazol-4-yl)methanol

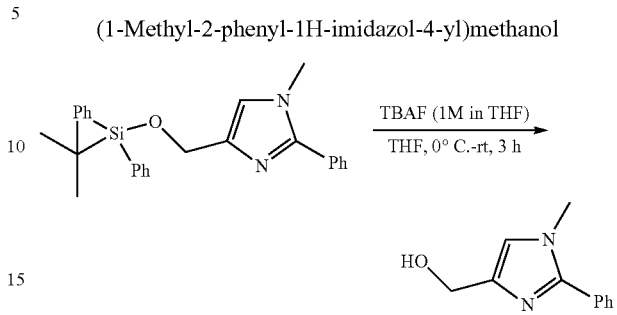

A solution of 4-(((tert-butyldiphenylsilyl)oxy)methyl)-1-methyl-2-phenyl-1H-imidazole (1.25 g, 2.93 mmol) in dry THF (25 mL) was cooled to 0° C. and tetrabutylammonium fluoride (5.9 mL, 5.86 mmol, 1M in THF) was added dropwise. The reaction mixture was allowed to warm up to room temperature and further stirred for 3 h. The reaction mixture was quenched with brine and extracted with EtOAc. The organic layer was dried over anhydrous Na₂SO₄ and concentrated under reduced pressure. The crude product was purified by column chromatography (silica 60-120 mesh, eluant 2-4% MeOH in CH₂Cl₂) to get (1-methyl-2-phenyl-1H-imidazol-4-yl)methanol (0.26 mg, yield 47%) as a white solid. ¹H NMR (400 MHz, DMSO-d₆) δ 7.68-7.66 (m, 2H), 7.50-7.41 (m, 3H), 7.11 (s, 1H), 4.92 (br s, 1H), 4.37 (s, 2H), 3.71 (s, 3H). MS (ESI) m/z: Calculated for $C_{11}H_{12}N_2O$: 188.09. found: 188.9 (M+H)⁺.

4-(Chloromethyl)-1-methyl-2-phenyl-1H-imidazole

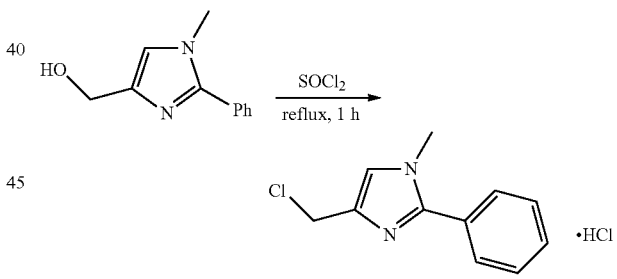

This compound was synthesized from (1-methyl-2-phenyl-1H-imidazol-4-yl)methanol as described in example 93 step 3 (0.28 g, crude) as hydrochloride salt as a brown solid. ¹H NMR (300 MHz, DMSO-d₆) δ 7.90 (s, 1H), 7.82-7.80 (m, 2H), 7.70-7.66 (m, 3H), 4.93 (s, 2H), 3.84 (s, 3H).

2-(1-Methyl-2-phenyl-1H-imidazol-4-yl)acetonitrile

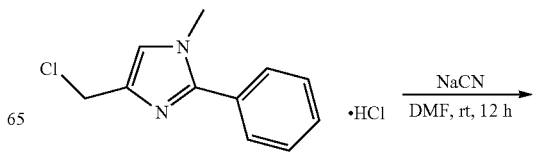

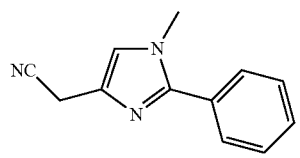

This compound was synthesized from 4-(chloromethyl)-1-methyl-2-phenyl-1H-imidazole as described in example 77 step 1 (120 mg, yield 44%) as a brown liquid. $^1$H NMR (300 MHz, CDCl$_3$) δ 7.61-7.58 (m, 2H), 7.49-7.43 (m, 3H), 7.02 (s, 1H), 3.75 (d, J=0.9 Hz, 2H), 3.73 (s, 3H). MS (ESI) m/z: Calculated for C$_{12}$H$_{11}$N$_3$: 197.10. found: 197.9 (M+H)$^+$.

2-(1-Methyl-2-phenyl-1H-imidazol-4-yl)propanenitrile

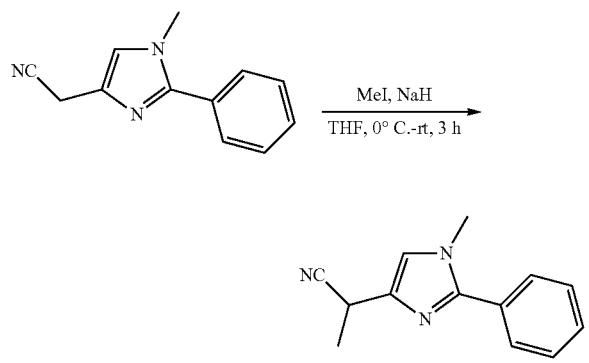

This compound was synthesized from 2-(1-methyl-2-phenyl-1H-imidazol-4-yl)acetonitrile as described in example 1 step 2 (60 mg, yield 47%) as light yellow oil. $^1$H NMR (300 MHz, CDCl$_3$) δ 7.62-7.59 (m, 2H), 7.47-7.45 (m, 3H), 7.01 (s, 1H), 4.01-3.94 (q, J=7.1 Hz, 1H), 3.72 (s, 3H), 1.71-1.69 (d, J=7.2 Hz, 3H). MS (ESI) m/z: Calculated for C$_{13}$H$_{13}$N$_3$: 211.11. found: 212.0 (M+H)$^+$.

2-(1-Methyl-2-phenyl-1H-imidazol-4-yl)propan-1-amine

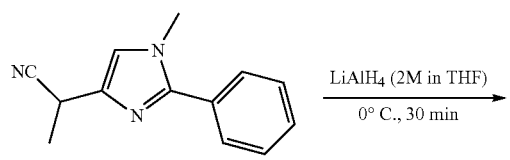

This compound was synthesized from 2-(1-methyl-2-phenyl-1H-imidazol-4-yl)propanenitrile as described in example 1 step 3 (60 mg, crude) and it was carried through without further purification. MS (ESI) m/z: Calculated for C$_{13}$H$_{17}$N$_3$: 215.14. found: 216.0 (M+H)$^+$.

N-(2-(1-Methyl-2-phenyl-1H-imidazol-4-yl)propyl)-5-(5-(trifluoromethyl)-1,2,4-oxadiazol-3-yl)nicotinamide

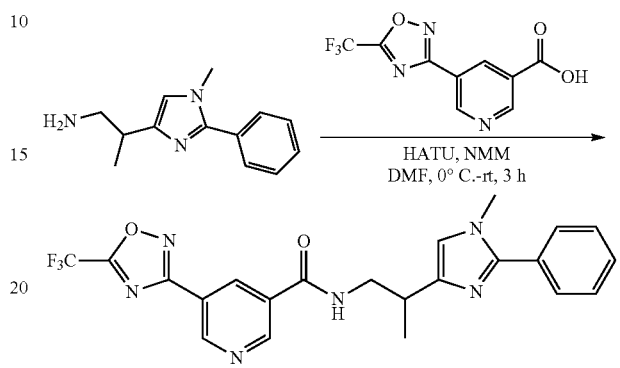

This compound was synthesized from 2-(1-methyl-2-phenyl-1H-imidazol-4-yl)propan-1-amine and 5-(5-(trifluoromethyl)-1,2,4-oxadiazol-3-yl)nicotinic acid as described in example 8 step 6 (10 mg, yield 16%). $^1$H NMR (400 MHz, CDCl$_3$) δ 9.40 (d, J=2.1 Hz, 1H), 9.31 (d, J=2.1 Hz, 1H), 9.16-9.15 (m, 1H), 8.87-8.86 (t, J=2.1 Hz, 1H), 7.62-7.59 (m, 2H), 7.42-7.40 (m, 3H), 6.81 (s, 1H), 4.02-3.96 (ddd, J=12.9 Hz, 6.2 Hz, 4.3 Hz, 1H), 3.75 (s, 3H), 3.42-3.35 (ddd, J=12.9 Hz, 9.4 Hz, 3.2 Hz, 1H), 3.15-3.10 (m, 1H), 1.40-1.38 (d, J=6.7 Hz, 3H). MS (ESI) m/z: Calculated for C$_{22}$H$_{19}$F$_3$N$_6$O$_2$: 456.15. found: 457.3 (M+H)$^+$.

Example 116

1-(5-Bromofuran-2-yl)-2,2,2-trifluoroethanol

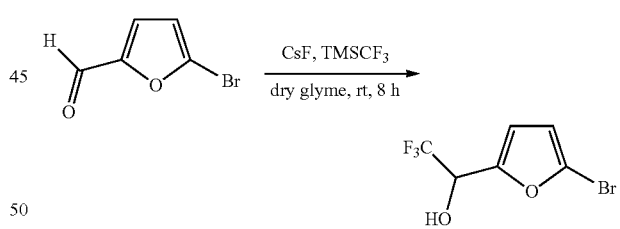

This compound was synthesized from 5-bromofuran-2-carbaldehyde as described in example 88 step 1 (2.6 g, yield 62%). $^1$H NMR (300 MHz, CDCl$_3$) δ 6.52-6.51 (d, J=3.5 Hz, 1H), 6.36-6.35 (d, J=3.5 Hz, 1H), 5.07-4.98 (m, 1H), 2.91-2.89 (d, J=7.2 Hz, 1H).

1-(5-Bromofuran-2-yl)-2,2,2-trifluoroethanone

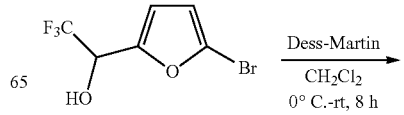

-continued

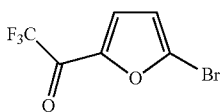

This compound was synthesized from 1-(5-bromofuran-2-yl)-2,2,2-trifluoroethanol as described in example 47 step 2 (1.2 g, yield 47%). $^1$H NMR (300 MHz, CDCl$_3$) δ 7.46-7.44 (m, 1H), 6.66-6.65 (d, J=3.7 Hz, 1H).

3-(5-(2,2,2-Trifluoroacetyl)furan-2-yl)benzoic acid

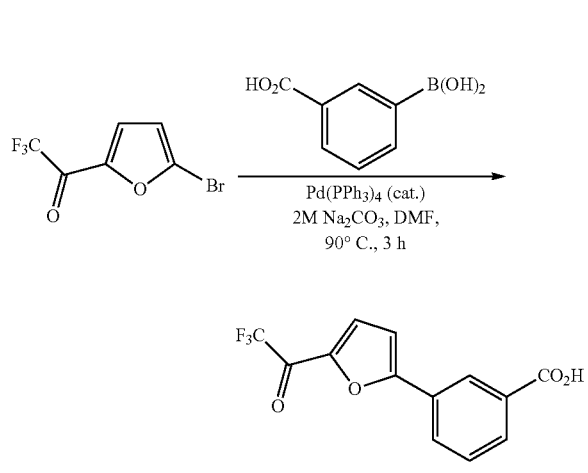

This compound was synthesized from 1-(5-bromofuran-2-yl)-2,2,2-trifluoroethanone as described in example 88 step 3 (500 mg, crude). $^1$H NMR (300 MHz, DMSO-d$_6$) δ 13.26 (br s, 1H), 8.41 (m, 1H), 8.19-8.16 (m, 1H), 8.05-8.03 (m, 1H), 7.98-7.97 (m, 1H), 7.70-7.67 (m, 1H), 7.58-7.57 (m, 1H).

N-(2-(2-(4-Fluorophenyl)oxazol-4-yl)-2-methylpropyl)-3-(5-(2,2,2-trifluoroacetyl)furan-2-yl)benzamide

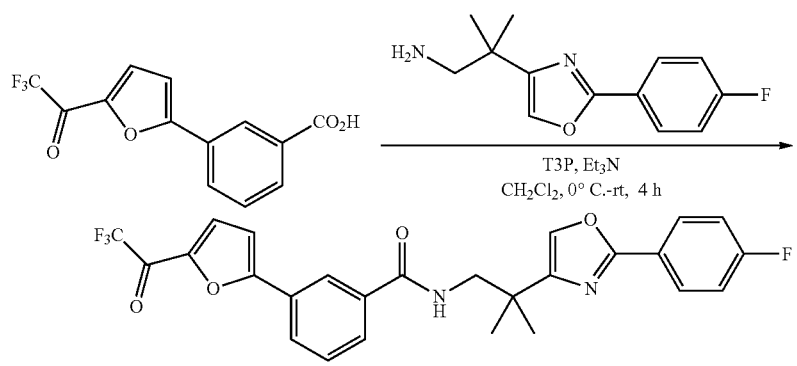

This compound was synthesized from 2-(2-(4-fluorophenyl)oxazol-4-yl)-2-methylpropan-1-amine and 3-(5-(2,2,2-trifluoroacetyl)furan-2-yl)benzoic acid as described in example 8 step 6 (20 mg, yield 6%). $^1$H NMR (400 MHz, DMSO-d$_6$) δ 8.52-8.49 (t, J=6.2 Hz, 1H), 8.30-8.29 (t, J=1.6 Hz, 1H), 8.09-8.06 (dt, J=8.1 Hz, 1.2 Hz, 1H), 8.01-7.98 (m, 4H), 7.94-7.92 (dt, J=8.1 Hz, 1.2 Hz, 1H), 7.66-7.62 (t, J=7.8 Hz, 1H), 7.51-7.50 (d, J=4.0 Hz, 1H), 7.35-7.31 (t, J=9.0 Hz, 2H), 3.52-3.50 (d, J=6.4 Hz, 2H), 1.29 (s, 6H). MS (ESI) m/z: Calculated for C$_{26}$H$_{20}$F$_4$N$_2$O$_4$: 500.14. found: 499.4 (M–H)$^-$.

Example 117

4-(Dimethoxymethyl)-2-(4-fluorophenyl)oxazole

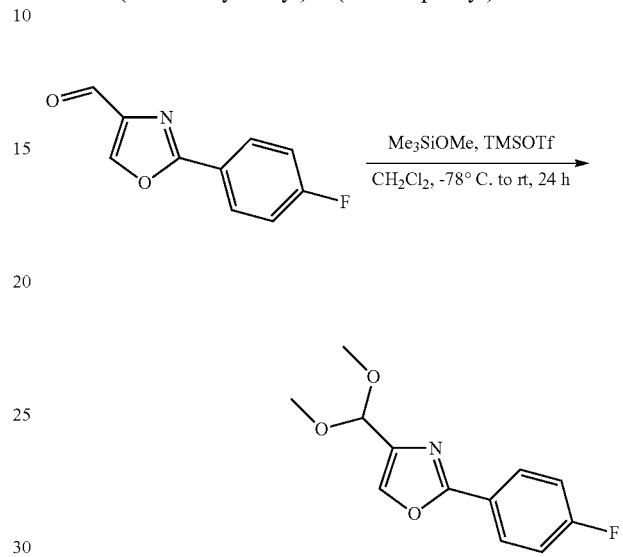

Methoxytrimethylsilane (545 mg, 5.23 mmol) and trimethylsilyl trifluoromethanesulfonate (30 mg, 0.13 mmol) were added to a solution of 2-(4-fluorophenyl)oxazole-4-carbaldehyde (500 mg, 2.62 mmol) in dry CH$_2$Cl$_2$ (2 mL) at −78° C. The reaction mixture was allowed to warm up to room temperature and stirred for 24 h, quenched with saturated aqueous NaHCO$_3$ solution, and the crude product was extracted with EtOAc. The organic layer was washed with 10% NaHCO$_3$ solution, water and brine and dried over anhydrous sodium sulfate. Solvent was removed under reduced pressure to get 4-(dimethoxymethyl)-2-(4-fluorophenyl)oxazole (400 mg, crude), which was carried through without further purification. $^1$H NMR (400 MHz, CDCl$_3$) δ 8.08-8.05 (m, 2H), 7.71 (d, J=1.2 Hz, 1H), 7.16-7.12 (m, 2H), 5.50 (d, J=0.9 Hz, 1H), 3.41 (s, 6H). MS (ESI) m/z: Calculated for C₁₂H₁₂FNO₃: 237.08. found: 259.9 (M+Na)⁺.

2-(2-(4-Fluorophenyl)oxazol-4-yl)-2-methoxyacetonitrile

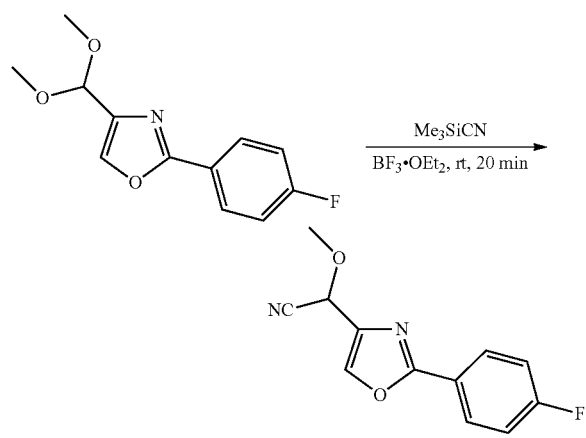

Trimethylsilyl cyanide (4.13 g, 41.76 mmol) was added to a solution of 4-(dimethoxymethyl)-2-(4-fluorophenyl)oxazole (400 mg, 1.69 mmol) at room temperature, followed by boron trifluoride diethyl etherate (37 mg, 0.26 mmol). The reaction mixture was stirred for 20 min, quenched with saturated aqueous NaHCO₃ solution, and extracted with EtOAc. The combined extracts were washed with H₂O and brine, dried over anhydrous sodium sulfate, and concentrated under reduced pressure. The crude product was purified by column chromatography (silica gel 60-120 mesh, eluent 8-10% EtOAc in petroleum ether) to afford 2-(2-(4-fluorophenyl)oxazol-4-yl)-2-methoxyacetonitrile (100 mg, yield 16%) as a light yellow liquid. ¹H NMR (400 MHz, CDCl₃) δ 8.08-8.06 (m, 2H), 7.90 (d, J=0.9 Hz, 1H), 7.19-7.15 (m, 2H), 5.29 (d, J=0.9 Hz, 1H), 3.62 (s, 3H). MS (ESI) m/z: Calculated for C₁₂H₉FN₂O₂: 232.21. found: 232.9 (M+H)⁺.

2-(2-(4-Fluorophenyl)oxazol-4-yl)-2-methoxyethanamine

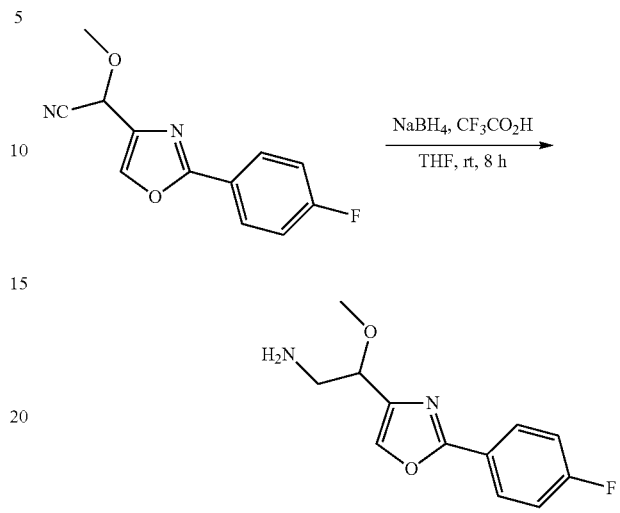

This compound was synthesized from 2-(2-(4-fluorophenyl)oxazol-4-yl)-2-methoxyacetonitrile as described in example 94 step 6 (100 mg, crude) and it was carried through without further purification. MS (ESI) m/z: Calculated for C₁₂H₁₃FN₂O₂: 236.10. found: 236.9 (M+H)⁺.

N-(2-(2-(4-Fluorophenyl)oxazol-4-yl)-2-methoxyethyl)-3-(5-(trifluoromethyl)-1,2,4-oxadiazol-3-yl)benzamide

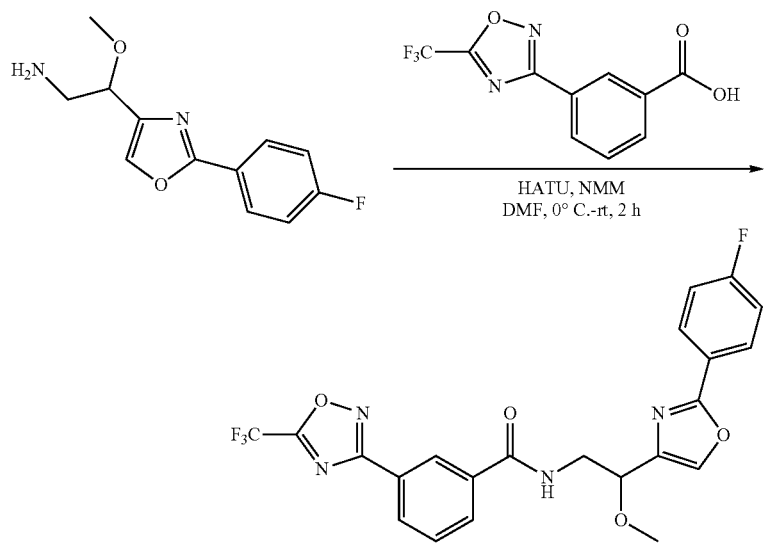

This compound was synthesized from 2-(2-(4-fluorophenyl)oxazol-4-yl)-2-methoxyethanamine and 3-(5-(trifluoromethyl)-1,2,4-oxadiazol-3-yl)benzoic acid as described in example 8 step 6 (44 mg, yield 22%) as an off-white solid. ¹H NMR (400 MHz, CDCl₃) δ 8.56-8.55 (t, J=1.6 Hz, 1H), 8.29-8.26 (dt, J=7.9 Hz, 1.3 Hz, 1H), 8.11-8.06 (m, 3H), 7.73 (s, 1H), 7.67-7.63 (t, J=7.7 Hz, 1H), 7.22-7.19 (m, 1H), 7.17-7.13 (t, J=8.7 Hz, 2H), 4.54-4.51 (dd, J=5.9 Hz, 5.1 Hz, 1H), 4.12-4.06 (ddd, J=13.9 Hz, 6.5 Hz, 4.9 Hz, 1H), 3.87-3.81

(ddd, J=13.9 Hz, 6.1 Hz, 4.8 Hz, 1H), 3.45 (s, 3H). MS (ESI) m/z: Calculated for $C_{22}H_{16}F_4N_4O_4$: 476.11. found: 475.6 (M)⁻.

Example 118

2-(4-(4-Fluorophenyl)thiazol-2-yl)propanenitrile

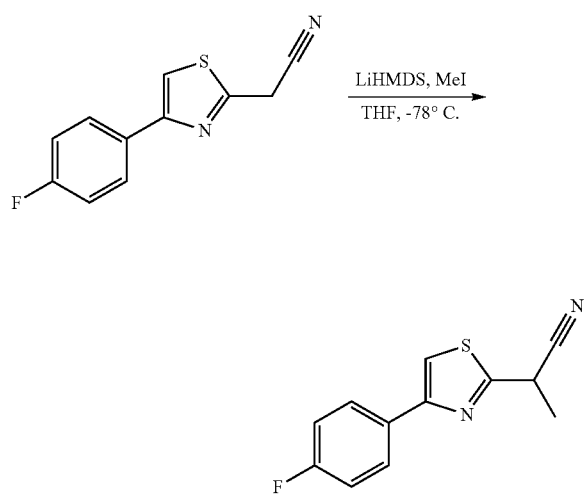

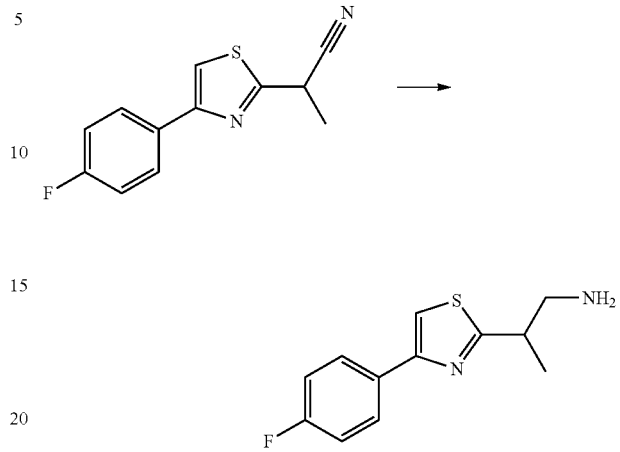

To a stirred solution of 2-(4-(4-fluorophenyl)thiazol-2-yl)acetonitrile (500 mg, 2.29 mmol) in THF (10 mL) at −78° C. was added LiHMDS (1M in THF; 2.06 mL, 2.06 mmol) and the reaction mixture was stirred at −78° C. for 10 min. Iodomethane (0.12 mL, 2.06 mmol) in THF (2 mL) was then added dropwise and the reaction mixture was stirred at −78° C. for 30 min. The reaction mixture was diluted with EtOAc, washed with saturated aqueous NH₄Cl solution, water, brine, and dried over anhydrous sodium sulfate. The organic layer was concentrated under reduced pressure to give the crude product; which was purified on a Teledyne ISCO automated column chromatography system (0-30% EtOAc/Hexanes) to give 2-(4-(4-fluorophenyl)thiazol-2-yl)propanenitrile (180 mg, yield 34%). MS (ESI) m/z: Calculated for $C_{12}H_9FN_2S$: 232.05. found: 233.1 (M+H)

2-(4-(4-Fluorophenyl)thiazol-2-yl)propan-1-amine

To a stirred solution of 2-(4-(4-fluorophenyl)thiazol-2-yl)propanenitrile (140 mg, 0.6 mmol) in THF (3 mL) at room temperature was added borane (1M in THF; 3.01 mL, 3.01 mmol) and the reaction mixture was stirred at room temperature for 1 h and then heated at 40° C. for 1 h. The reaction mixture was then cooled to 0° C. and quenched with MeOH (~5 eq, ~0.2 mL), and allowed to warm to room temperature where 2N HCl solution was added until the pH ~2. The reaction mixture was refluxed at 65° C. for 15 min and then cooled to room temperature and concentrated under reduced pressure. The solid obtained was triturated with ether twice and dichloromethane another two times. The remaining solid was dissolved in water (~50 mL) and basified to pH ~11 with NaOH pellets. The aqueous mixture was then extracted with ether and dried over sodium sulfate and concentrated under reduced pressure to give 2-(4-(4-fluorophenyl)thiazol-2-yl)propan-1-amine (75 mg, yield 52%), which was carried through without further purification; MS (ESI) m/z: Calculated for $C_{12}H_{13}FN_2S$: 236.08. found: 237.1 (M+H)⁺.

N-(2-(4-(4-Fluorophenyl)thiazol-2-yl)propyl)-3-(5-(trifluoromethyl)-1,2,4-oxadiazol-3-yl)benzamide

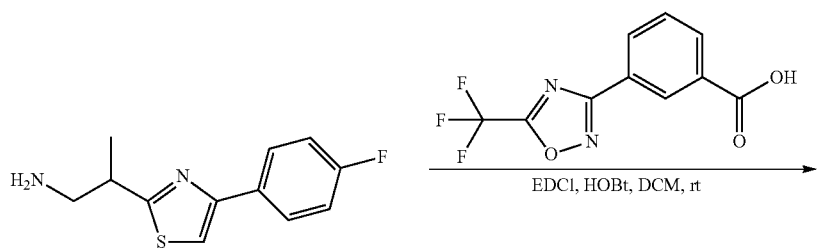

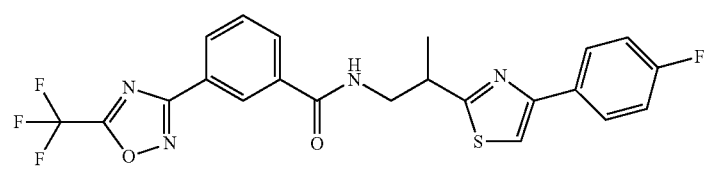

2-(4-(4-Fluorophenyl)thiazol-2-yl)propan-1-amine (50 mg, 0.21 mmol), 3-(5-(trifluoromethyl)-1,2,4-oxadiazol-3-yl)benzoic acid (54.62 mg, 0.21 mmol), N-(3-dimethylaminopropyl)-N'-ethylcarbodiimide hydrochloride (EDC) (81.12 mg, 0.42 mmol), and 1-hydroxybenzotriazole (HOBt) (45.74 mg, 0.39 mmol) were dissolved in dichloromethane (3 mL) at room temperature. Diisopropylethylamine (DIEA) (0.147 mL, 0.85 mmol) was then introduced at room temperature and the reaction mixture was stirred at room temperature overnight. The reaction mixture was diluted with dichloromethane (100 mL) and washed with water (1×20 mL) and brine (1×20 mL). The organic layer was then dried over anhydrous sodium sulfate and concentrated under reduced pressure to give the crude product, which was purified on a Teledyne ISCO automated column chromatography system (0-30% EtOAc/Hexanes) to give N-(2-(4-(4-fluorophenyl)thiazol-2-yl)propyl)-3-(5-(trifluoromethyl)-1,2,4-oxadiazol-3-yl)benzamide (36 mg, 36% yield). $^1$H NMR (CDCl$_3$) δ 8.50 (1h, s), 8.23 (1H, d, J=8 Hz), 8.03 (1H, 1H, d, J=8 Hz), 7.85-7.81 (3H, m), 7.58 (1H, t), 7.35 (1H, s), 7.03 (2H, m), 4.05 (1H, m), 3.65 (1H, m), 1.54 (3H, d, J=8 Hz). MS (ESI) m/z: Calculated for C$_{22}$H$_{16}$F$_4$N$_4$O$_2$S: 476.09. found: 477.1 (M+H)$^+$.

Example 119

N-((4-(4-Phenylthiazol-2-yl)tetrahydro-2H-pyran-4-yl)methyl)-3-(5-(2,2,2-trifluoroacetyl)thiophen-2-yl)benzamide

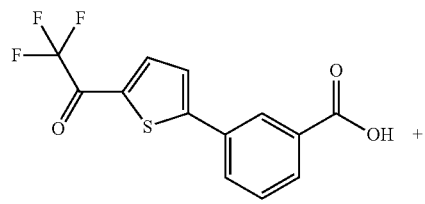

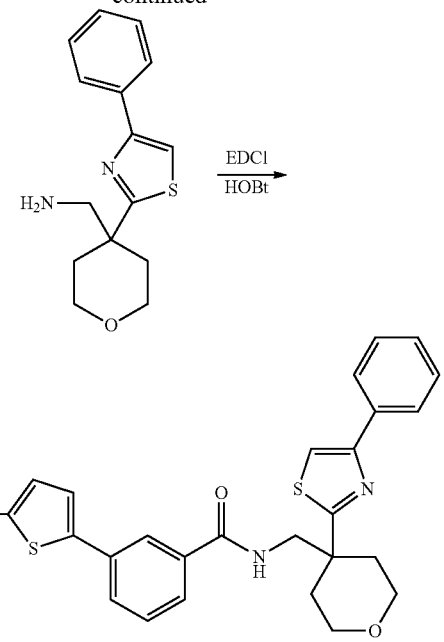

This compound was synthesized from (4-(4-phenylthiazol-2-yl)tetrahydro-2H-pyran-4-yl)methanamine and 3-(5-(2,2,2-trifluoroacetyl)thiophen-2-yl)benzoic acid as described in example 118 step 3 (0.022 g, yield 15%). $^1$H NMR (400 MHz, DMSO) δ 8.650-8.681 (t, 1H), δ 8.132 (s, 2H), δ 8.071 (s, 1H), δ 7.973-7.991 (d, 1H), δ 7.897-7.915 (d, 1H), 7.826-7.846 (d, 1H), 7.786-7.797 (d, 1H), 7.532-7.571 (t, 1H), 7.320-7.357 (t, 2H), 7.254-7.272 (d, 1H), 3.814-3.843 (d 2H), 3.553-3.568 (d, 2H), 3.282-3.409 (d, 2H), 2.22-2.26 (d, 2H), 1.936-2.006 (m, 2H); MS (ESI+) m/z 555.1 (M–H).

Example 120

N-(2-(2-(4-Fluorophenyl)oxazol-4-yl)ethyl)-3-(5-(trifluoromethyl)-1,2,4-oxadiazol-3-yl)benzamide

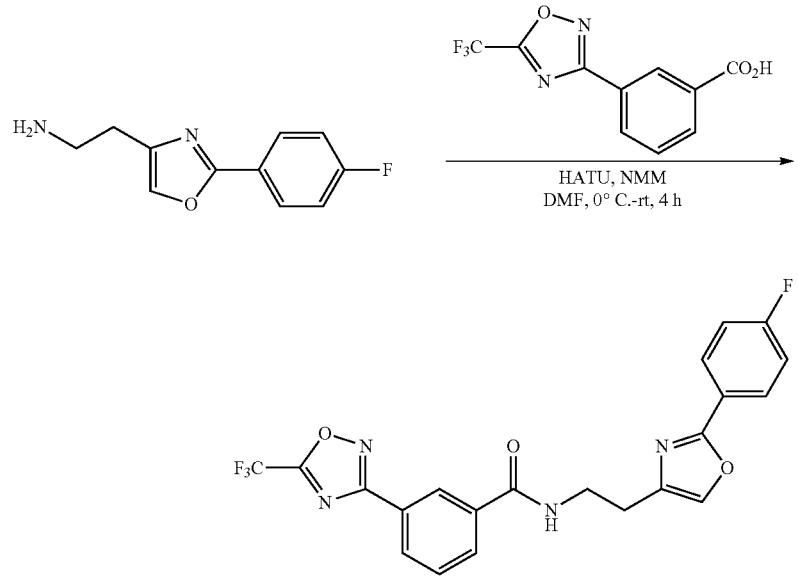

This compound was synthesized from 2-(2-(4-fluorophenyl)oxazol-4-yl)ethanamine and 3-(5-(trifluoromethyl)-1,2,4-oxadiazol-3-yl)benzoic acid as described in example 8 step 6 (45 mg, yield 27%). $^1$H NMR (400 MHz, DMSO-d$_6$) δ 8.91 (t, J=5.4 Hz, 1H), 8.51 (s, 1H), 8.20 (d, J=7.9 Hz, 1H), 8.12 (d, J=8.2 Hz, 1H), 8.00-7.97 (m, 3H), 7.74-7.70 (t, J=7.8 Hz, 1H), 7.37-7.32 (t, J=8.8 Hz, 2H), 3.61-3.56 (m, 2H), 2.84-2.80 (t, J=7.0 Hz, 2H). MS (ESI) m/z: Calculated for C$_{21}$H$_{14}$F$_4$N$_4$O$_3$: 446.10. found: 447.2 (M+H)$^+$.

Example 121

N-(2-(2-(4-Fluorophenyl)oxazol-4-yl)-2-methylpropyl)-5-(5-(trifluoromethyl)-1,2,4-oxadiazol-3-yl)nicotinamide

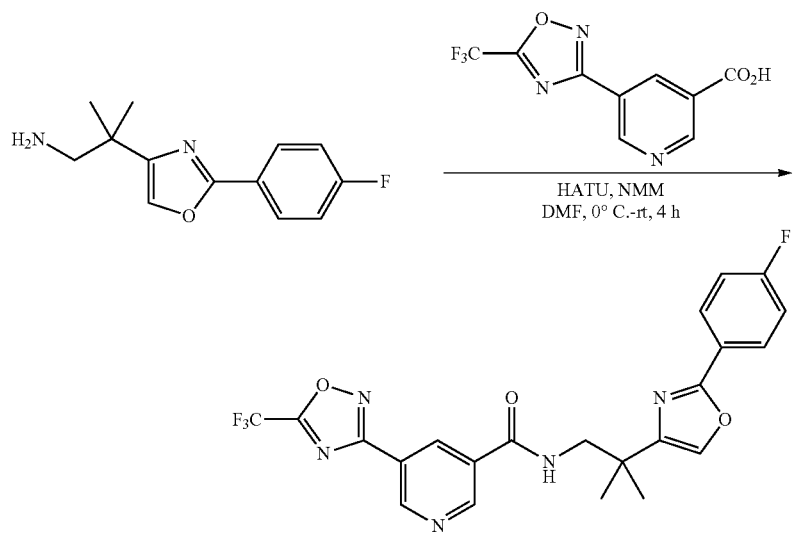

This compound was synthesized from 2-(2-(4-fluorophenyl)oxazol-4-yl)-2-methylpropan-1-amine and 5-(5-trifluoromethyl-[1,2,4]oxadiazol-3-yl)-nicotinic acid as described in example 8 step 6 (19 mg, yield 13%). $^1$H NMR (400 MHz, MeOD) δ 9.38 (d, J=1.5 Hz, 1H), 9.17 (d, J=1.8 Hz, 1H), 8.84 (d, J=1.8 Hz, 1H), 8.09-8.05 (m, 2H), 7.78 (s, 1H), 7.25-7.20 (m, 2H), 3.68 (s, 2H), 1.42 (s, 6H). MS (ESI) m/z: Calculated for C$_{22}$H$_{17}$F$_4$N$_5$O$_3$: 475.13. found: 476.2 (M+H)$^+$.

Example 122

2-(3-Bromophenyl)-2-methylpropanenitrile

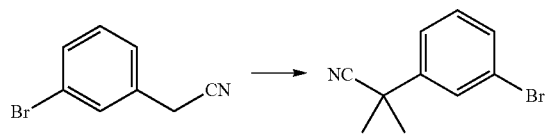

This compound was synthesized from 2-(3-bromophenyl)acetonitrile as described in example 1 step 2 using iodomethane, (1.2 g, used crude) and it was carried through without further purification. MS (ESI) m/z: Calculated for C$_{10}$H$_{10}$BrN: 223.00. found: 224.0 (M+H)$^+$.

2-(3-Bromophenyl)-2-methylpropan-1-amine

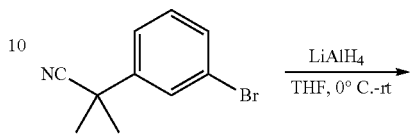

-continued

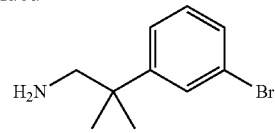

This compound was synthesized from 2-(3-bromophenyl)-2-methylpropanenitrile as described in example 1 step 3 (1.3 g, used crude), and it was carried through without further purification. MS (ESI) m/z: Calculated for C$_{10}$H$_{14}$BrN: 227.03. found: 228.0 (M+H)$^+$.

N-(2-(3-Bromophenyl)-2-methylpropyl)-3-(5-(trifluoromethyl)-1,2,4-oxadiazol-3-yl)benzamide

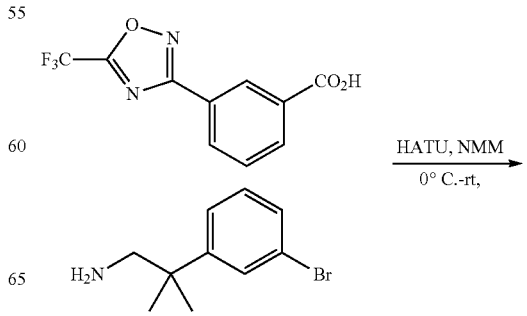

265

-continued

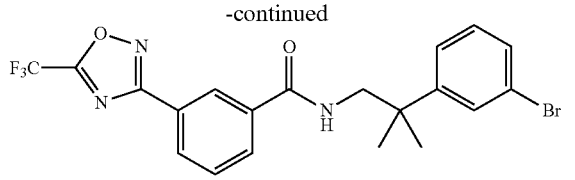

This compound was synthesized from 2-(3-bromophenyl)-2-methylpropan-1-amine and 3-(5-(trifluoromethyl)-1,2,4-oxadiazol-3-yl)benzoic acid as described in example 8 step 6 (90 mg, yield 83%). MS (ESI) m/z: Calculated for $C_{20}H_{17}BrF_3N_3O_2$: 467.05. found: 468.0 (M+H)$^+$.

N-(2-([1,1'-Biphenyl]-3-yl)-2-methylpropyl)-3-(5-(trifluoromethyl)-1,2,4-oxadiazol-3-yl)benzamide

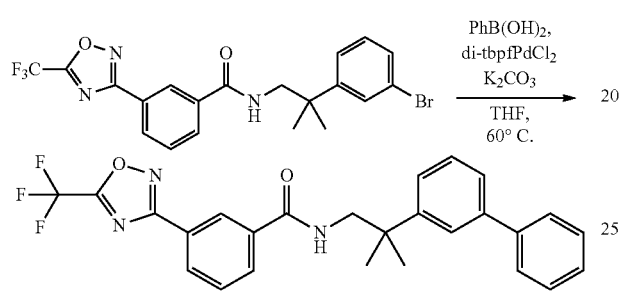

A solution of N-(2-(3-bromophenyl)-2-methylpropyl)-3-(5-(trifluoromethyl)-1,2,4-oxadiazol-3-yl)benzamide (30 mg, 0.064 mmol) and phenyl boronic acid (39 mgs, 0.32 mmol) in THF (1.2 mL) was degassed with nitrogen. Dichloro[1,1' bis(di-tert-butylphosphino)]ferrocene palladium (II) (5 mgs, 0.006 mmol) and 1 M potassium carbonate (1.2 mL) were added. The reaction was heated overnight at 60° C. The reaction was extracted with ethyl acetate and dried over sodium sulfate. The crude was purified by prep TLC using 30% EA/hexanes to yield N-(2-([1,1'-biphenyl]-3-yl)-2-methylpropyl)-3-(5-(trifluoromethyl)-1,2,4-oxadiazol-3-yl)benzamide (6 mgs, yield 18%). $^1$H NMR (300 MHz, CDCl$_3$) δ 8.29 (s, 1H) 8.18 (d, J=7.2 Hz, 1H), 7.81 (d, J=7.2 Hz, 1H), 7.64-7.30 (m, 10H) 5.88 (s, 1H), 3.73 (d, J=7.2 Hz, 2H), 1.48 (s, 6H). MS (ESI) m/z: Calculated for $C_{26}H_{22}F_3N_3O_2$: 465.17. found: 466.2 (M+H)$^+$.

Example 123

N-(2-(4'-Fluoro-[1,1'-biphenyl]-3-yl)-2-methylpropyl)-3-(5-(trifluoromethyl)-1,2,4-oxadiazol-3-yl)benzamide

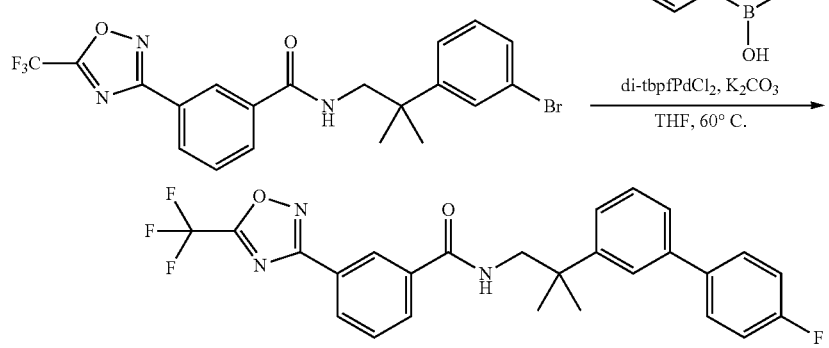

266

This compound was synthesized from N-(2-(3-bromophenyl)-2-methylpropyl)-3-(5-(trifluoromethyl)-1,2,4-oxadiazol-3-yl)benzamide and 4-fluoroboronic acid as described in example 122 step 4 (8 mg, 25% yield). $^1$H NMR (300 MHz, CDCl3) δ 8.27 (s, 1H) 8.18 (d, J=7.2 Hz, 1H), 7.82 (d, J=7.2 Hz, 1H), 7.60-7.38 (m, 8H) 7.11 (m, 1H), 5.71 (s, 1H), 3.73 (d, J=7.2 Hz, 2H), 1.47 (s, 6H). MS (ESI) m/z: Calculated for $C_{26}H_{21}F_4N_3O_2$: 483.16. found: 484.2 (M+H)$^+$.

Example 124

2-(4-(3,5-Difluorophenyl)thiazol-2-yl)acetonitrile

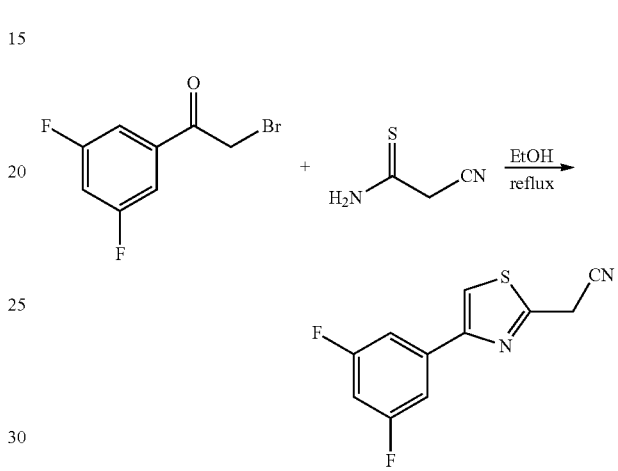

This compound was synthesized from 2-bromo-1-(3,5-difluorophenyl)ethanone as described in example 1 step 1 (3 g, yield 94%). MS (ESI) m/z: Calculated for $C_{11}H_6F_2N_2S$: 236.02. found: 237.1 (M+H)$^+$.

4-(4-(3,5-Difluorophenyl)thiazol-2-yl)tetrahydro-2H-pyran-4-carbonitrile

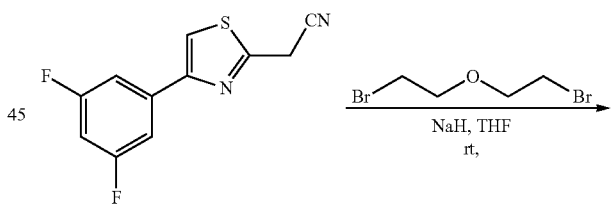

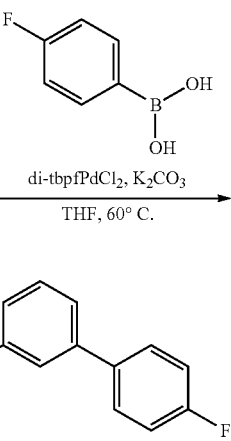

268

N-((4-(4-(3,5-Difluorophenyl)thiazol-2-yl)tetrahydro-2H-pyran-4-yl)methyl)-3-(5-(trifluoromethyl)-1,2,4-oxadiazol-3-yl)benzamide

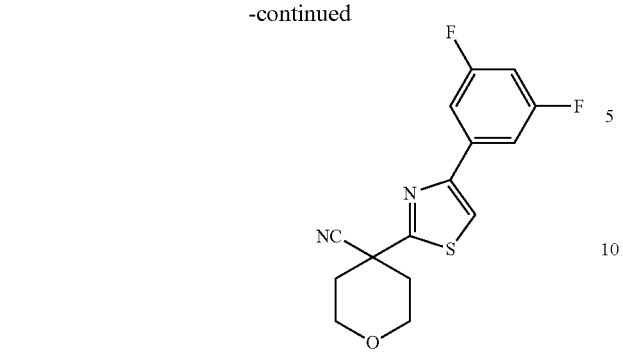

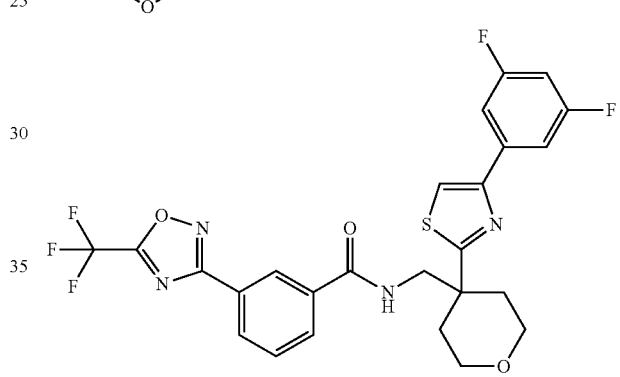

This compound was synthesized from (4-(4-(3,5-difluorophenyl)thiazol-2-yl)tetrahydro-2H-pyran-4-yl)methanamine and 3-(5-(trifluoromethyl)-1,2,4-oxadiazol-3-yl)benzoic acid as described in example 8 step 6 (20 mg, 10% yield). $^1$H NMR (300 MHz, CDCl$_3$) δ 8.45 (s, 1H), 8.24 (d, J=8.3 Hz, 1H), 7.88 (d, J=8.3 Hz, 1H), 7.64-7.54 (m, 2H), 7.35 (d, J=5.5 Hz, 1H), 6.73 (m, 2H), 3.95 (m, 2H), 3.85 (d, J=5.5 Hz, 2H), 3.70 (m, 2H), 2.28 (m, 2H), 2.05 (m, 2H). MS (ESI) m/z: Calculated for C$_{25}$H$_{19}$F$_5$N$_4$O$_3$S: 550.11. found: 551.1 (M+H)$^+$.

267

-continued

This compound was synthesized from 2-(4-(3,5-difluorophenyl)thiazol-2-yl)acetonitrile using 2-bromoethyl ether as described in example 1 step 2 (1.0 g, yield 59%). MS (ESI) m/z: Calculated for C$_{15}$H$_{12}$F$_2$N$_2$OS: 306.06. found: 307.1 (M+H)$^+$.

(4-(4-(3,5-Difluorophenyl)thiazol-2-yl)tetrahydro-2H-pyran-4-yl)methanamine

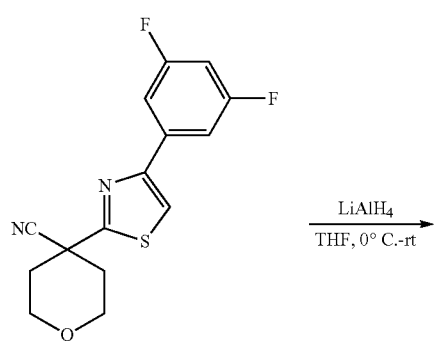

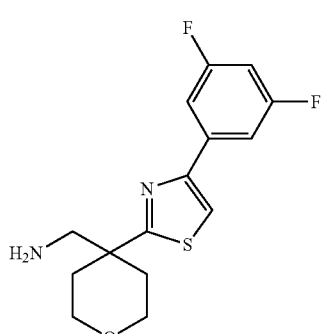

This compound was synthesized from 4-(4-(3,5-difluorophenyl)thiazol-2-yl)tetrahydro-2H-pyran-4-carbonitrile as described in example 1 step 3 (1 g, crude), and it was carried through without further purification. MS (ESI) m/z: Calculated for C$_{15}$H$_{16}$F$_2$N$_2$OS: 310.10. found: 311.1 (M+H)$^+$.

Example 125

2-(4-(3,5-Difluorophenyl)thiazol-2-yl)-2-methylpropanenitrile

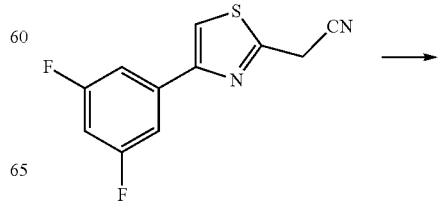

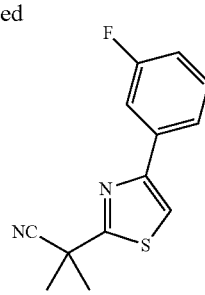

This compound was synthesized from 2-(4-(3,5-difluorophenyl)thiazol-2-yl)acetonitrile using iodomethane as described in example 1 step 2 (1.0 g, yield 60%). MS (ESI) m/z: Calculated for $C_{13}H_{10}F_2N_2S$: 264.05. found: 265.1 $(M+H)^+$.

2-(4-(3,5-Difluorophenyl)thiazol-2-yl)-2-methylpropan-1-amine

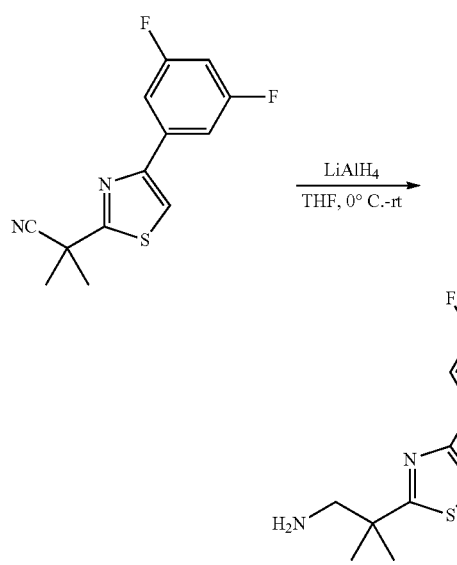

This compound was synthesized from 2-(4-(3,5-difluorophenyl)-2-methylpropanenitrile as described in example 1 step 3 (1 g, crude) and it was carried through without further purification. MS (ESI) m/z: Calculated for $C_{13}H_{14}F_2N_2S$: 268.08. found: 269.1 $(M+H)^+$.

N-(2-(4-(3,6-Difluorophenyl)thiazol-2-yl)-2-methylpropyl)-3-(6-(trifluoromethyl)-1,2,4-oxadiazol-3-yl)benzamide

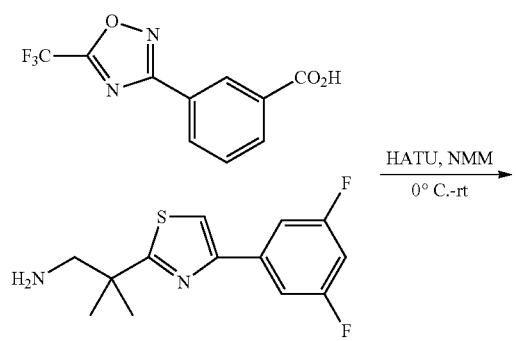

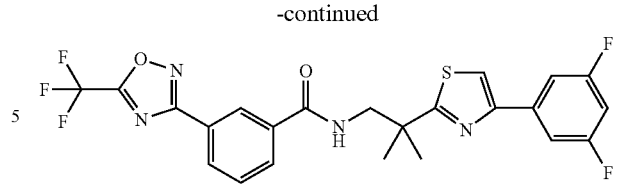

This compound was synthesized from 2-(4-(3,5-difluorophenyl)thiazol-2-yl)-2-methylpropan-1-amine and 3-(5-(trifluoromethyl)-1,2,4-oxadiazol-3-yl)benzoic acid as described in example 8 step 6 (85 mg, yield 24%). $^1$H NMR (300 MHz, CDCl$_3$) δ 8.54 (s, 1H), 8.25 (d, J=7.6 Hz, 1H), 8.04 (m, 1H) 7.62 (t, J=9.2 Hz, 1H), 7.47 (s, 1H), 7.35 (d, J=7.6 Hz, 2H), 6.72 (m, 1H), 3.79 (d, J=2.8 Hz, 2H), 1.55 (s, 6H). MS (ESI) m/z: Calculated for $C_{23}H_{17}F_5N_4O_2S$: 508.10. found: 509.1 $(M+H)^+$.

Example 126

2-(2-Phenyloxazol-4-yl)ethanamine

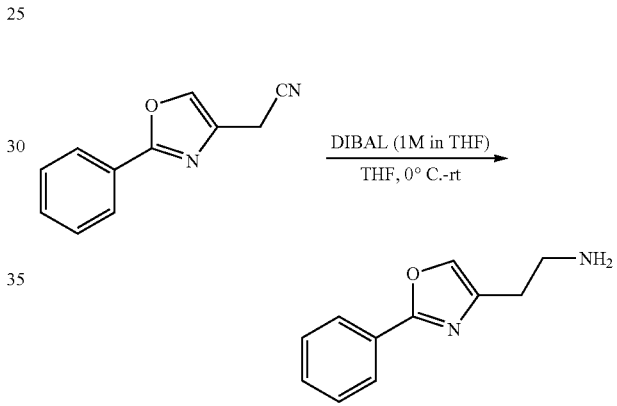

This compound was synthesized from 2-(2-phenyloxazol-4-yl)acetonitrile as described in example 64 step 4 (400 mg, crude) and it was carried through without further purification. MS (ESI) m/z: Calculated for $C_{11}H_{12}N_2O$: 188.09. found: 189.1 $(M+H)^+$.

N-(2-(2-Phenyloxazol-4-yl)ethyl)-3-(5-(trifluoromethyl)-1,2,4-oxadiazol-3-yl)benzamide

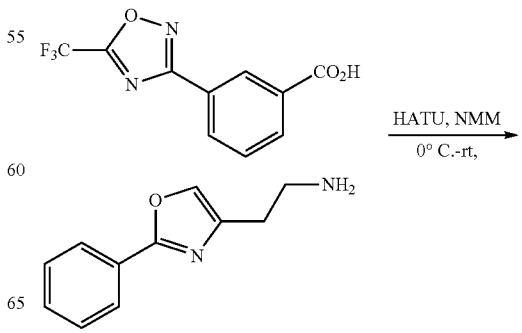

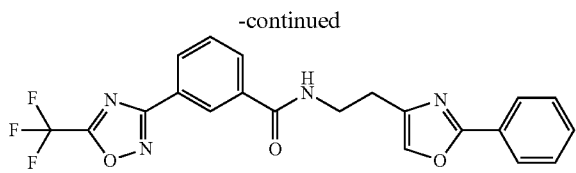

This compound was synthesized from 2-(2-phenyloxazol-4-yl)ethanamine and 3-(5-(trifluoromethyl)-1,2,4-oxadiazol-3-yl)benzoic acid as described in example 8 step 6 (40 mgs, yield 25%). $^1$H NMR (CDCl$_3$) δ 8.59 (s, 1H), 8.26 (d, J=7.8 Hz, 1H), 8.13 (d, J=8.1 Hz, 1H), 8.05 (m, 2H), 7.62-7.56 (m, 3H), 7.43 (m, 2H), 3.84 (m, 2H), 2.93 (m, 2H). MS (ESI) m/z: Calculated for C$_{21}$H$_{15}$F$_3$N$_4$O$_3$: 428.11. found: 429.1 (M+H)$^+$.

Example 127

N-(2-(2-Phenyloxazol-4-yl)ethyl)-5-(5-(trifluoromethyl)-1,2,4-oxadiazol-3-yl)nicotinamide

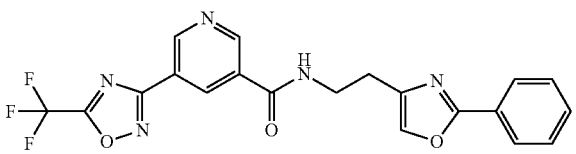 [SMILES: O=C(NCCc1coc(-c2ccccc2)n1)c1cncc(-c2noc(C(F)(F)F)n2)c1]

This compound was synthesized from 2-(2-phenyloxazol-4-yl)ethanamine and 5-(5-(trifluoromethyl)-1,2,4-oxadiazol-3-yl)nicotinic acid as described in example 8 step 6 (42 mgs, yield 32%). $^1$H NMR (CDCl$_3$) δ 9.46 (d, J=2.1 Hz, 1H), 9.32 (d, J=2.1 Hz, 1H), 8.87 (t, J=2.7 Hz, 1H), 8.06-7.96 (m, 3H), 7.57-7.44 (m, 3H), 3.85 (m, 2H), 2.93 (t, J=6.3 Hz, 2H). MS (ESI) m/z: Calculated for C$_{20}$H$_{14}$F$_3$N$_5$O$_3$: 429.10. found: 430.1 (M+H)$^+$.

Example 128

2-(2-(4-Chlorophenyl)oxazol-4-yl)ethanamine

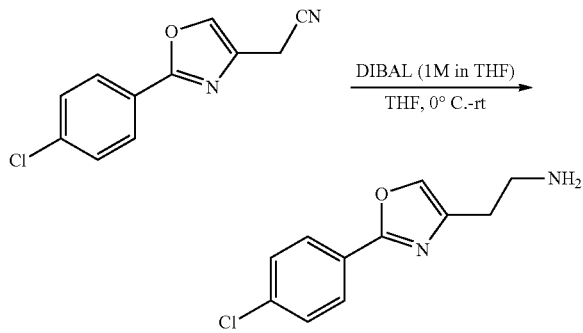

This compound was synthesized from 2-(2-(4-chlorophenyl)oxazol-4-yl)acetonitrile as described in example 64 step 4 (466 mg, crude) and it was carried through without further purification. MS (ESI) m/z: Calculated for C$_{11}$H$_{11}$ClN$_2$O: 222.06. found: 223.1 (M+H)$^+$.

N-(2-(2-(4-Chlorophenyl)oxazol-4-yl)ethyl)-3-(5-(trifluoromethyl)-1,2,4-oxadiazol-3-yl)benzamide

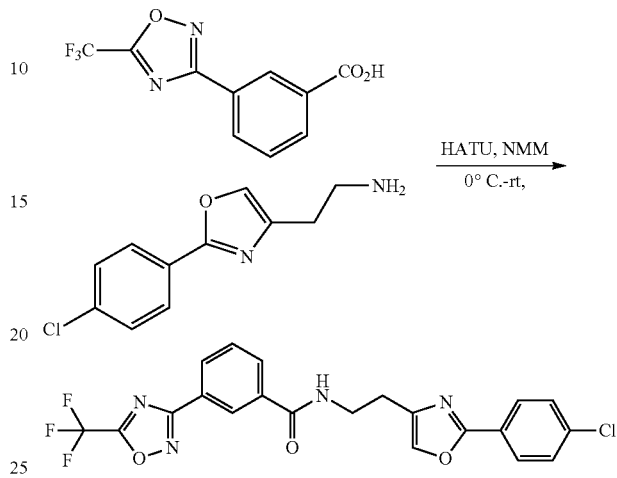

This compound was synthesized from 2-(2-(4-chlorophenyl)oxazol-4-yl)ethanamine and 3-(5-(trifluoromethyl)-1,2,4-oxadiazol-3-yl)benzoic acid as described in example 8 step 6 (4 mgs, 2% yield). $^1$H NMR (CDCl$_3$) δ 8.55 (s, 1H), 8.25 (d, J=7.8 Hz, 1H), 8.12 (d, J=7.8 Hz, 1H), 7.98 (d, J=7.8 Hz, 2H), 7.68-7.54 (m, 2H), 7.41 (d, J=8.4 Hz, 2H), 3.86 (m, 2H), 3.94 (m, 2H). MS (ESI) m/z: Calculated for C$_{21}$H$_{14}$ClF$_3$N$_4$O$_3$: 462.07. found: 463.1 (M+H)$^+$.

Example 129

N-(2-(2-(4-Chlorophenyl)oxazol-4-yl)ethyl)-5-(5-(trifluoromethyl)-1,2,4-oxadiazol-3-yl)nicotinamide

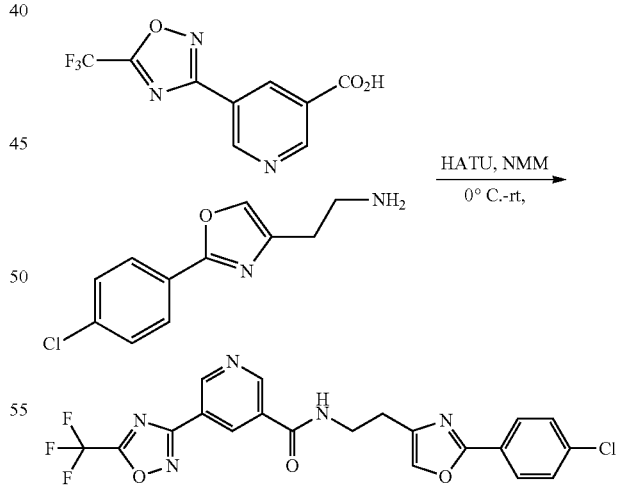

This compound was synthesized from 2-(2-(4-chlorophenyl)oxazol-4-yl)ethanamine and 5-(5-(trifluoromethyl)-1,2,4-oxadiazol-3-yl)nicotinic acid as described in example 8 step 6 (14 mgs, 10% yield). $^1$H NMR (CDCl$_3$) δ 9.45 (s, 1H), 9.29 (s, 1H), 8.84 (s, 1H), 7.97 (d, J=8.4 Hz, 1H), 7.80 (s, 1H), 7.57 (s, 1H), 7.43 (d, J=8.1 Hz, 1H), 7.26 (s, 1H), 3.85 (d, J=5.1 Hz, 2H), 2.93 (t, J=5.4 Hz, 2H). MS (ESI) m/z: Calculated for C$_{20}$H$_{13}$ClF$_3$N$_5$O$_3$: 463.07. found: 464.1 (M+H)$^+$.

Example 130

N-(2-Methyl-2-(2-phenyloxazol-4-yl)propyl)-5-(5-(trifluoromethyl)-1,2,4-oxadiazol-3-yl)nicotinamide

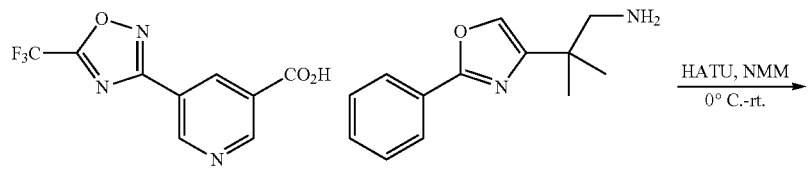

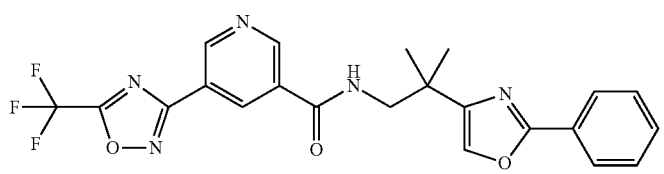

This compound was synthesized from 2-methyl-2-(2-phenyloxazol-4-yl)propan-1-amine and 5-(5-(trifluoromethyl)-1,2,4-oxadiazol-3-yl)nicotinic acid as described in example 8 step 6 (19 mgs, 13% yield). $^1$H NMR (CDCl$_3$) δ 9.45 (t, J=9.0 Hz, 1H), 9.35 (s, 1H), 8.42 (s, 1H), 8.03 (s, 2H), 7.51-7.40 (m, 4H), 3.62 (bs, 2H), 1.42 (s, 6H). MS (ESI) m/z: Calculated for C$_{22}$H$_{18}$F$_3$N$_5$O$_3$: 457.14. found: 458.1 (M+H)$^+$.

Example 131

2-(2-(4-Chlorophenyl)oxazol-4-yl)-2-methylpropanenitrile

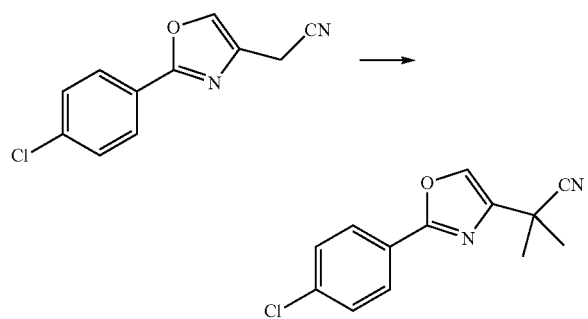

This compound was synthesized from 2-(2-(4-chlorophenyl)oxazol-4-yl)acetonitrile using iodomethane as described in example 1 step 2 (100 mg, crude) and it was carried through without further purification MS (ESI) m/z: Calculated for C$_{13}$H$_{11}$ClN$_2$O: 246.06. found: 247.1 (M+H)$^+$.

2-(2-(4-Chlorophenyl)oxazol-4-yl)-2-methylpropan-1-amine

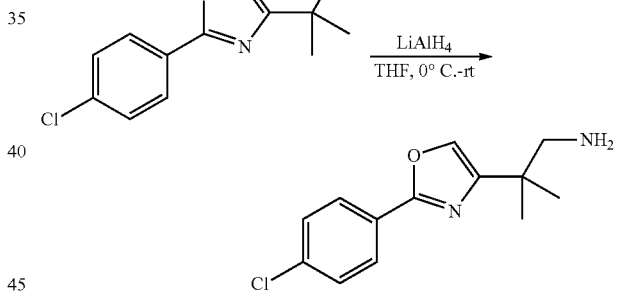

This compound was synthesized from 2-(2-(4-chlorophenyl)oxazol-4-yl)-2-methylpropanenitrile as described in example 1 step 3 (100 mg, crude) and it was carried through without further purification. MS (ESI) m/z: Calculated for C$_{13}$H$_{15}$ClN$_2$O: 250.09. found: 251.1 (M+H)$^+$.

N-(2-(2-(4-Chlorophenyl)oxazol-4-yl)-2-methylpropyl)-3-(5-(trifluoromethyl)-1,2,4-oxadiazol-3-yl)benzamide

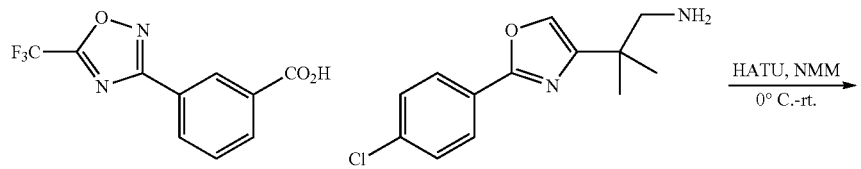

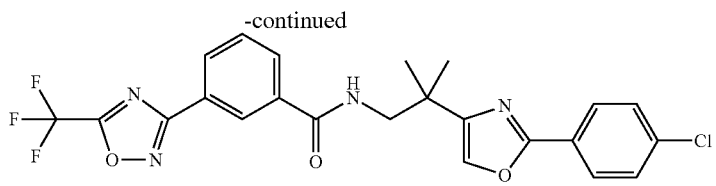

This compound was synthesized from 2-(2-(4-chlorophenyl)oxazol-4-yl)-2-methylpropan-1-amine and 3-(5-(trifluoromethyl)-1,2,4-oxadiazol-3-yl)benzoic acid as described in example 8 step 6 (8 mg, yield 14%). $^1$H NMR (CDCl$_3$) δ 8.59 (t, J=1.7 Hz, 1H), 8.25 (d, J=7.9 Hz, 1H), 8.12 (d, J=6.7 Hz, 1H), 7.99 (d, J=6.6 Hz, 2H), 7.64 (t, J=7.7 Hz, 2H) 7.49 (s, 1H), 7.38 (d, J=4.9 Hz, 1H), 2.03 (s, 2H), 1.40 (s, 6H). MS (ESI) m/z: Calculated for C$_{23}$H$_{18}$ClF$_3$N$_4$O$_3$: 490.10. found: 491.1 (M+H)$^+$.

Example 132

Methyl 3-(3-(5-(trifluoromethyl)-1,2,4-oxadiazol-3-yl)benzamido)propanoate

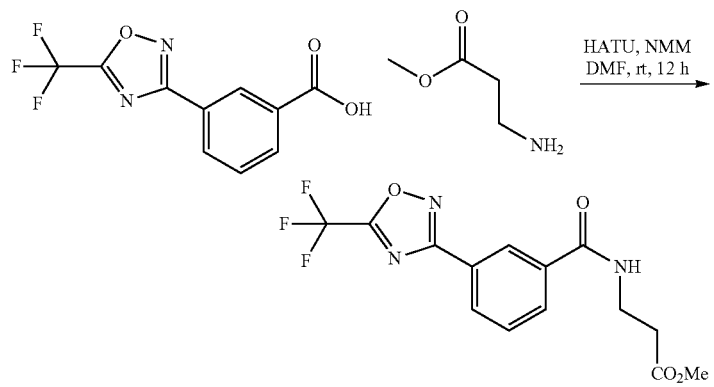

This compound was synthesized from methyl 3-aminopropanoate and 3-(5-(trifluoromethyl)-1,2,4-oxadiazol-3-yl)benzoic acid as described in example 8 step 6 (120 mgs, yield 75%). MS (ESI) m/z: Calculated for C$_{14}$H$_{12}$F$_3$N$_3$O$_4$: 343.08. found: 344.1 (M+H)$^+$.

3-(3-(5-(Trifluoromethyl)-1,2,4-oxadiazol-3-yl)benzamido)propanoic acid

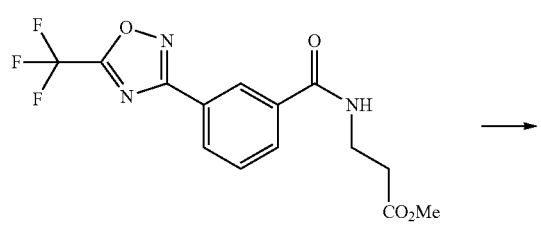

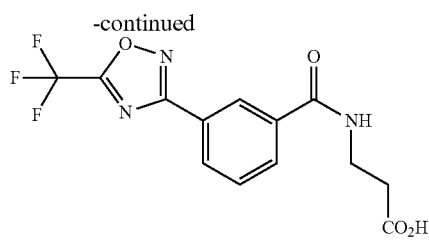

A sodium hydroxide solution (0.2 mL, 5 M) was added to a solution of methyl 3-(3-(5-(trifluoromethyl)-1,2,4-oxadiazol-3-yl)benzamido)propanoate in THF/MeOH/water (4:1:1, 15 mL). The reaction was stirred for 30 min and acidified with 2 M HCl. The reaction was extracted with ethyl acetate several times, dried over sodium sulfate, and used crude. MS (ESI) m/z: Calculated for C$_{13}$H$_{10}$F$_3$N$_3$O$_4$: 329.06. found: 330.1 (M+H)$^+$.

N-(2-(3-Phenyl-1,2,4-oxadiazol-5-yl)ethyl)-3-(5-(trifluoromethyl)-1,2,4-oxadiazol-3-yl)benzamide HOBt (47 mg, 0.35 mmol), EDCI (67 mg, 0.35 mmol), and diisopropylethylamine (0.7 mL, 1.0 mmol) were added to a solution of 3-(3-(5-(trifluoromethyl)-1,2,4-oxadiazol-3-yl)benzamido)propanoic acid (115 mg, 0.35 mmol) and N'-hydroxybenzimidamide (47 mg, 0.35 mmol) in dichloromethane (3.5 mL) with a few drops of DMF. The reaction was stirred 1 h and then toluene was added and the reaction was heated to 90° C. for 1 h. The reaction was diluted with ethyl acetate and the organic layer was washed with saturated sodium bicarbonate and dried over sodium sulfate. The product was purified on reverse phase using water/acetonitrile to give N-(2-(3-phenyl-1,2,4-oxadiazol-5-yl)ethyl)-3-(5-(trifluoromethyl)-1,2,4-oxadiazol-3-yl)benzamide (10 mg, yield 7%). $^1$H NMR (CDCl$_3$) δ 8.60 (s, 1H), 8.22 (m, 1H), 8.10 (m, 3H,) 7.60 (m, 1H), 7.55-7.45 (m, 3H), 4.05 (m, 2H), 3.26 (m, 2H). MS (ESI) m/z: Calculated for $C_{20}H_{14}F_3N_5O_3$: 429.10. found: 430.1 (M+H)$^+$.

Example 133

Ethyl 1-benzyl-5-phenyl-1H-pyrazole-3-carboxylate

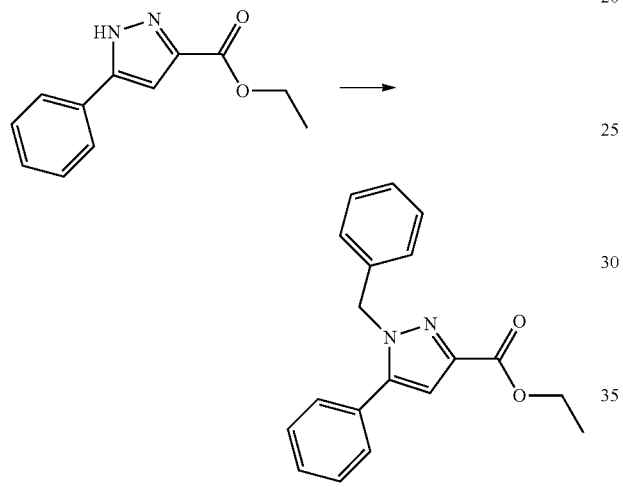

Benzyl bromide (696 mg, 4.01 mmol) was added to ethyl 5-phenyl-1H-pyrazole-3-carboxylate (880 mg, 4.1 mmol) and potassium carbonate (562 mg, 4.01) in DMF (8 mL). The reaction was stirred for several h and then diluted with water. The mixture was washed several times with ethyl acetate and the combine extracts were dried over sodium sulfate. The solvent was removed under reduced pressure and the residue was purified on ISCO using 0-100% ethyl acetate/hexane gradient to give ethyl 1-benzyl-5-phenyl-1H-pyrazole-3-carboxylate (1.3 g, quantitative). MS (ESI) m/z: Calculated for $C_{19}H_{18}N_2O_2$: 306.14. found: 307.1 (M+H)$^+$.

(1-Benzyl-5-phenyl-1H-pyrazol-3-yl)methanol

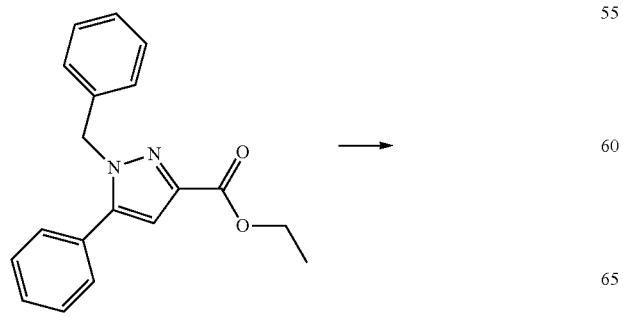

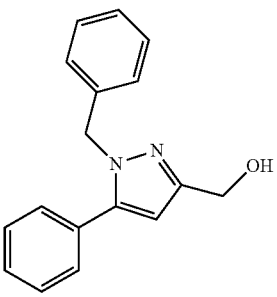

At 0° C., LAH (1.8 mL, 3.7 mmol, 2M in THF) was added to ethyl 1-benzyl-5-phenyl-1H-pyrazole-3-carboxylate (560 mg, 1.8 mmol) in THF (18 mL). The reaction was stirred for 10 min and then warmed to room temperature for 1 h. Minimal water was slowly added to the reaction followed by 1 mL of 5 M sodium hydroxide. The reaction was stirred for 30 min, sodium sulfate was added, and the solids were removed by filtration. The filtrate was concentrated under reduced pressure to yield crude (1-benzyl-5-phenyl-1H-pyrazol-3-yl)methanol, which was carried through without further purification. MS (ESI) m/z: Calculated for $C_{17}H_{16}N_2O$: 264.13. found: 265.1 (M+H)$^+$.

1-Benzyl-3-(bromomethyl)-5-phenyl-1H-pyrazole

Carbon tetrabromide (2.5 g, 7.6 mmol) and then triphenylphosphine (2.0 g, 7.6 mmol) was added to (1-benzyl-5-phenyl-1H-pyrazol-3-yl)methanol (1.0 g, 3.8 mmol) in dicholomethane (38 mL) at 0° C. Upon completion of the reaction as monitored by LCMS, the reaction was filtered through silica washing with methylene chloride and then purified on an ISCO using 0-30% ethyl acetate/hexanes to give 1-benzyl-3-(bromomethyl)-5-phenyl-1H-pyrazole (0.5 g, yield 43%). MS (ESI) m/z: Calculated for $C_{17}H_{15}BrN_2$: 326.04. found: 327.0 (M+H)⁺.

2-(1-Benzyl-5-phenyl-1H-pyrazol-3-yl)acetonitrile

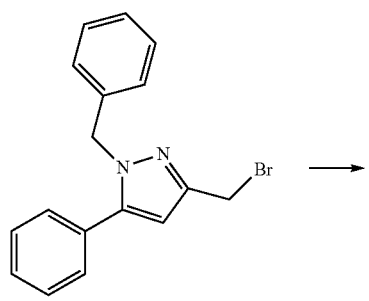

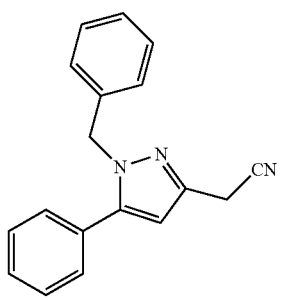

1-Benzyl-3-(bromomethyl)-5-phenyl-1H-pyrazole (200 mg, 0.6 mmol) and sodium cyanide (30 mg, 0.6 mmol) were stirred in DMF (6 mL). After several h, more sodium cyanide (60 mg, 1.2 mmol) was added to the reaction. A 25% ammonium hydroxide solution in water was added to the reaction and the reaction mixture was extracted with ethyl acetate. The combined extracts were dried over sodium sulfate and concentrated under reduced pressure to yield 2-(1-benzyl-5-phenyl-1H-pyrazol-3-yl)acetonitrile (130 mg, yield 80%) MS (ESI) m/z: Calculated for $C_{18}H_{15}N_3$: 273.13. found: 274.1 (M+H)⁺.

2-(1-Benzyl-5-phenyl-1H-pyrazol-3-yl)-2-methyl-propanenitrile

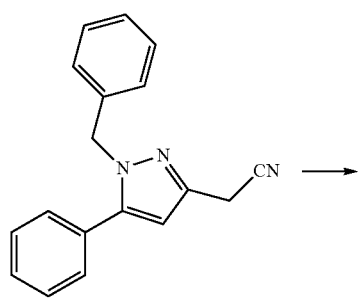

-continued

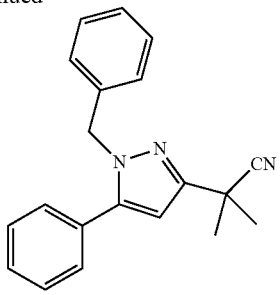

This compound was synthesized from 2-(1-benzyl-5-phenyl-1H-pyrazol-3-yl)acetonitrile using iodomethane as described in example 1 step 2 (500 mg, yield 91%). MS (ESI) m/z: Calculated for $C_{20}H_{19}N_3$: 301.16. found: 302.2 (M+H)⁺.

2-(1-Benzyl-5-phenyl-1H-pyrazol-3-yl)-2-methyl-propan-1-amine

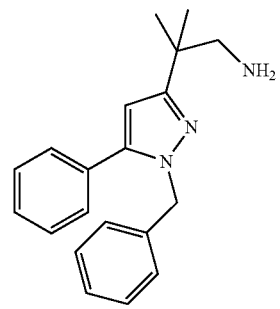

2-(1-Benzyl-5-phenyl-1H-pyrazol-3-yl)-2-methylpropanenitrile (50 mg, 0.16 mmol) was dissolved in THF (1.6 mL). Borane-tetrahydrofuran (0.8 mL, 1 M solution) was added and the reaction was heated to 60° C. for 3 h. Minimal water was added to quench the reaction. Ethyl acetate was added followed by sodium sulfate and the solids were removed by filtration. The filtrate was concentrated under reduced pressure to yield 2-(1-benzyl-5-phenyl-1H-pyrazol-3-yl)-2-methylpropan-1-amine (50 mg, crude), which was carried through without further purification. MS (ESI) m/z: Calculated for $C_{20}H_{23}N_3$: 305.19. found: 306.2 (M+H)⁺.

281

2-Methyl-2-(5-phenyl-1H-pyrazol-3-yl)propan-1-amine

282

2-(1-Benzyl-5-phenyl-1H-pyrazol-3-yl)-2-methylpropan-1-amine (50 mg, 0.2 mmol) was stirred under an atmosphere of hydrogen in methanol/concentrated sulfuric acid (5:1, 5 mL) with 5% palladium on carbon (350 mg). After several h, more palladium on carbon was added (350 mg). The reaction was stopped after 3 days with starting material remaining. The solution was degassed and filtered through Celite. Methanol was removed under vacuum and 1 M potassium carbonate was added until the reaction was basic. The slurry was extracted multiple times with 30% isopropanol/chloroform. The combined organic layers were dried over sodium sulfate and concentrated under reduced pressure to yield 2-methyl-2-(5-phenyl-1H-pyrazol-3-yl)propan-1-amine, which was carried through without further purification.

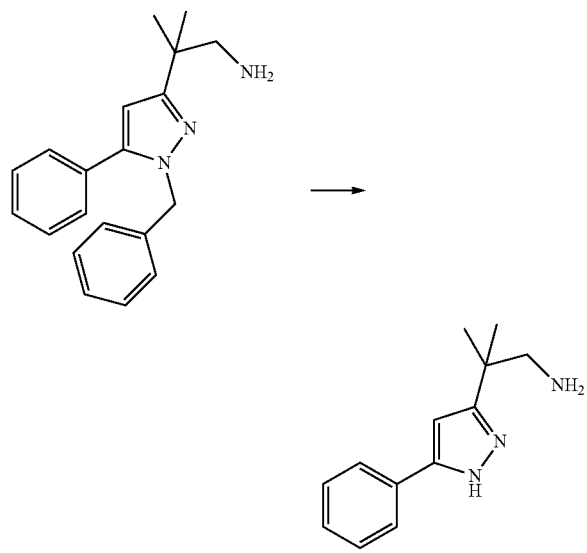

N-(2-Methyl-2-(3-phenyl-1H-pyrazol-5-yl)propyl)-3-(5-(trifluoromethyl)-1,2,4-oxadiazol-3-yl)benzamide

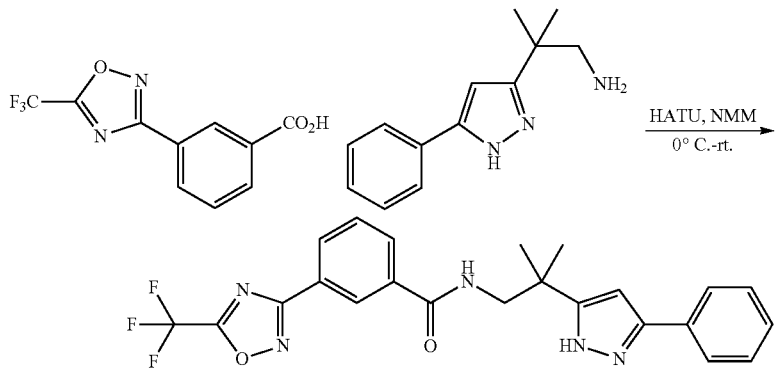

This compound was synthesized from 2-methyl-2-(5-phenyl-1H-pyrazol-3-yl)propan-1-amine and 3-(5-(trifluoromethyl)-1,2,4-oxadiazol-3-yl)benzoic acid as described in example 8 step 6 (10 mg, yield 11%). $^1$H NMR (CDCl$_3$) δ 8.52 (s, 1H) 8.20 (d, J=7.4, 1H), 8.05 (d, J=7.4, 1H), 7.64-7.52 (m, 3H), 7.46-7.32 (m, 3H), 6.47 (s, 1H), 3.70 (d, J=4.5, 2H), 1.44 (s, 6H). MS (ESI) m/z: Calculated for C$_{23}$H$_{20}$F$_3$N$_5$O$_2$: 455.16. found: 456.2 (M+H)$^+$.

Example 134

N-(2-(2-(4-Fluorophenyl)oxazol-4-yl)propyl)-5-(5-(trifluoromethyl)-1,2,4-oxadiazol-3-yl)nicotinamide

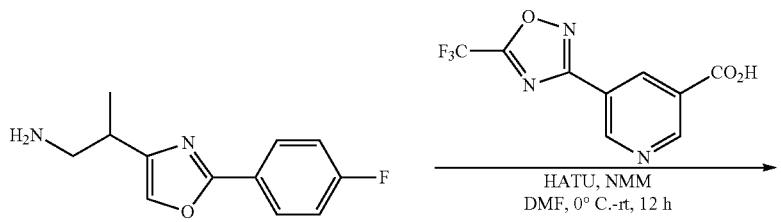

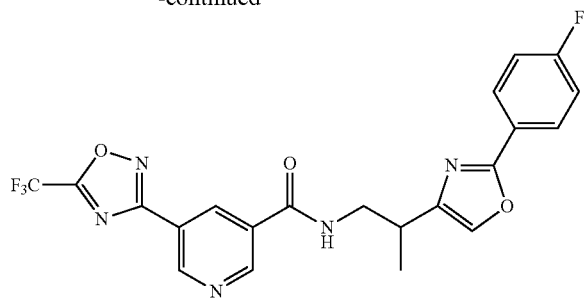

This compound was synthesized from 2-(2-(4-fluorophenyl)oxazol-4-yl)propan-1-amine and 5-(5-(trifluoromethyl)-1,2,4-oxadiazol-3-yl)nicotinic acid as described in example 8 step 6 (75 mg, yield 28%) as a yellow solid. $^1$H NMR (400 MHz, CDCl$_3$) δ 9.47-9.46 (d, J=2.0 Hz, 1H), 9.33 (d, J=2.0 Hz, 1H), 8.88-8.87 (t, J=2.1 Hz, 1H), 8.11-8.04 (m, 3H), 7.54 (d, J=1.0 Hz, 1H), 7.18-7.14 (t, J=8.8 Hz, 2H), 4.02-3.96 (ddd, J=13.2 Hz, 6.5 Hz, 4.1 Hz, 1H), 3.53-3.46 (ddd, J=13.1 Hz, 9.0 Hz, 4.3 Hz, 1H), 3.20-3.11 (m, 1H), 1.42-1.40 (d, J=7.0 Hz, 3H). MS (ESI) m/z: Calculated for C$_{21}$H$_{15}$F$_4$N$_5$O$_3$: 461.11. found: 462.1 (M+H)$^+$.

Example 135

N-(2-(4-(4-Chlorophenyl)thiazol-2-yl)-2-methylpropyl)-6-(5-(trifluoromethyl)-1,2,4-oxadiazol-3-yl)nicotinamide

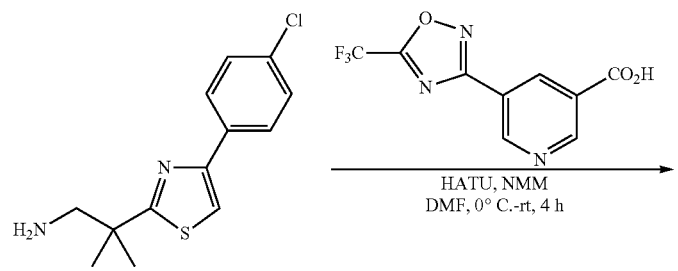

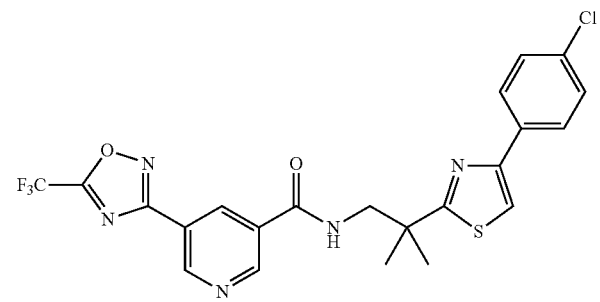

This compound was synthesized from 2-(4-(4-chlorophenyl)thiazol-2-yl)-2-methylpropan-1-amine and 5-(5-(trifluoromethyl)-1,2,4-oxadiazol-3-yl)nicotinic acid as described in example 8 step 6 (18 mg, yield 16%). $^1$H NMR (400 MHz, CDCl$_3$) δ 9.46 (d, J=2.0 Hz, 1H), 9.23 (d, J=2.3 Hz, 1H), 8.80 (t, J=2.1 Hz, 1H), 8.21 (m, 1H), 7.81-7.78 (m, 2H), 7.43 (m, 1H), 7.38-7.35 (m, 2H), 3.85 (d, J=5.8 Hz, 2H), 1.56 (s, 6H). MS (ESI) m/z: Calculated for C$_{22}$H$_{17}$ClF$_3$N$_5$O$_2$S: 507.07. found: 508.0 (M+H)$^+$.

Example 136

N-((4-([1,1'-Biphenyl]-3-yl)-1-methylpiperidin-4-yl)methyl)-5-(5-(trifluoromethyl)-1,2,4-oxadiazol-3-yl)nicotinamide

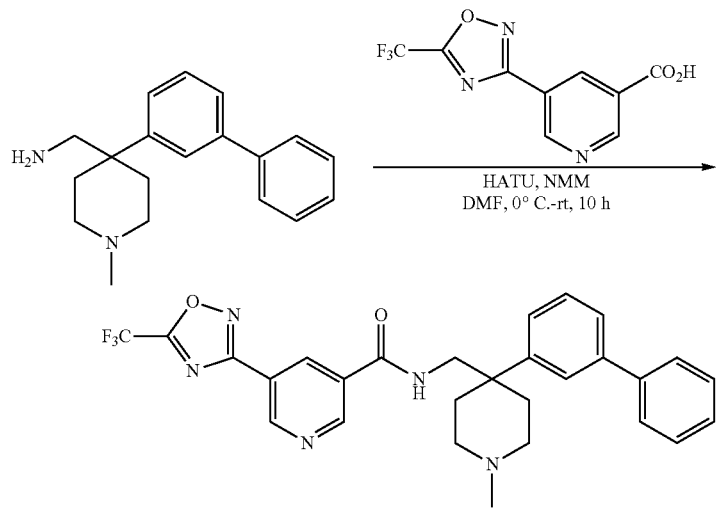

This compound was synthesized from (4-([1,1'-biphenyl]-3-yl)-1-methylpiperidin-4-yl)methanamine and 5-(5-(trifluoromethyl)-1,2,4-oxadiazol-3-yl)nicotinic acid as described in example 8 step 6 (60 mg, yield 30%) as an off white solid. $^1$H NMR (400 MHz, MeOD) δ 9.32 (d, J=2.0 Hz, 1H), 9.01 (d, J=2.0 Hz, 1H), 8.68-8.67 (t, J=2.0 Hz, 1H), 7.65 (m, 1H), 7.57-7.55 (m, 2H), 7.50-7.47 (m, 3H), 7.40-7.36 (t, J=7.4 Hz, 2H), 7.31-7.28 (m, 1H), 3.62 (m, 2H), 2.79-2.76 (m, 2H), 2.44-2.31 (m, 4H), 2.24 (m, 3H), 2.11-2.05 (m, 2H). MS (ESI) m/z: Calculated for $C_{23}H_{26}F_3N_5O_2$: 521.20. found: 522.2 (M+H)$^+$.

Example 137

5-Bromothiophene-3-carbaldehyde

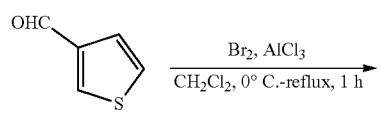

Anhydrous aluminum chloride (5.9 g, 44.5 mmol) was added in small portions over a period of 2 h to a solution of thiophene-3-carbaldehyde (2.0 g, 17.8 mmol) in $CH_2Cl_2$ (100 mL) maintaining the temperature at 0° C. Bromine (2.56 g, 16.0 mmol) in $CH_2Cl_2$ (50 mL) was then added dropwise to the reaction mixture at 0° C. The reaction mixture was refluxed at 40° C. for 1 h, quenched with water, and extracted with $CH_2Cl_2$. The combined extracts were dried over anhydrous $Na_2SO_4$, and concentrated under reduced pressure. The crude product was purified by column chromatography (silica 60-120 mesh, eluant 10% EtOAc in petroleum ether) to give 5-bromothiophene-3-carbaldehyde (3.0 g, yield 88%).

1-(5-Bromothiophen-3-yl)-2,2,2-trifluoroethanol

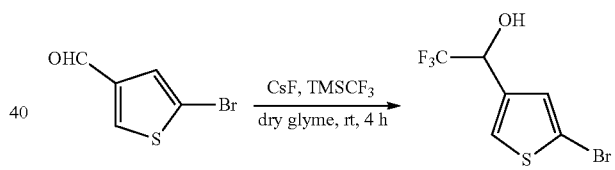

This compound was synthesized from 5-bromothiophene-3-carbaldehyde as described in example 88 step 1 (3.0 g, yield 73%) as a yellow liquid. $^1$H NMR (300 MHz, $CDCl_3$) δ 7.36 (s, 1H), 7.15 (s, 1H), 5.05-5.03 (m, 1H), 3.28 (br s, 1H).

1-(5-Bromothiophen-3-yl)-2,2,2-trifluoroethanone

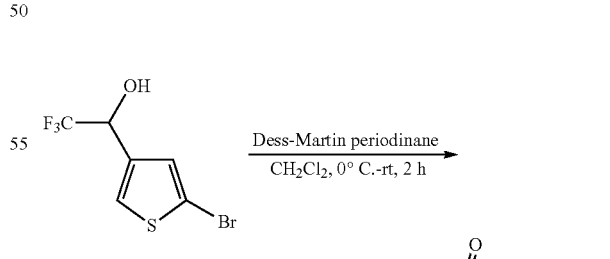

This compound was synthesized from 1-(5-bromothiophen-3-yl)-2,2,2-trifluoroethanol as described in example 47 step 2 (1.85 g, yield 62%). ¹H NMR (400 MHz, CDCl₃) δ 8.25 (m, 1H), 7.62 (d, J=1.1 Hz, 1H).

3-(4-(2,2,2-Trifluoroacetyl)thiophen-2-yl)benzoic acid

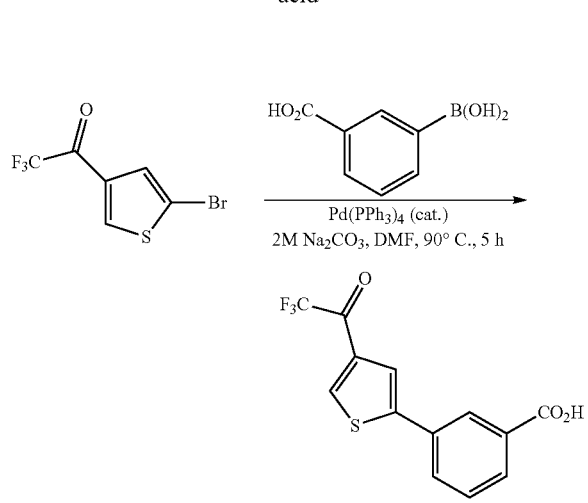

This compound was synthesized from 1-(5-bromothiophen-3-yl)-2,2,2-trifluoroethanone and 3-carboxyphenylboronic acid as described in example 88 step 3 (150 mg, yield 16%) as a yellow solid. ¹H NMR (300 MHz, DMSO-d₆) δ 13.26 (br s, 1H), 8.85 (s, 1H), 8.19 (s, 1H), 8.07-8.05 (m, 2H), 7.96-7.93 (d, J=7.9 Hz, 1H), 7.62-7.57 (t, J=7.7 Hz, 1H).

N-(2-(2-(4-Fluorophenyl)oxazol-4-yl)-2-methylpropyl)-3-(4-(2,2,2-trifluoroacetyl)thiophen-2-yl)benzamide

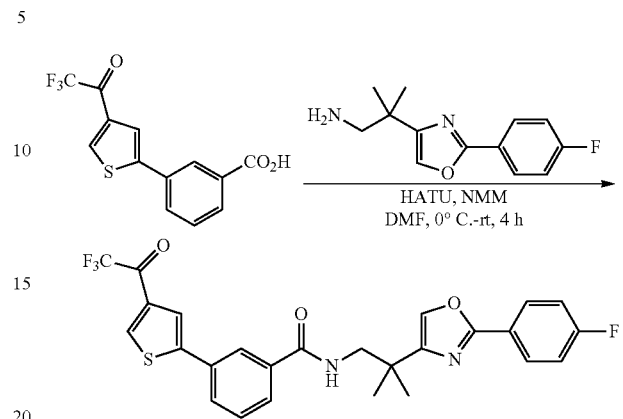

This compound was synthesized from 2-(2-(4-fluorophenyl)oxazol-4-yl)-2-methylpropan-1-amine and 3-(4-(2,2,2-trifluoroacetyl)thiophen-2-yl)benzoic acid as described in example 8 step 6 (75 mg, yield 30%). ¹H NMR (400 MHz, DMSO-d₆) δ 8.21-8.16 (m, 1H), 8.11-8.10 (m, 1H), 8.02-7.96 (m, 3H), 7.91-7.90 (m, 1H), 7.88-7.83 (m, 1H), 7.77-7.75 (m, 1H), 7.67-7.48 (m, 2H), 7.31-7.25 (m, 2H), 3.56-3.54 (m, 2H), 1.33 (d, J=2.1 Hz, 6H). MS (ESI) m/z: Calculated for $C_{26}H_{20}F_4N_2O_3S$: 516.11. found: 515.7 (M−H)⁻.

Example 138

N-(2-(2-(4-Fluorophenyl)oxazol-4-yl)-2-oxoethyl)-3-(5-(trifluoromethyl)-1,2,4-oxadiazol-3-yl)benzamide

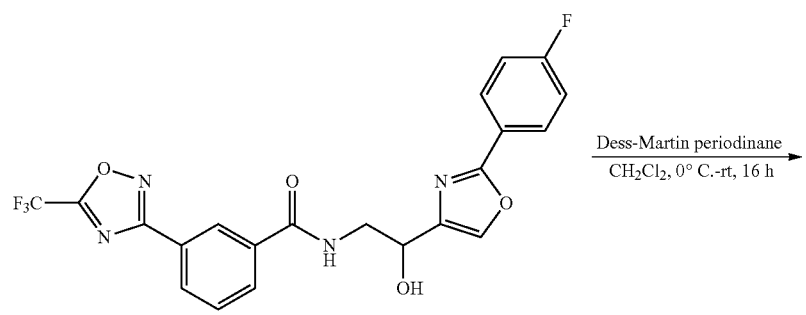

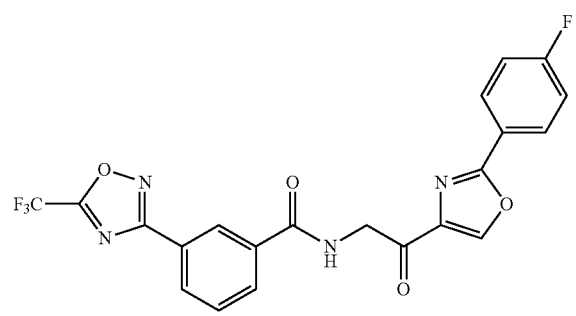

This compound was synthesized from N-(2-(2-(4-fluorophenyl)oxazol-4-yl)-2-hydroxyethyl)-3-(5-(trifluoromethyl)-1,2,4-oxadiazol-3-yl)benzamide as described in example 47 step 2 (150 mg, yield 43%) as an off-white solid. $^1$H NMR (300 MHz, CDCl$_3$) δ 8.62 (t, J=1.5 Hz, 1H), 8.40 (s, 1H), 8.32-8.29 (dt, J=7.8 Hz, 1.2 Hz, 1H), 8.15-8.11 (m, 3H), 7.70-7.65 (t, J=7.8 Hz, 1H), 7.25-7.19 (t, J=8.7 Hz, 3H), 5.02-5.00 (d, J=4.6 Hz, 2H). MS (ESI) m/z: Calculated for C$_{21}$H$_{12}$F$_4$N$_4$O$_4$: 460.08. found: 459.4 (M−H)$^−$.

N-(2-(2-(4-Fluorophenyl)oxazol-4-yl)-2-hydroxypropyl)-3-(5-(trifluoromethyl)-1,2,4-oxadiazol-3-yl)benzamide

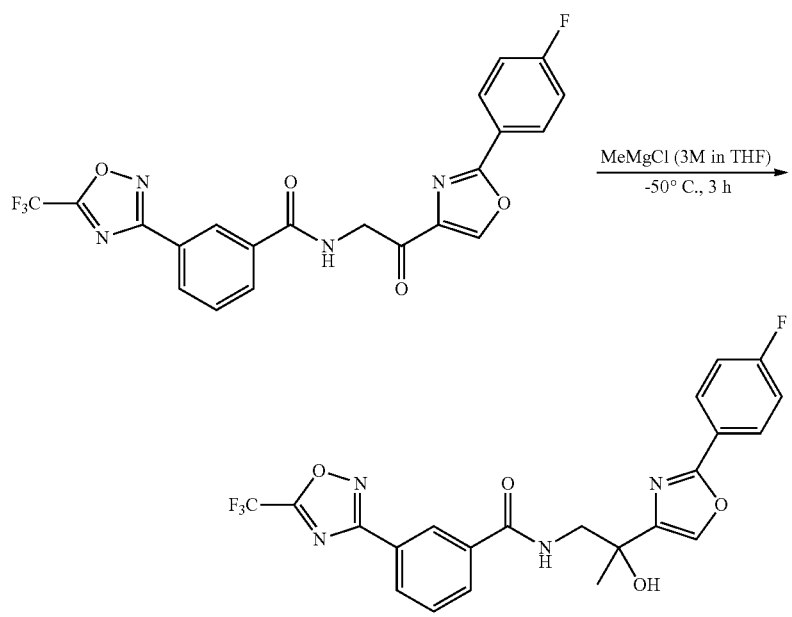

N-(2-(2-(4-Fluorophenyl)oxazol-4-yl)-2-oxoethyl)-3-(5-(trifluoromethyl)-1,2,4-oxadiazol-3-yl)benzamide (150 mg, 0.33 mmol) was dissolved in dry THF (10 mL) and the reaction mixture was cooled to −50° C. Methylmagnesium chloride (0.32 mL, 0.98 mmol, 3M in THF) was then added and the reaction mixture was stirred at −50° C. for 3 h. The reaction mixture was quenched with aqueous saturated NH$_4$Cl solution, and extracted with EtOAc. The combined extracts were washed with water and brine, and concentrated under reduced pressure. The crude product was purified by column chromatography (silica gel 60-120 mesh, eluent 25-30% EtOAc in petroleum ether) followed by preparative TLC (eluent 30% EtOAc in petroleum ether) to afford N-(2-(2-(4-fluorophenyl)oxazol-4-yl)-2O2-hydroxypropyl)-3-(5-(trifluoromethyl)-1,2,4-oxadiazol-3-yl)benzamide (15 mg, yield 10%) as a white solid. $^1$H NMR (400 MHz, CDCl$_3$) δ 8.49 (t, J=1.5 Hz, 1H), 8.28-8.25 (dt, J=7.9 Hz, 1.3 Hz, 1H), 8.05-8.01 (m, 3H), 7.70 (s, 1H), 7.64-7.61 (t, J=7.8 Hz, 1H), 7.16-7.11 (t, J=8.7 Hz, 2H), 7.05-7.02 (m, 1H), 3.96-3.85 (m, 2H), 3.81 (s, 1H), 1.65 (s, 3H). MS (ESI) m/z: Calculated for C$_{22}$H$_{16}$F$_4$N$_4$O$_4$: 476.11. found: 475.5 (M−H)$^−$.

Example 139

1-(4-Bromofuran-2-yl)-2,2,2-trifluoroethanol

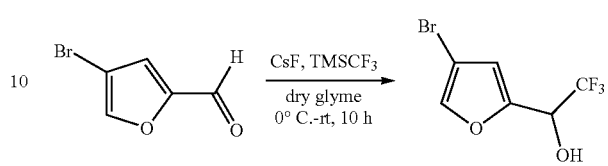

This compound was synthesized from 4-bromofuran-2-carbaldehyde as described in example 88 step 1 (1.0 g, yield 72%) as a pale yellow liquid. $^1$H NMR (400 MHz, DMSO-d$_6$) δ 7.99 (d, J=0.9 Hz, 1H), 7.10-7.08 (d, J=6.4 Hz, 1H), 6.75 (s, 1H), 5.29-5.22 (m, 1H).

1-(4-Bromofuran-2-yl)-2,2,2-trifluoroethanone

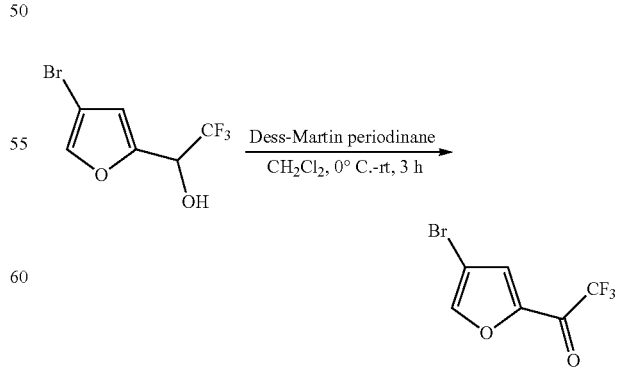

This compound was synthesized from 1-(4-bromofuran-2-yl)-2,2,2-trifluoroethanol as described in example 47 step 2

(0.8 g, yield 81%), which was used in the next step without further purification. $^1$H NMR (400 MHz, CDCl$_3$) δ 7.82 (m, 1H), 7.52-7.51 (m, 1H).

3-(5-(2,2,2-Trifluoroacetyl)furan-3-yl)benzoic acid

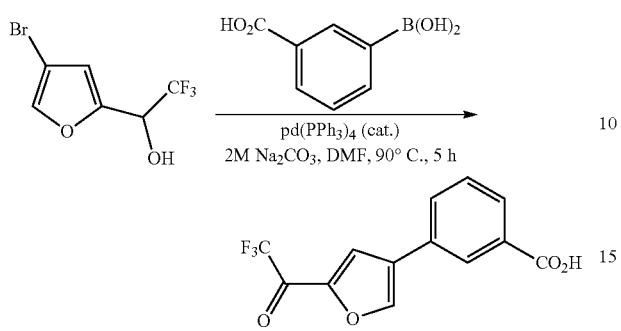

This compound was synthesized from 1-(4-bromofuran-2-yl)-2,2,2-trifluoroethanone and 3-carboxyphenylboronic acid as described in example 88 step 3 (150 mg, yield 26%) as a pale yellow solid. $^1$H NMR (300 MHz, DMSO-d$_6$) δ 13.14 (br s, 1H), 8.99 (s, 1H), 8.44 (s, 1H), 8.31 (m, 1H), 8.07-8.04 (m, 1H), 7.93-7.90 (m, 1H), 7.60-7.55 (t, J=7.7 Hz, 1H). MS (ESI) m/z: Calculated for C$_{13}$H$_7$F$_3$O$_4$: 284.03. found: 282.9 (M−H)$^-$.

N-(2-(2-(4-Fluorophenyl)oxazol-4-yl)-2-methylpropyl)-3-(5-(2,2,2-trifluoroacetyl)furan-3-yl)benzamide

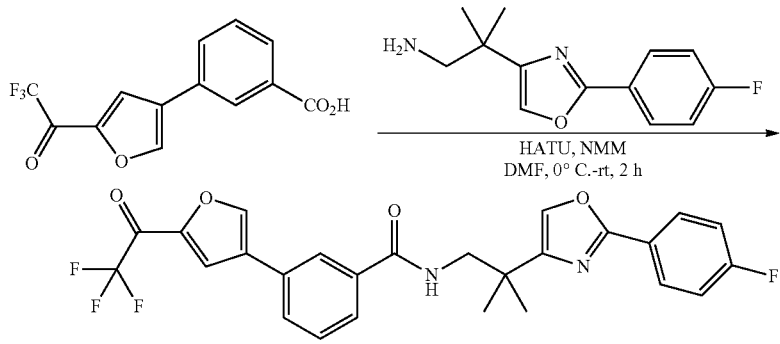

This compound was synthesized from 2-(2-(4-fluorophenyl)oxazol-4-yl)-2-methylpropan-1-amine and 3-(5-(2,2,2-trifluoroacetyl)furan-3-yl)benzoic acid as described in example 8 step 6 (30 mg, yield 14%). $^1$H NMR (400 MHz, DMSO-d$_6$) δ 8.91 (s, 1H), 8.40-8.35 (m, 2H), 8.16 (m, 1H), 8.02-7.94 (m, 4H), 7.82-7.80 (m, 1H), 7.57-7.53 (t, J=7.8 Hz, 1H), 7.36-7.31 (t, J=9.0 Hz, 2H), 3.53-3.51 (d, J=6.1 Hz, 2H), 1.30 (s, 6H). MS (ESI) m/z: Calculated for C$_{26}$H$_{20}$F$_4$N$_2$O$_4$: 500.14. found: 499.5 (M−H)$^-$.

Example 140

1-(4-Bromothiophen-2-yl)-2,2,2-trifluoroethanol

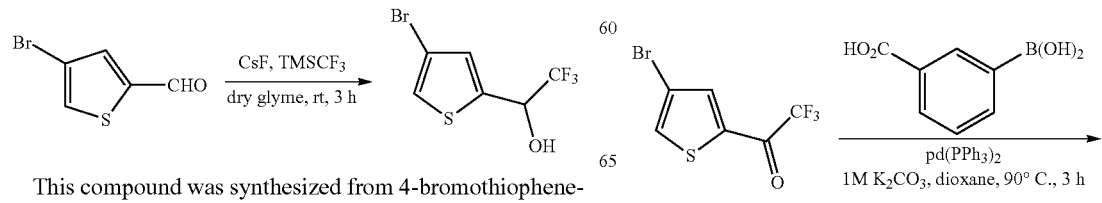

This compound was synthesized from 4-bromothiophene-2-carbaldehyde as described in example 88 step 1 (2.0 g, yield 74%) as a pale yellow liquid. $^1$H NMR (300 MHz, CDCl$_3$) δ 7.30 (d, J=1.3 Hz, 1H), 7.12 (m, 1H), 5.27-5.22 (m, 1H), 3.17 (br s, 1H).

1-(4-Bromothiophen-2-yl)-2,2,2-trifluoroethanone

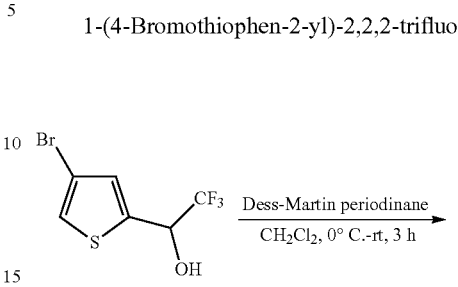

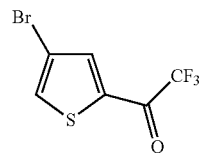

This compound was synthesized from 1-(4-bromothiophen-2-yl)-2,2,2-trifluoroethanol as described in example 47 step 2 (1.5 g, yield 75%) as dark brown liquid. $^1$H NMR (300 MHz, CDCl$_3$) δ 7.86 (m, 1H), 7.80 (d, J=0.9 Hz, 1H).

3-(5-(2,2,2-Trifluoroacetyl)thiophen-3-yl)benzoic acid

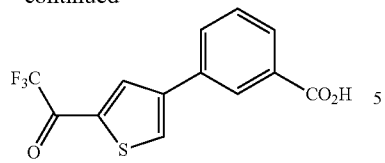

This compound was synthesized from 1-(4-bromothiophen-2-yl)-2,2,2-trifluoroethanone and 3-carboxyphenylboronic acid as described in example 88 step 3 (400 mg, yield 46%) as a pale yellow solid. $^1$H NMR (400 MHz, DMSO-$d_6$) δ 13.19 (br s, 1H), 8.85 (d, J=1.2 Hz, 1H), 8.50 (s, 1H), 8.29 (m, 1H), 8.10-8.08 (d, J=7.6 Hz, 1H), 7.96-7.94 (d, J=7.6 Hz, 1H), 7.62-7.59 (t, J=7.8 Hz, 1H). MS (ESI) m/z: Calculated for $C_{13}H_7F_3O_3S$: 300.01. found: 298.9 (M−H)$^−$.

N-(2-(2-(4-Fluorophenyl)oxazol-4-yl)-2-methylpropyl)-3-(5-(2,2,2-trifluoroacetyl)thiophen-3-yl)benzamide

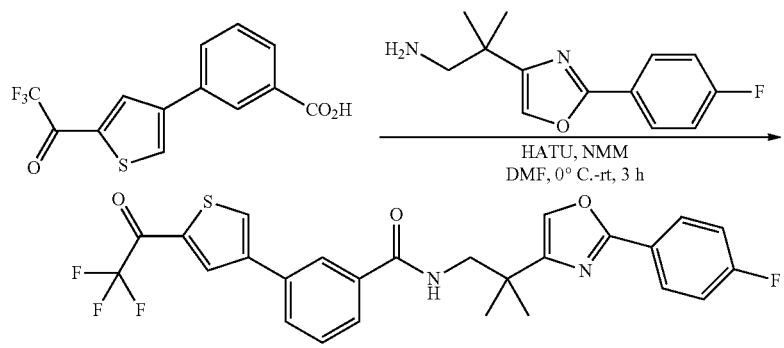

This compound was synthesized from 2-(2-(4-fluorophenyl)oxazol-4-yl)-2-methylpropan-1-amine and 3-(5-(2,2,2-trifluoroacetyl)thiophen-3-yl)benzoic acid as described in example 8 step 6 (30 mg, yield 17%). $^1$H NMR (400 MHz, DMSO-$d_6$) δ 8.67 (d, J=1.2 Hz, 1H), 8.43 (m, 1H), 8.16-8.12 (m, 2H), 8.00-7.97 (dd, J=9.0 Hz, 5.3 Hz, 2H), 7.92-7.90 (m, 2H), 7.84-7.82 (m, 1H), 7.57-7.53 (t, J=7.8 Hz, 1H), 7.30-7.25 (t, J=9.0 Hz, 2H), 3.56 (d, J=6.4 Hz, 2H), 1.34 (s, 6H). MS (ESI) m/z: Calculated for $C_{26}H_{20}F_4N_2O_3S$: 516.11. found: 515.5 (M−H)$^−$.

Example 141

3-Cyano-N-((4-(4-phenylthiazol-2-yl)tetrahydro-2H-pyran-4-yl)methyl)benzamide

This compound was synthesized from (4-(4-phenylthiazol-2-yl)tetrahydro-2H-pyran-4-yl)methanamine and 3-cyanobenzoic acid as described in example 8 step 6 (6.6 g, yield 89%) as a white solid. $^1$H NMR (300 MHz, CDCl$_3$) δ 8.11-8.10 (m, 1H), 8.02-7.99 (dt, J=7.9 Hz, 1.5 Hz, 1H), 7.91-7.88 (m, 2H), 7.78-7.74 (dt, J=7.7 Hz, 1.3 Hz, 1H), 7.71-7.68 (m, 1H), 7.53-7.46 (m, 3H), 7.42-7.36 (m, 1H), 3.97-3.90 (m, 2H), 3.85-3.83 (d, J=5.7 Hz, 2H), 3.77-3.69 (m, 2H), 2.35-2.29 (m, 2H), 2.07-1.98 (m, 2H). MS (ESI) m/z: Calculated for $C_{23}H_{21}N_3O_2S$: 403.14. found: 402.2 (M−H)$^−$.

(N'-Hydroxycarbamimidoyl)-N-((4-(4-phenylthiazol-2-yl)tetrahydro-2H-pyran-4-yl)methyl)benzamide

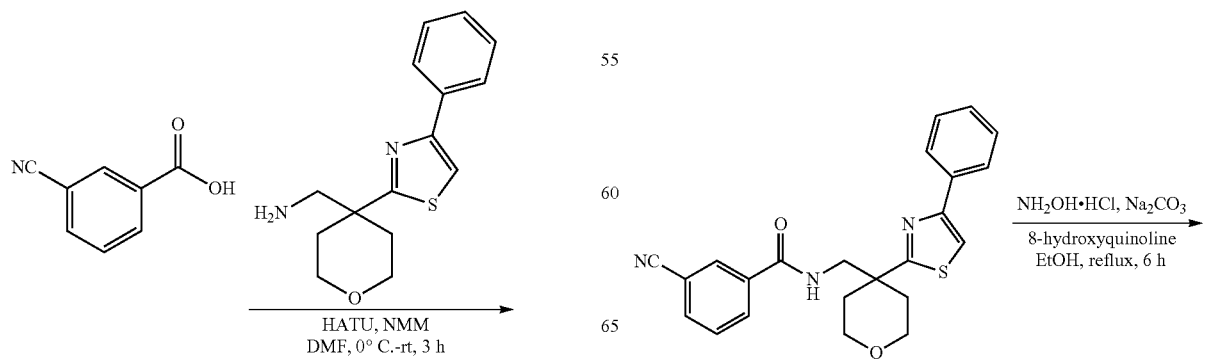

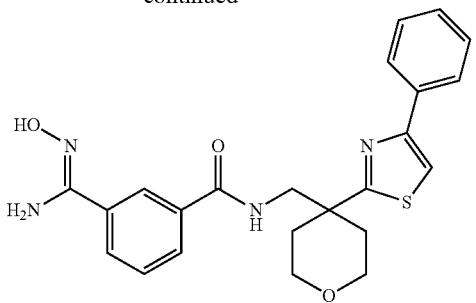

This compound was synthesized from 3-cyano-N-((4-(4-phenylthiazol-2-yl)tetrahydro-2H-pyran-4-yl)methyl)benzamide as described in example 1 step 4 (6.8 g, crude), which was used without further purification. ¹H NMR (400 MHz, MeOD) δ 8.05-8.04 (m, 1H), 7.93-7.91 (m, 2H), 7.78-7.75 (m, 3H), 7.43-7.37 (m, 3H), 7.32-7.28 (m, 1H), 3.94-3.91 (m, 2H), 3.69 (m, 2H), 3.63-3.56 (m, 2H), 2.43-2.39 (d, J=13.8 Hz, 2H), 2.10-2.06 (m, 2H). MS (ESI) m/z: Calculated for C$_{23}$H$_{24}$N$_4$O$_3$S: 436.16. found: 437.2 (M+H)⁺.

Ethyl 3-(3-(((4-(4-phenylthiazol-2-yl)tetrahydro-2H-pyran-4-yl)methyl)carbamoyl)phenyl)-1,2,4-oxadiazole-5-carboxylate

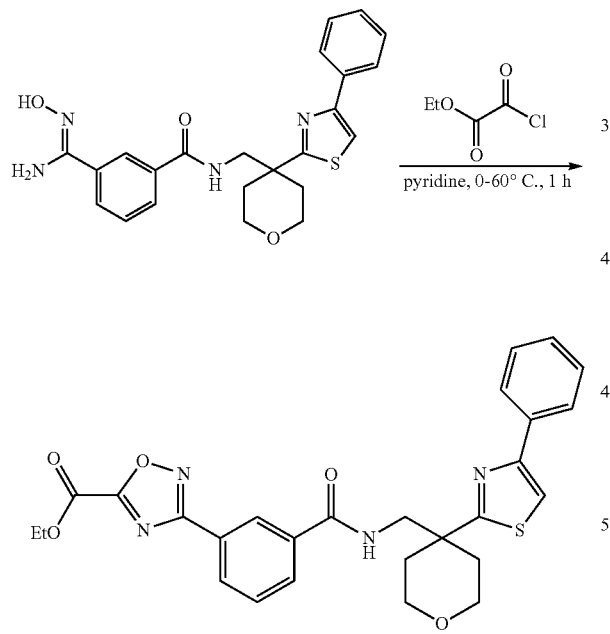

3-(N'-Hydroxycarbamimidoyl)-N-((4-(4-phenylthiazol-2-yl)tetrahydro-2H-pyran-4-yl)methyl)benzamide (6.8 g, 15.57 mmol) was dissolved in anhydrous pyridine (68 mL) and the reaction mixture was cooled to 0° C. Ethyl chlorooxoacetate (5.2 mL, 46.73 mmol) was added dropwise, and the reaction mixture was heated at 60° C. for 1 h, quenched with 1.5N HCl solution, and diluted with EtOAc. The organic layer was washed with water and brine, dried over anhydrous sodium sulfate and concentrated under reduced pressure. The crude product was purified by column chromatography (silica gel 60-120 mesh, eluent 25-30% EtOAc in petroleum ether) to afford ethyl 3-(3-(((4-(4-phenylthiazol-2-yl)tetrahydro-2H-pyran-4-yl)methyl)carbamoyl)phenyl)-1,2,4-oxadiazole-5-carboxylate (6.8 g, yield 87%). ¹H NMR (400 MHz, CDCl$_3$) δ 8.21 (d, J=7.9 Hz, 1H), 8.11-8.09 (m, 1H), 7.78-7.76 (m, 1H), 7.61-7.59 (m, 2H), 7.44 (s, 1H), 7.32-7.27 (m, 1H), 7.23-7.21 (m, 3H), 4.62-4.57 (q, J=7.0 Hz, 2H), 3.97-3.94 (m, 2H), 3.81-3.76 (m, 2H), 3.56-3.50 (m, 2H), 2.41-2.37 (m, 2H), 2.19-2.12 (m, 2H), 1.53-1.50 (t, J=7.2 Hz, 3H). MS (ESI) m/z: Calculated for C$_{27}$H$_{26}$N$_4$O$_5$S: 518.16. found: 517.1 (M−H)⁻.

3-(5-(Hydroxymethyl)-1,2,4-oxadiazol-3-yl)-N-((4-(4-phenylthiazol-2-yl)tetrahydro-2H-pyran-4-yl)methyl)benzamide

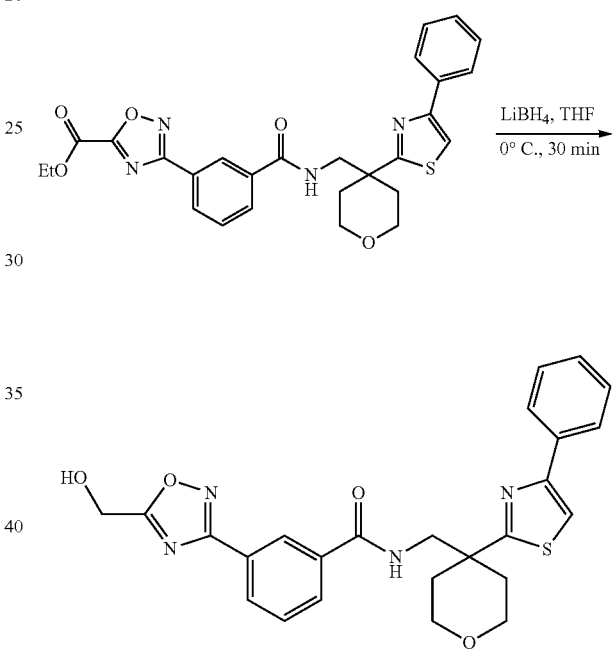

Ethyl 3-(3-(((4-(4-phenylthiazol-2-yl)tetrahydro-2H-pyran-4-yl)methyl)carbamoyl)phenyl)-1,2,4-oxadiazole-5-carboxylate (1.0 g, 1.93 mmol) was dissolved in anhydrous THF (20 mL) and the reaction mixture was cooled to 0° C. Lithium borohydride (1.15 mL, 2.3 mmol, 2M in THF) was added, and the reaction mixture was stirred for 30 min, quenched with ice, and diluted with EtOAc. The organic layer was washed with water and brine, and concentrated under reduced pressure. The crude product was purified by column chromatography (silica gel 60-120 mesh, eluant: 70-80% EtOAc in petroleum ether) to afford 3-(5-(hydroxymethyl)-1,2,4-oxadiazol-3-yl)-N-((4-(4-phenylthiazol-2-yl)tetrahydro-2H-pyran-4-yl)methyl)benzamide (300 mg, yield 32%). ¹H NMR (300 MHz, DMSO-d$_6$) δ 8.46 (m, 1H), 8.20-8.17 (m, 1H), 7.96 (m, 1H), 7.91-7.88 (m, 2H), 7.62 (m, 1H), 7.53-7.51 (m, 2H), 7.36-7.34 (m, 3H), 4.89 (s, 2H), 3.99-3.92 (m, 2H), 3.90-3.88 (d, J=5.7 Hz, 2H), 3.78-3.70 (m, 2H), 2.35-2.27 (m, 2H), 2.08-2.00 (m, 2H). MS (ESI) m/z: Calculated for C$_{26}$H$_{24}$N$_4$O$_4$S: 476.15. found: 475.7 (M−H)⁻.

3-(5-Formyl-1,2,4-oxadiazol-3-yl)-N-((4-(4-phenylthiazol-2-yl)tetrahydro-2H-pyran-4-yl)methyl)benzamide

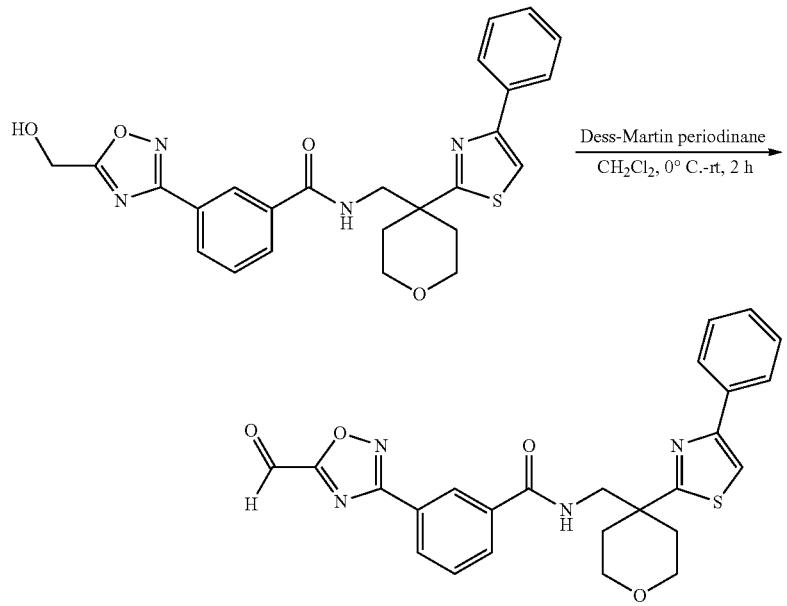

This compound was synthesized from 3-(5-(hydroxymethyl)-1,2,4-oxadiazol-3-yl)-N-((4-(4-phenylthiazol-2-yl)tetrahydro-2H-pyran-4-yl)methyl)benzamide as described in example 47 step 2 (340 mg, yield 57%). $^1$H NMR (300 MHz, CDCl$_3$) δ 9.89 (s, 1H), 8.49 (m, 1H), 8.27-8.17 (m, 1H), 8.04-8.01 (m, 1H), 7.90-7.88 (m, 2H), 7.71-7.69 (m, 1H), 7.60-7.52 (m, 2H), 7.37-7.30 (m, 2H), 4.00-3.92 (m, 2H), 3.91-3.89 (d, J=5.7 Hz, 2H), 3.78-3.71 (m, 2H), 2.36-2.28 (m, 2H), 2.09-2.01 (m, 2H). MS (ESI) m/z: Calculated for C$_{25}$H$_{22}$N$_4$O$_4$S: 474.14. found: 473.4 (M−H)$^−$.

N-((4-(4-Phenylthiazol-2-yl)tetrahydro-2H-pyran-4-yl)methyl)-3-(5-(2,2,2-trifluoro-1-hydroxyethyl)-1,2,4-oxadiazol-3-yl)benzamide

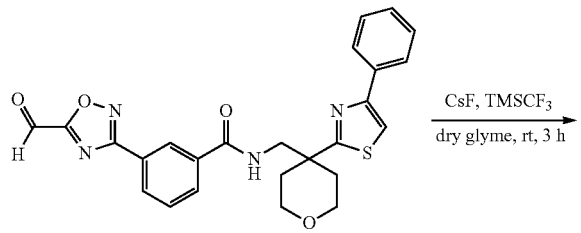

This compound was synthesized from 3-(5-formyl-1,2,4-oxadiazol-3-yl)-N-((4-(4-phenylthiazol-2-yl)tetrahydro-2H-pyran-4-yl)methyl)benzamide as described in example 88 step 1 (30 mg, yield 17%). MS (ESI) m/z: Calculated for C$_{26}$H$_{23}$F$_3$N$_4$O$_4$S: 544.14. found: 545.2 (M+H)$^+$.

N-((4-(4-Phenylthiazol-2-yl)tetrahydro-2H-pyran-4-yl)methyl)-3-(5-(2,2,2-trifluoroacetyl)-1,2,4-oxadiazol-3-yl)benzamide

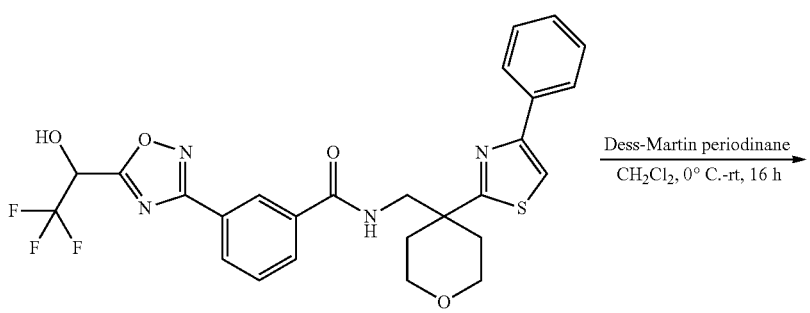

-continued

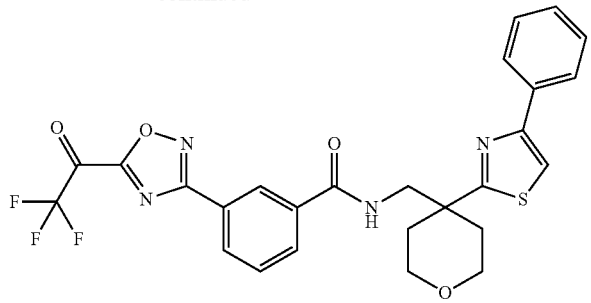

This compound was synthesized from N-((4-(4-phenylthiazol-2-yl)tetrahydro-2H-pyran-4-yl)methyl)-3-(5-(2,2,2-trifluoro-1-hydroxyethyl)-1,2,4-oxadiazol-3-yl)benzamide as described in example 47 step 2 (5 mg, yield 17%). $^1$H NMR (400 MHz, CDCl$_3$) δ 8.56 (s, 1H), 8.15-8.13 (m, 1H), 7.89-7.87 (m, 2H), 7.79-7.77 (m, 1H), 7.54 (s, 1H), 7.44-7.36 (m, 4H), 4.00-3.94 (m, 2H), 3.90-3.89 (d, J=5.3 Hz, 2H), 3.79-3.74 (m, 2H), 2.34-2.30 (m, 2H), 2.07-2.02 (m, 2H). MS (ESI) m/z: Calculated for $C_{26}H_{21}F_3N_4O_4S$: 542.12. found: 541.5 (M–H)$^-$.

Pharmaceutical Compositions

Example A

Tablets are prepared using conventional methods and are formulated as follows:

| Ingredient | Amount per tablet |
|---|---|
| Compound of Example I | 5 mg |
| Microcrystalline cellulose | 100 mg |
| Lactose | 100 mg |
| Sodium starch glycollate | 30 mg |
| Magnesium stearate | 2 mg |
| Total | 237 mg |

Example B

Capsules are prepared using conventional methods and are formulated as follows:

| Ingredient | Amount per tablet |
|---|---|
| Compound of Example 3 | 15 mg |
| Dried starch | 178 mg |
| Magnesium stearate | 2 mg |
| Total | 195 mg |

Histone Deacetylase 9 (HDAC9) Inhibition Assay:

Novel histone deacetylase 9 (HDAC9) inhibitors were characterized in an in vitro biochemical functional assay. The assay measures the increased fluorescent signal due to deacetylation, by HDAC9, of a fluorogenic substrate. The commercial available substrate is Class IIa HDAC-specific and contains an acetylated lysine residue and would releases the fluorescent signal upon trypsin cleavage after deacetylation.

Specifically, test compounds diluted to various concentrations in 100% DMSO are first dispensed into 384-well assay plates. Recombinant HDAC9 isoform 4 (purchased from BPS Bioscience) in complete assay buffer (50 mM Tris-HCl, pH 8.0, 137 mM NaCl, 2.7 mM KCl, 1 mM MgCl$_2$, 0.05% BSA & 0.005% Tween 20) were then added to each well (5 uL/well) using Multidrop Combi (Thermo Scientific), followed by 5 uL/well substrate (purchased from BPS Bioscience, 4.5 uM final). After 45 minutes incubation at room temperature, 10 uL 2× developer solution (assay buffer with 40 uM Trypsin and 20 uM Trichostatin A) was added. The plates were then incubated 1 hour at room temperature before reading in fluorescent intensity mode at 450 nm in an Envision (Perkin Elmer) plate reader. Percent Inhibition of HDAC9 activity by compounds in each test wells was calculated by normalizing to fluorescent signal in control wells containing DMSO only. The pIC50s value of test compounds were calculated from non-linear curve fitting, using ActivityBase5 data analysis tool (IDBS), from 11 point 3× dilution series starting from 100 uM final compound concentration.

For dose response experiments, normalized data were fit by ABASE/XC50 using the equation $y=a+(b-a)/(1+(10^x/10^c))^d$, where a is the minimum % activity, b is the maximum % activity, c is the pIC$_{50}$, d is the Hill slope.

The pIC$_{50}$s are averaged to determine a mean value, for a minimum of 2 experiments. As determined using the above method, the compounds of Examples 1-141 exhibited a pIC$_{50}$ greater than 4.8. For instance, the compounds of Examples 21, 32, 78, 110 and 132 inhibited HDAC9 in the above method with a mean pIC$_{50}$>6.

REFERENCES

US 20060269559, U.S. Pat. No. 7,521,044, WO2007084775

"Deacetylase inhibition promotes the generation and function of regulatory T cells," R. Tao, E. F. de Zoeten, E. Ozkaynak, C. Chen, L. Wang, P. M. Porrett, B. Li, L. A. Turka, E. N. Olson, M. I. Greene, A. D. Wells, W. W. Hancock, Nature Medicine, 13 (11), 2007.

"Expression of HDAC9 by T Regulatory Cells Prevents Colitis in Mice," E. F. de Zoeten, L. Wang, H. Sai, W. H. Dillmann, W. W. Hancock, Gastroenterology. 2009 Oct. 28.

"Immunomodulatory effects of deacetylase inhibitors: therapeutic targeting of FOXP3+ regulatory T cells," L. Wang, E. F. de Zoeten, M. I. Greene and W. W. Hancock, Nature Review Drug Discovery. 8(12):969-81, 2009 and references therein.

"HDAC7 targeting enhances FOXP3+ Treg function and induces long-term allograft survival," L. Wang, et al., Am. J. Transplant 9, S621 (2009).

"Selective class II HDAC inhibitors impair myogenesis by modulating the stability and activity of HDACMEF2 complexes," A. Nebbioso, F. Manzo, M. Miceli, M. Conte, L.

Manente, A. Baldi, A. De Luca, D. Rotili, S. Valente, A. Mai, A. Usiello, H. Gronemeyer, L. Altucci, EMBO reports 10 (7), 776-782, 2009. and references therein.

"Myocyte Enhancer Factor 2 and Class II Histone Deacetylases Control a Gender-Specific Pathway of Cardioprotection Mediated by the Estrogen Receptor," E. van Rooij, J. Fielitz, L. B. Sutherland, V. L. Thijssen, H. J. Crijns, M. J. Dimaio, J. Shelton, L. J. De Windt, J. A. Hill, E. N. Olson, Circulation Research, January 2010.

What is claimed is:

1. A compound according to Formula I:

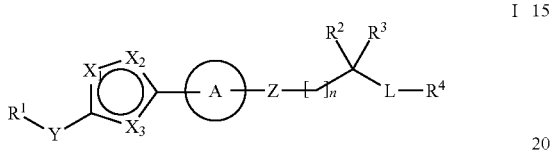

wherein:
- $R^1$ is halo($C_1$-$C_4$)alkyl, wherein said halo($C_1$-$C_4$)alkyl contains at least 2 halo atoms;
- Y is a bond and $X_1$ is O, N or NH, $X_2$ is N or CH and $X_3$ is N or NH,
- A is optionally substituted ($C_3$-$C_6$)cycloalkyl, phenyl, naphthyl, 4-7 membered heterocycloalkyl, 5-6 membered heteroaryl, or 9-10 membered heteroaryl, wherein any optionally substituted cycloalkyl, phenyl, naphthyl, heterocycloalkyl, or heteroaryl is optionally substituted by 1-3 groups independently selected from ($C_1$-$C_4$)alkyl, halogen, cyano, halo($C_1$-$C_4$)alkyl, ($C_1$-$C_4$)alkoxy, halo($C_1$-$C_4$)alkoxy, —$NR^A R^A$ and —(($C_1$-$C_4$)alkyl)$NR^A R^A$;
- Z is —C(=O)$NR^X$—, —$NR^X$C(=O)$NR^X$, —$NR^X$C(=O)—, —$SO_2$—, —$SO_2 NR^X$—, —$NR^X SO_2$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—;
- n is 0-4;
  - when n is 0, $R^2$ and $R^3$ are independently selected from H and optionally substituted ($C_1$-$C_4$)alkyl, aryl($C_1$-$C_4$)alkyl-, and ($C_3$-$C_7$)cycloalkyl($C_1$-$C_4$)alkyl-, or
  - when n is 1-4, $R^2$ and $R^3$ are independently selected from H, fluoro, and optionally substituted ($C_1$-$C_4$)alkyl, aryl($C_1$-$C_4$)alkyl-, and ($C_3$-$C_7$)cycloalkyl($C_1$-$C_4$)alkyl-, wherein, when n is 1, $R^2$ is F and $R^3$ is H, then Z is —C(=O)$NR^X$—, —$NR^X$C(=O)$NR^X$, —$SO_2 NR^X$—, —NHCH($CF_3$)—, —CH($CF_3$)NH—, —CH($CF_3$)—, —($C_1$-$C_4$)alkyl-, —$NR^X$—, or —($C_1$-$C_3$)alkyl-$NR^X$—, or
  - when n is 1-4, $R^2$ is selected from —$NR^A R^B$, —($C_1$-$C_4$)alkyl-$NR^A R^B$, —CONR$^A R^B$, —($C_1$-$C_4$)alkyl-CON-$R^A R^B$, —$CO_2$H, —($C_1$-$C_4$)alkyl-$CO_2$H, hydroxyl, hydroxy($C_1$-$C_4$)alkyl-, ($C_1$-$C_3$)alkoxy, and ($C_1$-$C_3$)alkoxy($C_1$-$C_4$)alkyl-, and $R^3$ is selected from H and optionally substituted ($C_1$-$C_4$)alkyl, aryl($C_1$-$C_4$)alkyl-, and ($C_3$-$C_7$)cycloalkyl($C_1$-$C_4$)alkyl-,
  - wherein the aryl, cycloalkyl and each of the ($C_1$-$C_4$) alkyl moieties of said optionally substituted ($C_1$-$C_4$)alkyl, aryl($C_1$-$C_4$)alkyl-, and ($C_3$-$C_7$)cycloalkyl($C_1$-$C_4$)alkyl- of any $R^2$ and $R^3$ are optionally substituted by 1, 2 or 3 groups independently selected from halogen, cyano, ($C_1$-$C_4$)alkyl, halo($C_1$-$C_4$)alkyl, ($C_1$-$C_4$) alkoxy, halo($C_1$-$C_4$)alkoxy, —$NR^A R^A$, —(($C_1$-$C_4$)alkyl)$NR^A R^A$, and hydroxyl;
- or $R^2$ and $R^3$ taken together with the atom to which they are connected form an optionally substituted 4, 5, 6, or 7 membered cycloalkyl or heterocycloalkyl group, wherein said heterocycloalkyl group contains 1 or 2 heteroatoms independently selected from N, O and S and said optionally substituted cycloalkyl or heterocycloalkyl group is optionally substituted by 1, 2 or 3 substituents independently selected from ($C_1$-$C_4$) alkyl, halo($C_1$-$C_4$)alkyl, halogen, cyano, aryl($C_1$-$C_4$) alkyl-, ($C_3$-$C_7$)cycloalkyl($C_1$-$C_4$)alkyl-, —$OR^Y$, —$NR^Y R^Y$, —C(=O)$OR^Y$, —C(=O)$NR^Y R^Y$, —$NR^Y$C(=O)$R^Y$, —$SO_2 NR^Y R^Y$, —$NR^Y SO_2 R^Y$, —OC(=O)$NR^Y R^Y$, —$NR^Y$C(=O)$OR^Y$, and —$NR^Y$C(=O)$NR^Y R^Y$; and
- L is 5-6 membered heteroaryl or phenyl which is substituted by $R^4$ and is optionally further substituted, wherein when L is further substituted, L is substituted by 1 or 2 substituents independently selected from halogen, cyano and ($C_1$-$C_4$)alkyl;
- $R^4$ is H, ($C_1$-$C_4$)alkyl, halo, halo($C_1$-$C_4$)alkyl, ($C_1$-$C_4$) alkoxy, (($C_1$-$C_4$)alkyl)(($C_1$-$C_4$)alkyl)N($C_1$-$C_4$) alkoxy, (($C_1$-$C_4$)alkyl)(($C_1$-$C_4$)alkyl)N($C_1$-$C_4$)alkyl-, ($C_1$-$C_4$)haloalkoxy-, ($C_1$-$C_4$)alkylamino, optionally substituted ($C_3$-$C_6$)cycloalkyl, optionally substituted phenyl, optionally substituted 5-6 membered heterocycloalkyl, or optionally substituted 5-6 membered heteroaryl, wherein said optionally substituted cycloalkyl, phenyl, heterocycloalkyl or heteroaryl is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$)alkylthio-, halo($C_1$-$C_4$)alkoxy, hydroxyl, —$NR^A R^C$ and —(($C_1$-$C_4$)alkyl)$NR^A R^C$;
- or L-$R^4$, taken together, form a 1,3-benzodioxolyl, 2,3-dihydro-1,4-benzodioxinyl, benzofuranyl, tetrahydroisoquinolyl or isoindolinyl group wherein said benzofuranyl, tetrahydroisoquinolyl or isoindolinyl group is optionally substituted by 1, 2 or 3 groups independently selected from ($C_1$-$C_4$)alkyl, halogen, cyano, halo($C_1$-$C_4$)alkyl, ($C_1$-$C_4$)alkoxy, ($C_1$-$C_4$) alkylthio-, halo($C_1$-$C_4$)alkoxy, hydroxyl, —$NR^A R^C$ and —(($C_1$-$C_4$)alkyl)$NR^A R^C$;
- wherein each $R^A$ is independently selected from H and ($C_1$-$C_4$)alkyl;
- $R^B$ is H, ($C_1$-$C_4$)alkyl, halo($C_1$-$C_4$)alkyl, —C(=O)($C_1$-$C_4$)alkyl, —C(=O)O($C_1$-$C_4$)alkyl, —C(=O)$NH_2$, —C(=O)NH($C_1$-$C_4$)alkyl, —C(=O)N(($C_1$-$C_4$) alkyl)(($C_1$-$C_4$)alkyl), —$SO_2$($C_1$-$C_4$)alkyl, or $R^A$ and $R^B$ taken together with the atom to which they are attached form a 4-6 membered heterocyclic ring, optionally containing one additional heteroatom selected from N, O and S and optionally substituted by ($C_1$-$C_4$)alkyl;
- $R^C$ is H, ($C_1$-$C_4$)alkyl, phenyl, 5-6 membered heterocycloalkyl, or 5-6 membered heteroaryl, or $R^A$ and $R^C$ taken together with the atom to which they are attached form a 4-8 membered heterocyclic ring, optionally containing one additional heteroatom selected from N, O and S and optionally substituted by ($C_1$-$C_4$)alkyl;
- each $R^X$ is independently selected from H, ($C_1$-$C_6$)alkyl, and optionally substituted ($C_2$-$C_6$)alkyl, where said optionally substituted ($C_2$-$C_6$)alkyl is optionally substituted by hydroxyl, cyano, amino, ($C_1$-$C_4$)alkoxy, ($C_1$-$C_4$)alkyl)NH—, or (($C_1$-$C_4$)alkyl)(($C_1$-$C_4$)alkyl) N—; and each $R^Y$ is independently selected from H, $(C_1$-$C_4)$alkyl, phenyl, and —$(C_1$-$C_4)$alkylphenyl;

provided that the compound is not:

4-methoxy-N-[2-[3-(trifluoromethyl)-1H-1,2,4-triazol-5-yl]-3-thienyl]-benzeneacetamide, N-[(4-methoxyphenyl)methyl]-4-[5-(trichloromethyl)-1,2,4-oxadiazol-3-yl]-1,2,5-oxadiazol-3-amine, 4-(trifluoromethyl)-N-[3-(trifluoromethyl)-4-[5-(trifluoromethyl)-1,2,4-oxadiazol-3-yl]phenyl]-benzenepropanamide, 3-{7-methyl-2-[4-(3-methyl-5-isoxazolyl)butyl]-1-benzofuran-5-yl}-5-(trifluoromethyl)-1,2,4-oxadiazole, 1-[3-(3-methyl-5-isoxazolyl)propyl]-5-[5-(trifluoromethyl)-1,2,4-oxadiazol-3-yl]-1H-indole, 7-methyl-1-[4-(3-methyl-5-isoxazolyl)butyl]-5-[5-(trifluoromethyl)-1,2,4-oxadiazol-3-yl]-1H-indole, 7-methyl-1-[5-(3-methyl-5-isoxazolyl)pentyl]-5-[5-(trifluoromethyl)-1,2,4-oxadiazol-3-yl]-1H-indole, 7-methyl-1-[3-(3-methyl-5-isoxazolyl)propyl]-5-[5-(trifluoromethyl)-1,2,4-oxadiazol-3-yl]-2,3-dihydro-1H-indole, or N-(phenylmethyl)-4-[5-(trifluoromethyl)-1,2,4-oxadiazol-3-yl]-1,2,5-oxadiazol-3-amine;

or a salt thereof.

2. The compound or salt according to claim 1, wherein $R^1$ is $CHF_2$ or $CF_3$.

3. The compound or salt according to claim 1, wherein when Y is a bond, $X_1$ is O, $X_2$ and $X_3$ are N.

4. The compound or salt according to claim 1, having the formula:

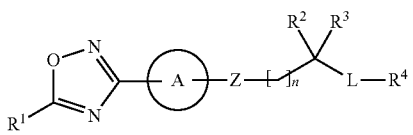

wherein:

$R^1$ is —$CF_3$;

A is optionally substituted $(C_3$-$C_6)$cycloalkyl, phenyl, naphthyl, 4-7 membered heterocycloalkyl, 5-6 membered heteroaryl, or 9-10 membered heteroaryl, wherein any optionally substituted cycloalkyl, phenyl, naphthyl, heterocycloalkyl, or heteroaryl is optionally substituted by 1-3 groups independently selected from $(C_1$-$C_4)$alkyl, halogen, cyano, halo$(C_1$-$C_4)$alkyl, $(C_1$-$C_4)$alkoxy, halo$(C_1$-$C_4)$alkoxy, —$NR^AR^A$ and —$((C_1$-$C_4)$alkyl)$NR^AR^A$;

Z is —C(=O)$NR^X$—, —$NR^X$C(=O)$NR^X$—, —$NR^X$C(=O)—, —$SO_2$—, —$SO_2NR^X$—, —$NR^XSO_2$—, —NHCH($CF_3$)—, —CH($CF_3$)NH—, —CH($CF_3$)—, —$(C_1$-$C_4)$alkyl-, —$NR^X$—, or —$(C_1$-$C_3)$alkyl-$NR^X$—;

n is 0-4;

when n is 0, $R^2$ and $R^3$ are independently selected from H and optionally substituted $(C_1$-$C_4)$alkyl, aryl$(C_1$-$C_4)$alkyl-, and $(C_3$-$C_7)$cycloalkyl$(C_1$-$C_4)$alkyl-, or when n is 1-4, $R^2$ and $R^3$ are independently selected from H, fluoro, and optionally substituted $(C_1$-$C_4)$alkyl, aryl$(C_1$-$C_4)$alkyl-, and $(C_3$-$C_7)$cycloalkyl$(C_1$-$C_4)$alkyl-, wherein, when n is 1, $R^2$ is F and $R^3$ is H, then Z is —C(=O)$NR^X$—, —$NR^X$C(=O)$NR^X$—, —$SO_2NR^X$—, —NHCH($CF_3$)—, —CH($CF_3$)NH—, —CH($CF_3$)—, —$(C_1$-$C_4)$alkyl-, —$NR^X$—, or —$(C_1$-$C_3)$alkyl-$NR^X$—, or when n is 1-4, $R^2$ is selected from amino, hydroxyl, and $(C_1$-$C_4)$alkoxy, and $R^3$ is selected from H and optionally substituted $(C_1$-$C_4)$alkyl, aryl$(C_1$-$C_4)$alkyl-, and $(C_3$-$C_7)$cycloalkyl$(C_1$-$C_4)$alkyl-, wherein the aryl, cycloalkyl and each of the $(C_1$-$C_4)$ alkyl moieties of said optionally substituted $(C_1$-$C_4)$ alkyl, aryl$(C_1$-$C_4)$alkyl-, and $(C_3$-$C_7)$cycloalkyl$(C_1$-$C_4)$alkyl- of any $R^2$ and $R^3$ are optionally substituted by 1, 2 or 3 groups independently selected from halogen, cyano, $(C_1$-$C_4)$alkyl, halo$(C_1$-$C_4)$alkyl, $(C_1$-$C_4)$alkoxy, halo$(C_1$-$C_4)$alkoxy, halogen, —$NR^AR^A$, —$((C_1$-$C_4)$alkyl)$NR^AR^A$, $(C_1$-$C_4)$alkoxy, hydroxyl, cyano, halo$(C_1$-$C_4)$alkyl, and halo$(C_1$-$C_4)$alkoxy;

or $R^2$ and $R^3$ taken together with the atom to which they are connected form an optionally substituted 4, 5, 6, or 7 membered cycloalkyl or heterocycloalkyl group, wherein said heterocycloalkyl group contains 1 or 2 heteroatoms independently selected from N, O and S and said optionally substituted cycloalkyl or heterocycloalkyl group is optionally substituted by 1, 2 or 3 substituents independently selected from $(C_1$-$C_4)$ alkyl, halo$(C_1$-$C_4)$alkyl, halogen, cyano, aryl$(C_1$-$C_4)$ alkyl-, $(C_3$-$C_7)$cycloalkyl$(C_1$-$C_4)$alkyl-, —$OR^Y$, —$NR^YR^Y$, —C(=O)$OR^Y$, —C(=O)$NR^YR^Y$, —$NR^YC$(=O)$R^Y$, —$SO_2NR^YR^Y$, —$NR^YSO_2R^Y$, —OC(=O)$NR^YR^Y$, —$NR^YC$(=O)$OR^Y$, and —$NR^YC$(=O)$NR^YR^Y$; and L is 5-6 membered heteroaryl or phenyl which is substituted by $R^4$ and is optionally further substituted, wherein when L is further substituted, L is substituted by 1 or 2 substituents independently selected from halogen, cyano and $(C_1$-$C_4)$alkyl;

$R^4$ is H, $(C_1$-$C_4)$alkyl, halo, halo$(C_1$-$C_4)$alkyl, $(C_1$-$C_4)$ alkoxy, $((C_1$-$C_4)$alkyl)$((C_1$-$C_4)$alkyl)$N(C_1$-$C_4)$ alkoxy, $((C_1$-$C_4)$alkyl)$((C_1$-$C_4)$alkyl)$N(C_1$-$C_4)$alkyl-, $(C_1$-$C_4)$haloalkoxy-, $(C_1$-$C_4)$alkylamino, optionally substituted $(C_3$-$C_6)$cycloalkyl, optionally substituted phenyl, optionally substituted 5-6 membered heterocycloalkyl, or optionally substituted 5-6 membered heteroaryl, wherein said optionally substituted cycloalkyl, phenyl, heterocycloalkyl or heteroaryl is optionally substituted by 1, 2 or 3 groups independently selected from $(C_1$-$C_4)$alkyl, halogen, cyano, halo$(C_1$-$C_4)$alkyl, $(C_1$-$C_4)$alkoxy, $(C_1$-$C_4)$alkylthio-, halo$(C_1$-$C_4)$alkoxy, hydroxyl, —$NR^AR^B$ and —$((C_1$-$C_4)$alkyl)$NR^AR^B$;

or L-$R^4$, taken together, form a 1,3-benzodioxolyl, 2,3-dihydro-1,4-benzodioxinyl, benzofuranyl, tetrahydroisoquinolyl or isoindolinyl group wherein said benzofuranyl, tetrahydroisoquinolyl or isoindolinyl group is optionally substituted by 1, 2 or 3 groups independently selected from $(C_1$-$C_4)$alkyl, halogen, cyano, halo$(C_1$-$C_4)$alkyl, $(C_1$-$C_4)$alkoxy, $(C_1$-$C_4)$ alkylthio-, halo$(C_1$-$C_4)$alkoxy, hydroxyl, —$NR^AR^B$ and —$((C_1$-$C_4)$alkyl)$NR^AR^B$;

wherein each $R^A$ is independently selected from H and $(C_1$-$C_4)$alkyl;

$R^B$ is H, $(C_1$-$C_4)$alkyl, phenyl, 5-6 membered heterocycloalkyl, or 5-6 membered heteroaryl, or $R^A$ and $R^B$ taken together with the atom to which they are attached form an optionally substituted 4-8 membered heterocyclic ring, optionally containing one additional heteroatom selected from N, O and S;

each $R^X$ is independently selected from H, $(C_1$-$C_6)$alkyl, and optionally substituted $(C_2$-$C_6)$alkyl, where said optionally substituted $(C_2$-$C_6)$alkyl is optionally substituted by hydroxyl, cyano, amino, $(C_1-C_4)$alkoxy, $(C_1-C_4)$alkyl)NH—, or $((C_1-C_4)$alkyl)$((C_1-C_4)$alkyl)N—; and each $R^Y$ is independently selected from H, $(C_1-C_4)$alkyl, phenyl, and —$(C_1-C_4)$alkylphenyl.

5. The compound or salt according to claim 1, wherein:

A is a phenyl group optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^4R^4$ and —$((C_1-C_4)$alkyl)$NR^4R^4$;

or A is a cyclopropyl, cyclopentyl or cyclohexyl group, optionally substituted by 1-2 groups independently selected from methyl, ethyl, tert-butyl, methoxy, ethoxy, —$NR^4R^4$ and —$((C_1-C_4)$alkyl)$NR^4R^4$, where each $R^4$ is independently H or methyl;

or A is naphthyl, optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^4R^4$ and —$((C_1-C_4)$alkyl)$NR^4R^4$;

or A is a 9-10 membered heteroaryl optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, oxo, —$NR^4R^4$ and —$((C_1-C_4)$alkyl)$NR^4R^4$;

or A is a 5-6 membered heteroaryl optionally substituted by 1-2 groups independently selected from $(C_1-C_4)$alkyl, halogen, cyano, halo$(C_1-C_4)$alkyl, $(C_1-C_4)$alkoxy, halo$(C_1-C_4)$alkoxy, —$NR^4R^4$ and —$((C_1-C_4)$alkyl)$NR^4R^4$.

6. The compound or salt according to claim 1, wherein:

A is isoquinolyl, indazolyl, tetrahydroisoquinolinonyl, isoindolinonyl, or indolinyl;

or A is oxazolyl, pyrazolyl, or thienyl, optionally substituted by a methyl group;

or A is a pyridyl or pyridyl-N-oxide group optionally substituted by 1 group selected from methyl, ethyl, fluoro, chloro, trifluoromethyl, methoxy, ethoxy, trifluoromethoxy, cyano, —$NR^4R^4$ and —$((C_1-C_4)$alkyl)$NR^4R^4$, where each $R^4$ is independently H or methyl.

7. The compound or salt according to claim 1, wherein Z is —C(=O)NH— or —CH$_2$NH—.

8. The compound or salt according to claim 1, wherein n is 0 or 1.

9. The compound or salt according to claim 1, wherein $R^2$ and $R^3$ are independently selected from H and optionally substituted $(C_1-C_4)$alkyl, phenyl$(C_1-C_2)$alkyl-, and $(C_3-C_6)$cycloalkyl$(C_1-C_2)$alkyl-.

10. The compound or salt according to claim 1, wherein: both $R^2$ and $R^3$ are H or both $R^2$ and $R^3$ are methyl;

or when n is 1, $R^2$ is hydroxyl and $R^3$ is H or methyl.

11. The compound or salt according to claim 1, wherein $R^2$ and $R^3$ taken together with the atom to which they are connected form an optionally substituted 4, 5 or 6 membered cycloalkyl or heterocycloalkyl group, wherein said heterocycloalkyl group contains 1 heteroatom selected from N and O and said optionally substituted cycloalkyl or heterocycloalkyl group is optionally substituted by a substituent selected from $(C_1-C_4)$alkyl, aryl$(C_1-C_2)$alkyl-, and $(C_3-C_6)$cycloalkyl$(C_1-C_2)$alkyl-.

12. The compound or salt according to claim 1, wherein $R^4$ is H, methyl, bromo, trifluoromethyl, dimethylaminoethoxy-, dimethylaminopropyl-, and optionally substituted pyridyl, cyclohexyl, piperidinyl, piperazinyl, imidazolyl, thienyl, or phenyl, where the pyridyl, cyclohexyl, piperidinyl, piperizinyl, imidazolyl, thienyl, or phenyl are optionally substituted by 1-2 substituents independently selected from methyl, chloro, bromo, fluoro, trifluoromethyl, methoxy, and cyano.

13. The compound or salt according to claim 1, wherein L-$R^4$, taken together, form a 1,3-benzodioxolyl, thienopyrimidinyl, benzo-isothiazolyl, 2,3-dihydro-1,4-benzodioxinyl, benzofuranyl, benzimidazolyl, benzimidazolonyl, tetrahydroisoquinolyl, indolinyl or isoindolinyl group, optionally substituted with 1 or 2 groups independently selected from methyl, trifluoromethyl, chloro, fluoro, cyano, methoxy, phenyl, and morpholinylpropyl-.

14. The compound or salt according to claim 1, wherein:

$R^1$ is $CHF_2$ or $CF_3$;

Y is a bond, $X_1$ is O, and $X_2$ and $X_3$ are N, or

A is an unsubstituted phenyl group or a phenyl group substituted by an ethyl, fluoro, cyano or methoxy group, or a thienyl, pyridyl, cyclopropyl, cyclopentyl or cyclohexyl group;

Z is —C(=O)NH— or —CH$_2$NH—;

n is 0 or 1 and both $R^2$ and $R^3$ are H or both $R^2$ and $R^3$ are methyl, or n is 1 and $R^2$ is hydroxyl and $R^3$ is H or methyl, or n is 0 or 1 and $R^2$ and $R^3$ taken together with the atom to which they are connected form a tetrahydropyranyl, 2,2-dimethyl-tetrahydropyranyl, cyclopentyl, 1-methyl-piperidinyl group;

L is thiazolyl, thienyl, triazolyl, pyridyl, phenyl, or oxazolyl, any of which is optionally substituted by a methyl group;

$R^4$ is H, methyl, bromo, trifluoromethyl, dimethylaminoethoxy-, phenyl, 4-chlorophenyl, 2-bromophenyl-, 4-fluorophenyl, 4-cyanophenyl, 3-trifluoromethylphenyl, 4-methoxyphenyl, cyclohexyl, imidazolyl, thienyl, pyrid-2-yl, pyrid-3-yl, or pyrid-4-yl; or L-$R^4$, taken together, form a 1,3-benzodioxolyl, tetrahydroisoquinolyl or isoindolinyl group.

15. The compound or salt according to claim 1, wherein:

$R^1$ is $CHF_2$ or $CF_3$;

Y is a bond, $X_1$ is O, and $X_2$ and $X_3$ are N;

A is an unsubstituted phenyl or pyridyl group;

Z is —C(=O)NH— or —CH$_2$NH—;

n is 1;

$R^2$ and $R^3$ are both methyl, or $R^2$ is hydroxyl and $R^3$ is methyl, or $R^2$ and $R^3$ are both hydrogen, or $R^2$ is methyl and $R^3$ is hydrogen, or $R^2$ is hydroxyl and $R^3$ is hydrogen, or $R^2$ is dimethylamino and $R^3$ is H, or $R^2$ is N,N-dimethylaminoethyl and $R^3$ is H, or $R^2$ and $R^3$ taken together with the atom to which they are connected form a tetrahydropyranyl, 2,2-dimethyl-tetrahydropyranyl, or a 1-methyl-piperidinyl group;

L is thiazolyl, thienyl, triazolyl, pyridyl, phenyl, or oxazolyl, any of which is optionally substituted by a methyl group;

$R^4$ is phenyl, optionally substituted by halo, cyano, halo $(C_1-C_2)$alkyl, or $(C_1-C_2)$alkoxy.

16. A compound which is:

N-(4-(2-(dimethylamino)ethoxy)benzyl)-3-(5-(trifluoromethyl)-1,2,4-oxadiazol-3-yl)benzamide, N-(2-(2-(dimethylamino)ethoxy)benzyl)-3-(5-(trifluoromethyl)-1,2,4-oxadiazol-3-yl)benzamide, N-(4-(1H-imidazol-1-yl)benzyl)-3-(5-(trifluoromethyl)-1,2,4-oxadiazol-3-yl)benzamide, N-(2-cyanoethyl)-N-(pyridin-3-ylmethyl)-3-(5-(trifluoromethyl)-1,2,4-oxadiazol-3-yl)benzamide, 3-(5-(trifluoromethyl)-1,2,4-oxadiazol-3-yl)-N-((4-(4-(trifluoromethyl)phenyl)tetrahydro-2H-pyran-4-yl)methyl)benzamide, 1-(4-(4-phenylthiazol-2-yl)tetrahydro-2H-pyran-4-yl)-N-(3-(5-(trifluoromethyl)-1,2,4-oxadiazol-3-yl)benzyl)methanamine, N-((4-(4-phenylthiazol-2-yl)tetrahydro-2H-pyran-4-yl)methyl)-5-(5-(trifluoromethyl)-1,2,4-oxadiazol-3-yl)nicotinamide, N-((4-(4-phenylthiophen-2-yl)tetrahydro-2H-pyran-4-yl)methyl)-3-(5-(trifluoromethyl)-1,2,4-oxadiazol-3-yl)benzamide, N-((1-(4-phenylthiazol-2-yl)cyclopentyl)methyl)-3-(5-(trifluoromethyl)-1,2,4-oxadiazol-3-yl)benzamide, N-((4-(3-phenyl-1H-1,2,4-triazol-5-yl)tetrahydro-2H-pyran-4-yl)methyl)-3-(5-(trifluoromethyl)-1,2,4-oxadiazol-3-yl)benzamide, N-((4-(2-phenylthiazol-4-yl)tetrahydro-2H-pyran-4-yl)methyl)-3-(5-(trifluoromethyl)-1,2,4-oxadiazol-3-yl)benzamide, N-((4-(4-(4-methoxyphenyl)thiazol-2-yl)tetrahydro-2H-pyran-4-yl)methyl)-3-(5-(trifluoromethyl)-1,2,4-oxadiazol-3-yl)benzamide, N-((4-(4-(4-chlorophenyl)thiazol-2-yl)tetrahydro-2H-pyran-4-yl)methyl)-3-(5-(trifluoromethyl)-1,2,4-oxadiazol-3-yl)benzamide, N-(2-methyl-2-(4-phenylthiazol-2-yl)propyl)-3-(5-(trifluoromethyl)-1,2,4-oxadiazol-3-yl)benzamide, N-((1-methyl-4-(4-phenylthiazol-2-yl)piperidin-4-yl)methyl)-3-(5-(trifluoromethyl)-1,2,4-oxadiazol-3-yl)benzamide, N-((4-(4-(4-fluorophenyl)thiazol-2-yl)tetrahydro-2H-pyran-4-yl)methyl)-3-(5-(trifluoromethyl)-1,2,4-oxadiazol-3-yl)benzamide, N-((4-(5-methyl-4-phenylthiazol-2-yl)tetrahydro-2H-pyran-4-yl)methyl)-3-(5-(trifluoromethyl)-1,2,4-oxadiazol-3-yl)benzamide, N-((4-(4-cyclohexylthiazol-2-yl)tetrahydro-2H-pyran-4-yl)methyl)-3-(5-(trifluoromethyl)-1,2,4-oxadiazol-3-yl)benzamide, N-((4-(4-(pyridin-2-yl)thiazol-2-yl)tetrahydro-2H-pyran-4-yl)methyl)-3-(5-(trifluoromethyl)-1,2,4-oxadiazol-3-yl)benzamide, N-((4-(4-(pyridin-4-yl)thiazol-2-yl)tetrahydro-2H-pyran-4-yl)methyl)-3-(5-(trifluoromethyl)-1,2,4-oxadiazol-3-yl)benzamide, N-((4-(4-phenylthiazol-2-yl)tetrahydro-2H-pyran-4-yl)methyl)-5-(5-(trifluoromethyl)-1,2,4-oxadiazol-3-yl)thiophene-2-carboxamide, N-((4-(4-(thiophen-2-yl)thiazol-2-yl)tetrahydro-2H-pyran-4-yl)methyl)-3-(5-(trifluoromethyl)-1,2,4-oxadiazol-3-yl)benzamide, N-(2-(4-(4-fluorophenyl)thiazol-2-yl)-2-methylpropyl)-3-(5-(trifluoromethyl)-1,2,4-oxadiazol-3-yl)benzamide, N-(2-(4-(4-chlorophenyl)thiazol-2-yl)-2-methylpropyl)-3-(5-(trifluoromethyl)-1,2,4-oxadiazol-3-yl)benzamide, 3-fluoro-N-(2-(4-(4-fluorophenyl)thiazol-2-yl)-2-methylpropyl)-5-(5-(trifluoromethyl)-1,2,4-oxadiazol-3-yl)benzamide, 3-cyano-N-((4-(4-phenylthiazol-2-yl)tetrahydro-2H-pyran-4-yl)methyl)-5-(5-(trifluoromethyl)-1,2,4-oxadiazol-3-yl)benzamide, 3-methoxy-N-((4-(4-phenylthiazol-2-yl)tetrahydro-2H-pyran-4-yl)methyl)-5-(5-(trifluoromethyl)-1,2,4-oxadiazol-3-yl)benzamide, N-(2-(4-(4-fluorophenyl)thiazol-2-yl)ethyl)-3-(5-(trifluoromethyl)-1,2,4-oxadiazol-3-yl)benzamide, N-((4-(4-(4-cyanophenyl)thiazol-2-yl)tetrahydro-2H-pyran-4-yl)methyl)-3-(5-(trifluoromethyl)-1,2,4-oxadiazol-3-yl)benzamide, N-((4-(4-(4-fluorophenyl)thiazol-2-yl)-2,2-dimethyltetrahydro-2H-pyran-4-yl)methyl)-3-(5-(trifluoromethyl)-1,2,4-oxadiazol-3-yl)benzamide, N-((4-(4-phenylthiazol-2-yl)tetrahydro-2H-pyran-4-yl)methyl)-3-(5-(trifluoromethyl)-1,2,4-oxadiazol-3-yl)benzenesulfonamide, 3-ethyl-N-((4-(4-phenylthiazol-2-yl)tetrahydro-2H-pyran-4-yl)methyl)-5-(5-(trifluoromethyl)-1,2,4-oxadiazol-3-yl)benzamide, N-((4-(3-bromophenyl)tetrahydro-2H-pyran-4-yl)methyl)-3-(5-(trifluoromethyl)-1,2,4-oxadiazol-3-yl)benzamide, 3-(5-(trifluoromethyl)-1,2,4-oxadiazol-3-yl)-N-((4-(4-(4-(trifluoromethyl)phenyl)thiazol-2-yl)tetrahydro-2H-pyran-4-yl)methyl)benzamide, N-(2-methyl-2-(4-(4-(trifluoromethyl)phenyl)thiazol-2-yl)propyl)-3-(5-(trifluoromethyl)-1,2,4-oxadiazol-3-yl)benzamide, N-((4-(4-phenylthiazol-2-yl)tetrahydro-2H-pyran-4-yl)methyl)-2-(5-(trifluoromethyl)-1,2,4-oxadiazol-3-yl)cyclopropanecarboxamide, N-((1-methyl-4-(2-phenylthiazol-4-yl)piperidin-4-yl)methyl)-5-(5-(trifluoromethyl)-1,2,4-oxadiazol-3-yl)nicotinamide, N-(2-(2-(4-chlorophenyl)thiazol-4-yl)-2-methylpropyl)-5-(5-(trifluoromethyl)-1,2,4-oxadiazol-3-yl)nicotinamide, N-((4-(2-(4-chlorophenyl)thiazol-4-yl)-1-methylpiperidin-4-yl)methyl)-5-(5-(trifluoromethyl)-1,2,4-oxadiazol-3-yl)nicotinamide, N-(2-(2-(4-chlorophenyl)thiazol-4-yl)-2-methylpropyl)-3-(5-(trifluoromethyl)-1,2,4-oxadiazol-3-yl)benzamide, N-(2-(2-(4-chlorophenyl)thiazol-4-yl)ethyl)-5-(5-(trifluoromethyl)-1,2,4-oxadiazol-3-yl)nicotinamide, N-(2-(4-(4-chlorophenyl)thiazol-2-yl)-2-methylpropyl)-2-(5-(trifluoromethyl)-1,2,4-oxadiazol-3-yl)isonicotinamide, N-(2-(2-(4-fluorophenyl)thiazol-4-yl)-2-methylpropyl)-3-(5-(trifluoromethyl)-1,2,4-oxadiazol-3-yl)benzamide, N-(2-(2-(4-fluorophenyl)thiazol-4-yl)-2-methylpropyl)-5-(5-(trifluoromethyl)-1,2,4-oxadiazol-3-yl)nicotinamide, N-(2-(4-(4-chlorophenyl)thiazol-2-yl)-2-methylpropyl)-6-(5-(trifluoromethyl)-1,2,4-oxadiazol-3-yl)picolinamide, N-(2-(dimethylamino)-2-(4-phenylthiazol-2-yl)ethyl)-3-(5-(trifluoromethyl)-1,2,4-oxadiazol-3-yl)benzamide, N-(2-(3-phenyl-1H-1,2,4-triazol-5-yl)ethyl)-3-(5-(trifluoromethyl)-1,2,4-oxadiazol-3-yl)benzamide, N-((1-(4-phenylthiazol-2-yl)cyclopropyl)methyl)-3-(5-(trifluoromethyl)-1,2,4-oxadiazol-3-yl)benzamide, 3-(4-(4-fluorophenyl)thiazol-2-yl)-N-(3-(5-(trifluoromethyl)-1,2,4-oxadiazol-3-yl)phenyl)propanamide, N-(2-(2-(4-chlorophenyl)thiazol-4-yl)ethyl)-3-(5-(trifluoromethyl)-1,2,4-oxadiazol-3-yl)benzamide, N-((4-phenylthiazol-2-yl)methyl)-3-(5-(trifluoromethyl)-1,2,4-oxadiazol-3-yl)benzamide, N-(2-(4-(4-fluorophenyl)thiazol-2-yl)ethyl)-5-(5-(trifluoromethyl)-1,2,4-oxadiazol-3-yl)nicotinamide, N-(2-(4-(4-chlorophenyl)thiazol-2-yl)ethyl)-3-(5-(trifluoromethyl)-1,2,4-oxadiazol-3-yl)benzamide, N-(2-(4-(4-chlorophenyl)thiazol-2-yl)ethyl)-5-(5-(trifluoromethyl)-1,2,4-oxadiazol-3-yl)nicotinamide,
N-((4-(3,4-dihydroisoquinolin-2(1H)-yl)tetrahydro-2H-pyran-4-yl)methyl)-3-(5-(trifluoromethyl)-1,2,4-oxadiazol-3-yl)benzamide,
N-methyl-N-((4-(4-phenylthiazol-2-yl)tetrahydro-2H-pyran-4-yl)methyl)-3-(5-(trifluoromethyl)-1,2,4-oxadiazol-3-yl)benzamide,
N-(2-(2-(4-fluorophenyl)thiazol-4-yl)ethyl)-5-(5-(trifluoromethyl)-1,2,4-oxadiazol-3-yl)nicotinamide,
N-(2-(2-(4-fluorophenyl)thiazol-4-yl)ethyl)-3-(5-(trifluoromethyl)-1,2,4-oxadiazol-3-yl)benzamide,
N-(2-(4-(4-fluorophenyl)thiazol-2-yl)-2-methylpropyl)-5-(5-(trifluoromethyl)-1,2,4-oxadiazol-3-yl)nicotinamide,
2,2,2-trifluoro-N-((4-(4-phenylthiazol-2-yl)tetrahydro-2H-pyran-4-yl)methyl)-1-(3-(5-(trifluoromethyl)-1,2,4-oxadiazol-3-yl)phenyl)ethanamine,
N-(2-(3-(4-fluorophenyl)-1H-1,2,4-triazol-5-yl)ethyl)-3-(5-(trifluoromethyl)-1,2,4-oxadiazol-3-yl)benzamide,
N-(2-(3-(4-chlorophenyl)-1H-1,2,4-triazol-5-yl)ethyl)-3-(5-(trifluoromethyl)-1,2,4-oxadiazol-3-yl)benzamide,
N-(2-methyl-2-(3-phenyl-1H-1,2,4-triazol-5-yl)propyl)-3-(5-(trifluoromethyl)-1,2,4-oxadiazol-3-yl)benzamide,
N-(2-methyl-2-(3-phenyl-1H-1,2,4-triazol-5-yl)propyl)-5-(5-(trifluoromethyl)-1,2,4-oxadiazol-3-yl)nicotinamide,
N-(2-(3-(4-fluorophenyl)-1H-1,2,4-triazol-5-yl)-2-methylpropyl)-3-(5-(trifluoromethyl)-1,2,4-oxadiazol-3-yl)benzamide,
N-(2-(3-(4-fluorophenyl)-1H-1,2,4-triazol-5-yl)-2-methylpropyl)-5-(5-(trifluoromethyl)-1,2,4-oxadiazol-3-yl)nicotinamide,
N-(2-(3-(4-chlorophenyl)-1H-1,2,4-triazol-5-yl)-2-methylpropyl)-3-(5-(trifluoromethyl)-1,2,4-oxadiazol-3-yl)benzamide,
N-(2-(4-(4-chlorophenyl)thiazol-2-yl)-2-methylpropyl)-6-methyl-5-(5-(trifluoromethyl)-1,2,4-oxadiazol-3-yl)nicotinamide,
N-(3-(4-phenylthiazol-2-yl)propyl)-3-(5-(trifluoromethyl)-1,2,4-oxadiazol-3-yl)benzamide,
N-(2-(2-(4-fluorophenyl)oxazol-4-yl)ethyl)-5-(5-(trifluoromethyl)-1,2,4-oxadiazol-3-yl)nicotinamide,
N-(2-(5-phenylthiazol-2-yl)ethyl)-3-(5-(trifluoromethyl)-1,2,4-oxadiazol-3-yl)benzamide,
N-(2-(2-(4-fluorophenyl)oxazol-4-yl)propyl)-3-(5-(trifluoromethyl)-1,2,4-oxadiazol-3-yl)benzamide,
N-(2-(2-(3-fluorophenyl)oxazol-4-yl)ethyl)-5-(5-(trifluoromethyl)-1,2,4-oxadiazol-3-yl)nicotinamide,
N-(2-(4-(4-chlorophenyl)thiazol-2-yl)-2-methylpropyl)-2-methyl-5-(5-(trifluoromethyl)-1,2,4-oxadiazol-3-yl)nicotinamide,
N-(2-methyl-2-(5-phenylthiazol-2-yl)propyl)-3-(5-(trifluoromethyl)-1,2,4-oxadiazol-3-yl)benzamide,
N-((4-([1,1'-biphenyl]-3-yl)tetrahydro-2H-pyran-4-yl)methyl)-3-(5-(trifluoromethyl)-1,2,4-oxadiazol-3-yl)benzamide,
N-((4-([1,1'-biphenyl]-3-yl)tetrahydro-2H-pyran-4-yl)methyl)-5-(5-(trifluoromethyl)-1,2,4-oxadiazol-3-yl)nicotinamide,
N-((2-(4-fluorophenyl)oxazol-4-yl)methyl)-3-(5-(trifluoromethyl)-1,2,4-oxadiazol-3-yl)benzamide,
N-((4-(2-(4-fluorophenyl)oxazol-4-yl)-1-methylpiperidin-4-yl)methyl)-3-(5-(trifluoromethyl)-1,2,4-oxadiazol-3-yl)benzamide,
N-(2-methyl-2-(2-phenyloxazol-4-yl)propyl)-3-(5-(trifluoromethyl)-1,2,4-oxadiazol-3-yl)benzamide,
2-(2-(4-fluorophenyl)oxazol-4-yl)-2-methyl-N-(3-(5-(trifluoromethyl)-1,2,4-oxadiazol-3-yl)benzyl)propan-1-amine,
3-(3-(4-(4-phenylthiazol-2-yl)butyl)phenyl)-5-(trifluoromethyl)-1,2,4-oxadiazole,
N-(2-methyl-2-(5-phenyloxazol-2-yl)propyl)-3-(5-(trifluoromethyl)-1,2,4-oxadiazol-3-yl)benzamide,
N-(2-(2-phenylthiazol-5-yl)ethyl)-3-(5-(trifluoromethyl)-1,2,4-oxadiazol-3-yl)benzamide,
N-(2-methyl-2-(2-phenylthiazol-5-yl)propyl)-3-(5-(trifluoromethyl)-1,2,4-oxadiazol-3-yl)benzamide,
N-((4-(2-(4-chlorophenyl)thiazol-4-yl)-1-methylpiperidin-4-yl)methyl)-3-(5-(trifluoromethyl)-1,2,4-oxadiazol-3-yl)benzamide,
2-fluoro-N-(2-(2-(4-fluorophenyl)oxazol-4-yl)-2-methylpropyl)-5-(5-(trifluoromethyl)-1,2,4-oxadiazol-3-yl)benzamide,
N-(2-(2-(4-fluorophenyl)oxazol-4-yl)-2-methylpropyl)-2-(5-(trifluoromethyl)-1,2,4-oxadiazol-3-yl)oxazole-4-carboxamide,
N-(2-(1-methyl-2-phenyl-1H-imidazol-5-yl)propyl)-5-(5-(trifluoromethyl)-1,2,4-oxadiazol-3-yl)nicotinamide,
N-(2-(2-(4-fluorophenyl)oxazol-4-yl)-2-hydroxyethyl)-3-(5-(trifluoromethyl)-1,2,4-oxadiazol-3-yl)benzamide,
5-(5-(difluoromethyl)-1,2,4-oxadiazol-3-yl)-N-(2-(2-(4-fluorophenyl)oxazol-4-yl)-2-methylpropyl)nicotinamide,
N-(2-(dimethylamino)-2-(2-(4-fluorophenyl)oxazol-4-yl)ethyl)-3-(5-(trifluoromethyl)-1,2,4-oxadiazol-3-yl)benzamide hydrochloride,
N-(2-(2-(4-fluorophenyl)oxazol-4-yl)-2-methylpropyl)-2-methoxy-5-(5-(trifluoromethyl)-1,2,4-oxadiazol-3-yl)benzamide,
N-(2-(2-(4-fluorophenyl)oxazol-5-yl)-2-methylpropyl)-3-(5-(trifluoromethyl)-1,2,4-oxadiazol-3-yl)benzamide,
N-(4-(dimethylamino)-2-(2-(4-fluorophenyl)oxazol-4-yl)butyl)-3-(5-(trifluoromethyl)-1,2,4-oxadiazol-3-yl)benzamide,
N-(4-(dimethylamino)-2-(2-(4-fluorophenyl)oxazol-4-yl)butyl)-5-(5-(trifluoromethyl)-1,2,4-oxadiazol-3-yl)nicotinamide,
N-(2-(2-(4-fluorophenyl)oxazol-4-yl)-2-hydroxyethyl)-5-(5-(trifluoromethyl)-1,2,4-oxadiazol-3-yl)nicotinamide,
N-((4-(2-(4-chlorophenyl)oxazol-4-yl)-1-methylpiperidin-4-yl)methyl)-3-(5-(trifluoromethyl)-1,2,4-oxadiazol-3-yl)benzamide,
2-(2-(4-chlorophenyl)oxazol-4-yl)-2-methyl-N-(3-(5-(trifluoromethyl)-1,2,4-oxadiazol-3-yl)benzyl)propan-1-amine,
N-(2-(2-(4-fluorophenyl)oxazol-5-yl)ethyl)-3-(5-(trifluoromethyl)-1,2,4-oxadiazol-3-yl)benzamide,
N-((4-([1,1'-biphenyl]-3-yl)-1-methylpiperidin-4-yl)methyl)-3-(5-(trifluoromethyl)-1,2,4-oxadiazol-3-yl)benzamide,
N-(2-(2-(4-methoxyphenyl)oxazol-4-yl)ethyl)-5-(5-(trifluoromethyl) 1,2,4-oxadiazol-3-yl)nicotinamide,
2-chloro-N-(2-(2-(4-fluorophenyl)oxazol-4-yl)-2-methylpropyl)-5-(5-(trifluoromethyl)-1,2,4-oxadiazol-3-yl)benzamide,
N-(2-(2-(4-fluorophenyl)oxazol-4-yl)-2-methylpropyl)-3-(5-(trifluoromethyl)-1,2,4-oxadiazol-3-yl)benzamide, N-(3-(2-(4-fluorophenyl)oxazol-4-yl)-3-hydroxypropyl)-3-(5-(trifluoromethyl)-1,2,4-oxadiazol-3-yl)benzamide, N-(2-(2-(4-cyanophenyl)oxazol-4-yl)ethyl)-5-(5-(trifluoromethyl) 1,2,4-oxadiazol-3-yl)nicotinamide, N-(2-(2-(2-fluorophenyl)oxazol-4-yl)ethyl)-5-(5-(trifluoromethyl)-1,2,4-oxadiazol-3-yl)nicotinamide, N-(2-(1-methyl-2-phenyl-1H-imidazol-4-yl)propyl)-5-(5-(trifluoromethyl)-1,2,4-oxadiazol-3-yl)nicotinamide, N-(2-(2-(4-fluorophenyl)oxazol-4-yl)-2-methoxyethyl)-3-(5-(trifluoromethyl)-1,2,4-oxadiazol-3-yl)benzamide, N-(2-(4-(4-fluorophenyl)thiazol-2-yl)propyl)-3-(5-(trifluoromethyl)-1,2,4-oxadiazol-3-yl)benzamide, N-(2-(2-(4-fluorophenyl)oxazol-4-yl)ethyl)-3-(5-(trifluoromethyl)-1,2,4-oxadiazol-3-yl)benzamide, N-(2-(2-(4-fluorophenyl)oxazol-4-yl)-2-methylpropyl)-5-(5-(trifluoromethyl)-1,2,4-oxadiazol-3-yl)nicotinamide, N-(2-([1,1'-biphenyl]-3-yl)-2-methylpropyl)-3-(5-(trifluoromethyl)-1,2,4-oxadiazol-3-yl)benzamide, N-(2-(4'-fluoro-[1,1'-biphenyl]-3-yl)-2-methylpropyl)-3-(5-(trifluoromethyl)-1,2,4-oxadiazol-3-yl)benzamide, N-((4-(4-(3,5-difluorophenyl)thiazol-2-yl)tetrahydro-2H-pyran-4-yl)methyl)-3-(5-(trifluoromethyl)-1,2,4-oxadiazol-3-yl)benzamide, N-(2-(4-(3,5-difluorophenyl)thiazol-2-yl)-2-methylpropyl)-3-(5-(trifluoromethyl)-1,2,4-oxadiazol-3-yl)benzamide, N-(2-(2-phenyloxazol-4-yl)ethyl)-3-(5-(trifluoromethyl)-1,2,4-oxadiazol-3-yl)benzamide, N-(2-(2-phenyloxazol-4-yl)ethyl)-5-(5-(trifluoromethyl)-1,2,4-oxadiazol-3-yl)nicotinamide, N-(2-(2-(4-chlorophenyl)oxazol-4-yl)ethyl)-3-(5-(trifluoromethyl)-1,2,4-oxadiazol-3-yl)benzamide, N-(2-(2-(4-chlorophenyl)oxazol-4-yl)ethyl)-5-(5-(trifluoromethyl)-1,2,4-oxadiazol-3-yl)nicotinamide, N-(2-methyl-2-(2-phenyloxazol-4-yl)propyl)-5-(5-(trifluoromethyl)-1,2,4-oxadiazol-3-yl)nicotinamide, N-(2-(2-(4-chlorophenyl)oxazol-4-yl)-2-methylpropyl)-3-(5-(trifluoromethyl)-1,2,4-oxadiazol-3-yl)benzamide, N-(2-(3-phenyl-1,2,4-oxadiazol-5-yl)ethyl)-3-(5-(trifluoromethyl)-1,2,4-oxadiazol-3-yl)benzamide, N-(2-methyl-2-(3-phenyl-1H-pyrazol-5-yl)propyl)-3-(5-(trifluoromethyl)-1,2,4-oxadiazol-3-yl)benzamide, N-(2-(2-(4-fluorophenyl)oxazol-4-yl)propyl)-5-(5-(trifluoromethyl)-1,2,4-oxadiazol-3-yl)nicotinamide, N-(2-(4-(4-chlorophenyl)thiazol-2-yl)-2-methylpropyl)-5-(5-(trifluoromethyl)-1,2,4-oxadiazol-3-yl)nicotinamide, N-((4-([1,1'-biphenyl]-3-yl)-1-methylpiperidin-4-yl)methyl)-5-(5-(trifluoromethyl)-1,2,4-oxadiazol-3-yl)nicotinamide, N-(2-(2-(4-fluorophenyl)oxazol-4-yl)-2-hydroxypropyl)-3-(5-(trifluoromethyl)-1,2,4-oxadiazol-3-yl)benzamide, or a pharmaceutically-acceptable salt thereof.

17. A pharmaceutical composition comprising the compound or salt according to claim 1 and one or more pharmaceutically-acceptable excipients.

18. The compound or salt according to claim 1, wherein A is a phenyl group optionally substituted by 1-2 groups independently selected from ($C_1$-$C_4$)alkyl, halogen, cyano, halo($C_1$-$C_4$)alkyl, ($C_1$-$C_4$)alkoxy, halo($C_1$-$C_4$)alkoxy, —$NR^AR^A$ and —(($C_1$-$C_4$)alkyl)$NR^AR^A$, where each $R^A$ is independently H or methyl.

19. The compound or salt according to claim 1, wherein A is an unsubstituted phenyl group or a phenyl group substituted by an ethyl, fluoro, cyano or methoxy group.

20. The compound or salt according to claim 1, wherein $R^2$ and $R^3$ taken together with the atom to which they are connected form a tetrahydropyranyl, 2,2-dimethyl-tetrahydropyranyl, cyclopentyl, 1-methyl-piperidinyl, cyclopropyl, cyclohexyl, 1-ethyl-piperidinyyl, tetrahydrofuranyl, piperidinyl, 1-methyl-pyrrolidinyl, 1-benzyl-pyrrolidinyl, 1-cyclopropylmethyl-pyrrolidinyl, oxetanyl, azetidinyl, 1-methyl-azetidinyl, 1-benzyl-azetidinyl, or 1-cyclopropylmethyl-azetidinyl group.

21. The compound or salt according to claim 1, wherein, L is a 5-membered heteroaryl, pyridyl or phenyl which is substituted by $R^4$ and is optionally further substituted, wherein when L is further substituted, L is substituted by 1 substituent selected from chloro, fluoro, cyano and methyl.

22. The compound or salt according to claim 1, wherein L is thiazolyl, thienyl, triazolyl, pyridyl, phenyl, or oxazolyl which is substituted by a methyl group.

* * * * *